United States Patent
Norris et al.

(10) Patent No.: US 9,725,449 B2
(45) Date of Patent: Aug. 8, 2017

(54) TRICYCLIC COMPOUNDS AS ANTICANCER AGENTS

(71) Applicant: BRISTOL-MYERS SQUIBB COMPANY, Princeton, NJ (US)

(72) Inventors: Derek J. Norris, Pennington, NJ (US); Wayne Vaccaro, Yardley, PA (US); Mikkel V. DeBenedetto, Middletown, CT (US); Andrew P. Degnan, Rocky Hill, CT (US); George V. Delucca, Pennington, NJ (US); Jeffrey A. Deskus, Marlborough, CT (US); Wen-Ching Han, Newtown, PA (US); Godwin Kwame Kumi, Rocky Hill, CT (US); William D. Schmitz, Cheshire, CT (US); John E. Starrett, Jr., Waterford, CT (US); Matthew D. Hill, Wallingford, CT (US); Hong Huang, Durham, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/150,492

(22) Filed: May 10, 2016

(65) Prior Publication Data

US 2016/0333013 A1 Nov. 17, 2016

Related U.S. Application Data

(60) Provisional application No. 62/159,991, filed on May 12, 2015.

(51) Int. Cl.

| | | |
|---|---|---|
| C07D 471/14 | (2006.01) | |
| A61K 31/4375 | (2006.01) | |
| A61K 31/439 | (2006.01) | |
| A61K 31/444 | (2006.01) | |
| A61K 31/4545 | (2006.01) | |
| A61K 31/496 | (2006.01) | |
| A61K 31/519 | (2006.01) | |
| A61K 31/5377 | (2006.01) | |
| A61K 31/541 | (2006.01) | |
| A61K 31/554 | (2006.01) | |
| A61K 31/675 | (2006.01) | |
| A61K 31/683 | (2006.01) | |
| C07D 519/00 | (2006.01) | |
| C07F 9/6561 | (2006.01) | |

(52) U.S. Cl.
CPC .......... *C07D 471/14* (2013.01); *A61K 31/439* (2013.01); *A61K 31/4375* (2013.01); *A61K 31/444* (2013.01); *A61K 31/4545* (2013.01); *A61K 31/496* (2013.01); *A61K 31/519* (2013.01); *A61K 31/5377* (2013.01); *A61K 31/541* (2013.01); *A61K 31/554* (2013.01); *A61K 31/675* (2013.01); *A61K 31/683* (2013.01); *C07D 519/00* (2013.01); *C07F 9/6561* (2013.01)

(58) Field of Classification Search
CPC .................................................... C07D 471/14
See application file for complete search history.

(56) References Cited

U.S. PATENT DOCUMENTS

| | | |
|---|---|---|
| 2014/0256700 A1 | 9/2014 | Poss et al. |
| 2014/0256706 A1 | 9/2014 | Wang et al. |
| 2016/0009701 A1 | 1/2016 | Poss et al. |
| 2016/0176864 A1 | 6/2016 | Norris et al. |

FOREIGN PATENT DOCUMENTS

| | | |
|---|---|---|
| WO | WO 2009/085185 | 7/2009 |
| WO | WO 2010/080429 | 7/2010 |
| WO | WO 2012/145173 | 10/2012 |
| WO | WO 2013/046635 | 4/2013 |
| WO | WO 2014/086739 | 6/2014 |
| WO | WO 2014/134232 | 9/2014 |
| WO | WO 2014/134267 | 9/2014 |
| WO | WO 2014/164596 | 10/2014 |
| WO | WO2015/100282 | 7/2015 |
| WO | WO 2015/110263 | 7/2015 |
| WO | WO 2015/131005 | 9/2015 |

OTHER PUBLICATIONS

Conway, S., ACS Med. Chem. Lett.; vol. 3 pp. 691-694 (2012).
Hewings et al., J. Med. Chem., vol. 55, pp. 9393-9413 (2012).
Gorlitzer, K. et. al., Die Pharmazie, Govi Verlag Pharmazeutischer Verlag GMBH, vol. 55 No. 4, pp. 273-281 (2000).

*Primary Examiner* — Bruck Kifle
(74) *Attorney, Agent, or Firm* — Elliott Korsen

(57) ABSTRACT

The present invention is directed to tricyclic compounds of the formula

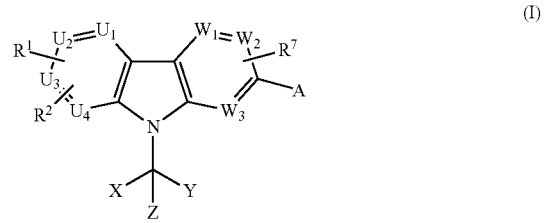

wherein all substituents are defined herein, as well as pharmaceutically acceptable compositions comprising compounds of the invention and methods of using said compositions in the treatment of various disorders.

17 Claims, No Drawings

TRICYCLIC COMPOUNDS AS ANTICANCER AGENTS

CROSS-REFERENCE TO RELATED APPLICATIONS

This application claims priority from U.S. Provisional Application No. 62/159,991 filed May 12, 2015, the disclosures of which are incorporated herein by reference in their entirety.

FIELD OF THE INVENTION

The invention provides novel tricyclic compounds, pharmaceutical compositions comprising the compounds, and methods of using them, for example, for the treatment or prophylaxis of certain cancers and to their use in therapy.

BACKGROUND OF THE INVENTION

The genomes of eukaryotic organisms are highly organized within the nucleus of the cell. The long strands of duplex DNA are wrapped around an octomer of histone proteins to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. There has been appreciation recently that chromatin templates form a fundamentally important set of gene control mechanisms referred to as epigenetic regulation. By conferring a wide range of specific chemical modifications to histones and DNA (such as acetylation, methylation, phosphorylation, ubiquitinylation and SUMOylation) epigenetic regulators modulate the structure, function and accessibility of our genome, thereby exerting a huge impact in gene expression.

Histone acetylation is most usually associated with the activation of gene transcription, as the modification loosens the interaction of the DNA and the histone octomer by changing the electrostatics. In addition to this physical change, specific proteins bind to acetylated lysine residues within histones to read the epigenetic code. Bromodomains are small (~110 amino acid) distinct domains within proteins that bind to acetylated lysine residues commonly but not exclusively in the context of histones. There is a family of around 50 proteins known to contain bromodomains, and they have a range of functions within the cell. The BET family of bromodomain containing proteins comprises 4 proteins (BRD2, BRD3, BRD4 and BRD-T) which contain tandem bromodomains capable of binding to two acetylated lysine residues in close proximity, increasing the specificity of the interaction.

BRD2 and BRD3 are reported to associate with histones along actively transcribed genes and may be involved in facilitating transcriptional elongation (Leroy et al., Mol. Cell. 2008 30(1):51-60), while BRD4 appears to be involved in the recruitment of the pTEF-I3 complex to inducible genes, resulting in phosphorylation of RNA polymerase and increased transcriptional output (Hargreaves et al., Cell, 2009 138(1): 1294145). All family members have been reported to have some function in controlling or executing aspects of the cell cycle, and have been shown to remain in complex with chromosomes during cell division—suggesting a role in the maintenance of epigenetic memory. In addition some viruses make use of these proteins to tether their genomes to the host cell chromatin, as part of the process of viral replication (You et al., Cell, 2004 117(3): 349-60).

Recent articles relating to this target include Prinjha et al., Trends in Pharmacological Sciences, March 2012, Vol. 33, No. 3, pp. 146-153; Conway, ACS Med. Chem. Lett., 2012, 3, 691-694 and Hewings et al., J. Med. Chem., 2012, 55, 9393-9413.

Small molecule BET inhibitors that are reported to be in development include GSK-525762A, OTX-015, TEN-010 as well as others from the University of Oxford and Constellation Pharmaceuticals Inc.

Hundreds of epigenetic effectors have been identified, many of which are chromatin-binding proteins or chromatin-modifying enzymes. These proteins have been associated with a variety of disorders such as neurodegenerative disorders, metabolic diseases, inflammation and cancer. Thus, these compounds which inhibit the binding of a bromodomain with its cognate acetylated proteins, promise new approaches in the treatment of a range of autoimmune and inflammatory diseases or conditions and in the treatment of various types of cancer.

SUMMARY OF THE INVENTION

There is provided a compound of formula (I)

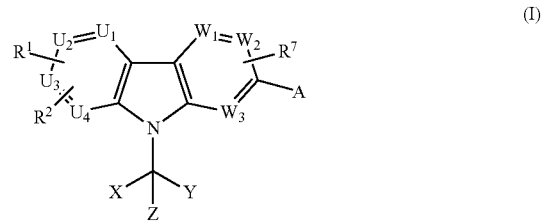

wherein
$U_1$, $U_2$, $U_3$ and $U_4$ are independently —N— or —CH—, provided that at least one of them is —N—;
$W_1$, $W_2$ and $W_3$ are independently —N— or —CH—, provided that at least one of them is —N—;
A is optionally substituted heterocyclo or optionally substituted heteroaryl, wherein the substituents are one or more R;
R is independently one or more hydrogen, $CD_3$, halogen, haloalkyl, hydroxyalkyl, CN, $CF_3$, $CH_2F$, $CHF_2$, optionally substituted ($C_1$-$C_6$)alkyl, optionally substituted ($C_1$-$C_6$)alkoxy, optionally substituted ($C_3$-$C_6$)cycloalkyl, optionally substituted heterocyclo, —$OR^4$, —$CONR^3R^4$, —$NR^3R^4$, $NR^3R^4(C_1$-$C_6)$alkyl-, —$NR^6OCOR^3$, —$NR^6COR^3$, $NR^6COR^3(C_1$-$C_6)$alkyl-, —$NR^6CO_2R^3$, $NR^6CO_2R^3(C_1$-$C_6)$alkyl-, —$NR^6CONR^3R^4$, —$SO_2NR^3R^4$, $SO_2(C_1$-$C_6)$alkyl-, —$NR^6SO_2NR^3R^4$, —$NR^6SO_2R^4$ or $NR^6SO_2R^4(C_1$-$C_6)$alkyl-;
X and Y are independently selected from hydrogen, optionally substituted ($C_1$-$C_6$)alkyl, optionally substituted ($C_3$-$C_8$)cycloalkyl, optionally substituted aryl, optionally substituted heteroaryl or optionally substituted heterocyclo;
Z is hydrogen, halogen, —OH, ($C_1$-$C_6$)alkyl or ($C_1$-$C_6$)alkoxy;
$R^1$ is, independently at each occurrence, one or more hydrogen, halogen, —CN, —$OR^4$, —$NR^3R^4$, —$CONR^3R^4$, —COOH, —$OCONR^3R^4$, —$NR^6OCOR^3$, —$NR^6CONR^3R^4$, —$NR^6SO_2NR^3R^4$, —$NR^6SO_2R^4$, optionally substituted ($C_1$-$C_6$)alkyl, optionally substituted $(C_2-C_6)$alkenyl, optionally substituted $(C_2-C_6)$alkynyl, optionally substituted $(C_1-C_6)$alkoxy, optionally substituted $(C_3-C_8)$cycloalkyl, optionally substituted $(C_3-C_8)$cycloalkyl $(C_1-C_6)$alkyl, optionally substituted $(C_3-C_8)$cycloalkyl-CO—, optionally substituted $(C_3-C_8)$cycloalkyl-$SO_2$—, optionally substituted aryl $(C_1-C_6)$alkoxy, optionally substituted $(C_3-C_8)$cycloalkyl $(C_1-C_6)$alkoxy, optionally substituted heterocyclyl-CO—, optionally substituted heterocyclyl, optionally substituted $(C_1-C_6)$alkyl-$SO_2$—, —$NR^6SO_2$— optionally substituted $(C_1-C_6)$alkyl, —$NR^6SO_2$— optionally substituted heterocyclo, optionally substituted $(C_1-C_6)$alkyl-$NR^6SO_2$— or optionally substituted heterocyclo-$NR^6SO_2$—;

$R^2$ is hydrogen, halogen, —CN, OH, —$CONR^3R^4$, —$NR^6COOR^4$, —$NR^6CONR^3R^4$, —$NR^6COR^4$, —$NR^6SO_2R^5$, —$SO_2NR^3R^4$, —$NR^6SO_2NR^3R^4$, optionally substituted $(C_1-C_6)$alkyl, optionally substituted $(C_3-C_8)$cycloalkyl, optionally substituted $(C_1-C_6)$ alkoxy, optionally substituted aryl, optionally substituted $(C_1-C_6)$alkyl-$SO_2$—, optionally substituted aryl-$SO_2$, optionally substituted heteroaryl or optionally substituted heterocyclo;

$R^3$ is hydrogen, optionally substituted $(C_1-C_6)$alkyl, optionally substituted $(C_3-C_8)$cycloalkyl, optionally substituted $(C_2-C_6)$alkenyl, optionally substituted $(C_2-C_6)$alkynyl, cyano$(C_1-C_6)$alkyl, hydroxy$(C_1-C_6)$alkyl, optionally substituted aryl, optionally substituted aryl$(C_1-C_6)$alkyl, optionally substituted aryloxy$(C_1-C_6)$alkyl, optionally substituted $(C_1-C_6)$alkyl-$SO_2$—, optionally substituted heterocyclyl, optionally substituted heterocyclyl$(C_1-C_6)$alkyl, optionally substituted heteroaryl or optionally substituted heteroaryl $(C_1-C_6)$alkyl, $R^4$ is hydrogen, optionally substituted $(C_1-C_6)$alkyl or optionally substituted $(C_3-C_8)$cycloalkyl;

$R^5$ is hydrogen, optionally substituted $(C_1-C_6)$alkyl, optionally substituted $(C_3-C_8)$cycloalkyl, optionally substituted $(C_2-C_6)$alkenyl, optionally substituted $(C_2-C_6)$alkynyl, cyano$(C_1-C_6)$alkyl, hydroxy$(C_1-C_6)$alkyl, optionally substituted aryl, optionally substituted aryl$(C_1-C_6)$alkyl, optionally substituted aryloxy$(C_1-C_6)$alkyl, optionally substituted $(C_1-C_6)$alkyl-$SO_2$—, optionally substituted heterocyclyl, optionally substituted heterocyclyl$(C_1-C_6)$alkyl, optionally substituted heteroaryl or optionally substituted heteroaryl $(C_1-C_6)$alkyl;

$R^6$ is hydrogen or optionally substituted $(C_1-C_6)$alkyl;

$R^7$ is hydrogen, optionally substituted $(C_1-C_6)$alkyl, —$OR^4$, CN or halogen;

and/or a pharmaceutically acceptable salt, tautomer or stereoisomer thereof.

In another aspect, there is provided a pharmaceutical composition comprising a compound of the invention or a pharmaceutically acceptable salt thereof and one or more pharmaceutically acceptable carriers, diluents or excipients.

In another aspect, there is provided a compound of the invention or a pharmaceutically acceptable salt thereof for use in therapy. In particular, the use is for the treatment of a disease or condition for which a bromodomain inhibitor is indicated.

In another aspect, there is provided a method of treating autoimmune and inflammatory diseases or conditions which comprises administering to a subject in need thereof a therapeutically effective amount of a bromodomain inhibitor.

In another aspect, there is provided a method of treating cancer which comprises administering to a subject in need thereof a therapeutically effective amount of a bromodomain inhibitor.

In another aspect of the present invention, there is provided a method for treating a bromodomain-containing protein mediated disorder in a patient in need thereof, comprising the step of administering to said patient a compound of the invention.

DETAILED DESCRIPTION OF THE INVENTION

In a first aspect of the present invention, there is provided a compound of formula (I)

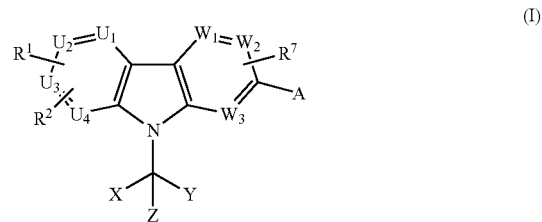

wherein $U_1$, $U_2$, $U_3$ and $U_4$ are independently —N— or —CH—, provided that at least one of them is —N—;

$W_1$, $W_2$ and $W_3$ are independently —N— or —CH—, provided that at least one of them is —N—;

A is optionally substituted heterocyclo or optionally substituted heteroaryl, wherein the substituents are one or more R;

R is independently one or more hydrogen, $CD_3$, halogen, haloalkyl, hydroxyalkyl, CN, $CF_3$, $CH_2F$, $CHF_2$, optionally substituted $(C_1-C_6)$alkyl, optionally substituted $(C_1-C_6)$alkoxy, optionally substituted $(C_3-C_6)$cycloalkyl, optionally substituted heterocyclo, —$OR^4$, —$CONR^3R^4$, —$NR^3R^4$, $NR^3R^4(C_1-C_6)$alkyl-, —$NR^6OCOR^3$, —$NR^6COR^3$, $NR^6COR^3(C_1-C_6)$alkyl-, —$NR^6CO_2R^3$, $NR^6CO_2R^3(C_1-C_6)$alkyl-, —$NR^6CONR^3R^4$, —$SO_2NR^3R^4$, $SO_2(C_1-C_6)$alkyl-, —$NR^6SO_2NR^3R^4$, —$NR^6SO_2R^4$ or $NR^6SO_2R^4(C_1-C_6)$alkyl-;

X and Y are independently selected from hydrogen, optionally substituted $(C_1-C_6)$alkyl, optionally substituted $(C_3-C_8)$cycloalkyl, optionally substituted aryl, optionally substituted heteroaryl or optionally substituted heterocyclo;

Z is hydrogen, halogen, —OH, $(C_1-C_6)$alkyl or $(C_1-C_6)$alkoxy;

$R^1$ is, independently at each occurrence, one or more hydrogen, halogen, —CN, —$OR^4$, —$NR^3R^4$, —$CONR^3R^4$, —COOH, —$OCONR^3R^4$, —$NR^6OCOR^3$, —$NR^6CONR^3R^4$, —$NR^6SO_2NR^3R^4$, —$NR^6SO_2R^4$, optionally substituted $(C_1-C_6)$alkyl, optionally substituted $(C_2-C_6)$alkenyl, optionally substituted $(C_2-C_6)$alkynyl, optionally substituted $(C_1-C_6)$alkoxy, optionally substituted $(C_3-C_8)$cycloalkyl, optionally substituted $(C_3-C_8)$cycloalkyl $(C_1-C_6)$alkyl, optionally substituted $(C_3-C_8)$cycloalkyl-CO—, optionally substituted $(C_3-C_8)$cycloalkyl-$SO_2$—, optionally substituted aryl $(C_1-C_6)$alkoxy, optionally substituted $(C_3-C_8)$cycloalkyl $(C_1-C_6)$alkoxy, optionally substituted heterocyclyl-CO—, optionally substituted heterocyclyl, optionally substituted $(C_1-C_6)$alkyl-$SO_2$—, —$NR^6SO_2$— optionally substituted $(C_1-C_6)$alkyl, —$NR^6SO_2$— optionally substituted heterocyclo, optionally substituted $(C_1-C_6)$alkyl-$NR^6SO_2$— or optionally substituted heterocyclo-$NR^6SO_2$—;

$R^2$ is hydrogen, halogen, —CN, OH, —$CONR^3R^4$, —$NR^6COOR^4$, —$NR^6CONR^3R^4$, —$NR^6COR^4$, —NR⁶SO₂R⁵, —SO₂NR³R⁴, —NR⁶SO₂NR³R⁴, optionally substituted ($C_1$-$C_6$)alkyl, optionally substituted ($C_3$-$C_8$)cycloalkyl, optionally substituted ($C_1$-$C_6$) alkoxy, optionally substituted aryl, optionally substituted ($C_1$-$C_6$)alkyl-SO₂—, optionally substituted aryl-SO₂, optionally substituted heteroaryl or optionally substituted heterocyclo;

R³ is hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-SO₂—, optionally substituted heterocyclyl, optionally substituted heterocyclyl($C_1$-$C_6$)alkyl, optionally substituted heteroaryl or optionally substituted heteroaryl ($C_1$-$C_6$)alkyl, R⁴ is hydrogen, optionally substituted ($C_1$-$C_6$)alkyl or optionally substituted ($C_3$-$C_8$)cycloalkyl;

R⁵ is hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-SO₂—, optionally substituted heterocyclyl, optionally substituted heterocyclyl($C_1$-$C_6$)alkyl, optionally substituted heteroaryl or optionally substituted heteroaryl ($C_1$-$C_6$)alkyl;

R⁶ is hydrogen or optionally substituted ($C_1$-$C_6$)alkyl;

R⁷ is hydrogen, optionally substituted ($C_1$-$C_6$)alkyl, —OR⁴, CN or halogen;

and/or a pharmaceutically acceptable salt, tautomer or stereoisomer thereof.

In a second aspect of the invention, there is provided a compound according to claim 1 of formula (II)

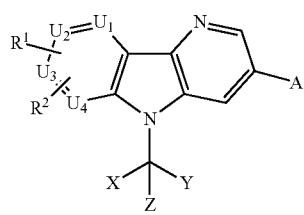

wherein:

$U_1$, $U_2$, $U_3$ and $U_4$ are independently —N— or —CH—, provided that at least one of them is —N—;

A is

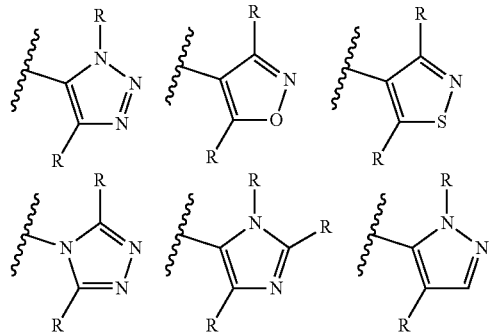

-continued

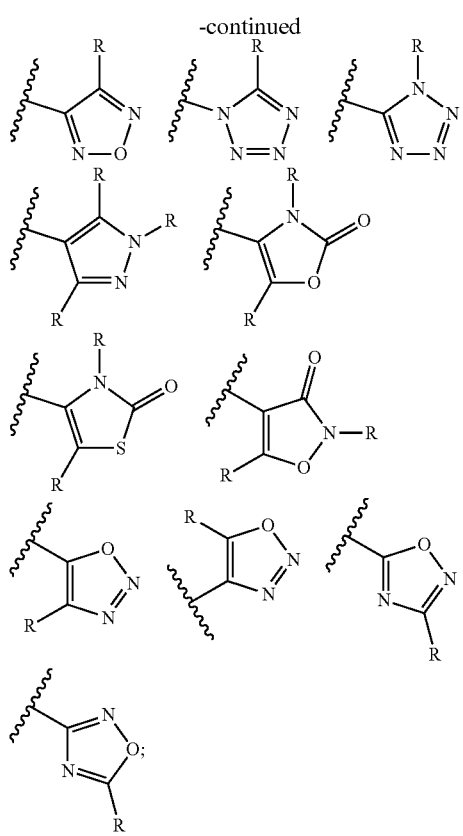

R is independently one or more hydrogen, CD₃, halogen, haloalkyl, hydroxyalkyl, CN, CF₃, CH₂F, CHF₂, optionally substituted ($C_1$-$C_6$)alkyl, optionally substituted ($C_1$-$C_6$) alkoxy, optionally substituted ($C_3$-$C_6$)cycloalkyl, optionally substituted heterocyclo, —OR⁴, —CONR³R⁴, —NR³R⁴, NR³R⁴($C_1$-$C_6$)alkyl-, —NR⁶OCOR³, —NR⁶COR³, NR⁶COR³($C_1$-$C_6$)alkyl-, —NR⁶CO₂R³, NR⁶CO₂R³($C_1$-$C_6$) alkyl-, —NR⁶CONR³R⁴, —SO₂NR³R⁴, SO₂($C_1$-$C_6$)alkyl-, —NR⁶SO₂NR³R⁴, —NR⁶SO₂R⁴ or NR⁶SO₂R⁴($C_1$-$C_6$) alkyl-;

X and Y are independently selected from hydrogen, optionally substituted ($C_1$-$C_6$)alkyl, optionally substituted ($C_3$-$C_8$)cycloalkyl, optionally substituted aryl, optionally substituted heteroaryl or optionally substituted heterocyclo;

Z is hydrogen, halogen, —OH, ($C_1$-$C_6$)alkyl or ($C_1$-$C_6$) alkoxy;

R¹ is, independently at each occurrence, one or more hydrogen, halogen, —CN, —OR⁴, —NR³R⁴, —CONR³R⁴, —COOH, —OCONR³R⁴, —NR⁶OCOR³, —NR⁶CONR³R⁴, —NR⁶SO₂NR³R⁴, —NR⁶SO₂R⁴, optionally substituted ($C_1$-$C_6$)alkyl, optionally substituted ($C_2$-$C_6$)alkenyl, optionally substituted ($C_2$-$C_6$)alkynyl, optionally substituted ($C_1$-$C_6$)alkoxy, optionally substituted ($C_3$-$C_8$)cycloalkyl, optionally substituted ($C_3$-$C_8$)cycloalkyl ($C_1$-$C_6$)alkyl, optionally substituted ($C_3$-$C_8$)cycloalkyl-CO—, optionally substituted ($C_3$-$C_8$)cycloalkyl-SO₂—, optionally substituted aryl ($C_1$-$C_6$)alkoxy, optionally substituted ($C_3$-$C_8$)cycloalkyl ($C_1$-$C_6$)alkoxy, optionally substituted heterocyclyl-CO—, optionally substituted heterocyclyl, optionally substituted ($C_1$-$C_6$)alkyl-SO₂—, —NR⁶SO₂— optionally substituted ($C_1$-$C_6$)alkyl, —NR⁶SO₂— optionally substituted heterocyclo, optionally substituted ($C_1$-$C_6$)alkyl-NR⁶SO₂— or optionally substituted heterocyclo-NR⁶SO₂—;

$R^2$ is hydrogen, halogen, —CN, OH, —CONR$^3$R$^4$, —NR$^6$COOR$^4$, —NR$^6$CONR$^3$R$^4$, —NR$^6$COR$^4$, —NR$^6$SO$_2$R$^5$, —SO$_2$NR$^3$R$^4$, —NR$^6$SO$_2$NR$^3$R$^4$, optionally substituted (C$_1$-C$_6$)alkyl, optionally substituted (C$_3$-C$_8$)cycloalkyl, optionally substituted (C$_1$-C$_6$) alkoxy, optionally substituted aryl, optionally substituted (C$_1$-C$_6$)alkyl-SO$_2$—, optionally substituted aryl-SO$_2$, optionally substituted heteroaryl or optionally substituted heterocyclo;

$R^3$ is hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl (C$_1$-C$_6$)alkyl, $R^4$ is hydrogen, optionally substituted (C$_1$-C$_6$)alkyl or optionally substituted (C$_3$-C$_8$)cycloalkyl;

$R^5$ is hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl (C$_1$-C$_6$)alkyl;

$R^6$ is hydrogen or optionally substituted (C$_1$-C$_6$)alkyl;

and/or a pharmaceutically acceptable salt, tautomer or stereoisomer thereof.

In a third aspect of the invention within the scope of the first two aspects, there is provided a compound of formula (II)

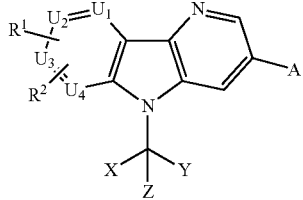

(II)

wherein:

$U_1$, $U_2$, $U_3$ and $U_4$ are independently —N— or —CH—, provided that at least one of them is —N—;

A is

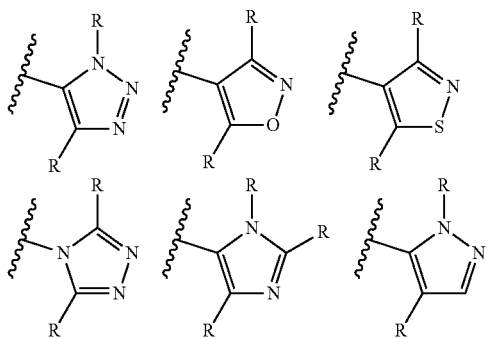

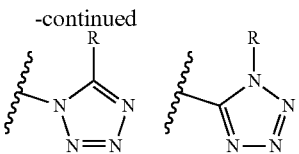

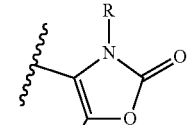

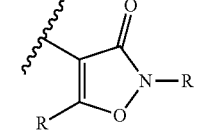

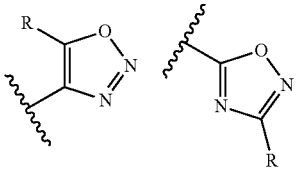

R is independently one or more hydrogen, CD$_3$, halogen, haloalkyl, hydroxyalkyl, CN, CF$_3$, CH$_2$F, CHF$_2$, optionally substituted (C$_1$-C$_6$)alkyl, optionally substituted (C$_1$-C$_6$) alkoxy, optionally substituted (C$_3$-C$_6$)cycloalkyl, optionally substituted heterocyclo, —OR$^4$, —CONR$^3$R$^4$, —NR$^3$R$^4$, NR$^3$R$^4$(C$_1$-C$_6$)alkyl-, —NR$^6$OCOR$^3$, —NR$^6$COR$^3$, NR$^6$COR$^3$(C$_1$-C$_6$)alkyl-, —NR$^6$CO$_2$R$^3$, NR$^6$CO$_2$R$^3$(C$_1$-C$_6$) alkyl-, —NR$^6$CONR$^3$R$^4$, —SO$_2$NR$^3$R$^4$, SO$_2$(C$_1$-C$_6$)alkyl-, —NR$^6$SO$_2$NR$^3$R$^4$, —NR$^6$SO$_2$R$^4$ or NR$^6$SO$_2$R$^4$(C$_1$-C$_6$) alkyl-;

X and Y are independently selected from hydrogen, optionally substituted (C$_1$-C$_6$)alkyl, optionally substituted (C$_3$-C$_8$)cycloalkyl, optionally substituted aryl, optionally substituted heteroaryl or optionally substituted heterocyclo;

Z is hydrogen, halogen, —OH, (C$_1$-C$_6$)alkyl or (C$_1$-C$_6$) alkoxy;

$R^1$ is, independently at each occurrence, one or more hydrogen, halogen, —CN, —OR$^4$, —NR$^3$R$^4$, —CONR$^3$R$^4$, —COOH, —OCONR$^3$R$^4$, —NR$^6$OCOR$^3$, —NR$^6$CONR$^3$R$^4$, —NR$^6$SO$_2$NR$^3$R$^4$, —NR$^6$SO$_2$R$^4$, optionally substituted (C$_1$-C$_6$)alkyl, optionally substituted (C$_2$-C$_6$)alkenyl, optionally substituted (C$_2$-C$_6$)alkynyl, optionally substituted (C$_1$-C$_6$)alkoxy, optionally substituted (C$_3$-C$_8$)cycloalkyl, optionally substituted (C$_3$-C$_8$)cycloalkyl (C$_1$-C$_6$)alkyl, optionally substituted (C$_3$-C$_8$)cycloalkyl-CO—, optionally substituted (C$_3$-C$_8$)cycloalkyl-SO$_2$—, optionally substituted aryl (C$_1$-C$_6$)alkoxy, optionally substituted (C$_3$-C$_8$)cycloalkyl (C$_1$-C$_6$)alkoxy, optionally substituted heterocyclyl-CO—, optionally substituted heterocyclyl, optionally substituted (C$_1$-C$_6$)alkyl-SO$_2$—, —NR$^6$SO$_2$— optionally substituted (C$_1$-C$_6$)alkyl, —NR$^6$SO$_2$— optionally substituted heterocyclo, optionally substituted (C$_1$-C$_6$)alkyl-NR$^6$SO$_2$— or optionally substituted heterocyclo-NR$^6$SO$_2$—;

$R^2$ is hydrogen, halogen, —CN, OH, optionally substituted ($C_1$-$C_6$)alkyl, optionally substituted ($C_3$-$C_8$)cycloalkyl, optionally substituted ($C_1$-$C_6$) alkoxy, optionally substituted aryl, optionally substituted heteroaryl or optionally substituted heterocyclo;

$R^3$ is hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl ($C_1$-$C_6$)alkyl, $R^4$ is hydrogen, optionally substituted ($C_1$-$C_6$)alkyl or optionally substituted ($C_3$-$C_8$)cycloalkyl;

$R^6$ is hydrogen or optionally substituted ($C_1$-$C_6$)alkyl;

and/or a pharmaceutically acceptable salt, tautomer or stereoisomer thereof.

In a 4$^{th}$ aspect within the scope of the prior aspects, there is provided a compound of the formula

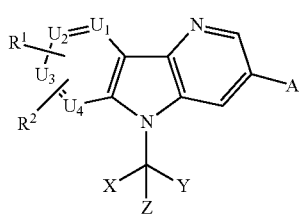

(II)

wherein
A is

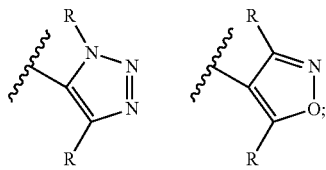

R is independently one or more hydrogen, $CD_3$, halogen, haloalkyl, hydroxyalkyl, CN, $CF_3$, $CH_2F$, $CHF_2$, optionally substituted ($C_1$-$C_6$)alkyl, optionally substituted ($C_1$-$C_6$) alkoxy, optionally substituted ($C_3$-$C_6$)cycloalkyl, optionally substituted heterocyclo, —$OR^4$, —$CONR^3R^4$, —$NR^3R^4$, $NR^3R^4$($C_1$-$C_6$)alkyl-, —$NR^6OCOR^3$, —$NR^6COR^3$, $NR^6COR^3$($C_1$-$C_6$)alkyl-, —$NR^6CO_2R^3$, $NR^6CO_2R^3$($C_1$-$C_6$)alkyl-, —$NR^6CONR^3R^4$, —$SO_2NR^3R^4$, $SO_2$($C_1$-$C_6$)alkyl-, —$NR^6SO_2NR^3R^4$, —$NR^6SO_2R^4$ or $NR^6SO_2R^4$($C_1$-$C_6$)alkyl-;

X and Y are independently selected from hydrogen, optionally substituted ($C_1$-$C_6$)alkyl, optionally substituted ($C_3$-$C_8$)cycloalkyl, optionally substituted aryl, optionally substituted heteroaryl or optionally substituted heterocyclo;

Z is hydrogen, halogen, —OH, ($C_1$-$C_6$)alkyl or ($C_1$-$C_6$) alkoxy;

$R^1$ is, independently at each occurrence, one or more hydrogen, halogen, —CN, —$OR^4$, —$NR^3R^4$, —$CONR^3R^4$, —COOH, —$OCONR^3R^4$, —$NR^6OCOR^3$, —$NR^6CONR^3R^4$, —$NR^6SO_2NR^3R^4$, —$NR^6SO_2R^4$, optionally substituted ($C_1$-$C_6$)alkyl, optionally substituted ($C_2$-$C_6$)alkenyl, optionally substituted ($C_2$-$C_6$)alkynyl, optionally substituted ($C_1$-$C_6$)alkoxy, optionally substituted ($C_3$-$C_8$)cycloalkyl, optionally substituted ($C_3$-$C_8$)cycloalkyl ($C_1$-$C_6$)alkyl, optionally substituted ($C_3$-$C_8$)cycloalkyl-CO—, optionally substituted ($C_3$-$C_8$)cycloalkyl-$SO_2$—, optionally substituted aryl ($C_1$-$C_6$)alkoxy, optionally substituted ($C_3$-$C_8$)cycloalkyl ($C_1$-$C_6$)alkoxy, optionally substituted heterocyclyl-CO—, optionally substituted heterocyclyl, optionally substituted ($C_1$-$C_6$)alkyl-$SO_2$—, —$NR^6SO_2$— optionally substituted ($C_1$-$C_6$)alkyl, —$NR^6SO_2$— optionally substituted heterocyclo, optionally substituted ($C_1$-$C_6$)alkyl-$NR^6SO_2$— or optionally substituted heterocyclo-$NR^6SO_2$—;

$R^2$ is hydrogen, halogen, —CN, OH, optionally substituted ($C_1$-$C_6$)alkyl, optionally substituted ($C_3$-$C_8$)cycloalkyl, optionally substituted ($C_1$-$C_6$) alkoxy, optionally substituted aryl, optionally substituted heteroaryl or optionally substituted heterocyclo;

$R^3$ is hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl ($C_1$-$C_6$)alkyl, $R^4$ is hydrogen, optionally substituted ($C_1$-$C_6$)alkyl or optionally substituted ($C_3$-$C_8$)cycloalkyl;

$R^6$ is hydrogen or optionally substituted ($C_1$-$C_6$)alkyl;

and/or a pharmaceutically acceptable salt, tautomer or stereoisomer thereof.

In a 5$^{th}$ aspect of the invention within the scope of the prior aspects, there is provided a compound of the formula

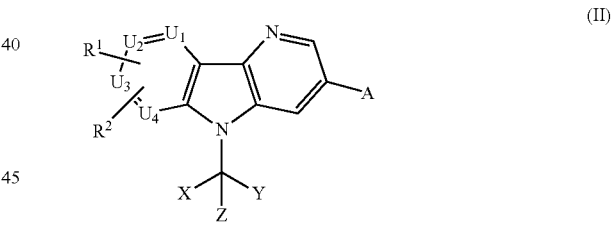

(II)

wherein:
A is

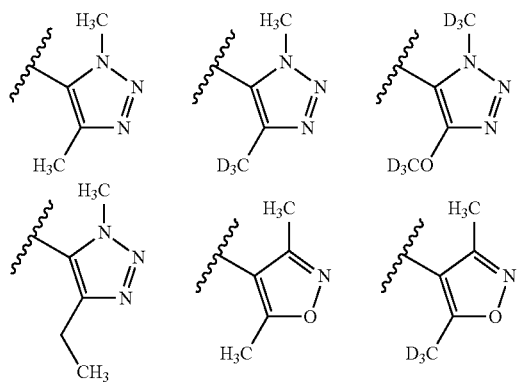

-continued

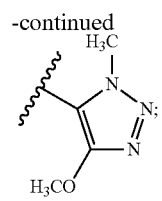

X and Y are independently selected from hydrogen, optionally substituted ($C_1$-$C_6$)alkyl, optionally substituted ($C_3$-$C_8$)cycloalkyl, optionally substituted aryl, optionally substituted heteroaryl or optionally substituted heterocyclo;

Z is hydrogen, halogen, —OH, ($C_1$-$C_6$)alkyl or ($C_1$-$C_6$) alkoxy;

$R^1$ is, independently at each occurrence, one or more hydrogen, halogen, —CN, —$OR^4$, —$NR^3R^4$, —$CONR^3R^4$, —COOH, —$OCONR^3R^4$, —$NR^6OCOR^3$, —$NR^6CONR^3R^4$, —$NR^6SO_2NR^3R^4$, —$NR^6SO_2R^4$, optionally substituted ($C_1$-$C_6$)alkyl, optionally substituted ($C_2$-$C_6$)alkenyl, optionally substituted ($C_2$-$C_6$)alkynyl, optionally substituted ($C_1$-$C_6$)alkoxy, optionally substituted ($C_3$-$C_8$)cycloalkyl, optionally substituted ($C_3$-$C_8$)cycloalkyl ($C_1$-$C_6$)alkyl, optionally substituted ($C_3$-$C_8$)cycloalkyl-CO—, optionally substituted ($C_3$-$C_8$)cycloalkyl-$SO_2$—, optionally substituted aryl ($C_1$-$C_6$)alkoxy, optionally substituted ($C_3$-$C_8$)cycloalkyl ($C_1$-$C_6$)alkoxy, optionally substituted heterocyclyl-CO—, optionally substituted heterocyclyl, optionally substituted ($C_1$-$C_6$)alkyl-$SO_2$—, —$NR^6SO_2$— optionally substituted ($C_1$-$C_6$)alkyl, —$NR^6SO_2$— optionally substituted heterocyclo, optionally substituted ($C_1$-$C_6$)alkyl-$NR^6SO_2$— or optionally substituted heterocyclo-$NR^6SO_2$—;

$R^2$ is hydrogen, halogen, —CN, OH, optionally substituted ($C_1$-$C_6$)alkyl, optionally substituted ($C_3$-$C_8$)cycloalkyl, optionally substituted ($C_1$-$C_6$) alkoxy, optionally substituted aryl, optionally substituted heteroaryl or optionally substituted heterocyclo;

$R^3$ is hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl ($C_1$-$C_6$)alkyl, $R^4$ is hydrogen, optionally substituted ($C_1$-$C_6$)alkyl or optionally substituted ($C_3$-$C_8$)cycloalkyl;

$R^6$ is hydrogen or optionally substituted ($C_1$-$C_6$)alkyl;

and/or a pharmaceutically acceptable salt, tautomer or stereoisomer thereof.

In a $6^{th}$ aspect of the invention within the scope of the prior aspects, there is provided a compound of the formula (III)

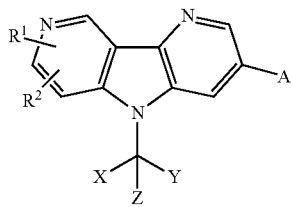

wherein:
A is

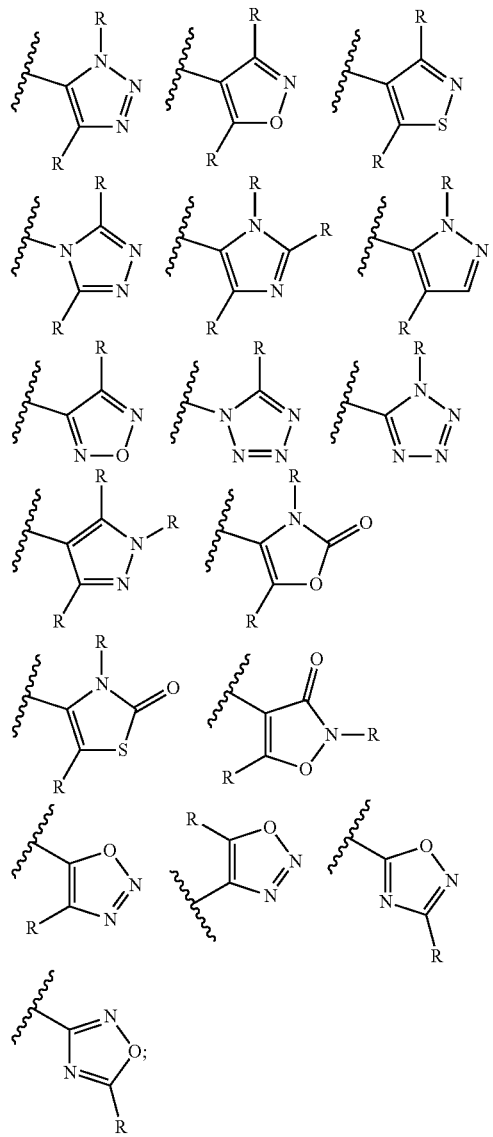

R is independently one or more hydrogen, $CD_3$, halogen, haloalkyl, hydroxyalkyl, CN, $CF_3$, $CH_2F$, $CHF_2$, optionally substituted ($C_1$-$C_6$)alkyl, optionally substituted ($C_1$-$C_6$) alkoxy, optionally substituted ($C_3$-$C_6$)cycloalkyl, optionally substituted heterocyclo, —$OR^4$, —$CONR^3R^4$, —$NR^3R^4$, $NR^3R^4$($C_1$-$C_6$)alkyl-, —$NR^6COR^3$, —$NR^6COR^3$, $NR^6COR^3$($C_1$-$C_6$)alkyl-, —$NR^6CO_2R^3$, $NR^6CO_2R^3$($C_1$-$C_6$) alkyl-, —$NR^6CONR^3R^4$, —$SO_2NR^3R^4$, $SO_2$($C_1$-$C_6$)alkyl-, —$NR^6SO_2NR^3R^4$, —$NR^6SO_2R^4$ or $NR^6SO_2R^4$($C_1$-$C_6$) alkyl-;

X and Y are independently selected from hydrogen, optionally substituted ($C_1$-$C_6$)alkyl, optionally substituted ($C_3$-$C_8$)cycloalkyl, optionally substituted aryl, optionally substituted heteroaryl or optionally substituted heterocyclo;

Z is hydrogen, halogen, —OH, ($C_1$-$C_6$)alkyl or ($C_1$-$C_6$) alkoxy;

$R^1$ is, independently at each occurrence, one or more hydrogen, halogen, —CN, —$OR^4$, —$NR^3R^4$, —$CONR^3R^4$, —COOH, —$OCONR^3R^4$, —$NR^6OCOR^3$, —NR⁶CONR³R⁴, —NR⁶SO₂NR³R⁴, —NR⁶SO₂R⁴, optionally substituted (C₁-C₆)alkyl, optionally substituted (C₂-C₆)alkenyl, optionally substituted (C₂-C₆)alkynyl, optionally substituted (C₁-C₆)alkoxy, optionally substituted (C₃-C₈)cycloalkyl, optionally substituted (C₃-C₈)cycloalkyl (C₁-C₆)alkyl, optionally substituted (C₃-C₈)cycloalkyl-CO—, optionally substituted (C₃-C₈)cycloalkyl-SO₂—, optionally substituted aryl (C₁-C₆)alkoxy, optionally substituted (C₃-C₈)cycloalkyl (C₁-C₆)alkoxy, optionally substituted heterocyclyl-CO—, optionally substituted heterocyclyl, optionally substituted (C₁-C₆)alkyl-SO₂—, —NR⁶SO₂— optionally substituted (C₁-C₆)alkyl, —NR⁶SO₂— optionally substituted heterocyclo, optionally substituted (C₁-C₆)alkyl-NR⁶SO₂— or optionally substituted heterocyclo-NR⁶SO₂—;

R² is hydrogen, halogen, —CN, OH, —CONR³R⁴, —NR⁶COOR⁴, —NR⁶CONR³R⁴, —NR⁶COR⁴, —NR⁶SO₂R⁵, —SO₂NR³R⁴, —NR⁶SO₂NR³R⁴, optionally substituted (C₁-C₆)alkyl, optionally substituted (C₃-C₈)cycloalkyl, optionally substituted (C₁-C₆) alkoxy, optionally substituted aryl, optionally substituted (C₁-C₆)alkyl-SO₂—, optionally substituted aryl-SO₂, optionally substituted heteroaryl or optionally substituted heterocyclo;

R³ is hydrogen, optionally substituted (C₁-C₆)alkyl, optionally substituted (C₃-C₈)cycloalkyl, optionally substituted (C₂-C₆)alkenyl, optionally substituted (C₂-C₆)alkynyl, cyano(C₁-C₆)alkyl, hydroxy(C₁-C₆)alkyl, optionally substituted aryl, optionally substituted aryl(C₁-C₆)alkyl, optionally substituted aryloxy(C₁-C₆)alkyl, optionally substituted (C₁-C₆)alkyl-SO₂—, optionally substituted heterocyclyl, optionally substituted heterocyclyl(C₁-C₆)alkyl, optionally substituted heteroaryl or optionally substituted heteroaryl (C₁-C₆)alkyl, R⁴ is hydrogen, optionally substituted (C₁-C₆)alkyl or optionally substituted (C₃-C₈)cycloalkyl;

R⁵ is hydrogen, optionally substituted (C₁-C₆)alkyl, optionally substituted (C₃-C₈)cycloalkyl, optionally substituted (C₂-C₆)alkenyl, optionally substituted (C₂-C₆)alkynyl, cyano(C₁-C₆)alkyl, hydroxy(C₁-C₆)alkyl, optionally substituted aryl, optionally substituted aryl(C₁-C₆)alkyl, optionally substituted aryloxy(C₁-C₆)alkyl, optionally substituted (C₁-C₆)alkyl-SO₂—, optionally substituted heterocyclyl, optionally substituted heterocyclyl(C₁-C₆)alkyl, optionally substituted heteroaryl or optionally substituted heteroaryl (C₁-C₆)alkyl;

R⁶ is hydrogen or optionally substituted (C₁-C₆)alkyl;

and/or a pharmaceutically acceptable salt, tautomer or stereoisomer thereof.

In a 7ᵗʰ aspect of the invention within the scope of the prior aspects, there is provided a compound of the formula A is

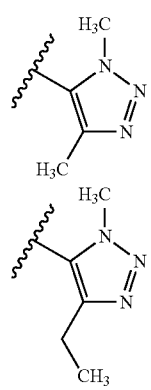

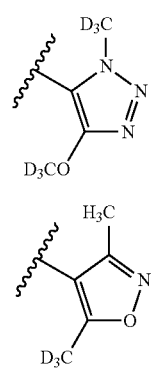
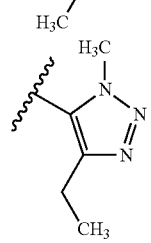
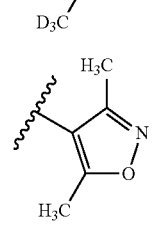
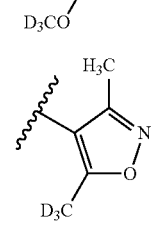

-continued

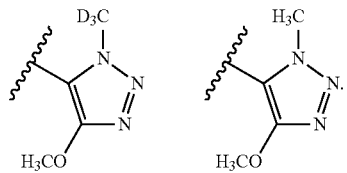

In an 8ᵗʰ aspect of the invention within the scope of the prior aspects, there is provided a compound of the formula

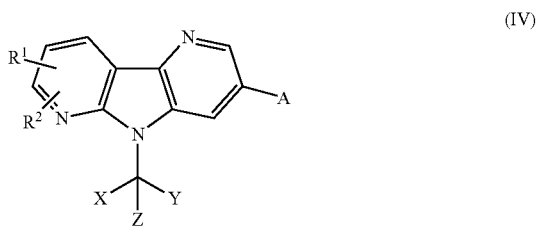

(IV)

wherein:

A is

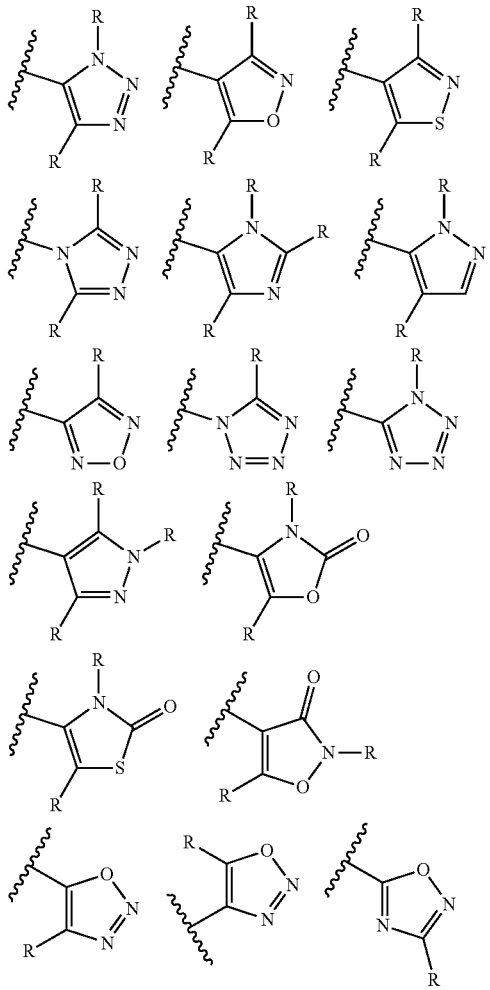

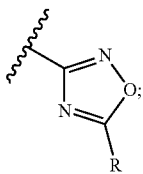

R is independently one or more hydrogen, CD₃, halogen, haloalkyl, hydroxyalkyl, CN, CF₃, CH₂F, CHF₂, optionally substituted (C₁-C₆)alkyl, optionally substituted (C₁-C₆) alkoxy, optionally substituted (C₃-C₆)cycloalkyl, optionally substituted heterocyclo, —OR⁴, —CONR³R⁴, —NR³R⁴, NR³R⁴(C₁-C₆)alkyl-, —NR⁶OCOR³, —NR⁶COR³, NR⁶COR³(C₁-C₆)alkyl-, —NR⁶CO₂R³, NR⁶CO₂R³(C₁-C₆)alkyl-, —NR⁶CONR³R⁴, —SO₂NR³R⁴, SO₂(C₁-C₆)alkyl-, —NR⁶SO₂NR³R⁴, —NR⁶SO₂R⁴ or NR⁶SO₂R⁴(C₁-C₆)alkyl-;

X and Y are independently selected from hydrogen, optionally substituted (C₁-C₆)alkyl, optionally substituted (C₃-C₈)cycloalkyl, optionally substituted aryl, optionally substituted heteroaryl or optionally substituted heterocyclo;

Z is hydrogen, halogen, —OH, (C₁-C₆)alkyl or (C₁-C₆) alkoxy;

R¹ is, independently at each occurrence, one or more hydrogen, halogen, —CN, —OR⁴, —NR³R⁴, —CONR³R⁴, —COOH, —OCONR³R⁴, —NR⁶OCOR³, —NR⁶CONR³R⁴, —NR⁶SO₂NR³R⁴, —NR⁶SO₂R⁴, optionally substituted (C₁-C₆)alkyl, optionally substituted (C₂-C₆)alkenyl, optionally substituted (C₂-C₆)alkynyl, optionally substituted (C₁-C₆)alkoxy, optionally substituted (C₃-C₈)cycloalkyl, optionally substituted (C₃-C₈)cycloalkyl (C₁-C₆)alkyl, optionally substituted (C₃-C₈)cycloalkyl-CO—, optionally substituted (C₃-C₈)cycloalkyl-SO₂—, optionally substituted aryl (C₁-C₆)alkoxy, optionally substituted (C₃-C₈)cycloalkyl (C₁-C₆)alkoxy, optionally substituted heterocyclyl-CO—, optionally substituted heterocyclyl, optionally substituted (C₁-C₆)alkyl-SO₂—, —NR⁶SO₂— optionally substituted (C₁-C₆)alkyl, —NR⁶SO₂— optionally substituted heterocyclo, optionally substituted (C₁-C₆)alkyl-NR⁶SO₂— or optionally substituted heterocyclo-NR⁶SO₂—;

R² is hydrogen, halogen, —CN, OH, —CONR³R⁴, —NR⁶COOR⁴, —NR⁶CONR³R⁴, —NR⁶COR⁴, —NR⁶SO₂R⁵, —SO₂NR³R⁴, —NR⁶SO₂NR³R⁴, optionally substituted (C₁-C₆)alkyl, optionally substituted (C₃-C₈)cycloalkyl, optionally substituted (C₁-C₆) alkoxy, optionally substituted aryl, optionally substituted (C₁-C₆)alkyl-SO₂—, optionally substituted aryl-SO₂, optionally substituted heteroaryl or optionally substituted heterocyclo;

R³ is hydrogen, optionally substituted (C₁-C₆)alkyl, optionally substituted (C₃-C₈)cycloalkyl, optionally substituted (C₂-C₆)alkenyl, optionally substituted (C₂-C₆)alkynyl, cyano(C₁-C₆)alkyl, hydroxy(C₁-C₆)alkyl, optionally substituted aryl, optionally substituted aryl(C₁-C₆)alkyl, optionally substituted aryloxy(C₁-C₆)alkyl, optionally substituted (C₁-C₆)alkyl-SO₂—, optionally substituted heterocyclyl, optionally substituted heterocyclyl(C₁-C₆)alkyl, optionally substituted heteroaryl or optionally substituted heteroaryl (C₁-C₆)alkyl, R⁴ is hydrogen, optionally substituted (C₁-C₆)alkyl or optionally substituted (C₃-C₈)cycloalkyl;

R⁵ is hydrogen, optionally substituted (C₁-C₆)alkyl, optionally substituted (C₃-C₈)cycloalkyl, optionally substituted (C₂-C₆)alkenyl, optionally substituted (C₂-C₆)alkynyl, cyano(C₁-C₆)alkyl, hydroxy(C₁-C₆)alkyl, optionally substituted aryl, optionally substituted aryl(C₁-C₆)alkyl, optionally substituted aryloxy(C₁-C₆)alkyl, optionally substituted (C₁-C₆)alkyl-SO₂—, optionally substituted heterocyclyl, optionally substituted heterocyclyl(C₁-C₆)alkyl, optionally substituted heteroaryl or optionally substituted heteroaryl (C₁-C₆)alkyl;

R⁶ is hydrogen or optionally substituted (C₁-C₆)alkyl;

and/or a pharmaceutically acceptable salt, tautomer or stereoisomer thereof.

In another aspect of the invention within the scope of the prior aspects, there is provided a compound of the formula

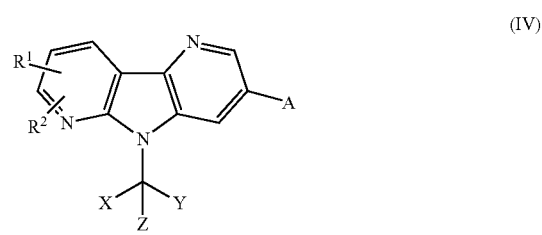

wherein:

A is

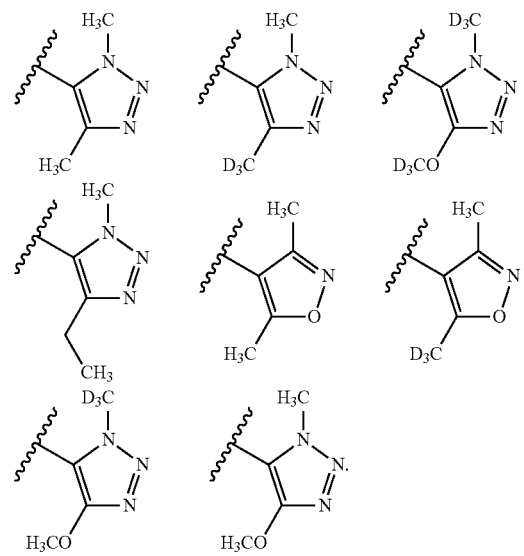

In another aspect of the invention within the scope of the prior aspects, there is provided a compound of the formula (V)

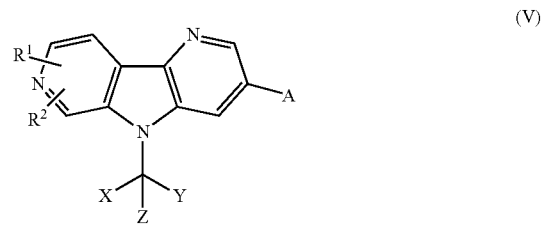

wherein:

A is

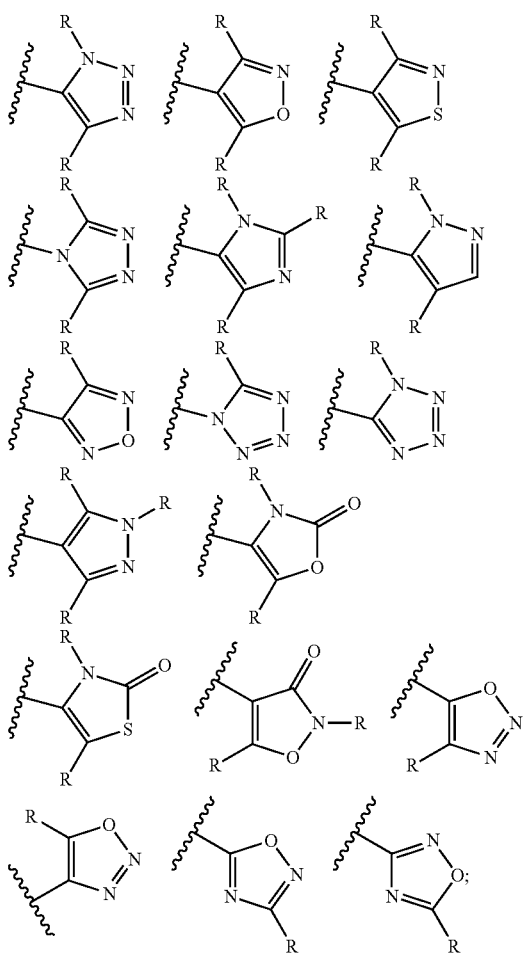

R is independently one or more hydrogen, CD$_3$, halogen, haloalkyl, hydroxyalkyl, CN, CF$_3$, CH$_2$F, CHF$_2$, optionally substituted (C$_1$-C$_6$)alkyl, optionally substituted (C$_1$-C$_6$) alkoxy, optionally substituted (C$_3$-C$_6$)cycloalkyl, optionally substituted heterocyclo, —OR$^4$, —CONR$^3$R$^4$, —NR$^3$R$^4$, NR$^3$R$^4$(C$_1$-C$_6$)alkyl-, —NR$^6$OCOR$^3$, —NR$^6$COR$^3$, NR$^6$COR$^3$(C$_1$-C$_6$)alkyl-, —NR$^6$CO$_2$R$^3$, NR$^6$CO$_2$R$^3$(C$_1$-C$_6$) alkyl-, —NR$^6$CONR$^3$R$^4$, —SO$_2$NR$^3$R$^4$, SO$_2$(C$_1$-C$_6$)alkyl-, —NR$^6$SO$_2$NR$^3$R$^4$, —NR$^6$SO$_2$R$^4$ or NR$^6$SO$_2$R$^4$(C$_1$-C$_6$) alkyl-;

X and Y are independently selected from hydrogen, optionally substituted (C$_1$-C$_6$)alkyl, optionally substituted (C$_3$-C$_8$)cycloalkyl, optionally substituted aryl, optionally substituted heteroaryl or optionally substituted heterocyclo;

Z is hydrogen, halogen, —OH, (C$_1$-C$_6$)alkyl or (C$_1$-C$_6$) alkoxy;

R$^1$ is, independently at each occurrence, one or more hydrogen, halogen, —CN, —OR$^4$, —NR$^3$R$^4$, —CONR$^3$R$^4$, —COOH, —OCONR$^3$R$^4$, —NR$^6$OCOR$^3$, —NR$^6$CONR$^3$R$^4$, —NR$^6$SO$_2$NR$^3$R$^4$, —NR$^6$SO$_2$R$^4$, optionally substituted (C$_1$-C$_6$)alkyl, optionally substituted (C$_2$-C$_6$)alkenyl, optionally substituted (C$_2$-C$_6$)alkynyl, optionally substituted (C$_1$-C$_6$)alkoxy, optionally substituted (C$_3$-C$_8$)cycloalkyl, optionally substituted (C$_3$-C$_8$)cycloalkyl (C$_1$-C$_6$)alkyl, optionally substituted (C$_3$-C$_8$)cycloalkyl-CO—, optionally substituted (C$_3$-C$_8$)cycloalkyl-SO$_2$—, optionally substituted aryl (C$_1$-C$_6$)alkoxy, optionally substituted (C$_3$-C$_8$)cycloalkyl (C$_1$-C$_6$)alkoxy, optionally substituted heterocyclyl-CO—, optionally substituted heterocyclyl, optionally substituted (C$_1$-C$_6$)alkyl-SO$_2$—, —NR$^6$SO$_2$— optionally substituted (C$_1$-C$_6$)alkyl, —NR$^6$SO$_2$— optionally substituted heterocyclo, optionally substituted (C$_1$-C$_6$)alkyl-NR$^6$SO$_2$— or optionally substituted heterocyclo-NR$^6$SO$_2$—;

R$^2$ is hydrogen, halogen, —CN, OH, —CONR$^3$R$^4$, —NR$^6$COOR$^4$, —NR$^6$CONR$^3$R$^4$, —NR$^6$COR$^4$, —NR$^6$SO$_2$R$^5$, —SO$_2$NR$^3$R$^4$, —NR$^6$SO$_2$NR$^3$R$^4$, optionally substituted (C$_1$-C$_6$)alkyl, optionally substituted (C$_3$-C$_8$)cycloalkyl, optionally substituted (C$_1$-C$_6$) alkoxy, optionally substituted aryl, optionally substituted (C$_1$-C$_6$)alkyl-SO$_2$—, optionally substituted aryl-SO$_2$, optionally substituted heteroaryl or optionally substituted heterocyclo;

R$^3$ is hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl (C$_1$-C$_6$)alkyl, R$^4$ is hydrogen, optionally substituted (C$_1$-C$_6$)alkyl or optionally substituted (C$_3$-C$_8$)cycloalkyl;

R$^5$ is hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl (C$_1$-C$_6$)alkyl;

R$^6$ is hydrogen or optionally substituted (C$_1$-C$_6$)alkyl;

and/or a pharmaceutically acceptable salt, tautomer or stereoisomer thereof.

In another aspect of the invention within the scope of the prior aspects, there is provided a compound of formula (V) wherein A is

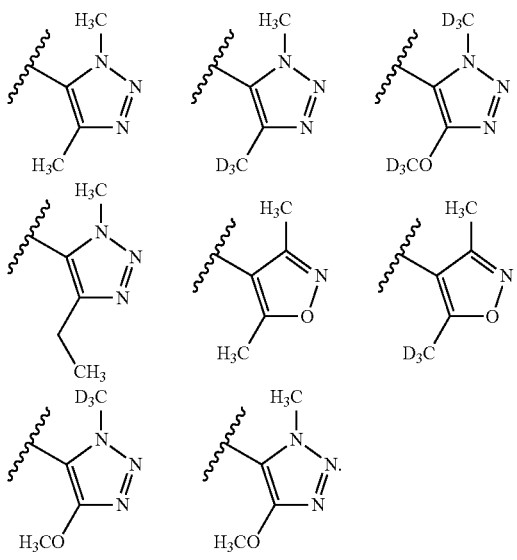

In another aspect of the invention within the scope of the prior aspects, there is provided a compound of the formula (VI)

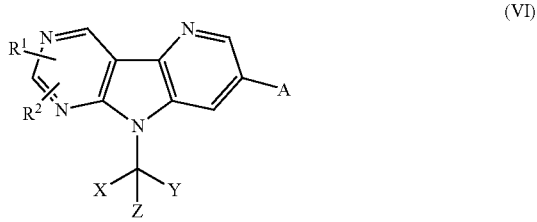

wherein:

A is

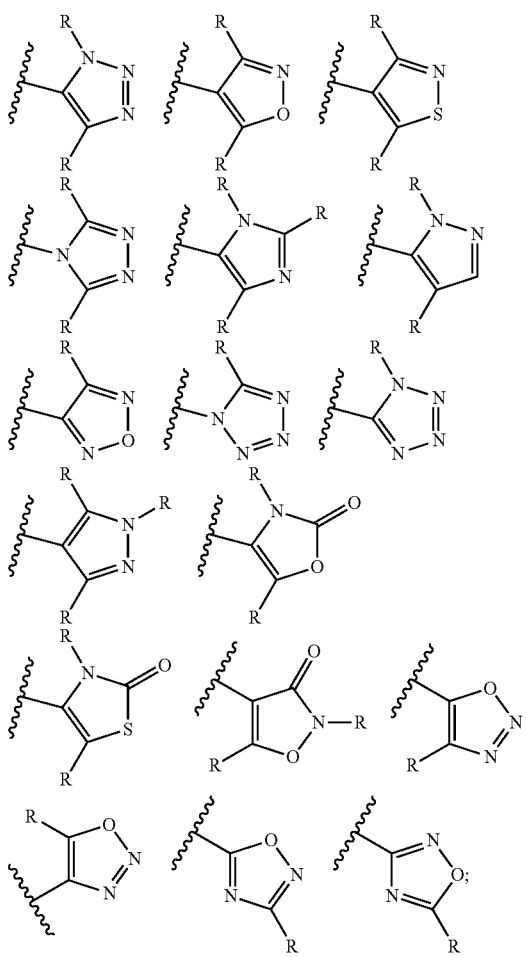

R is independently one or more hydrogen, CD$_3$, halogen, haloalkyl, hydroxyalkyl, CN, CF$_3$, CH$_2$F, CHF$_2$, optionally substituted (C$_1$-C$_6$)alkyl, optionally substituted (C$_1$-C$_6$)alkoxy, optionally substituted (C$_3$-C$_6$)cycloalkyl, optionally substituted heterocyclo, —OR$^4$, —CONR$^3$R$^4$, —NR$^3$R$^4$, NR$^3$R$^4$(C$_1$-C$_6$)alkyl-, —NR$^6$OCOR$^3$, —NR$^6$COR$^3$, NR$^6$COR$^3$(C$_1$-C$_6$)alkyl-, —NR$^6$CO$_2$R$^3$, NR$^6$CO$_2$R$^3$(C$_1$-C$_6$)alkyl-, —NR$^6$CONR$^3$R$^4$, —SO$_2$NR$^3$R$^4$, SO$_2$(C$_1$-C$_6$)alkyl-, —NR$^6$SO$_2$NR$^3$R$^4$, —NR$^6$SO$_2$R$^4$ or NR$^6$SO$_2$R$^4$(C$_1$-C$_6$)alkyl-;

X and Y are independently selected from hydrogen, optionally substituted (C$_1$-C$_6$)alkyl, optionally substituted (C$_3$-C$_8$)cycloalkyl, optionally substituted aryl, optionally substituted heteroaryl or optionally substituted heterocyclo;

Z is hydrogen, halogen, —OH, (C$_1$-C$_6$)alkyl or (C$_1$-C$_6$) alkoxy;

R$^1$ is, independently at each occurrence, one or more hydrogen, halogen, —CN, —OR$^4$, —NR$^3$R$^4$, —CONR$^3$R$^4$, —COOH, —OCONR$^3$R$^4$, —NR$^6$OCOR$^3$, —NR$^6$CONR$^3$R$^4$, —NR$^6$SO$_2$NR$^3$R$^4$, —NR$^6$SO$_2$R$^4$, optionally substituted (C$_1$-C$_6$)alkyl, optionally substituted (C$_2$-C$_6$)alkenyl, optionally substituted (C$_2$-C$_6$)alkynyl, optionally substituted (C$_1$-C$_6$)alkoxy, optionally substituted (C$_3$-C$_8$)cycloalkyl, optionally substituted (C$_3$-C$_8$)cycloalkyl (C$_1$-C$_6$)alkyl, optionally substituted (C$_3$-C$_8$)cycloalkyl-CO—, optionally substituted (C$_3$-C$_8$)cycloalkyl-SO$_2$—, optionally substituted aryl (C$_1$-C$_6$)alkoxy, optionally substituted (C$_3$-C$_8$)cycloalkyl (C$_1$-C$_6$)alkoxy, optionally substituted heterocyclyl-CO—, optionally substituted heterocyclyl, optionally substituted (C$_1$-C$_6$)alkyl-SO$_2$—, —NR$^6$SO$_2$— optionally substituted (C$_1$-C$_6$)alkyl, —NR$^6$SO$_2$— optionally substituted heterocyclo, optionally substituted (C$_1$-C$_6$)alkyl-NR$^6$SO$_2$— or optionally substituted heterocyclo-NR$^6$SO$_2$—;

R$^2$ is hydrogen, halogen, —CN, OH, —CONR$^3$R$^4$, —NR$^6$COOR$^4$, —NR$^6$CONR$^3$R$^4$, —NR$^6$COR$^4$, —NR$^6$SO$_2$R$^5$, —SO$_2$NR$^3$R$^4$, —NR$^6$SO$_2$NR$^3$R$^4$, optionally substituted (C$_1$-C$_6$)alkyl, optionally substituted (C$_3$-C$_8$)cycloalkyl, optionally substituted (C$_1$-C$_6$) alkoxy, optionally substituted aryl, optionally substituted (C$_1$-C$_6$)alkyl-SO$_2$—, optionally substituted aryl-SO$_2$, optionally substituted heteroaryl or optionally substituted heterocyclo;

R$^3$ is hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl (C$_1$-C$_6$)alkyl, R$^4$ is hydrogen, optionally substituted (C$_1$-C$_6$)alkyl or optionally substituted (C$_3$-C$_8$)cycloalkyl;

R$^5$ is hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl (C$_1$-C$_6$)alkyl;

R$^6$ is hydrogen or optionally substituted (C$_1$-C$_6$)alkyl;

and/or a pharmaceutically acceptable salt, tautomer or stereoisomer thereof.

In another aspect of the invention within the scope of the prior aspects, there is provided a compound of formula (VI) wherein A is

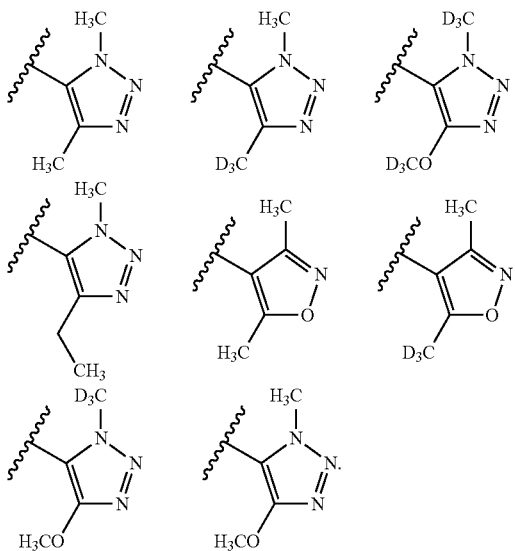

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

In another aspect, there is provided a compound selected from the following 5-(dimethyl-1H-1,2,3-triazol-5-yl)-10-methanesulfonyl-13-methoxy-8-[(S)-oxan-4-yl(phenyl)methyl]-3,8,12-triazatricyclo[7.4.0.0$^{2,7}$]trideca-1(13),2(7),3,5,9,11-hexaene, 10-methanesulfonyl-13-methoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene, 5-(dimethyl-1H-1,2,3-triazol-5-yl)-8-[(S)-(2-fluorophenyl)(oxan-4-yl)methyl]-10-methanesulfonyl-13-methoxy-3,8,12-triazatricyclo[7.4.0.0$^{2,7}$]trideca-1(13),2(7),3,5,9,11-hexaene, 8-[(S)-(2-fluorophenyl)(oxan-4-yl)methyl]-10-methanesulfonyl-13-methoxy-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene, 5-(dimethyl-1H-1,2,3-triazol-5-yl)-8-[(S)-(4-fluorophenyl)(oxan-4-yl)methyl]-10-methanesulfonyl-13-methoxy-3,8,12-triazatricyclo[7.4.0.0$^{2,7}$]trideca-1(13),2(7),3,5,9,11-hexaene, 5-(dimethyl-1H-1,2,3-triazol-5-yl)-13-ethoxy-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaene, 10-methanesulfonyl-13-($^2$H$_3$)methoxy-5-[5-($^2$H$_3$)methyl-3-methyl-1,2-oxazol-4-yl]-8-[(S)-oxan-4-yl(phenyl)methyl]-3,8,12-triazatricyclo[7.4.0.0$^{2,7}$]trideca-1(13),2(7),3,5,9,11-hexaene, 8-[(S)-(4-fluorophenyl)(oxan-4-yl)methyl]-10-methanesulfonyl-13-($^2$H$_3$)methoxy-5-[5-($^2$H$_3$)methyl-3-methyl-1,2-oxazol-4-yl]-3,8,12-triazatricyclo[7.4.0.0$^{2,7}$]trideca-1(13),2(7),3,5,9,11-hexaene, 13-ethoxy-10-methanesulfonyl-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene, 13-(cyclopropylmethoxy)-10-methanesulfonyl-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene, 8-[(S)-(3-fluoropyridin-2-yl)(oxan-4-yl)methyl]-10-methanesulfonyl-13-methoxy-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene, 8-[(S)-(4,4-difluorocyclohexyl)(3-fluoropyridin-2-yl)methyl]-10-methanesulfonyl-13-methoxy-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene, 13-(cyclopropylmethoxy)-8-[(S)-(2-fluorophenyl)(oxan-4-yl)methyl]-10-methanesulfonyl-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene, 13-ethoxy-8-[(S)-(4-fluorophenyl)(oxan-4-yl)methyl]-10-methanesulfonyl-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene, 13-(cyclopropylmethoxy)-8-[(S)-(4-fluorophenyl)(oxan-4-yl)methyl]-10-methanesulfonyl-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene, 8-[(S)-(4,4-difluorocyclohexyl)(phenyl)methyl]-10-methanesulfonyl-13-methoxy-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene, 10-methanesulfonyl-13-methoxy-5-[4-($^2$H$_3$)methyl-1-methyl-1H-1,2,3-triazol-5-yl]-8-[oxan-4-yl(2,4,6-trifluorophenyl)methyl]-3,8,12-triazatricyclo[7.4.0.0$^{2,7}$]trideca-1(13),2(7),3,5,9,11-hexaene, 8-[(4,4-difluorocyclohexyl)(phenyl)methyl]-5-(dimethyl-1H-1,2,3-triazol-5-yl)-10-methanesulfonyl-13-methoxy-3,8,12-triazatricyclo[7.4.0.0$^{2,7}$]trideca-1(13),2(7),3,5,9,11-hexaene, 13-(cyclopropylmethoxy)-8-[(S)-(4,4-difluorocyclohexyl)(phenyl)methyl]-10-methanesulfonyl-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene, N-[5-(dimethyl-1,2-oxazol-4-yl)-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaen-13-yl]cyclopropanesulfonamide, 13-(cyclopropylmethoxy)-5-(dimethyl-1H-1,2,3-triazol-5-yl)-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaene, 10-methanesulfonyl-13-methoxy-5-(4-methoxy-1-methyl-H-1,2,3-triazol-5-yl)-8-[(S)-oxan-4-yl(phenyl)methyl]-3,8,12-triazatricyclo[7.4.0.0$^{2,7}$]trideca-1(9),2(7),3,5,10,12-hexaene

[5-(dimethyl-1H-1,2,3-triazol-5-yl)-13-methoxy-8-[(S)-oxan-4-yl(phenyl)methyl]-3,8,12-triazatricyclo[7.4.0.0$^{2,7}$]trideca-1(9),2,4,6,10,12-hexaen-10-yl]methanol, 2-{13-methoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaen-10-yl}propan-2-ol, 13-methoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(9),2,4,6,10,12-hexaen-10-yl}methanol, 2-[5-(dimethyl-1H-1,2,3-triazol-5-yl)-13-methoxy-8-[(S)-oxan-4-yl(phenyl)methyl]-3,8,12-triazatricyclo[7.4.0.0$^{2,7}$]trideca-1(9),2,4,6,10,12-hexaen-10-yl]propan-2-ol, 2-[5-(dimethyl-1,2-oxazol-4-yl)-8-[(4-fluorophenyl)(oxan-4-yl)methyl]-3,8,12-triazatricyclo[7.4.0.0²,⁷]trideca-1(9),2(7),3,5,10,12-hexaen-11-yl]propan-2-ol, 2-[5-(dimethyl-1,2-oxazol-4-yl)-13-methoxy-8-[(S)-oxan-4-yl(phenyl)methyl]-3,8,12-triazatricyclo[7.4.0.0²,⁷]trideca-1(9),2,4,6,10,12-hexaen-10-yl]propan-2-ol, 2-{5-[4-(²H₃)methyl-1-methyl-1H-1,2,3-triazol-5-yl]-8-[(S)-oxan-4-yl(phenyl)methyl]-3,8,12-triazatricyclo[7.4.0.0²,⁷]trideca-1(9),2(7),3,5,10,12-hexaen-11-yl}propan-2-ol, 2-{5-[4-(²H₃)methyl-1-methyl-1H-1,2,3-triazol-5-yl]-8-[(S)-oxan-4-yl(phenyl)methyl]-3,8,12-triazatricyclo[7.4.0.0²,⁷]trideca-1(9),2,4,6,10,12-hexaen-10-yl}propan-2-ol, 2-[5-(dimethyl-1H-1,2,3-triazol-5-yl)-8-[(S)-oxan-4-yl(phenyl)methyl]-3,8,12-triazatricyclo[7.4.0.0²,⁷]trideca-1(9),2(7),3,5,10,12-hexaen-11-yl]propan-2-ol, 2-{5-[4-(²H₃)methyl-1-methyl-1H-1,2,3-triazol-5-yl]-8-[(S)-oxan-4-yl(phenyl)methyl]-3,8,10-triazatricyclo[7.4.0.0²,⁷]trideca-1(13),2(7),3,5,9,11-hexaen-12-yl}propan-2-ol, 2-[5-(dimethyl-1H-1,2,3-triazol-5-yl)-8-[(S)-oxan-4-yl(phenyl)methyl]-3,8,10-triazatricyclo[7.4.0.0²,⁷]trideca-1(13),2(7),3,5,9,11-hexaen-12-yl]propan-2-ol, 2-[5-(dimethyl-1,2-oxazol-4-yl)-8-[(S)-oxan-4-yl(phenyl)methyl]-3,8,12-triazatricyclo[7.4.0.0²,⁷]trideca-1(9),2(7),3,5,10,12-hexaen-11-yl]propan-2-ol, 2-[5-(4-ethyl-1-methyl-1H-1,2,3-triazol-5-yl)-8-[(S)-oxan-4-yl(phenyl)methyl]-3,8,12-triazatricyclo[7.4.0.0²,⁷]trideca-1(9),2(7),3,5,10,12-hexaen-11-yl]propan-2-ol, 4-{5-[4-(²H₃)methyl-1-methyl-1H-1,2,3-triazol-5-yl]-8-[(S)-oxan-4-yl(phenyl)methyl]-3,8,10-triazatricyclo[7.4.0.0²,⁷]trideca-1(9),2(7),3,5,10,12-hexaen-11-yl}-1λ⁶,4-thiomorpholine-1,1-dione, or 2-{8-[(S)-(4-fluorophenyl)(oxan-4-yl)methyl]-5-[5-(²H₃)methyl-3-methyl-1,2-oxazol-4-yl]-3,8,12-triazatricyclo[7.4.0.0²,⁷]trideca-1(13),2(7),3,5,9,11-hexaen-11-yl}propan-2-ol, and/or a pharmaceutically acceptable salt, tautomer or stereoisomer thereof.

One embodiment of the invention provides compounds wherein A is optionally substituted heterocyclo or optionally substituted heteroaryl, wherein the substituents are one or more R;

Another embodiment of the invention provides compounds wherein A is

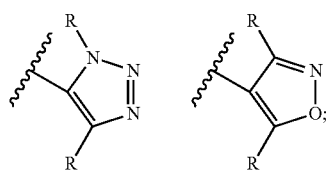

and R is independently one or more hydrogen, $CD_3$, $OCD_3$, $CF_3$, $CHF_2$ or $(C_1-C_3)$alkyl.

Another embodiment of the invention provides compounds wherein A is and R is independently one or more hydrogen, $CD_3$, $OCD_3$, $CF_3$, $CHF_2$ or $(C_1-C_3)$alkyl.

Other Embodiments of the Invention

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a method for inhibiting activity of a bromodomain-containing protein mediated disorder in a patient in need thereof comprising the step of administering to said patient at least one compound of the invention.

In another embodiment, the invention provides a method for the treatment and/or prophylaxis of various types of cancer, comprising administering to a patient in need of such treatment and/or prophylaxis a therapeutically effective amount of one or more compounds of the invention, alone, or, optionally, in combination with another compound of the invention and/or at least one other type of therapeutic agent.

In another embodiment, the invention provides a method for the treatment and/or prophylaxis of various types of cancer, including without limitation, small cell lung cancer, non-small cell lung cancer, colorectal cancer, multiple myeloma, acute myeloid leukemia (AML), acute lymphoblastic leukemia (ALL), pancreatic cancer, liver cancer, hepatocellular cancer, neuroblastoma, other solid tumors or other hematological cancers.

In another embodiment, the invention provides a method for the treatment and/or prophylaxis of various types of cancer, including without limitation, small cell lung cancer, non-small cell lung cancer, colorectal cancer, multiple myeloma or AML.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

In another embodiment, the invention provides a method of inhibiting a bromodomain-containing protein comprising contacting said protein with any exemplified compound or a pharmaceutically acceptable salt or composition thereof.

Therapeutic Applications

The compounds of formula (I) of the invention are bromodomain inhibitors and have potential utility in the treatment of diseases and conditions for which a bromodomain inhibitor is indicated.

In one embodiment there is provided a method for the treatment of a disease or condition, for which a bromodomain inhibitor is indicated, in a subject in need thereof which comprises administering a therapeutically effective amount of compound of formula (I) or a pharmaceutically acceptable salt thereof.

In another embodiment there is provided a method for treatment of a chronic autoimmune and/or inflammatory condition, in a subject in need thereof which comprises administering a therapeutically effective amount of one or more compounds of formula (I) or a pharmaceutically acceptable salt thereof.

In a further embodiment there is provided a method for treatment of cancer in a subject in need thereof which comprises administering a therapeutically effective amount of one or more compounds of formula (I) or a pharmaceutically acceptable salt thereof.

In one embodiment the subject in need thereof is a mammal, particularly a human.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of chronic autoimmune and inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes and acute rejection of transplanted organs.

Bromodomain inhibitors may be useful in the treatment of a wide variety of acute inflammatory conditions such as acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis and acute rejection of transplanted organs.

Bromodomain inhibitors may be useful in the prevention or treatment of diseases or conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria, SIRS associated with viral infections such as influenza, herpes zoster, herpes simplex and coronavirus.

Bromodomain inhibitors may be useful in the prevention or treatment of conditions associated with ischaemia-reperfusion injury such as myocardial infarction, cerebrovascular ischaemia (stroke), acute coronary syndromes, renal reperfusion injury, organ transplantation, coronary artery bypass grafting, cardio-pulmonary bypass procedures and pulmonary, renal, hepatic, gastro-intestinal or peripheral limb embolism.

Bromodomain inhibitors may be useful in the treatment of disorders of lipid metabolism via the regulation of APO-A1 such as hypercholesterolemia, atherosclerosis and Alzheimer's disease.

Bromodomain inhibitors may be useful in the treatment of fibrotic conditions such as idiopathic pulmonary fibrosis, renal fibrosis, post-operative stricture, keloid formation, scleroderma and cardiac fibrosis.

Bromodomain inhibitors may be useful in the prevention and treatment of viral infections such as herpes virus, human papilloma virus, adenovirus, poxvirus and other DNA viruses.

Bromodomain inhibitors may also be useful in the treatment of cancer, including hematological, epithelial including lung, breast and colon carcinomas, midline carcinomas, mesenchymal, hepatic, renal and neurological tumours.

In one embodiment the disease or condition for which a bromodomain inhibitor is indicated is selected from diseases associated with systemic inflammatory response syndrome, such as sepsis, burns, pancreatitis, major trauma, hemorrhage and ischemia. In this embodiment, the bromodomain inhibitor would be administered at the point of diagnosis to reduce the incidence of SIRS, the onset of shock, multi-organ dysfunction syndrome, which includes the onset of acute lung injury, ARDS, acute renal, hepatic, cardiac and gastro-intestinal injury and mortality. In another embodiment the bromodomain inhibitor would be administered prior to surgical or other procedures associated with a high risk of sepsis, hemorrhage, extensive tissue damage, SIRS or MODS (multiple organ dysfunction syndrome). In a particular embodiment the disease or condition for which a bromodomain inhibitor is indicated is sepsis, sepsis syndrome, septic shock and endotoxemia. In another embodiment, the bromodomain inhibitor is indicated for the treatment of acute or acute on chronic pancreatitis. In another embodiment the bromodomain inhibitor is indicated for the treatment of burns.

In one embodiment the disease or condition for which a bromodomain inhibitor is indicated is selected from herpes simplex infections and reactivations, cold sores, herpes zoster infections and reactivations, chickenpox, shingles, human papilloma virus, cervical neoplasia, adenovirus infections, including acute respiratory disease, and poxvirus infections such as cowpox and smallpox and African swine fever virus.

The term "diseases or conditions for which a bromodomain inhibitor is indicated" is intended to include any of or all of the above disease states.

In one embodiment, there is provided a method for inhibiting a bromodomain which comprises contacting the bromodomain with a compound of formula (1) or a pharmaceutically acceptable salt thereof.

While it is possible that for use in therapy, a compound of formula (I) as well as pharmaceutically acceptable salts thereof may be administered as the compound itself, it is more commonly presented as a pharmaceutical composition.

Pharmaceutical compositions may be presented in unit dose forms containing a predetermined amount of active ingredient pep unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

In addition to apoptosis defects found in tumors, defects in the ability to eliminate self-reactive cells of the immune system due to apoptosis resistance are considered to play a key role in the pathogenesis of autoimmune diseases. Autoimmune diseases are characterized in that the cells of the immune system produce antibodies against its own organs and molecules or directly attack tissues resulting in the destruction of the latter. A failure of those self-reactive cells to undergo apoptosis leads to the manifestation of the disease. Defects in apoptosis regulation have been identified in autoimmune diseases such as systemic lupus erythematosus or rheumatoid arthritis.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus. Sharp's syndrome, CREST syndrome (calcinosis, Raynaud's syndrome, esophageal dysmotility, telangiectasia), dermatomyositis, vasculitis (Morbus Wegener's) and Sjogren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, malaria and Chagas disease.

Compounds of the invention are useful for the treatment of certain types of cancer by themselves or in combination or co-administration with other therapeutic agents or radiation therapy. Thus, in one embodiment, the compounds of the invention are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin or topotecan; (vii) topoisomerase II poisons, (viii) microtubule-directed agents, (ix) kinase inhibitors (x) miscellaneous investigational agents (xi) hormones and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

Further provided herein are methods of treatment wherein compounds of the invention are administered with one or more immuno-oncology agents. The immuno-oncology agents used herein, also known as cancer immunotherapies, are effective to enhance, stimulate, and/or up-regulate immune responses in a subject. In one aspect, the administration of a compound of the invention with an immuno-oncology agent has a synergic effect in inhibiting tumor growth.

In one aspect, the compound(s) of the invention are sequentially administered prior to administration of the immuno-oncology agent. In another aspect, compound(s) of the invention are administered concurrently with the immunology-oncology agent. In yet another aspect, compound(s) of the invention are sequentially administered after administration of the immuno-oncology agent.

In another aspect, compounds of the invention may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LT$\beta$R, LIGHT, DcR3, HVEM, VEGI/TL1A, TRAMP/DR3, EDAR, EDA1, XEDAR, EDA2, TNFR1, Lymphotoxin $\alpha$/TNF$\beta$, TNFR2, TNF$\alpha$, LT$\beta$R, Lymphotoxin $\alpha$1$\beta$2, FAS, FASL, RELT, DR6, TROY, NGFR.

In another aspect, the immuno-oncology agent is a cytokine that inhibits T cell activation (e.g., IL-6, IL-10, TGF-$\beta$, VEGF, and other immunosuppressive cytokines) or a cytokine that stimulates T cell activation, for stimulating an immune response.

In one aspect, T cell responses can be stimulated by a combination of a compound of the invention and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of the invention for the treatment of cancer include antagonists of inhibitory receptors on NK cells or agonists of activating receptors on NK cells. For example, compounds of the invention can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, compounds of the invention can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. Suitable PD-L1 antibodies include, for example, MPDL3280A (RG7446; WO2010/077634), durvalumab (MEDI4736), BMS-936559 (WO2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO008/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO006/105021, WO009/009116) and MK-4166 (WO11/028683).

In another aspect, the immuno-oncology agent is an IDO antagonist. Suitable IDO antagonists include, for example, INCB-024360 (WO2006/122150, WO07/75598, WO08/36653, WO008/36642), indoximod, or NLG-919 (WO09/73620, WO009/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained release formulation; (3) topical application, for example, as a cream, ointment, or a controlled release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the patient being treated and the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, troches and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

DEFINITIONS

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

When a substituent is noted as "optionally substituted", the substituents are selected from, for example, substituents such as alkyl, cycloalkyl, aryl, heteroaryl, heterocyclo, halo, haloalkyl, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. —SO$_2$NH$_2$, substituted sulfonamido, nitro, cyano, carboxy, carbamyl, e.g. —CONH$_2$, substituted carbamyl e.g. —CONH alkyl, —CONH aryl, —CONH arylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl, unless otherwise defined.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

As used herein, the term "alkyl" or "alkylene" is intended to include both branched and straight-chain saturated aliphatic hydrocarbon groups having the specified number of carbon atoms. For example, "C$_1$-C$_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkenyl" denotes a straight- or branch-chained hydrocarbon radical containing one or more double bonds and typically from 2 to 20 carbon atoms in length. For example, "C$_2$-C$_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" denotes a straight- or branch-chained hydrocarbon radical containing one or more triple bonds and typically from 2 to 20 carbon atoms in length. For example, "C$_2$-C$_8$ alkenyl" contains from two to eight carbon atoms. Representative alkynyl groups include, but are not limited to, for example, ethynyl, 1-propynyl, 1-butynyl, heptynyl, octynyl and the like.

The term "alkoxy" or "alkyloxy" refers to an —O-alkyl group. "C$_{1-6}$ alkoxy" (or alkyloxy), is intended to include C$_1$, C$_2$, C$_3$, C$_4$, C$_5$, and C$_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

The term "aryl", either alone or as part of a larger moiety such as "aralkyl", "aralkoxy", or aryloxyalkyl", refers to monocyclic, bicyclic and tricyclic ring systems having a total of five to 15 ring members, wherein at least one ring in the system is aromatic and wherein each ring in the system contains three to seven ring members. In certain embodiments of the invention, "aryl" refers to an aromatic ring system which includes, but not limited to phenyl, biphenyl, indanyl, 1-naphthyl, 2-naphthyl and terahydronaphthyl. The term "aralkyl" or "arylalkyl" refers to an alkyl residue attached to an aryl ring. Non-limiting examples include benzyl, phenethyl and the like. The fused aryls may be connected to another group either at a suitable position on the cycloalkyl ring or the aromatic ring. For example:

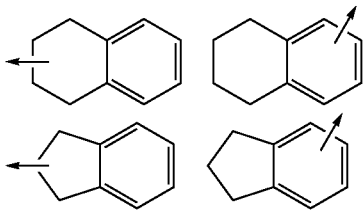

Arrowed lines drawn from the ring system indicate that the bond may be attached to any of the suitable ring atoms.

The term "cycloalkyl" refers to cyclized alkyl groups. $C_{3-6}$ cycloalkyl is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbomyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

The term "cycloalkylalkyl" refers to a cycloalkyl or substituted cycloalkyl bonded to an alkyl group connected to the core of the compound.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "benzyl," as used herein, refers to a methyl group on which one of the hydrogen atoms is replaced by a phenyl group.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heterocyclylalkyl" refers to a heterocyclyl or substituted heterocyclyl bonded to an alkyl group connected to the core of the compound.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

The term "electron withdrawing group" (EWG) refers to a substituent which polarizes a bond, drawing electron density towards itself and away from other bonded atoms. Examples of EWGs include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —O-phenyl, and —O— heteroaryl. Preferred examples of EWG include, but are not limited to, $CF_3$, $CF_2CF_3$, CN, halogen, $SO_2(C_{1-4}$ alkyl), $CONH(C_{1-4}$ alkyl), $CON(C_{1-4}$ alkyl$)_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis,* 4th Edition, Wiley (2007) and *The Peptides: Analysis, Synthesis, Biology,* Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The present invention is intended to include all isotopes of atoms occurring in the present compounds. Isotopes include those atoms having the same atomic number but different mass numbers. By way of general example and without limitation, isotopes of hydrogen include deuterium and tritium. The isotopes of hydrogen can be denoted as $^1H$ (hydrogen), $^2H$ (deuterium) and $^3H$ (tritium). They are also commonly denoted as D for deuterium and T for tritium. In the application, $CD_3$ denotes a methyl group wherein all of the hydrogen atoms are deuterium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy*, $22^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:
a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);
c) Bundgaard, H., *Adv. Drug Deliv. Rev.*, 8:1-38 (1992);
d) Bundgaard, H. et al., *J. Pharm. Sci.*, 77:285 (1988);
e) Kakeya, N. et al., *Chem. Pharm. Bull.*, 32:692 (1984); and
f) Rautio, J (Editor). *Prodrugs and Targeted Delivery (Methods and Principles in Medicinal Chemistry)*, Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK ($2^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, $3^{rd}$ edition, Academic Press, San Diego, Calif. (2008).

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated by reference in their entirety.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Fourth Edition, Wiley and Sons, 2007).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

General routes to compounds described in the invention are illustrated in Schemes 1-7, where the $R^1$, $R^2$, $R^7$, X, Y, Z, $U_1$, $U_2$, $U_3$, $U_4$, and A substituents are defined previously in the text or a functional group that can be converted to the desired final substituent. The substituent L is a leaving group such as a halide or OH that can be easily converted to a leaving group such as a triflate. As shown in Scheme 1, a general procedure for the preparation of compounds of the invention involves starting with a suitably substituted heterocycle 1 and the nitropyridine 2 as shown in Scheme 1. A Suzuki reaction between 1 (where M is a suitable coupling partner, such as boronic acid or boronic ester) and 2 (for example, 2,5-dibromo-3-nitropyridine) can give the functionalized pyridine 3. Reductive cyclization mediated by a phosphine reagent, such as 1,2-bis(diphenylphosphino)ethane (dppe), can provide the tricycle 4. Coupling of 4 with the aromatic heterocycle A (5, where M is a suitable coupling partner, such as boronic acid, boronic ester or stannane) using a suitable catalyst then generates 6 as shown in Scheme 1.

In the final step, the nitrogen of 6 can be substituted under Mitsunobu conditions using triphenylphosphine and diisopropyl azodicarboxylate (DIAD) with an alcohol 7. Alternatively, the nitrogen of 6 can be substituted to obtain functionalized tricyclic 9 by a displacement reaction between the nitrogen of 6 and an alkylating agent 8, where L is a leaving group such as a halide, mesylate or triflate, in the presence of a base, such as potassium carbonate.

Alternately, the nitrogen of intermediate 4 can be first substituted under Mitsunobu conditions with alcohol 7 or with alkylating agent 8, where L is a leaving group such as a halide, mesylate or triflate, in the presence of a base, such as potassium carbonate to give intermediate 10. Then coupling of 10 with the aromatic heterocycle A (5, where M is a suitable coupling partner, such as boronic acid, boronic ester or stannane) using a suitable catalyst then generates the final tricyclic 9. The intermediate 10 can also be directly coupled with a suitable aromatic heterocycle A (5, where M is H), via palladium-mediated C—H activation to afford compounds 9 as shown in Scheme 1.

In cases where 9 is a racemate, chiral separation can provide enantiomerically pure products. Further derivatization of $R^1$ and $R^2$ can provide additional compounds of the invention. For example, when $R^1$ is an ester, addition of a Grignard reagent or alkyl lithium can generate tertiary alcohols. The same $R^1$ ester could instead be hydrolyzed using, for example, sodium hydroxide to give a carboxylic acid ($R^1$=$CO_2H$) as the final substituent.

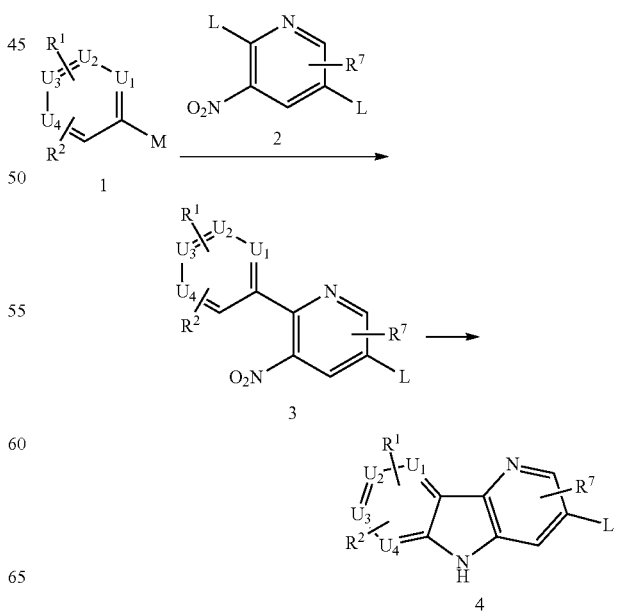

Scheme 1

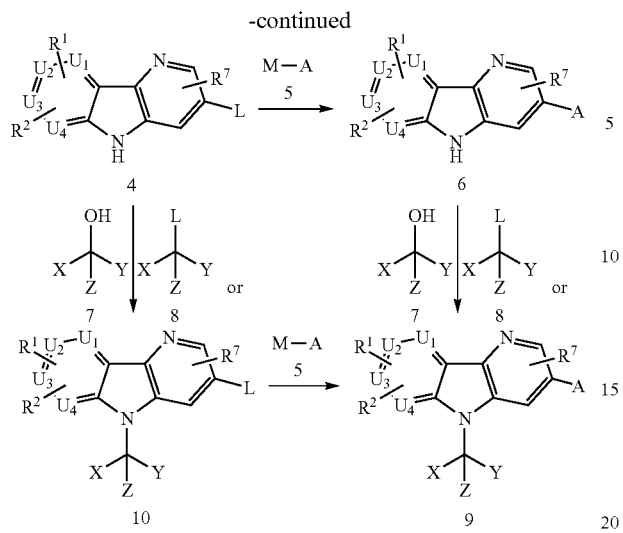

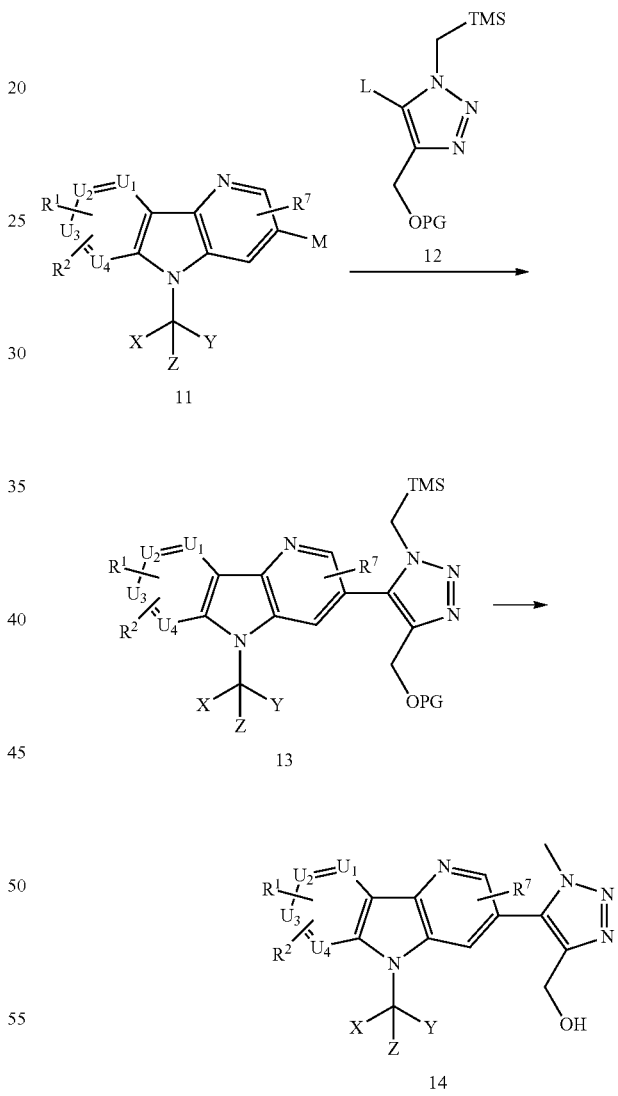

catalyst. Triazole 12 is available in one step from a copper-mediated cycloaddition reaction of (azidomethyl)trimethylsilane with a protected propargyl alcohol. Intermediate 13 can then be deprotected using a variety of conditions. For example, when PG is tert-butyldimethylsilyl, treatment with tetrabutylammonium fluoride can give the final compound 14. Further derivatization of the hydroxyl group (for example: alkylation, conversion to a leaving group and displacement, oxidation to either an aldehyde or carboxylic acid and subsequent elaboration) can provide additional compounds of the invention by application of methods which will be readily apparent to one of ordinary skill in the art.

An alternate synthesis of tricyclic 9 can be achieved as outlined in Scheme 2. The leaving group L, of 10 (prepared as in Scheme 1) can be converted to a suitable coupling partner, M (preferably a boronic ester or boronic acid) by the action of a palladium catalyst, affording 11. Coupling of 11 with the aromatic heterocycle A (5.1, where L is a suitable leaving group, such as a halogen or triflate) using a suitable catalyst can give the tricycle 9.

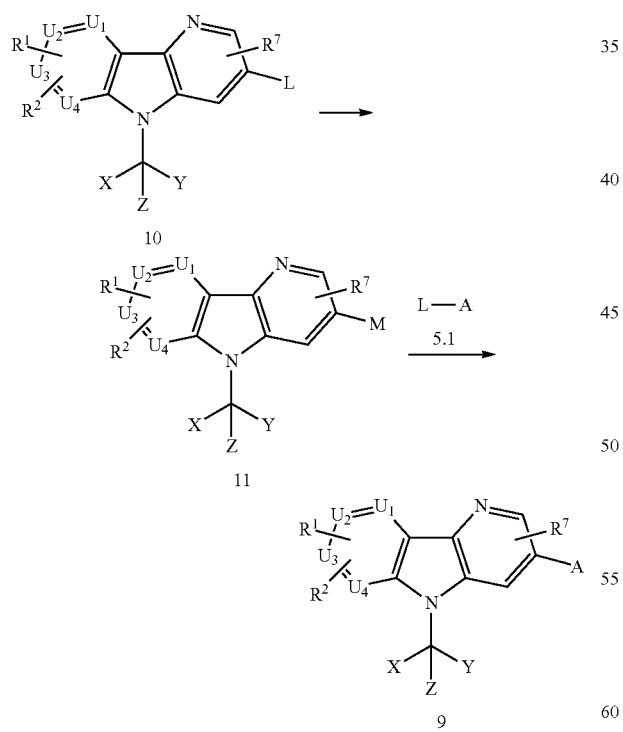

Hydroxymethyl pyrazole derivatives such as 14 can be accessed according to Scheme 3. Intermediate 11 (where M is a suitable coupling partner such as a boronic acid or boronic ester; prepared as in Scheme 2) can be coupled to an appropriately protected triazole 12 by the action of a suitable An alternate synthesis of the tricycle 4 can be achieved as outlined in Scheme 4. Aniline 15 can be coupled to pyridine 16, where L and L' are two leaving groups such as halide or triflate, using a Buchwald N-arylation reaction to give intermediate 17. Oxidative ring closure, using an appropriate catalyst such as Pd(OAc)$_2$ in an acidic media such as trifluoroacetic acid, can afford tricycle 4 as shown in Scheme 4.

Scheme 4

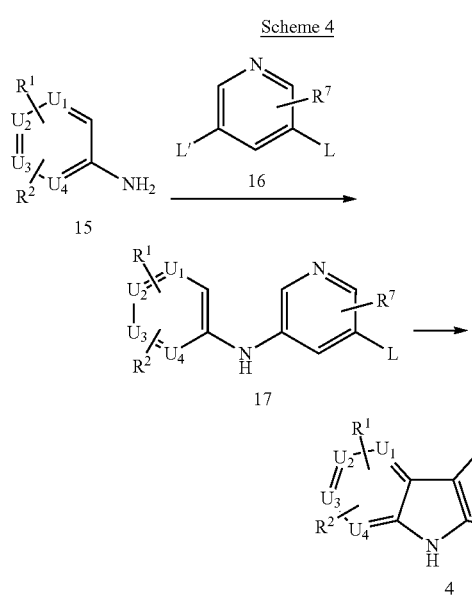

Alkoxy-substituted triazoles 23 can be prepared as illustrated in Scheme 5. Aldehyde 18 can be converted to acetal 20 by treatment with alcohol 19 (where Alk is a $C_1$-$C_6$ alkyl or $C_3$-$C_6$ cycloalkyl optionally substituted with deuterium) in the presence of acid or a dehydrating agent such as $CaCl_2$. Acetal 20 can be converted to alkoxy-substituted alkynes 21 by treatment with a strong base such as lithium diethylamide or sodium amide. Compounds 21 can be converted to triazoles 23 through a copper-catalyzed 3+2 cycloaddition reaction with azide 22. Triazoles 23 can be directly coupled to the tricycle 10 as in Scheme 1. In most cases, said coupling results in loss of the trimethylsilyl group. In cases where the trimethylsilyl group is not lost, it can be removed by treatment with tetrabutylammonium fluoride.

Scheme 5

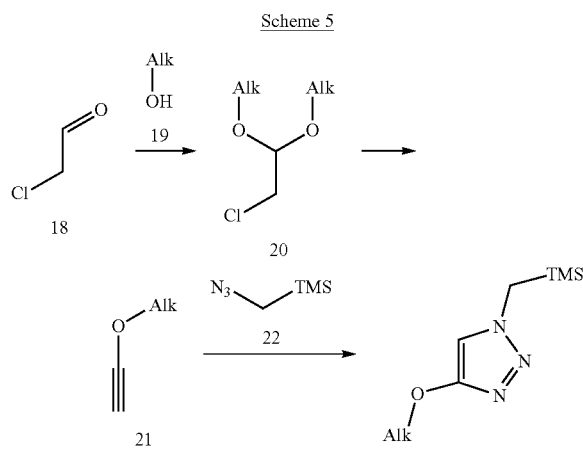

Alkyl-substituted triazoles 31 can be prepared as illustrated in Scheme 6. Acetylene 24 can be alkylated with 25 (where Alk is a $C_1$-$C_6$ alkyl or $C_3$-$C_6$ cycloalkyl optionally substituted with deuterium and where L is an appropriate leaving group such as iodide, bromide, chloride, or sulfonate) by the action of a strong base such as n-BuLi. Alkyne 26 can be converted to triazoles 28 through a copper-catalyzed 3+2 cycloaddition reaction with 27. Triazoles 28 can be directly coupled to the tricycle 10 as illustrated in Scheme 1. Alternately, the trimethylsilyl group of 28 can be removed directly by the action of tetrabutyl ammonium fluoride to give N-methyl-triazole 29. Deprotonation of 29 with a strong base such as n-BuLi, followed by reaction with an appropriate electrophile 30 (where L is a leaving group such as a halide or alkoxide and M is an appropriate group to facilitate metal-mediated couplings such as tributyltin or a boronic ester; e.g. M-L=$Bu_3SnCl$ or $B(OMe)_3$) can afford triazoles 31 which can readily be coupled as illustrated in Scheme 1.

Scheme 6

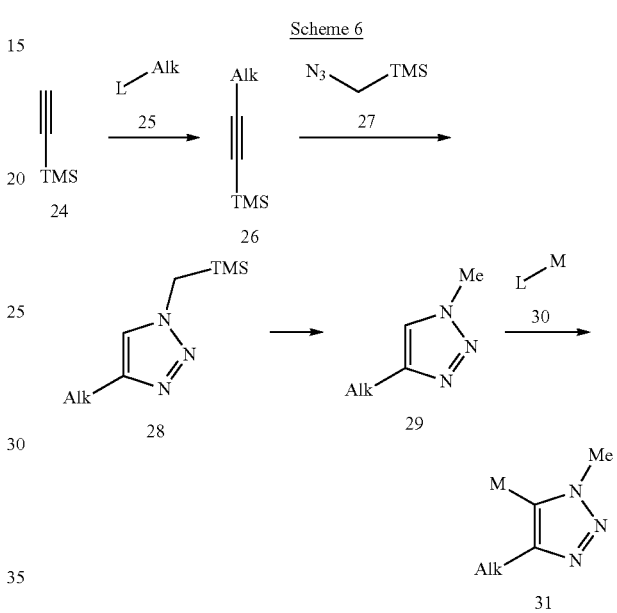

One can vary the substituents of the triazole as shown in Scheme 7. The leaving group of 25 (where Alk is a $C_1$-$C_6$ alkyl or $C_3$-$C_6$ cycloalkyl optionally substituted with deuterium and where L is an appropriate leaving group such as iodide, bromide, chloride, or sulfonate) can be displaced by treatment with sodium azide to afford 32. Alkynes 33 or 34 can be coupled to azides 32 to give triazoles 35 through a copper-catalyzed 3+2 cycloaddition reaction. Triazoles 35 can be directly coupled to the tricycle as illustrated in Scheme 1. Alternately, deprotonation of 35 with a strong base such as n-BuLi, followed by reaction with an appropriate electrophile 30 (where L is a leaving group such as a halide or alkoxide and M is an appropriate group to facilitate metal-mediated couplings such as tributyltin or a boronic ester; e.g. M-L=$Bu_3SnCl$ or $B(OMe)_3$) can afford triazoles 36 which can readily be coupled as illustrated in Scheme 1.

Scheme 7

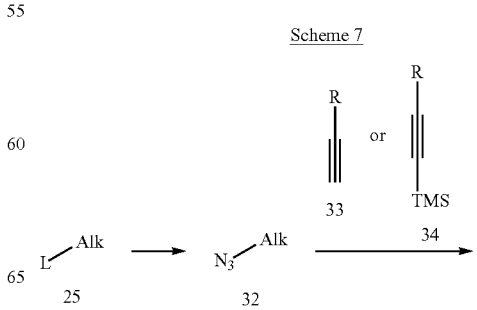

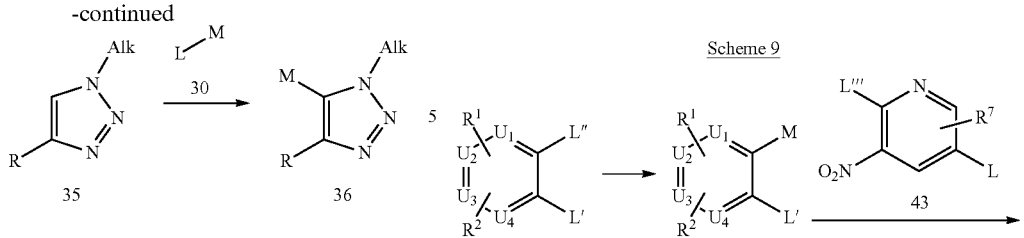

An alternate synthesis of tricyclic 6 can be achieved as outlined in Scheme 8. Selective coupling of one of the two leaving groups (L,L') of 37 to the aromatic heterocycle A (5, where M is a suitable coupling partner, such as boronic acid, boronic ester or stannane) using a suitable catalyst then generates 38. Coupling of the amino group of 38 with 39 (where L″ is a suitable leaving group such as a halide) can be achieved via either $S_NAr$ chemistry or a Buchwald N-arylation reaction to afford 40. Cyclization with a suitable catalyst such as bis(triphenylphosphine)palladium(II)chloride can afford tricycle 6 which can be further elaborated to tricycle 9 as outlined in Schemes 1-2.

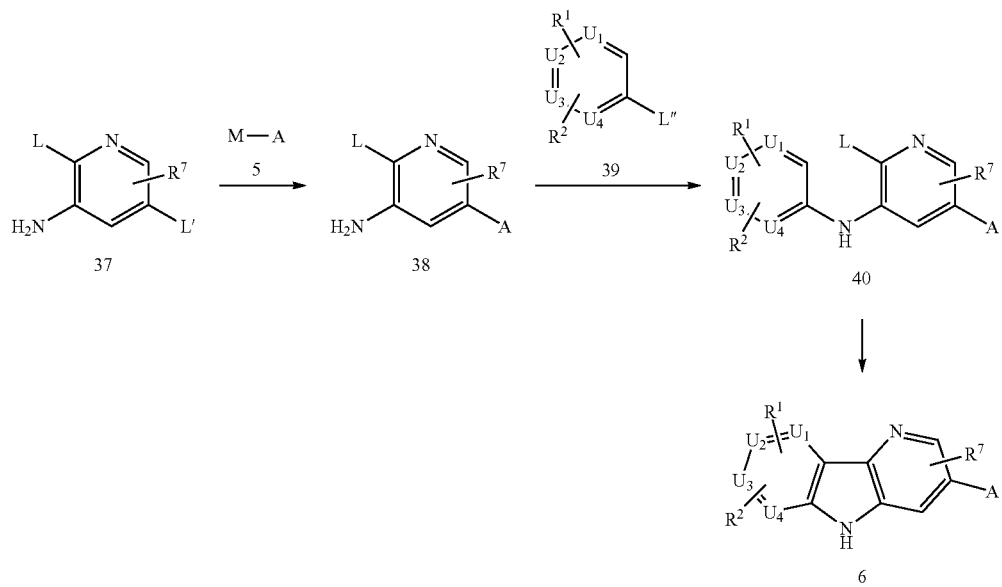

An alternate synthesis of tricyclic 4 can be achieved as outlined in Scheme 9. Selective conversion of one of the two leaving groups (L',L″) of 41 to a suitable coupling partner, M (preferably a boronic ester or boronic acid) can be achieved by the action of a palladium catalyst to afford 42. 42 can, in turn, be selectively coupled at one of the two leaving groups (L,L‴) of 43 by the action of a suitable catalyst to give biaryl 44. The nitro group of 44 can be reduced to the corresponding amine using methods known to one skilled in the art to give 45. Cyclization to tricycle 4 can be achieved using a base (e.g. NaHMDS or potassium tert-butoxide) in an intramolecular $S_NAr$ reaction or via an intramolecular Buchwald N-arylation reaction. Tricycle 4 can be further elaborated to tricycle 9 as outlined in Schemes 1-2.

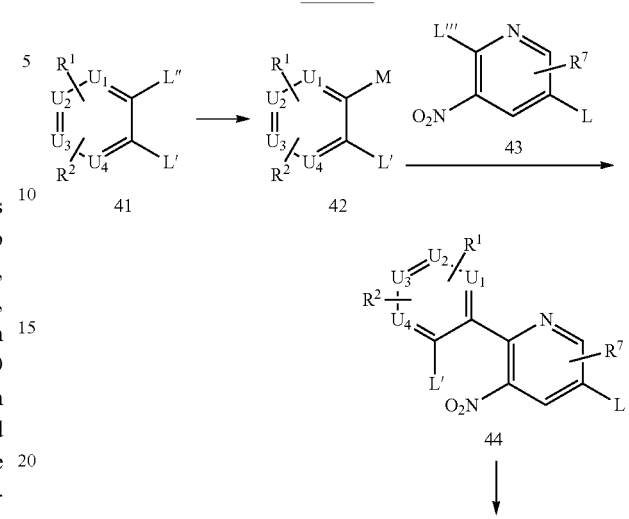

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather is defined by the claims appended hereto.

ABBREVIATIONS

| | |
|---|---|
| ACN | acetonitrile |
| AcOH | acetic acid |
| AlMe$_3$ | trimethyl aluminum |
| aq | aqueous |
| Bn | benzyl |
| Boc | tert-butoxycarbonyl |
| Boc$_2$O | di-tert-butyl dicarbonate |
| CBz | benzyloxycarbonyl |
| DCC | 1,3-dicyclohexylcarbodiimide |
| DCM | dichloromethane |
| DDQ | 2,3-dichloro-5,6-dicyano-1,4-benzoquinone |
| DIAD | diisopropyl azodicarboxylate |
| DIEA | diisopropylethylamine |
| DMAP | 4-dimethylaminopyridine |
| DMA | dimethylacetamide |
| DME | dimethoxyethane |
| DMF | dimethylformamide |
| DMSO | dimethyl sulfoxide |
| EDC | 1-(3-dimethylaminopropyl)-3-ethylcarbodiimide hydrochloride |
| Et$_2$AlCl | diethyl aluminum chloride |
| Et$_3$N | triethyl amine |
| Et$_2$O | diethyl ether |
| EtOH | ethanol |
| EtOAc | ethyl acetate |
| equiv. | equivalent(s) |
| g | gram(s) |
| h or hr | hour(s) |
| HOBt | hydroxybenzotriazole |
| HPLC | high pressure liquid chromatography |
| iPrOH | isopropyl alcohol |
| KOtBu | potassium tert-butoxide |
| LCMS | Liquid Chromatography-Mass Spectroscopy |
| LDA | lithium diisopropylamide |
| LiHMDS | lithium bis(trimethylsilyl)amide |
| Me | methyl |
| MeCN | acetonitrile |
| MeI | methyl iodide |
| MeOH | methanol |
| min | min(s) |
| mL | milliliter(s) |
| mmol | millimole |
| mM | millimolar |
| MTBE | methyl t-butyl ether |
| NaHMDS | sodium bis(trimethylsilyl)amide |
| n-BuLi | n-butyl lithium |
| NH$_4$OAc | ammonium acetate |
| NMP | N-methylpyrrolidinone |
| Pd(OAc)$_2$ | palladium acetate |
| Pd(dppf)Cl$_2$ | [1,1'bis(diphenylphosphino)ferrocene]dichloropalladium(II) |
| RT or Rt | retention time |
| RuPhos | 2-Dicyclohexylphosphino-2'6'-di-i-propoxy-1,1'-biphenyl |
| RuPhos Precatalyst | Chloro(2-dicyclohexylphosphino-2'6'-di-i-propoxy-1,1'-biphenyl)[2-(2-aaminoethylphenyl)]palladium(II), methyl-t-butylether adduct |
| sat | saturated |
| SFC | supercritical fluid chromatography |
| t-Bu | tertiary butyl |
| t-BuLi | t-butyl lithium |
| t-BuOH | tertiary butyl alcohol |
| t-BuOMe | tert-butyl methyl ether |
| TBAF | tretabutylammonium fluoride |
| TBTU | O-(1H-benzotriazol-1-yl)-N,N,N',N'-tetramethyluronium tetrafluoroborate |
| TCTU | O-(1H-6-chlorobenzotriazol-1-yl)-N,N,N',N'-tetramethyluronium tetrafluoroborate |
| TEA | triethylamine |
| TFA | trifluoroacetic acid |
| Tf$_2$O | trifluoromethylsulfonic anhydride |
| THF | tetrahydrofuran |

Examples 1 and 2

2-[5-(Dimethyl-1,2-oxazol-4-yl)-8-[(4-fluorophenyl)(oxan-4-yl)methyl]-3,8,12-triazatricyclo[7.4.0.0$^{2,7}$]trideca-1(9),2(7),3,5,10,12-hexaen-11-yl]propan-2-ol Example 1

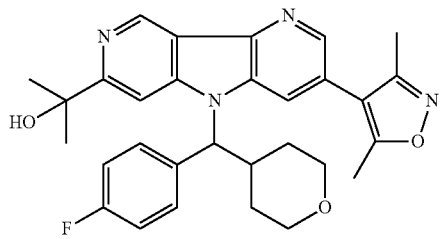

Enantiomer 1

Example 2

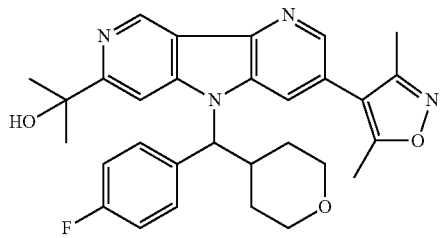

Enantiomer 2

Step 1: 2-Chloro-5-(3,5-dimethylisoxazol-4-yl)pyridin-3-amine

A mixture of 5-bromo-2-chloropyridin-3-amine (5.11 g, 24.6 mmol), (3,5-dimethylisoxazol-4-yl)boronic acid (3.47 g, 24.6 mmol), PdCl$_2$(dppf) (0.216 g, 0.296 mmol), was vacuum purged with nitrogen (3×). Tripotassium phosphate (3M in water, 24.6 mL, 73.9 mmol) and THF (30 mL) were added and the mixture was again vacuum purged with nitrogen (3×). The resulting mixture was warmed with stirred overnight at 75° C. The mixture was cooled to room temperature, transferred to a separatory funnel, and the aqueous layer was removed. The organic layer was dried with anhydrous sodium sulfate, filtered, and concentrated to provide a dark residue. The residue was suspended in DCM and ethyl acetate, and concentrated onto enough silica gel to provide a free flowing powder. The powder was loaded into an ISCO solid load cartridge and purified on an ISCO companion chromatography system (120 g silica cartridge, eluting with 0-100% ethyl acetate/hexanes, 85 mL/min) to provide 2-chloro-5-(3,5-dimethylisoxazol-4-yl)pyridin-3-amine (3.82 g, 17.1 mmol, 69.3% yield) as a white solid. $^1$H NMR (400 MHz, DMSO-d$_6$) δ 7.61 (d, J=2.0 Hz, 1H), 7.14 (d, J=2.0 Hz, 1H), 5.67 (s, 2H), 2.41 (s, 3H), 2.23 (s, 3H).

HPLC: RT=0.908 min (Waters Acquity BEH C18 1.7 μm 2.0×50 mm, $CH_3CN/H_2O/0.1\%$ TFA, 1.5 min gradient, wavelength=254 nm); MS (ES): m/z=224 $[M+H]^+$.

Step 2: Methyl 4-((2-chloro-5-(3,5-dimethylisoxazol-4-yl)pyridin-3-yl)amino)picolinate The reaction was performed in a thick walled vessel with a Teflon screw cap. A solution of methyl 4-chloropicolinate (3.95 g, 23.0 mmol) and 2-chloro-5-(3,5-dimethylisoxazol-4-yl)pyridin-3-amine (1.03 g, 4.61 mmol) in MeOH (25 mL) was treated with hydrogen chloride (4M in dioxane, 1.151 mL, 4.61 mmol). The resulting mixture was stirred at 80° C. overnight. The mixture was cooled to room temperature. LC/MS indicates 54/11 ratio of desired product m/z 359 (m+1) to starting aniline m/z 224 (m+1). The reaction was concentrated to dryness on a rotary evaporator. The resulting the residue was treated with saturated $NaHCO_3$ solution until pH 9, sonicated, filtered through a sintered glass funnel and washed with water. The product was air dried for a few hours, then overnight under vacuum to provide methyl 4-((2-chloro-5-(3,5-dimethylisoxazol-4-yl)pyridin-3-yl)amino)picolinate (0.943 g, 2.63 mmol, 57.1% yield) as a white solid. $^1$H NMR (400 MHz, DMSO-$d_6$) δ 9.04 (s, 1H), 8.36 (d, J=5.5 Hz, 1H), 8.28 (d, J=2.2 Hz, 1H), 7.98 (d, J=2.2 Hz, 1H), 7.71-7.58 (m, 1H), 7.18-7.07 (m, 1H), 3.84 (s, 3H), 2.47 (s, 3H), 2.33-2.26 (m, 3H). HPLC: RT=0.862 min (Waters Acquity BEH C18 1.7 μm 2.0×50 mm, $CH_3CN/H_2O/0.1\%$ TFA, 1.5 min gradient, wavelength=254 nm); MS (ES): m/z=359 $[M+H]^+$.

Step 3: Methyl 3-(3,5-dimethylisoxazol-4-yl)-5H-pyrrolo[3,2-b:4,5-c']dipyridine-7-carboxylate A mixture of methyl 4-((2-chloro-5-(3,5-dimethylisoxazol-4-yl)pyridin-3-yl)amino)picolinate (943 mg, 2.63 mmol), bis(triphenylphosphine)palladium(II)chloride (184 mg, 0.263 mmol) and sodium acetate trihydrate (539 mg, 6.57 mmol) in DMA (15 mL) in a round bottom flask equipped with a reflux condenser and nitrogen inlet was vacuum purged with nitrogen (3×). The resulting mixture was warmed to 170° C. After 1 h, the mixture was cooled to room temperature, diluted with chloroform (15 mL), filtered through Celite, washing with chloroform (3×10 mL). Resulting filtrate was concentrated to provide an amber residue. The residue was dissolved in a mixture of DCM/MeOH, concentrated onto enough silica gel to provide a free flowing powder. The powder was loaded into an ISCO solid load cartridge and purified on an ISCO companion chromatography system (40 g silica cartridge, eluting with 0-10% MeOH/DCM, followed by 10-30% MeOH/DCM, 40 mL/min). Note that the compound has poor solubility and eluted slowly. Like fractions were combined and concentrated to provide methyl 3-(3,5-dimethylisoxazol-4-yl)-5H-pyrrolo[3,2-b:4,5-c']dipyridine-7-carboxylate (500 mg, 1.55 mmol, 59.0% yield) as a light yellow solid. $^1$H NMR (400 MHz, DMSO-$d_6$) δ 12.27 (br. s., 1H), 9.49 (d, J=0.9 Hz, 1H), 8.65 (d, J=1.8 Hz, 1H), 8.32 (d, J=1.1 Hz, 1H), 8.12 (d, J=2.0 Hz, 1H), 3.95 (s, 3H), 2.51 (3H, under DMSO peak), 2.30 (s, 3H). HPLC: RT=1.118 min (Waters Acquity BEH C18 1.7 μm 2.0×50 mm, $CH_3CN/H_2O/0.1\%$ TFA, 1.5 min gradient, wavelength=254 nm); MS (ES): m/z=323 $[M+H]^+$.

Step 4: Methyl 3-(3,5-dimethylisoxazol-4-yl)-5-((4-fluorophenyl)(tetrahydro-2H-pyran-4-yl)methyl)-5H-pyrrolo[3,2-b:4,5-c']dipyridine-7-carboxylate Diisopropyl diazene-1,2-dicarboxylate (DIAD) (0.206 mL, 1.05 mmol) was drop wise added to a 0° C. suspension of methyl 3-(3,5-dimethylisoxazol-4-yl)-5H-pyrrolo[3,2-b:4,5-c']dipyridine-7-carboxylate (225 mg, 0.698 mmol), (4-fluorophenyl)(tetrahydro-2H-pyran-4-yl)methanol (220 mg, 1.05 mmol) and triphenylphosphine (275 mg, 1.05 mmol) in dichloromethane (20 mL). The cooling bath was removed and the orange suspension was stirred at room temperature overnight. The reaction was concentrated in vacuo. The residue was dissolved in a minimum of DCM and purified on an ISCO companion chromatography system (40 g silica cartridge, eluting with 0-100% ethyl acetate/DCM, followed by 0-30% MeOH/DCM 40 mL/min). Like fractions were combined and concentrated to provide an amber residue. The residue was dissolved in a minimum of DCM and again purified on an ISCO companion chromatography system (40 g silica cartridge, eluting with 0-10% MeOH/DCM, followed by 0-30% MeOH/DCM, 40 mL/min). Like fractions were combined to provide methyl 3-(3,5-dimethylisoxazol-4-yl)-5-((4-fluorophenyl)(tetrahydro-2H-pyran-4-yl)methyl)-5H-pyrrolo[3,2-b:4,5-c']dipyridine-7-carboxylate (225 mg, 0.437 mmol, 62.6% yield).

Step 5: 2-[5-(Dimethyl-1,2-oxazol-4-yl)-8-[(4-fluorophenyl)(oxan-4-yl)methyl]-3,8,12-triazatricyclo[7.4.0.0$^{2,7}$]trideca-1(9),2(7),3,5,10,12-hexaen-11-yl]propan-2-ol Methylmagnesium bromide (3M in $Et_2O$, 2.186 mL, 6.56 mmol) was added to a −10° C. (MeOH/ice) solution of methyl 3-(3,5-dimethylisoxazol-4-yl)-5-((4-fluorophenyl)(tetrahydro-2H-pyran-4-yl)methyl)-5H-pyrrolo[3,2-b:4,5-c']dipyridine-7-carboxylate (225 mg, 0.437 mmol) in DCM (10 mL). After ~2 h LC/MS indicates consumption of SM m/z 515 (m+1) and formation of product m/z 515 (m+1). The reaction was quenched with saturated ammonium chloride solution, transferred to a separatory funnel, and extracted with DCM. The extracts were combined, washed with saturated $NH_4Cl$ solution, dried over anhydrous sodium sulfate, filtered and concentrated to provide an orange residue. The residue was dissolved in a minimum of DCM and purified on an ISCO companion chromatography system (24 g silica cartridge, eluting with 0-10% MeOH/DCM, then flushed with 10-30% MeOH/DCM, 35 mL/min) to provide racemic 2-(3-(3,5-dimethylisoxazol-4-yl)-5-((4-fluorophenyl)(tetrahydro-2H-pyran-4-yl)methyl)-5H-pyrrolo[3,2-b:4,5-c']dipyridin-7-yl)propan-2-ol (83 mg, 0.161 mmol, 36.9% yield) as an orange solid. The enantiomers were separated by chiral SFC. Preparative SFC Chromatographic Conditions: Instrument: Berger SFC MGII: Column: Chiral OD-H 25×3 cm ID, 5 m, Flow rate: 50.0 mL/min, Mobile Phase: 80/20 $CO_2$/MeOH, Detector Wavelength: 220 nm. Sample Prep and Inj. Volume: 3000 μL of 86 mg dissolved in 7 mL MeOH, to provide Example 1 (Enantiomer 1); 25.6 mg and Example 2 (Enantiomer 2); 26.0 mg. The stereoisomer purity of each enantiomer was estimated to be >99%. For Example 1 (Enantiomer 1): 2-[5-(Dimethyl-1,2-oxazol-4-yl)-8-[(4-fluorophenyl)(oxan-4-yl)methyl]-3,8,12-triazatricyclo[7.4.0.0$^{2,7}$]trideca-1(9),2(7),3,5,10,12-hexaen-11-yl]propan-2-ol: $^1$H NMR (400 MHz, DMSO-$d_6$) δ 9.30 (d, J=0.9 Hz, 1H), 8.53 (d, J=1.5 Hz, 1H), 8.38-8.29 (m, 1H), 8.28-8.21 (m, 1H), 7.72 (d, J=3.3 Hz, 2H), 7.32-7.07 (m, 2H), 5.93-5.79 (m, 1H), 5.41 (s, 1H), 3.99-3.87 (m, 1H), 3.85-3.67 (m, 1H), 3.55-3.42 (m, 1H), 3.41-3.33 (m, 1H), 3.30-3.22 (m, 1H), 2.48 (s, 3H), 2.30 (s, 3H), 1.75-1.63 (m, 1H), 1.59 (s, 3H), 1.57 (s, 3H), 1.39-1.21 (m, 1H), 1.09-1.08 (m, 1H), 1.05-0.90 (m, 1H). Account for 30 of 31H. Other H may be under solvent peak. HPLC: RT=0.996 min (Waters Acquity BEH C18 1.7 μm 2.0×50 mm, CH$_3$CN/H$_2$O/0.1% TFA, 1.5 min gradient, wavelength=254 nm); MS (ES): m/z=515 [M+H]$^+$; HPLC Purity: 95/5 to 5/95 H$_2$O/CH$_3$CN/0.05% TFA, flow=0.5 mL/min, gradient=15 minSunfire C18 3.5 μm, 3.0×150 mm: RT=6.12 min; Purity @220 nm:100%; @254 nm:100% Xbridge Phenyl 3.5 um, 3.0×150 mm: RT=7.41 min; Purity @220 nm:100%; @254 nm: 100%. Analytical SFC Chromatographic Conditions: Instrument: Berger analytical SFC. Column: Chiral OD-H 250×4.6 mm ID, 5 μm Flow rate: 2.0 mL/min Mobile Phase: 80/20 CO$_2$/MeOH. Enantiomer 1, RT: 8.888 min. For Example 2 (Enantiomer 2): 2-[5-(Dimethyl-1,2-oxazol-4-yl)-8-[(4-fluorophenyl)(oxan-4-yl)methyl]-3,8,12-triazatricyclo[7.4.0.0$^{2,7}$]trideca-1(9),2(7),3,5,10,12-hexaen-11-yl]propan-2-ol: $^1$H NMR (400 MHz, DMSO-d$_6$) δ 9.30 (d, J=0.7 Hz, 1H), 8.53 (d, J=1.5 Hz, 1H), 8.37-8.28 (m, 1H), 8.25 (br. s., 1H), 7.72 (dd, J=8.7, 5.4 Hz, 2H), 7.19 (t, J=8.8 Hz, 2H), 5.83 (d, J=11.2 Hz, 1H), 5.41 (s, 1H), 3.98-3.86 (m, 1H), 3.82-3.69 (m, 1H), 3.47 (s, 1H), 3.43-3.34 (m, 1H), 3.27 (d, J=11.9 Hz, 1H), 2.48 (s, 3H), 2.30 (s, 3H), 1.66 (br. s., 1H), 1.59 (s, 3H), 1.57 (s, 3H), 1.39-1.19 (m, 1H), 1.05-0.90 (m, 1H). Account for 30 of 31H. Other H may be under solvent peak. HPLC: RT=0.995 min (Waters Acquity BEH C18 1.7 μm 2.0×50 mm, CH$_3$CN/H$_2$O/0.1% TFA, 1.5 min gradient, wavelength=254 nm); MS (ES): m/z=515 [M+H]$^+$; HPLC Purity: 95/5 to 5/95 H$_2$O/CH$_3$CN/0.05% TFA, flow=0.5 mL/min, gradient=15 min. Sunfire C18 3.5 μm, 3.0×150 mm: RT=6.12 min; Purity @220 nm:100%; @254 nm:100% Xbridge Phenyl 3.5 um, 3.0×150 mm: RT=7.41 min; Purity @220 nm:100%; @254 nm:98.8%. Analytical SFC Chromatographic Conditions: Instrument: Berger analytical SFC. Column: Chiral OD-H 250×4.6 mm ID, 5 μm Flow rate: 2.0 mL/min Mobile Phase: 80/20 CO$_2$/MeOH. Enantiomer 2, RT: 13.039 min.

Example 3

5-(Dimethyl-1H-1,2,3-triazol-5-yl)-13-fluoro-8-[(S)-oxan-4-yl(phenyl)methyl]-3,8,12-triazatricyclo[7.4.0.0$^{2,7}$]trideca-1(13),2(7),3,5,9,11-hexaene

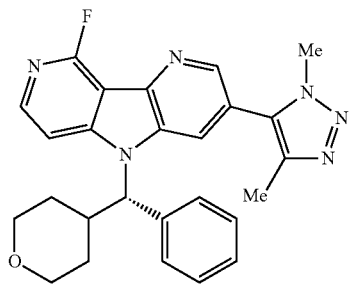 [SMILES: Cc1nnn(C)c1-c1cnc2c3c(F)nccc3n([C@H](c3ccccc3)C3CCOCC3)c2c1]

Step 1: 5-Bromo-2'-fluoro-3-nitro-2,3'-bipyridine

A mixture of 2,5-dibromo-3-nitropyridine (3.00 g, 10.7 mmol) and (2-fluoropyridin-3-yl)boronic acid (1.5 g, 10.7 mmol) in tetrahydrofuran (20 mL) in a 40 mL vial was purged under a stream of nitrogen and then treated with 2 M aqueous potassium phosphate (10.65 mL, 21.3 mmol) and then with PdCl$_2$(dppf)-CH$_2$Cl$_2$Adduct (0.435 g, 0.532 mmol). The vial was capped with septum and evacuated and purged with nitrogen 3 times before heating in a heating block at 80° C. for 5 h. The mixture was cooled to room temperature diluted with water and extracted into ethyl acetate. Washed with water and brine and concentrated to give black residue. The material was chromatographed on an ISCO Companion 80 g silica gel column and eluted with EtOAc/Hexane gradient (20-100%) to give 5-bromo-2'-fluoro-3-nitro-2,3'-bipyridine (1.0 g, 3.35 mmol, 31.5% yield) as an off-white solid. LCMS: RT=0.86 min; (ES): m/z (M+H)$^+$=298.0, 300.0: (Waters Acquity SDS. Column: BEH C18 2.1×50 mm 1.7 u (1.6 min grad) 2-98% B. Flow Rate=0.8 mL/min. Solvent A: H$_2$O—0.1% TFA. Solvent B: ACN—0.1% TFA). $^1$H NMR (400 MHz, CDCl$_3$) δ 9.00 (d, J=2.0 Hz, 1H), 8.57 (s, 1H), 8.37 (dt, J=4.8, 1.4 Hz, 1H), 8.15 (ddd, J=9.3, 7.4, 2.0 Hz, 1H), 7.41 (ddd, J=7.3, 5.1, 1.9 Hz, 1H).

Step 2: 3-Bromo-9-fluoro-5H-pyrrolo[3,2-b:4,5-c']dipyridine

In a 40 mL vial was added a mixture of 5-bromo-2'-fluoro-3-nitro-2,3'-bipyridine (1 g, 3.35 mmol) and 1,2-bis(diphenylphosphino)ethane (1.671 g, 4.19 mmol) in 1,2-dichlorobenzene (15 mL) and the vial capped and heated in a heating block at 170° C. for 5 h. Concentrated on a rotary evaporator using high vacuum pump and the residue was chromatographed on an ISCO Companion 40 g silica gel column and eluted with EtOAc/Hexane gradient (30-100%) to give 3-bromo-9-fluoro-5H-pyrrolo[3,2-b:4,5-c']dipyridine (460 mg, 1.73 mmol, 51.5% yield) as a light-tan solid. LCMS: RT=0.69 min; (ES): m/z (M+H)$^+$=265.9, 267.9: (Waters Acquity SDS. Column: BEH C18 2.1×50 mm 1.7 u (1.6 min grad) 2-98% B. Flow Rate=0.8 mL/min. Solvent A: H$_2$O—0.1% TFA. Solvent B: ACN—0.1% TFA).

Step 3: 3-(1,4-Dimethyl-1H-1,2,3-triazol-5-yl)-9-fluoro-5H-pyrrolo[3,2-b:4,5-c']dipyridine In a 20 mL scintillation vial was added a mixture of 1,4-dimethyl-5-(tributylstannyl)-1H-1,2,3-triazole (1001 mg, 2.59 mmol), 3-bromo-9-fluoro-5H-pyrrolo[3,2-b:4,5-c']dipyridine (460 mg, 1.73 mmol), copper(I) iodide (65.9 mg, 0.346 mmol), and Pd(Ph$_3$P)$_4$ (200 mg, 0.173 mmol) in DMF (10 mL). Added triethylamine (0.482 mL, 3.46 mmol) and the vial was capped with septum and heated in a heating block at 90° C. for 5 h and cooled to room temperature. Diluted with ammonium hydroxide and water and extracted into ethyl acetate and concentrated to give a light-brown oil. The material was dissolved in DCM and chromatographed on an ISCO Companion 40 g silica gel column and eluted with MeOH/CH$_2$Cl$_2$ gradient (0-10%). Collected product fractions to give 3-(1,4-dimethyl-1H-1,2,3-triazol-5-yl)-9-fluoro-5H-pyrrolo[3,2-b:4,5-c']dipyridine (340 mg, 1.20 mmol, 69.7% yield) as a white solid. LCMS: RT=0.58 min; (ES): m/z (M+H)$^+$=283.1: Waters Acquity SDS. Column: BEH C18 2.1×50 mm 1.7 u (1.6 min grad) 2-98% B. Flow Rate=0.8 mL/min. Solvent A: H$_2$O—0.1% TFA. Solvent B: ACN—0.1% TFA. $^1$H NMR (400 MHz, CDCl$_3$) δ 10.13 (br. s., 1H), 8.69 (d, J=1.8 Hz, 1H), 8.26 (dd, J=5.8, 1.0 Hz, 1H), 7.81 (d, J=1.8 Hz, 1H), 7.39 (dd, J=5.7, 2.4 Hz, 1H), 4.04 (s, 3H), 2.40 (s, 3H).

Step 4: 5-(Dimethyl-1H-1,2,3-triazol-5-yl)-13-fluoro-8-[(S)-oxan-4-yl(phenyl)methyl]-3,8,12-triazatricyclo[7.4.0.0$^{2,7}$]trideca-1(13),2(7),3,5,9,11-hexaene In a RB flask was added a mixture of 3-(1,4-dimethyl-1H-1,2,3-triazol-5-yl)-9-fluoro-5H-pyrrolo[3,2-b:4,5-c']

dipyridine (100 mg, 0.354 mmol), (R)-phenyl(tetrahydro-2H-pyran-4-yl)methanol (136 mg, 0.709 mmol), and Ph$_3$P (186 mg, 0.709 mmol) in dichloromethane (5 mL) and stirred at room temperature. Then DIAD (0.138 mL, 0.709 mmol) was added drop wise and the resulting mixture stirred at room temperature overnight. The material was chromatographed on an ISCO Companion 40 g silica gel column and eluted first with Ethyl acetate (100%) and then switched to 10% MeOH/DCM. Collected fractions with product to give 15 mg of a white solid which was further purified via preparative LC/MS with the following conditions: Column: Waters XBridge C18, 19×100 mm, 5-μm particles; Mobile Phase A: 5:95 ACN: water with 10-mM NH$_4$OAc; Mobile Phase B: 95:5 ACN: water with 10-mM NH$_4$OAc; Gradient: 0-100% B over 10 min, then a 3-min hold at 100% B; Flow: 20 mL/min. Fractions containing the desired product were combined and dried via centrifugal evaporation to give 1.5 mg of title compound. LCMS: RT=1.52 min; (ES): m/z (M+H)$^+$=457.2: (Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75-min hold at 100% B; Flow: 1.11 mL/min.). $^1$H NMR (500 MHz, DMSO-d$_6$) δ 8.72 (s, 1H), 8.64 (br. s., 1H), 8.27 (d, J=4.4 Hz, 1H), 8.21 (br. s., 1H), 7.71 (d, J=7.4 Hz, 2H), 7.39-7.33 (m, 2H), 7.32-7.26 (m, 1H), 5.93 (d, J=11.4 Hz, 1H), 4.02 (br. s., 3H), 3.90 (d, J=9.4 Hz, 1H), 3.74 (d, J=8.8 Hz, 1H), 3.47 (t, J=11.1 Hz, 1H), 3.27 (t, J=11.3 Hz, 1H), 2.31 (s, 3H), 1.69 (d, J=12.8 Hz, 1H), 1.59-1.50 (m, 1H), 1.35-1.26 (m, 1H), 0.98 (d, J=12.5 Hz, 1H).

Example 4

12-Chloro-5-(dimethyl-1H-1,2,3-triazol-5-yl)-8-[(S)-(2-fluorophenyl)(oxan-4-yl)methyl]-3,8,11-triazatricyclo[7.4.0.0$^{2,7}$]trideca-1(13),2(7),3,5,9,11-hexaene

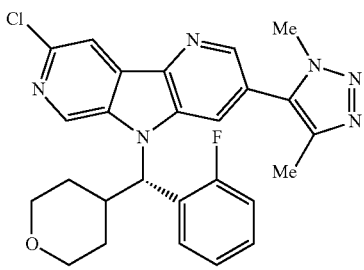 [SMILES: Cc1nnn(C)c1-c1cnc2c3cc(Cl)ncc3n([C@H](c3ccccc3F)C3CCOCC3)c2c1]

Step 1: 5-Bromo-2'-chloro-3-nitro-2,4'-bipyridine

In a RB flask was added a mixture of 2,5-dibromo-3-nitropyridine (8.78 g, 31.1 mmol) and (2-chloropyridin-4-yl)boronic acid (5 g, 31.8 mmol) in tetrahydrofuran (60 mL) and the solution was purged under a stream of nitrogen. Added 2 M aqueous potassium phosphate (39.7 mL, 79 mmol) and continued purging with nitrogen and then added PdCl$_2$(dppf)-CH$_2$Cl$_2$Adduct (1.297 g, 1.59 mmol) and the mixture was then heated to reflux under nitrogen for 2.5 h. Let cool to room temperature and diluted with water and extracted into ethyl acetate. Washed with water and concentrated. The material was dissolved in DCM and chromatographed on an ISCO Companion 120 g silica gel column and eluted with EtOAc/Hexane gradient (20-50%) to give 5-bromo-2'-chloro-3-nitro-2,4'-bipyridine (5 g, 15.9 mmol, 50.0% yield). LCMS: RT=0.92 min; (ES): m/z (M+H)$^+$=314.0, 316.0. (Waters Acquity SDS. Column: BEH C18 2.1×50 mm 1.7 u (1.6 min grad) 2-98% B. Flow Rate=0.8 mL/min. Solvent A: H$_2$O—0.1% TFA. Solvent B: Acetonitrile—0.1% TFA).

Step 2: 3-Bromo-8-chloro-5H-pyrrolo[3,2-b:5,4-c']dipyridine

In each of two 40 mL vial was added a mixture of 5-bromo-2'-chloro-3-nitro-2,4'-bipyridine (1 g, 3.18 mmol) and 1,2-bis(diphenylphosphino)ethane (1.583 g, 3.97 mmol) in 1,2-dichlorobenzene (10 mL). The vials was capped and heated in a heating block at 160° C. for 3 h. Both vials were removed from heating block combined and concentrated under high vacuum and the remaining residue dissolved in DCM and chromatographed on an ISCO Companion 40 g silica gel column and eluted with EtOAc/Hexane gradient (30-60-100%) to give two isomeric products. The major isomer gave 3-bromo-6-chloro-5H-pyrrolo[3,2-b:5,4-c']dipyridine (420 mg, 0.779 mmol, 24.49% yield). LCMS: RT=0.80 min; (ES): m/z (M+H)$_+$=282, 284 (Waters Acquity SDS. Column: BEH C18 2.1×50 mm 1.7 u (1.6 min grad) 2-98% B. Flow Rate=0.8 mL/min. Solvent A: H$_2$O—0.1% TFA. Solvent B: ACN—0.1% TFA). $^1$H NMR (400 MHz, DMSO-d$_6$) δ 12.39 (s, 1H), 8.71 (d, J=2.0 Hz, 1H), 8.27 (d, J=5.3 Hz, 1H), 8.24 (d, J=2.0 Hz, 1H), 8.17 (d, J=5.3 Hz, 1H). The minor isomer gave (3-bromo-8-chloro-5H-pyrrolo[3,2-b:5,4-c']dipyridine (100 mg, 0.177 mmol, 5.57% yield). LCMS: RT=0.83 min; (ES): m/z (M+H)$^+$=282, 284.: Waters Acquity SDS. Column: BEH C18 2.1×50 mm 1.7 u (1.6 min grad) 2-98% B. Flow Rate=0.8 mL/min. Solvent A: H$_2$O—0.1% TFA. Solvent B: ACN—0.1% TFA). $^1$H NMR (400 MHz, DMSO-d$_6$) δ 12.09 (br. s., 1H), 8.85 (d, J=1.0 Hz, 1H), 8.67 (d, J=2.0 Hz, 1H), 8.37 (d, J=2.1 Hz, 1H), 8.18 (d, J=1.0 Hz, 1H).

Step 3: (S)-3-Bromo-8-chloro-5-((2-fluorophenyl)(tetrahydro-2H-pyran-4-yl)methyl)-5H-pyrrolo[3,2-b:5,4-c']dipyridine In a RB flask was added a suspension of 3-bromo-8-chloro-5H-pyrrolo[3,2-b:5,4-c']dipyridine (100 mg, 0.354 mmol), (R)-(2-fluorophenyl)(tetrahydro-2H-pyran-4-yl)methanol (149 mg, 0.708 mmol), and triphenylphosphine (186 mg, 0.708 mmol) in dichloromethane (5 mL). The suspension was stirred at room temperature and treated drop wise with DIAD (0.138 mL, 0.708 mmol) and then stirred at room temperature for 5 h. The mixture was directly added to silica gel column and chromatographed on an ISCO Companion 40 g silica gel column and eluted with EtOAc/Hexane gradient (10-60%) to give (S)-3-bromo-8-chloro-5-((2-fluorophenyl)(tetrahydro-2H-pyran-4-yl)methyl)-5H-pyrrolo[3,2-b:5,4-c']dipyridine (160 mg, 0.337 mmol, 95% yield). LCMS: RT=1.10 min; (ES): m/z (M+H)$^+$=474.2, 476.2: (Waters Acquity SDS. Column: BEH C18 2.1×50 mm 1.7 u (1.6 min grad) 2-98% B. Flow Rate=0.8 mL/min. Solvent A: H$_2$O—0.1% TFA. Solvent B: ACN—0.1% TFA).

Step 4: 12-Chloro-5-(dimethyl-1H-1,2,3-triazol-5-yl)-8-[(S)-(2-fluorophenyl)(oxan-4-yl)methyl]-3,8,11-triazatricyclo[7.4.0.0$^{2,7}$]trideca-1(13),2(7),3,5,9,11-hexaene In a 20 mL vial was added a mixture of (S)-3-bromo-8-chloro-5-((2-fluorophenyl)(tetrahydro-2H-pyran-4-yl)

methyl)-5H-pyrrolo[3,2-b:5,4-c']dipyridine (160 mg, 0.337 mmol), 1,4-dimethyl-5-(tributylstannyl)-1H-1,2,3-triazole (156 mg, 0.404 mmol), copper(I) iodide (12.84 mg, 0.067 mmol), Pd(Ph$_3$P)$_4$ (38.9 mg, 0.034 mmol), and triethylamine (0.141 mL, 1.01 mmol) in DMF (2 mL). The vial was capped and heated in a heating block at 100° C. for 3 h. Diluted with ammonium hydroxide and water and extracted into ethyl acetate. Washed with water and brine and concentrated. The material was chromatographed on an ISCO Companion 40 g silica gel column and eluted first with Ethyl acetate (100%) and then with 10% MeOH/DCM. Collected fractions to give 65 mg of 12-chloro-5-(dimethyl-1H-1,2,3-triazol-5-yl)-8-[(S)-(2-fluorophenyl)(oxan-4-yl)methyl]-3,8,11-triazatricyclo[7.4.0.0$^{2,7}$]trideca-1(13),2(7),3,5,9,11-hexaene as an off-white solid. LCMS: RT=0.90 min; (ES): m/z (M+H)$^+$=491.4 (Waters Acquity SDS. Column: BEH C18 2.1×50 mm 1.7 u (1.6 min grad) 2-98% B. Flow Rate=0.8 mL/min. Solvent A: H$_2$O—0.1% TFA. Solvent B: ACN—0.1% TFA). $^1$H NMR (400 MHz, CD$_3$OD) δ 9.16 (s, 1H), 8.73-8.64 (m, 1H), 8.56 (br. s., 1H), 8.31 (d, J=0.9 Hz, 1H), 8.16 (td, J=7.4, 2.1 Hz, 1H), 7.77-7.62 (m, 1H), 7.62-7.51 (m, 1H), 7.18-7.00 (m, 1H), 6.12 (d, J=11.5 Hz, 1H), 4.10-4.05 (m, 3H), 4.04-3.96 (m, 1H), 3.84 (dd, J=11.6, 3.4 Hz, 1H), 3.62 (td, J=11.9, 2.0 Hz, 1H), 3.45-3.36 (m, 2H), 2.37 (s, 3H), 1.93 (d, J=13.3 Hz, 1H), 1.67 (td, J=12.3, 7.8 Hz, 1H), 1.49 (td, J=12.3, 7.6 Hz, 1H), 1.03-0.95 (m, 1H).

Example 5

10-Chloro-5-(dimethyl-1H-1,2,3-triazol-5-yl)-8-[(S)-(2-fluorophenyl)(oxan-4-yl)methyl]-3,8,11-triazatricyclo[7.4.0.0$^{2,7}$]trideca-1(13),2(7),3,5,9,11-hexaene

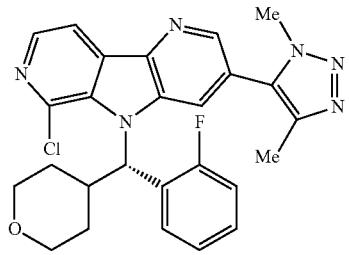 [SMILES: Cc1nnn(C)c1-c1cnc2c3ccnc(Cl)c3n([C@H](c3ccccc3F)C3CCOCC3)c2c1]

The title compound was synthesized using the procedure described for the synthesis of 12-chloro-5-(dimethyl-1H-1,2,3-triazol-5-yl)-8-[(S)-(2-fluorophenyl)(oxan-4-yl)methyl]-3,8,11-triazatricyclo[7.4.0.0$^{2,7}$]trideca-1(13),2(7),3,5,9,11-hexaene except using 3-bromo-6-chloro-5H-pyrrolo[3,2-b:5,4-c']dipyridine (the major isomer obtained in step 2). LCMS: RT=0.89 min; (ES): m/z (M+H)$^+$=491.1.: (Waters Acquity SDS. Column: BEH C18 2.1×50 mm 1.7 u (1.6 min grad) 2-98% B. Flow Rate=0.8 mL/min. Solvent A: H$_2$O—0.1% TFA. Solvent B: ACN—0.1% TFA). $^1$H NMR (500 MHz, DMSO-d$_6$) δ 8.70 (s, 1H), 8.38 (d, J=5.0 Hz, 1H), 8.33-8.23 (m, 3H), 7.42-7.31 (m, 2H), 7.14 (d, J=11.4 Hz, 1H), 7.11-7.04 (m, 1H), 3.92 (d, J=9.1 Hz, 1H), 3.86 (s, 3H), 3.79 (d, J=9.1 Hz, 1H), 3.62-3.39 (m, 2H), 3.26 (t, J=11.3 Hz, 1H), 2.18 (s, 3H), 1.88 (d, J=13.5 Hz, 1H), 1.66-1.54 (m, 1H), 1.54-1.43 (m, 1H), 0.93 (d, J=12.8 Hz, 1H).

Example 6

10-Chloro-5-(dimethyl-1H-1,2,3-triazol-5-yl)-8-[(S)-oxan-4-yl(phenyl)methyl]-3,8,11-triazatricyclo[7.4.0.0$^{2,7}$]trideca-1(13),2(7),3,5,9,11-hexaene

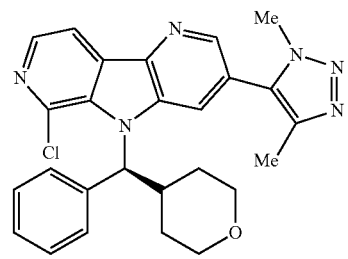 [SMILES: Cc1nnn(C)c1-c1cnc2c3ccnc(Cl)c3n([C@H](c3ccccc3)C3CCOCC3)c2c1]

Step 1: (S)-3-Bromo-6-chloro-5-(phenyl(tetrahydro-2H-pyran-4-yl)methyl)-5H-pyrrolo[3,2-b:5,4-c']dipyridine A mixture of 3-bromo-6-chloro-5H-pyrrolo[3,2-b:5,4-c']dipyridine (0.25 g, 0.885 mmol) and (R)-phenyl(tetrahydro-2H-pyran-4-yl)methanol (0.340 g, 1.77 mmol) in THF (2 mL) was added triphenylphosphine (0.464 g, 1.77 mmol) and DIAD (0.344 mL, 1.77 mmol) was added drop wise over the period of 10 min at 25° C. and then stirred at room temperature for 16 h. The mixture was added to silica gel column and chromatographed on an ISCO Companion 24 g silica gel column and eluted with 0 to 5% DCM/MeOH to give (S)-3-bromo-6-chloro-5-(phenyl(tetrahydro-2H-pyran-4-yl)methyl)-5H-pyrrolo[3,2-b:5,4-c']dipyridine (180 mg, 0.394 mmol, 44.5% yield) as a white solid. LCMS: HPLC: RT=1.12 min. MS (ES): m/z=458 [M+H]$^+$ (ACN/H$_2$O with NH$_4$OAc, Acquity BEH C18 1.7 μm (50×2.1) mm, gradient=3 min, wavelength=220 nm).

Step 2: 10-Chloro-5-(dimethyl-1H-1,2,3-triazol-5-yl)-8-[(S)-oxan-4-yl(phenyl)methyl]-3,8,11-triazatricyclo[7.4.0.0$^{2,7}$]trideca-1(13),2(7),3,5,9,11-hexaene To a stirred solution of (S)-3-bromo-6-chloro-5-(phenyl(tetrahydro-2H-pyran-4-yl)methyl)-5H-pyrrolo[3,2-b:5,4-c']dipyridine (100 mg, 0.219 mmol), 1,4-dimethyl-5-(tributylstannyl)-1H-1,2,3-triazole (85 mg, 0.219 mmol) and Et$_3$N (0.122 mL, 0.876 mmol) in DMF (2.5 mL) was degasified by bubbling N$_2$. The mixture was treated with Pd(Ph$_3$P)$_4$ (25.3 mg, 0.022 mmol) and copper(I) iodide (6.25 mg, 0.033 mmol) and heated 95° C. for 2 h. The mixture was quenched with water and ammonium hydroxide and water and extracted into ethyl acetate. Washed with water and brine and concentrated. The material was chromatographed on an ISCO Companion 12 g silica gel column and eluted with CHCl$_3$/MeOH (2%). Further purification by preparative-HPLC (Column: Sunfire C18(250×30*7 u) Mobile Phase A: 10 mm NH$_4$OAc in water, Mobile Phase B: ACN Solubility: MEOH+THF, Flow: 15 mL/min, T/% B: 0/10,11/60) gave title compound (35 mg, 0.072 mmol, 32.8% yield) as a white color solid. LCMS: HPLC: RT=1.90 min (ACN/H$_2$O with HCOONH$_4$, Ascentis Express C8 2.7 m (5×2.1) mm, gradient=4 min, wavelength=220 nm); MS (ES): m/z=473 [M+H]$^+$. HPLC RT=8.99 min, Column: XBridge (150×4.6 mm) 3.5 micron, Mobile phase A: 0.05% TFA in Water: ACN: (95:5), Mobile phase B: ACN:0.05% TFA in Water:

(95:5), FLOW: 1.0 mL/min, wavelength=220 nm & 254 nm); HPLC RT=9.89 min Sunfire C18 (4.6×150) mm, 3.5 micron, Mobile Phase A:0.05% TFA in water:ACN (95:5), Mobile Phase B:ACN:0.05% TFA in water (95:5), FLOW: 1 mL/min, wavelength=220 nm & 254 nm. $^1$H NMR (400 MHz, CD$_3$OD) δ =8.63 (d, J=2.0 Hz, 1H), 8.40-8.35 (m, 2H), 8.18 (d, J=1.5 Hz, 1H), 7.63 (d, J=7.5 Hz, 2H), 7.44-7.36 (m, 2H), 7.34-7.27 (m, 1H), 7.08 (d, J=11.0 Hz, 1H), 4.03-3.97 (m, 1H), 3.87 (s, 3H), 3.82 (dd, J=3.0, 11.5 Hz, 1H), 3.66-3.58 (m, 1H), 3.43-3.34 (m, 2H), 2.22 (s, 3H), 2.12 (d, J=12.5 Hz, 1H), 1.68-1.52 (m, 2H), 0.86 (d, J=14.1 Hz, 1H).

Example 7

5-(Dimethyl-1H-1,2,3-triazol-5-yl)-10-(morpholin-4-yl)-8-[(S)-oxan-4-yl(phenyl)methyl]-3,8,11-triazatricyclo[7.4.0.0$^{2,7}$]trideca-1(13),2(7),3,5,9,11-hexaene

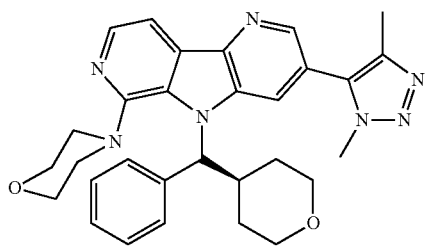

A mixture of 10-chloro-5-(dimethyl-1H-1,2,3-triazol-5-yl)-8-[(S)-oxan-4-yl(phenyl)methyl]-3,8,11-triazatricyclo[7.4.0.0$^{2,7}$]trideca-1(13),2(7),3,5,9,11-hexaene (25 mg, 0.053 mmol) and morpholine (92 mg, 1.06 mmol) was irradiated in microwave at 170° C. for 5 hrs. This was purified by preparative-HPLC (Column: Sunfire C18(250× 30 mm 7 u) Mobile Phase A: 10 mm NH$_4$OAc in water, Mobile Phase B: ACN Gradient 10-60% B Over 30 min. Flow: 15 mL/min) to give the title compound (8.0 mg, 0.014 mmol, 26.6% yield) as a white solid. LCMS: RT=1.82 min; MS (ES): m/z=524 [M+H]$^+$ (Column: Ascentis Express C8 (50×2.1 mm; 2.7 μm), ACN/H$_2$O with NH$_4$OAc, gradient=4 min, wavelength=220 nm); HPLC RT=7.94 min (Column: Sunfire C18 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). HPLC RT=7.49 min. (Column: XBridge Phenyl 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). 1H NMR (400 MHz, CD$_3$OD) δ 8.58 (d, J=2.01 Hz, 1H), 8.35 (s, 1H), 8.13 (d, J=5.52 Hz, 1H), 8.00 (d, J=1.51 Hz, 1H), 7.57 (d, J=7.03 Hz, 2H), 7.32-7.39 (m, 2H), 7.23-7.31 (m, 2H), 4.11 (d, J=10.04 Hz, 1H), 3.95-4.04 (m, 3H), 3.89 (s, 3H), 3.77-3.85 (m, 2H), 3.61 (dd, J=12.05, 10.04 Hz, 1H), 3.47-3.52 (m, 1H), 3.39 (dd, J=11.80, 9.79 Hz, 3H), 2.23 (s, 3H), 2.04-2.13 (m, 1H), 1.66 (dd, J=12.55, 3.51 Hz, 1H), 1.42 (dd, J=13.05, 4.52 Hz, 1H), 0.93-1.01 (m, 2H).

Example 8

5-(Dimethyl-1H-1,2,3-triazol-5-yl)-10-(4-methylpiperazin-1-yl)-8-[(S)-oxan-4-yl(phenyl)methyl]-3,8,11-triazatricyclo[7.4.0.0$^{2,7}$]trideca-1(13),2(7),3,5,9,11-hexaene

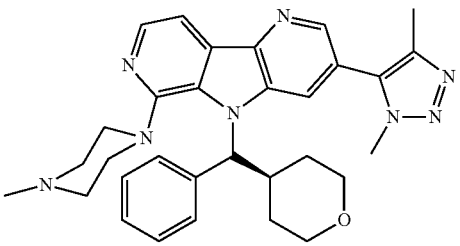

A mixture of 10-chloro-5-(dimethyl-1H-1,2,3-triazol-5-yl)-8-[(S)-oxan-4-yl(phenyl)methyl]-3,8,11-triazatricyclo[7.4.0.0$^{2,7}$]trideca-1(13),2(7),3,5,9,11-hexaene (25 mg, 0.053 mmol) and 1-methylpiperazine (106 mg, 1.06 mmol) was irradiated in microwave at 170° C. for 3 hrs. This was purified by preparative-HPLC (Column: Sunfire C18(250× 30 mm 7 u) Mobile Phase A: 10 mm NH$_4$OAc in water, Mobile Phase B: ACN Gradient 10-60% B Over 30 min. Flow: 15 mL/min) to give the title compound (14 mg, 0.026 mmol, 34% yield) as a white solid. LCMS: RT=1.80 min; MS (ES): m/z=537 [M+H]$^+$ (Column: Ascentis Express C8 (50×2.1 mm; 2.7 μm), ACN/H$_2$O with NH$_4$OAc, gradient=4 min, wavelength=220 nm); HPLC RT=5.66 min (Column: Sunfire C18 3.5 m, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). HPLC RT=5.98 min. (Column: XBridge Phenyl 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). 1H NMR (400 MHz, CD$_3$OD) δ 8.56-8.60 (m, 1H), 8.30-8.34 (m, 1H), 8.10 (d, J=5.02 Hz, 1H), 7.99 (d, J=2.01 Hz, 1H), 7.57 (d, J=7.53 Hz, 2H), 7.32-7.38 (m, 2H), 7.25-7.31 (m, 1H), 7.16 (d, J=10.04 Hz, 1H), 3.99 (dd, J=11.55, 3.01 Hz, 1H), 3.89 (s, 3H), 3.78-3.83 (m, 1H), 3.60 (dd, J=11.80, 9.79 Hz, 1H), 3.33-3.52 (m, 6H), 3.11-3.18 (m, 1H), 3.02 (d, J=11.04 Hz, 1H), 2.59-2.68 (m, 1H), 2.49 (d, J=8.53 Hz, 1H), 2.43 (s, 3H), 2.23 (s, 3H), 2.05 (d, J=13.55 Hz, 3H), 1.60-1.71 (m, 1H), 1.43 (dd, J=13.05, 4.52 Hz, 1H), 0.98 (d, J=12.55 Hz, 1H).

Example 9

5-(Dimethyl-1H-1,2,3-triazol-5-yl)-N-(2-methoxyethyl)-8-[(S)-oxan-4-yl(phenyl)methyl]-3,8,11-triazatricyclo[7.4.0.0²,⁷]trideca-1(13),2(7),3,5,9,11-hexaen-10-amine

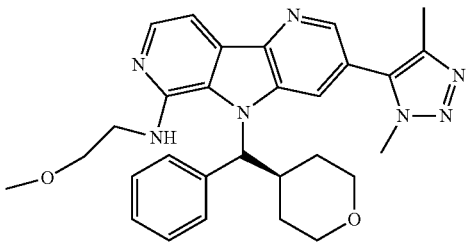

A mixture of 10-chloro-5-(dimethyl-1H-1,2,3-triazol-5-yl)-8-[(S)-oxan-4-yl(phenyl)methyl]-3,8,11-triazatricyclo[7.4.0.0²,⁷]trideca-1(13),2(7),3,5,9,11-hexaene (25 mg, 0.053 mmol) and 2-methoxyethanamine (79 mg, 1.06 mmol) was irradiated in microwave at 170° C. for 3 hrs. This was purified by preparative-HPLC (Column: Sunfire C18(250×30 mm 7 u) Mobile Phase A: 10 mm NH$_4$OAc in water, Mobile Phase B: ACN Gradient 10-60% B Over 30 min. Flow: 15 mL/min) to give the title compound (9 mg, 0.017 mmol, 27% yield) as a white solid. LCMS: RT=1.85 min; MS (ES): m/z=512 [M+H]⁺ (Column: Ascentis Express C8 (50×2.1 mm; 2.7 μm), ACN/H$_2$O with NH$_4$OAc, gradient=4 min, wavelength=220 nm); HPLC RT=5.87 min (Column: Sunfire C18 3.5 m, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). HPLC RT=6.44 min. (Column: XBridge Phenyl 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). 1H NMR (400 MHz, CD$_3$OD) δ 8.53 (s, 1H), 8.21 (br. s., 1H), 8.03 (d, J=5.52 Hz, 1H), 7.67 (d, J=5.52 Hz, 1H), 7.50 (d, J=7.53 Hz, 2H), 7.33-7.41 (m, 2H), 7.27-7.32 (m, 1H), 6.20 (d, J=11.04 Hz, 1H), 4.00 (d, J=8.53 Hz, 1H), 3.93 (s, 3H), 3.84 (d, J=8.53 Hz, 1H), 3.75 (br. s., 3H), 3.57-3.65 (m, 1H), 3.46 (s, 3H), 3.39-3.44 (m, 1H), 2.27 (s, 3H), 2.05 (br. s., 1H), 1.66 (d, J=10.04 Hz, 1H), 1.39-1.50 (m, 1H), 0.98-1.06 (m, 1H), 0.90 (br. s., 1H).

Example 10

(2-{[5-(Dimethyl-1H-1,2,3-triazol-5-yl)-8-[(S)-oxan-4-yl(phenyl)methyl]-3,8,11-triazatricyclo[7.4.0.0²,⁷]trideca-1(13),2(7),3,5,9,11-hexaen-10-yl]oxy}ethyl)dimethylamine

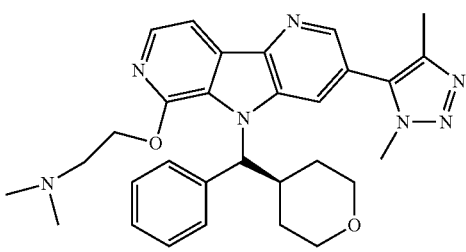

A mixture of 10-chloro-5-(dimethyl-1H-1,2,3-triazol-5-yl)-8-[(S)-oxan-4-yl(phenyl)methyl]-3,8,11-triazatricyclo[7.4.0.0²,⁷]trideca-1(13),2(7),3,5,9,11-hexaene (25 mg, 0.053 mmol) and 2-(dimethylamino)ethanol (94 mg, 1.06 mmol) was irradiated in microwave at 170° C. for 3 hrs. This was purified by preparative-HPLC (Column: Sunfire C18 (250×30 mm 7 u) Mobile Phase A: 10 mm NH$_4$OAc in water, Mobile Phase B: ACN Gradient 10-60% B Over 30 min. Flow: 15 mL/min) to give the title compound (11 mg, 0.021 mmol, 32% yield) as a white solid. LCMS: RT=1.82 min; MS (ES): m/z=526 [M+H]⁺ (Column: Ascentis Express C8 (50×2.1 mm; 2.7 μm), ACN/H$_2$O with NH$_4$OAc, gradient=4 min, wavelength=220 nm); HPLC RT=5.87 min (Column: Sunfire C18 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). HPLC RT=6.40 min. (Column: XBridge Phenyl 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). 1H NMR (400 MHz, CD$_3$OD) δ 8.54 (d, J=1.51 Hz, 1H), 8.16 (br. s., 1H), 8.06 (d, J=5.52 Hz, 1H), 7.90 (d, J=5.52 Hz, 1H), 7.64 (d, J=7.53 Hz, 2H), 7.36 (t, J=7.53 Hz, 2H), 7.24-7.30 (m, 1H), 6.83 (br. s., 1H), 4.86 (br. s., 2H), 3.99 (d, J=12.05 Hz, 1H), 3.89 (s, 3H), 3.78-3.85 (m, 1H), 3.60 (td, J=12.05, 2.01 Hz, 1H), 3.35-3.42 (m, 1H), 2.95-3.03 (m, 2H), 2.41 (s, 6H), 2.24 (s, 3H), 2.04 (d, J=13.55 Hz, 1H), 1.49-1.64 (m, 2H), 0.89 (d, J=14.06 Hz, 1H).

Example 11

2-{[5-(Dimethyl-1H-1,2,3-triazol-5-yl)-8-[(S)-oxan-4-yl(phenyl)methyl]-3,8,11-triazatricyclo[7.4.0.0²,⁷]trideca-1(13),2(7),3,5,9,11-hexaen-10-yl]amino}ethan-1-ol

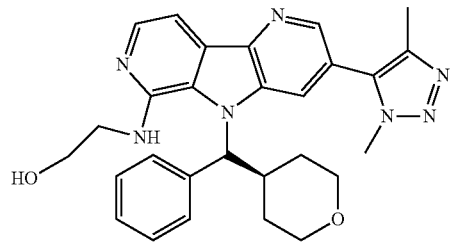

A mixture of 10-chloro-5-(dimethyl-1H-1,2,3-triazol-5-yl)-8-[(S)-oxan-4-yl(phenyl)methyl]-3,8,11-triazatricyclo[7.4.0.0²,⁷]trideca-1(13),2(7),3,5,9,11-hexaene (25 mg, 0.053 mmol) and 2-aminoethanol (64.6 mg, 1.06 mmol) was irradiated in microwave at 170° C. for 3 hrs. This was purified by preparative-HPLC (Column: Sunfire C18 (250×30 mm 7 u) Mobile Phase A: 10 mm NH$_4$OAc in water, Mobile Phase B: ACN Gradient 10-60% B Over 30 min. Flow: 15 mL/min) to give the title compound (7 mg, 0.014 mmol, 26% yield) as a white solid. LCMS: RT=1.74 min; MS (ES): m/z=498 [M+H]⁺ (Column: Ascentis Express C8 (50×2.1 mm; 2.7 μm), ACN/H$_2$O with NH$_4$OAc, gradient=4 min, wavelength=220 nm); HPLC RT=5.47 min (Column: Sunfire C18 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min;

Flow: 1 mL/min; Detection: UV at 220 nm). HPLC RT=5.81 min. (Column: XBridge Phenyl 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). $^1$H NMR (400 MHz, CD$_3$OD) δ 8.56 (s, 1H), 8.22 (br. s., 1H), 8.00 (d, J=5.02 Hz, 1H), 7.56 (d, J=7.53 Hz, 2H), 7.49 (d, J=5.52 Hz, 1H), 7.32 (t, J=7.28 Hz, 2H), 7.25 (d, J=7.53 Hz, 1H), 6.08 (d, J=11.55 Hz, 1H), 4.91 (br. s., 1H), 3.84-3.96 (m, 4H), 3.73 (br. s., 5H), 3.50 (t, J=11.55 Hz, 3H), 2.21 (br. s., 3H), 1.86 (s, 1H), 1.64 (br. s., 2H), 1.23 (br. s., 1H).

Example 12

5-(Dimethyl-1H-1,2,3-triazol-5-yl)-11-methoxy-8-[(S)-oxan-4-yl(phenyl)methyl]-3,8,10-triazatricyclo[7.4.0.0$^{2,7}$]trideca-1(13),2(7),3,5,9,11-hexaene

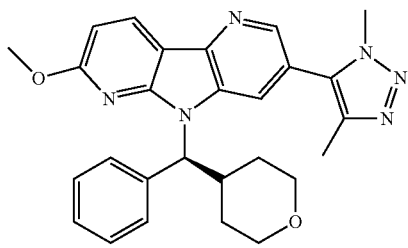 [SMILES: COc1ccc2c3ncc(-c4c(C)nnn4C)cc3n([C@H](c3ccccc3)C3CCOCC3)c2n1]

The title compound was synthesized using the procedure described for the synthesis of 10-chloro-5-(dimethyl-1H-1,2,3-triazol-5-yl)-8-[(S)-oxan-4-yl(phenyl)methyl]-3,8,11-triazatricyclo[7.4.0.0$^{2,7}$]trideca-1(13),2(7),3,5,9,11-hexaene starting with (6-methoxypyridin-3-yl)boronic acid (as shown in Scheme 1). LCMS: HPLC: RT=2.054 min (ACN/H$_2$O with NH$_4$HCO$_2$, Column-Ascentis Express C8 (50×2.1 nm-2.7 μm), gradient=4 min, wave-length=254 nm); MS (ES): m/z=469.4 [M+H]. $^1$H NMR: (400 MHz, d4-MeOH) δ 8.51 (d, J=8.4 Hz, 1H), 8.44 (m, 1H), 8.28 (m, 1H), 7.74 (d, J=7.2 Hz, 2H), 7.32 (m, 2H), 7.25 (m, 1H), 6.84 (d, J=8.4, 1H), 5.81 (d, J=10.8 Hz, 1H), 4.20 (s, 3H), 4.01-3.96 (s+m, 4H), 3.76 (m, 1H), 3.72 (m, 1H), 3.49 (m, 1H), 3.43 (m, 1H), 2.32 (s, 3H), 1.69 (m, 1H), 1.53-1.41 (m, 2H), 1.39 (m, 1H). HPLC RT=9.121 min. (XBridge Phenyl (4.6×150 nm), 3.5 micron, 5/95 to 95/5 H$_2$O/ACN, 0.05% TFA, flow=1 mL/min. gradient=15 min.). HPLC RT=10.043 min (Sunfire C18 (4.6×150) nm, 3.5 micron, 5/95 to 95/5 H$_2$O/ACN, 0.05% TFA, flow=1 mL/min. gradient=15 min.).

Example 13

5-(Dimethyl-1H-1,2,3-triazol-5-yl)-10-methoxy-8-[(S)-oxan-4-yl(phenyl)methyl]-3,8,11-triazatricyclo[7.4.0.0$^{2,7}$]trideca-1(13),2(7),3,5,9,11-hexaene

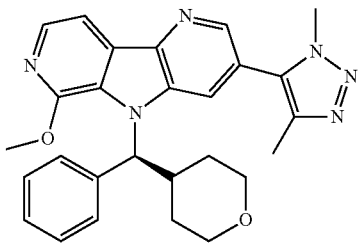 [SMILES: COc1nccc2c3ncc(-c4c(C)nnn4C)cc3n([C@H](c3ccccc3)C3CCOCC3)c12]

The title compound was synthesized using the procedure described for the synthesis of 10-chloro-5-(dimethyl-1H-1,2,3-triazol-5-yl)-8-[(S)-oxan-4-yl(phenyl)methyl]-3,8,11-triazatricyclo[7.4.0.0$^{2,7}$]trideca-1(13),2(7),3,5,9,11-hexaene except starting with (2-methoxypyridin-4-yl)boronic acid (according to Scheme 1). LCMS: HPLC: RT=1.898 min., MS (ES): m/z=469.2[M+H]. (ACN/H$_2$O with HCOONH$_4$, Ascentis Express C8 (50×2.1 mm; 2.7 u), gradient=4 min, wavelength=220 nm); $^1$H NMR (400 MHz, CD$_3$OD) δ 8.54 (d, J=1.0 Hz, 1H), 8.17 (br. s., 1H), 8.07 (d, J=5.5 Hz, 1H), 7.89 (d, J=5.5 Hz, 1H), 7.60 (d, J=7.5 Hz, 2H), 7.42-7.32 (m, 2H), 7.30-7.22 (m, 1H), 6.69 (br. s., 1H), 4.31 (s, 3H), 3.98 (dd, J=2.8, 11.8 Hz, 1H), 3.89 (s, 3H), 3.81 (dd, J=3.0, 11.5 Hz, 1H), 3.60 (dt, J=2.3, 11.9 Hz, 1H), 3.43-3.33 (m, 2H), 2.23 (s, 3H), 2.03 (d, J=13.1 Hz, 1H), 1.60-1.39 (m, 2H), 0.92 (d, J=14.1 Hz, 1H). HPLC: RT=15.331 min (Sunfire C18 3.5 um, 4.6×150 mm 95/5 to 5/95 H$_2$O/CH$_3$CN/0.05% TFA, flow=1 mL/min, gradient=25 min).

Example 14

11-Chloro-5-(dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaene

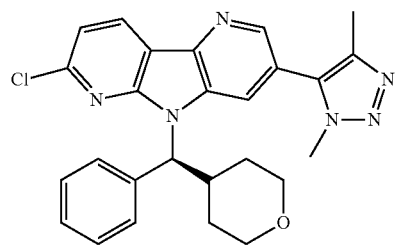 [SMILES: Cc1nnn(C)c1-c1cnc2c3ccc(Cl)nc3n([C@H](c3ccccc3)C3CCOCC3)c2c1]

The title compound was synthesized using the procedure described for the synthesis of 10-chloro-5-(dimethyl-1H-1,2,3-triazol-5-yl)-8-[(S)-oxan-4-yl(phenyl)methyl]-3,8,11-triazatricyclo[7.4.0.0$^{2,7}$]trideca-1(13),2(7),3,5,9,11-hexaene except starting with (6-chloropyridin-3-yl)boronic acid (according to Scheme 1). LCMS: HPLC: RT=2.028 min MS (ES): m/z=473.2 [M+H] (ACN/H$_2$O with HCOONH$_4$, Ascentis Express C8 (50×2.1 mm; 2.7μ), gradient=4 min, wavelength=220 nm); $^1$H NMR (400 MHz, CD$_3$OD) δ 8.68 (d, J=8.53 Hz, 1H), 8.59 (d, J=1.51 Hz, 1H), 8.40 (d, J=1.51 Hz, 1H), 7.71-7.79 (m, 2H), 7.44-7.51 (m, 1H), 7.32-7.39

(m, 2H), 7.24-7.31 (m, 1H), 5.93 (d, J=11.55 Hz, 1H), 3.95-4.04 (m, 4H), 3.82-3.91 (m, 1H), 3.65 (d, J=11.55 Hz, 1H), 3.56 (dd, J=11.80, 9.29 Hz, 1H), 3.43 (td, J=11.80, 2.51 Hz, 1H), 2.33 (s, 3H), 1.75 (d, J=14.05 Hz, 1H), 1.37-1.61 (m, 2H), 1.22 (d, J=11.55 Hz, 1H). Chiral HPLC SFC RT=6.90 min (Column: Lux Cellulose-2, 250×4.6 mm, 5 μm; Mobile Phase: 60/40 CO$_2$/(0.3% DEA in MeOH); Flow: 4 mL/min).

Example 15

11-Chloro-5-(dimethyl-1H-1,2,3-triazol-5-yl)-8-[(R)-oxan-4-yl(phenyl)methyl]-3,8,10-triazatricyclo[7.4.0.0$^{2,7}$]trideca-1(9),2(7),3,5,10,12-hexaene

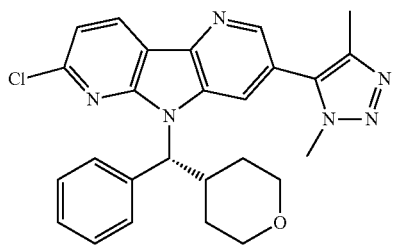 [SMILES: Cc1nnn(C)c1-c1cnc2c3ccc(Cl)nc3n([C@@H](c3ccccc3)C3CCOCC3)c2c1]

The title compound was synthesized using the procedure described for the synthesis of 10-chloro-5-(dimethyl-1H-1,2,3-triazol-5-yl)-8-[(S)-oxan-4-yl(phenyl)methyl]-3,8,11-triazatricyclo[7.4.0.0$^{2,7}$]trideca-1(13),2(7),3,5,9,11-hexaene except starting with (6-chloropyridin-3-yl)boronic acid (according to Scheme 1). LCMS: HPLC: RT=2.028 min MS (ES): m/z=473.2 [M+H] (ACN/H$_2$O with HCOONH$_4$, Ascentis Express C8 (50×2.1 mm; 2.7μ), gradient=4 min, wavelength=220 nm); $^1$H NMR (400 MHz, CD$_3$OD) δ 8.68 (d, J=8.53 Hz, 1H), 8.59 (d, J=1.51 Hz, 1H), 8.40 (d, J=1.51 Hz, 1H), 7.71-7.79 (m, 2H), 7.44-7.51 (m, 1H), 7.32-7.39 (m, 2H), 7.24-7.31 (m, 1H), 5.93 (d, J=11.55 Hz, 1H), 3.95-4.04 (m, 4H), 3.82-3.91 (m, 1H), 3.65 (d, J=11.55 Hz, 1H), 3.56 (dd, J=11.80, 9.29 Hz, 1H), 3.43 (td, J=11.80, 2.51 Hz, 1H), 2.33 (s, 3H), 1.75 (d, J=14.05 Hz, 1H), 1.37-1.61 (m, 2H), 1.22 (d, J=11.55 Hz, 1H). Chiral HPLC SFC RT=4.59 min (Column: Lux Cellulose—2, 250×4.6 mm, 5 μm; Mobile Phase: 60/40 CO$_2$/(0.3% DEA in MeOH); Flow: 4 mL/min).

Example 16

5-(Dimethyl-1H-1,2,3-triazol-5-yl)-8-[(3-fluorophenyl)(oxan-4-yl)methyl]-11-methoxy-3,8,10-triazatricyclo[7.4.0.0$^{2,7}$]trideca-1(13),2(7),3,5,9,11-hexaene (Rac)

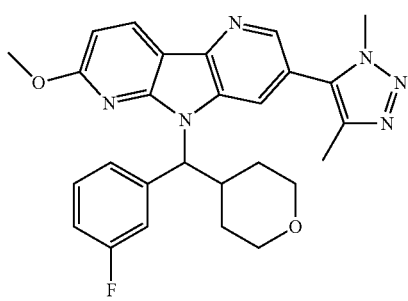 [SMILES: COc1ccc2c3ncc(-c4c(C)nnn4C)cc3n(C(c3cccc(F)c3)C3CCOCC3)c2n1]

The title compound was synthesized using the procedure described for the synthesis of 10-chloro-5-(dimethyl-1H-1,2,3-triazol-5-yl)-8-[(S)-oxan-4-yl(phenyl)methyl]-3,8,11-triazatricyclo[7.4.0.0$^{2,7}$]trideca-1(13),2(7),3,5,9,11-hexaene except starting with (6-methoxypyridin-3-yl)boronic acid and using racemic (3-fluorophenyl)(tetrahydro-2H-pyran-4-yl)methanol (according to Scheme 1). LCMS: HPLC: RT=1.991 min MS (ES): m/z=487.2 [M+H] (ACN/H$_2$O with HCOONH$_4$, Ascentis Express C8 (50×2.1 mm; 2.7μ), gradient=4 min, wavelength=220 nm); HPLC RT=9.874 min (Column: Sunfire C18 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). HPLC RT=9.021 min. (Column: XBridge Phenyl 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). $^1$H NMR (400 MHz, CD$_3$OD) δ 8.55 (d, J=8.4 Hz, 1H), 8.49 (m, 1H), 8.37 (m, 1H), 7.64 (m, 1H), 7.57 (m, 1H), 7.36 (m, 1H), 7.03 (m, 1H), 6.88 (d, J=8.4 Hz, 1H), 5.81 (d, J=12.0 Hz, 1H), 4.23 (s, 3H), 4.02 (s, 3H), 4.01 (m, 1H), 3.89 (m, 1H), 3.58 (m, 1H), 3.52 (m, 1H), 2.36 (s, 3H), 1.67 (m, 1H), 1.55 (m, 1H), 1.42 (m, 1H), 1.34 (m, 2H).

Example 17

8-[(2,3-Difluorophenyl)(oxan-4-yl)methyl]-5-(dimethyl-1H-1,2,3-triazol-5-yl)-11-methoxy-3,8,10-triazatricyclo[7.4.0.0$^{2,7}$]trideca-1(13),2(7),3,5,9,11-hexaene (Rac)

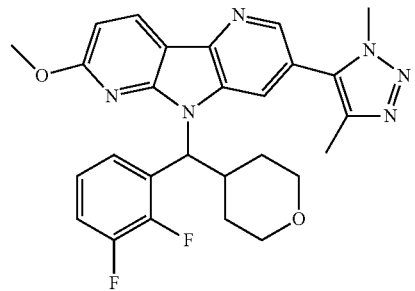 [SMILES: COc1ccc2c3ncc(-c4c(C)nnn4C)cc3n(C(c3cccc(F)c3F)C3CCOCC3)c2n1]

The title compound was synthesized using the procedure described for the synthesis of 10-chloro-5-(dimethyl-1H-1,2,3-triazol-5-yl)-8-[(S)-oxan-4-yl(phenyl)methyl]-3,8,11-triazatricyclo[7.4.0.0$^{2,7}$]trideca-1(13),2(7),3,5,9,11-hexaene except starting with (6-methoxypyridin-3-yl)boronic acid and using racemic (2,3-difluorophenyl)(tetrahydro-2H-pyran-4-yl)methanol (according to Scheme 1). LCMS: RT=1.983 min; MS (ES): m/z=505.2 [M+H]$^+$ (Column: Ascentis Express C8 (50×2.1 mm; 2.7 μm), ACN/H$_2$O with NH$_4$OAc, gradient=4 min, wavelength=220 nm); HPLC RT=10.125 min (Column: Sunfire C18 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). HPLC RT=9.163 min. (Column: XBridge Phenyl 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). $^1$H NMR (400 MHz, CD$_3$OD) δ 8.51-8.48 (m, 2H), 8.33 (m, 1H), 7.99 (m, 1H), 7.20 (m, 2H), 6.81 (d, J=8.4 Hz, 1H), 6.09 (d, J=11.2 Hz, 1H), 4.15 (s, 3H), 4.05 (s, 3H), 3.99 (m, 1H), 3.96 (m, 1H), 3.71 (M, 1H), 3.51 (M, 1H), 3.39 (M, 1H), 2.35 (s, 3H), 1.71 (m, 1H), 1.57-1.47 (m, 2H), 1.44 (m, 1H).

Example 18

5-(Dimethyl-1H-1,2,3-triazol-5-yl)-8-[(2-fluorophenyl)(oxan-4-yl)methyl]-10-methoxy-3,8,11-triazatricyclo[7.4.0.0²,⁷]trideca-1(13),2(7),3,5,9,11-hexaene Enantiomer 1

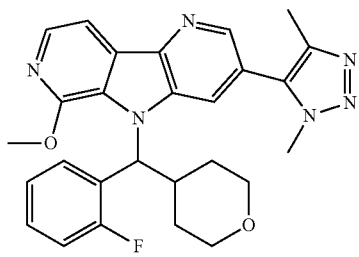 [SMILES: COc1nccc2c3ncc(-c4c(C)nnn4C)cc3n(C(c3ccccc3F)C3CCOCC3)c12]

The title compound was synthesized using the procedure described for the synthesis of 10-chloro-5-(dimethyl-1H-1,2,3-triazol-5-yl)-8-[(S)-oxan-4-yl(phenyl)methyl]-3,8,11-triazatricyclo[7.4.0.0²,⁷]trideca-1(13),2(7),3,5,9,11-hexaene except using racemic (2-fluorophenyl)-(tetrahydro-2H-pyran-4-yl)methanol and separating final enantiomer using Chiral preparative SFC (Column: Chiral OD-H 25×2.1 cm, 5 μm; Mobile Phase: 60/40 CO₂/(0.25% DEA in MeOH); Flow: 70 mL/min). For Enatiomer 1: LCMS: RT=1.91 min; MS (ES): m/z=487.2 [M+H]⁺ (Ascentis Express C8 (50×2.1 mm; 2.7 μm), ACN/H₂O with NH₄OAc, gradient=4 min, wavelength=220 nm); HPLC RT=9.806 min (Column: Sunfire C18 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). HPLC RT=8.666 min. (Column: XBridge Phenyl 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). ¹H NMR (400 MHz, CD₃OD) δ ppm 8.56 (s, 1H), 8.16 (br. s., 1H), 8.03-8.10 (m, 2H), 7.87-7.93 (m, 1H), 7.29-7.41 (m, 2H), 6.92-7.08 (m, 2H), 4.29 (br. s., 3H), 3.97-4.06 (m, 1H), 3.82-3.96 (m, 4H), 3.57-3.66 (m, 1H), 3.35-3.44 (m, 2H), 2.25 (br. s., 3H), 2.01 (d, J=14.05 Hz, 1H), 1.48-1.68 (m, 2H), 0.88-1.01 (m, 1H). Chiral SFC RT=5.28 min (Column: Chiralcel OD-H 250×4.6 mm, 5 μm; Mobile Phase: 70/30 CO₂/(0.25% DEA in MeOH); Flow: 3 mL/min).

Example 19

5-(Dimethyl-1H-1,2,3-triazol-5-yl)-8-[(2-fluorophenyl)(oxan-4-yl)methyl]-10-methoxy-3,8,11-triazatricyclo[7.4.0.0²,⁷]trideca-1(13),2(7),3,5,9,11-hexaene Enantiomer 2

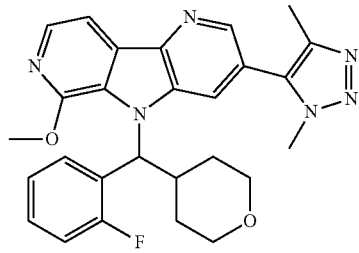 [SMILES: COc1nccc2c3ncc(-c4c(C)nnn4C)cc3n(C(c3ccccc3F)C3CCOCC3)c12]

The title compound was synthesized using the procedure described for the synthesis of 10-chloro-5-(dimethyl-1H-1,2,3-triazol-5-yl)-8-[(S)-oxan-4-yl(phenyl)methyl]-3,8,11-triazatricyclo[7.4.0.0²,⁷]trideca-1(13),2(7),3,5,9,11-hexaene except using racemic (2-fluorophenyl)-(tetrahydro-2H-pyran-4-yl)methanol and separating final enantiomer using Chiral preparative SFC (Column: Chiral OD-H 25×2.1 cm, 5 μm; Mobile Phase: 60/40 CO₂/(0.25% DEA in MeOH); Flow: 70 mL/min). For Enatiomer 2: LCMS: RT=1.91 min; MS (ES): m/z=487.2 [M+H]⁺ (Ascentis Express C8 (50×2.1 mm; 2.7 μm), ACN/H₂O with NH₄OAc, gradient=4 min, wavelength=220 nm); HPLC RT=9.806 min (Column: Sunfire C18 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). HPLC RT=8.666 min. (Column: XBridge Phenyl 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). ¹H NMR (400 MHz, CD₃OD) δ ppm 8.56 (s, 1H), 8.16 (br. s., 1H), 8.03-8.10 (m, 2H), 7.87-7.93 (m, 1H), 7.29-7.41 (m, 2H), 6.92-7.08 (m, 2H), 4.29 (br. s., 3H), 3.97-4.06 (m, 1H), 3.82-3.96 (m, 4H), 3.57-3.66 (m, 1H), 3.35-3.44 (m, 2H), 2.25 (br. s., 3H), 2.01 (d, J=14.05 Hz, 1H), 1.48-1.68 (m, 2H), 0.88-1.01 (m, 1H). Chiral SFC RT=3.88 min (Column: Chiralcel OD-H 250×4.6 mm, 5 μm; Mobile Phase: 70/30 CO₂/(0.25% DEA in MeOH); Flow: 3 mL/min).

Example 20

5-(Dimethyl-1H-1,2,3-triazol-5-yl)-8-[(3-fluorophenyl)(oxan-4-yl)methyl]-10-methoxy-3,8,11-triazatricyclo[7.4.0.0²,⁷]trideca-1(13),2(7),3,5,9,11-hexaene Enantiomer 1

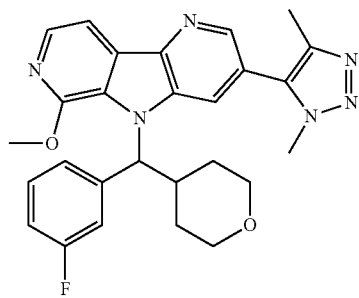 [SMILES: COc1nccc2c3ncc(-c4c(C)nnn4C)cc3n(C(c3cccc(F)c3)C3CCOCC3)c12]

Example 21

5-(Dimethyl-1H-1,2,3-triazol-5-yl)-8-[(3-fluorophenyl)(oxan-4-yl)methyl]-10-methoxy-3,8,11-triazatricyclo[7.4.0.0²,⁷]trideca-1(13),2(7),3,5,9,11-hexaene Enantiomer 2

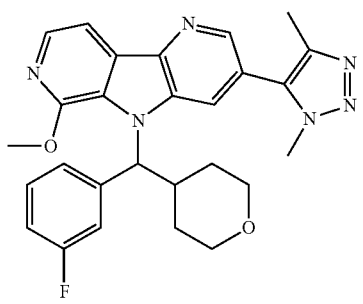 [SMILES: COc1nccc2c3ncc(-c4c(C)nnn4C)cc3n(C(c3cccc(F)c3)C3CCOCC3)c12]

The title compound was synthesized using the procedure described for the synthesis of 10-chloro-5-(dimethyl-1H-1,2,3-triazol-5-yl)-8-[(S)-oxan-4-yl(phenyl)methyl]-3,8,11-triazatricyclo[7.4.0.0²,⁷]trideca-1(13),2(7),3,5,9,11-hexaene except using racemic (3-fluorophenyl)-(tetrahydro-2H-pyran-4-yl)methanol and separating final enantiomer using Chiral preparative SFC (Column: Whelk-01(R,R), 25×2.1 cm, 5 μm; Mobile Phase: 65/35 CO₂/(0.25% DEA in MeOH); Flow: 75 mL/min). For Enatiomer 1: LCMS: RT=1.91 min; MS (ES): m/z=487.2 [M+H]⁺ (Ascentis Express C8 (50×2.1 mm; 2.7 μm), ACN/H₂O with NH₄OAc, gradient=4 min, wavelength=220 nm); HPLC RT=10.155 min (Column: Sunfire C18 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). HPLC RT=9.123 min. (Column: XBridge Phenyl 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). ¹H NMR (400 MHz, CD₃OD) δ ppm 8.54-8.61 (m, 1H), 8.26 (br. s., 1H), 8.10 (d, J=5.52 Hz, 1H), 7.92 (d, J=5.52 Hz, 1H), 7.34-7.50 (m, 3H), 6.99-7.09 (m, 1H), 6.73 (br. s., 1H), 4.34 (s, 3H), 3.94-4.04 (m, 4H), 3.80-3.87 (m, 1H), 3.61-3.66 (m, 1H), 3.35-3.44 (m, 2H), 2.25-2.31 (m, 3H), 2.01 (d, J=13.55 Hz, 1H), 1.40-1.58 (m, 2H), 0.99 (d, J=15.06 Hz, 1H). Chiral SFC RT=4.95 min (Column: Whelk-01(R,R), 250×4.6 mm, 5 μm; Mobile Phase: 60/40 CO₂/(0.25% DEA in MeOH); Flow: 4 mL/min).

The title compound was synthesized using the procedure described for the synthesis of 10-chloro-5-(dimethyl-1H-1,2,3-triazol-5-yl)-8-[(S)-oxan-4-yl(phenyl)methyl]-3,8,11-triazatricyclo[7.4.0.0²,⁷]trideca-1(13),2(7),3,5,9,11-hexaene except using racemic (3-fluorophenyl)-(tetrahydro-2H-pyran-4-yl)methanol and separating final enantiomer using Chiral preparative SFC (Column: Whelk-01(R,R), 25×2.1 cm, 5 μm; Mobile Phase: 65/35 CO₂/(0.25% DEA in MeOH); Flow: 75 mL/min). For Enatiomer 2: LCMS: RT=1.91 min; MS (ES): m/z=487.2 [M+H]⁺ (Ascentis Express C8 (50×2.1 mm; 2.7 μm), ACN/H₂O with NH₄OAc, gradient=4 min, wavelength=220 nm); HPLC RT=10.155 min (Column: Sunfire C18 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). HPLC RT=9.123 min. (Column: XBridge Phenyl 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). ¹H NMR (400 MHz, CD₃OD) δ ppm 8.54-8.61 (m, 1H), 8.26 (br. s., 1H), 8.10 (d, J=5.52 Hz, 1H), 7.92 (d, J=5.52 Hz, 1H), 7.34-7.50 (m, 3H), 6.99-7.09 (m, 1H), 6.73 (br. s., 1H), 4.34 (s, 3H), 3.94-4.04 (m, 4H), 3.80-3.87 (m, 1H), 3.61-3.66 (m, 1H), 3.35-3.44 (m, 2H), 2.25-2.31 (m, 3H), 2.01 (d, J=13.55 Hz, 1H), 1.40-1.58 (m, 2H), 0.99 (d, J=15.06 Hz, 1H). Chiral SFC RT=5.76 min (Column: Whelk-01(R,R), 250×4.6 mm, 5 μm; Mobile Phase: 60/40 CO₂/(0.25% DEA in MeOH); Flow: 4 mL/min).

Example 22

8-[(2,3-Difluorophenyl)(oxan-4-yl)methyl]-5-(dimethyl-1H-1,2,3-triazol-5-yl)-10-methoxy-3,8,11-triazatricyclo[7.4.0.0²,⁷]trideca-1(13),2(7),3,5,9,11-hexaene Enantiomer 1

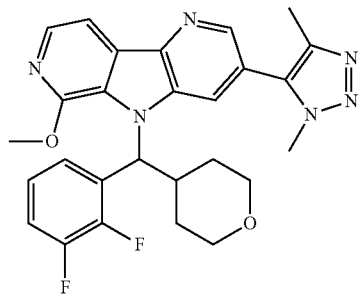 [SMILES: COc1nccc2c3ncc(-c4c(C)nnn4C)cc3n(C(c3cccc(F)c3F)C3CCOCC3)c12]

The title compound was synthesized using the procedure described for the synthesis of 10-chloro-5-(dimethyl-1H-1,2,3-triazol-5-yl)-8-[(S)-oxan-4-yl(phenyl)methyl]-3,8,11-triazatricyclo[7.4.0.0²,⁷]trideca-1(13),2(7),3,5,9,11-hexaene except using racemic (2,3-difluorophenyl)-(tetrahydro-2H-pyran-4-yl)methanol and separating final enantiomer using Chiral preparative SFC (Column: Chiral OD-H 25×2.1 cm, 5 μm; Mobile Phase: 65/35 CO₂/(0.25% DEA in MeOH); Flow: 70 mL/min). For Enatiomer 1: LCMS: RT=1.94 min; MS (ES): m/z=505.2 [M+H]⁺ (Ascentis Express C8 (50×2.1 mm; 2.7 μm), ACN/H₂O with NH₄OAc, gradient=4 min, wavelength=220 nm); HPLC RT=10.419 min (Column: Sunfire C18 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). HPLC RT=9.158 min. (Column: XBridge Phenyl 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). ¹H NMR (400 MHz, CD₃OD) δ ppm 8.55-8.62 (m, 1H), 8.18 (br. s., 1H), 8.08 (d, J=5.52 Hz, 1H), 7.82-7.95 (m, 2H), 7.21-7.37 (m, 2H), 6.94-7.08 (m, 1H), 4.30 (br. s., 3H), 3.80-4.05 (m, 5H), 3.54-3.66 (m, 1H), 3.35-3.44 (m, 2H), 2.26 (br. s., 3H), 1.93-2.03 (m, 1H), 1.59 (br. s., 2H), 0.97 (d, J=14.06 Hz, 1H). Chiral SFC RT=4.82 min (Column: Chiralcel OD-H 250×4.6 mm, 5 μm; Mobile Phase: 75/25 CO₂/(0.25% DEA in MeOH); Flow: 3 mL/min).

Example 23

8-[(2,3-Difluorophenyl)(oxan-4-yl)methyl]-5-(dimethyl-1H-1,2,3-triazol-5-yl)-10-methoxy-3,8,11-triazatricyclo[7.4.0.0²,⁷]trideca-1(13),2(7),3,5,9,11-hexaene Enantiomer 2

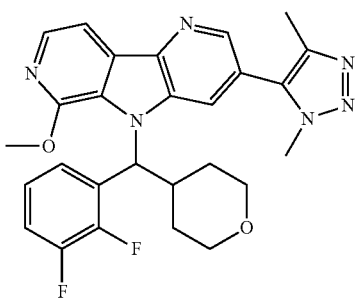 [SMILES: COc1nccc2c3ncc(-c4c(C)nnn4C)cc3n(C(c3cccc(F)c3F)C3CCOCC3)c12]

The title compound was synthesized using the procedure described for the synthesis of 10-chloro-5-(dimethyl-1H-1,2,3-triazol-5-yl)-8-[(S)-oxan-4-yl(phenyl)methyl]-3,8,11-triazatricyclo[7.4.0.0²,⁷]trideca-1(13),2(7),3,5,9,11-hexaene except using racemic (2,3-difluorophenyl)-(tetrahydro-2H-pyran-4-yl)methanol and separating final enantiomer using Chiral preparative SFC (Column: Chiral OD-H 25×2.1 cm, 5 μm; Mobile Phase: 65/35 CO₂/(0.25% DEA in MeOH); Flow: 70 mL/min). For Enatiomer 2: LCMS: RT=1.94 min; MS (ES): m/z=505.2 [M+H]⁺ (Ascentis Express C8 (50×2.1 mm; 2.7 μm), ACN/H₂O with NH₄OAc, gradient=4 min, wavelength=220 nm); HPLC RT=10.419 min (Column: Sunfire C18 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). HPLC RT=9.158 min. (Column: XBridge Phenyl 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). ¹H NMR (400 MHz, CD₃OD) δ ppm 8.55-8.62 (m, 1H), 8.18 (br. s., 1H), 8.08 (d, J=5.52 Hz, 1H), 7.82-7.95 (m, 2H), 7.21-7.37 (m, 2H), 6.94-7.08 (m, 1H), 4.30 (br. s., 3H), 3.80-4.05 (m, 5H), 3.54-3.66 (m, 1H), 3.35-3.44 (m, 2H), 2.26 (br. s., 3H), 1.93-2.03 (m, 1H), 1.59 (br. s., 2H), 0.97 (d, J=14.06 Hz, 1H). Chiral SFC RT=7.27 min (Column: Chiralcel OD-H 250×4.6 mm, 5 μm; Mobile Phase: 75/25 CO₂/(0.25% DEA in MeOH); Flow: 3 mL/min).

Example 24

5-(Dimethyl-1H-1,2,3-triazol-5-yl)-10-methoxy-8-[oxan-4-yl(2,4,6-trifluorophenyl)methyl]-3,8,11-triazatricyclo[7.4.0.0²,⁷]trideca-1(13),2(7),3,5,9,11-hexaene (Rac)

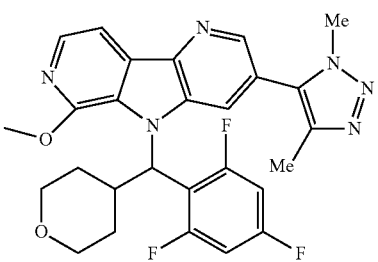 [SMILES: COc1nccc2c3ncc(-c4c(C)nnn4C)cc3n(C(c3c(F)cc(F)cc3F)C3CCOCC3)c12]

The title compound was synthesized using the procedure described for the synthesis of 10-chloro-5-(dimethyl-1H-1,2,3-triazol-5-yl)-8-[(S)-oxan-4-yl(phenyl)methyl]-3,8,11-triazatricyclo[7.4.0.0²,⁷]trideca-1(13),2(7),3,5,9,11-hexaene except starting with (6-methoxypyridin-3-yl)boronic acid and using racemic (tetrahydro-2H-pyran-4-yl)(2,4,6-trifluorophenyl)methanol (according to Scheme 1). LCMS: RT=1.935 min; MS (ES): m/z=523.2 [M+H]⁺ (Column: Ascentis Express C8 (50×2.1 mm; 2.7 μm), ACN/H₂O with NH₄OAc, gradient=4 min, wavelength=220 nm); HPLC RT=9.661 min (Column: Sunfire C18 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). HPLC RT=9.216 min. (Column: XBridge Phenyl 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). ¹H NMR (400 MHz, CD₃OD) δ 8.64 (d, J=1.51 Hz, 1H), 8.21 (br. s., 1H), 8.07 (d, J=5.52 Hz, 1H), 7.89 (d, J=5.52 Hz, 1H), 6.97 (t, J=9.04 Hz, 3H), 4.26 (br. s., 3H), 4.00-4.09 (m, 4H), 3.84 (d, J=9.04 Hz, 1H), 3.55 (dd, J=11.80, 9.79 Hz, 1H), 3.37 (br. s., 1H), 2.34 (s, 3H), 1.85 (br. s., 1H), 1.58 (br. s., 2H), 1.27 (d, J=6.02 Hz, 1H), 1.07 (br. s., 1H).

Example 25

8-[(2,4-Difluorophenyl)(oxan-4-yl)methyl]-5-(dimethyl-1H-1,2,3-triazol-5-yl)-10-methoxy-3,8,11-triazatricyclo[7.4.0.0²,⁷]trideca-1(13),2(7),3,5,9,11-hexaene (Rac)

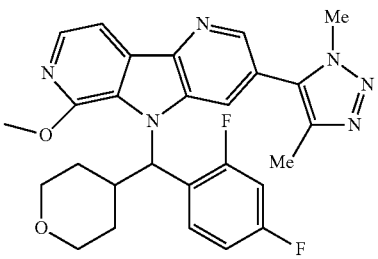 [SMILES: COc1nccc2c3ncc(-c4c(C)nnn4C)cc3n(C(c3ccc(F)cc3F)C3CCOCC3)c12]

The title compound was synthesized using the procedure described for the synthesis of 10-chloro-5-(dimethyl-1H-1,2,3-triazol-5-yl)-8-[(S)-oxan-4-yl(phenyl)methyl]-3,8,11-triazatricyclo[7.4.0.0²,⁷]trideca-1(13),2(7),3,5,9,11-hexaene except starting with (6-methoxypyridin-3-yl)boronic acid and using racemic (2,4-difluorophenyl)(tetrahydro-2H-pyran-4-yl)methanol (according to Scheme 1). LCMS: RT=1.941 min; MS (ES): m/z=505.2 [M+H]⁺ (Column: Ascentis Express C8 (50×2.1 mm; 2.7 μm), ACN/H₂O with NH₄OAc, gradient=4 min, wavelength=220 nm); HPLC RT=9.281 min (Column: Sunfire C18 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). HPLC RT=9.041 min. (Column: XBridge Phenyl 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). $^1$H NMR (400 MHz, CD₃OD) δ ppm 8.58 (s, 1H), 8.04-8.20 (m, 3H), 7.90 (d, J=5.52 Hz, 1H), 7.12 (t, J=7.28 Hz, 1H), 6.87-7.01 (m, 2H), 4.30 (br. s., 3H), 3.92-4.05 (m, 4H), 3.85 (d, J=9.04 Hz, 1H), 3.61 (t, J=11.80 Hz, 1H), 3.36-3.44 (m, 2H), 2.27 (br. s., 3H), 1.96 (br. s., 1H), 1.58 (br. s., 2H), 0.90-1.01 (m, 1H).

Example 26

8-[(2,5-Difluorophenyl)(oxan-4-yl)methyl]-5-(dimethyl-1H-1,2,3-triazol-5-yl)-10-methoxy-3,8,11-triazatricyclo[7.4.0.0²,⁷]trideca-1(13),2(7),3,5,9,11-hexaene (Rac)

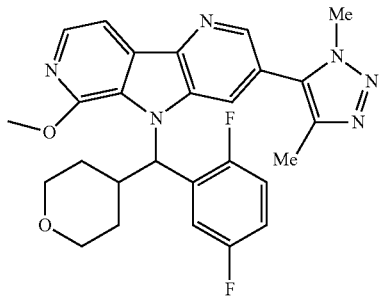 [SMILES: COc1nccc2c3ncc(-c4c(C)nnn4C)cc3n(C(c3cc(F)ccc3F)C3CCOCC3)c12]

The title compound was synthesized using the procedure described for the synthesis of 10-chloro-5-(dimethyl-1H-1,2,3-triazol-5-yl)-8-[(S)-oxan-4-yl(phenyl)methyl]-3,8,11-triazatricyclo[7.4.0.0²,⁷]trideca-1(13),2(7),3,5,9,11-hexaene except starting with (6-methoxypyridin-3-yl)boronic acid and using racemic (2,5-difluorophenyl)(tetrahydro-2H-pyran-4-yl)methanol (according to Scheme 1). LCMS: RT=1.924 min; MS (ES): m/z=505.2 [M+H]⁺ (Column: Ascentis Express C8 (50×2.1 mm; 2.7 μm), ACN/H₂O with NH₄OAc, gradient=4 min, wavelength=220 nm); HPLC RT=9.029 min (Column: Sunfire C18 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). HPLC RT=8.922 min. (Column: XBridge Phenyl 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). 1H NMR (400 MHz, CD₃OD) δ 8.59 (s, 1H), 8.25 (br. s., 1H), 8.08 (d, J=5.52 Hz, 1H), 7.87-7.99 (m, 2H), 6.90-7.18 (m, 3H), 4.30 (br. s., 3H), 3.94-4.06 (m, 4H), 3.82-3.91 (m, 1H), 3.62 (t, J=10.79 Hz, 1H), 3.35-3.45 (m, 2H), 2.22-2.34 (m, 3H), 1.92-2.01 (m, 1H), 1.47-1.68 (m, 2H), 1.00 (d, J=12.05 Hz, 1H).

Example 27

8-[(2,6-Difluorophenyl)(oxan-4-yl)methyl]-5-(dimethyl-1H-1,2,3-triazol-5-yl)-10-methoxy-3,8,11-triazatricyclo[7.4.0.0²,⁷]trideca-1(13),2(7),3,5,9,11-hexaene (Rac)

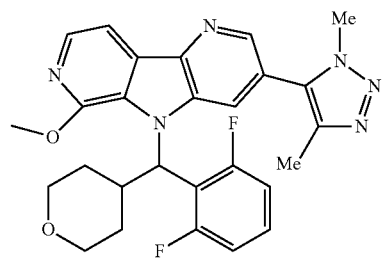 [SMILES: COc1nccc2c3ncc(-c4c(C)nnn4C)cc3n(C(c3c(F)cccc3F)C3CCOCC3)c12]

The title compound was synthesized using the procedure described for the synthesis of 10-chloro-5-(dimethyl-1H-1,2,3-triazol-5-yl)-8-[(S)-oxan-4-yl(phenyl)methyl]-3,8,11-triazatricyclo[7.4.0.0²,⁷]trideca-1(13),2(7),3,5,9,11-hexaene except starting with (6-methoxypyridin-3-yl)boronic acid and using racemic (2,6-difluorophenyl)(tetrahydro-2H-pyran-4-yl)methanol (according to Scheme 1). LCMS: RT=1.915 min; MS (ES): m/z=505.2 [M+H]⁺ (Column: Ascentis Express C8 (50×2.1 mm; 2.7 μm), ACN/H₂O with NH₄OAc, gradient=4 min, wavelength=220 nm); HPLC RT=8.953 min (Column: Sunfire C18 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). HPLC RT=8.792 min. (Column: XBridge Phenyl 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). 1H NMR (400 MHz, CD₃OD) δ 8.63 (d, J=2.01 Hz, 1H), 8.25 (br. s., 1H), 8.08 (d, J=5.52 Hz, 1H), 7.90 (d, J=5.52 Hz, 1H), 7.35-7.48 (m, 1H), 7.05 (dd, J=10.04, 8.53 Hz, 2H), 4.28 (s, 3H), 4.05 (s, 4H), 3.80-3.91 (m, 1H), 3.49-3.63 (m, 1H), 3.38 (d, J=2.51 Hz, 2H), 2.33 (s, 3H), 1.85-1.98 (m, 1H), 1.57 (d, J=9.04 Hz, 2H), 1.05 (d, J=13.05 Hz, 1H).

Example 28

5-(Dimethyl-1H-1,2,3-triazol-5-yl)-8-[(2-fluorophenyl)(oxan-4-yl)methyl]-11-methoxy-3,8,10-triazatricyclo[7.4.0.0²,⁷]trideca-1(13),2(7),3,5,9,11-hexaene (Rac)

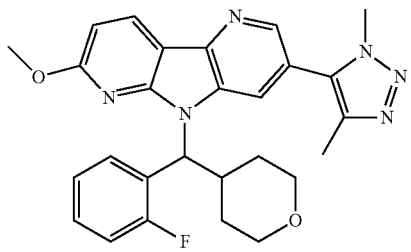 [SMILES: COc1ccc2c3ncc(-c4c(C)nnn4C)cc3n(C(c3ccccc3F)C3CCOCC3)c2n1]

The title compound was synthesized using the procedure described for the synthesis of 10-chloro-5-(dimethyl-1H-1,2,3-triazol-5-yl)-8-[(S)-oxan-4-yl(phenyl)methyl]-3,8,11-triazatricyclo[7.4.0.0²,⁷]trideca-1(13),2(7),3,5,9,11-hexaene except starting with (6-methoxypyridin-3-yl)boronic acid and using racemic (2-fluorophenyl)(tetrahydro-2H-pyran-4-yl)methanol (according to Scheme 1). LCMS: RT=1.967 min; MS (ES): m/z=487.2 [M+H]⁺ (Column: Ascentis Express C8 (50×2.1 mm; 2.7 μm), ACN/H₂O with NH₄OAc, gradient=4 min, wavelength=220 nm); HPLC RT=8.983 min (Column: Sunfire C18 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). HPLC RT=9.053 min. (Column: XBridge Phenyl 3.5 μm, 4.6×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). ¹H NMR (400 MHz, CD₃OD) δ 8.51-8.47 (m, 2H), 8.30 (m, 1H), 8.19 (m, 1H), 7.31 (m, 1H), 7.24 (m, 1H), 7.06 (m, 1H), 6.81 (d, J=8.4 Hz, 1H), 6.08 (d, J=12.0 Hz, 1H), 4.17 (s, 3H), 4.04 (s, 3H), 3.97 (m, 1H), 3.74 (m, 1H), 3.85 (m, 1H), 3.57-3.32 (m, 2H), 2.35 (s, 3H), 1.75 (m, 1H), 1.59-1.40 (m, 2H), 1.19 (m, 1H).

Example 29

5-(Dimethyl-1H-1,2,3-triazol-5-yl)-10-fluoro-8-[(S)-(2-fluorophenyl)(oxan-4-yl)methyl]-3,8,11-triazatricyclo[7.4.0.0²,⁷]trideca-1(13),2(7),3,5,9,11-hexaene

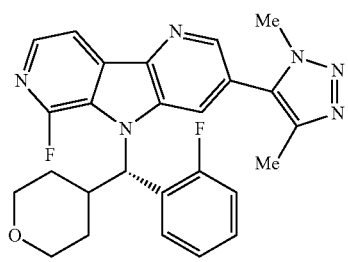 [SMILES: Cc1nnn(C)c1-c1cnc2c3ccnc(F)c3n([C@H](c3ccccc3F)C3CCOCC3)c2c1]

The title compound was synthesized using the procedure described for the synthesis of 10-chloro-5-(dimethyl-1H-1,2,3-triazol-5-yl)-8-[(S)-(2-fluorophenyl)(oxan-4-yl)methyl]-3,8,11-triazatricyclo[7.4.0.0²,⁷]trideca-1(13),2(7),3,5,9,11-hexaene except starting with (2-fluoropyridin-4-yl)boronic acid. LCMS: RT=1.59 min; (ES): m/z (M+H)⁺=475.3 (Waters Acquity SDS. Column: BEH C18 2.1×50 mm 1.7 u (1.6 min grad) 2-98% B. Flow Rate=0.8 mL/min. Solvent A: H₂O—0.1% TFA. Solvent B: ACN—0.1% TFA). ¹H NMR (500 MHz, DMSO-d₆) δ 8.72 (br. s., 1H), 8.43-8.26 (m, 2H), 8.19 (br. s., 1H), 8.10 (br. s., 1H), 7.43-7.28 (m, 2H), 7.12 (br. s., 1H), 6.20 (d, J=11.4 Hz, 1H), 3.91 (br. s., 3H), 3.76 (br. s., 2H), 3.57-3.37 (m, 2H), 3.26 (t, J=11.4 Hz, 1H), 2.22 (br. s., 3H), 1.83 (d, J=12.5 Hz, 1H), 1.39 (br. s., 2H), 1.00 (br. s., 1H).

Example 30

5-(Dimethyl-1H-1,2,3-triazol-5-yl)-8-[(S)-(2-fluorophenyl)(oxan-4-yl)methyl]-13-methoxy-3,8,12-triazatricyclo[7.4.0.0²,⁷]trideca-1(9),2(7),3,5,10,12-hexaene

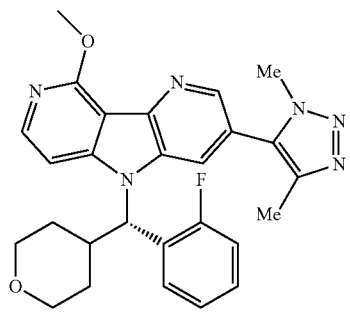 [SMILES: COc1nccc2c1c1ncc(-c3c(C)nnn3C)cc1n2[C@H](c1ccccc1F)C1CCOCC1]

The title compound was synthesized using the procedure described for the synthesis of 12-chloro-5-(dimethyl-1H-1,2,3-triazol-5-yl)-8-[(S)-(2-fluorophenyl)(oxan-4-yl)methyl]-3,8,11-triazatricyclo[7.4.0.0²,⁷]trideca-1(13),2(7),3,5,9,11-hexaene except starting with (2-methoxypyridin-3-yl)boronic acid. LCMS: RT=1.45 min; (ES): m/z (M+H)⁺=487.3 (Column: Waters Acquity UPLC BEH C18, 2.1×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75-min hold at 100% B; Flow: 1.11 mL/min.). ¹H NMR (500 MHz, DMSO-d6) δ 8.62 (br. s., 1H), 8.23 (t, J=7.1 Hz, 3H), 7.95 (s, 1H), 7.43-7.27 (m, 2H), 7.12 (t, J=9.3 Hz, 1H), 6.03 (d, J=11.1 Hz, 1H), 4.09 (s, 3H), 3.98 (br. s., 3H), 3.89 (d, J=11.8 Hz, 1H), 3.71 (d, J=9.4 Hz, 1H), 3.52-3.35 (m, 2H), 3.21 (t, J=11.4 Hz, 1H), 2.28 (br. s., 3H), 1.73 (d, J=13.5 Hz, 1H), 1.66-1.52 (m, 1H), 1.32 (d, J=12.5 Hz, 1H), 0.76 (d, J=12.5 Hz, 1H).

Example 31

5-(Dimethyl-1H-1,2,3-triazol-5-yl)-8-[(S)-(2-fluorophenyl)(oxan-4-yl)methyl]-10-(methylsulfanyl)-3,8,11-triazatricyclo[7.4.0.0²,⁷]trideca-1(13),2(7),3,5,9,11-hexaene

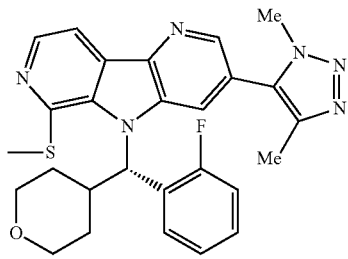 [SMILES: CSc1nccc2c3ncc(-c4c(C)nnn4C)cc3n([C@H](c3ccccc3F)C3CCOCC3)c12]

In a 2 dram vial was added a mixture of 10-chloro-5-(dimethyl-1H-1,2,3-triazol-5-yl)-8-[(S)-(2-fluorophenyl)(oxan-4-yl)methyl]-3,8,11-triazatricyclo[7.4.0.0²,⁷]trideca-1(13),2(7),3,5,9,11-hexaene (50 mg, 0.102 mmol) and sodium thiomethoxide (28.6 mg, 0.407 mmol) in DMSO (2 mL) and the vial was capped and heated in a heating block at 80° C. for 3 h. Mixture was diluted with methanol and purified via preparative LC/MS (Column: Waters XBridge C18, 19×200 mm, 5-μm particles; Mobile Phase A: 5:95 ACN: water with 10-mM NH₄OAc; Mobile Phase B: 95:5 ACN: water with 10-mM NH₄OAc; Gradient: 37-77% B over 20 min, then a 5-min hold at 100% B; Flow: 20 mL/min.) to give the title compound in 59% yield. LCMS: RT=1.847 min; (ES): m/z (M+H)⁺=503.10: (Column: Waters Acquity UPLC BEH C18, 2.1×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75-min hold at 100% B; Flow: 1.11 mL/min.). ¹H NMR (500 MHz, DMSO-d6) δ 8.61 (s, 1H), 8.46 (d, J=5.0 Hz, 1H), 8.21 (t, J=6.6 Hz, 1H), 8.10 (s, 1H), 8.00 (d, J=5.0 Hz, 1H), 7.40-7.28 (m, 2H), 7.11-7.02 (m, 1H), 6.90 (d, J=11.3 Hz, 1H), 3.96-3.88 (m, 1H), 3.82 (s, 3H), 3.77 (d, J=9.0 Hz, 1H), 3.63-3.46 (m, 2H), 3.25 (t, J=11.4 Hz, 1H), 2.81 (s, 3H), 2.14 (s, 3H), 1.88 (d, J=12.6 Hz, 1H), 1.79-1.67 (m, 1H), 1.58-1.45 (m, 1H), 0.79 (d, J=11.8 Hz, 1H).

Example 32

5-(Dimethyl-1H-1,2,3-triazol-5-yl)-8-[(S)-(2-fluorophenyl)(oxan-4-yl)methyl]-12-methanesulfonyl-3,8,11-triazatricyclo[7.4.0.0²,⁷]trideca-1(13),2(7),3,5,9,11-hexaene

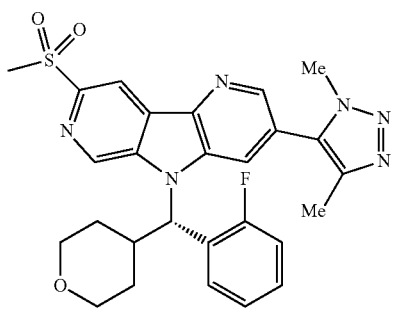 [SMILES: Cc1nnn(C)c1-c1cnc2c3cc(S(C)(=O)=O)ncc3n([C@H](c3ccccc3F)C3CCOCC3)c2c1]

In a 2 dram vial was added a mixture of 12-chloro-5-(dimethyl-1H-1,2,3-triazol-5-yl)-8-[(S)-(2-fluorophenyl)(oxan-4-yl)methyl]-3,8,11-triazatricyclo[7.4.0.0²,⁷]trideca-1(13),2(7),3,5,9,11-hexaene (40 mg, 0.081 mmol), sodium methanesulfinate (41.6 mg, 0.407 mmol), copper(I) iodide (7.76 mg, 0.041 mmol), proline (9.38 mg, 0.081 mmol) and Cs₂CO₃ (26.5 mg, 0.081 mmol) in DMSO (1 mL) and the vial was capped and heated in a heating block at 95° C. for 7 days. Mixture was diluted with methanol and purified via preparative LC/MS (Column: Waters XBridge C18, 19×200 mm, 5-μm particles; Mobile Phase A: 5:95 ACN: water with 10-mM NH₄OAc; Mobile Phase B: 95:5 ACN: water with 10-mM NH₄OAc; Gradient: 37-77% B over 20 min, then a 5-min hold at 100% B; Flow: 20 mL/min.) to give the title compound (18 mg, 0.033 mmol, 53% yield). LCMS: RT=1.324 min; (ES): m/z (M+H)⁺=535.0 (Column: Waters Acquity UPLC BEH C18, 2.1×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75-min hold at 100% B; Flow: 1.11 mL/min.). ¹H NMR (500 MHz, DMSO-d6) δ 8.84 (m., 2H), 8.79-8.70 (m, 2H), 8.36 (br. s., 1H), 7.44-7.31 (m, 2H), 7.21-7.07 (m, 1H), 6.31 (d, J=11.1 Hz, 1H), 4.05 (br. s., 3H), 3.92 (d, J=12.1 Hz, 1H), 3.72 (d, J=8.8 Hz, 1H), 3.47 (br. s., 2H), 3.34 (s, 3H), 3.24 (t, J=11.3 Hz, 1H), 2.33 (br. s., 3H), 1.78 (d, J=12.5 Hz, 1H), 1.65 (d, J=10.1 Hz, 1H), 1.40 (br. s., 1H), 0.81 (d, J=12.5 Hz, 1H).

Example 33

5-(Dimethyl-1H-1,2,3-triazol-5-yl)-13-methanesulfonyl-8-[(S)-oxan-4-yl(phenyl)methyl]-3,8,12-triazatricyclo[7.4.0.0²,⁷]trideca-1(13),2(7),3,5,9,11-hexaene

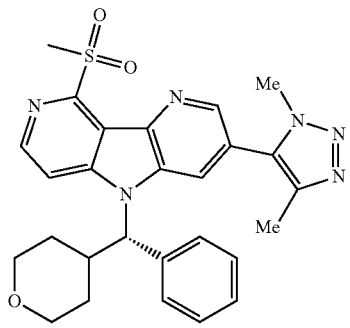 [SMILES: Cc1nnn(C)c1-c1cnc2c3c(S(C)(=O)=O)nccc3n([C@H](c3ccccc3)C3CCOCC3)c2c1]

The title compound was synthesized using the procedure described for the synthesis of 10-chloro-5-(dimethyl-1H-1,2,3-triazol-5-yl)-13-methanesulfonyl-8-[(S)-oxan-4-yl(phenyl)methyl]-3,8,12-triazatricyclo[7.4.0.0²,⁷]trideca-1(13),2(7),3,5,9,11-hexaene. LCMS: RT=1.366 min; (ES): m/z (M+H)⁺=517.15 (Column: Waters Acquity UPLC BEH C18, 2.1×50 mm, 1.7-μm particles; Mobile Phase A: 5:95 ACN: water with 10 mM NH₄OAc; Mobile Phase B: 95:5 ACN: water with 10 mM NH₄OAc; Temperature: 50° C.; Gradient: 0-100% B over 3 min, then a 0.75-min hold at 100% B; Flow: 1.11 mL/min.). ¹H NMR (500 MHz, DMSO-d6) δ 8.84 (s, 1H), 8.75 (br. s., 1H), 8.60 (br. s., 1H), 7.95 (s, 1H), 7.70 (d, J=7.7 Hz, 2H), 7.39-7.33 (m, 2H), 7.32-7.25 (m, 1H), 6.03 (d, J=11.4 Hz, 1H), 4.03 (br. s., 3H), 3.94-3.87 (m, 1H), 3.76-3.68 (m, 4H), 3.55-3.42 (m, 2H), 3.27 (t, J=11.4

Hz, 1H), 2.31 (br. s., 3H), 1.74 (d, J=12.8 Hz, 1H), 1.63-1.53 (m, 1H), 1.32 (m, 1H), 0.94 (d, J=12.5 Hz, 1H).

Example 34

10-Chloro-5-(dimethyl-1H-1,2,3-triazol-5-yl)-8-[(S)-oxan-4-yl(phenyl)methyl]-3,8,12-triazatricyclo[7.4.0.0²,⁷]trideca-1(13),2(7),3,5,9,11-hexaene

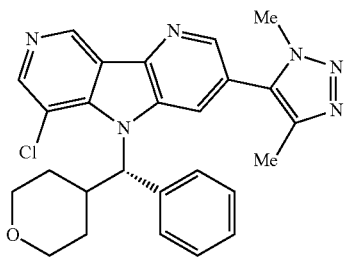 [SMILES: Cc1nnn(C)c1-c1cnc2c3cncc(Cl)c3n([C@H](c3ccccc3)C3CCOCC3)c2c1]

The title compound was synthesized using the procedure described for the synthesis of 10-chloro-5-(dimethyl-1H-1,2,3-triazol-5-yl)-13-fluoro-8-[(S)-oxan-4-yl(phenyl)methyl]-3,8,12-triazatricyclo[7.4.0.0²,⁷]trideca-1(13),2(7),3,5,9,11-hexaene. LCMS: RT=2.05 min; (ES): m/z (M+H)⁺= 473.3 (Column: Waters Acquity UPLC BEH C18, 2.1×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75-min hold at 100% B; Flow: 1.11 mL/min. ¹H NMR (500 MHz, DMSO-d₆) δ 8.78 (d, J=2.0 Hz, 1H), 8.74 (d, J=2.0 Hz, 1H), 8.66 (s, 1H), 8.62 (br. s., 1H), 7.79 (d, J=7.4 Hz, 2H), 7.35-7.28 (m, 2H), 7.27-7.21 (m, 1H), 5.91 (br. s., 1H), 4.03 (s, 3H), 3.87 (d, J=10.8 Hz, 1H), 3.74 (d, J=10.4 Hz, 1H), 3.54-3.36 (m, 2H), 3.25 (t, J=11.3 Hz, 1H), 2.31 (s, 3H), 1.52 (d, J=10.1 Hz, 1H), 1.45-1.33 (m, 1H), 1.32-1.19 (m, 1H), 1.11 (d, J=12.1 Hz, 1H).

Example 35

5-(Dimethyl-1H-1,2,3-triazol-5-yl)-8-[(S)-oxan-4-yl(phenyl)methyl]-3,8,12-triazatricyclo[7.4.0.0²,⁷]trideca-1(13),2(7),3,5,9,11-hexaene

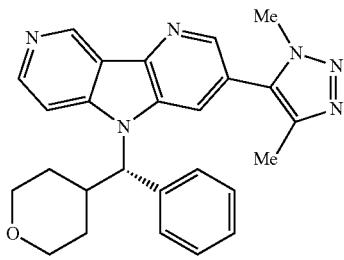 [SMILES: Cc1nnn(C)c1-c1cnc2c3cnccc3n([C@H](c3ccccc3)C3CCOCC3)c2c1]

The title compound was synthesized using the procedure described for the synthesis of 5-(dimethyl-1H-1,2,3-triazol-5-yl)-13-fluoro-8-[(S)-oxan-4-yl(phenyl)methyl]-3,8,12-triazatricyclo[7.4.0.0²,⁷]trideca-1(13),2(7),3,5,9,11-hexaene. LCMS: RT=1.71 min; (ES): m/z (M+H)⁺=439.3 (Column: Waters Acquity UPLC BEH C18, 2.1×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75-min hold at 100% B; Flow: 1.11 mL/min. ¹H NMR (500 MHz, DMSO-d₆) δ 8.76 (d, J=3.7 Hz, 1H), 8.66 (d, J=7.1 Hz, 1H), 8.62 (s, 1H), 8.57 (br. s., 1H), 7.81 (d, J=7.4 Hz, 2H), 7.45 (dd, J=7.6, 4.9 Hz, 1H), 7.34-7.28 (m, 2H), 7.27-7.20 (m, 1H), 5.96 (br. s., 1H), 4.03 (s, 3H), 3.88 (d, J=9.4 Hz, 1H), 3.74 (d, J=11.4 Hz, 1H), 3.57-3.35 (m, 2H), 3.26 (t, J=11.3 Hz, 1H), 2.31 (s, 3H), 1.54 (dd, J=11.1, 2.4 Hz, 1H), 1.46-1.35 (m, 1H), 1.32-1.20 (m, 1H), 1.11 (d, J=11.8 Hz, 1H).

Example 36

10,13-Dichloro-5-(dimethyl-1H-1,2,3-triazol-5-yl)-8-[(S)-oxan-4-yl(phenyl)methyl]-3,8,12-triazatricyclo[7.4.0.0²,⁷]trideca-1(13),2(7),3,5,9,11-hexaene

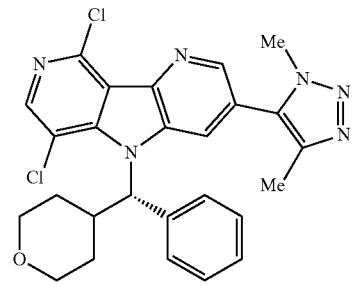 [SMILES: Cc1nnn(C)c1-c1cnc2c3c(Cl)ncc(Cl)c3n([C@H](c3ccccc3)C3CCOCC3)c2c1]

The title compound was synthesized using the procedure described for the synthesis of 12-chloro-5-(dimethyl-1H-1,2,3-triazol-5-yl)-8-[(S)-(2-fluorophenyl)(oxan-4-yl)methyl]-3,8,11-triazatricyclo[7.4.0.0²,⁷]trideca-1(13),2(7),3,5,9,11-hexaene except starting with (2,5-dichloropyridin-3-yl)boronic acid. LCMS: RT=1.85 min; (ES): m/z (M+H)⁺= 507.3.: Column: Waters Acquity UPLC BEH C18, 2.1×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75-min hold at 100% B; Flow: 1.11 mL/min. ¹H NMR (500 MHz, DMSO-d₆) δ 8.58 (bs, 1H), 8.40 (s, 1H), 8.04 (bs, 1H), 7.46 (d, J=7.7 Hz, 2H), 7.23-7.15 (m, 2H), 7.13-7.07 (m, J=7.4 Hz, 1H), 6.68 (d, J=11.1 Hz, 1H), 3.74-3.68 (m, 1H), 3.66 (s, 3H), 3.53 (d, J=8.8 Hz, 1H), 3.38-3.26 (m, 2H), 3.04 (t, J=11.3 Hz, 1H), 1.96 (s, 3H), 1.72 (d, J=12.8 Hz, 1H), 1.30-1.11 (m, 2H), 0.67 (d, J=12.5 Hz, 1H).

Example 37

10-Chloro-5-(dimethyl-1H-1,2,3-triazol-5-yl)-13-fluoro-8-[(S)-oxan-4-yl(phenyl)methyl]-3,8,12-triazatricyclo[7.4.0.0²,⁷]trideca-1(13),2(7),3,5,9,11-hexaene

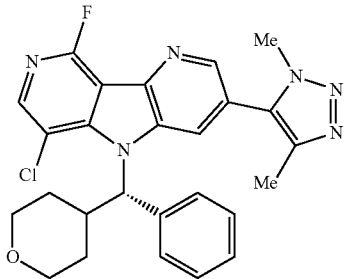 [SMILES: Cc1nnn(C)c1-c1cnc2c3c(F)ncc(Cl)c3n([C@H](c3ccccc3)C3CCOCC3)c2c1]

The title compound was synthesized using the procedure described for the synthesis of 12-chloro-5-(dimethyl-1H-1,2,3-triazol-5-yl)-8-[(S)-(2-fluorophenyl)(oxan-4-yl)methyl]-3,8,11-triazatricyclo[7.4.0.0²,⁷]trideca-1(13),2(7),3,5,9,11-hexaene except starting with (5-chloro-2-fluoropyridin-3-yl)boronic acid. LCMS: RT=1.78 min; (ES): m/z (M+H)⁺=491.3 (Column: Waters Acquity UPLC BEH C18, 2.1×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75-min hold at 100% B; Flow: 1.11 mL/min. ¹H NMR (500 MHz, DMSO-d₆) δ 8.49 (s, 1H), 8.18 (s, 1H), 8.02 (s, 1H), 7.44 (d, J=7.7 Hz, 2H), 7.20-7.10 (m, 2H), 7.10-7.02 (m, 1H), 6.63 (d, J=11.1 Hz, 1H), 3.66 (d, J=9.8 Hz, 1H), 3.62 (s, 3H), 3.50 (d, J=10.4 Hz, 1H), 3.36-3.22 (m, 2H), 3.00 (t, J=11.3 Hz, 1H), 1.92 (s, 3H), 1.67 (d, J=12.8 Hz, 1H), 1.27-1.06 (m, 2H), 0.65 (d, J=11.8 Hz, 1H).

Example 38

10-Bromo-5-(dimethyl-1H-1,2,3-triazol-5-yl)-13-methoxy-8-[(S)-oxan-4-yl(phenyl)methyl]-3,8,12-triazatricyclo[7.4.0.0²,⁷]trideca-1(13),2(7),3,5,9,11-hexaene

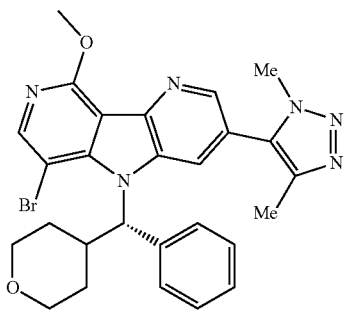 [SMILES: COc1ncc(Br)c2c1c1ncc(-c3c(C)nnn3C)cc1n2[C@H](c1ccccc1)C1CCOCC1]

The title compound was synthesized using the procedure described for the synthesis of 12-chloro-5-(dimethyl-1H-1,2,3-triazol-5-yl)-8-[(S)-(2-fluorophenyl)(oxan-4-yl)methyl]-3,8,11-triazatricyclo[7.4.0.0²,⁷]trideca-1(13),2(7),3,5,9,11-hexaene except starting with (5-bromo-2-methoxypyridin-3-yl)boronic acid. LCMS: RT=1.82 min; (ES): m/z (M+H)⁺=547.3 (Column: Waters Acquity UPLC BEH C18, 2.1×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75-min hold at 100% B; Flow: 1.11 mL/min. ¹H NMR (500 MHz, DMSO-d₆) δ 8.42 (s, 1H), 8.22 (s, 1H), 7.90 (s, 1H), 7.41 (d, J=7.7 Hz, 2H), 7.15 (t, J=7.6 Hz, 2H), 7.09-7.04 (m, J=7.1 Hz, 1H), 6.86 (d, J=11.1 Hz, 1H), 3.89 (s, 3H), 3.72-3.65 (m, 1H), 3.61 (s, 3H), 3.30 (m, 2H), 3.51 (d, J=11.4 Hz, 1H), 3.06-2.97 (m, 1H), 1.93 (s, 3H), 1.71 (d, J=11.8 Hz, 1H), 1.30-1.13 (m, 2H), 0.58 (d, J=12.1 Hz, 1H).

Example 39

10-Chloro-5-(dimethyl-1H-1,2,3-triazol-5-yl)-13-methoxy-8-[(S)-oxan-4-yl(phenyl)methyl]-3,8,11-triazatricyclo[7.4.0.0²,⁷]trideca-1(13),2(7),3,5,9,11-hexaene

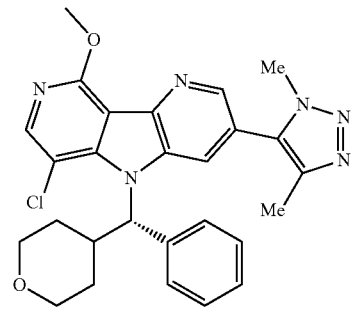 [SMILES: COc1ncc(Cl)c2c1c1ncc(-c3c(C)nnn3C)cc1n2[C@H](c1ccccc1)C1CCOCC1]

The title compound was synthesized using the procedure described for the synthesis of 12-chloro-5-(dimethyl-1H-1,2,3-triazol-5-yl)-8-[(S)-(2-fluorophenyl)(oxan-4-yl)methyl]-3,8,11-triazatricyclo[7.4.0.0²,⁷]trideca-1(13),2(7),3,5,9,11-hexaene except starting with (2-chloro-5-methoxypyridin-3-yl)boronic acid. LCMS: RT=1.62 min; (ES): m/z (M+H)⁺=503.3 (Column: Waters Acquity UPLC BEH C18, 2.1×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75-min hold at 100% B; Flow: 1.11 mL/min. ¹H NMR (500 MHz, DMSO-d₆) δ 8.42 (s, 1H), 7.95 (s, 1H), 7.89 (s, 1H), 7.38 (d, J=7.7 Hz, 2H), 7.18-7.07 (m, 2H), 7.06-6.98 (m, 1H), 6.71 (d, J=10.8 Hz, 1H), 3.89 (s, 3H), 3.71-3.63 (m, 1H), 3.61 (s, 3H), 3.45-3.34 (m, 1H), 3.30-3.20 (m, J=11.4 Hz, 1H), 3.00 (t, J=11.4 Hz, 1H), 1.92 (s, 3H), 1.68 (d, J=12.1 Hz, 1H), 1.27-1.10 (m, 2H), 0.58 (d, J=11.8 Hz, 1H).

Example 40

10-Chloro-5-(dimethyl-1H-1,2,3-triazol-5-yl)-13-methoxy-8-[(S)-oxan-4-yl(phenyl)methyl]-3,8,12-triazatricyclo[7.4.0.0²,⁷]trideca-1(13),2(7),3,5,9,11-hexaene

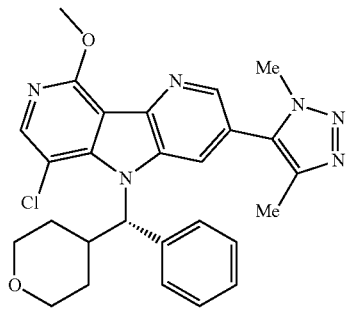 [SMILES: COc1ncc(Cl)c2c1c1ncc(-c3c(C)nnn3C)cc1n2[C@H](c1ccccc1)C1CCOCC1]

The title compound was synthesized using the procedure described for the synthesis of 12-chloro-5-(dimethyl-1H-1,2,3-triazol-5-yl)-8-[(S)-(2-fluorophenyl)(oxan-4-yl)methyl]-3,8,11-triazatricyclo[7.4.0.0²,⁷]trideca-1(13),2(7),3,5,9,11-hexaene except starting with (5-chloro-2-methoxypyridin-3-yl)boronic acid. LCMS: RT=1.85 min; (ES): m/z (M+H)⁺=503.2 (Column: Waters Acquity UPLC BEH C18, 2.1×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75-min hold at 100% B; Flow: 1.11 mL/min. ¹H NMR (500 MHz, DMSO-d₆) δ 8.67 (br. s., 1H), 8.35 (s, 1H), 8.18 (s, 1H), 7.67 (d, J=7.4 Hz, 2H), 7.38 (t, J=7.6 Hz, 2H), 7.32-7.24 (m, 1H), 6.87 (d, J=11.1 Hz, 1H), 4.13 (s, 3H), 3.94-3.83 (m, 4H), 3.75 (d, J=8.8 Hz, 1H), 3.52 (d, J=11.8 Hz, 1H), 3.46-3.33 (m, 1H), 3.25 (t, J=11.4 Hz, 1H), 2.18 (s, 3H), 1.92 (d, J=13.1 Hz, 1H), 1.51-1.32 (m, 2H), 0.86 (d, J=13.1 Hz, 1H).

Example 41

10-Chloro-5-(dimethyl-1H-1,2,3-triazol-5-yl)-N,N-dimethyl-8-[(S)-oxan-4-yl(phenyl)methyl]-3,8,12-triazatricyclo[7.4.0.0²,⁷]trideca-1(13),2(7),3,5,9,11-hexaen-13-amine

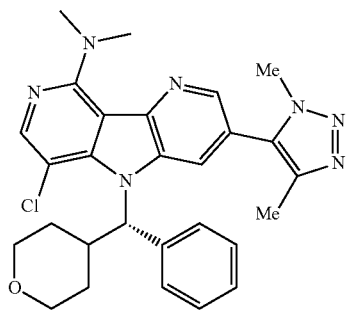 [SMILES: Cc1nnn(C)c1-c1cnc2c3c(N(C)C)ncc(Cl)c3n([C@H](c3ccccc3)C3CCOCC3)c2c1]

In a 2 dram vial was added a solution of 10-chloro-5-(dimethyl-1H-1,2,3-triazol-5-yl)-13-fluoro-8-[(S)-oxan-4-yl(phenyl)methyl]-3,8,12-triazatricyclo[7.4.0.0²,⁷]trideca-1(13),2(7),3,5,9,11-hexaene (20 mg, 0.041 mmol) in a 2 M solution of dimethylamine in THF (1 ml, 2.00 mmol) and the solution was stirred at room temperature for 2 h. Diluted with methanol and purified via preparative LC/MS (Column: Waters XBridge C18, 19×200 mm, 5-μm particles; Mobile Phase A: 5:95 ACN: water with 10-mM NH₄OAc; Mobile Phase B: 95:5 ACN: water with 10-mM NH₄OAc; Gradient: 37-77% B over 20 min, then a 5-min hold at 100% B; Flow: 20 mL/min.) to give the title compound (14.5 mg, 0.028 mmol, 69.0% yield). LCMS: RT=2.04 min; (ES): m/z (M+H)⁺=516. (Column: Waters Acquity UPLC BEH C18, 2.1×50 mm, 1.7-μm particles; Mobile Phase A: 5:95 ACN: water with 10 mM NH₄OAc; Mobile Phase B: 95:5 ACN: water with 10 mM NH₄OAc; Temperature: 50° C.; Gradient: 0-100% B over 3 min, then a 0.75-min hold at 100% B; Flow: 1.11 mL/min.). ¹H NMR (500 MHz, DMSO-d6) δ 8.63 (s, 1H), 8.27 (s, 1H), 8.07 (s, 1H), 7.64 (d, J=7.4 Hz, 2H), 7.37 (t, J=7.6 Hz, 2H), 7.31-7.23 (m, 1H), 6.93 (d, J=11.1 Hz, 1H), 3.88 (d, J=8.8 Hz, 1H), 3.84 (s, 3H), 3.74 (d, J=10.4 Hz, 1H), 3.62-3.45 (m, 2H), 3.30-3.23 (m, 1H), 3.21 (s, 6H), 2.15 (s, 3H), 1.92 (d, J=12.1 Hz, 1H), 1.50-1.33 (m, 2H), 0.84 (d, J=12.8 Hz, 1H).

Example 42

10-Chloro-5-(dimethyl-1H-1,2,3-triazol-5-yl)-13-methanesulfonyl-8-[(S)-oxan-4-yl(phenyl)methyl]-3,8,12-triazatricyclo[7.4.0.0²,⁷]trideca-1(13),2(7),3,5,9,11-hexaene

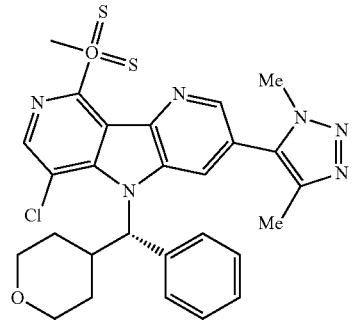

In a 2 dram vial was added a solution of 10-chloro-5-(dimethyl-1H-1,2,3-triazol-5-yl)-13-fluoro-8-[(S)-oxan-4-yl(phenyl)methyl]-3,8,12-triazatricyclo[7.4.0.0²,⁷]trideca-1(13),2(7),3,5,9,11-hexaene (20 mg, 0.041 mmol) and sodium methanesulfinate (20.79 mg, 0.204 mmol) in DMSO (1 mL) and the solution was heated in heating block at 75° C. overnight. Additional sodium methanesulfinate was added (20.79 mg, 0.204 mmol) and heated at 95° C. for an additional 4 h. Diluted with methanol and purified via preparative LC/MS (Column: Waters XBridge C18, 19×200 mm, 5-μm particles; Mobile Phase A: 5:95 ACN: water with 10-mM NH₄OAc; Mobile Phase B: 95:5 ACN: water with 10-mM NH₄OAc; Gradient: 37-77% B over 20 min, then a 5-min hold at 100% B; Flow: 20 mL/min.) to give the title compound (6.9 mg, 0.012 mmol, 30% yield). LCMS: RT=1.61 min; (ES): m/z (M+H)⁺=551.0 (Column: Waters Acquity UPLC BEH C18, 2.1×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75-min hold at 100% B; Flow: 1.11 mL/min.). ¹H NMR (500 MHz, DMSO-d6) δ 8.90 (s, 1H), 8.85 (s, 1H), 8.29 (s, 1H), 7.67 (d, J=7.4 Hz, 2H), 7.43-7.35 (m, 2H), 7.34-7.28 (m, 1H), 7.01 (d, J=11.1 Hz, 1H), 3.91 (d, J=11.8 Hz, 1H), 3.87 (s, 3H), 3.74 (d, J=9.1 Hz, 1H), 3.70 (s, 3H), 3.61-3.46 (m, 2H), 3.25 (t, J=11.4 Hz, 1H), 2.16 (s, 3H), 1.95 (d, J=12.5 Hz, 1H), 1.54-1.33 (m, 2H), 0.86 (d, J=12.5 Hz, 1H).

Example 43

10-Chloro-5-(dimethyl-1H-1,2,3-triazol-5-yl)-13-ethoxy-8-[(S)-oxan-4-yl(phenyl)methyl]-3,8,12-triazatricyclo[7.4.0.0$^{2,7}$]trideca-1(13),2(7),3,5,9,11-hexaene

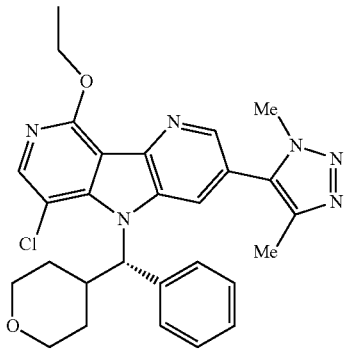 [SMILES: CCOc1ncc(Cl)c2c1c1ncc(-c3c(C)nnn3C)cc1n2[C@H](c1ccccc1)C1CCOCC1]

In a 2 dram vial was added a solution of 10-chloro-5-(dimethyl-1H-1,2,3-triazol-5-yl)-13-fluoro-8-[(S)-oxan-4-yl(phenyl)methyl]-3,8,12-triazatricyclo[7.4.0.0$^{2,7}$]trideca-1(13),2(7),3,5,9,11-hexaene (30 mg, 0.061 mmol) and KOtBu (41.1 mg, 0.367 mmol) in ethanol (1 ml, 17.1 mmol) and the resulting solution stirred at room temperature overnight. Mixture was quenched with 1N HCl and diluted with methanol and purified via preparative LC/MS (Column: Waters XBridge C18, 19×200 mm, 5-µm particles; Mobile Phase A: 5:95 ACN: water with 10-mM NH$_4$OAc; Mobile Phase B: 95:5 ACN: water with 10-mM NH$_4$OAc; Gradient: 37-77% B over 20 min, then a 5-min hold at 100% B; Flow: 20 mL/min.) to give the title compound (5.8 mg, 0.010 mmol, 16% yield). LCMS: RT=2.02 min; (ES): m/z (M+H)$^+$=517.0 (Column: Waters Acquity UPLC BEH C18, 2.1×50 mm, 1.7-µm particles; Mobile Phase A: 5:95 ACN: water with 10 mM NH$_4$OAc; Mobile Phase B: 95:5 ACN: water with 10 mM NH$_4$OAc; Temperature: 50° C.; Gradient: 0-100% B over 3 min, then a 0.75-min hold at 100% B; Flow: 1.11 mL/min.). $^1$H NMR (500 MHz, DMSO-d6) δ 8.65 (s, 1H), 8.31 (s, 1H), 8.13 (s, 1H), 7.64 (d, J=7.7 Hz, 2H), 7.42-7.33 (m, 2H), 7.32-7.24 (m, 1H), 6.86 (d, J=11.1 Hz, 1H), 4.61 (q, J=6.5 Hz, 2H), 3.89 (d, J=7.4 Hz, 1H), 3.85 (s, 3H), 3.74 (d, J=9.8 Hz, 1H), 3.65-3.45 (m, 2H), 3.30-3.18 (m, 1H), 2.16 (s, 3H), 1.91 (d, J=13.1 Hz, 1H), 1.49-1.35 (m, 5H), 0.85 (d, J=10.8 Hz, 1H).

Example 44

10-Chloro-N-(cyclopropylmethyl)-5-(dimethyl-1H-1,2,3-triazol-5-yl)-8-[(S)-oxan-4-yl(phenyl)methyl]-3,8,12-triazatricyclo[7.4.0.0$^{2,7}$]trideca-1(13),2(7),3,5,9,11-hexaen-13-amine

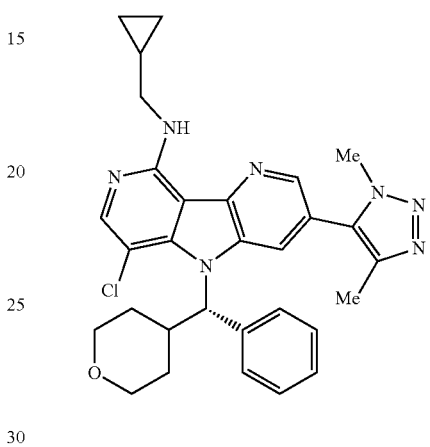

In a 2 dram vial was added a solution of 10-chloro-5-(dimethyl-1H-1,2,3-triazol-5-yl)-13-fluoro-8-[(S)-oxan-4-yl(phenyl)methyl]-3,8,12-triazatricyclo[7.4.0.0$^{2,7}$]trideca-1(13),2(7),3,5,9,11-hexaene (30 mg, 0.061 mmol) and cyclopropylamine (44 mg, 0.631 mmol) in DMSO (1 ml) and the resulting solution stirred at room temperature overnight. Mixture was diluted with methanol and purified via preparative LC/MS (Column: Waters XBridge C18, 19×200 mm, 5-µm particles; Mobile Phase A: 5:95 ACN: water with 10-mM NH$_4$OAc; Mobile Phase B: 95:5 ACN: water with 10-mM NH$_4$OAc; Gradient: 37-77% B over 20 min, then a 5-min hold at 100% B; Flow: 20 mL/min.) to give the title compound (18 mg, 0.033 mmol, 53% yield). LCMS: RT=2.37 min; (ES): m/z (M+H)$^+$=542.1 (Column: Waters Acquity UPLC BEH C18, 2.1×50 mm, 1.7-µm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75-min hold at 100% B; Flow: 1.11 mL/min.). $^1$H NMR (500 MHz, DMSO-d6) δ 8.60 (bs, 1H), 8.15 (bs, 1H), 8.13 (bs, 1H), 7.65 (d, J=7.7 Hz, 2H), 7.44 (t, J=5.6 Hz, 1H), 7.37 (t, J=7.6 Hz, 2H), 7.32-7.22 (m, 1H), 6.73 (d, J=11.1 Hz, 1H), 3.92-3.83 (m, 4H), 3.75 (d, J=9.4 Hz, 1H), 3.62 (d, J=14.1 Hz, 2H), 3.55-3.40 (m, 2H), 3.25 (t, J=11.6 Hz, 1H), 2.16 (s, 3H), 1.87 (d, J=12.1 Hz, 1H), 1.46-1.32 (m, 2H), 1.23-1.13 (m, 1H), 0.91 (d, J=12.1 Hz, 1H), 0.48 (d, J=7.1 Hz, 2H), 0.30 (d, J=4.0 Hz, 2H).

Example 45

5-(Dimethyl-1,2-oxazol-4-yl)-10-methanesulfonyl-13-methoxy-8-[(S)-oxan-4-yl(phenyl)methyl]-3,8,12-triazatricyclo[7.4.0.0²,⁷]trideca-1(13),2(7),3,5,9,11-hexaene

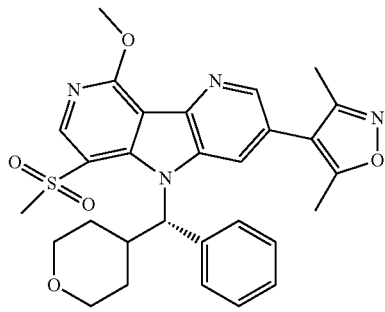 [SMILES: COc1ncc(S(C)(=O)=O)c2c1c1ncc(-c3c(C)noc3C)cc1n2[C@H](c1ccccc1)C1CCOCC1]

Step 1: 5-Bromo-2-(5-methanesulfonyl-2-methoxypyridin-3-yl)-3-nitropyridine

To a 100 mL round bottom flask containing 5-methanesulfonyl-2-methoxy-3-(tetramethyl-1,3,2-dioxaborolan-2-yl)pyridine (664 mg, 2.12 mmol) and 2,5-dibromo-3-nitropyridine (598 mg, 2.12 mmol) in THF (12 mL) was added tripotassium phosphate (2M aq., 3.18 mL, 6.36 mmol) and Pd(dppf)Cl₂—CH₂Cl₂ (87 mg, 0.106 mmol). Nitrogen gas was bubbled through the reaction mixture for 2 min before heating to reflux for 1 h. The reaction mixture was cooled to room temperature and then concentrated. Water was added and the mixture extracted twice with CHCl₃. The combined organic layers were dried over MgSO₄, filtered and then concentrated. The residue was purified on an 80 g silica gel column eluting with a gradient from CH₂Cl₂ to 20% EtOAc/CH₂Cl₂. The tubes containing product were collected and concentrated give the title compound as a pale yellow solid (405 mg, 49.2%). ¹H NMR (500 MHz, CDCl₃) δ 8.97 (d, J=2.0 Hz, 1H), 8.84 (d, J=2.4 Hz, 1H), 8.49 (d, J=2.0 Hz, 1H), 8.47 (d, J=2.4 Hz, 1H), 3.97 (s, 3H), 3.18 (s, 3H); LCMS (M+H)=388; HPLC RT=2.033 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2: 5-Bromo-10-methanesulfonyl-13-methoxy-3,8,12-triazatricyclo[7.4.0.0²,⁷]trideca-1(13),2(7),3,5,9,11-hexaene To a 50 mL round bottom flask containing 5-bromo-2-(5-methanesulfonyl-2-methoxypyridin-3-yl)-3-nitropyridine (405 mg, 1.04 mmol) in 1,2-dichlorobenzene (10 mL) was added Ph₃P (821 mg, 3.13 mmol) and the reaction mixture was heated to 170° C. for 1.5 h. After cooling to room temperature the reaction mixture was purified directly on an 80 g silica gel column eluting with a gradient from CH₂Cl₂ to 60% EtOAc/CH₂Cl₂. The tubes with product were concentrated and the resulting solid was triturated with Et₂O. The solid was filtered to give the title compound as a cream color solid (148.9 mg, 40.1%)¹H NMR (500 MHz, DMSO-d₆) δ 12.22 (br. s., 1H), 8.69 (br. s., 1H), 8.59 (s, 1H), 8.26 (s, 1H), 4.19 (s, 3H), 3.40 (s, 3H); LCMS (M+H)=356; HPLC RT=1.880 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 3: 5-Bromo-10-methanesulfonyl-13-methoxy-8-[(S)-oxan-4-yl(phenyl)methyl]-3,8,12-triazatricyclo[7.4.0.0²,⁷]trideca-1(13),2(7),3,5,9,11-hexaene To a 20 mL vial containing 5-bromo-10-methanesulfonyl-13-methoxy-3,8,12-triazatricyclo-[7.4.0.0²,⁷]trideca-1(13),2(7),3,5,9,11-hexaene (100 mg, 0.281 mmol) and (R)-oxan-4-yl(phenyl)methanol (108 mg, 0.561 mmol) in toluene (2 mL) cooled in an ice/water bath was added Ph₃P (147 mg, 0.561 mmol) and DIAD (0.109 mL, 0.561 mmol). The reaction mixture was removed from the ice/water bath and allowed to stir at room temperature for 1 h and then purified directly on an 80 g silica gel column eluting with a gradient from CH₂Cl₂ to EtOAc. The tubes with product were collected and concentrated to give the title compound (147 mg, 99%). ¹H NMR (500 MHz, CDCl₃) δ 8.99 (s, 1H), 8.76 (d, J=1.8 Hz, 1H), 7.77 (d, J=2.0 Hz, 1H), 7.51-7.48 (m, 2H), 7.43-7.38 (m, 2H), 7.37-7.32 (m, 1H), 6.89 (d, J=10.1 Hz, 1H), 4.39 (s, 3H), 4.06 (dd, J=11.5, 2.8 Hz, 1H), 3.78 (dd, J=11.7, 3.1 Hz, 1H), 3.54 (td, J=11.9, 1.9 Hz, 1H), 3.31-3.22 (m, 4H), 3.00-2.88 (m, 1H), 2.13 (d, J=13.4 Hz, 1H), 1.96-1.85 (m, 1H), 1.54-1.48 (m, 1H), 0.36 (d, J=12.4 Hz, 1H); LCMS (M+H)=530; HPLC RT=2.783 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 4: 5-(Dimethyl-1,2-oxazol-4-yl)-10-methanesulfonyl-13-methoxy-8-[(S)-oxan-4-yl(phenyl)methyl]-3,8,12-triazatricyclo[7.4.0.0²,⁷]trideca-1(13),2(7),3,5,9,11-hexaene To an 8 mL vial containing 5-bromo-10-methanesulfonyl-13-methoxy-8-[(S)-oxan-4-yl(phenyl)methyl]-3,8,12-triazatricyclo[7.4.0.0²,⁷]trideca-1(13),2(7),3,5,9,11-hexaene (50 mg, 0.094 mmol) and (dimethyl-1,2-oxazol-4-yl)boronic acid (19.9 mg, 0.141 mmol) in THF (1 mL) was added tripotassium phosphate (2M aq., 0.141 mL, 0.283 mmol) and Pd(dppf)Cl₂—CH₂Cl₂ (7.7 mg, 0.009 mmol). Nitrogen gas was bubbled through the reaction mixture for 30 seconds then sealed under N₂ and heated on an 80° C. heating block for 1 h. The reaction mixture was cooled to room temperature and then concentrated. The residue was purified on a 40 g silica gel column eluting with a gradient from CH₂Cl₂ to 3% MeOH/CH₂Cl₂. The tubes containing product were collected and concentrated give the title compound as an off white solid (36.4 mg, 70.6%). ¹H NMR (500 MHz, CDCl₃) δ 8.99 (s, 1H), 8.64 (d, J=1.7 Hz, 1H), 7.50 (d, J=7.9 Hz, 2H), 7.42-7.36 (m, 3H), 7.36-7.30 (m, 1H), 6.91 (d, J=9.9 Hz, 1H), 4.42 (s, 3H), 4.07 (dd, J=11.6, 2.7 Hz, 1H), 3.80-3.76 (m, 1H), 3.53 (td, J=11.9, 1.9 Hz, 1H), 3.36 (s, 3H), 3.21 (td, J=11.9, 1.9 Hz, 1H), 3.00-2.89 (m, 1H), 2.24 (s, 3H), 2.21-2.15 (m, 1H), 2.06 (s, 3H), 2.01-1.91 (m, 1H), 1.64-1.57 (m, 1H), 0.37 (d, J=12.5 Hz, 1H); LCMS (M+H)=547; HPLC RT=2.632 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 46

5-(Dimethyl-1H-1,2,3-triazol-5-yl)-10-methanesulfonyl-13-methoxy-8-[(S)-oxan-4-yl(phenyl)methyl]-3,8,12-triazatricyclo[7.4.0.0²,⁷]trideca-1(13),2(7),3,5,9,11-hexaene

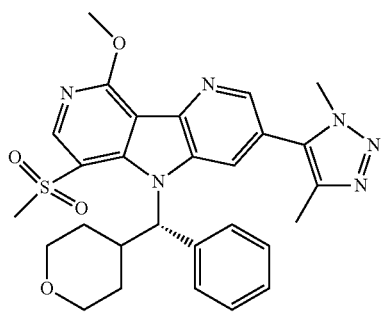 [SMILES: COc1ncc(S(C)(=O)=O)c2c1c1ncc(-c3c(C)nnn3C)cc1n2[C@H](c1ccccc1)C1CCOCC1]

To an 8 mL vial containing 5-bromo-10-methanesulfonyl-13-methoxy-8-[(S)-oxan-4-yl(phenyl)methyl]-3,8,12-triazatricyclo[7.4.0.0²,⁷]trideca-1(13),2(7),3,5,9,11-hexaene (50 mg, 0.094 mmol) in DMF (1 mL) was added 1,4-dimethyl-5-(tributylstannyl)-1H-1,2,3-triazole (54.6 mg, 0.141 mmol), CuI (2.69 mg, 0.014 mmol), Et₃N (0.026 mL, 0.189 mmol) and Pd(Ph₃P)₄ (8.17 mg, 0.007 mmol). Nitrogen gas was bubbled through the reaction mixture for 30 seconds then sealed under N₂ and heated on a 100° C. heating block for 30 min. The reaction mixture was cooled to room temperature and then diluted with water. The resulting precipitate was collected by filtration and purified on silica gel column (40 g) eluting with a gradient from CH₂Cl₂ to 4% MeOH/CH₂Cl₂. The tubes with the desired compound were concentrated and dried under vacuum to give the title compound (33.6 mg, 64%). $^1$H NMR (500 MHz, CDCl₃) δ 9.02 (s, 1H), 8.69 (d, J=1.8 Hz, 1H), 7.49 (d, J=7.8 Hz, 2H), 7.46 (d, J=1.8 Hz, 1H), 7.43-7.38 (m, 2H), 7.37-7.32 (m, 1H), 6.93 (d, J=9.9 Hz, 1H), 4.43 (s, 3H), 4.07 (dd, J=11.6, 2.7 Hz, 1H), 3.79 (dd, J=11.7, 3.2 Hz, 1H), 3.71 (s, 3H), 3.54 (td, J=11.9, 1.9 Hz, 1H), 3.39 (s, 3H), 3.22 (td, J=12.0, 2.0 Hz, 1H), 3.00-2.90 (m, 1H), 2.19 (d, J=13.7 Hz, 1H), 2.16 (s, 3H), 2.02-1.91 (m, 1H), 1.67-1.57 (m, 1H), 0.37 (d, J=12.2 Hz, 1H); LCMS (M+H)=547; HPLC RT=2.400 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 47

10-Methanesulfonyl-13-methoxy-5-[4-($^2$H₃)methyl-1-methyl-1H-1,2,3-triazol-5-yl]-8-[(S)-oxan-4-yl(phenyl)methyl]-3,8,12-triazatricyclo[7.4.0.0²,⁷]trideca-1(13),2(7),3,5,9,11-hexaene

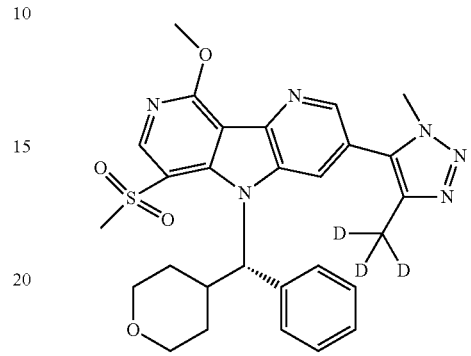

To a 4 mL vial containing 5-bromo-10-methanesulfonyl-13-methoxy-8-[(S)-oxan-4-yl(phenyl)methyl]-3,8,12-triazatricyclo[7.4.0.0²,⁷]trideca-1(13),2(7),3,5,9,11-hexaene (35 mg, 0.066 mmol) in NMP (0.13 mL) was added 4-($^2$H₃)methyl-1-[(trimethylsilyl)methyl]-1H-1,2,3-triazole (22.7 mg, 0.132 mmol), tetrabutylammonium acetate (39.8 mg, 0.132 mmol) and Pd(dppf)Cl₂—CH₂Cl₂ (6.8 mg, 0.006 mmol). The vial was sealed under N₂ and heated on a 100° C. heating block for 2 h. The reaction mixture was cooled to room temperature and then TBAF, 1M in THF (0.66 mL, 0.66 mmol) was added, stirred at room temperature for 15 min then diluted with saturated aq. ammonium hydroxide. The reaction was concentrated and the residue purified on preparative HPLC (Column: Phen Luna C18, 30×100 mm, 5 µm particles; Mobile Phase A: 5:95 ACN:water with 0.1% TFA; Mobile Phase B: 95:5 ACN:water with 0.1% TFA; Gradient: 10-100% B over 12 min, then a 3-min hold at 100% B; Flow: 40 mL/min). The tubes with the desired compound were neutralized with saturated aq. K₂CO₃ and concentrated to remove CH₃CN. A white precipitate formed which was diluted with water, filtered and dried under vacuum to give the title compound (12.2 mg, 33%). $^1$H NMR (500 MHz, CDCl₃) δ 9.02 (s, 1H), 8.69 (d, J=1.8 Hz, 1H), 7.49 (d, J=7.9 Hz, 2H), 7.46 (d, J=1.8 Hz, 1H), 7.43-7.37 (m, 2H), 7.37-7.32 (m, 1H), 6.93 (d, J=9.9 Hz, 1H), 4.43 (s, 3H), 4.07 (dd, J=11.7, 2.7 Hz, 1H), 3.79 (dd, J=11.8, 3.1 Hz, 1H), 3.71 (s, 3H), 3.54 (t, J=11.9 Hz, 1H), 3.39 (s, 3H), 3.22 (td, J=11.9, 1.9 Hz, 1H), 3.00-2.90 (m, 1H), 2.19 (d, J=13.4 Hz, 1H), 2.02-1.91 (m, 1H), 1.67-1.58 (m, 1H), 0.37 (d, J=12.8 Hz, 1H); LCMS (M+H)=550; HPLC RT=2.387 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 48

5-(Dimethyl-1,2-oxazol-4-yl)-8-[(S)-(2-fluorophenyl)(oxan-4-yl)methyl]-10-methanesulfonyl-13-methoxy-3,8,12-triazatricyclo[7.4.0.0²,⁷]trideca-1(13),2(7),3,5,9,11-hexaene

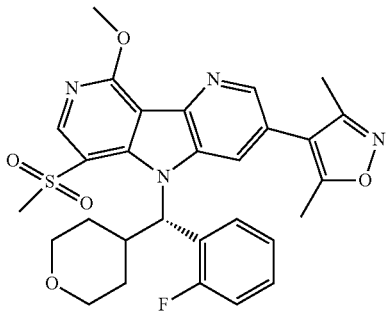 [SMILES: COc1ncc(S(C)(=O)=O)c2c1c1ncc(-c3c(C)noc3C)cc1n2[C@H](c1ccccc1F)C1CCOCC1]

Step 1: 5-Bromo-8-[(S)-(2-fluorophenyl)(oxan-4-yl)methyl]-10-methanesulfonyl-13-methoxy-3,8,12-triazatricyclo[7.4.0.0²,⁷]trideca-1(13),2(7),3,5,9,11-hexaene Following procedures analogous to those described for 5-bromo-10-methanesulfonyl-13-methoxy-8-[(S)-oxan-4-yl(phenyl)methyl]-3,8,12-triazatricyclo[7.4.0.0²,⁷]trideca-1(13),2(7),3,5,9,11-hexaene, 5-bromo-10-methanesulfonyl-13-methoxy-3,8,12-triazatricyclo[7.4.0.0²,⁷]trideca-1(13),2(7),3,5,9,11-hexaene (75 mg, 0.211 mmol) and (R)-(2-fluorophenyl)(oxan-4-yl)methanol (89 mg, 0.421 mmol) was converted to the title compound (85.5 mg, 74%). ¹H NMR (500 MHz, CDCl₃) δ 9.07 (s, 1H), 8.72 (d, J=1.8 Hz, 1H), 7.82-7.77 (m, 1H), 7.75 (d, J=1.8 Hz, 1H), 7.42-7.32 (m, 2H), 7.15 (d, J=10.2 Hz, 1H), 6.98 (ddd, J=11.6, 7.7, 1.6 Hz, 1H), 4.38 (s, 3H), 4.08 (d, J=11.3 Hz, 1H), 3.86 (dd, J=11.5, 3.0 Hz, 1H), 3.57 (td, J=11.7, 2.2 Hz, 1H), 3.39 (s, 3H), 3.32 (td, J=11.9, 1.8 Hz, 1H), 3.04 (q, J=11.0 Hz, 1H), 2.11-1.85 (m, 3H), 0.51 (d, J=13.0 Hz, 1H); LCMS (M+H)=548; HPLC RT=2.703 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2: 5-(Dimethyl-1,2-oxazol-4-yl)-8-[(S)-(2-fluorophenyl)(oxan-4-yl)methyl]-10-methanesulfonyl-13-methoxy-3,8,12-triazatricyclo[7.4.0.0²,⁷]trideca-1(13),2(7),3,5,9,11-hexaene Following procedures analogous to those described for 5-(dimethyl-1,2-oxazol-4-yl)-10-methanesulfonyl-13-methoxy-8-[(S)-oxan-4-yl(phenyl)methyl]-3,8,12-triazatricyclo[7.4.0.0²,⁷]trideca-1(13),2(7),3,5,9,11-hexaene, 5-bromo-8-[(S)-(2-fluorophenyl)(oxan-4-yl)methyl]-10-methanesulfonyl-13-methoxy-3,8,12-triazatricyclo[7.4.0.0²,⁷]trideca-1(13),2(7),3,5,9,11-hexaene (30 mg, 0.055 mmol) was converted to the title compound (22.5 mg, 72%). ¹H NMR (500 MHz, CDCl₃) δ 9.09 (s, 1H), 8.62 (d, J=1.8 Hz, 1H), 7.77 (t, J=7.5 Hz, 1H), 7.46 (d, J=1.7 Hz, 1H), 7.40-7.30 (m, 2H), 7.19 (d, J=10.1 Hz, 1H), 7.00 (ddd, J=11.6, 8.0, 1.2 Hz, 1H), 4.41 (s, 3H), 4.08 (dd, J=11.3, 2.4 Hz, 1H), 3.85 (dd, J=11.6, 3.4 Hz, 1H), 3.54 (td, J=11.8, 2.1 Hz, 1H), 3.41 (s, 3H), 3.27 (td, J=11.9, 1.9 Hz, 1H), 3.04 (q, J=10.9 Hz, 1H), 2.25 (s, 3H), 2.13-2.02 (m, 4H), 2.01-1.89 (m, 2H), 0.51 (d, J=13.0 Hz, 1H); LCMS (M+H)=565; HPLC RT=2.532 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 49

5-(Dimethyl-1,2-oxazol-4-yl)-8-[(S)-(4-fluorophenyl)(oxan-4-yl)methyl]-10-methanesulfonyl-13-methoxy-3,8,12-triazatricyclo[7.4.0.0²,⁷]trideca-1(13),2(7),3,5,9,11-hexaene

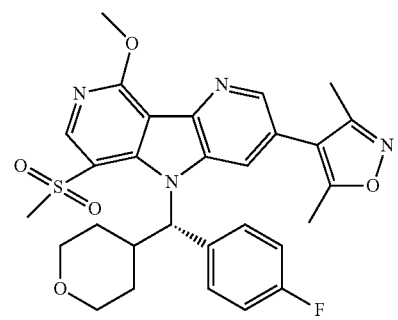 [SMILES: COc1ncc(S(C)(=O)=O)c2c1c1ncc(-c3c(C)noc3C)cc1n2[C@H](c1ccc(F)cc1)C1CCOCC1]

Step 1: 5-Bromo-8-[(S)-(4-fluorophenyl)(oxan-4-yl)methyl]-10-methanesulfonyl-13-methoxy-3,8,12-triazatricyclo[7.4.0.0²,⁷]trideca-1(13),2(7),3,5,9,11-hexaene Following procedures analogous to those described for 5-bromo-10-methanesulfonyl-13-methoxy-8-[(S)-oxan-4-yl(phenyl)methyl]-3,8,12-triazatricyclo[7.4.0.0²,⁷]trideca-1(13),2(7),3,5,9,11-hexaene, 5-bromo-10-methanesulfonyl-13-methoxy-3,8,12-triazatricyclo[7.4.0.0²,⁷]trideca-1(13),2(7),3,5,9,11-hexaene (75 mg, 0.211 mmol) and (R)-(4-fluorophenyl)(oxan-4-yl)methanol (89 mg, 0.421 mmol) was converted to the title compound (91.4 mg, 79%). ¹H NMR (500 MHz, CDCl₃) δ 8.95 (s, 1H), 8.77 (d, J=1.8 Hz, 1H), 7.75 (d, J=1.8 Hz, 1H), 7.53 (dd, J=8.5, 5.2 Hz, 2H), 7.10 (t, J=8.5 Hz, 2H), 6.83 (d, J=10.1 Hz, 1H), 4.38 (s, 3H), 4.06 (dd, J=11.4, 2.7 Hz, 1H), 3.77 (dd, J=11.5, 3.0 Hz, 1H), 3.53 (td, J=11.9, 1.7 Hz, 1H), 3.34 (s, 3H), 3.25 (td, J=11.9, 1.7 Hz, 1H), 2.96-2.85 (m, 1H), 2.08 (d, J=13.4 Hz, 1H), 1.90-1.80 (m, 1H), 1.54-1.44 (m, 1H), 0.34 (d, J=12.8 Hz, 1H); LCMS (M+H)=548; HPLC RT=2.873 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Step 2: 5-(Dimethyl-1,2-oxazol-4-yl)-8-[(S)-(4-fluorophenyl)(oxan-4-yl)methyl]-10-methanesulfonyl-13-methoxy-3,8,12-triazatricyclo[7.4.0.0²,⁷]trideca-1(13),2(7),3,5,9,11-hexaene Following procedures analogous to those described for 5-(dimethyl-1,2-oxazol-4-yl)-10-methanesulfonyl-13-methoxy-8-[(S)-oxan-4-yl(phenyl)methyl]-3,8,12-triazatricyclo[7.4.0.0²,⁷]trideca-1(13),2(7),3,5,9,11-hexaene, 5-bromo-8-[(S)-(4-fluorophenyl)(oxan-4-yl)methyl]-10-methanesulfonyl-13-methoxy-3,8,12-triazatricyclo[7.4.0.0$^{2,7}$]trideca-1(13),2(7),3,5,9,11-hexaene (30 mg, 0.055 mmol) was converted to the title compound (21 mg, 66%). $^1$H NMR (500 MHz, CDCl$_3$) δ 8.95 (s, 1H), 8.66 (d, J=1.7 Hz, 1H), 7.53 (dd, J=8.5, 5.2 Hz, 2H), 7.41 (d, J=1.8 Hz, 1H), 7.09 (t, J=8.5 Hz, 2H), 6.87 (d, J=9.9 Hz, 1H), 4.41 (s, 3H), 4.07 (dd, J=11.7, 2.6 Hz, 1H), 3.77 (dd, J=11.5, 3.1 Hz, 1H), 3.51 (t, J=11.1 Hz, 1H), 3.39 (s, 3H), 3.20 (td, J=11.9, 1.8 Hz, 1H), 2.97-2.85 (m, 1H), 2.29 (s, 3H), 2.16-2.09 (m, 4H), 1.96-1.85 (m, 1H), 1.54-1.47 (m, 1H), 0.35 (d, J=13.1 Hz, 1H); LCMS (M+H)=565; HPLC RT=2.686 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 50

5-(Dimethyl-1H-1,2,3-triazol-5-yl)-8-[(S)-(2-fluorophenyl)(oxan-4-yl)methyl]-10-methanesulfonyl-13-methoxy-3,8,12-triazatricyclo[7.4.0.0$^{2,7}$]trideca-1(13),2(7),3,5,9,11-hexaene

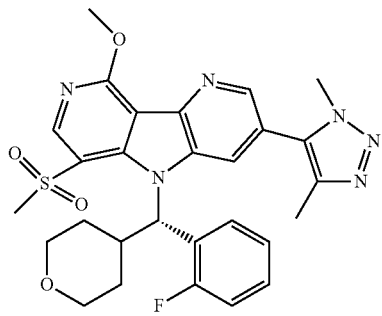 [SMILES: COc1ncc(S(C)(=O)=O)c2c1c1ncc(-c3c(C)nnn3C)cc1n2[C@H](c1ccccc1F)C1CCOCC1]

Following procedures analogous to those described for 5-(dimethyl-1H-1,2,3-triazol-5-yl)-10-methanesulfonyl-13-methoxy-8-[(S)-oxan-4-yl(phenyl)methyl]-3,8,12-triazatricyclo[7.4.0.0$^{2,7}$]trideca-1(13),2(7),3,5,9,11-hexaene, 5-bromo-8-[(S)-(2-fluorophenyl)(oxan-4-yl)methyl]-10-methanesulfonyl-13-methoxy-3,8,12-triazatricyclo[7.4.0.0$^{2,7}$]trideca-1(13),2(7),3,5,9,11-hexaene (30 mg, 0.055 mmol) was converted to the title compound (15.9 mg, 51%). $^1$H NMR (500 MHz, CDCl$_3$) δ 9.12 (s, 1H), 8.66 (d, J=1.8 Hz, 1H), 7.78 (t, J=7.4 Hz, 1H), 7.52 (d, J=1.8 Hz, 1H), 7.41-7.36 (m, 1H), 7.35-7.31 (m, 1H), 7.21 (d, J=10.2 Hz, 1H), 7.00 (ddd, J=11.7, 8.0, 1.3 Hz, 1H), 4.42 (s, 3H), 4.08 (dd, J=11.7, 2.5 Hz, 1H), 3.86 (dd, J=11.7, 3.1 Hz, 1H), 3.76 (s, 3H), 3.54 (td, J=11.9, 2.1 Hz, 1H), 3.43 (s, 3H), 3.27 (td, J=12.0, 2.0 Hz, 1H), 3.08-2.97 (m, 1H), 2.14 (s, 3H), 2.12-1.93 (m, 3H), 0.53 (d, J=11.9 Hz, 1H); LCMS (M+H)=565; HPLC RT=2.345 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 51

8-[(S)-(2-Fluorophenyl)(oxan-4-yl)methyl]-10-methanesulfonyl-13-methoxy-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene

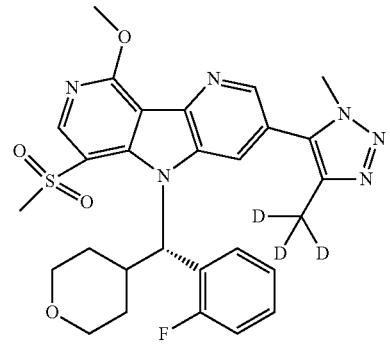 [SMILES: [2H]C([2H])([2H])c1nnn(C)c1-c1cnc2c3c(OC)ncc(S(C)(=O)=O)c3n([C@H](c3ccccc3F)C3CCOCC3)c2c1]

Following procedures analogous to those described for 10-methanesulfonyl-13-methoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene, 5-bromo-8-[(S)-(2-fluorophenyl)(oxan-4-yl)methyl]-10-methanesulfonyl-13-methoxy-3,8,12-triazatricyclo[7.4.0.0$^{2,7}$]trideca-1(13),2(7),3,5,9,11-hexaene (24 mg, 0.044 mmol) was converted to the title compound (9 mg, 35%). $^1$H NMR (500 MHz, CDCl$_3$) δ 9.12 (s, 1H), 8.66 (d, J=1.8 Hz, 1H), 7.77 (t, J=7.6 Hz, 1H), 7.52 (d, J=1.8 Hz, 1H), 7.42-7.36 (m, 1H), 7.35-7.31 (m, 1H), 7.21 (d, J=10.1 Hz, 1H), 7.04-6.95 (m, 1H), 4.42 (s, 3H), 4.08 (d, J=9.0 Hz, 1H), 3.86 (dd, J=11.7, 3.4 Hz, 1H), 3.76 (s, 3H), 3.59-3.51 (m, 1H), 3.43 (s, 3H), 3.31-3.22 (m, 1H), 3.08-2.96 (m, 1H), 2.13-1.93 (m, 3H), 0.53 (d, J=11.3 Hz, 1H); LCMS (M+H)=568; HPLC RT=2.348 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 52

5-(Dimethyl-1H-1,2,3-triazol-5-yl)-8-[(S)-(4-fluorophenyl)(oxan-4-yl)methyl]-10-methanesulfonyl-13-methoxy-3,8,12-triazatricyclo[7.4.0.0$^{2,7}$]trideca-1(13),2(7),3,5,9,11-hexaene

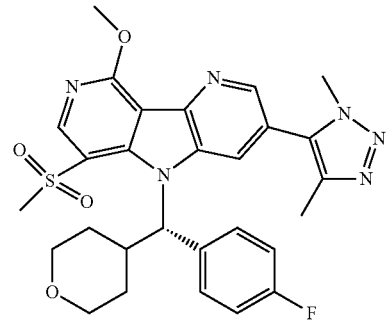 [SMILES: COc1ncc(S(C)(=O)=O)c2c1c1ncc(-c3c(C)nnn3C)cc1n2[C@H](c1ccc(F)cc1)C1CCOCC1]

Following procedures analogous to those described for 5-(dimethyl-1H-1,2,3-triazol-5-yl)-10-methanesulfonyl-13-methoxy-8-[(S)-oxan-4-yl(phenyl)methyl]-3,8,12-triazatricyclo[7.4.0.0$^{2,7}$]trideca-1(13),2(7),3,5,9,11-hexaene, 5-bromo-8-[(S)-(4-fluorophenyl)(oxan-4-yl)methyl]-10-methanesulfonyl-13-methoxy-3,8,12-triazatricyclo[7.4.0.0$^{2,7}$]trideca-1(13),2(7),3,5,9,11-hexaene (30 mg, 0.055 mmol) was converted to the title compound (21.4 mg, 68%). $^1$H NMR (500 MHz, CDCl$_3$) δ 8.98 (s, 1H), 8.70 (d, J=1.7 Hz, 1H), 7.53 (dd, J=8.5, 5.2 Hz, 2H), 7.47 (d, J=1.7 Hz, 1H), 7.10 (t, J=8.5 Hz, 2H), 6.89 (d, J=10.1 Hz, 1H), 4.42 (s, 3H), 4.07 (dd, J=11.7, 2.7 Hz, 1H), 3.83-3.75 (m, 4H), 3.56-3.48 (m, 1H), 3.42 (s, 3H), 3.20 (td, J=12.0, 1.8 Hz, 1H), 2.97-2.85 (m, 1H), 2.19 (s, 3H), 2.13 (d, J=13.6 Hz, 1H), 1.98-1.85 (m, 1H), 1.63-1.56 (m, 1H), 0.35 (d, J=12.5 Hz, 1H); LCMS (M+H)=565; HPLC RT=2.477 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 53

5-(Dimethyl-1H-1,2,3-triazol-5-yl)-13-ethoxy-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaene

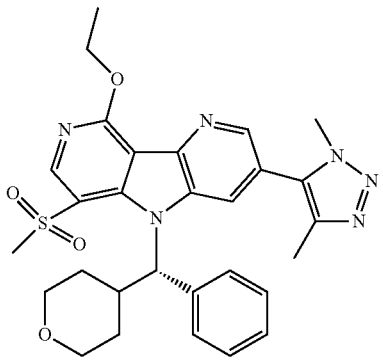 [SMILES: CCOc1ncc(S(C)(=O)=O)c2c1c1ncc(-c3c(C)nnn3C)cc1n2[C@H](c1ccccc1)C1CCOCC1]

To a 4 mL vial containing 5-(dimethyl-1H-1,2,3-triazol-5-yl)-10-methanesulfonyl-13-methoxy-8-[(S)-oxan-4-yl(phenyl)methyl]-3,8,12-triazatricyclo[7.4.0.0$^{2,7}$]trideca-1(13),2(7),3,5,9,11-hexaene (16 mg, 0.029 mmol) in EtOH (0.75 mL) was added KOtBu (23 mg, 0.205 mmol) and the reaction mixture was stirred at room temperature for 15 h. The reaction mixture diluted with 0.15 mL NMP and stirred an additional 3 h at room temperature and then 1M aq. citric acid solution (0.073 mL, 0.073 mmol) was added. The reaction mixture was concentrated then diluted with water and the resulting precipitate was collected by filtration and dried under vacuum to give the title compound (10.7 mg, 61%). $^1$H NMR (500 MHz, CDCl$_3$) δ 9.00 (s, 1H), 8.68 (d, J=1.7 Hz, 1H), 7.48 (d, J=7.6 Hz, 2H), 7.44 (d, J=1.7 Hz, 1H), 7.42-7.36 (m, 2H), 7.36-7.31 (m, 1H), 6.92 (d, J=9.9 Hz, 1H), 4.95 (q, J=7.0 Hz, 2H), 4.07 (dd, J=11.0, 3.2 Hz, 1H), 3.79 (dd, J=11.9, 2.9 Hz, 1H), 3.69 (s, 3H), 3.53 (td, J=11.8, 1.3 Hz, 1H), 3.39 (s, 3H), 3.27-3.17 (m, J=10.5 Hz, 1H), 2.99-2.89 (m, J=11.3, 11.3, 11.3 Hz, 1H), 2.20 (br. s., 1H), 2.15 (s, 3H), 2.02-1.91 (m, J=4.9 Hz, 1H), 1.64 (s, 4H), 0.39 (d, J=13.3 Hz, 1H); LCMS (M+H)=561; HPLC RT=2.587 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 54

10-Methanesulfonyl-13-($^2$H$_3$)methoxy-5-[5-($^2$H$_3$)methyl-3-methyl-1,2-oxazol-4-yl]-8-[(S)-oxan-4-yl(phenyl)methyl]-3,8,12-triazatricyclo[7.4.0.0$^{2,7}$]trideca-1(13),2(7),3,5,9,11-hexaene

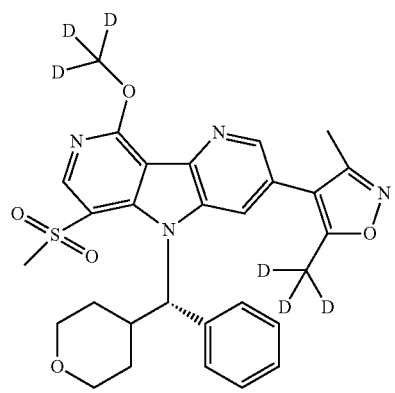 [SMILES: [2H]C([2H])([2H])Oc1ncc(S(C)(=O)=O)c2c1c1ncc(-c3c(C)noc3C([2H])([2H])[2H])cc1n2[C@H](c1ccccc1)C1CCOCC1]

To a 4 mL vial containing 5-(dimethyl-1H-1,2,3-triazol-5-yl)-10-methanesulfonyl-13-methoxy-8-[(S)-oxan-4-yl(phenyl)methyl]-3,8,12-triazatricyclo[7.4.0.0$^{2,7}$]trideca-1(13),2(7),3,5,9,11-hexaene (23.4 mg, 0.043 mmol) in CD$_3$OD (1.5 mL) was added KOtBu (22.1 mg, 0.197 mmol) and the reaction mixture was heated on an 80° C. heating block for 17 h. The reaction mixture was cooled to room temperature and 1M aq. citric acid solution (0.043 mL, 0.043 mmol) was added. The reaction mixture was concentrated then diluted with water and the resulting precipitate was collected by filtration and dried under vacuum. The crude solid was dissolved in MeOH (1 mL) and KOtBu (22.1 mg, 0.197 mmol) was added and the reaction stirred for 20 min at room temperature. The reaction was then diluted with saturated aq. NaHCO$_3$, then MeOH was removed by evaporation and diluted with water to give a white precipitate. The white precipitate was collected by filtration and dried under vacuum to give the title compound (15.5 mg, 61%). $^1$H NMR (500 MHz, CDCl$_3$) δ 8.99 (s, 1H), 8.64 (d, J=1.5 Hz, 1H), 7.49 (d, J=7.6 Hz, 2H), 7.44-7.36 (m, 3H), 7.36-7.31 (m, 1H), 6.91 (d, J=9.9 Hz, 1H), 4.11-3.99 (m, 1H), 3.78 (dd, J=11.6, 2.9 Hz, 1H), 3.53 (t, J=11.2 Hz, 1H), 3.36 (s, 3H), 3.25-3.17 (m, 1H), 3.02-2.89 (m, 1H), 2.18 (d, J=13.4 Hz, 1H), 2.06 (s, 3H), 2.01-1.90 (m, 1H), 1.64-1.58 (m, 1H), 0.37 (d, J=12.7 Hz, 1H); LCMS (M+H)=553; HPLC RT=2.636 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 55

8-[(S)-(4-Fluorophenyl)(oxan-4-yl)methyl]-10-methanesulfonyl-13-($^2$H$_3$)methoxy-5-[5-($^2$H$_3$)methyl-3-methyl-1,2-oxazol-4-yl]-3,8,12-triazatricyclo[7.4.0.0$^{2,7}$]trideca-1(13),2(7),3,5,9,11-hexaene

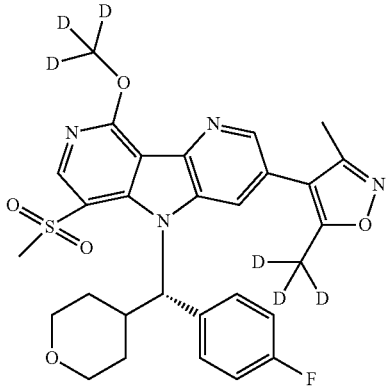 [SMILES: [2H]C([2H])([2H])Oc1ncc(S(C)(=O)=O)c2c1c1ncc(-c3c(C)noc3C([2H])([2H])[2H])cc1n2[C@H](c1ccc(F)cc1)C1CCOCC1]

Following procedures analogous to those described for 10-methanesulfonyl-13-($^2$H$_3$)methoxy-5-[5-($^2$H$_3$)methyl-3-methyl-1,2-oxazol-4-yl]-8-[(S)-oxan-4-yl(phenyl)methyl]-3,8,12-triazatricyclo-[7.4.0.0$^{2,7}$]trideca-1(13),2(7),3,5,9,11-hexaene, 5-(dimethyl-1,2-oxazol-4-yl)-8-[(S)-(4-fluorophenyl)(oxan-4-yl)methyl]-10-methanesulfonyl-13-methoxy-3,8,12-triazatricyclo[7.4.0.0$^{2,7}$]trideca-1(13),2(7),3,5,9,11-hexaene (15 mg, 0.027 mmol) was converted to the title compound (3.4 mg, 21%). $^1$H NMR (500 MHz, CDCl$_3$) δ 8.95 (s, 1H), 8.66 (d, J=1.7 Hz, 1H), 7.53 (dd, J=8.5, 5.1 Hz, 2H), 7.41 (d, J=1.7 Hz, 1H), 7.09 (t, J=8.5 Hz, 2H), 6.87 (d, J=9.9 Hz, 1H), 4.07 (d, J=8.9 Hz, 1H), 3.77 (dd, J=11.8, 3.0 Hz, 1H), 3.51 (t, J=11.1 Hz, 1H), 3.39 (s, 3H), 3.20 (t, J=11.1 Hz, 1H), 2.96-2.82 (m, 1H), 2.12 (s, 4H), 1.96-1.86 (m, 1H), 1.53-1.48 (m, 1H), 0.35 (d, J=12.5 Hz, 1H); LCMS (M+H)=571; HPLC RT=2.700 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 56

13-Ethoxy-10-methanesulfonyl-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene

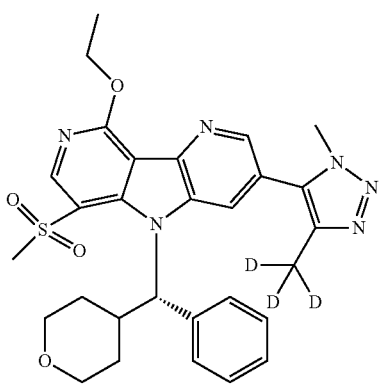 [SMILES: [2H]C([2H])([2H])c1nnn(C)c1-c1cnc2c3c(OCC)ncc(S(C)(=O)=O)c3n([C@H](c3ccccc3)C3CCOCC3)c2c1]

Following procedures analogous to those described for 5-(dimethyl-1H-1,2,3-triazol-5-yl)-13-ethoxy-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaene, 10-methanesulfonyl-13-methoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene (31 mg, 0.056 mmol) was converted to the title compound (6.4 mg, 19.9%). $^1$H NMR (500 MHz, CDCl$_3$) δ 9.00 (s, 1H), 8.68 (d, J=1.8 Hz, 1H), 7.48 (d, J=7.9 Hz, 2H), 7.44 (d, J=1.8 Hz, 1H), 7.42-7.37 (m, 2H), 7.36-7.31 (m, J=7.3 Hz, 1H), 6.92 (d, J=9.9 Hz, 1H), 4.95 (qd, J=7.0, 1.0 Hz, 2H), 4.07 (dd, J=11.6, 2.7 Hz, 1H), 3.79 (dd, J=11.5, 3.0 Hz, 1H), 3.69 (s, 3H), 3.53 (td, J=11.9, 1.8 Hz, 1H), 3.39 (s, 3H), 3.22 (td, J=11.9, 1.9 Hz, 1H), 3.01-2.89 (m, 1H), 2.19 (d, J=13.4 Hz, 1H), 2.03-1.91 (m, J=4.4 Hz, 1H), 1.70-1.59 (m, J=7.1, 7.1 Hz, 4H), 0.39 (d, J=12.8 Hz, 1H); LCMS (M+H)=564; HPLC RT=2.590 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 57

5-(Dimethyl-1H-1,2,3-triazol-5-yl)-10-methanesulfonyl-8-[(S)-oxan-4-yl(phenyl)methyl]-13-(propan-2-yloxy)-3,8,12-triazatricyclo[7.4.0.0$^{2,7}$]trideca-1(13),2(7),3,5,9,11-hexaene

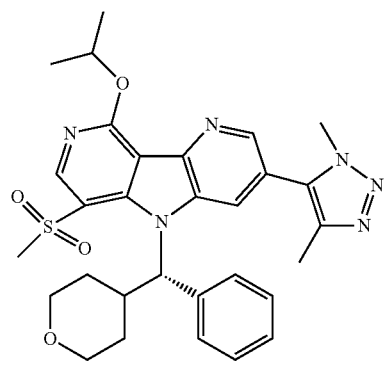 [SMILES: Cc1nnn(C)c1-c1cnc2c3c(OC(C)C)ncc(S(C)(=O)=O)c3n([C@H](c3ccccc3)C3CCOCC3)c2c1]

Following procedures analogous to those described for 5-(dimethyl-1H-1,2,3-triazol-5-yl)-13-ethoxy-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaene, 5-(dimethyl-1H-1,2,3-triazol-5-yl)-10-methanesulfonyl-13-methoxy-8-[(S)-oxan-4-yl(phenyl)methyl]-3,8,12-triazatricyclo[7.4.0.0$^{2,7}$]trideca-1(13),2(7),3,5,9,11-hexaene (20 mg, 0.037 mmol) in iPrOH (0.75 mL) was converted to the title compound (18.7 mg, 84%). $^1$H NMR (500 MHz, CDCl$_3$) δ 8.99 (s, 1H), 8.65 (d, J=1.8 Hz, 1H), 7.47 (d, J=8.5 Hz, 2H), 7.41 (s, 1H), 7.40-7.36 (m, 2H), 7.35-7.30 (m, J=7.2 Hz, 1H), 6.91 (d, J=9.9 Hz, 1H), 5.84 (spt, J=6.2 Hz, 1H), 4.07 (dd, J=11.8, 2.7 Hz, 1H), 3.79 (dd, J=12.0, 3.3 Hz, 1H), 3.68 (s, 3H), 3.53 (td, J=11.9, 1.7 Hz, 1H), 3.38 (s, 3H), 3.21 (td, J=12.0, 1.8 Hz, 1H), 3.00-2.88 (m, 1H), 2.19 (d, J=13.4 Hz, 1H), 2.14 (s, 3H), 2.02-1.89 (m, 1H), 1.67-1.59 (m, J=11.4, 6.3 Hz, 7H), 0.40 (d, J=12.8 Hz, 1H); LCMS (M+H)=575; HPLC RT=2.745 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 58

10-Methanesulfonyl-5-[4-($^2$H$_3$)methyl-1-methyl-1H-1,2,3-triazol-5-yl]-8-[(S)-oxan-4-yl(phenyl)methyl]-13-(propan-2-yloxy)-3,8,12-triazatricyclo[7.4.0.0$^{2,7}$]trideca-1(13),2(7),3,5,9,11-hexaene

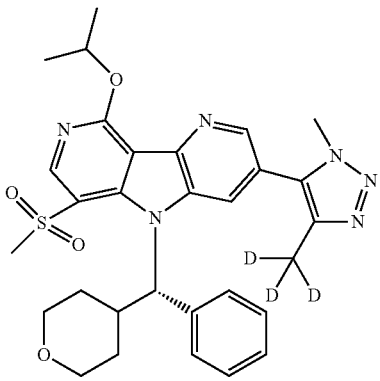 [SMILES: [2H]C([2H])([2H])c1nnn(C)c1-c1cnc2c3c(OC(C)C)ncc(S(C)(=O)=O)c3n([C@H](c3ccccc3)C3CCOCC3)c2c1]

Following procedures analogous to those described for 5-(dimethyl-1H-1,2,3-triazol-5-yl)-13-ethoxy-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaene, 10-methanesulfonyl-13-methoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene (30 mg, 0.055 mmol) in iPrOH (1 mL) was converted to the title compound (16.9 mg, 50%). $^1$H NMR (400 MHz, CDCl$_3$) δ 8.99 (s, 1H), 8.65 (d, J=1.8 Hz, 1H), 7.49-7.45 (m, 2H), 7.42 (d, J=1.8 Hz, 1H), 7.38 (s, 3H), 6.92 (d, J=9.8 Hz, 1H), 5.84 (spt, J=6.2 Hz, 1H), 4.07 (dd, J=11.6, 2.9 Hz, 1H), 3.79 (dd, J=11.3, 3.9 Hz, 1H), 3.68 (s, 3H), 3.53 (td, J=11.9, 1.8 Hz, 1H), 3.37 (s, 3H), 3.21 (td, J=11.9, 1.8 Hz, 1H), 3.01-2.87 (m, 1H), 2.18 (d, J=13.0 Hz, 1H), 2.03-1.90 (m, J=4.3 Hz, 1H), 1.63 (dd, J=9.0, 6.2 Hz, 7H), 0.41 (d, J=12.7 Hz, 1H); LCMS (M+H)=578; HPLC RT=2.741 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 59

13-(Cyclopropylmethoxy)-10-methanesulfonyl-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene

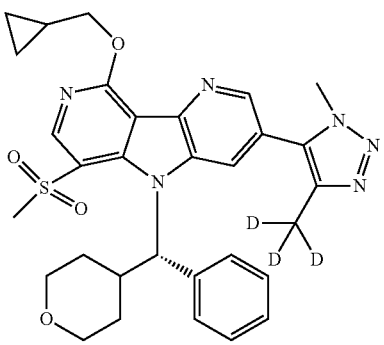 [SMILES: [2H]C([2H])([2H])c1nnn(C)c1-c1cnc2c3c(OCC4CC4)ncc(S(C)(=O)=O)c3n([C@H](c3ccccc3)C3CCOCC3)c2c1]

Following procedures analogous to those described for 5-(dimethyl-1H-1,2,3-triazol-5-yl)-13-ethoxy-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaene, 10-methanesulfonyl-13-methoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene (27 mg, 0.049 mmol) in cyclopropylmethanol (0.4 mL) was converted to the title compound (14.2 mg, 48.5%). $^1$H NMR (500 MHz, CDCl$_3$) δ 8.98 (s, 1H), 8.69 (d, J=1.7 Hz, 1H), 7.51-7.46 (m, 2H), 7.44 (d, J=1.8 Hz, 1H), 7.42-7.36 (m, 2H), 7.36-7.31 (m, 1H), 6.92 (d, J=9.8 Hz, 1H), 4.79-4.67 (m, 2H), 4.12-4.03 (m, 1H), 3.79 (dd, J=11.9, 3.1 Hz, 1H), 3.69 (s, 3H), 3.57-3.50 (m, 1H), 3.38 (s, 3H), 3.22 (t, J=11.1 Hz, 1H), 3.00-2.89 (m, 1H), 2.19 (d, J=13.1 Hz, 1H), 2.04-1.92 (m, 1H), 1.69-1.58 (m, 2H), 0.75-0.64 (m, 2H), 0.60-0.51 (m, 2H), 0.41 (d, J=12.8 Hz, 1H); LCMS (M+H)=590; HPLC RT=2.793 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 60

10-Methanesulfonyl-13-methoxy-5-[5-($^2$H$_3$)methyl-3-methyl-1,2-oxazol-4-yl]-8-[(S)-oxan-4-yl(phenyl)methyl]-3,8,12-triazatricyclo[7.4.0.0$^{2,7}$]trideca-1(13),2(7),3,5,9,11-hexaene

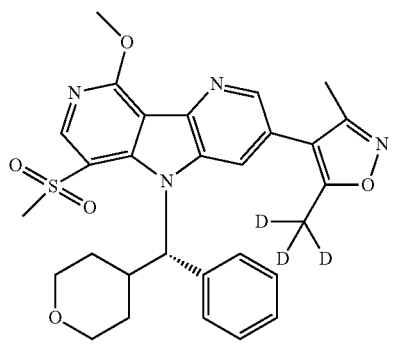 [SMILES: [2H]C([2H])([2H])c1onc(C)c1-c1cnc2c3c(OC)ncc(S(C)(=O)=O)c3n([C@H](c3ccccc3)C3CCOCC3)c2c1]

Following procedures analogous to those described for 10-methanesulfonyl-13-($^2$H$_3$)methoxy-5-[5-($^2$H$_3$)methyl-3-methyl-1,2-oxazol-4-yl]-8-[(S)-oxan-4-yl(phenyl)methyl]-3,8,12-triazatricyclo[7.4.0.0$^{2,7}$]trideca-1(13),2(7),3,5,9,11-hexaene, 5-(dimethyl-1H-1,2,3-triazol-5-yl)-10-methanesulfonyl-13-methoxy-8-[(S)-oxan-4-yl(phenyl)methyl]-3,8,12-triazatricyclo[7.4.0.0$^{2,7}$]trideca-1(13),2(7),3,5,9,11-hexaene (20 mg, 0.037 mmol) in CH$_3$OD (1.5 mL) was converted to the title compound (9 mg, 44%). $^1$H NMR (400 MHz, CDCl$_3$) δ 8.99 (s, 1H), 8.64 (d, J=1.7 Hz, 1H), 7.52-7.46 (m, 2H), 7.43-7.33 (m, 4H), 6.92 (d, J=9.8 Hz, 1H), 4.42 (s, 3H), 4.07 (dd, J=11.8, 3.4 Hz, 1H), 3.78 (dd, J=12.2, 3.2 Hz, 1H), 3.53 (td, J=11.9, 1.8 Hz, 1H), 3.36 (s, 3H), 3.21 (td, J=12.0, 2.0 Hz, 1H), 3.01-2.88 (m, 1H), 2.18 (d, J=14.1 Hz, 1H), 2.06 (s, 3H), 2.02-1.90 (m, J=4.3 Hz, 1H), 1.65-1.59 (m, 1H), 0.37 (d, J=11.9 Hz, 1H); LCMS (M+H)=550; HPLC RT=2.631 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 61

2-({10-Methanesulfonyl-5-[4-($^2H_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaen-13-yl}oxy)ethan-1-ol

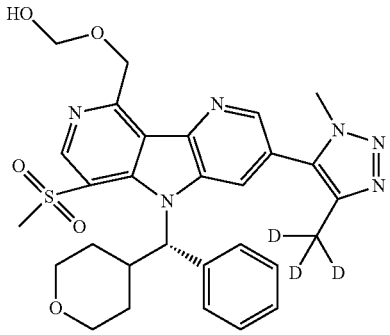 [SMILES: [2H]C([2H])([2H])c1nnn(C)c1-c1cnc2c3c(COCO)ncc(S(C)(=O)=O)c3n([C@H](c3ccccc3)C3CCOCC3)c2c1]

Following procedures analogous to those described for 5-(dimethyl-1H-1,2,3-triazol-5-yl)-13-ethoxy-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaene, 10-methanesulfonyl-13-methoxy-5-[4-($^2H_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene (14 mg, 0.025 mmol) in ethylene glycol (0.6 mL) was converted to the title compound (9.3 mg, 61%). $^1$H NMR (500 MHz, CDCl$_3$) δ 8.99 (s, 1H), 8.64 (d, J=1.7 Hz, 1H), 7.52-7.44 (m, 3H), 7.40 (t, J=7.5 Hz, 2H), 7.38-7.32 (m, 1H), 6.93 (d, J=9.9 Hz, 1H), 5.02-4.90 (m, J=3.5 Hz, 2H), 4.16 (br. s., 2H), 4.07 (dd, J=11.6, 2.6 Hz, 1H), 3.89 (br. s., 1H), 3.80 (dd, J=11.7, 3.1 Hz, 1H), 3.70 (s, 3H), 3.54 (td, J=11.9, 1.3 Hz, 1H), 3.40 (s, 3H), 3.23 (td, J=11.9, 1.7 Hz, 1H), 3.02-2.89 (m, 1H), 2.20 (d, J=13.3 Hz, 1H), 2.03-1.91 (m, J=4.3 Hz, 1H), 1.68-1.62 (m, J=4.3 Hz, 1H), 0.39 (d, J=12.5 Hz, 1H); LCMS (M+H)=580; HPLC RT=2.285 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 62

13-Ethoxy-8-[(S)-(2-fluorophenyl)(oxan-4-yl)methyl]-10-methanesulfonyl-5-[4-($^2H_3$)methyl-1-methyl-1H-1,2,3-triazol-5-yl]-3,8,12-triazatricyclo[7.4.0.0$^{2,7}$]trideca-1(13),2(7),3,5,9,11-hexaene

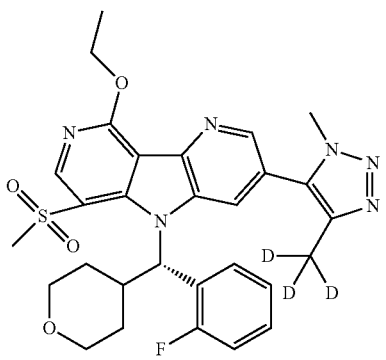

Following procedures analogous to those described for 5-(dimethyl-1H-1,2,3-triazol-5-yl)-13-ethoxy-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaene, 8-[(S)-(2-fluorophenyl)(oxan-4-yl)methyl]-10-methanesulfonyl-13-methoxy-5-[4-($^2H_3$)methyl-1-methyl-1H-1,2,3-triazol-5-yl]-3,8,12-triazatricyclo[7.4.0.0$^{2,7}$]trideca-1(13),2(7),3,5,9,11-hexaene (20 mg, 0.035 mmol) was converted to the title compound (13.9 mg, 66%). $^1$H NMR (500 MHz, CDCl$_3$) δ 9.09 (s, 1H), 8.65 (d, J=1.7 Hz, 1H), 7.77 (t, J=7.5 Hz, 1H), 7.50 (d, J=1.8 Hz, 1H), 7.40-7.29 (m, 2H), 7.19 (d, J=10.2 Hz, 1H), 6.99 (ddd, J=11.6, 8.0, 1.1 Hz, 1H), 4.94 (q, J=7.0 Hz, 2H), 4.08 (br dd, J=11.4, 2.4 Hz, 1H), 3.86 (br dd, J=11.7, 3.2 Hz, 1H), 3.75 (s, 3H), 3.54 (td, J=11.9, 1.9 Hz, 1H), 3.42 (s, 3H), 3.27 (td, J=12.0, 1.8 Hz, 1H), 3.03 (q, J=11.1 Hz, 1H), 2.13-1.94 (m, 3H), 1.63 (t, J=7.0 Hz, 3H), 0.54 (br d, J=12.4 Hz, 1H); LCMS (M+H)=582; HPLC RT=2.538 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min).

Example 63

2-({8-[(S)-(2-Fluorophenyl)(oxan-4-yl)methyl]-10-methanesulfonyl-5-[4-($^2H_3$)methyl-1-methyl-1H-1,2,3-triazol-5-yl]-3,8,12-triazatricyclo[7.4.0.0$^{2,7}$]trideca-1(13),2(7),3,5,9,11-hexaen-13-yl}oxy)ethan-1-ol

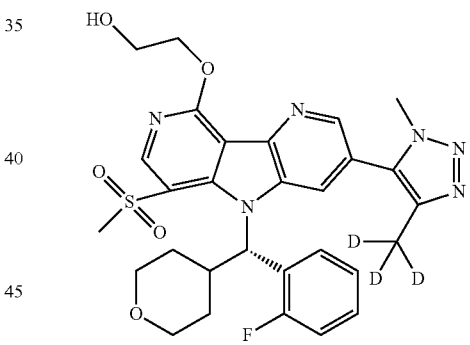

Following procedures analogous to those described for 5-(dimethyl-1H-1,2,3-triazol-5-yl)-13-ethoxy-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaene, 8-[(S)-(2-fluorophenyl)(oxan-4-yl)methyl]-10-methanesulfonyl-13-methoxy-5-[4-($^2H_3$)methyl-1-methyl-1H-1,2,3-triazol-5-yl]-3,8,12-triazatricyclo[7.4.0.0$^{2,7}$]trideca-1(13),2(7),3,5,9,11-hexaene (25.6 mg, 0.045 mmol) in ethylene glycol (1 mL) was converted to the title compound (16 mg, 58.8%). $^1$H NMR (500 MHz, CDCl$_3$) δ 9.08 (s, 1H), 8.60 (d, J=1.7 Hz, 1H), 7.78 (br t, J=7.5 Hz, 1H), 7.52 (d, J=1.7 Hz, 1H), 7.43-7.32 (m, 2H), 7.20 (br d, J=10.2 Hz, 1H), 7.00 (ddd, J=11.6, 8.0, 1.2 Hz, 1H), 5.02-4.88 (m, 2H), 4.14 (br s, 2H), 4.08 (br dd, J=11.8, 2.2 Hz, 2H), 3.87 (br dd, J=12.1, 3.5 Hz, 1H), 3.75 (s, 3H), 3.58-3.50 (m, 1H), 3.43 (s, 3H), 3.27 (td, J=11.9, 1.8 Hz, 1H), 3.03 (q, J=10.9 Hz, 1H), 2.14-1.93 (m, 3H), 0.53 (br d, J=13.1 Hz, 1H); LCMS (M+H)=598; HPLC RT=2.247 min (Column: Chromolith ODS S5 4.6×50 mm; Mobile Phase A: 10:90 MeOH:water with 0.1% TFA;

Mobile Phase B: 90:10 MeOH:water with 0.1% TFA; Temperature: 40° C.; Gradient: 0-100% B over 4 min; Flow: 4 mL/min).

Examples 64 and 65

8-[(3-Fluoropyridin-2-yl)(oxan-4-yl)methyl]-10-methanesulfonyl-13-methoxy-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene

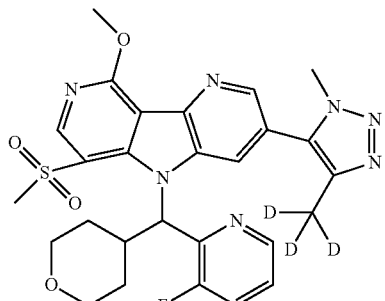

Example 64
Enantiomer A

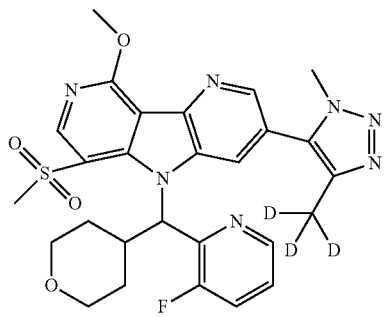

Example 65
Enantiomer B

Step 1: 5-Bromo-8-[(3-fluoropyridin-2-yl)(oxan-4-yl)methyl]-10-methanesulfonyl-13-methoxy-3,8,12-triazatricyclo[7.4.0.0$^{2,7}$]trideca-1(13),2(7),3,5,9,11-hexaene Following procedures analogous to those described for 5-bromo-10-methanesulfonyl-13-methoxy-8-[(S)-oxan-4-yl(phenyl)methyl]-3,8,12-triazatricyclo[7.4.0.0$^{2,7}$]trideca-1(13),2(7),3,5,9,11-hexaene, 5-bromo-10-methanesulfonyl-13-methoxy-3,8,12-triazatricyclo[7.4.0.0$^{2,7}$]trideca-1(13),2(7),3,5,9,11-hexaene (150 mg, 0.421 mmol) and racemic (3-fluoropyridin-2-yl)(oxan-4-yl)methanol (178 mg, 0.842 mmol) was converted to the title compound (154.9 mg, 66.9%). $^1$H NMR (500 MHz, CDCl$_3$) δ 9.04 (s, 1H), 8.73 (d, J=1.8 Hz, 1H), 8.57 (br d, J=2.7 Hz, 1H), 8.18 (d, J=1.8 Hz, 1H), 7.39-7.33 (m, 2H), 7.25 (s, 1H), 4.37 (s, 3H), 4.03 (br dd, J=11.5, 2.5 Hz, 1H), 3.83 (br dd, J=11.4, 3.3 Hz, 1H), 3.55 (td, J=11.7, 2.3 Hz, 1H), 3.48-3.37 (m, 4H), 3.35-3.28 (m, 1H), 1.95-1.76 (m, 3H), 0.49 (br d, J=11.7 Hz, 1H); LCMS (M+H)=549; HPLC RT=2.615 min (Column: Chromolith ODS S5 4.6×50 mm; Mobile Phase A: 10:90 MeOH: water with 0.1% TFA; Mobile Phase B: 90:10 MeOH:water with 0.1% TFA; Temperature: 40° C.; Gradient: 0-100% B over 4 min; Flow: 4 mL/min).

Step 2: 8-[(3-Fluoropyridin-2-yl)(oxan-4-yl)methyl]-10-methanesulfonyl-13-methoxy-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene To a 20 mL vial containing 5-bromo-8-[(3-fluoropyridin-2-yl)(oxan-4-yl)methyl]-10-methanesulfonyl-13-methoxy-3,8,12-triazatricyclo[7.4.0.0$^{2,7}$]trideca-1(13),2(7),3,5,9,11-hexaene (154.9 mg, 0.282 mmol) in DMF (4 mL) was added 4-($^2$H$_3$)methyl-5-(tributylstannyl)-1-[(trimethylsilyl)methyl]-1H-1,2,3-triazole (195 mg, 0.423 mmol), CuI (8.0 mg, 0.042 mmol), Et$_3$N (0.079 mL, 0.564 mmol) and Pd(Ph$_3$P)$_4$ (24.4 mg, 0.021 mmol). Nitrogen gas was bubbled through the reaction mixture for 30 seconds then sealed under N$_2$ and heated on a 95° C. heating block for 1 h. The reaction mixture was cooled to room temperature and diluted with 1M TBAF in THF (0.564 mL, 0.564 mmol). After stirring at room temperature for 25 min the reaction was concentrated. The residue was diluted with water and the resulting precipitate was collected by filtration and purified on silica gel column (40 g) eluting with a gradient from CH$_2$Cl$_2$ to 6% MeOH/CH$_2$Cl$_2$. The tubes containing product were collected and concentrated to give the racemic title compound (125.2 mg, 78%). Chiral separation was performed on the racemic compound (41 mg, 0.072 mmol) on chiral preparative SFC to give enantiomer A (18.2 mg, 44%) and enantiomer B (18.6 mg, 45%). Enantiomer A: $^1$H NMR (500 MHz, CDCl$_3$) δ 9.08 (s, 1H), 8.69 (d, J=1.8 Hz, 1H), 8.51 (dt, J=3.8, 1.9 Hz, 1H), 8.01 (d, J=1.8 Hz, 1H), 7.40-7.35 (m, 2H), 7.34-7.30 (m, 1H), 4.41 (s, 3H), 4.06-4.00 (m, 1H), 3.92 (s, 3H), 3.84 (br dd, J=11.4, 3.4 Hz, 1H), 3.50 (td, J=11.3, 3.1 Hz, 1H), 3.45 (s, 3H), 3.43-3.36 (m, 1H), 3.24 (td, J=11.8, 1.8 Hz, 1H), 1.91-1.80 (m, 3H), 0.52 (br dd, J=13.1, 1.5 Hz, 1H); LCMS (M+H)=569; HPLC RT=2.173 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=11.1 min (Column: Chiral OD-H, 250×4.6 mm, 5 μm; Mobile Phase: 80/20 CO$_2$/MeOH; Flow: 2 mL/min). Enantiomer B: $^1$H NMR (500 MHz, CDCl$_3$) δ 9.11 (s, 1H), 8.78 (br s, 1H), 8.51 (d, J=4.1 Hz, 1H), 8.19 (br s, 1H), 7.44-7.33 (m, 3H), 4.45 (s, 3H), 4.07-4.00 (m, 1H), 3.96 (s, 3H), 3.85 (br dd, J=11.6, 3.4 Hz, 1H), 3.54-3.46 (m, 1H), 3.45 (s, 3H), 3.37 (br s, 1H), 3.24 (td, J=11.9, 1.8 Hz, 1H), 1.91-1.84 (m, 3H), 0.51 (br d, J=11.6 Hz, 1H); LCMS (M+H)=569; HPLC RT=2.163 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=15.6 min (Column: Chiral OD-H, 250×4.6 mm, 5 μm; Mobile Phase: 80/20 CO$_2$/MeOH; Flow: 2 mL/min)

Examples 66 and 67

8-[(3-Fluoropyridin-2-yl)(oxan-4-yl)methyl]-10-($^2$H$_3$)methanesulfonyl-13-methoxy-5-[5-($^2$H$_3$)methyl-3-methyl-1,2-oxazol-4-yl]-3,8,12-triazatricyclo[7.4.0.0$^{2,7}$]trideca-1(13),2(7),3,5,9,11-hexaene

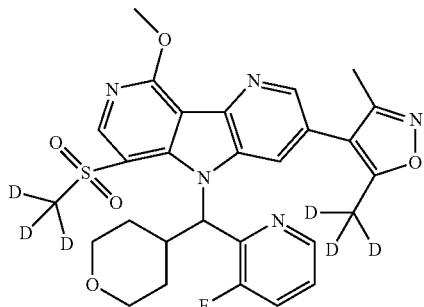

Example 66
Enantiomer A

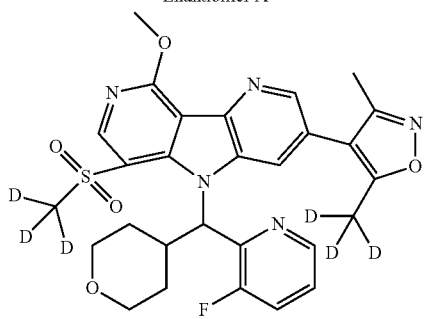

Example 67
Enantiomer B

Following procedures analogous to those described for 10-methanesulfonyl-13-methoxy-5-[5-($^2$H$_3$)methyl-3-methyl-1,2-oxazol-4-yl]-8-[(S)-oxan-4-yl(phenyl)methyl]-3,8,12-triazatricyclo[7.4.0.0$^{2,7}$]trideca-1(13),2(7),3,5,9,11-hexaene, 5-(dimethyl-1,2-oxazol-4-yl)-8-[(3-fluoropyridin-2-yl)(oxan-4-yl)methyl]-10-methanesulfonyl-13-methoxy-3,8,12-triazatricyclo[7.4.0.0$^{2,7}$]trideca-1(13),2(7),3,5,9,11-hexaene (76 mg, 0.134 mmol) was converted to the racemic title compound. Chiral separation was performed on the racemic compound on chiral preparative SFC to give enantiomer A (29.1 mg, 37.9%) and enantiomer B (28.8 mg, 37.5%). Enantiomer A: $^1$H NMR (500 MHz, CDCl$_3$) δ 9.05 (s, 1H), 8.64 (d, J=1.8 Hz, 1H), 8.52 (dd, J=4.7, 1.4 Hz, 1H), 7.87 (d, J=1.8 Hz, 1H), 7.39-7.33 (m, 1H), 7.32-7.28 (m, 2H), 4.40 (s, 3H), 4.03 (br dd, J=11.5, 2.7 Hz, 1H), 3.84 (br dd, J=11.6, 3.2 Hz, 1H), 3.52 (td, J=11.7, 2.4 Hz, 1H), 3.44-3.39 (m, 1H), 3.25 (td, J=11.9, 2.1 Hz, 1H), 2.21 (s, 3H), 1.97-1.91 (m, 1H), 1.85 (quind, J=12.5, 4.5 Hz, 2H), 0.58-0.46 (m, 1H); LCMS (M+H)=572; HPLC RT=2.380 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=9.1 min (Column: Chiral OD-H, 250×4.6 mm, 5 μm; Mobile Phase: 80/20 CO$_2$/MeOH; Flow: 2 mL/min). Enantiomer B: $^1$H NMR (500 MHz, CDCl$_3$) δ 9.05 (s, 1H), 8.64 (s, 1H), 8.52 (br s, 1H), 7.87 (s, 1H), 7.39-7.28 (m, 3H), 4.40 (s, 3H), 4.03 (br d, J=11.1 Hz, 1H), 3.84 (br d, J=11.1 Hz, 1H), 3.52 (br t, J=11.7 Hz, 1H), 3.44 (br d, J=8.1 Hz, 1H), 3.26 (br t, J=11.7 Hz, 1H), 2.21 (s, 3H), 1.98-1.91 (m, 1H), 1.91-1.77 (m, 2H), 0.51 (br d, J=12.7 Hz, 1H); LCMS (M+H)=572; HPLC RT=2.383 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=11.7 min (Column: Chiral OD-H, 250×4.6 mm, 5 μm; Mobile Phase: 80/20 CO$_2$/MeOH; Flow: 2 mL/min)

Examples 68 and 69

13-Ethoxy-8-[(3-fluoropyridin-2-yl)(oxan-4-yl)methyl]-10-methanesulfonyl-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene

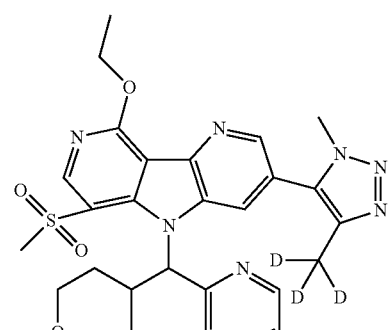

Example 68
Enantiomer A

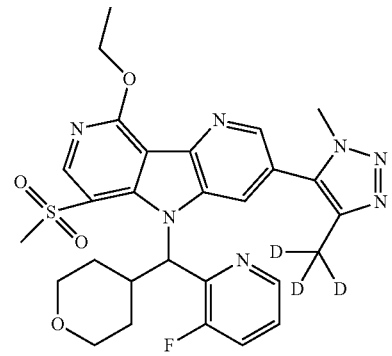 [SMILES: [2H]C([2H])([2H])c1nnn(C)c1-c1cnc2c3c(OCC)ncc(S(C)(=O)=O)c3n([C@H](c3ccccc3F)C3CCOCC3)c2c1]

Example 69
Enantiomer B

Following procedures analogous to those described for 5-(dimethyl-1H-1,2,3-triazol-5-yl)-13-ethoxy-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaene, 8-[(3-fluoropyridin-2-yl)(oxan-4-yl)methyl]-10-methanesulfonyl-13-methoxy-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene (42 mg, 0.074 mmol) was converted to the racemic title compound. Chiral separation was performed on the racemic compound on chiral preparative SFC to give enantiomer A (15.3 mg, 35.6%) and enantiomer B (15.8 mg, 36%). Enantiomer A: $^1$H NMR (500 MHz, CDCl$_3$) δ 9.05 (s, 1H), 8.68 (d, J=1.7 Hz, 1H), 8.53-8.48 (m, 1H), 7.98 (d, J=1.8 Hz, 1H), 7.40-7.29 (m, 3H), 4.94 (q, J=7.0 Hz, 2H), 4.05-4.00 (m, 1H), 3.91 (s, 3H), 3.84 (br dd, J=11.4, 3.1 Hz, 1H), 3.50 (td, J=11.4, 3.2 Hz, 1H), 3.45 (s, 3H), 3.41 (br d, J=12.2 Hz, 1H), 3.24 (td, J=11.9, 2.1 Hz, 1H), 1.92-1.80 (m, 3H), 1.63 (t, J=7.0 Hz, 3H), 0.53 (br d, J=11.3 Hz, 1H); LCMS (M+H)=583; HPLC RT=2.352 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=10.8 min (Column: Chiral OD-H, 250×4.6 mm, 5 μm; Mobile Phase: 80/20 CO$_2$/MeOH; Flow: 2 mL/min). Enantiomer B: $^1$H NMR (500 MHz, CDCl$_3$) δ 9.05 (s, 1H), 8.68 (d, J=1.8 Hz, 1H), 8.52-8.48 (m, 1H), 7.98 (d, J=1.8 Hz, 1H), 7.40-7.29 (m, 3H), 4.94 (q, J=7.0 Hz, 2H), 4.02 (br d, J=11.1 Hz, 1H), 3.91 (s, 3H), 3.84 (br dd, J=11.4, 3.2 Hz, 1H), 3.50 (td, J=11.4, 3.2 Hz, 1H), 3.45 (s, 3H), 3.43-3.36 (m, 1H), 3.24 (td, J=11.9, 2.1 Hz, 1H), 1.93-1.80 (m, 3H), 1.63 (t, J=7.0 Hz, 3H), 0.53 (br d, J=13.0 Hz, 1H); LCMS (M+H)=583; HPLC RT=2.353 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=11.2 min (Column: Chiral OD-H, 250×4.6 mm, 5 μm; Mobile Phase: 80/20 CO$_2$/MeOH; Flow: 2 mL/min)

Examples 70 and 71

8-[(3-Fluoropyridin-2-yl)(oxan-4-yl)methyl]-10-methanesulfonyl-5-[4-($^2$H$_3$)methyl-1-methyl-1H-1,2,3-triazol-5-yl]-13-(propan-2-yloxy)-3,8,12-triazatricyclo[7.4.0.0$^{2,7}$]trideca-1(13),2(7),3,5,9,11-hexaene

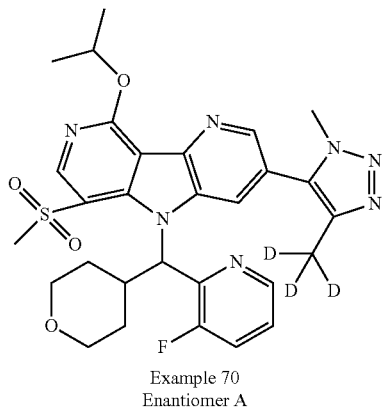

Example 70
Enantiomer A

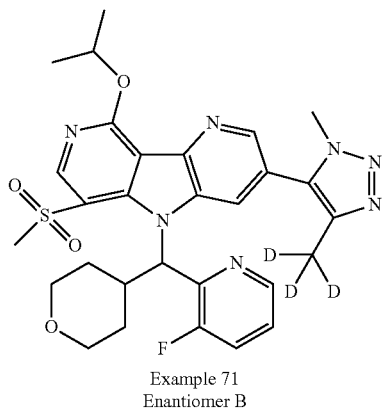

Example 71
Enantiomer B

Following procedures analogous to those described for 10-methanesulfonyl-5-[4-($^2$H$_3$)methyl-1-methyl-1H-1,2,3-triazol-5-yl]-8-[(S)-oxan-4-yl(phenyl)methyl]-13-(propan-2-yloxy)-3,8,12-triazatricyclo[7.4.0.0$^{2,7}$]trideca-1(13),2(7),3,5,9,11-hexaene, 8-[(3-fluoropyridin-2-yl)(oxan-4-yl)methyl]-10-methanesulfonyl-13-methoxy-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene (42 mg, 0.074 mmol) was converted to the racemic title compound. Chiral separation was performed on the racemic compound on chiral preparative SFC to give enantiomer A (9.0 mg, 20.4%) and enantiomer B (11.2 mg, 25.5%). Enantiomer A: $^1$H NMR (500 MHz, CDCl$_3$) δ 9.04 (s, 1H), 8.65 (d, J=1.7 Hz, 1H), 8.53-8.47 (m, 1H), 7.94 (d, J=1.8 Hz, 1H), 7.38-7.29 (m, 3H), 5.83 (spt, J=6.3 Hz, 1H), 4.06-3.99 (m, 1H), 3.90 (s, 3H), 3.84 (br dd, J=11.5, 3.0 Hz, 1H), 3.50 (td, J=11.4, 3.1 Hz, 1H), 3.44 (s, 3H), 3.43-3.35 (m, 1H), 3.24 (td, J=11.9, 2.0 Hz, 1H), 1.93-1.80 (m, 3H), 1.62 (dd, J=9.5, 6.3 Hz, 6H), 0.54 (br d, J=11.3 Hz, 1H); LCMS (M+H)=597; HPLC RT=2.532 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=10.0 min (Column: Chiral OD-H, 250×4.6 mm, 5 μm; Mobile Phase: 80/20 CO$_2$/MeOH; Flow: 2 mL/min). Enantiomer B: $^1$H NMR (500 MHz, CDCl$_3$) δ 9.04 (s, 1H), 8.65 (d, J=1.8 Hz, 1H), 8.52-8.48 (m, 1H), 7.94 (d, J=1.8 Hz, 1H), 7.38-7.30 (m, 3H), 5.83 (spt, J=6.3 Hz, 1H), 4.06-3.98 (m, 1H), 3.90 (s, 3H), 3.84 (br dd, J=11.2, 3.0 Hz, 1H), 3.50 (td, J=11.4, 3.1 Hz, 1H), 3.44 (s, 3H), 3.42-3.35 (m, 1H), 3.24 (td, J=12.0, 2.0 Hz, 1H), 1.92-1.83 (m, 3H), 1.62 (dd, J=9.6, 6.3 Hz, 6H), 0.54 (br d, J=12.8 Hz, 1H); LCMS (M+H)=597; HPLC RT=2.537 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=12.5 min (Column: Chiral OD-H, 250×4.6 mm, 5 μm; Mobile Phase: 80/20 CO$_2$/MeOH; Flow: 2 mL/min)

Examples 72 and 73

8-[(4,4-Difluorocyclohexyl)(3-fluoropyridin-2-yl)methyl]-10-methanesulfonyl-13-methoxy-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene

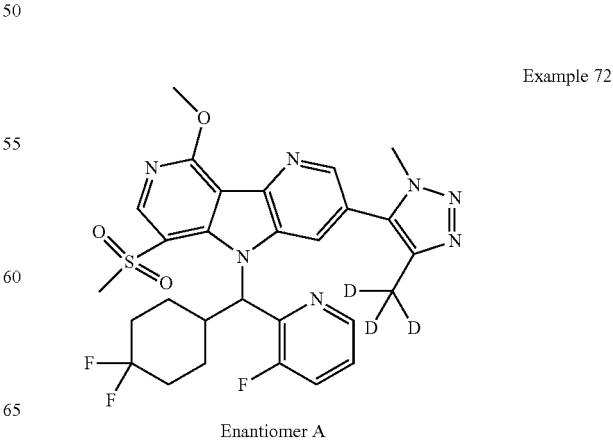

Example 72
Enantiomer A

-continued

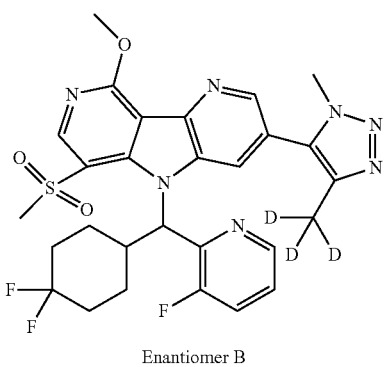

Example 73
Enantiomer B

Step 1: 5-Bromo-8-[(4,4-difluorocyclohexyl)(3-fluoropyridin-2-yl)methyl]-10-methanesulfonyl-13-methoxy-3,8,12-triazatricyclo[7.4.0.0²,⁷]trideca-1(13),2(7),3,5,9,11-hexaene Following procedures analogous to those described for 5-bromo-10-methanesulfonyl-13-methoxy-8-[(S)-oxan-4-yl(phenyl)methyl]-3,8,12-triazatricyclo[7.4.0.0²,⁷]trideca-1(13),2(7),3,5,9,11-hexaene, 5-bromo-10-methanesulfonyl-13-methoxy-3,8,12-triazatricyclo[7.4.0.0²,⁷]trideca-1(13),2(7),3,5,9,11-hexaene (100 mg, 0.281 mmol) and racemic (4,4-difluorocyclohexyl)(3-fluoropyridin-2-yl)methanol (138 mg, 0.561 mmol) was converted to the title compound.

Step 2: 8-[(4,4-Difluorocyclohexyl)(3-fluoropyridin-2-yl)methyl]-10-methanesulfonyl-13-methoxy-5-[4-(²H₃)methyl-1-methyl-1H-1,2,3-triazol-5-yl]-3,8,12-triazatricyclo[7.4.0.0²,⁷]trideca-1(13),2(7),3,5,9,11-hexaene Following procedures analogous to those described for 8-[(3-fluoropyridin-2-yl)(oxan-4-yl)methyl]-10-methanesulfonyl-13-methoxy-5-[4-(²H₃)methyl-1-methyl-1H-1,2,3-triazol-5-yl]-3,8,12-triazatricyclo[7.4.0.0²,⁷]trideca-1(13),2(7),3,5,9,11-hexaene, 5-bromo-8-[(4,4-difluorocyclohexyl)(3-fluoropyridin-2-yl)methyl]-10-methanesulfonyl-13-methoxy-3,8,12-triazatricyclo[7.4.0.0²,⁷]trideca-1(13),2(7),3,5,9,11-hexaene (164 mg, 0.281 mmol) was converted to the racemic title compound (92.1 mg, 54.4%). Chiral separation was performed on the racemic compound (46 mg, 0.076 mmol) on chiral preparative SFC to give enantiomer A (23 mg, 49.5%) and enantiomer B (21.6 mg, 47%). Enantiomer A: ¹H NMR (400 MHz, CDCl₃) δ 9.08 (s, 1H), 8.68 (d, J=1.8 Hz, 1H), 8.52 (dt, J=3.9, 1.8 Hz, 1H), 7.90 (d, J=1.8 Hz, 1H), 7.39-7.34 (m, 2H), 7.33-7.28 (m, 2H), 4.42 (s, 3H), 3.90 (s, 3H), 3.45 (s, 3H), 3.36-3.24 (m, 1H), 2.17 (br s, 1H), 2.07 (br d, J=6.0 Hz, 1H), 2.03-1.81 (m, 4H), 0.79 (br d, J=13.2 Hz, 1H); LCMS (M+H)=603; HPLC RT=2.690 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=7.0 min (Column: Chiral AS, 250×4.6 mm, 5 μm; Mobile Phase: 80/20 CO₂/MeOH; Flow: 2 mL/min). Enantiomer B: ¹H NMR (400 MHz, CDCl₃) δ 9.08 (s, 1H), 8.68 (d, J=1.8 Hz, 1H), 8.52 (dt, J=3.9, 1.8 Hz, 1H), 7.90 (d, J=1.8 Hz, 1H), 7.39-7.34 (m, 2H), 7.33-7.28 (m, 2H), 4.42 (s, 3H), 3.90 (s, 3H), 3.45 (s, 3H), 3.36-3.23 (m, 1H), 2.18 (br s, 1H), 2.07 (br d, J=6.0 Hz, 1H), 2.02-1.80 (m, 4H), 0.79 (br d, J=16.1 Hz, 1H); LCMS (M+H)=603; HPLC RT=2.690 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=10.9 min (Column: Chiral AS, 250×4.6 mm, 5 μm; Mobile Phase: 80/20 CO₂/MeOH; Flow: 2 mL/min)

Examples 74 and 75

8-[(4,4-Difluorocyclohexyl)(3-fluoropyridin-2-yl)methyl]-13-ethoxy-10-methanesulfonyl-5-[4-(²H₃)methyl-1-methyl-1H-1,2,3-triazol-5-yl]-3,8,12-triazatricyclo[7.4.0.0²,⁷]trideca-1(13),2(7),3,5,9,11-hexaene

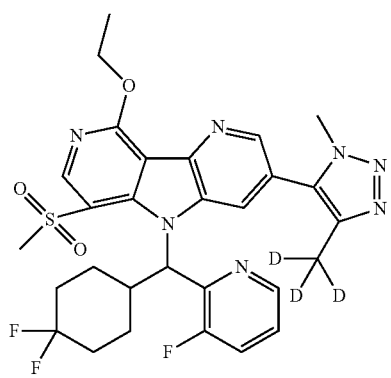

Example 74
Enantiomer A

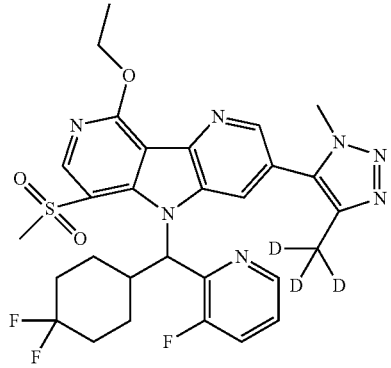

Example 75
Enantiomer B

Following procedures analogous to those described for 5-(dimethyl-1H-1,2,3-triazol-5-yl)-13-ethoxy-10-methanesulfonyl-8-[(S)-oxan-4-yl(phenyl)methyl]-3,8,12-triazatricyclo[7.4.0.0²,⁷]trideca-1(13),2(7),3,5,9,11-hexaene, 8-[(4,4-difluorocyclohexyl)(3-fluoropyridin-2-yl)methyl]-10-methanesulfonyl-13-methoxy-5-[4-(²H₃)methyl-1-methyl-1H-1,2,3-triazol-5-yl]-3,8,12-triazatricyclo[7.4.0.0²,⁷]trideca-1(13),2(7),3,5,9,11-hexaene (46 mg, 0.076 mmol) was converted to the racemic title compound. Chiral separation was performed on the racemic compound on chiral preparative SFC to give enantiomer A (18.6 mg, 39%) and enantiomer B (21.4 mg, 45.5%). Enantiomer A: ¹H NMR (400 MHz, CDCl₃) δ 9.05 (s, 1H), 8.67 (d, J=1.7 Hz, 1H), 8.55-8.50 (m, 1H), 7.88 (d, J=1.8 Hz, 1H), 7.38-7.34 (m, 2H), 7.31-7.29 (m, 1H), 4.94 (q, J=7.1 Hz, 2H), 3.89 (s, 3H), 3.45 (s, 3H), 3.29 (br d, J=12.8 Hz, 1H), 2.17 (br s, 1H), 2.07 (br d, J=6.0 Hz, 1H), 2.03-1.80 (m, 4H), 1.63 (t, J=7.0 Hz, 4H), 0.79 (br d, J=13.3 Hz, 1H); LCMS (M+H)=617; HPLC RT=2.831 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=7.5 min (Column: Chiral AS, 250×4.6 mm, 5 μm; Mobile Phase: 80/20 CO$_2$/MeOH; Flow: 2 mL/min). Enantiomer B: $^1$H NMR (400 MHz, CDCl$_3$) δ 9.05 (s, 1H), 8.68 (d, J=1.8 Hz, 1H), 8.54-8.49 (m, 1H), 7.88 (d, J=1.7 Hz, 1H), 7.38-7.34 (m, 2H), 7.30 (dd, J=1.9, 1.0 Hz, 1H), 4.94 (q, J=7.0 Hz, 2H), 3.89 (s, 3H), 3.45 (s, 3H), 3.35-3.23 (m, 1H), 2.17 (br s, 1H), 2.11-2.05 (m, 1H), 2.03-1.81 (m, 4H), 1.63 (t, J=7.0 Hz, 4H), 0.80 (br d, J=14.3 Hz, 1H); LCMS (M+H)=617; HPLC RT=2.840 min (Column: Chromolith ODS S5 4.6×50 mm; Mobile Phase A: 10:90 MeOH:water with 0.1% TFA; Mobile Phase B: 90:10 MeOH:water with 0.1% TFA; Temperature: 40° C.; Gradient: 0-100% B over 4 min; Flow: 4 mL/min); SFC RT=14.2 min (Column: Chiral AS, 250×4.6 mm, 5 μm; Mobile Phase: 80/20 CO$_2$/MeOH; Flow: 2 mL/min).

Examples 76 through 96 were synthesized using the procedures described for the synthesis of Examples 45, 46, 47, and 56.

Example 76

13-(Cyclopropylmethoxy)-8-[(S)-(2-fluorophenyl) (oxan-4-yl)methyl]-10-methanesulfonyl-5-[4-($^2$H$_3$) methyl-1-methyl-1H-1,2,3-triazol-5-yl]-3,8,12-triazatricyclo[7.4.0.0$^{2,7}$]trideca-1(13),2(7),3,5,9,11-hexaene

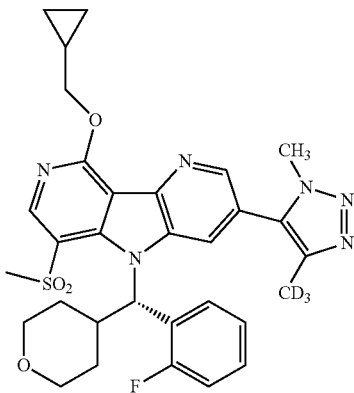 [SMILES: [2H]C([2H])([2H])c1nnn(C)c1-c1cnc2c3c(OCC4CC4)ncc(S(C)(=O)=O)c3n([C@H](c3ccccc3F)C3CCOCC3)c2c1]

LCMS: RT=1.736 min; (ES): m/z (M+H)$^+$=608.15: Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75-min hold at 100% B; Flow: 1.11 mL/min. $^1$H NMR (500 MHz, DMSO-d6) δ 8.91 (s, 1H), 8.71 (s, 1H), 8.20-8.10 (m, 1H), 7.96 (s, 1H), 7.42-7.31 (m, 2H), 7.12-7.01 (m, 1H), 6.92 (d, J=10.4 Hz, 1H), 4.59-4.52 (m, 2H), 3.89 (d, J=8.1 Hz, 1H), 3.81-3.69 (m, 4H), 3.59 (s, 3H), 3.55-3.43 (m, 2H), 3.32-3.21 (m, 1H), 1.85 (d, J=12.1 Hz, 1H), 1.75 (m, 2H), 1.51-1.38 (m, 1H), 0.67 (d, J=11.1 Hz, 1H), 0.61 (d, J=6.7 Hz, 2H), 0.46 (d, J=3.7 Hz, 2H).

Example 77

13-Ethoxy-8-[(S)-(4-fluorophenyl)(oxan-4-yl) methyl]-10-methanesulfonyl-5-[4-($^2$H$_3$)methyl-1-methyl-1H-1,2,3-triazol-5-yl]-3,8,12-triazatricyclo [7.4.0.0$^{2,7}$]trideca-1(13),2(7),3,5,9,11-hexaene

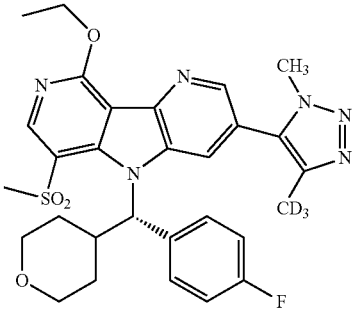 [SMILES: [2H]C([2H])([2H])c1nnn(C)c1-c1cnc2c3c(OCC)ncc(S(C)(=O)=O)c3n([C@H](c3ccc(F)cc3)C3CCOCC3)c2c1]

LCMS: RT=1.615 min; (ES): m/z (M+H)$^+$=582.25.: Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75-min hold at 100% B; Flow: 1.11 mL/min. $^1$H NMR (500 MHz, DMSO-d6) δ 8.90 (s, 1H), 8.73 (s, 1H), 7.89 (s, 1H), 7.73-7.63 (m, 2H), 7.19 (t, J=8.8 Hz, 2H), 6.68 (d, J=10.4 Hz, 1H), 4.75 (q, J=6.7 Hz, 2H), 3.88 (d, J=12.5 Hz, 1H), 3.82 (s, 3H), 3.72 (s, 3H), 3.66 (d, J=8.4 Hz, 1H), 3.56-3.40 (m, 2H), 3.19 (t, J=11.3 Hz, 1H), 1.94 (d, J=13.1 Hz, 1H), 1.72-1.53 (m, 2H), 1.49 (t, J=7.1 Hz, 3H), 0.44 (d, J=12.5 Hz, 1H).

Example 78

13-(Cyclopropylmethoxy)-8-[(S)-(4-fluorophenyl) (oxan-4-yl)methyl]-10-methanesulfonyl-5-[4-($^2$H$_3$) methyl-1-methyl-1H-1,2,3-triazol-5-yl]-3,8,12-triazatricyclo[7.4.0.0$^{2,7}$]trideca-1(13),2(7),3,5,9,11-hexaene

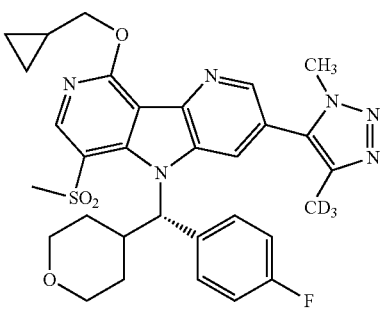 [SMILES: [2H]C([2H])([2H])c1nnn(C)c1-c1cnc2c3c(OCC4CC4)ncc(S(C)(=O)=O)c3n([C@H](c3ccc(F)cc3)C3CCOCC3)c2c1]

LCMS: RT=1.551 min; (ES): m/z (M+H)$^+$=608.00: Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75-min hold at 100% B; Flow: 1.11 mL/min. $^1$H NMR (500 MHz, DMSO-d6) δ 8.88 (s, 1H), 8.75 (d, J=1.2 Hz, 1H), 7.89 (d, J=1.5 Hz, 1H), 7.69 (dd, J=8.4, 5.3

Hz, 2H), 7.19 (t, J=8.7 Hz, 2H), 6.69 (d, J=10.1 Hz, 1H), 4.55 (d, J=7.0 Hz, 2H), 3.88 (d, J=8.5 Hz, 1H), 3.82 (s, 3H), 3.71 (s, 3H), 3.66 (dd, J=11.6, 3.4 Hz, 1H), 3.55-3.50 (m, 2H), 3.23-3.14 (m, 1H), 1.94 (d, J=12.8 Hz, 1H), 1.70-1.52 (m, 2H), 1.50-1.39 (m, 1H), 0.65-0.57 (m, 2H), 0.49-0.42 (m, J=4.6 Hz, 3H).

Example 79

8-[(S)-(4-Fluorophenyl)(oxan-4-yl)methyl]-10-methanesulfonyl-5-[4-($^2$H$_3$)methyl-1-methyl-1H-1,2,3-triazol-5-yl]-13-(propan-2-yloxy)-3,8,12-triazatricyclo[7.4.0.0$^{2,7}$]trideca-1(13),2(7),3,5,9,11-hexaene

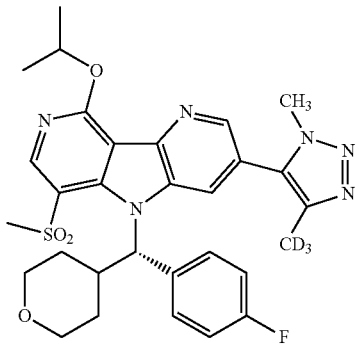 [SMILES: [2H]C([2H])([2H])c1nnn(C)c1-c1cnc2c3c(OC(C)C)ncc(S(C)(=O)=O)c3n([C@H](c3ccc(F)cc3)C3CCOCC3)c2c1]

LCMS: RT=1.544 min; (ES): m/z (M+H)$^+$=596.1: Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75-min hold at 100% B; Flow: 1.11 mL/min. $^1$H NMR (500 MHz, DMSO-d6) δ 8.88 (s, 1H), 8.73 (d, J=1.5 Hz, 1H), 7.86 (d, J=1.5 Hz, 1H), 7.68 (dd, J=8.2, 5.5 Hz, 2H), 7.19 (t, J=8.7 Hz, 2H), 6.68 (d, J=10.1 Hz, 1H), 5.80-5.68 (m, 1H), 3.92-3.85 (m, 1H), 3.82 (s, 3H), 3.70 (s, 3H), 3.66 (d, J=11.0 Hz, 2H), 3.57-3.50 (m, 2H), 3.23-3.15 (m, 1H), 1.94 (d, J=13.1 Hz, 1H), 1.69-1.53 (m, 2H), 1.48 (t, J=5.5 Hz, 6H), 0.49-0.41 (m, 1H).

Example 80

8-[(S)-(2-Fluorophenyl)(oxan-4-yl)methyl]-10-methanesulfonyl-5-[4-($^2$H$_3$)methyl-1-methyl-1H-1,2,3-triazol-5-yl]-13-(propan-2-yloxy)-3,8,12-triazatricyclo[7.4.0.0$^{2,7}$]trideca-1(13),2(7),3,5,9,11-hexaene

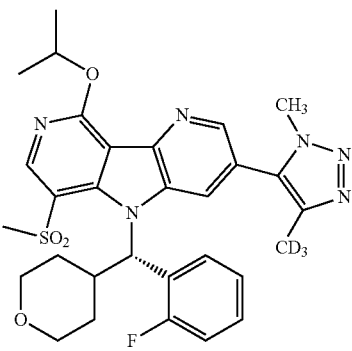 [SMILES: [2H]C([2H])([2H])c1nnn(C)c1-c1cnc2c3c(OC(C)C)ncc(S(C)(=O)=O)c3n([C@H](c3ccccc3F)C3CCOCC3)c2c1]

LCMS: RT=1.739 min; (ES): m/z (M+H)+=596.1: Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75-min hold at 100% B; Flow: 1.11 mL/min. $^1$H NMR (500 MHz, DMSO-d6) δ 8.92 (s, 1H), 8.70 (d, J=0.9 Hz, 1H), 8.18-8.12 (m, 1H), 7.95 (s, 1H), 7.41-7.33 (m, 2H), 7.06 (dd, J=11.6, 9.2 Hz, 1H), 6.91 (d, J=10.1 Hz, 1H), 5.76 (quin, J=6.2 Hz, 1H), 3.93-3.86 (m, 1H), 3.76 (s, 3H), 3.73 (d, J=7.6 Hz, 1H), 3.59 (s, 3H), 3.57-3.51 (m, 2H), 3.27 (t, J=11.1 Hz, 1H), 1.85 (d, J=12.8 Hz, 2H), 1.76 (d, J=10.4 Hz, 1H), 1.48 (d, J=6.1 Hz, 6H), 0.71-0.63 (m, 1H).

Example 81

8-[(S)-(4,4-Difluorocyclohexyl)(phenyl)methyl]-10-methanesulfonyl-13-methoxy-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene

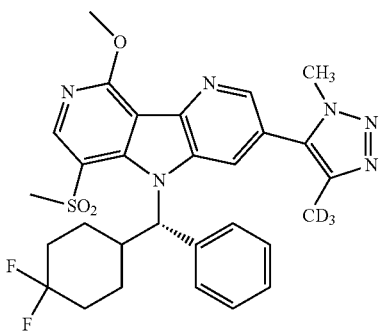

LCMS: RT=0.89 min; (ES): m/z (M+H)$^+$=584.2: (Waters Acquity SDS. Column: BEH C18 2.1×50 mm 1.7 u (1.6 min grad) 2-98% B. Flow Rate=0.8 mL/min. Solvent A: H$_2$O—0.1% TFA. Solvent B: ACN—0.1% TFA). HPLC RT=11.87 min (Column: Sunfire C18 3.5 μm, 3.0×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). HPLC RT=11.67 min. (Column: XBridge Phenyl 3.5 μm, 3.0×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). 1H NMR (400 MHz, CD$_3$OD) δ 9.01 (s, 1H), 8.70 (d, J=1.7 Hz, 1H), 7.52-7.46 (m, 2H), 7.45-7.34 (m, 4H), 6.94 (d, J=9.9 Hz, 1H), 4.44 (s, 3H), 3.70 (s, 3H), 3.43 (s, 3H), 2.80 (d, J=10.5 Hz, 1H), 2.43-2.21 (m, 2H), 2.05-1.84 (m, 3H), 1.72-1.19 (m, 3H). Chiral SFC RT=6.389 min (Column: Chiral OD-H 250×4.6 mm ID, 5 mm, Flow rate: 2.0 mL/min, Mobile Phase: 70/30 CO$_2$/MeOH).

Example 82

8-[(R)-(4,4-Difluorocyclohexyl)(phenyl)methyl]-10-methanesulfonyl-13-methoxy-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene

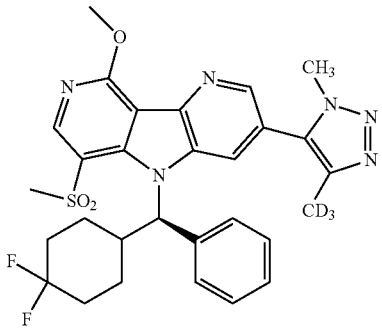 [SMILES: [2H]C([2H])([2H])c1nnn(C)c1-c1cnc2c3c(OC)ncc(S(C)(=O)=O)c3n([C@@H](c3ccccc3)C3CCC(F)(F)CC3)c2c1]

LCMS: RT=0.89 min; (ES): m/z (M+H)$^+$=584.2: (Waters Acquity SDS. Column: BEH C18 2.1×50 mm 1.7 u (1.6 min grad) 2-98% B. Flow Rate=0.8 mL/min. Solvent A: H$_2$O—0.1% TFA. Solvent B: ACN—0.1% TFA). HPLC RT=11.87 min (Column: Sunfire C18 3.5 μm, 3.0×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). HPLC RT=11.67 min. (Column: XBridge Phenyl 3.5 μm, 3.0×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). 1H NMR (400 MHz, CD$_3$OD) δ 9.01 (s, 1H), 8.70 (d, J=1.7 Hz, 1H), 7.52-7.46 (m, 2H), 7.45-7.34 (m, 4H), 6.94 (d, J=9.9 Hz, 1H), 4.44 (s, 3H), 3.70 (s, 3H), 3.43 (s, 3H), 2.80 (d, J=10.5 Hz, 1H), 2.43-2.21 (m, 2H), 2.05-1.84 (m, 3H), 1.72-1.19 (m, 3H). Chiral SFC RT=11.069 min (Column: Chiral OD-H 250×4.6 mm ID, 5 mm, Flow rate: 2.0 mL/min, Mobile Phase: 70/30 CO$_2$/MeOH).

Example 83

10-Methanesulfonyl-13-methoxy-5-[4-($^2$H$_3$)methyl-1-methyl-1H-1,2,3-triazol-5-yl]-8-[oxan-4-yl(2,4,6-trifluorophenyl)methyl]-3,8,12-triazatricyclo[7.4.0.0$^{2,7}$]trideca-1(13),2(7),3,5,9,11-hexaene—Enantiomer 1

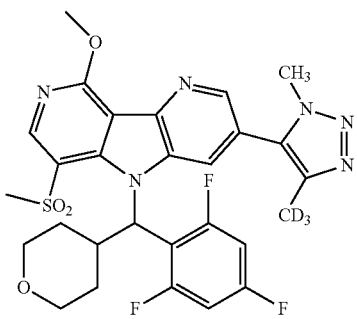 [SMILES: [2H]C([2H])([2H])c1nnn(C)c1-c1cnc2c3c(OC)ncc(S(C)(=O)=O)c3n(C(c3c(F)cc(F)cc3F)C3CCOCC3)c2c1]

LCMS: RT=1.515 min; (ES): m/z (M+H)$^+$=604.1: (Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75-min hold at 100% B; Flow: 1.11 mL/min.). $^1$H NMR (500 MHz, DMSO-d6) δ 9.00 (s, 1H), 8.77 (s, 1H), 8.04 (s, 1H), 7.38 (d, J=11.1 Hz, 1H), 7.26 (t, J=9.9 Hz, 2H), 4.23 (s, 3H), 4.01-3.86 (m, 4H), 3.72 (d, J=10.4 Hz, 1H), 3.57 (s, 1H), 3.52-3.36 (m, 2H), 3.31-3.19 (m, 1H), 1.82-1.49 (m, 3H), 0.82 (d, J=12.5 Hz, 1H). Chiral HPLC RT=7.53 min (Column: Chiralcel OD-H 250×4.6 mm, 5 μm; Mobile Phase: 45% Ethanol in Heptane (0.1% DEA); Flow: 1 mL/min).

Example 84

10-Methanesulfonyl-13-methoxy-5-[4-($^2$H$_3$)methyl-1-methyl-1H-1,2,3-triazol-5-yl]-8-[oxan-4-yl(2,4,6-trifluorophenyl)methyl]-3,8,12-triazatricyclo[7.4.0.0$^{2,7}$]trideca-1(13),2(7),3,5,9,11-hexaene—Enantiomer 2

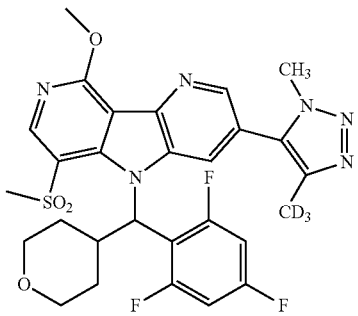 [SMILES: [2H]C([2H])([2H])c1nnn(C)c1-c1cnc2c3c(OC)ncc(S(C)(=O)=O)c3n(C(c3c(F)cc(F)cc3F)C3CCOCC3)c2c1]

LCMS: RT=1.515 min; (ES): m/z (M+H)$^+$=604.1: (Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75-min hold at 100% B; Flow: 1.11 mL/min.). $^1$H NMR (500 MHz, DMSO-d6) δ 9.00 (s, 1H), 8.77 (s, 1H), 8.04 (s, 1H), 7.38 (d, J=11.1 Hz, 1H), 7.26 (t, J=9.9 Hz, 2H), 4.23 (s, 3H), 4.01-3.86 (m, 4H), 3.72 (d, J=10.4 Hz, 1H), 3.57 (s, 1H), 3.52-3.36 (m, 2H), 3.31-3.19 (m, 1H), 1.82-1.49 (m, 3H), 0.82 (d, J=12.5 Hz, 1H). Chiral HPLC RT=9.34 min (Column: Chiralcel OD-H 250×4.6 mm, 5 μm; Mobile Phase: 45% Ethanol in Heptane (0.1% DEA); Flow: 1 mL/min).

Example 85

8-[(S)-(2-Fluorophenyl)(oxan-4-yl)methyl]-13-(3-fluoropropoxy)-10-methanesulfonyl-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene

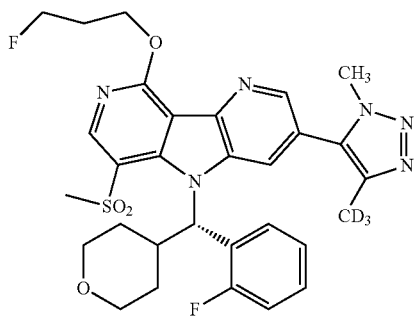 [SMILES: [2H]C([2H])([2H])c1nnn(C)c1-c1cnc2c3c(OCCCF)ncc(S(C)(=O)=O)c3n([C@H](c3ccccc3F)C3CCOCC3)c2c1]

LCMS: RT=1.457 min; (ES): m/z (M+H)$^+$=614.1: Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75-min hold at 100% B; Flow: 1.11 mL/min. $^1$H NMR (500 MHz, DMSO-d6) δ 8.92 (s, 1H), 8.67 (s, 1H), 8.13 (br. s., 1H), 7.95 (s, 1H), 7.36 (br. s., 2H), 7.11-6.99 (m, 1H), 6.91 (d, J=10.4 Hz, 1H), 4.84-4.73 (m, 3H), 4.69 (t, J=5.7 Hz, 1H), 3.89 (d, J=7.1 Hz, 1H), 3.74 (s, 3H), 3.70-3.61 (m, 2H), 3.58 (s, 3H), 3.51 (t, J=11.3 Hz, 1H), 3.26 (t, J=11.4 Hz, 1H), 2.34-2.21 (m, 2H), 1.89-1.69 (m, 3H), 0.66 (d, J=12.1 Hz, 1H).

Example 86

8-[(3-Fluorophenyl)(oxan-4-yl)methyl]-10-methanesulfonyl-13-methoxy-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene—Enantiomer 1

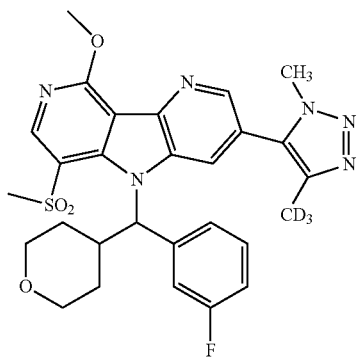 [SMILES: [2H]C([2H])([2H])c1nnn(C)c1-c1cnc2c3c(OC)ncc(S(C)(=O)=O)c3n(C(c3cccc(F)c3)C3CCOCC3)c2c1]

LCMS: RT=0.79 min; (ES): m/z (M+H)$^+$=568.2 (Waters Acquity SDS. Column: BEH C18 2.1×50 mm 1.7 u (1.6 min grad) 2-98% B. Flow Rate=0.8 mL/min. Solvent A: H$_2$O—0.1% TFA. Solvent B: ACN—0.1% TFA). HPLC RT=10.576 min (Column: Sunfire C18 3.5 μm, 3.0×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). HPLC RT=10.563 min. (Column: XBridge Phenyl 3.5 μm, 3.0×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). $^1$H NMR (400 MHz, CDCl$_3$) δ 9.00 (s, 1H), 8.73 (d, J=1.8 Hz, 1H), 7.51 (d, J=1.8 Hz, 1H), 7.44-7.36 (m, 1H), 7.35-7.21 (m, 2H), 7.11-7.04 (m, 1H), 6.95 (d, J=9.9 Hz, 1H), 4.44 (s, 3H), 4.08 (dd, J=11.0, 3.1 Hz, 1H), 3.84-3.76 (m, 4H), 3.59-3.48 (m, 1H), 3.42 (s, 3H), 3.29-3.16 (m, 1H), 2.93 (m, 1H), 2.16 (d, J=13.6 Hz, 1H), 1.95 (dd, J=12.9, 4.1 Hz, 1H), 1.68-1.54 (m, 1H), 0.40 (d, J=12.8 Hz, 1H). Chiral SFC RT=8.378 min (Column: Chiral OD-H 250×4.6 mm ID, 5 mm, Flow rate: 2.0 mL/min, Mobile Phase: 70/30 CO$_2$/MeOH).

Example 87

8-[(3-Fluorophenyl)(oxan-4-yl)methyl]-10-methanesulfonyl-13-methoxy-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene—Enantiomer 2

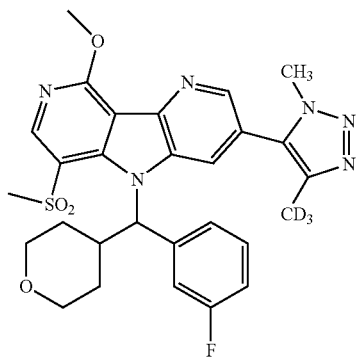 [SMILES: [2H]C([2H])([2H])c1nnn(C)c1-c1cnc2c3c(OC)ncc(S(C)(=O)=O)c3n(C(c3cccc(F)c3)C3CCOCC3)c2c1]

LCMS: RT=0.79 min; (ES): m/z (M+H)$^+$=568.2 (Waters Acquity SDS. Column: BEH C18 2.1×50 mm 1.7 u (1.6 min grad) 2-98% B. Flow Rate=0.8 mL/min. Solvent A: H$_2$O—0.1% TFA. Solvent B: ACN—0.1% TFA). HPLC RT=10.576 min (Column: Sunfire C18 3.5 μm, 3.0×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). HPLC RT=10.563 min. (Column: XBridge Phenyl 3.5 μm, 3.0×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). $^1$H NMR (400 MHz, CDCl$_3$) δ 9.00 (s, 1H), 8.73 (d, J=1.8 Hz, 1H), 7.51 (d, J=1.8 Hz, 1H), 7.44-7.36 (m, 1H), 7.35-7.21 (m, 2H), 7.11-7.04 (m, 1H), 6.95 (d, J=9.9 Hz, 1H), 4.44 (s, 3H), 4.08 (dd, J=11.0, 3.1 Hz, 1H), 3.84-3.76 (m, 4H), 3.59-3.48 (m, 1H), 3.42 (s, 3H), 3.29-3.16 (m, 1H), 2.93 (m, 1H), 2.16 (d, J=13.6 Hz, 1H), 1.95 (dd, J=12.9, 4.1 Hz, 1H), 1.68-1.54 (m, 1H), 0.40 (d, J=12.8 Hz, 1H). Chiral SFC RT=10.680 min (Column: Chiral OD-H 250×4.6 mm ID, 5 mm, Flow rate: 2.0 mL/min, Mobile Phase: 70/30 CO$_2$/MeOH).

Example 88

8-[(4,4-Difluorocyclohexyl)(phenyl)methyl]-5-(dimethyl-1,2-oxazol-4-yl)-10-methanesulfonyl-13-methoxy-3,8,12-triazatricyclo[7.4.0.0²,⁷]trideca-1(13),2(7),3,5,9,11-hexaene—Enantiomer 1

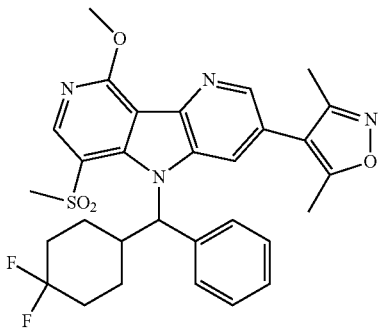 [SMILES: COc1ncc(S(C)(=O)=O)c2c1c1ncc(-c3c(C)noc3C)cc1n2C(c1ccccc1)C1CCC(F)(F)CC1]

LCMS: RT=1.95 min; (ES): m/z (M+H)+=581.1: (Column: Waters Acquity UPLC BEH C18, 2.1×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75-min hold at 100% B; Flow: 1.11 mL/min.). ¹H NMR (500 MHz, DMSO-d6) δ 8.89 (s, 1H), 8.63 (s, 1H), 7.71 (s, 1H), 7.61 (d, J=7.8 Hz, 2H), 7.43-7.33 (m, 2H), 7.32-7.25 (m, 1H), 6.70 (d, J=10.4 Hz, 1H), 4.23 (s, 3H), 3.71 (s, 3H), 2.26 (s, 3H), 2.13 (d, J=12.8 Hz, 3H), 2.06 (s, 4H), 1.84 (br. s., 1H), 1.65 (d, J=19.3 Hz, 3H), 0.66 (br. s., 1H). Chiral HPLC RT=18.1 min (Column: Chiralcel OD-H 250×4.6 mm, 5 μm; Mobile Phase: 14% Ethanol in Heptane (0.1% DEA); Flow: 1 mL/min).

Example 89

8-[(4,4-Difluorocyclohexyl)(phenyl)methyl]-5-(dimethyl-1,2-oxazol-4-yl)-10-methanesulfonyl-13-methoxy-3,8,12-triazatricyclo[7.4.0.0²,⁷]trideca-1(13),2(7),3,5,9,11-hexaene—Enantiomer 2

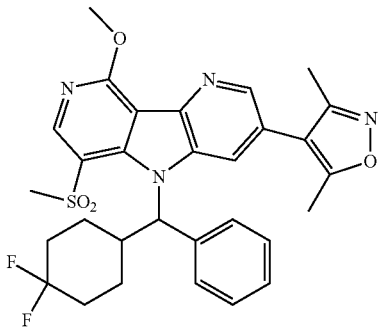 [SMILES: COc1ncc(S(C)(=O)=O)c2c1c1ncc(-c3c(C)noc3C)cc1n2C(c1ccccc1)C1CCC(F)(F)CC1]

LCMS: RT=1.95 min; (ES): m/z (M+H)+=581.1: (Column: Waters Acquity UPLC BEH C18, 2.1×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75-min hold at 100% B; Flow: 1.11 mL/min.). ¹H NMR (500 MHz, DMSO-d6) δ 8.89 (s, 1H), 8.63 (s, 1H), 7.71 (s, 1H), 7.61 (d, J=7.8 Hz, 2H), 7.43-7.33 (m, 2H), 7.32-7.25 (m, 1H), 6.70 (d, J=10.4 Hz, 1H), 4.23 (s, 3H), 3.71 (s, 3H), 2.26 (s, 3H), 2.13 (d, J=12.8 Hz, 3H), 2.06 (s, 4H), 1.84 (br. s., 1H), 1.65 (d, J=19.3 Hz, 3H), 0.66 (br. s., 1H). Chiral HPLC RT=20.2 min (Column: Chiralcel OD-H 250×4.6 mm, 5 μm; Mobile Phase: 14% Ethanol in Heptane (0.1% DEA); Flow: 1 mL/min).

Example 90

8-[(4,4-Difluorocyclohexyl)(phenyl)methyl]-5-(dimethyl-1H-1,2,3-triazol-5-yl)-10-methanesulfonyl-13-methoxy-3,8,12-triazatricyclo[7.4.0.0²,⁷]trideca-1(13),2(7),3,5,9,11-hexaene—Enantiomer 1

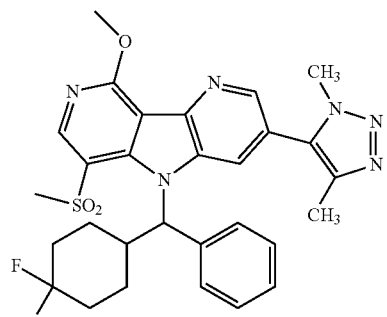

LCMS: RT=1.749 min; (ES): m/z (M+H)+=581.15.: (Column: Waters Acquity UPLC BEH C18, 2.1×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75-min hold at 100% B; Flow: 1.11 mL/min.). ¹H NMR (500 MHz, DMSO-d6) δ 8.92 (s, 1H), 8.71 (s, 1H), 7.86 (s, 1H), 7.60 (d, J=7.7 Hz, 2H), 7.40-7.34 (m, 2H), 7.32-7.26 (m, 1H), 6.71 (d, J=10.4 Hz, 1H), 4.24 (s, 3H), 3.77 (s, 3H), 3.72 (s, 3H), 2.17-2.04 (m, 7H), 1.85 (br. s., 1H), 1.67 (d, J=17.8 Hz, 3H), 0.71 (d, J=8.6 Hz, 1H). Chiral SFC RT=4.58 min (Column: Chiralpak IB, 250×4.6 mm, 5 μm; Mobile Phase: 70/30 CO₂/MeOH; Flow: 2 mL/min).

Example 91

8-[(4,4-Difluorocyclohexyl)(phenyl)methyl]-5-(dimethyl-1H-1,2,3-triazol-5-yl)-10-methanesulfonyl-13-methoxy-3,8,12-triazatricyclo[7.4.0.0²,⁷]trideca-1(13),2(7),3,5,9,11-hexaene—Enantiomer 2

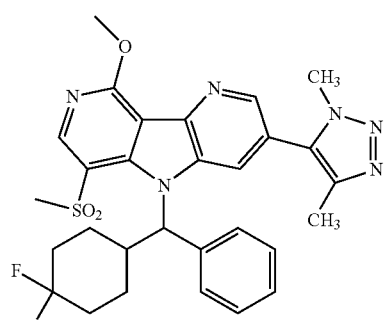

LCMS: RT=1.749 min; (ES): m/z (M+H)⁺=581.15.: (Column: Waters Acquity UPLC BEH C18, 2.1×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75-min hold at 100% B; Flow: 1.11 mL/min.). ¹H NMR (500 MHz, DMSO-d6) δ 8.92 (s, 1H), 8.71 (s, 1H), 7.86 (s, 1H), 7.60 (d, J=7.7 Hz, 2H), 7.40-7.34 (m, 2H), 7.32-7.26 (m, 1H), 6.71 (d, J=10.4 Hz, 1H), 4.24 (s, 3H), 3.77 (s, 3H), 3.72 (s, 3H), 2.17-2.04 (m, 7H), 1.85 (br. s., 1H), 1.67 (d, J=17.8 Hz, 3H), 0.71 (d, J=8.6 Hz, 1H). Chiral SFC RT=5.45 min (Column: Chiralpak IB, 250×4.6 mm, 5 μm; Mobile Phase: 70/30 CO₂/MeOH; Flow: 2 mL/min).

Example 92

8-[(S)-(4,4-Difluorocyclohexyl)(phenyl)methyl]-10-methanesulfonyl-5-[4-(²H₃)methyl-1-methyl-1H-1,2,3-triazol-5-yl]-3,8,12-triazatricyclo[7.4.0.0²,⁷]trideca-1(13),2(7),3,5,9,11-hexaen-13-ol

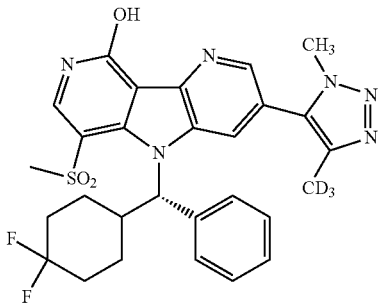 [SMILES: [2H]C([2H])([2H])c1nnn(C)c1-c1cnc2c3c(O)ncc(S(C)(=O)=O)c3n([C@H](c3ccccc3)C3CCC(F)(F)CC3)c2c1]

LCMS: RT=1.542 min; (ES): m/z (M+H)⁺=570.2 (Column: Waters Acquity UPLC BEH C18, 2.1×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75-min hold at 100% B; Flow: 1.11 mL/min.). ¹H NMR (500 MHz, DMSO-d6) δ 8.60 (s, 1H), 8.28 (br. s., 1H), 7.73 (s, 1H), 7.58 (d, J=7.7 Hz, 3H), 7.38 (t, J=7.6 Hz, 3H), 7.33-7.28 (m, 1H), 6.54 (d, J=10.3 Hz, 1H), 3.74 (s, 3H), 3.58 (s, 3H), 3.32 (d, J=11.4 Hz, 1H), 2.22-1.99 (m, 4H), 1.94-1.82 (m, 1H), 1.77-1.56 (m, 4H), 0.74 (br. s., 1H).

Example 93

5-(Dimethyl-1H-1,2,3-triazol-5-yl)-10-methanesulfonyl-8-[(S)-oxan-4-yl(phenyl)methyl]-3,8,12-triazatricyclo[7.4.0.0²,⁷]trideca-1(13),2(7),3,5,9,11-hexaen-13-ol

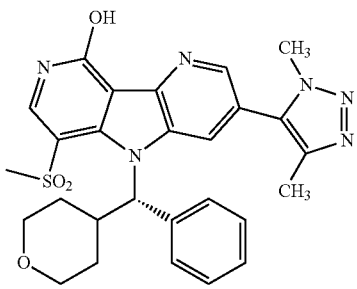 [SMILES: Cc1nnn(C)c1-c1cnc2c3c(O)ncc(S(C)(=O)=O)c3n([C@H](c3ccccc3)C3CCOCC3)c2c1]

LCMS: RT=1.13 min; (ES): m/z (M+H)⁺=533.2 (Column: Waters Acquity UPLC BEH C18, 2.1×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75-min hold at 100% B; Flow: 1.11 mL/min.). ¹H NMR (500 MHz, DMSO-d6) δ 8.60 (s, 1H), 8.28 (s, 1H), 7.78 (s, 1H), 7.61 (d, J=7.7 Hz, 2H), 7.42-7.35 (m, 2H), 7.33-7.27 (m, 1H), 6.56 (d, J=10.1 Hz, 1H), 3.88 (d, J=9.8 Hz, 1H), 3.75-3.67 (m, 4H), 3.59 (s, 3H), 3.52 (t, J=11.4 Hz, 1H), 3.42-3.34 (m, 1H), 3.22 (t, J=11.3 Hz, 1H), 2.06 (s, 3H), 1.98 (d, J=13.1 Hz, 1H), 1.92 (s, 1H), 1.74-1.53 (m, 2H), 0.48 (d, J=11.8 Hz, 1H).

Example 94

13-(Cyclopropylmethoxy)-8-[(S)-(4,4-difluorocyclohexyl)(phenyl)methyl]-10-methanesulfonyl-5-[4-(²H₃)methyl-1-methyl-1H-1,2,3-triazol-5-yl]-3,8,12-triazatricyclo[7.4.0.0²,⁷]trideca-1(13),2(7),3,5,9,11-hexaene

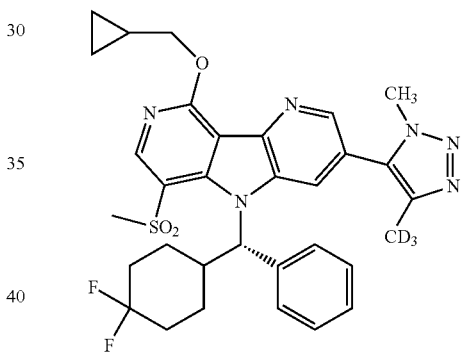

LCMS: RT=0.98 min; (ES): m/z (M+H)⁺=624.3: (Waters Acquity SDS. Column: BEH C18 2.1×50 mm 1.7 u (1.6 min grad) 2-98% B. Flow Rate=0.8 mL/min. Solvent A: H₂O—0.1% TFA. Solvent B: ACN—0.1% TFA). HPLC RT=13.529 min (Column: Sunfire C18 3.5 μm, 3.0×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). HPLC RT=13.169 min. (Column: XBridge Phenyl 3.5 μm, 3.0×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). 1H NMR (400 MHz, CDCl₃) δ 8.97 (s, 1H), 8.70 (d, J=1.8 Hz, 1H), 7.52-7.45 (m, 2H), 7.43-7.33 (m, 4H), 6.93 (d, J=9.9 Hz, 1H), 4.81-4.67 (m, 2H), 3.69 (s, 3H), 3.42 (s, 3H), 2.80 (d, J=10.3 Hz, 1H), 2.37 (d, J=9.8 Hz, 1H), 2.26 (br. s., 1H), 2.02-1.90 (m, 3H), 1.69-1.53 (m, 2H), 0.95-0.84 (m, 1H), 0.76-0.61 (m, 3H), 0.60-0.52 (m, 2H).

Example 95

8-[(S)-(4,4-Difluorocyclohexyl)(4-fluorophenyl)methyl]-10-methanesulfonyl-13-methoxy-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene

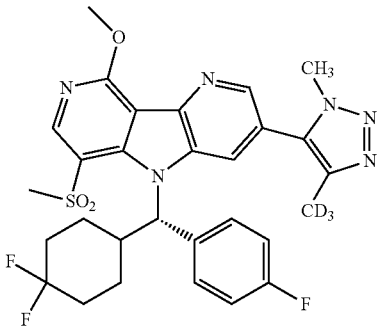

LCMS: RT=0.90 min; (ES): m/z (M+H)$^+$ 602.2: (Waters Acquity SDS. Column: BEH C18 2.1×50 mm 1.7 u (1.6 min grad) 2-98% B. Flow Rate=0.8 mL/min. Solvent A: H$_2$O—0.1% TFA. Solvent B: ACN—0.1% TFA). HPLC RT=10.849 min (Column: Sunfire C18 3.5 µm, 3.0×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). HPLC RT=10.483 min. (Column: XBridge Phenyl 3.5 µm, 3.0×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). 1H NMR (400 MHz, CDCl$_3$) δ 8.97 (s, 1H), 8.72 (d, J=1.8 Hz, 1H), 7.53 (dd, J=8.5, 5.1 Hz, 2H), 7.46 (d, J=1.8 Hz, 1H), 7.12 (t, J=8.6 Hz, 2H), 6.91 (d, J=10.0 Hz, 1H), 4.44 (s, 3H), 3.79 (s, 3H), 3.46 (s, 3H), 2.78 (d, J=9.7 Hz, 1H), 2.37-2.19 (m, 2H), 2.06-1.82 (m, 3H), 1.36-1.23 (m, 2H), 0.60 (d, J=9.7 Hz, 1H). Chiral SFC RT=12.40 min (Column: Chiralcel OD-H 250×4.6 mm, 5 µm; Mobile Phase: 80/20 CO$_2$/MeOH; Flow: 2 mL/min).

Example 96

8-[(R)-(4,4-Difluorocyclohexyl)(4-fluorophenyl)methyl]-10-methanesulfonyl-13-methoxy-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene

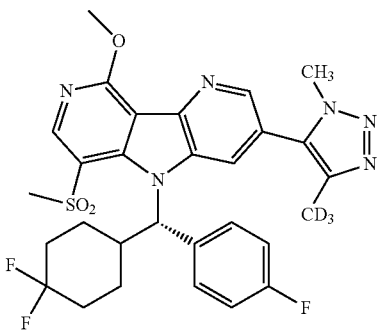 [SMILES: [2H]C([2H])([2H])c1nnn(C)c1-c1cnc2c3c(OC)ncc(S(C)(=O)=O)c3n([C@H](c3ccc(F)cc3)C3CCC(F)(F)CC3)c2c1]

LCMS: RT=0.90 min; (ES): m/z (M+H)$^+$ 602.2: (Waters Acquity SDS. Column: BEH C18 2.1×50 mm 1.7 u (1.6 min grad) 2-98% B. Flow Rate=0.8 mL/min. Solvent A: H$_2$O—0.1% TFA. Solvent B: ACN—0.1% TFA). HPLC RT=10.849 min (Column: Sunfire C18 3.5 µm, 3.0×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). HPLC RT=10.483 min. (Column: XBridge Phenyl 3.5 µm, 3.0×150 mm; Mobile Phase A: 5:95 ACN:water with 0.05% TFA; Mobile Phase B: 95:5 ACN:water with 0.05% TFA; Gradient 10-100% B over 15 min; Flow: 1 mL/min; Detection: UV at 220 nm). 1H NMR (400 MHz, CDCl$_3$) δ 8.97 (s, 1H), 8.72 (d, J=1.8 Hz, 1H), 7.53 (dd, J=8.5, 5.1 Hz, 2H), 7.46 (d, J=1.8 Hz, 1H), 7.12 (t, J=8.6 Hz, 2H), 6.91 (d, J=10.0 Hz, 1H), 4.44 (s, 3H), 3.79 (s, 3H), 3.46 (s, 3H), 2.78 (d, J=9.7 Hz, 1H), 2.37-2.19 (m, 2H), 2.06-1.82 (m, 3H), 1.36-1.23 (m, 2H), 0.60 (d, J=9.7 Hz, 1H). Chiral SFC RT=14.75 min (Column: Chiralcel OD-H 250×4.6 mm, 5 µm; Mobile Phase: 80/20 CO$_2$/MeOH; Flow: 2 mL/min).

Example 97

N-[5-(Dimethyl-1H-1,2,3-triazol-5-yl)-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaen-13-yl]cyclopropanesulfonamide

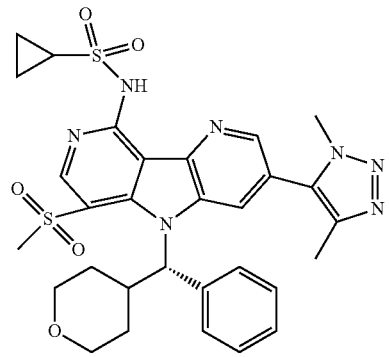 [SMILES: Cc1nnn(C)c1-c1cnc2c3c(NS(=O)(=O)C4CC4)ncc(S(C)(=O)=O)c3n([C@H](c3ccccc3)C3CCOCC3)c2c1]

To a stirred solution of 5-(dimethyl-1H-1,2,3-triazol-5-yl)-10-methanesulfonyl-13-methoxy-8-[(S)-oxan-4-yl(phenyl)methyl]-3,8,12-triazatricyclo[7.4.0.0$^{2,7}$]trideca-1(13),2(7),3,5,9,11-hexaene (40.0 mg, 0.073 mmol) and cyclopropanesulfonamide (35.5 mg, 0.293 mmol) in NMP (0.50 mL) was added t-BuOK (20.5 mg, 0.183 mmol). The reaction mixture was heated at 95° C. for 5.5 h and then cooled to room temperature. The mixture was diluted with saturated NH$_4$Cl solution and extracted with EtOAc. Combined EtOAc extracts were dried over MgSO$_4$, filtered and concentrated. The crude was purified via preparative LC/MS with the following conditions: Column: Waters XBridge Phenyl, 19×200 mm, 5-µm particles; Mobile Phase A: 5:95 ACN: water with 10-mM NH$_4$OAc; Mobile Phase B: 95:5 ACN: water with 10-mM NH$_4$OAc; Gradient: 15-70% B over 20 min, then a 5-min hold at 100% B; Flow: 20 mL/min. Fractions containing the desired product were combined and dried via centrifugal evaporation to give N-[5-(dimethyl-1H-1,2,3-triazol-5-yl)-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaen-13-yl]cyclopropanesulfonamide (12.2 mg, 26.2%). $^1$H NMR (500 MHz, DMSO-d$_6$) δ 8.97 (s, 1H), 8.76 (s, 1H), 7.98 (s, 1H), 7.63 (br d, J=7.4 Hz, 2H), 7.39-7.32 (m, 2H), 7.31-7.24 (m, 1H), 6.68 (br d, J=10.1 Hz, 1H), 3.87 (br d, J=7.1 Hz, 1H), 3.76 (s, 3H), 3.70 (s, 1H), 3.61 (br d, J=10.4 Hz, 1H), 3.53-3.44 (m, 1H), 3.42 (br d, J=12.1 Hz, 1H), 3.20 (br t, J=11.9 Hz, 1H), 2.54 (s, 3H), 2.06 (s, 3H), 1.96 (br d, J=12.5 Hz, 1H), 1.66-1.52 (m, 3H), 1.32 (br s, 2H), 1.17 (br d, J=6.7 Hz, 2H), 0.50 (br d, J=11.8 Hz, 1H); LCMS: RT=1.588 min; (ES): m/z (M+H)$^+$=636.0; LCMS: Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75-min hold at 100% B; Flow: 1.11 mL/min. HPLC Purity @ 220 nm: 100%.

Example 98

N-[5-(Dimethyl-1,2-oxazol-4-yl)-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaen-13-yl]cyclopropanesulfonamide

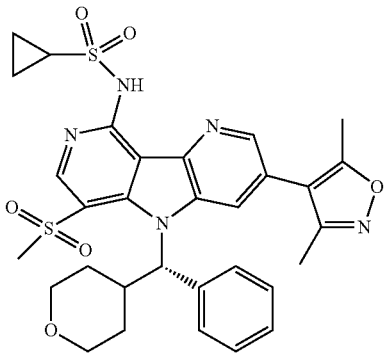 [SMILES: Cc1noc(C)c1-c1cnc2c3c(NS(=O)(=O)C4CC4)ncc(S(C)(=O)=O)c3n([C@H](c3ccccc3)C3CCOCC3)c2c1]

To a stirred solution of 5-(dimethyl-1,2-oxazol-4-yl)-10-methanesulfonyl-13-methoxy-8-[(S)-oxan-4-yl(phenyl)methyl]-3,8,12-triazatricyclo[7.4.0.0$^{2,7}$]trideca-1(13),2(7),3,5,9,11-hexaene (23.0 mg, 0.042 mmol) and ethanesulfonamide (90.4 mg, 0.579 mmol) in NMP (1.20 mL) was added t-BuOK (55.6 mg, 0.496 mmol). The reaction mixture was heated at 95° C. for 14.5 h and cooled to room temperature. The mixture was diluted with EtOAc and washed with 10% LiCl solution. The organic layer was dried over MgSO$_4$, filtered and concentrated to give the crude. This was purified by flash chromatography (Teledyne ISCO CombiFlash 0% to 100% solvent A/B=DCM/10% MeOH in DCM, RediSep SiO$_2$ 24 g, detecting at 254 nM, and monitoring at 220 nM). Concentration of appropriate fractions provided an impure compound. It was further purified by preparative HPLC. (3-LUNA C18 100×30 mm, 40 mL min, 30 to 80% 12 min gradient, 6 min 100% hold; A: 90% water-10% MeOH-0.1% TFA; B: 90% MeOH-10% water-0.1% TFA, detection at 220 nM). The desired fractions were concentrated and lyophilized to a TFA salt. This TFA salt in EtOAc was liberated to free amine base by saturated NaHCO$_3$ solution wash. The concentrated EtOAc layer gave an oil and then was purified via preparative LC/MS with the following conditions: Column: Waters XBridge Phenyl, 19×200 mm, 5-μm particles; Mobile Phase A: 5:95 ACN:water with 10-mM NH$_4$OAc; Mobile Phase B: 95:5 ACN:water with 10-mM NH$_4$OAc; Gradient: 15-70% B over 20 min, then a 5-min hold at 100% B; Flow: 20 mL/min. Fractions containing the desired product were combined and dried via centrifugal evaporation to give (N-[5-(dimethyl-1,2-oxazol-4-yl)-10-methanesulfonyl-8-[(S)-oxan-4-yl-(phenyl)methyl]-3,8,12-triazatricyclo[7.4.0.0$^{2,7}$]trideca-1(13),2 (7),3,5,9,11-hexaen-13-yl]cyclopropanesulfonamide (6.5 mg, 6.1%). $^1$H NMR (500 MHz, DMSO-d$_6$) δ 8.95 (br s, 1H), 8.69 (br s, 1H), 7.85 (br s, 1H), 7.66 (br d, J=7.4 Hz, 2H), 7.36 (br t, J=7.6 Hz, 2H), 7.27 (br s, 1H), 6.69 (br d, J=10.1 Hz, 1H), 3.90 (s, 1H), 3.87 (br s, 1H), 3.70 (br s, 1H), 3.67 (br d, J=11.1 Hz, 1H), 3.55-3.45 (m, 1H), 3.20 (br t, J=11.8 Hz, 1H), 2.54 (s, 3H), 2.48-2.46 (m, 1H), 2.27 (s, 3H), 2.07 (s, 3H), 1.98 (br d, J=12.5 Hz, 1H), 1.69-1.51 (m, 2H), 1.31 (br s, 2H), 1.15 (br s, 2H), 0.46 (br d, J=11.8 Hz, 1H); LCMS: RT=1.878 min; (ES): m/z (M+H)$^+$=636.5; LCMS: Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75-min hold at 100% B; Flow: 1.11 mL/min. HPLC Purity @ 220 nm: 98%.

Example 99

N-[5-(Dimethyl-1,2-oxazol-4-yl)-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaen-13-yl]ethane-1-sulfonamide

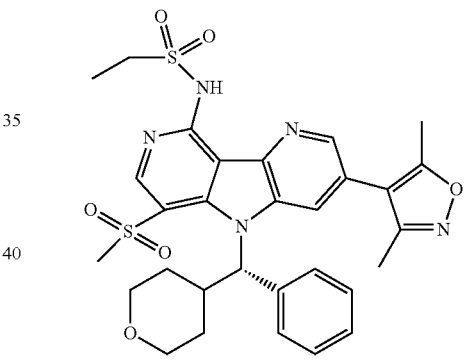

To a stirred solution of 5-(dimethyl-1,2-oxazol-4-yl)-10-methanesulfonyl-13-methoxy-8-[(S)-oxan-4-yl(phenyl)methyl]-3,8,12-triazatricyclo[7.4.0.0$^{2,7}$]trideca-1(13),2(7), 3,5,9,11-hexaene (23.0 mg, 0.042 mmol) and ethanesulfonamide (16.1 mg, 0.147 mmol) in DMF (0.25 mL; note; if NMP used instead of DMF it can avoid the byproduct generated from DMF from heating in base). The reaction mixture was heated at 95° C. for 14 h and cooled to room temperature. The mixture was diluted with brine and extracted with EtOAc. The EtOAc extracts were dried over MgSO$_4$, filtered and concentrated to give the crude. This was purified via preparative LC/MS with the following conditions: Column: Waters XBridge Phenyl, 19×200 mm, 5-μm particles; Mobile Phase A: 5:95 ACN: water with 10-mM NH$_4$OAc; Mobile Phase B: 95:5 ACN: water with 10-mM NH$_4$OAc; Gradient: 15-70% B over 20 min, then a 5-min hold at 100% B; Flow: 20 mL/min. Fractions containing the desired product were combined and dried via centrifugal evaporation to give N-[5-(dimethyl-1,2-oxazol-4-yl)-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaen-13-yl]ethane-1-sulfonamide (2.8 mg, 10.7%). $^1$H NMR (500

MHz, DMSO-$d_6$) δ 8.93 (br s, 1H), 8.68 (s, 1H), 7.82 (br s, 1H), 7.64 (br d, J=7.4 Hz, 2H), 7.40-7.32 (m, 2H), 7.30-7.24 (m, 1H), 7.23 (br s, 1H), 6.66 (br d, J=10.1 Hz, 1H), 3.86 (br d, J=6.7 Hz, 1H), 3.65 (br s, 1H), 3.50 (br t, J=11.6 Hz, 1H), 3.37 (br d, J=11.4 Hz, 1H), 3.19 (br t, J=11.6 Hz, 1H), 2.54 (s, 3H), 2.51-2.50 (m, 2H), 2.24 (s, 3H), 2.04 (s, 3H), 1.97 (br d, J=12.5 Hz, 1H), 1.66-1.49 (m, 2H), 1.33 (t, J=7.2 Hz, 3H), 0.43 (br d, J=12.5 Hz, 1H); LCMS: RT=1.596 min; (ES): m/z (M+H)$^+$=625.0; LCMS: Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75-min hold at 100% B; Flow: 1.11 mL/min. HPLC Purity @ 220 nm: 100%.

Example 100

N-[5-(Dimethyl-1,2-oxazol-4-yl)-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaen-13-yl]propane-2-sulfonamide

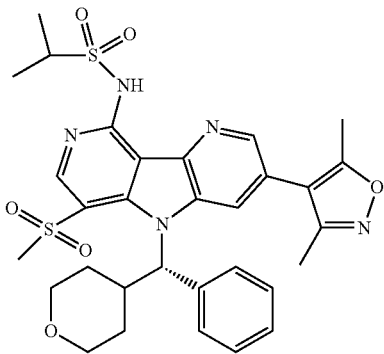 [SMILES: Cc1noc(C)c1-c1cnc2c3c(NS(=O)(=O)C(C)C)ncc(S(C)(=O)=O)c3n([C@H](c3ccccc3)C3CCOCC3)c2c1]

Following procedures analogous to those described in the preparation of N-[5-(dimethyl-1,2-oxazol-4-yl)-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaen-13-yl]ethane-1-sulfonamide, 5-(dimethyl-1,2-oxazol-4-yl)-10-methanesulfonyl-13-methoxy-8-[(S)-oxan-4-yl(phenyl)methyl]-3,8,12-triazatricyclo[7.4.0.0$^{2,7}$]trideca-1(13),2(7),3,5,9,11-hexaene (23.0 mg, 0.042 mmol) and propane-2-sulfonamide (18.1 mg, 0.147 mmol) were converted to N-[5-(dimethyl-1,2-oxazol-4-yl)-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaen-13-yl]propane-2-sulfonamide (2.2 mg, 7.5%). $^1$H NMR (500 MHz, DMSO-$d_6$) δ 8.93 (br s, 1H), 8.69 (s, 1H), 7.83 (br s, 1H), 7.65 (br d, J=7.7 Hz, 2H), 7.38-7.32 (m, 2H), 7.31-7.25 (m, 1H), 6.67 (br d, J=10.4 Hz, 1H), 3.87 (br d, J=8.4 Hz, 1H), 3.65 (br d, J=12.8 Hz, 1H), 3.57 (br s, 1H), 3.38 (br s, 1H), 3.19 (br t, J=11.1 Hz, 2H), 2.54 (s, 3H), 2.56-2.52 (m, 1H), 2.25 (s, 3H), 2.05 (s, 3H), 1.97 (br d, J=11.8 Hz, 1H), 1.60 (br t, J=12.5 Hz, 2H), 1.40 (br t, J=5.9 Hz, 6H), 0.43 (br s, 1H); LCMS: RT=1.940 min; (ES): m/z (M+H)$^+$=638; LCMS: Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75-min hold at 100% B; Flow: 1.11 mL/min. HPLC Purity @ 220 nm: 91%.

Example 101

13-(Cyclopropylmethoxy)-5-(dimethyl-1H-1,2,3-triazol-5-yl)-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaene

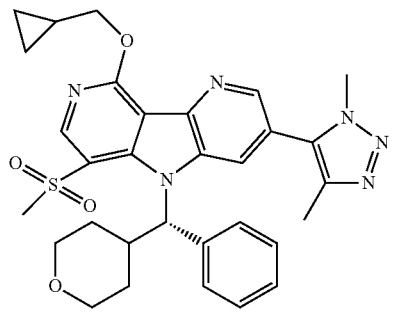 [SMILES: Cc1nnn(C)c1-c1cnc2c3c(OCC4CC4)ncc(S(C)(=O)=O)c3n([C@H](c3ccccc3)C3CCOCC3)c2c1]

Step 1: 5-Bromo-13-(cyclopropylmethoxy)-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaene To a stirred solution of 5-bromo-10-methanesulfonyl-13-methoxy-8-[(S)-oxan-4-yl(phenyl)methyl]-3,8,12-triazatricyclo[7.4.0.0$^{2,7}$]trideca-1(13),2(7),3,5,9,11-hexaene (50.0 mg, 0.094 mmol) in cyclopropyl alcohol (1.20 mL, 16.8 mmol) was added t-BuOK (22.0 mg, 0.196 mmol). The reaction mixture was stirred at room temperature for 21.5 h and diluted with EtOAc. The resulting mixture was washed with 10% LiCl solution. The EtOAc layer was dried over MgSO$_4$, filtered and concentrated. The crude was purified by flash chromatography (Teledyne ISCO CombiFlash 0% to 100% solvent A/B=Hexane/EtOAc, RediSep SiO$_2$ 12 g, detecting at 254 nM, and monitoring at 220 nM). Concentration of appropriate fractions provided 5-bromo-13-(cyclopropylmethoxy)-10-methanesulfonyl-8-[(S)-oxan-4-yl (phenyl)methyl]-3,8,12-triazatricyclo[7.4.0.0$^{2,7}$]trideca-1(13),2(7),3,5,9,11-hexaene (53.4 mg, 99%). $^1$H NMR (400 MHz, CDCl$_3$) δ 8.94 (s, 1H), 8.75 (d, J=1.8 Hz, 1H), 7.75 (d, J=1.8 Hz, 1H), 7.51-7.45 (m, 2H), 7.43-7.30 (m, 4H), 6.88 (d, J=10.0 Hz, 1H), 4.67 (s, 1H), 4.06 (dd, J=11.6, 2.9 Hz, 1H), 3.78 (dd, J=11.7, 3.1 Hz, 1H), 3.53 (td, J=11.9, 1.9 Hz, 1H), 3.27 (s, 3H), 3.26-3.19 (m, 1H), 2.98-2.81 (m, 1H), 2.12 (d, J=13.6 Hz, 1H), 1.97-1.83 (m, 1H), 1.58-1.48 (m, 2H), 0.70-0.62 (m, 2H), 0.57-0.49 (m, 2H), 0.39 (d, J=12.5 Hz, 1H); HPLC: RT=3.145 min (Chromolith ODS 4.6×50 mm (4 min grad) eluting with 10-90% aqueous MeOH over 4 min containing 0.% TFA, 4 mL/min, monitoring at 220 nm); MS (ES): m/z=570.4 [M+H]$^+$.

Step 2: 13-(Cyclopropylmethoxy)-5-(dimethyl-1H-1,2,3-triazol-5-yl)-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaene To a stirred mixture of 5-bromo-13-(cyclopropylmethoxy)-10-methanesulfonyl-8-[(S)-oxan-4-yl(phenyl)methyl]-3,8,12-triazatricyclo[7.4.0.0$^{2,7}$]trideca-1(13),2(7), 3,5,9,11-hexaene (25.0 mg, 0.044 mmol), 1,4-dimethyl-5-(tributylstannyl)-1H-1,2,3-triazole (30.5 mg, 0.079 mmol), and tetrakis(triphenylphosphine) palladium(0) (3.8 mg, 3.29

μmol) in DMF (1.0 mL) was purged with nitrogen. While purging, cuprous iodide (1.25 mg, 6.57 μmol) and Et₃N (0.013 mL, 0.096 mmol) were added. The nitrogen purging was continued for 5 min. The mixture was heated at 85° C. for 4 h and cooled to room temperature. Another batch of 1,4-dimethyl-5-(tributylstannyl)-1H-1,2,3-triazole (30.5 mg, 0.079 mmol), Et₃N (0.013 mL, 0.096 mmol), cuprous iodide (1.25 mg, 6.57 μmol) and tetrakis(triphenylphosphine)palladium(0) (3.8 mg, 3.29 μmol) were added with nitrogen purging. The mixture was heated at 95° C. for 14 h and cooled to room temperature. The mixture was diluted with 1:1 MeOH/DCM (10 mL), filtered and concentrated. The crude was purified via preparative LC/MS with the following conditions: Column: Waters XBridge Phenyl, 19×200 mm, 5-μm particles; Mobile Phase A: 5:95 ACN: water with 10-mM NH₄OAc; Mobile Phase B: 95:5 ACN: water with 10-mM NH₄OAc; Gradient: 15-70% B over 20 min, then a 5-min hold at 100% B; Flow: 20 mL/min. Fractions containing the desired product were combined and dried via centrifugal evaporation to give 13-(cyclopropylmethoxy)-5-(dimethyl-1H-1,2,3-triazol-5-yl)-10-methanesulfonyl-8-[(S)-oxan-4-yl(phenyl)methyl]-3,8,12-triazatricyclo[7.4.0.0²,⁷]trideca-1(13),2(7),3,5,9,11-hexaene (10.9 mg, 42.4%). ¹H NMR (500 MHz, DMSO-d₆) δ 8.87 (s, 1H), 8.72 (s, 1H), 7.86 (s, 1H), 7.61 (br d, J=7.7 Hz, 2H), 7.39-7.31 (m, 2H), 7.31-7.22 (m, 1H), 6.70 (br d, J=10.4 Hz, 1H), 4.54 (d, J=7.1 Hz, 2H), 3.87 (br d, J=9.8 Hz, 1H), 3.64 (br s, 1H), 3.46 (br s, 1H), 3.19 (br t, J=11.6 Hz, 1H), 2.54 (s, 6H), 2.06 (s, 3H), 1.97 (br d, J=12.8 Hz, 1H), 1.72-1.52 (m, 2H), 1.44 (br s, 1H), 0.60 (br d, J=6.7 Hz, 2H), 0.45 (br d, J=3.7 Hz, 3H), 0.31-0.30 (m, 1H); LCMS: RT=1.70 min; (ES): m/z (M+H)⁺=587.4; LCMS: Column: Waters Acquity UPLC BEH C18, 2.1×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75-min hold at 100% B; Flow: 1.11 mL/min. HPLC Purity @ 220 nm: 97%.

Example 102

N-[5-(Dimethyl-1,2-oxazol-4-yl)-10-methanesulfonyl-8-[(S)-oxan-4-yl(phenyl)methyl]-3,8,12-triazatricyclo[7.4.0.0²,⁷]trideca-1(13),2(7),3,5,9,11-hexaen-13-yl]methanesulfonamide

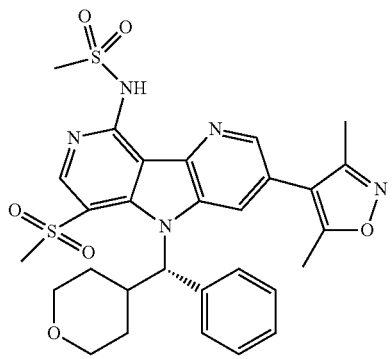 [SMILES: Cc1noc(C)c1-c1cnc2c3c(NS(C)(=O)=O)ncc(S(C)(=O)=O)c3n([C@H](c3ccccc3)C3CCOCC3)c2c1]

Step 1: N-{5-Bromo-10-methanesulfonyl-8-[(S)-oxan-4-yl(phenyl)methyl]-3,8,12-triazatricyclo[7.4.0.0²,⁷]trideca-1(13),2(7),3,5,9,11-hexaen-13-yl}methanesulfonamide To a stirred solution of 5-bromo-10-methanesulfonyl-13-methoxy-8-[(S)-oxan-4-yl(phenyl)methyl]-3,8,12-triazatricyclo[7.4.0.0²,⁷]trideca-1(13),2(7),3,5,9,11-hexaene (45.0 mg, 0.085 mmol) and methanesulfonamide (72.6 mg, 0.764 mmol) in DMF (1.00 mL) was added t-BuOK (60.0 mg, 0.535 mmol). The reaction mixture was heated at 95° C. for 13.5 h and cooled to room temperature. The mixture was diluted with EtOAc, washed with 10% LiCl solution, dried over MgSO₄, filtered and concentrated. The crude was purified by flash chromatography (Teledyne ISCO CombiFlash 0% to 100% solvent A/B=DCM/10% MeOH in DCM, RediSep SiO₂ 24 g, detecting at 254 nM, and monitoring at 220 nM). Concentration of appropriate fractions provided N-{5-bromo-10-methanesulfonyl-8-[(S)-oxan-4-yl(phenyl)methyl]-3,8,12-triazatricyclo[7.4.0.0²,⁷]trideca-1(13),2(7),3,5,9,11-hexaen-13-yl}methanesulfonamide (24.0 mg, 47.7%). ¹H NMR (400 MHz, CDCl₃) δ 9.07 (s, 1H), 8.64 (d, J=1.7 Hz, 1H), 7.82 (d, J=1.7 Hz, 1H), 7.56-7.45 (m, 2H), 7.41-7.27 (m, 3H), 6.85 (d, J=10.3 Hz, 1H), 6.02 (br. s., 1H), 4.11-4.00 (m, 1H), 3.87-3.77 (m, 2H), 3.59-3.51 (m, 1H), 3.36 (s, 3H), 3.28 (d, J=3.5 Hz, 1H), 2.13 (d, J=13.2 Hz, 1H), 1.95-1.79 (m, 1H), 1.60 (qd, J=12.4, 4.5 Hz, 1H), 0.41 (d, J=12.7 Hz, 1H); HPLC: RT=2.780 min (Chromolith ODS 4.6×50 mm (4 min grad) eluting with 10-90% aqueous MeOH over 4 min containing 0.% TFA, 4 mL/min, monitoring at 220 nm); MS (ES): m/z=593; 595 [M+H]⁺.

Step 2: N-[5-(Dimethyl-1,2-oxazol-4-yl)-10-methanesulfonyl-8-[(S)-oxan-4-yl(phenyl)methyl]-3,8,12-triazatricyclo[7.4.0.0²,⁷]trideca-1(13),2(7),3,5,9,11-hexaen-3-yl]methanesulfonamide To a stirred solution of N-{5-bromo-10-methanesulfonyl-8-[(S)-oxan-4-yl(phenyl)methyl]-3,8,12-triazatricyclo[7.4.0.0²,⁷]trideca-1(13),2(7),3,5,9,11-hexaen-13-yl}methanesulfonamide (12.0 mg, 0.020 mmol) and (3,5-dimethylisoxazol-4-yl)boronic acid (5.7 mg, 0.040 mmol) in dioxane (0.50 mL) was added 2M K₃PO₄ solution (0.025 mL, 0.051 mmol). The mixture was purged with nitrogen and PdCl₂(dppf)-CH₂Cl₂ Adduct (5.33 mg, 6.53 μmol) was added, and then heated to 95° C. for 1 h. The cooled mixture was diluted with 1:1 MeOH/DCM (10 mL), filtered and concentrated. The crude was purified via preparative LC/MS with the following conditions: Column: Waters XBridge Phenyl, 19×200 mm, 5-μm particles; Mobile Phase A: 5:95 ACN: water with 10-mM NH₄OAc; Mobile Phase B: 95:5 ACN: water with 10-mM NH₄OAc; Gradient: 15-70% B over 20 min, then a 5-min hold at 100% B; Flow: 20 mL/min. Fractions containing the desired product were combined and dried via centrifugal evaporation to give N-[5-(dimethyl-1,2-oxazol-4-yl)-10-methanesulfonyl-8-[(S)-oxan-4-yl(phenyl)methyl]-3,8,12-triazatricyclo[7.4.0.0²,⁷]trideca-1(13),2(7),3,5,9,11-hexaen-13-yl]methanesulfonamide (3.5 mg, 28.4%). ¹H NMR (500 MHz, DMSO-d₆) δ 8.93 (br s, 1H), 8.66 (br s, 1H), 7.80 (br s, 1H), 7.65 (br d, J=7.4 Hz, 2H), 7.37 (br t, J=7.6 Hz, 2H), 7.29 (br t, J=7.2 Hz, 1H), 6.68 (br d, J=10.1 Hz, 1H), 3.89 (s, 1H), 3.87 (br s, 1H), 3.68 (br s, 1H), 3.58 (br s, 2H), 3.38 (br s, 1H), 3.21 (br t, J=11.4 Hz, 2H), 2.58-2.54 (m, 3H), 2.26 (s, 3H), 2.06 (s, 3H), 1.99 (br d, J=12.8 Hz, 1H), 1.71-1.55 (m, 2H), 0.44 (br d, J=12.5 Hz, 1H); LCMS: RT=1.75 min; (ES): m/z (M+H)⁺=610.3; LCMS: Column: Waters Acquity UPLC BEH C18, 2.1×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75-min hold at 100% B; Flow: 1.11 mL/min. HPLC Purity @ 220 nm: 96%.

Example 103

13-(Cyclopropylmethoxy)-5-(dimethyl-1,2-oxazol-4-yl)-10-methanesulfonyl-8-[(S)-oxan-4-yl(phenyl)methyl]-3,8,12-triazatricyclo[7.4.0.0²,⁷]trideca-1(13),2(7),3,5,9,11-hexaene

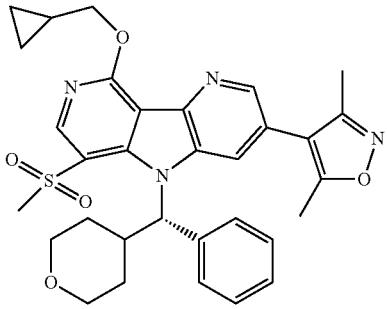 [SMILES: Cc1noc(C)c1-c1cnc2c3c(OCC4CC4)ncc(S(C)(=O)=O)c3n([C@H](c3ccccc3)C3CCOCC3)c2c1]

Following procedures analogous to those described in the preparation of step 2 of N-[5-(dimethyl-1,2-oxazol-4-yl)-10-methanesulfonyl-8-[(S)-oxan-4-yl(phenyl)methyl]-3,8,12-triazatricyclo[7.4.0.0²,⁷]trideca-1(13),2(7),3,5,9,11-hexaen-13-yl]methanesulfonamide, 5-bromo-10-methanesulfonyl-13-methoxy-8-[(S)-oxan-4-yl(phenyl)methyl]-3,8,12-triazatricyclo[7.4.0.0²,⁷]trideca-1(13),2(7),3,5,9,11-hexaene (25.0 mg, 0.044 mmol) and (3,5-dimethylisoxazol-4-yl)boronic acid (12.4 mg, 0.088 mmol) were converted to 13-(cyclopropylmethoxy)-5-(dimethyl-1,2-oxazol-4-yl)-10-methanesulfonyl-8-[(S)-oxan-4-yl(phenyl)methyl]-3,8,12-triazatricyclo[7.4.0.0²,⁷]-trideca-1(13),2(7),3,5,9,11-hexaene (15.7 mg, 61.1%). ¹H NMR (500 MHz, DMSO-d₆) δ 8.84 (s, 1H), 8.64 (s, 1H), 7.69 (s, 1H), 7.61 (br d, J=7.7 Hz, 2H), 7.37-7.31 (m, 2H), 7.29-7.23 (m, 1H), 6.69 (br d, J=10.4 Hz, 1H), 4.53 (d, J=7.1 Hz, 2H), 3.87 (br d, J=14.1 Hz, 1H), 3.67 (s, 3H), 3.19 (br t, J=11.4 Hz, 1H), 2.54 (s, 3H), 2.24 (s, 3H), 2.04 (s, 3H), 1.98 (br s, 1H), 1.67 (br d, J=10.1 Hz, 1H), 1.56 (br d, J=8.4 Hz, 1H), 1.44 (br s, 1H), 0.60 (br d, J=6.7 Hz, 2H), 0.45 (br d, J=4.4 Hz, 2H), 0.38 (br d, J=12.1 Hz, 1H); LCMS: RT=1.84 min; (ES): m/z (M+H)⁺=587.2; LCMS: Column: Waters Acquity UPLC BEH C18, 2.1×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75-min hold at 100% B; Flow: 1.11 mL/min. HPLC Purity @ 220 nm: 100%.

Example 104

1-Cyclopropyl-N-[5-(dimethyl-1H-1,2,3-triazol-5-yl)-10-methanesulfonyl-8-[(S)-oxan-4-yl(phenyl)methyl]-3,8,12-triazatricyclo[7.4.0.0²,⁷]trideca-1(13),2(7),3,5,9,11-hexaen-13-yl]methanesulfonamide

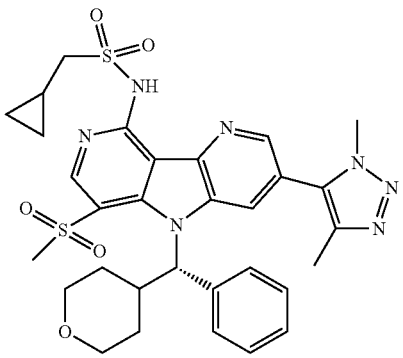 [SMILES: Cc1nnn(C)c1-c1cnc2c3c(NS(=O)(=O)CC4CC4)ncc(S(C)(=O)=O)c3n([C@H](c3ccccc3)C3CCOCC3)c2c1]

Step 1: N-{5-Bromo-10-methanesulfonyl-8-[(S)-oxan-4-yl(phenyl)methyl]-3,8,12-triazatricyclo[7.4.0.0²,⁷]trideca-1(13),2(7),3,5,9,11-hexaen-13-yl}-1-yclopropylmethanesulfonamide Following procedures analogous to those described in the preparation of N-{5-bromo-10-methanesulfonyl-8-[(S)-oxan-4-yl(phenyl)methyl]-3,8,12-triazatricyclo[7.4.0.0²,⁷]trideca-1(13),2(7),3,5,9,11-hexaen-13-yl}methanesulfonamide, 5-bromo-10-methanesulfonyl-13-methoxy-8-[(S)-oxan-4-yl(phenyl)methyl]-3,8,12-triazatricyclo[7.4.0.0²,⁷]trideca-1(13),2(7),3,5,9,11-hexaene (40.0 mg, 0.075 mmol) and cyclopropylmethanesulfonamide (88.0 mg, 0.651 mmol) were converted to N-{5-bromo-10-methanesulfonyl-8-[(S)-oxan-4-yl(phenyl)methyl]-3,8,12-triazatricyclo[7.4.0.0²,⁷]trideca-1(13),2(7),3,5,9,11-hexaen-13-yl}-1-cyclopropylmethanesulfonamide (50.0 mg. quantitative yield). ¹H NMR (400 MHz, CDCl₃) δ 10.15 (br s, 1H), 9.05 (s, 1H), 8.63 (d, J=1.7 Hz, 1H), 7.80 (d, J=1.8 Hz, 1H), 7.52-7.43 (m, 2H), 7.43-7.30 (m, 3H), 6.84 (d, J=10.0 Hz, 1H), 4.08-3.99 (m, 1H), 3.81 (br dd, J=11.7, 3.2 Hz, 1H), 3.74 (d, J=7.2 Hz, 1H), 3.60-3.48 (m, 1H), 3.33 (s, 3H), 3.04 (d, J=7.2 Hz, 2H), 2.11 (br d, J=13.4 Hz, 1H), 1.92-1.81 (m, 1H), 1.57 (qd, J=12.4, 4.4 Hz, 1H), 1.34-1.22 (m, 1H), 1.21-1.12 (m, 1H), 0.76-0.64 (m, 2H), 0.45-0.37 (m, 2H); HPLC: RT=3.058 min (Chromolith ODS 4.6×50 mm (4 min grad) eluting with 10-90% aqueous MeOH over 4 min containing 0.% TFA, 4 mL/min, monitoring at 220 nm); MS (ES): m/z=633; 635 [M+H]⁺.

Step 2: 1-Cyclopropyl-N-[5-(dimethyl-1H-1,2,3-triazol-5-yl)-10-methanesulfonyl-8-[(S)-oxan-4-yl(phenyl)methyl]-3,8,12-triazatricyclo[7.4.0.0²,⁷]trideca-1(13),2(7),3,5,9,11-hexaen-13-yl]methanesulfonamide Following procedures analogous to those described in the step 2 preparation of 13-(cyclopropylmethoxy)-5-(dimethyl-1H-1,2,3-triazol-5-yl)-10-methanesulfonyl-8-[(S)-oxan-4-yl(phenyl)methyl]-3,8,12-triazatricyclo[7.4.0.0²,⁷]trideca-1(13),2(7),3,5,9,11-hexaene, N-{5-bromo-10-methanesulfonyl-8-[(S)-oxan-4-yl(phenyl)methyl]-3,8,12-triazatricyclo[7.4.0.0²,⁷]trideca-1(13),2(7),3,5,9,11-hexaen-13-yl}-1-cyclopropylmethanesulfonamide (25.0 mg, 0.039 mmol) and 1,4-dimethyl-5-(tributylstannyl)-1H-1,2,3-triazole (27.4 mg, 0.071 mmol) were converted to 1-cyclopropyl-N-[5-(dimethyl-1H-1,2,3-triazol-5-yl)-10-methanesulfonyl-8-[(S)-oxan-4-yl(phenyl)methyl]-3,8,12-triazatricyclo[7.4.0.0²,⁷]trideca-1(13),2(7),3,5,9,11-hexaen-13-yl]methanesulfonamide (2.9 mg, 11.3%). ¹H NMR (500 MHz, DMSO-d₆) δ 8.97 (br s, 1H), 8.79 (br s, 1H), 8.03 (br s, 1H), 7.66 (br d, J=7.4 Hz, 2H), 7.38-7.32 (m, 3H), 7.30-7.25 (m, 1H), 6.69 (br d, J=10.1 Hz, 1H), 3.89 (s, 1H), 3.87 (br s, 1H), 3.78 (s, 3H), 3.72 (br s, 2H), 3.67 (br d, J=8.8 Hz, 1H), 3.47 (br s, 1H), 3.20 (br t, J=11.4 Hz, 1H), 2.54 (s, 3H), 2.08 (s, 3H), 1.95 (br d, J=12.5 Hz, 1H), 1.62 (br d, J=8.4 Hz, 2H), 1.15 (br s, 1H), 0.57 (br d, J=6.1 Hz, 2H), 0.50 (br d, J=12.1 Hz, 1H), 0.35 (br d, J=4.0 Hz, 2H); LCMS: RT=1.698 min; (ES): m/z (M+H)⁺=650.2; LCMS: Column: Waters Acquity UPLC BEH C18, 2.1×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75-min hold at 100% B; Flow: 1.11 mL/min. HPLC Purity @ 220 nm: 100%.

Example 105

N-[5-(Dimethyl-1H-1,2,3-triazol-5-yl)-10-methanesulfonyl-8-[(S)-oxan-4-yl(phenyl)methyl]-3,8,12-triazatricyclo[7.4.0.0²,⁷]trideca-1(13),2(7),3,5,9,11-hexaen-13-yl]methanesulfonamide

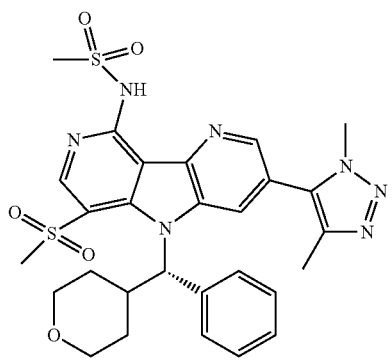 [SMILES: Cc1nnn(C)c1-c1cnc2c3c(NS(C)(=O)=O)ncc(S(C)(=O)=O)c3n([C@H](c3ccccc3)C3CCOCC3)c2c1]

Following procedures analogous to those described in the preparation of 1-cyclopropyl-N-[5-(dimethyl-1H-1,2,3-triazol-5-yl)-10-methanesulfonyl-8-[(S)-oxan-4-yl(phenyl)methyl]-3,8,12-triazatricyclo[7.4.0.0²,⁷]trideca-1(13),2(7),3,5,9,11-hexaen-13-yl]methanesulfonamide, N-{5-bromo-10-methanesulfonyl-8-[(S)-oxan-4-yl(phenyl)methyl]-3,8,12-triazatricyclo[7.4.0.0²,⁷]trideca-1(13),2(7),3,5,9,11-hexaen-13-yl}methanesulfonamide (12.0 mg, 0.020 mmol) and 1,4-dimethyl-5-(tributylstannyl)-1H-1,2,3-triazole (14.5 mg, 0.036 mmol) were converted to N-[5-(dimethyl-1H-1,2,3-triazol-5-yl)-10-methanesulfonyl-8-[(S)-oxan-4-yl(phenyl)methyl]-3,8,12-triazatricyclo[7.4.0.0²,⁷]trideca-1(13),2(7),3,5,9,11-hexaen-13-yl]methanesulfonamide (3.2 mg, 26.0%). $^1$H NMR (500 MHz, DMSO-$d_6$) δ 8.98 (br s, 1H), 8.77 (br s, 1H), 7.99 (br s, 1H), 7.64 (br d, J=7.7 Hz, 2H), 7.40-7.32 (m, 2H), 7.31-7.22 (m, 1H), 6.69 (br d, J=10.1 Hz, 1H), 3.89 (s, 1H), 3.86 (br s, 1H), 3.77 (s, 3H), 3.72-3.61 (m, 2H), 3.20 (br t, J=11.3 Hz, 1H), 2.54 (s, 1H), 2.07 (s, 6H), 1.96 (br d, J=12.5 Hz, 1H), 1.62 (br s, 2H), 0.49 (br d, J=12.5 Hz, 1H); LCMS: RT=1.418 min; (ES): m/z (M+H)⁺=610.05; LCMS: Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75-min hold at 100% B; Flow: 1.11 mL/min. HPLC Purity @ 220 nm: 100%.

Example 106

3-({[5-(Dimethyl-1H-1,2,3-triazol-5-yl)-13-methoxy-8-[(S)-oxan-4-yl(phenyl)methyl]-3,8,12-triazatricyclo[7.4.0.0²,⁷]trideca-1(13),2(7),3,5,9,11-hexaen-10-yl]sulfonyl}methyl)oxetan-3-ol

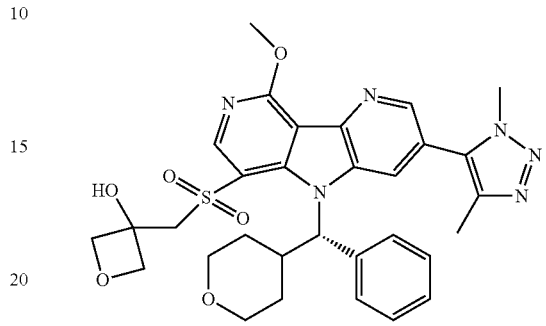

To a stirred solution of 5-(dimethyl-1H-1,2,3-triazol-5-yl)-10-methanesulfonyl-13-methoxy-8-[(S)-oxan-4-yl(phenyl)methyl]-3,8,12-triazatricyclo[7.4.0.0²,⁷]trideca-1(13),2(7),3,5,9,11-hexaene (24.0 mg, 0.044 mmol) in THF (1.50 mL) under nitrogen at room temperature was added 1M KHMDS in THF (0.077 mL, 0.077 mmol). The mixture was stirred at room temperature for 15 min and oxetane-3-one (11.2 mg, 0.155 mmol) was added. The resulting mixture was stirred at room temperature for another 10 min and was poured into MeOH (10 mL). The mixture was concentrated and purified via preparative LC/MS with the following conditions: Column: Waters XBridge Phenyl, 19×200 mm, 5-μm particles; Mobile Phase A: 5:95 ACN: water with 10-mM NH$_4$OAc; Mobile Phase B: 95:5 ACN: water with 10-mM NH$_4$OAc; Gradient: 15-70% B over 20 min, then a 5-min hold at 100% B; Flow: 20 mL/min. Fractions containing the desired product were combined and dried via centrifugal evaporation to give 3-({[5-(dimethyl-1H-1,2,3-triazol-5-yl)-13-methoxy-8-[(S)-oxan-4-yl(phenyl)methyl]-3,8,12-triazatricyclo[7.4.0.0²,⁷]trideca-1(13),2(7),3,5,9,11-hexaen-10-yl]sulfonyl}methyl)oxetan-3-ol (11.3 mg, 41.6%). $^1$H NMR (500 MHz, DMSO-$d_6$) δ 8.85 (s, 1H), 8.68 (s, 1H), 7.79 (s, 1H), 7.59 (d, J=7.7 Hz, 2H), 7.38-7.32 (m, 2H), 7.31-7.23 (m, 1H), 6.70 (d, J=10.1 Hz, 1H), 6.37 (s, 1H), 4.75 (d, J=6.7 Hz, 1H), 4.59 (d, J=6.7 Hz, 1H), 4.48 (d, J=7.1 Hz, 1H), 4.42 (d, J=6.7 Hz, 1H), 4.27 (s, 1H), 4.23 (s, 3H), 4.13 (d, J=14.5 Hz, 1H), 3.91-3.84 (m, 1H), 3.72 (s, 3H), 3.64 (d, J=8.4 Hz, 1H), 3.18 (t, J=11.8 Hz, 1H), 2.54 (s, 5H), 1.98 (br. s., 1H), 1.78-1.66 (m, 1H), 1.60-1.47 (m, 1H), 0.42 (d, J=12.1 Hz, 1H); LCMS: RT=1.25 min; (ES): m/z (M+H)⁺=619.3; LCMS: Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75-min hold at 100% B; Flow: 1.11 mL/min. HPLC Purity @ 220 nm: 98%.

Example 107

10-Methanesulfonyl-13-methoxy-5-(4-methoxy-1-methyl-1H-1,2,3-triazol-5-yl)-8-[(S)-oxan-4-yl(phenyl)methyl]-3,8,12-triazatricyclo[7.4.0.0²,⁷]trideca-1(9),2(7),3,5,10,12-hexaene

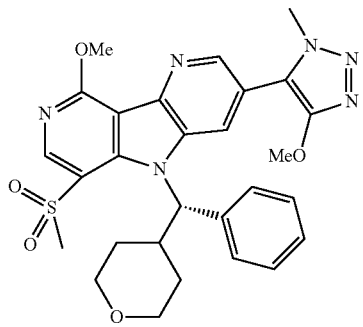 [SMILES: COc1nnn(C)c1-c1cnc2c3c(OC)ncc(S(C)(=O)=O)c3n([C@H](c3ccccc3)C3CCOCC3)c2c1]

A dry, nitrogen flushed, 1 dram vial was charged with tetramethylammonium acetate (30.1 mg, 0.226 mmol), bis(triphenylphosphine)palladium(II) dichloride (7.94 mg, 0.011 mmol), and (S)-3-bromo-9-methoxy-6-(methylsulfonyl)-5-(phenyl(tetrahydro-2H-pyran-4-yl)methyl)-5H-pyrrolo[3,2-b:4,5-c]dipyridine (60.0 mg, 0.113 mmol). To this was added 4-methoxy-1-((trimethylsilyl)methyl)-1H-1,2,3-triazole (41.9 mg, 0.226 mmol). The vial was again flushed with nitrogen. To this was added N-methyl-2-pyrrolidone (0.8 ml). The resulting mixture was stirred vigorously under a stream of nitrogen for 10 min. The vial was placed in a pre-heated oil bath at 95° C. and heated overnight. Tetramethylammonium acetate (30.1 mg, 0.226 mmol) was added and the reaction heated at 95° C. for an additional 30 min. The reaction was cooled to room temperature, diluted with ethyl acetate, washed with saturated ammonium chloride, then water, then brine, dried over magnesium sulfate, filtered, and concentrated. The residue was purified by preparative HPLC (Column: XBridge C18, 19×200 mm, 5-μm particles; Mobile Phase A: 5:95 ACN: water with 0.1% trifluoroacetic acid; Mobile Phase B: 95:5 ACN: water with 0.1% trifluoroacetic acid; Gradient: 20-50% B over 30 min, then a 5-min hold at 100% B; Flow: 20 mL/min.) to give 39.4 mg (62%). $^1$H NMR (500 MHz, DMSO-d$_6$) δ 8.91 (s, 1H), 8.74 (s, 1H), 7.94 (brs, 1H), 7.65 (d, c, 2H), 7.38 (m, 2H), 7.31 (m, 1H), 6.72 (d, 3.92 (d, J=10.3 Hz, 1H), 4.24 (s, 3H), 3.97 (s, 3H), 3.89 (d, J=9.2 Hz, 1H), 3.8 (s, 3H), 3.71 (s, 3H), 3.64 (d, J=10.3 Hz, 1H), 3.54-3.33 (m, 2H), 3.18 (t, J=11×2 Hz, 1H), 2.0 (d, J=13.6 Hz, 1H), 1.61 (m, 2H), 0.35 (d, J=12.8 Hz, 1H); LCMS (M+H)$^+$=365.5.

Example 108

10-Methanesulfonyl-5-[4-($^2$H$_3$)methyl-1-methyl-1H-1,2,3-triazol-5-yl]-13-(2-methylpropoxy)-8-[(S)-oxan-4-yl(phenyl)methyl]-3,8,12-triazatricyclo[7.4.0.0²,⁷]trideca-1(13),2(7),3,5,9,11-hexaene

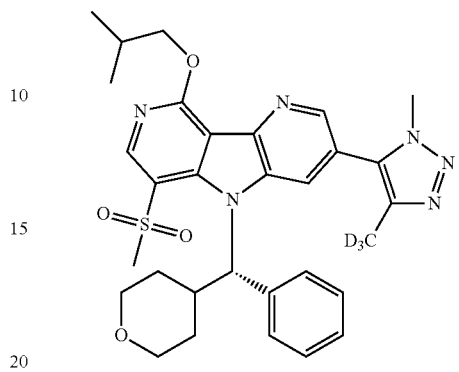

A 2-dram pressure vial was charged with 10-methanesulfonyl-13-methoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0²,⁷]trideca-1(13),2(7),3,5,9,11-hexaene (20 mg, 0.036 mmol) and KOtBu (20.41 mg, 0.182 mmol). To that mixture was added 2-methyl-1-propanol (500 μl, 5.40 mmol) at room temperature. After 2.5 h, the reaction mixture was quenched with a few drops of 1.0N HCl and purified by preparative HPLC: Column: XBridge C18, 19×mm, 5-μm particles; Mobile Phase A: 5:95 ACN: water with 10-mM NH$_4$OAc; Mobile Phase B: 95:5 ACN: water with 10-mM NH$_4$OAc; Gradient: 40-80% B over 15 min, then a 5-min hold at 100% B; Flow: 20 mL/min. The fractions were collected to give 7.2 mg (33% yield) of product. $^1$H NMR (500 MHz, DMSO-d$_6$) δ 8.89 (s, 1H), 8.74 (s, 1H), 7.87 (s, 1H), 7.63 (d, J=7.7 Hz, 2H), 7.39-7.32 (m, 2H), 7.32-7.25 (m, 1H), 6.72 (d, J=10.6 Hz, 1H), 4.47 (d, J=3.7 Hz, 2H), 3.88 (d, J=11.4 Hz, 1H), 3.76 (s, 3H), 3.72-3.62 (m, 4H), 3.56-3.47 (m, 1H), 3.43 (d, J=11.4 Hz, 1H), 3.21 (t, J=12.5 Hz, 1H), 2.23 (dt, J=13.0, 6.7 Hz, 1H), 1.98 (d, J=11.7 Hz, 1H), 1.76-1.55 (m, 2H), 1.09 (d, J=6.2 Hz, 6H), 0.46 (d, J=11.7 Hz, 1H). Mass found 592 (M+H)$^+$.

Example 109

10-Methanesulfonyl-5-[4-($^2$H$_3$)methyl-1-methyl-1H-1,2,3-triazol-5-yl]-8-[(S)-oxan-4-yl(phenyl)methyl]-13-[(2R)-oxolan-2-ylmethoxy]-3,8,12-triazatricyclo[7.4.0.0²,⁷]trideca-1(13),2(7),3,5,9,11-hexaene

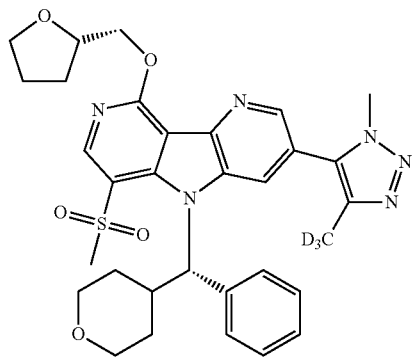

The title compound was prepared from (R)-(-)-tetrahydrofuryl alcohol following a procedure analogous to that described for the synthesis of 10-methanesulfonyl-5-[4-($^2$H$_3$)methyl-1-methyl-1H-1,2,3-triazol-5-yl]-13-(2-methylpropoxy)-8-[(S)-oxan-4-yl(phenyl)methyl]-3,8,12-triazatricyclo-[7.4.0.0$^{2,7}$]trideca-1(13),2(7),3,5,9,11-hexaene to give 8.6 mg (38% yield) of product. $^1$H NMR (400 MHz, CDCl$_3$) δ 8.98 (s, 1H), 8.65 (d, J=1.8 Hz, 1H), 7.51-7.44 (m, 2H), 7.44-7.30 (m, 4H), 6.91 (d, J=9.8 Hz, 1H), 4.90-4.81 (m, 2H), 4.61-4.53 (m, 1H), 4.11-3.99 (m, 2H), 3.92-3.84 (m, 1H), 3.83-3.74 (m, 1H), 3.69 (s, 3H), 3.54 (t, J=11.2 Hz, 1H), 3.38 (s, 3H), 3.27-3.16 (m, 1H), 3.01-2.88 (m, 1H), 2.26-2.08 (m, 1H), 2.05-1.83 (m, 1H), 1.62 (qd, J=12.4, 4.3 Hz, 2H), 0.94-0.79 (m, 3H), 0.40 (d, J=12.8 Hz, 1H). Chiral HPLC: Chiralpak ID column, 60% MeOH, 2 mL/min, 150 bar, Temp: 35 C, Flow rate: 40 mL/min for 17 min, UV monitored @ 252 nm, Injection: 0.25 mL of ~6 mg/mL in MeOH (12 mg purified by stacked injections. SFC RT: 11 min. Mass found 620 (M+H)$^+$.

Example 110

10-Methanesulfonyl-5-[4-($^2$H$_3$)methyl-1-methyl-1H-1,2,3-triazol-5-yl]-8-[(S)-oxan-4-yl(phenyl)methyl]-13-[(2S)-oxolan-2-ylmethoxy]-3,8,12-triazatricyclo[7.4.0.0$^{2,7}$]trideca-1(13),2(7),3,5,9,11-hexaene

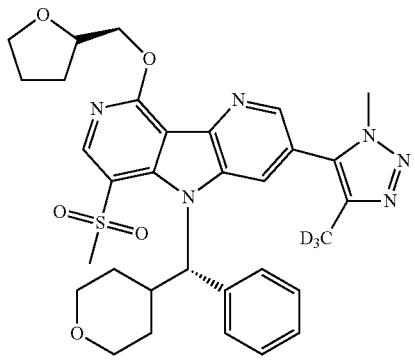

The title compound was prepared from tetrahydrofurfuryl alcohol following a procedure analogous to that described for the synthesis of 10-methanesulfonyl-5-[4-($^2$H$_3$)methyl-1-methyl-1H-1,2,3-triazol-5-yl]-13-(2-methylpropoxy)-8-[(S)-oxan-4-yl(phenyl)methyl]-3,8,12-triazatricyclo[7.4.0.0$^{2,7}$]trideca-1(13),2(7),3,5,9,11-hexaene to give 5.9 mg (26% yield) of product. The diastereomers generated in the last step were separated by Chiral SFC. Chiralpak ID preparative column, 21×250 mm, 5 μm particle size, Mobile phase: 60% MeOH in CO$_2$, 130 bar, Temp: 35 C, Flow rate: 40 mL/min. for 17 min. UV monitored @ 252 nm Injection: 0.25 mL of ~6 mg/mL in MeOH. 1H NMR (400 MHz, CDCl$_3$) δ 8.98 (s, 1H), 8.66 (d, J=1.8 Hz, 1H), 7.50-7.45 (m, 2H), 7.43-7.31 (m, 4H), 6.91 (d, J=9.8 Hz, 1H), 4.91 (dd, J=11.3, 3.8 Hz, 1H), 4.81-4.74 (m, 1H), 4.58 (qd, J=6.8, 3.8 Hz, 1H), 4.13-3.98 (m, 2H), 3.93-3.83 (m, 1H), 3.82-3.74 (m, 2H), 3.69 (s, 3H), 3.60-3.48 (m, 1H), 3.38 (s, 3H), 3.21 (t, J=11.0 Hz, 1H), 3.02-2.87 (m, 1H), 2.27-2.08 (m, 2H), 2.05-1.88 (m, 1H), 1.71-1.51 (m, 2H), 0.95-0.77 (m, 3H), 0.39 (d, J=13.3 Hz, 1H). Chiral SFC RT: 13.5 min. Mass found 620 (M+H)$^+$.

Example 111

10-Methanesulfonyl-5-[4-($^2$H$_3$)methyl-1-methyl-1H-1,2,3-triazol-5-yl]-8-[(S)-oxan-4-yl(phenyl)methyl]-13-(oxetan-3-yloxy)-3,8,12-triazatricyclo[7.4.0.0$^{2,7}$]trideca-1(13),2(7),3,5,9,11-hexaene

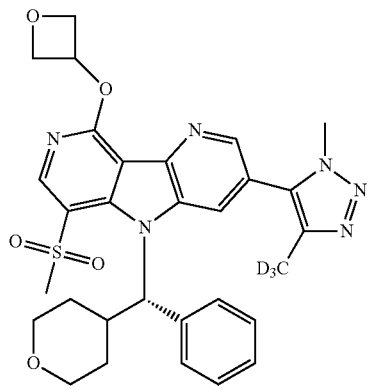 [SMILES: [2H]C([2H])([2H])c1nnn(C)c1-c1cnc2c3c(OC4COC4)ncc(S(C)(=O)=O)c3n([C@H](c3ccccc3)C3CCOCC3)c2c1]

Step 1: 13-Chloro-10-methanesulfonyl-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene A 24/40-50 mL round bottom flask was charged with 10-methanesulfonyl-13-methoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.02,7]trideca-1(13),2(7),3,5,9,11-hexaene (336 mg, 0.611 mmol) and dissolved in DMF (6113 μl). To that solution was added POCl$_3$ (570 μl, 6.11 mmol). The flask was placed into an oil bath preheated to 80° C. and vented into a balloon partially filled with nitrogen. After 1.5 h, the reaction mixture was poured onto ice and diluted with ethyl acetate. The reaction mixture was slowly quenched with solid sodium bicarbonate. The solution was transferred into a separatory funnel and the layers were separated and the organic was washed with water. The aqueous was extracted with ethyl acetate and the aqueous was discarded. The combined organics were washed with brine, dried with magnesium sulfate, filtered, concentrated under reduced pressure and purified by flash chromatography: (24 g ISCO RediSep Rf, loaded in/with: DCM and dried, fraction size: 9 mL 13×100 mm, and eluted with acetone in DCM 0% [75 mL], 0-25% [250 mL], 25% [200 mL], 25-100% [400 mL]). The fractions were collected to give 282 mg (83% yield). $^1$H NMR (400 MHz, CDCl$_3$) δ 9.13 (s, 1H), 8.77 (d, J=1.8 Hz, 1H), 7.55-7.52 (m, 1H), 7.52-7.47 (m, 2H), 7.46-7.34 (m, 3H), 6.97 (d, J=10.0 Hz, 1H), 4.11-4.04 (m, 1H), 3.85-3.77 (m, 1H), 3.72 (s, 3H), 3.59-3.50 (m, 1H), 3.48 (s, 3H), 3.29-3.18 (m, 1H), 3.04-2.89 (m, 1H), 2.26-2.13 (m, 1H), 2.06-1.92 (m, 1H), 1.71-1.59 (m, 1H), 0.37 (d, J=13.3 Hz, 1H). Mass found 555 (M+H)$^+$.

Step 2: 10-Methanesulfonyl-5-[4-($^2$H$_3$)methyl-1-methyl-1H-1,2,3-triazol-5-yl]-8-[(S)-oxan-4-yl(phenyl)methyl]-13-(oxetan-3-yloxy)-3,8,12-triazatricyclo[7.4.0.0$^{2,7}$]trideca-1(13),2(7),3,5,9,11-hexaene A 2-dram pressure vial was charged with 13-chloro-10-methanesulfonyl-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0²,⁷]trideca-1(13),2(7),3,5,9,11-hexaene (38 mg, 0.069 mmol) and KOtBu (38.5 mg, 0.343 mmol). To that mixture was added oxetan-3-ol (750 μl, 11.82 mmol). After 2 h, the volatiles were evaporated with a stream of nitrogen. The mixture was diluted with 2 mL of methanol, filtered through a 0.45 syringe tip filter and purified by preparative HPLC: Column: Waters XBridge C18 100×30 mm 5 u, Solvents: A:95:5water/ACN; B:95:5 ACN/water; Buffer: 10 mM NH₄OAc, % B: 33% isocratic (10 min), Flow Rate: 30 mL/min, 4 injections monitored at 254 nM. The fractions containing product were concentrated on the speed vacuum overnight. The product was filtered through a small plug of silica gel washing with DCM and eluted with acetone to give 18.5 mg (45% yield) of product. $^1$H NMR (400 MHz, CDCl₃) δ 8.92 (s, 1H), 8.67 (d, J=1.8 Hz, 1H), 7.52-7.46 (m, 3H), 7.43-7.31 (m, 3H), 6.93 (d, J=9.8 Hz, 1H), 6.02 (quin, J=6.0 Hz, 1H), 5.19-5.11 (m, 2H), 5.04 (ddd, J=9.8, 7.5, 5.8 Hz, 2H), 4.07 (dd, J=11.9, 2.6 Hz, 1H), 3.79 (dd, J=11.8, 3.0 Hz, 1H), 3.71 (s, 3H), 3.53 (t, J=11.0 Hz, 1H), 3.38 (s, 3H), 3.22 (td, J=11.9, 2.0 Hz, 1H), 3.03-2.88 (m, 1H), 2.24-2.12 (m, 1H), 2.06-1.90 (m, 1H), 1.69-1.60 (m, 1H), 0.38 (d, J=12.3 Hz, 1H). Mass found 592 (M+H)⁺.

Example 112

13-(2,2-Difluoroethoxy)-10-methanesulfonyl-5-[4-(²H₃)methyl-1-methyl-1H-1,2,3-triazol-5-yl]-8-[(S)-oxan-4-yl(phenyl)methyl]-3,8,12-triazatricyclo[7.4.0.0²,⁷]trideca-1(13),2(7),3,5,9,11-hexaene

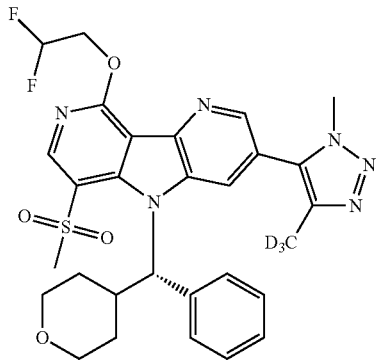 [SMILES: [2H]C([2H])([2H])c1nnn(C)c1-c1cnc2c3c(OCC(F)F)ncc(S(C)(=O)=O)c3n([C@H](c3ccccc3)C3CCOCC3)c2c1]

Step 1: 13-(2,2-Difluoroethoxy)-10-methanesulfonyl-5-[4-(²H₃)methyl-1-methyl-1H-1,2,3-triazol-5-yl]-8-[(S)-oxan-4-yl(phenyl)methyl]-3,8,12-triazatricyclo[7.4.0.0²,⁷]trideca-1(13),2(7),3,5,9,11-hexaene The title compound was prepared from 2,2-difluoroethanol following a procedure analogous to that described for the synthesis of 10-methanesulfonyl-5-[4-(²H₃)methyl-1-methyl-1H-1,2,3-triazol-5-yl]-8-[(S)-oxan-4-yl(phenyl)methyl]-13-(oxetan-3-yloxy)-3,8,12-triazatricyclo[7.4.0.0²,⁷]trideca-1(13),2(7),3,5,9,11-hexaene to give 5.7 mg (23% yield) of product. $^1$H NMR (400 MHz, CDCl₃) δ 8.99 (s, 1H), 8.70 (d, J=1.8 Hz, 1H), 7.51-7.45 (m, 3H), 7.44-7.33 (m, 3H), 6.93 (d, J=10.0 Hz, 1H), 6.59-6.25 (m, 1H), 5.17-4.97 (m, 2H), 4.08 (d, J=9.0 Hz, 1H), 3.85-3.75 (m, 1H), 3.70 (s, 3H), 3.54 (t, J=11.0 Hz, 1H), 3.41 (s, 3H), 3.28-3.16 (m, 1H), 3.03-2.90 (m, 1H), 2.27-2.14 (m, 1H), 2.08-1.91 (m, 1H), 1.71-1.54 (m, 1H), 0.39 (d, J=12.8 Hz, 1H). Mass found 600 (M+H)⁺.

Example 113

N-[(1S)-1-Cyclopropylethyl]-10-methanesulfonyl-5-[4-(²H₃)methyl-1-methyl-1H-1,2,3-triazol-5-yl]-8-[(S)-oxan-4-yl(phenyl)methyl]-3,8,12-triazatricyclo[7.4.0.0²,⁷]trideca-1(13),2(7),3,5,9,11-hexaen-13-amine

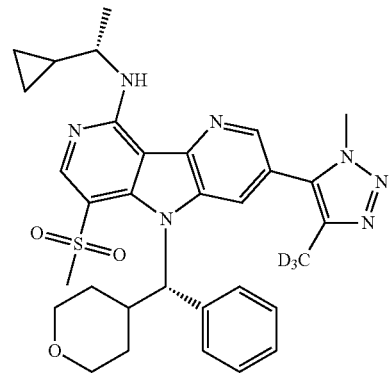 [SMILES: [2H]C([2H])([2H])c1nnn(C)c1-c1cnc2c3c(N[C@@H](C)C4CC4)ncc(S(C)(=O)=O)c3n([C@H](c3ccccc3)C3CCOCC3)c2c1]

A 1-dram pressure vial was charged with 13-chloro-10-methanesulfonyl-5-[4-(²H₃)methyl-1-methyl-1H-1,2,3-triazol-5-yl]-8-[(S)-oxan-4-yl(phenyl)methyl]-3,8,12-triazatricyclo[7.4.0.0²,⁷]trideca-1(13),2(7),3,5,9,11-hexaene (17.3 mg, 0.031 mmol) and dissolved in DMSO (250 μL). To that solution was added (S)-1-cyclopropylethanamine (53.2 mg, 0.624 mmol). After 2 h, the mixture was diluted with 500 μL of methanol, filtered through a 0.45 syringe tip filter, and purified by preparative HPLC. Column: Waters XBridge C18 100×30 mm 5 u, Solvents: A:95:5water/ACN; B:95:5 ACN/water; Buffer: 10 mM NH₄OAc, % B gradient 52% (15 min), Flow Rate: 30 mL/min, 1 injection monitored @ 254 nm. The fractions containing product were concentrated on the speed vacuum overnight. The product was filtered through a small plug of silica gel washing with DCM and eluted with acetone to give 17.2 mg (91% yield). $^1$H NMR (400 MHz, CDCl₃) δ 8.91 (s, 1H), 8.47 (d, J=1.8 Hz, 1H), 8.16 (d, J=8.3 Hz, 1H), 7.49 (d, J=7.8 Hz, 2H), 7.42-7.30 (m, 4H), 6.89 (d, J=10.0 Hz, 1H), 4.14-4.00 (m, 2H), 3.83 (dd, J=11.5, 3.3 Hz, 1H), 3.70 (s, 3H), 3.59-3.48 (m, 1H), 3.32 (s, 3H), 3.24 (td, J=11.9, 1.8 Hz, 1H), 3.01-2.87 (m, 1H), 2.22-2.12 (m, 1H), 2.07-1.85 (m, 1H), 1.75-1.58 (m, 1H), 1.48 (d, J=6.8 Hz, 3H), 0.69-0.46 (m, 5H), 0.41 (dq, J=9.1, 4.7 Hz, 1H). Mass found 603 (M+H)⁺.

Example 114

N-[(1R)-1-Cyclopropylethyl]-10-methanesulfonyl-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaen-13-amine

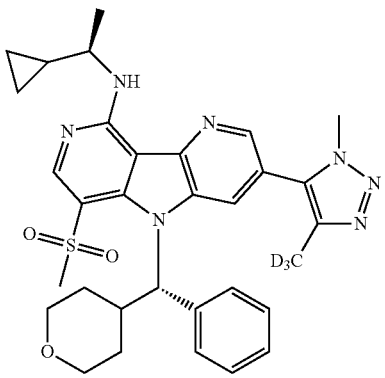 [SMILES: [2H]C([2H])([2H])c1nnn(C)c1-c1cnc2c3c(N[C@H](C)C4CC4)ncc(S(C)(=O)=O)c3n([C@H](c3ccccc3)C3CCOCC3)c2c1]

The title compound was prepared from (R)-1-cyclopropylethanamine, 0.5 sulfate dibasic salt following a procedure analogous to that described for the synthesis of N-[(1S)-1-cyclopropylethyl]-10-methanesulfonyl-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaen-13-amine to give 6.8 mg (52% yield) of product. $^1$H NMR (400 MHz, CDCl$_3$) δ 8.91 (s, 1H), 8.48 (d, J=1.8 Hz, 1H), 8.15 (d, J=8.3 Hz, 1H), 7.50 (d, J=7.8 Hz, 2H), 7.42-7.29 (m, 4H), 6.89 (d, J=10.0 Hz, 1H), 4.16-4.02 (m, 2H), 3.86-3.77 (m, 1H), 3.69 (s, 3H), 3.53 (td, J=11.9, 1.8 Hz, 1H), 3.32 (s, 3H), 3.28-3.19 (m, 1H), 3.00-2.87 (m, 1H), 2.21-2.13 (m, 1H), 2.02-1.87 (m, 1H), 1.73-1.62 (m, 1H), 1.50 (d, J=6.5 Hz, 3H), 0.66-0.44 (m, 5H), 0.42-0.34 (m, 1H). Mass found 603 (M+H)$^+$.

Example 115

N-Ethyl-10-methanesulfonyl-N-methyl-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaen-13-amine

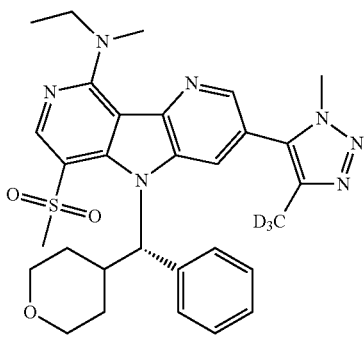 [SMILES: [2H]C([2H])([2H])c1nnn(C)c1-c1cnc2c3c(N(C)CC)ncc(S(C)(=O)=O)c3n([C@H](c3ccccc3)C3CCOCC3)c2c1]

The title compound was prepared from N-ethylmethylamine following a procedure analogous to that described for the synthesis of N-[(1S)-1-cyclopropylethyl]-10-methanesulfonyl-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaen-13-amine to give 14.8 mg (93% yield) of product. $^1$H NMR (400 MHz, CDCl$_3$) δ 8.90 (s, 1H), 8.51 (d, J=2.0 Hz, 1H), 7.49 (d, J=7.8 Hz, 2H), 7.41-7.30 (m, 4H), 6.93 (d, J=9.8 Hz, 1H), 4.11-3.98 (m, 3H), 3.84-3.76 (m, 1H), 3.68 (s, 3H), 3.53 (td, J=11.9, 1.8 Hz, 1H), 3.46 (s, 3H), 3.34 (s, 3H), 3.23 (td, J=11.9, 1.9 Hz, 1H), 3.01-2.89 (m, 1H), 2.24-2.12 (m, 1H), 2.06-1.88 (m, 1H), 1.73-1.59 (m, 1H), 1.38 (t, J=7.0 Hz, 3H), 0.46 (d, J=12.8 Hz, 1H). Mass found 577 (M+H)$^+$.

Example 116

10-Methanesulfonyl-N-methyl-5-[4-($^2$H$_3$)methyl-1-methyl-1H-1,2,3-triazol-5-yl]-8-[(S)-oxan-4-yl(phenyl)methyl]-N-(propan-2-yl)-3,8,12-triazatricyclo[7.4.0.0$^{2,7}$]trideca-1(13),2(7),3,5,9,11-hexaen-13-amine

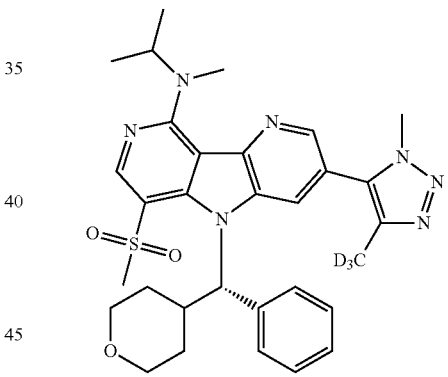

The title compound was prepared from N-isopropylmethylamine following a procedure analogous to that described for the synthesis of N-[(1S)-1-cyclopropylethyl]-10-methanesulfonyl-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaen-13-amine to give 15.7 mg (96% yield) of product. $^1$H NMR (400 MHz, CDCl$_3$) δ 8.90 (s, 1H), 8.51 (d, J=2.0 Hz, 1H), 7.48 (d, J=7.8 Hz, 2H), 7.41-7.29 (m, 4H), 6.91 (d, J=9.8 Hz, 1H), 5.13 (spt, J=6.7 Hz, 1H), 4.06 (dd, J=11.5, 2.8 Hz, 1H), 3.85-3.76 (m, 1H), 3.67 (s, 3H), 3.53 (td, J=11.9, 1.6 Hz, 1H), 3.35 (s, 3H), 3.29 (s, 3H), 3.23 (td, J=11.9, 2.0 Hz, 1H), 3.02-2.89 (m, 1H), 2.23-2.13 (m, 1H), 2.06-1.89 (m, 1H), 1.73-1.59 (m, 1H), 1.41 (dd, J=6.5, 2.8 Hz, 6H), 0.46 (d, J=13.1 Hz, 1H). Mass found 591 (M+H)$^+$.

Example 117

N-(2,2-Difluoroethyl)-10-methanesulfonyl-5-[4-($^2H_3$)methyl-1-methyl-1H-1,2,3-triazol-5-yl]-8-[(S)-oxan-4-yl(phenyl)methyl]-3,8,12-triazatricyclo [7.4.0.0$^{2,7}$]trideca-1(13),2(7),3,5,9,11-hexaen-13-amine

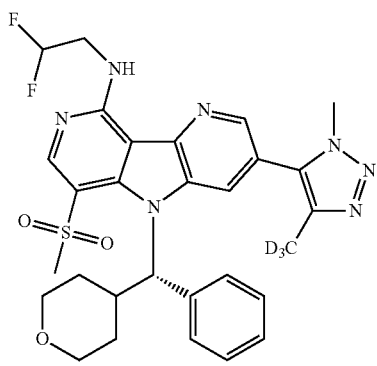 [SMILES: [2H]C([2H])([2H])c1nnn(C)c1-c1cnc2c3c(NCC(F)F)ncc(S(C)(=O)=O)c3n([C@H](c3ccccc3)C3CCOCC3)c2c1]

The title compound was prepared from 2,2-difluoroethylamine following a procedure analogous to that described for the synthesis of N-[(1S)-1-cyclopropylethyl]-10-methanesulfonyl-5-[4-($^2H_3$)methyl-1-methyl-1H-1,2,3-triazol-5-yl]-8-[(S)-oxan-4-yl(phenyl)methyl]-3,8,12-triazatricyclo [7.4.0.0$^{2,7}$]trideca-1(13),2(7),3,5,9,11-hexaen-13-amine to give 18.4 mg (56% yield) of product. 1H NMR (400 MHz, CDCl$_3$) δ 8.95 (s, 1H), 8.49 (d, J=1.8 Hz, 1H), 8.25 (t, J=6.4 Hz, 1H), 7.53-7.46 (m, 2H), 7.44-7.30 (m, 4H), 6.90 (d, J=10.0 Hz, 1H), 6.32-5.96 (m, 1H), 4.25 (tdd, J=14.5, 6.3, 4.0 Hz, 2H), 4.07 (dd, J=11.7, 2.6 Hz, 1H), 3.82 (dd, J=11.7, 3.1 Hz, 1H), 3.70 (s, 3H), 3.58-3.49 (m, 1H), 3.34 (s, 3H), 3.24 (td, J=11.9, 1.8 Hz, 1H), 3.01-2.87 (m, 1H), 2.21-2.13 (m, 1H), 2.00-1.86 (m, 1H), 1.73-1.56 (m, 1H), 0.45 (d, J=12.5 Hz, 1H) Mass found 599 (M+H)$^+$.

Examples 118 and 119

8-[(4,4-Difluorocyclohexyl)(phenyl)methyl]-5-(dimethyl-1H-1,2,3-triazol-5-yl)-10-methanesulfonyl-13-(propan-2-yloxy)-3,8,12-triazatricyclo[7.4.0.0$^{2,7}$]trideca-1(13),2(7),3,5,9,11-hexaene Example 118

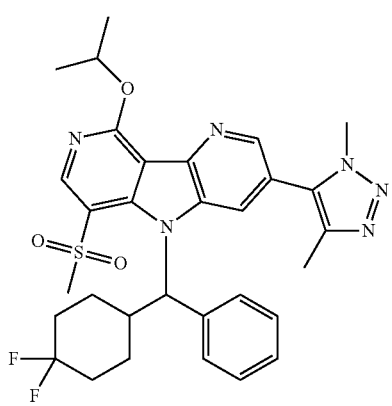

Enantiomer A

Example 119

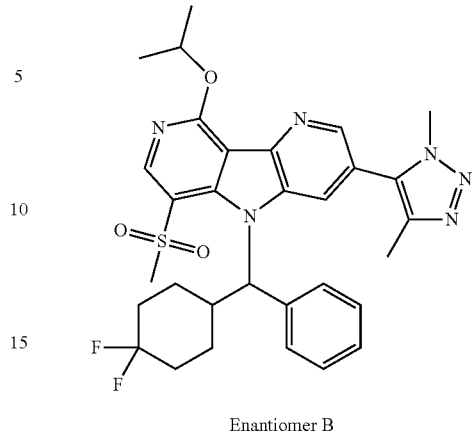

Enantiomer B

Step 1: 3-(1,4-Dimethyl-H-1,2,3-triazol-5-yl)-9-methoxy-6-(methylsulfonyl)-5H-pyrrolo[3,2-b:4,5-c']dipyridine A 10-20 mL microwave vial was charged with 1,4-dimethyl-5-(tributylstannyl)-1H-1,2,3-triazole (650 mg, 1.68 mmol) and diluted with DMF (7019 μl). To that solution was added 3-bromo-9-methoxy-6-(methylsulfonyl)-5H-pyrrolo[3,2-b:4,5-c']dipyridine (500 mg, 1.40 mmol), copper(I) iodide (40.1 mg, 0.211 mmol), triethylamine (293 μl, 2.11 mmol) and Pd(Ph$_3$P)$_4$ (122 mg, 0.105 mmol). The vial was sealed and degassed using ultra pure argon and sonication for 2 min. The vial was placed into an oil bath preheated to 80° C. After 1.5 h, the warm reaction was filtered through a pad of Celite and concentrated under reduced pressure. The resulting solids were suspended in DCM and collected by filtration. The filter cake was washed with a small amount of DCM followed by several volumes of hexanes to give 165 mg of desired product. The supernatant was loaded directly onto the column and purified by flash chromatography: (24 g ISCO RediSep Rf, loaded in/with: DCM and dried, fraction size: 9 mL 13×100 mm, and eluted with methanol in DCM 0% [75 mL], 0-4% [201 mL], 4% [201 mL], 4-10% [200 mL]). The fractions containing product were concentrated under reduced pressure and combined with previously filtered material to give 370 mg (71% yield). $^1$H NMR (400 MHz, CDCl$_3$) δ 9.88 (s, 1H), 8.75 (d, J=2.0 Hz, 1H), 8.72 (s, 1H), 7.83 (d, J=2.0 Hz, 1H), 4.41 (s, 3H), 4.04 (s, 3H), 3.27 (s, 3H), 2.40 (s, 3H). Mass found 373 (M+H)$^+$.

Step 2: 5-((4,4-Difluorocyclohexyl)(phenyl)methyl)-3-(1,4-dimethyl-1H-1,2,3-triazol-5-yl)-9-methoxy-6-(methylsulfonyl)-5H-pyrrolo[3,2-b:4,5-c']dipyridine A 24/40-50 mL was charged with triphenylphosphine (423 mg, 1.61 mmol) and dissolved in THF (4028 μl). The mixture was cooled to 0° C. and di-tert-butyl azodicarboxylate (371 mg, 1.61 mmol) was added in one portion. After 30 min, a thick milky solid formed and (4,4-difluorocyclohexyl)(phenyl)methanol (365 mg, 1.61 mmol) was added. After 20 min, 3-(1,4-dimethyl-1H-1,2,3-triazol-5-yl)-9-methoxy-6-(methylsulfonyl)-5H-pyrrolo[3,2-b:4,5-c'] dipyridine (300 mg, 0.806 mmol) was added as a solid. 4 mL of THF was used to wash the remaining carboline into the reaction mixture. After 1 h, TFA (621 μl, 8.06 mmol) was added and the mixture was let stir for 30 min and concentrated under reduced pressure. The yellow oil was diluted with ethyl acetate and quenched with a 1.5M tripotassium phosphate solution and transferred into a separatory funnel. The layers were separated. A thick emulsion persisted and was collected by filtration to give 65 mg of desired product. The organic was washed with water and brine, dried with magnesium sulfate, filtered, concentrated under reduced pressure and purified by flash chromatography: (40 g ISCO RediSep Rf, loaded in/with: DCM and dried, fraction size: 21 mL 16×150 mm, and eluted with acetone in DCM 0% [102 mL], 0-30% [400 mL], 30% [400 mL], 30-100% [400 mL]). The fractions were collected and the lots were combined to give 343 mg (73.3% yield) of product. $^1$H NMR (400 MHz, CDCl$_3$) δ 9.00 (s, 1H), 8.69 (d, J=2.0 Hz, 1H), 7.51-7.45 (m, 2H), 7.44-7.34 (m, 4H), 6.92 (d, J=10.0 Hz, 1H), 4.43 (s, 3H), 3.68 (s, 3H), 3.42 (s, 3H), 2.77 (br. s., 1H), 2.35 (br. s., 1H), 2.30-2.18 (m, 1H), 2.14 (s, 3H), 2.00-1.83 (m, 3H), 1.71-1.42 (m, 2H), 0.57 (br. s., 1H). Mass found 581 (M+H)$^+$.

Step 3: 9-Chloro-5-((4,4-difluorocyclohexyl)(phenyl)methyl)-3-(1,4-dimethyl-1H-1,2,3-triazol-5-yl)-6-(methylsulfonyl)-5H-pyrrolo[3,2-b:4,5-c']dipyridine A 24/40-100 mL round bottom flask was charged with (S)-5-((4,4-difluorocyclohexyl)(phenyl)methyl)-3-(1,4-dimethyl-1H-1,2,3-triazol-5-yl)-9-methoxy-6-(methylsulfonyl)-5H-pyrrolo[3,2-b:4,5-c']dipyridine (343 mg, 0.591 mmol) and dissolved in DMF (1737 μL) and POCl$_3$ (50 μL, 0.536 mmol) was added. The flask was placed into a reaction block preheated to 80° C. After 2 h, the mixture was poured onto ice and diluted with ethyl acetate. The reaction mixture was slowly quenched with solid sodium bicarbonate. The quenched solution was transferred into a separatory funnel and the layers were separated. The organic was washed with water. The aqueous was extracted with ethyl acetate and the aqueous was discarded. The combined organics were washed with brine, dried with magnesium sulfate, filtered and concentrated under reduced pressure. While attempting to dissolve the product in DCM to load onto a column, a white solid persisted. The solids were collected by filtration and NMR showed it to be the desired product. The supernatant was concentrated and the trituration process was repeated three more to give a combined yield of 197 mg of pure product. The supernatant was purified by flash chromatography: (24 g ISCO RediSep Rf, loaded in/with: DCM and dried, fraction size: 9 mL 13×100 mm, and eluted with ethyl acetate in DCM 0% [102 mL], 0-30% [252 mL], 30% [300 mL], 30-100% [252 mL]). The fractions were collected to give 70 mg of desired product which was combined with the previously collected lots to give 267 mg (77% yield) of product. $^1$H NMR (400 MHz, CDCl$_3$) δ 9.10 (s, 1H), 8.77 (d, J=1.8 Hz, 1H), 7.52-7.46 (m, 3H), 7.46-7.33 (m, 3H), 6.96 (d, J=10.0 Hz, 1H), 3.70 (s, 3H), 3.50 (s, 3H), 2.79 (br. s., 1H), 2.36 (br. s., 1H), 2.26 (br. s., 1H), 2.15 (s, 3H), 2.01-1.88 (m, 3H), 1.75-1.56 (m, 2H), 0.59 (d, J=14.3 Hz, 1H). Mass found 585 (M+H)$^+$.

Step 4: 8-[(4,4-Difluorocyclohexyl)(phenyl)methyl]-5-(dimethyl-1H-1,2,3-triazol-5-yl)-10-methanesulfonyl-13-(propan-2-yloxy)-3,8,12-triazatricyclo[7.4.0.0$^{2,7}$]trideca-1(13),2(7),3,5,9,11-hexaene A 1-dram pressure vial was charged with 2-propanol (500 μl, 6.49 mmol). KOtBu (96 mg, 0.855 mmol) was added and let stir for 30 min. 9-chloro-5-((4,4-difluorocyclohexyl)(phenyl)methyl)-3-(1,4-dimethyl-1H-1,2,3-triazol-5-yl)-6-(methylsulfonyl)-5H-pyrrolo[3,2-b:4,5-c']dipyridine (50 mg, 0.085 mmol) was added followed by NMP (500 μL). After 10 min, the mixture was quenched with a saturated solution of sodium bicarbonate and diluted with DCM. The layers were separated and the organic was washed with water and brine and the aqueous was discarded. The combined organics were washed with brine, dried with magnesium sulfate, filtered, concentrated under high vacuum pressure and purified by preparative HPLC. Crude mass: 44 mg. The crude material was dissolved in 2 mL NMP. Column: Waters XBridge C18 100×30 mm 5 u, Solvents: A:95:5water/ACN; B:95:5 ACN/water; Buffer: 10 mM NH$_4$OAc, % B gradient 50% (13 min), Flow Rate: 30 mL/min, Product RT: 10.45 min, 4 injections monitored @ 254 nm. The fractions containing product were concentrated on the speed vacuum overnight to give 36 mg of racemic product. The racemic mixture was separated by Chiral SFC: Chiralcel OD-H preparative column, 30×250 mm, 5 μm particle size. Mobile phase: 20% MeOH in CO$_2$, 130 bar, Temp: 35 C, Flow rate: 70 mL/min. for 15 min. UV monitored @ 220 nm, Injection: 0.35 mL of ~7 mg/mL in 1:1 CHCl$_3$:MeOH (36 mg purified by stacked injection) to give Enantiomer A (15.2 mg, 29% yield) and Enantiomer B (13.5 mg, 26% yield). Enantiomer A: $^1$H NMR (400 MHz, CDCl$_3$) δ 8.97 (s, 1H), 8.65 (d, J=2.0 Hz, 1H), 7.50-7.43 (m, 2H), 7.42-7.31 (m, 4H), 6.90 (d, J=9.8 Hz, 1H), 5.84 (spt, J=6.3 Hz, 1H), 3.65 (s, 3H), 3.40 (s, 3H), 2.85-2.72 (m, 1H), 2.40-2.32 (m, 1H), 2.29-2.21 (m, 1H), 2.12 (s, 3H), 2.03-1.87 (m, 3H), 1.72-1.60 (m, 4H), 0.67-0.58 (m, 1H). SFC RT: 10.95 min. Mass found 609 (M+H)$^+$. Enantiomer B: $^1$H NMR (400 MHz, CDCl$_3$) δ 8.97 (s, 1H), 8.65 (d, J=1.8 Hz, 1H), 7.49-7.43 (m, 2H), 7.42-7.31 (m, 4H), 6.90 (d, J=10.0 Hz, 1H), 5.84 (spt, J=6.2 Hz, 1H), 3.69-3.63 (m, 3H), 3.40 (s, 3H), 2.85-2.71 (m, 1H), 2.36 (d, J=10.0 Hz, 1H), 2.29-2.21 (m, 1H), 2.12 (s, 3H), 2.02-1.84 (m, 3H), 1.69-1.62 (m, 4H), 0.68-0.58 (m, 1H). SFC RT: 13 min. Mass found 609 (M+H)$^+$.

Examples 120 and 121

8-[(4,4-Difluorocyclohexyl)(phenyl)methyl]-5-(dimethyl-1H-1,2,3-triazol-5-yl)-10-methanesulfonyl-13-(3-methoxyazetidin-1-yl)-3,8,12-triazatricyclo[7.4.0.0$^{2,7}$]trideca-1(13),2(7),3,5,9,11-hexaene

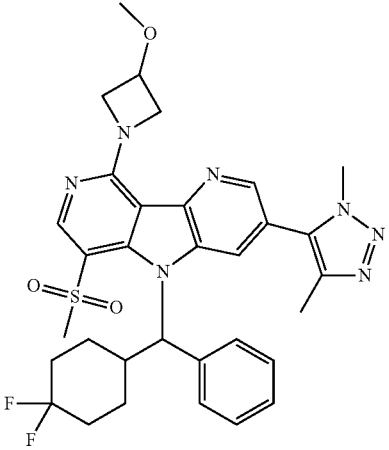

Example 120

Enantiomer A

Example 121

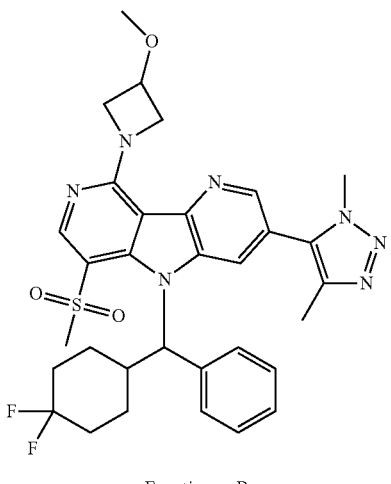

Enantiomer B

The title compound was prepared from 3-methoxyazetidine, HCl following a procedure analogous to that described for the synthesis of 8-[(4,4-difluorocyclohexyl)(phenyl)methyl]-5-(dimethyl-1H-1,2,3-triazol-5-yl)-10-methanesulfonyl-13-(propan-2-yloxy)-3,8,12-triazatricyclo[7.4.0.0$^{2,7}$]trideca-1(13),2(7),3,5,9,11-hexaene to give 33 mg of racemic product. The enantiomers were separated by Chiral SFC: Chiralcel OD-H preparative column, 30×250 mm, 5 μm particle size, Mobile phase: 20% MeOH in CO$_2$, 150 bar, Temp: 35 C, Flow rate: 70 mL/min for 39 min. UV monitored @ 220 nm, Injection: 0.75 mL of ~8 mg/mL in 1:1 CHCl$_3$:MeOH (33 mg purified by stacked injection) to give Enantiomer A (13.2 mg, 40% yield) and Enantiomer B (13 mg, 39% yield). Enantiomer A: $^1$H NMR (400 MHz, CDCl$_3$) δ 8.91 (s, 1H), 8.44 (d, J=1.8 Hz, 1H), 7.49-7.43 (m, 2H), 7.42-7.28 (m, 4H), 6.91 (d, J=9.8 Hz, 1H), 5.23-4.75 (m, 2H), 4.72-4.46 (m, 2H), 4.42 (tt, J=6.3, 4.2 Hz, 1H), 3.65 (s, 3H), 3.41 (s, 3H), 3.34 (s, 3H), 2.83-2.71 (m, J=9.8 Hz, 1H), 2.34 (d, J=9.8 Hz, 1H), 2.22 (d, J=13.6 Hz, 1H), 2.16 (s, 3H), 2.04-1.79 (m, 3H), 1.75-1.57 (m, 2H), 0.65 (d, J=10.5 Hz, 1H). SFC RT: 25 min. Mass found 636 (M+H)$^+$. Enantiomer B: $^1$H NMR (400 MHz, CDCl$_3$) δ 8.91 (s, 1H), 8.44 (d, J=1.8 Hz, 1H), 7.49-7.43 (m, 2H), 7.42-7.28 (m, 4H), 6.91 (d, J=9.8 Hz, 1H), 5.23-4.75 (m, 2H), 4.75-4.45 (m, 2H), 4.42 (tt, J=6.3, 4.1 Hz, 1H), 3.65 (s, 3H), 3.41 (s, 3H), 3.34 (s, 3H), 2.84-2.69 (m, J=9.5 Hz, 1H), 2.39-2.29 (m, 1H), 2.28-2.18 (m, 1H), 2.16 (s, 3H), 2.02-1.80 (m, 3H), 1.74-1.61 (m, 2H), 0.65 (d, J=10.8 Hz, 1H). SFC RT: 33.75 min. Mass found 636 (M+H)$^+$.

Examples 122 and 123

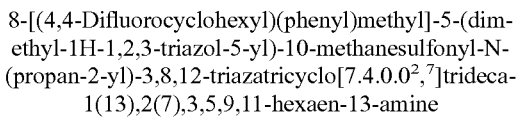

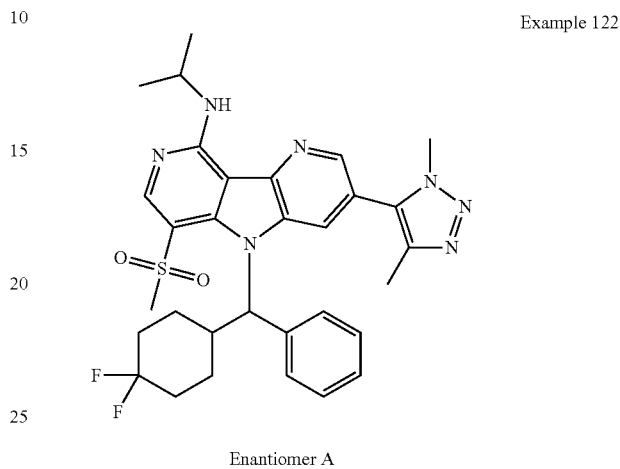

Enantiomer A

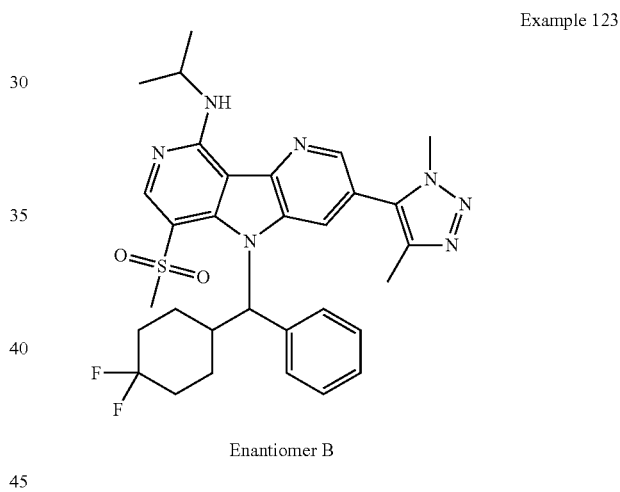

Enantiomer B

The title compound was prepared from isopropylamine following a procedure analogous to that described for the synthesis of 8-[(4,4-difluorocyclohexyl)(phenyl)methyl]-5-(dimethyl-1H-1,2,3-triazol-5-yl)-10-methanesulfonyl-13-(propan-2-yloxy)-3,8,12-triazatricyclo[7.4.0.0$^{2,7}$]trideca-1(13),2(7),3,5,9,11-hexaene to give 30 mg of racemic product. The enantiomers were separated by Chiral SFC: Chiralcel OD-H preparative column, 30×250 mm, 5 μm particle size, Mobile phase: 20% MeOH in CO$_2$, 130 bar, Temp: 35 C, Flow rate: 70 mL/min for 19 min. UV monitored @ 220 nm, Injection: 0.35 mL of ~11 mg/mL in 1:1 CHCl$_3$:MeOH (23 mg purified by stacked injection) to give Enantiomer A (11.6 mg, 31% yield) and Enantiomer B (11.8 mg, 31% yield). Enantiomer A: $^1$H NMR (400 MHz, CDCl$_3$) δ 8.93 (s, 1H), 8.46 (d, J=1.5 Hz, 1H), 8.00 (d, J=7.8 Hz, 1H), 7.51-7.45 (m, 2H), 7.43-7.30 (m, 4H), 6.88 (d, J=9.8 Hz, 1H), 4.75-4.65 (m, 1H), 3.67 (s, 3H), 3.33 (s, 3H), 2.77 (d, J=10.5 Hz, 1H), 2.33 (d, J=9.3 Hz, 1H), 2.27-2.13 (m, 4H), 2.04-1.81 (m, 3H), 1.77-1.63 (m, 2H), 1.46 (dd, J=8.5, 6.5 Hz, 6H), 0.73-0.62 (m, 1H). SFC RT: 12.6 min. Mass found 608 (M+H)$^+$. Enantiomer B: $^1$H NMR (400 MHz, CDCl$_3$) δ 8.93 (s, 1H), 8.46 (d, J=1.8 Hz, 1H), 8.00 (d, J=8.0 Hz, 1H), 7.51-7.45 (m, 2H), 7.42-7.29 (m, 4H), 6.88 (d, J=10.0 Hz, 1H), 4.75-4.64 (m, 1H), 3.67 (s, 3H), 3.33 (s, 3H), 2.77 (d, J=10.5 Hz, 1H), 2.33 (d, J=9.5 Hz, 1H), 2.28-2.13 (m, 4H), 2.05-1.80 (m, 3H), 1.76-1.62 (m, 2H), 1.46 (dd, J=8.5, 6.5 Hz, 6H), 0.74-0.63 (m, 1H). SFC RT: 15.5 min. Mass found 608 (M+H)$^+$.

Examples 124 and 125

8-[(4,4-Difluorocyclohexyl)(phenyl)methyl]-5-(dimethyl-1H-1,2,3-triazol-5-yl)-10-methanesulfonyl-N-(2-methylpropyl)-3,8,12-triazatricyclo[7.4.0.0$^{2,7}$]trideca-1(13),2(7),3,5,9,11-hexaen-13-amine

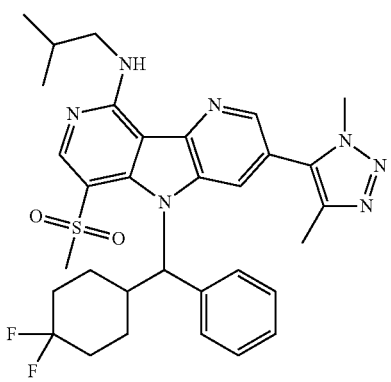

Example 124

Enantiomer A

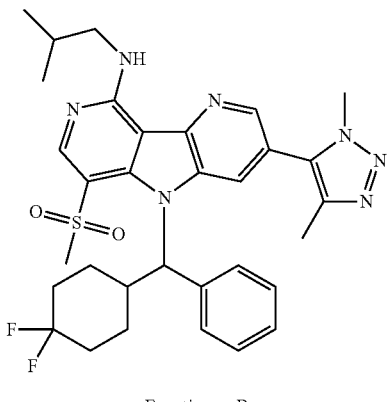

Example 125

Enantiomer B

The title compound was prepared from isobutylamine following a procedure analogous to that described for the synthesis of 8-[(4,4-difluorocyclohexyl)(phenyl)methyl]-5-(dimethyl-1H-1,2,3-triazol-5-yl)-10-methanesulfonyl-13-(propan-2-yloxy)-3,8,12-triazatricyclo[7.4.0.0$^{2,7}$]trideca-1(13),2(7),3,5,9,11-hexaene to give 19.6 mg of racemic product. The enantiomers were separated by Chiral SFC: Chiralcel OD-H preparative column, 30×250 mm, 5 μm particle size, Mobile phase: 20% MeOH in CO$_2$, 150 bar, Temp: 35 C, Flow rate: 70 mL/min for 18 min, UV monitored @ 220 nm Injection: 0.25 mL of ~7 mg/mL in MeOH (20 mg purified by stacked injection) to give Enantiomer A (7.8 mg, 20.6% yield) and Enantiomer B (9.8 mg, 26% yield). Enantiomer A: $^1$H NMR (400 MHz, CDCl$_3$) δ 8.93 (s, 1H), 8.46 (d, J=1.8 Hz, 1H), 8.22 (t, J=5.9 Hz, 1H), 7.51-7.45 (m, 2H), 7.43-7.36 (m, 2H), 7.36-7.30 (m, 2H), 6.89 (d, J=9.8 Hz, 1H), 3.70-3.65 (m, 5H), 3.34 (s, 3H), 2.84-2.71 (m, J=9.8 Hz, 1H), 2.33 (d, J=8.0 Hz, 1H), 2.23 (d, J=11.0 Hz, 1H), 2.17 (s, 3H), 2.05-1.82 (m, 4H), 1.77-1.60 (m, 2H), 1.12 (d, J=6.5 Hz, 6H), 0.73-0.64 (m, 1H). SFC RT: 12.9 min. Mass found 622 (M+H)$^+$. Enantiomer B: $^1$H NMR (400 MHz, CDCl$_3$) δ 8.93 (s, 1H), 8.46 (d, J=1.5 Hz, 1H), 8.22 (t, J=5.9 Hz, 1H), 7.52-7.46 (m, 2H), 7.42-7.36 (m, 2H), 7.36-7.30 (m, 2H), 6.89 (d, J=10.3 Hz, 1H), 3.70-3.65 (m, 5H), 3.34 (s, 3H), 2.84-2.71 (m, J=9.0 Hz, 1H), 2.38-2.30 (m, 1H), 2.29-2.22 (m, 1H), 2.17 (s, 3H), 2.05-1.83 (m, 4H), 1.76-1.63 (m, 2H), 1.12 (d, J=6.5 Hz, 6H), 0.76-0.66 (m, 1H). SFC RT: 14.5 min. Mass found 622 (M+H)$^+$.

Examples 126 and 127

8-[(4,4-Difluorocyclohexyl)(phenyl)methyl]-5-(dimethyl-1H-1,2,3-triazol-5-yl)-10-methanesulfonyl-N-methyl-N-(propan-2-yl)-3,8,12-triazatricyclo[7.4.0.0$^{2,7}$]trideca-1(13),2(7),3,5,9,11-hexaen-13-amine

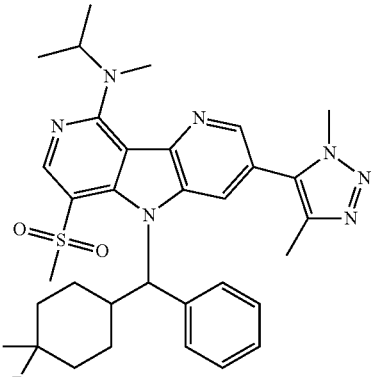

Example 126

Enantiomer A

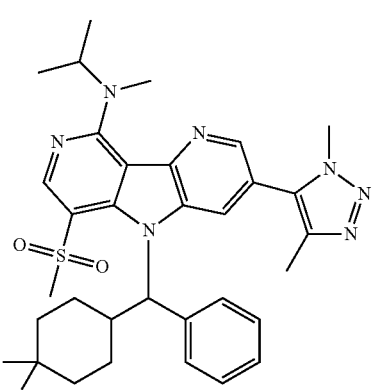

Example 127

Enantiomer B

The title compound was prepared from N-isopropylmethylamine following a procedure analogous to that described for the synthesis of 8-[(4,4-difluorocyclohexyl)(phenyl)methyl]-5-(dimethyl-1H-1,2,3-triazol-5-yl)-10-methanesulfonyl-13-(propan-2-yloxy)-3,8,12-triazatricyclo[7.4.0.0$^{2,7}$]trideca-1(13),2(7),3,5,9,11-hexaene to give 30.3 mg of racemic product. The enantiomers were separated by Chiral SFC: Chiralcel OD-H preparative column, 30×250 mm, 5 μm particle size, Mobile phase: 35% MeOH in CO$_2$, 150 bar, Temp: 35 C, Flow rate: 70 mL/min for 12 min, UV monitored @ 220 nm, Injection: 0.5 mL of ~10 mg/mL in MeOH (30 mg purified by stacked injection) to give Enantiomer A (14.4 mg, 44.5% yield) and Enantiomer B (14.5 mg, 44.8% yield). Enantiomer A: 1H NMR (400 MHz, CDCl$_3$) δ 8.88 (s, 1H), 8.51 (d, J=2.0 Hz, 1H), 7.50-7.43 (m, 2H), 7.41-7.35 (m, 2H), 7.35-7.31 (m, 2H), 6.90 (d, J=9.8 Hz, 1H), 5.13 (spt, J=6.6 Hz, 1H), 3.65 (s, 3H), 3.37 (s, 3H), 3.29 (s, 3H), 2.85-2.72 (m, 1H), 2.40-2.30 (m, 1H), 2.28-2.20 (m, 1H), 2.16 (s, 3H), 2.05-1.91 (m, 3H), 1.77-1.61 (m, 2H), 1.41 (t, J=6.3 Hz, 6H), 0.67 (d, J=13.3 Hz, 1H). SFC RT: 16.1 min. Mass found 622 (M+H)$^+$. Enantiomer B: $^1$H NMR (400 MHz, CDCl$_3$) δ 8.88 (s, 1H), 8.51 (d, J=1.8 Hz, 1H), 7.50-7.43 (m, 2H), 7.41-7.35 (m, 2H), 7.35-7.30 (m, 2H), 6.90 (d, J=9.8 Hz, 1H), 5.13 (spt, J=6.6 Hz, 1H), 3.67-3.62 (m, 3H), 3.37 (s, 3H), 3.29 (s, 3H), 2.78 (s, 1H), 2.40-2.30 (m, 1H), 2.24 (br. s., 1H), 2.16 (s, 3H), 2.05-1.89 (m, 3H), 1.76-1.62 (m, 2H), 1.41 (t, J=6.4 Hz, 6H), 0.67 (s, 1H). SFC RT: 18.6 min. Mass found 622 (M+H)$^+$.

Example 128

13-Methoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene

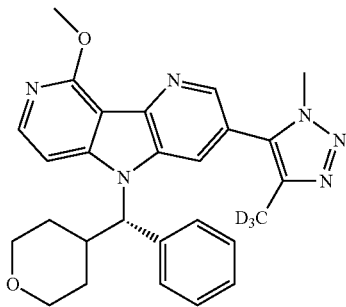 [SMILES: [2H]C([2H])([2H])c1nnn(C)c1-c1cnc2c3c(OC)nccc3n([C@H](c3ccccc3)C3CCOCC3)c2c1]

Step 1: 5-Bromo-2'-methoxy-3-nitro-2,3'-bipyridine

A 24/40-200 mL round bottom flask was charged with 2,5-dibromo-3-nitropyridine (3.54 g, 12.6 mmol), (2-methoxypyridin-3-yl)boronic acid (2.017 g, 13.2 mmol) and PdCl$_2$(dppf)-CH$_2$Cl$_2$ Adduct (0.513 g, 0.628 mmol). The mixture was dissolved in THF (50.2 ml) and 2M tripotassium phosphate (18.84 ml, 37.7 mmol) was added. The mixture was degassed using sonication and ultra pure argon for 5 min. The mixture was heated to 80° C. After 4.5 h, the mixture was cooled, concentrated to remove most of the THF then diluted with ethyl acetate and washed with water and brine. The organics were dried over MgSO$_4$, filtered and concentrated to give a brown solid. This material was purified on SiO$_2$ (40 g) loaded on dry column in DCM/blown dry and eluted using hexane (96 mL), 50% DCM/hexane (480 mL), 50 to 100% DCM/hexane (384 mL, linear gradient), DCM (240 mL), 0 to 10% ethyl acetate/DCM (384 mL, linear gradient), 10% ethyl acetate/DCM (360 mL). To give 2.6 g (67% yield) of product. $^1$H NMR (400 MHz, CDCl$_3$) δ 8.94 (d, J=2.0 Hz, 1H), 8.42 (d, J=2.0 Hz, 1H), 8.30 (dd, J=5.0, 2.0 Hz, 1H), 7.99 (dd, J=7.4, 1.9 Hz, 1H), 7.11 (dd, J=7.3, 5.0 Hz, 1H), 3.87 (s, 3H). Mass found 310 (M+H)$^+$.

Step 2: 3-Bromo-9-methoxy-5H-pyrrolo[3,2-b:4,5-c']dipyridine

To a mixture of 5-bromo-2'-methoxy-3-nitro-2,3'-bipyridine (2.6 g, 8.38 mmol) and DPPE (5.01 g, 12.6 mmol) in a 40 mL pressure rated vial was added 1,2-dichlorobenzene (20 mL). The vial was sealed and heated to 165° C. After 3 h the vial was allowed to cool to ambient temperature then the solution was diluted with diethyl ether and filtered. The filtrate was concentrated, triturated with DCM and filtered. This solid was re-triturated and filtered from DCM to give 1.02 g (44% yield) of product. $^1$H NMR (400 MHz, CDCl$_3$) δ 8.76 (d, J=2.0 Hz, 1H), 8.41 (br. s., 1H), 8.20 (d, J=5.8 Hz, 1H), 7.92 (d, J=2.0 Hz, 1H), 7.06 (d, J=5.8 Hz, 1H), 4.29 (s, 3H). Mass found 279 (M+H)$^+$.

Step 3: 13-Methoxy-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene An oven dried 2-5 mL microwave vial was charged with 4-($^2$H$_3$)methyl-1-methyl-5-(tributylstannyl)-1H-1,2,3-triazole (420 mg, 1.08 mmol) and diluted with DMF (4495 μl). To that solution was added 3-bromo-9-methoxy-5H-pyrrolo[3,2-b:4,5-c']dipyridine (250 mg, 0.899 mmol), copper(I) iodide (25.7 mg, 0.135 mmol), triethylamine (188 μl, 1.35 mmol) and Pd(Ph$_3$P)$_4$ (78 mg, 0.067 mmol). The vial was sealed and degassed using ultra pure argon and sonication for 2 min. The vial was sealed and placed into an oil bath preheated to 80° C. After 35 min, the mixture was cooled to room temperature and filtered through a pad of Celite. The solution was concentrated under reduced pressure and purified by flash chromatography: (24 g ISCO RediSep Rf, loaded in/with: DCM and dried, fraction size: 9 mL 13×100 mm, and eluted with methanol in DCM 0% [100 mL], 0-5% [175 mL], 5% [125 mL], 5-7% [201 mL], 7% [150 mL]). The fractions were collected to give 260 mg (97% yield) of product. $^1$H NMR (400 MHz, CDCl$_3$) δ 8.73 (br. s., 1H), 8.68 (d, J=1.8 Hz, 1H), 8.25 (d, J=6.0 Hz, 1H), 7.72 (d, J=2.0 Hz, 1H), 7.13 (d, J=5.8 Hz, 1H), 4.33 (s, 3H), 4.03 (s, 3H). Mass found 298 (M+H)$^+$.

Step 4: 13-Methoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene A 24/40-50 mL was charged with triphenylphosphine (459 mg, 1.75 mmol) and dissolved in THF (4372 μl). The mixture was cooled to 0° C. and di-tert-butyl azodicarboxylate (403 mg, 1.75 mmol) was added in one portion. After 30 min, the yellow solution became a thick milky slurry. (R)-phenyl(tetrahydro-2H-pyran-4-yl)methanol (336 mg, 1.75 mmol) was added and after 10 min, 13-methoxy-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene (260 mg, 0.874 mmol) was added as a solid and an additional amount of THF (4372 μl) was added to dissolve the rest of the carboline and add it to was added to the reaction mixture. The ice bath was removed. After 45 min, TFA (674 μl, 8.74 mmol) was added to quench the reaction and the mixture was let stir for 10 min and concentrated under reduced pressure. The yellow oil was diluted with ethyl acetate and quenched with a 1.5M tripotassium phosphate solution and transferred into a separatory funnel. The layers were separated and the organic was washed with water, brine, filtered, dried with magnesium sulfate, concentrated under reduced pressure and purified by flash chromatography: (40 g ISCO RediSep Rf, loaded in/with: DCM and dried, fraction size: 9 mL 13×100 mm, and eluted with acetone in DCM 0% [130 mL], 0-30% [250 mL], 30% [250 mL], 30-50% [250 mL], 50% [250 mL], 50-70% [250 mL]). The fractions were collected to give 194 mg, 47.0% yield) of product. 10 mg of the purified product was diluted with 1 mL of methanol and purified by preparative HPLC. Waters XBridge C18 100×30 mm 5 u, Solvents: A:95:5water/ACN; B:95:5 ACN/water; Buffer: 10 mM NH$_4$OAc, % B gradient 30% (15 min), Flow Rate: 30 mL/min. The fractions containing product were concentrated under reduced pressure. The resulting solids were filtered through a plug of silica gel, eluting the product with acetone. $^1$H NMR (400 MHz, CDCl$_3$) δ 8.62 (d, J=2.0 Hz, 1H), 8.29 (d, J=6.3 Hz, 1H), 7.60 (d, J=1.8 Hz, 1H), 7.46-7.41 (m, 2H), 7.40-7.28 (m, 4H), 5.46 (d, J=10.8 Hz, 1H), 4.32 (s, 3H), 4.06 (dd, J=11.7, 2.9 Hz, 1H), 3.91-3.83 (m, 4H), 3.54 (td, J=11.9, 1.9 Hz, 1H), 3.36 (td, J=11.9, 2.0 Hz, 1H), 3.07 (qt, J=11.1, 3.6 Hz, 1H), 2.07-1.98 (m, 1H), 1.66-1.52 (m, 1H), 1.45-1.32 (m, 1H), 1.06 (d, J=12.8 Hz, 1H). Mass found 472 (M+H)$^+$.

Example 129

13-Ethoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene

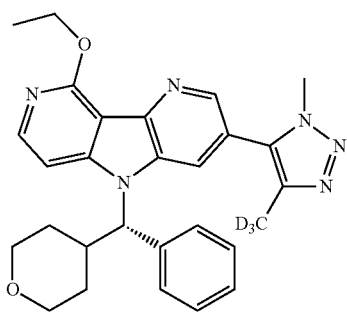 [SMILES: [2H]C([2H])([2H])c1nnn(C)c1-c1cnc2c3c(OCC)nccc3n([C@H](c3ccccc3)C3CCOCC3)c2c1]

Step 1: 13-Chloro-5-[4-(2H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene A 2.0-5.0 mL microwave vial was charged with 13-methoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene (196 mg, 0.416 mmol) and dissolved in DMF (4156 μl). To that solution was added POCl$_3$ (387 μl, 4.16 mmol). The vial was sealed and placed into a reaction block preheated to 80° C. After 4 h, the reaction mixture was poured into ice water and neutralized with solid sodium bicarbonate. The crude mixture was diluted with ethyl acetate and transferred into a separatory funnel where the layers were separated. The organic was washed with brine (×3). The combined aqueous was extracted with ethyl acetate and the aqueous was discarded. The combined organics were washed with brine, dried with magnesium sulfate, filtered, concentrated under reduced pressure and purified by flash chromatography: (24 g ISCO RediSep Rf, loaded in/with: DCM and dried, fraction size: 9 mL 13×100 mm, and eluted with acetone in DCM 0% [125 mL], 0-35% [333 mL], 35% [165 mL], 35-100% [201 mL]). The fractions were collected to give 133 mg (67.2% yield) of product. $^1$H NMR (400 MHz, CDCl$_3$) δ 8.72 (d, J=1.8 Hz, 1H), 8.51 (d, J=6.0 Hz, 1H), 7.67 (d, J=1.5 Hz, 1H), 7.60 (d, J=6.0 Hz, 1H), 7.45-7.33 (m, 5H), 5.52 (d, J=10.8 Hz, 1H), 4.11-4.05 (m, 1H), 3.92-3.86 (m, 4H), 3.60-3.51 (m, 1H), 3.36 (td, J=11.8, 2.0 Hz, 1H), 3.08 (s, 1H), 2.05 (d, J=13.3 Hz, 1H), 1.66-1.52 (m, 1H), 1.45-1.32 (m, 1H), 1.06 (d, J=12.5 Hz, 1H). Mass found 476 (M+H)$^+$.

Step 2: 13-Ethoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene A 1-dram pressure vial was charged with ethanol (250 μL, 4.28 mmol) and KOtBu (23.57 mg, 0.210 mmol) was added in one portion. After 10 min, 13-chloro-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene (10 mg, 0.021 mmol) dissolved in NMP (150 μL) was added. The vial was placed into a reaction block preheated to 55° C. After 2 h, the mixture was quenched with a saturated solution of sodium bicarbonate and diluted with methanol. The inorganic solids were filtered off through a 0.45 syringe tip filter and the clear solution was purified by preparative HPLC: Column: Waters XBridge C18 100×30 mm 5 u, Solvents: A:95:5water/ACN; B:95:5 ACN/water; Buffer: 10 mM NH$_4$OAc, % B: 32% (20 min), Flow Rate: 30 mL/min, 1 injection monitored @ 254 nm. The fractions containing product were collected and concentrated under reduced pressure. The resulting solids were filtered through a plug of silica gel, eluting the product with acetone to give 5.1 mg (49.5% yield) of product. $^1$H NMR (400 MHz, CDCl$_3$) δ 8.62 (d, J=1.8 Hz, 1H), 8.27 (d, J=6.0 Hz, 1H), 7.57 (d, J=1.8 Hz, 1H), 7.45-7.39 (m, 2H), 7.39-7.29 (m, 3H), 7.26 (d, J=6.3 Hz, 1H), 5.46 (d, J=10.8 Hz, 1H), 4.84 (q, J=7.1 Hz, 2H), 4.06 (dd, J=11.8, 2.8 Hz, 1H), 3.91-3.83 (m, 4H), 3.54 (td, J=11.9, 2.0 Hz, 1H), 3.35 (td, J=11.9, 2.0 Hz, 1H), 3.13-3.00 (m, 1H), 2.03 (d, J=13.1 Hz, 1H), 1.66-1.52 (m, 4H), 1.46-1.32 (m, 1H), 1.07 (d, J=13.3 Hz, 1H). Mass found 486 (M+H)$^+$.

Example 130

13-(Cyclopropylmethoxy)-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene

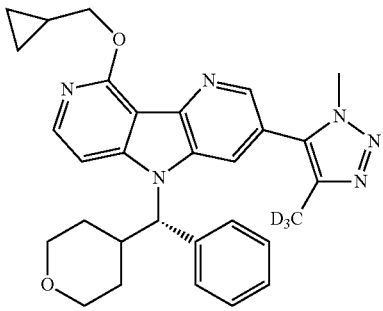 [SMILES: [2H]C([2H])([2H])c1nnn(C)c1-c1cnc2c3c(OCC4CC4)nccc3n([C@H](c3ccccc3)C3CCOCC3)c2c1]

The title compound was prepared from cyclopropanemethanol following a procedure analogous to that described for the synthesis of 13-ethoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene to give 5.8 mg (53.4% yield) of product. $^1$H NMR (400 MHz, CDCl$_3$) δ 8.62 (d, J=1.8 Hz, 1H), 8.25 (d, J=6.0 Hz, 1H), 7.57 (d, J=1.8 Hz, 1H), 7.45-7.40 (m, 2H), 7.38-7.30 (m, 3H), 7.26 (d, J=6.0 Hz, 1H), 5.46 (d, J=10.5 Hz, 1H), 4.66-4.54 (m, 2H), 4.06 (dd, J=11.8, 3.0 Hz, 1H), 3.91-3.82 (m, 4H), 3.54 (td, J=11.9, 2.0 Hz, 1H), 3.35 (td, J=11.9, 1.9 Hz, 1H), 3.13-3.00 (m, 1H), 2.03 (d, J=12.8 Hz, 1H), 1.62-1.51 (m, 2H), 1.46-1.32 (m, 1H), 1.08 (d, J=13.1 Hz, 1H), 0.68-0.61 (m, 2H), 0.54-0.48 (m, 2H). Mass found 512 (M+H)$^+$.

Example 131

5-[4-($^2$H$_3$)Methyl-1-methyl-1H-1,2,3-triazol-5-yl]-8-[(S)-oxan-4-yl(phenyl)methyl]-13-(propan-2-yloxy)-3,8,12-triazatricyclo[7.4.0.0$^{2,7}$]trideca-1(13),2(7),3,5,9,11-hexaene

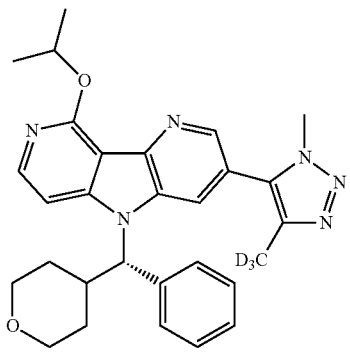 [SMILES: [2H]C([2H])([2H])c1nnn(C)c1-c1cnc2c3c(OC(C)C)nccc3n([C@H](c3ccccc3)C3CCOCC3)c2c1]

The title compound was prepared from 2-propanol following a procedure analogous to that described for the synthesis of 13-ethoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene to give 5.6 mg (52.8% yield) of product. $^1$H NMR (400 MHz, CDCl$_3$) δ 8.60 (d, J=2.0 Hz, 1H), 8.26 (d, J=6.0 Hz, 1H), 7.54 (d, J=1.8 Hz, 1H), 7.44-7.39 (m, 2H), 7.39-7.30 (m, 3H), 7.23 (d, J=6.0 Hz, 1H), 5.73 (spt, J=6.3 Hz, 1H), 5.45 (d, J=10.8 Hz, 1H), 4.05 (dd, J=11.8, 2.8 Hz, 1H), 3.92-3.81 (m, 4H), 3.54 (td, J=11.9, 2.0 Hz, 1H), 3.35 (td, J=11.9, 2.0 Hz, 1H), 3.13-2.99 (m, 1H), 2.03 (d, J=14.1 Hz, 1H), 1.59 (dd, J=6.3, 4.3 Hz, 7H), 1.46-1.32 (m, 1H), 1.11-1.02 (m, 1H). Mass found 500 (M+H)$^+$.

Example 132

N-Ethyl-N-methyl-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaen-13-amine

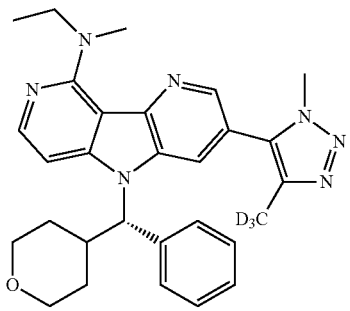 [SMILES: [2H]C([2H])([2H])c1nnn(C)c1-c1cnc2c3c(N(C)CC)nccc3n([C@H](c3ccccc3)C3CCOCC3)c2c1]

A 1-dram pressure vial was charged with 13-chloro-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene (10 mg, 0.021 mmol) and dissolved in NMP (150 µL). N-ethylmethylamine (150 µl, 1.73 mmol) was added and the reaction was placed into a heating block preheated to 90° C. After 4 h, the completed reaction was purified directly by preparative HPLC: Column: Waters XBridge C18 100×30 mm 5 u, Solvents: A:95:5water/ACN; B:95:5 ACN/water; Buffer: 10 mM NH$_4$OAc, % B: 43% (10 min), Flow Rate: 30 mL/min, 1 injection monitored @ 254 nm. The fractions containing product were concentrated under reduced pressure. The resulting solids were washed through a plug of silica gel, eluting the product with acetone to give 7.5 mg (69.4% yield) of product. $^1$H NMR (400 MHz, CDCl$_3$) δ 8.51 (d, J=2.0 Hz, 1H), 8.32 (d, J=6.0 Hz, 1H), 7.52 (d, J=2.0 Hz, 1H), 7.46-7.40 (m, 2H), 7.39-7.28 (m, 3H), 7.09 (d, J=6.0 Hz, 1H), 5.47 (d, J=10.5 Hz, 1H), 4.09-3.96 (m, 3H), 3.90-3.84 (m, 4H), 3.54 (td, J=11.9, 1.9 Hz, 1H), 3.40-3.30 (m, 4H), 3.14-3.00 (m, 1H), 2.04 (d, J=13.6 Hz, 1H), 1.68-1.52 (m, 1H), 1.48-1.34 (m, 1H), 1.33-1.28 (m, 3H), 1.10-1.03 (m, 1H). Mass found 499 (M+H)$^+$.

Example 133

N-(2,2-Difluoroethyl)-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaen-13-amine

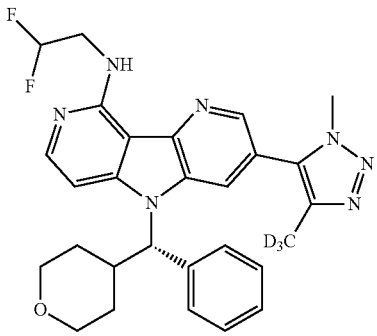 [SMILES: [2H]C([2H])([2H])c1nnn(C)c1-c1cnc2c3c(NCC(F)F)nccc3n([C@H](c3ccccc3)C3CCOCC3)c2c1]

The title compound was prepared from 2,2-difluoroethylamine following a procedure analogous to that described for the synthesis of N-ethyl-N-methyl-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaen-13-amine to give 12.4 mg (89% yield) of product. $^1$H NMR (400 MHz, CDCl$_3$) δ 8.43 (d, J=1.8 Hz, 1H), 8.23 (d, J=6.0 Hz, 1H), 7.54 (d, J=1.8 Hz, 1H), 7.46-7.41 (m, 2H), 7.39-7.29 (m, 3H), 7.25 (t, J=6.4 Hz, 1H), 7.01 (d, J=6.0 Hz, 1H), 6.32-5.97 (m, 1H), 5.38 (d, J=10.5 Hz, 1H), 4.23-4.09 (m, 2H), 4.05 (dd, J=11.7, 2.6 Hz, 1H), 3.93-3.85 (m, 4H), 3.53 (td, J=11.9, 2.0 Hz, 1H), 3.37 (td, J=11.9, 2.0 Hz, 1H), 3.11-2.99 (m, 1H), 1.96 (d, J=13.1 Hz, 1H), 1.62-1.50 (m, 1H), 1.47-1.34 (m, 1H), 1.12 (d, J=12.8 Hz, 1H). Mass found 521 (M+H)$^+$.

Example 134

5-[4-($^2$H$_3$)Methyl-1-methyl-1H-1,2,3-triazol-5-yl]-8-[(S)-oxan-4-yl(phenyl)methyl]-N-(2,2,2-trifluoroethyl)-3,8,12-triazatricyclo[7.4.0.0$^{2,7}$]trideca-1(13),2(7),3,5,9,11-hexaen-13-amine

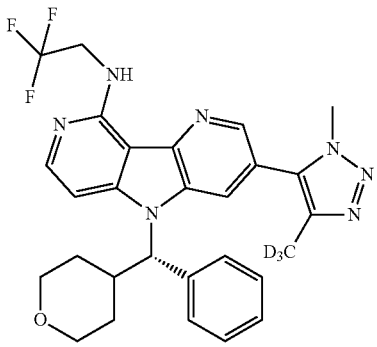 [SMILES: [2H]C([2H])([2H])c1nnn(C)c1-c1cnc2c3c(NCC(F)(F)F)nccc3n([C@H](c3ccccc3)C3CCOCC3)c2c1]

The title compound was prepared from 2,2,2-trifluoroethylamine following a procedure analogous to that described for the synthesis of N-ethyl-N-methyl-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7), 3,5,9,11-hexaen-13-amine to give 6.3 mg (55% yield) of product. $^1$H NMR (400 MHz, CDCl$_3$) δ 8.43 (d, J=1.8 Hz, 1H), 8.26 (d, J=6.0 Hz, 1H), 7.55 (d, J=1.5 Hz, 1H), 7.46-7.41 (m, 2H), 7.39-7.28 (m, 4H), 7.04 (d, J=6.3 Hz, 1H), 5.38 (d, J=10.5 Hz, 1H), 4.51 (qd, J=9.1, 6.8 Hz, 2H), 4.08-4.01 (m, 1H), 3.93-3.84 (m, 4H), 3.53 (td, J=11.9, 2.0 Hz, 1H), 3.37 (td, J=11.9, 2.0 Hz, 1H), 3.12-2.99 (m, 1H), 1.96 (d, J=12.8 Hz, 1H), 1.59-1.49 (m, 1H), 1.47-1.33 (m, 1H), 1.16 (d, J=13.6 Hz, 1H). Mass found 539 (M+H)$^+$.

Example 135

Methyl 5-(dimethyl-1H-1,2,3-triazol-5-yl)-13-methoxy-8-[(S)-oxan-4-yl(phenyl)methyl]-3,8,12-triazatricyclo[7.4.0.0$^{2,7}$]trideca-1(9),2,4,6,10,12-hexaene-10-carboxylate

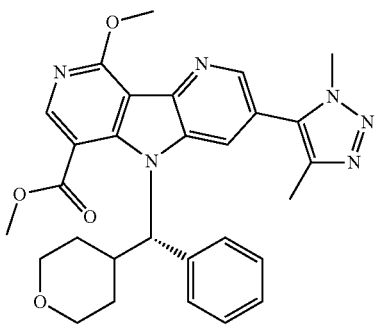 [SMILES: COC(=O)c1cnc(OC)c2c3ncc(-c4c(C)nnn4C)cc3n([C@H](c3ccccc3)C3CCOCC3)c12]

Step 1: Methyl 6-methoxy-5-(4,4,5,5-tetramethyl-1,3,2-dioxaborolan-2-yl)nicotinate A 250 mL round bottom flask was charged with methyl 5-bromo-6-methoxynicotinate (3.77 g, 15.3 mmol) and dissolved in dioxane (61.3 ml). To that stirring solution was added potassium acetate (3.01 g, 30.6 mmol), bis(pinacolato)diboron (4.47 g, 17.6 mmol) and PdCl$_2$(dppf) (0.112 g, 0.153 mmol). The flask was sealed and degassed by sonication while bubbling argon gas through the solution for 5 min. The reaction flask was placed into an oil bath preheated to 80° C. and stirred overnight. After 17.5 h the mixture was cooled to room temperature and an additional amount of bis(pinacolato)diboron (2.0 g, 7.87 mmol) and PdCl$_2$(dppf) (450 mg, 0.615 mmol) was added. The flask was sealed and degassed as previously described and heating was continued for 4 h then the mixture was cooled and concentrated under reduced pressure to give a black solid. This solid was dissolved in ethyl acetate. Water was added and the mixture was filtered through a pad of Celite. The filtrate was transferred into a separatory funnel and the layers were separated. The organic was washed with water (×1) and brine (×2), dried with magnesium sulfate, filtered and concentrated under reduced pressure. The crude residue was purified by flash chromatography: (40 g ISCO RediSep Rf) loaded on dry column in DCM, dried under a stream of nitrogen and eluted with 0%-50% ethyl acetate/hexanes to give the title compound (3.52 g, 12.0 mmol, 78% yield) as a crystalline white solid. $^1$H NMR (400 MHz, CDCl$_3$) δ 8.89 (d, J=2.5 Hz, 1H), 8.56 (d, J=2.5 Hz, 1H), 4.04 (s, 3H), 3.92 (s, 3H), 1.37 (s, 12H). LCMS: Rt=0.97 min; (ES): m/z (M+H)$^+$ 294: (Waters Acquity SDS. Column: BEH C18 2.1×50 mm 1.7

μm (1.5 min grad) 2-98% B. Flow Rate=0.8 mL/min. Solvent A: H$_2$O—0.1% TFA. Solvent B: ACN—0.1% TFA).

Step 2: Methyl 5-bromo-2'-methoxy-3-nitro-[2,3'-bipyridine]-5'-carboxylate

To a 250 mL round bottom flask containing methyl 6-methoxy-5-(4,4,5,5-tetramethyl-1,3,2-dioxaborolan-2-yl)nicotinate (3.52 g, 12.0 mmol) was added THF (100 mL). To this solution was added 2,5-dibromo-3-nitropyridine (4.06 g, 14.4 mmol), potassium phosphate tribasic, 2.0M (12.01 mL, 24.0 mmol) and PdCl$_2$(dppf) (0.300 g, 0.410 mmol). The flask was sealed and degassed by sonication while bubbling argon gas through the solution. The flask was then placed into an oil bath preheated to 65° C. After 1 h, the mixture was cooled and concentrated under reduced pressure. The resulting brown solid was dissolved in ethyl acetate and diluted with water. The biphasic mixture was filtered through a pad of Celite and transferred into a separatory funnel where the layers were separated. The organic layer was washed with water (×1) and brine (×2), dried over magnesium sulfate, filtered and concentrated. The crude product was purified by flash chromatography: (40 g ISCO RediSep Rf, loaded on dry column in DCM, dried under a stream of nitrogen and eluted with 0-15% ethyl acetate/hexanes to give the title compound (1.67 g, 4.54 mmol, 37.8% yield) as a solid. $^1$H NMR (400 MHz, CDCl$_3$) δ 8.97 (d, J=2.0 Hz, 1H), 8.94 (d, J=2.5 Hz, 1H), 8.57 (d, J=2.3 Hz, 1H), 8.46 (d, J=2.0 Hz, 1H), 3.97-3.95 (m, 3H), 3.94 (s, 3H). LCMS: Rt=1.24 min; (ES): m/z (M+H)$^+$ 369: (Waters Acquity SDS. Column: BEH C18 2.1×50 mm 1.7 μm (1.5 min grad) 2-98% B. Flow Rate=0.8 mL/min. Solvent A: H$_2$O—0.1% TFA. Solvent B: ACN—0.1% TFA).

Step 3: Methyl 3-bromo-9-methoxy-5H-pyrrolo[3,2-b:4,5-c']dipyridine-6-carboxylate A 100 mL round bottom flask was charged with methyl 5-bromo-2'-methoxy-3-nitro-[2,3'-bipyridine]-5'-carboxylate (2.42 g, 6.57 mmol) and 1,2-bis(diphenylphosphino)ethane (3.93 g, 9.86 mmol). The mixture was suspended in 1,2-dichlorobenzene (21.9 ml), sealed under a balloon atmosphere of nitrogen, and placed into an oil bath preheated to 160° C. After 30 min, the mixture was allowed to cool to room temperature and diethyl ether was added resulting in the formation of a precipitate which was collected by filtration. Trituration of the crude material with DCM gave 250 mg of a the desired product as a tan solid which was collected by filtration and characterized by 1H NMR. The supernatant was concentrated under reduced pressure and purified by flash chromatography (40 g ISCO RediSep Rf, loaded on dry column in DCM, dried under a stream of nitrogen and eluted with ethyl acetate in DCM 0% [150 mL], 0-15% [500 mL], 15% [600 mL]). The product containing fractions were concentrated to give a brown impure solid. This solid was triturated with DCM and the desired product was collected by filtration. Multiple repetitive triturations of the filtrates in this way and combination of the lots gave the title compound (950 mg, 2.83 mmol, 43.0% yield) as a light brown solid. $^1$H NMR (400 MHz, CDCl$_3$) δ 10.04 (br. s., 1H), 8.86 (s, 1H), 8.78 (d, J=2.0 Hz, 1H), 8.00 (d, J=1.8 Hz, 1H), 4.36 (s, 3H), 4.05 (s, 3H).

Step 4: (S)-Methyl 3-bromo-9-methoxy-5-(phenyl (tetrahydro-2H-pyran-4-yl)methyl)-5H-pyrrolo[3,2-b:4,5-c']dipyridine-6-carboxylate A 100 mL round bottom flask was charged with triphenylphosphine (624 mg, 2.38 mmol) and dissolved in THF (5 mL). The solution was cooled with an ice bath and di-tert-butyl azodicarboxylate (548 mg, 2.38 mmol) dissolved in THF (1 mL) was added drop wise to give a yellow solution which turned to a thick white suspension after 30 min. (R)-phenyl(tetrahydro-2H-pyran-4-yl)methanol (458 mg, 2.38 mmol) was then added in one portion and the mixture was stirred for 45 min. methyl 3-bromo-9-methoxy-5H-pyrrolo[3,2-b:4,5-c']dipyridine-6-carboxylate (400 mg, 1.19 mmol) was partially suspended in THF (20 mL) and added drop wise to the reaction over 10 min. The ice bath was removed and the reaction was allowed to warm to room temperature. After 2.5 h, trifluoroacetic acid (0.917 mL, 11.9 mmol) was added and the mixture was stirred for 20 min and then concentrated under reduced pressure. The mixture was diluted with ethyl acetate and quenched with 1.5M aqueous potassium phosphate solution. The contents of the flask were transferred into a separatory funnel and the layers were separated. The organic was washed with water (×2) and brine (×1). The combined aqueous was back extracted with ethyl acetate (×2) and discarded. The combined organics were washed with brine (×1), dried over magnesium sulfate, concentrated under reduced pressure, and purified by flash chromatography: (40 g ISCO RediSep Rf, loaded on dry column in DCM, dried under a stream of nitrogen and eluted with ethyl acetate in DCM 0% [102 mL], 0-15% [352 mL], 15% [552 mL], 15-50% [1000 mL]). The product containing fractions gave (S)-methyl 3-bromo-9-methoxy-5-(phenyl (tetrahydro-2H-pyran-4-yl)methyl)-5H-pyrrolo[3,2-b:4,5-c']dipyridine-6-carboxylate (581 mg, 1.14 mmol, 96% yield) as an amorphous white solid which contained 28% of methyl 3-bromo-9-methoxy-5H-pyrrolo[3,2-b:4,5-c']dipyridine-6-carboxylate as an impurity. The material was taken on as is. $^1$H NMR (400 MHz, CDCl$_3$) δ 8.81 (s, 1H), 8.69 (d, J=1.8 Hz, 1H), 7.80 (d, J=2.0 Hz, 1H), 7.57 (d, J=7.5 Hz, 2H), 7.42-7.36 (m, 2H), 7.33 (d, J=7.3 Hz, 1H), 6.55-6.48 (m, 1H), 4.35 (s, 3H), 4.04 (s, 3H), 4.05-4.00 (m, 1H), 3.83-3.76 (m, J=4.0 Hz, 1H), 3.59-3.51 (m, J=1.8 Hz, 1H), 3.30 (td, J=11.9, 2.3 Hz, 1H), 3.00-2.88 (m, 1H), 2.06 (d, J=13.8 Hz, 1H), 1.64-1.50 (m, 1H), 1.44-1.30 (m, J=4.8 Hz, 1H), 0.53 (d, J=12.8 Hz, 1H). LCMS: Rt=1.02 min; (ES): m/z (M+H)$^+$ 512: (Waters Acquity SDS. Column: BEH C18 2.1×50 mm 1.7 μm (1.5 min grad) 2-98% B. Flow Rate=0.8 mL/min. Solvent A: H$_2$O—0.1% TFA. Solvent B: ACN—0.1% TFA).

Step 5: Methyl 5-(dimethyl-1H-1,2,3-triazol-5-yl)-13-methoxy-8-[(S)-oxan-4-yl(phenyl)methyl]-3,8,12-triazatricyclo[7.4.0.0$^{2,7}$]trideca-1(9),2,4,6,10,12-hexaene-10-carboxylate A solution of (S)-methyl 3-bromo-9-methoxy-5-(phenyl (tetrahydro-2H-pyran-4-yl)methyl)-5H-pyrrolo[3,2-b:4,5-c']dipyridine-6-carboxylate (292 mg, 0.572 mmol), copper (I) iodide (16.34 mg, 0.086 mmol), tetrakis (triphenylphosphine)palladium(0) (49.6 mg, 0.043 mmol), 1,4-dimethyl-5-(tributylstannyl)-1H-1,2,3-triazole (331 mg, 0.858 mmol) and triethylamine (0.120 mL, 0.858 mmol) in DMF (3.0 mL) in a 20 mL scintillation vial was degassed by bubbling through argon while sonicating for 2 min. The vial was sealed and heated to 100° C. After 2 h the reaction vial was cooled, diluted with ethyl acetate, filtered through Celite and washed with water. The aqueous portion was extracted with ethyl acetate and the combined organics were washed with brine, dried over MgSO$_4$, filtered and concentrated to give a yellow solid. The crude material was purified by flash chromatography: (24 g ISCO RediSep Rf loaded on dry column in DCM, dried under a stream of nitrogen and eluted with methanol in DCM 0% [5 CV], 0-5% [20 CV], 5-10%

[5 CV]). The product containing fractions gave 309 mg of a glassy white solid. The white solid was further purified by flash chromatography: (24 g ISCO RediSep Rf, loaded on dry column in DCM, dried under a stream of nitrogen and eluted with methanol in DCM 0% [165 mL], 0-3% [165 mL], 3% [660 mL], 3-10% [330 mL]). The product containing fractions gave the title compound (109 mg, 201 mmol, 35%) as a white solid. $^1$H NMR (400 MHz, CDCl$_3$) δ 8.85 (s, 1H), 8.60 (s, 1H), 7.58 (d, J=7.5 Hz, 2H), 7.53 (s, 1H), 7.37 (t, J=7.5 Hz, 2H), 7.33-7.28 (m, 1H), 6.64 (d, J=10.3 Hz, 1H), 4.36 (s, 3H), 4.04 (s, 3H), 4.00 (d, J=11.0 Hz, 1H), 3.81-3.73 (m, 1H), 3.70 (s, 3H), 3.51 (t, J=11.7 Hz, 1H), 3.29-3.17 (m, 1H), 3.03-2.85 (m, J=8.5 Hz, 1H), 2.16 (s, 3H), 2.10 (d, J=13.6 Hz, 1H), 1.66-1.51 (m, 1H), 1.37 (qd, J=12.3, 4.4 Hz, 1H), 0.49 (d, J=12.8 Hz, 1H). LCMS: Rt=1.254 min; (ES): m/z (M+H)$^+$ 527: (Waters Acquity SDS. Column: BEH C18 2.1×50 mm 1.7 μm (1.5 min grad) 2-98% B. Flow Rate=0.8 mL/min. Solvent A: H$_2$O—0.1% TFA. Solvent B: ACN—0.1% TFA). HPLC Rt=7.94 min (Column: XSELECT CSH C18 3.5 μm, 3.0×150 mm; Mobile Phase A: 0.1% TFA/95% H$_2$O/5% ACN; Mobile Phase B: 95:5 0.1% TFA/5% H$_2$O/95% ACN; Gradient 10-100% B over 15 min; Flow: 1 mL/min; Detection: UV at 220 nm and 254 nM). HPLC Rt=6.46 min (Column: Zorbax Bonus-RP 3.5 μm, 3.0×150 mm; Mobile Phase A: 0.1% TFA/95% H$_2$O/5% ACN; Mobile Phase B: 95:5 0.1% TFA/5% H$_2$O/95% ACN; Gradient 10-100% B over 15 min; Flow: 1 mL/min; Detection: UV at 220 nm and 254 nM).

Example 136

[5-(Dimethyl-1H-1,2,3-triazol-5-yl)-13-methoxy-8-[(S)-oxan-4-yl(phenyl)methyl]-3,8,12-triazatricyclo[7.4.0.0$^{2,7}$]trideca-1(9),2,4,6,10,12-hexaen-10-yl]methanol

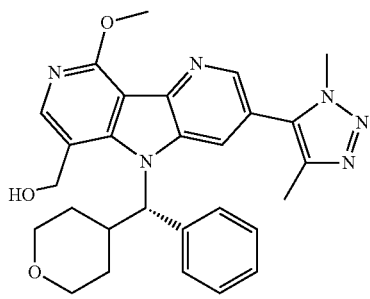 [SMILES: COc1ncc(CO)c2c1c1ncc(-c3c(C)nnn3C)cc1n2[C@H](c1ccccc1)C1CCOCC1]

A suspension of(S)-methyl 3-(1,4-dimethyl-1H-1,2,3-triazol-5-yl)-9-methoxy-5-(phenyl(tetrahydro-2H-pyran-4-yl)methyl)-5H-pyrrolo[3,2-b:4,5-c']dipyridine-6-carboxylate (16 mg, 0.030 mmol) in THF (0.5 mL) was cooled in an ice water bath and lithium aluminum hydride 2.0 M in THF (0.030 mL, 0.061 mmol) was added. After 40 min, the mixture was quenched with one drop of water, one drop of aqueous 3N NaOH and after five min of stirring excess solid sodium sulfate was added. This mixture was diluted with ethyl acetate, filtered and concentrated to give 14 mg of a crude yellow film. The crude material was purified via preparative LC/MS with the following conditions: Column: XBridge C18, 19×mm, 5-μm particles; Mobile Phase A: 5:95 ACN: water with 10-mM NH$_4$OAc; Mobile Phase B: 95:5 ACN: water with 10-mM NH$_4$OAc; Gradient: 10-50% B over 20 min, then a 5-min hold at 100% B; Flow: 20 mL/min. Fractions containing the desired product were combined and dried via centrifugal evaporation to give the title compound (4.1 mg, 21%). The estimated purity by LCMS analysis was 99%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. $^1$H NMR (500 MHz, DMSO-d$_6$) δ 8.57 (s, 1H), 8.16 (s, 1H), 7.98 (s, 1H), 7.68 (d, J=7.7 Hz, 2H), 7.40-7.30 (m, 2H), 7.28-7.22 (m, 1H), 6.36 (d, J=11.0 Hz, 1H), 5.87 (t, J=4.8 Hz, 1H), 5.01 (d, J=4.8 Hz, 2H), 4.11 (s, 3H), 3.88 (d, J=7.7 Hz, 1H), 3.82 (s, 3H), 3.69 (d, J=8.4 Hz, 1H), 3.51-3.49 (m, 1H), 3.48-3.37 (m, 1H), 3.22 (t, J=11.6 Hz, 1H), 2.14 (s, 3H), 1.91 (t, J=6.2 Hz, 1H), 1.57-1.38 (m, 2H), 0.63 (d, J=12.5 Hz, 1H). LC/MS (499, [M+H]$^+$). LCMS: Rt=1.29 min; (ES): m/z (M+H)$^+$ 499: (Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm).

Example 137

5-(dimethyl-1H-1,2,3-triazol-5-yl)-10-(3-fluoroazetidine-1-carbonyl)-13-methoxy-8-[(S)-oxan-4-yl(phenyl)methyl]-3,8,12-triazatricyclo[7.4.0.0$^{2,7}$]trideca-1(9),2,4,6,10,12-hexaene

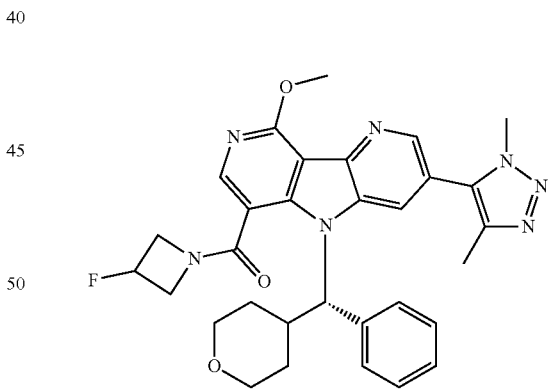

Step 1: (S)-3-(1,4-Dimethyl-1H-1,2,3-triazol-5-yl)-9-methoxy-5-(phenyl(tetrahydro-2H-pyran-4-yl)methyl)-5H-pyrrolo[3,2-b:4,5-c']dipyridine-6-carboxylic acid To a solution of (S)-methyl 3-(1,4-dimethyl-1H-1,2,3-triazol-5-yl)-9-methoxy-5-(phenyl(tetrahydro-2H-pyran-4-yl)methyl)-5H-pyrrolo[3,2-b:4,5-c']dipyridine-6-carboxylate (15.6 mg, 0.030 mmol) in THF (700 μL) and water (100 μL) was added lithium hydroxide monohydrate (6.2 mg, 0.148 mmol). The mixture was stirred at room temperature.

After 40 h, the mixture was treated with a small amount (~200 μL) of a pH 5 buffer prepared from citric acid and sodium hydroxide then extracted into ethyl acetate. The organic extracts were dried over MgSO₄, filtered and concentrated to give the title compound (15.1 mg, 99%) as a white solid. $^1$H NMR (400 MHz, CDCl₃) δ 9.09 (s, 1H), 8.70 (d, J=1.8 Hz, 1H), 7.59-7.53 (m, 3H), 7.40-7.32 (m, 2H), 7.30 (d, J=7.3 Hz, 1H), 7.05 (d, J=10.5 Hz, 1H), 4.41 (s, 3H), 4.12-4.07 (m, 1H), 3.91-3.83 (m, 1H), 3.73 (s, 3H), 3.56 (t, J=11.2 Hz, 1H), 3.37-3.25 (m, 1H), 2.95 (d, J=10.8 Hz, 1H), 2.19 (s, 3H), 2.10 (d, J=13.6 Hz, 1H), 1.69 (d, J=10.5 Hz, 1H), 1.55 (dd, J=12.4, 3.9 Hz, 1H), 0.60 (d, J=12.8 Hz, 1H). LCMS: Rt=1.24 min; (ES): m/z (M+H)⁺ 513: (Waters Acquity SDS; Column Type: ACQUITY UPLC® BEH C18 1.7 μm 2.1×50 mm; Run Time: 2.20 min; 0-100% B; Solvent A: 100% water/0.05% TFA; Solvent B: 100% ACN w/0.05% TFA; Flow: 0.8 mL/min; Detection: UV=220 nm).

Step 2: [5-(Dimethyl-1H-1,2,3-triazol-5-yl)-13-methoxy-8-[(S)-oxan-4-yl(phenyl)methyl]-3,8,12-triazatricyclo[7.4.0.0²,⁷]trideca-1(9),2,4,6,10,12-hexaen-10-yl]methanol A mixture of (S)-3-(1,4-dimethyl-1H-1,2,3-triazol-5-yl)-9-methoxy-5-(phenyl(tetrahydro-2H-pyran-4-yl)methyl)-5H-pyrrolo[3,2-b:4,5-c']dipyridine-6-carboxylic acid (15.1 mg, 0.029 mmol), 3-fluoroazetidine hydrochloride (6.57 mg, 0.059 mmol), HATU (13.4 mg, 0.035 mmol) and Hunig's base (0.013 mL, 0.074 mmol) in DMF (0.5 mL) was stirred at room temperature. After 21 h, the mixture was diluted with ethyl acetate, washed with brine (3×), dried over MgSO₄, filtered and concentrated to give 20.8 mg of a clear film. The crude material was purified via preparative LC/MS as a single injection in 1.0 mL of methanol with the following conditions: Column: XBridge C18, 30×100 mm, 5-μm particles; Mobile Phase A: 5:95 ACN: water with 10 mM NH₄OAc; Mobile Phase B: 95:5 ACN: water with 10 mM NH₄OAc; Gradient: 0-100% B over 15 min, then a 1-min hold at 100% B; Flow: 30 mL/min; 254 nm detection. Fractions containing the desired product were combined and dried via centrifugal evaporation then the material was taken up in ethyl acetate, washed with brine, dried over MgSO₄, filtered and concentrated to give the title compound (4.6 mg, 26%) as a white solid film. The estimated purity by HPLC analysis was 95%. $^1$H NMR (400 MHz, CDCl₃) δ 8.65 (d, J=1.8 Hz, 1H), 8.26 (br. s., 1H), 7.65-7.50 (m, 3H), 7.40-7.29 (m, 3H), 6.27 (br. s., 1H), 4.40 (d, J=6.8 Hz, 3H), 4.36 (s, 4H), 4.04 (d, J=11.5 Hz, (m, 1H), 2.23 (1H), 3.83 (d, J=11.8 Hz, 1H), 3.78 (s, 3H), 3.51 (t, J=11.4 Hz, 1H), 3.28 (t, J=11.9 Hz, 1H), 3.03-2.85 s, 3H), 2.09-2.00 (m, 1H), 1.56-1.52 (m, 1H), 1.46-1.32 (m, 1H), 0.81-0.71 (m, 2H). LCMS: Rt=1.079 min; (ES): m/z (M+H)⁺ 570: (Column: Waters Acquity UPLC BEH C18, 2.1×50 mm, 1.7 μm particles; Mobile Phase A: water/0.05% TFA; Mobile Phase B: ACN/0.05% TFA; Gradient: 2-98% B over 1 min, then a 0.5-min hold at 98% B; Flow: 0.8 mL/min; Detection: UV=220 nm). HPLC Rt=11.11 min (Column: XSELECT CSH C18 3.5 μm, 3.0×150 mm; Mobile Phase A: 0.1% TFA/95% H₂O/5% ACN; Mobile Phase B: 95:5 0.1% TFA/5% H₂O/95% ACN; Gradient 10-100% B over 15 min; Flow: 1 mL/min; Detection: UV at 220 nm and 254 nM). HPLC Rt=13.06 min (Column: Zorbax Bonus-RP 3.5 μm, 3.0×150 mm; Mobile Phase A: 0.1% TFA/95% H₂O/5% ACN; Mobile Phase B: 95:5 0.1% TFA/5% H₂O/95% ACN; Gradient 10-100% B over 15 min; Flow: 1 mL/min; Detection: UV at 220 nm and 254 nM).

Example 138

2-{13-Methoxy-5-[4-(²H₃)methyl-1-methyl-1H-1,2,3-triazol-5-yl]-8-[(S)-oxan-4-yl(phenyl)methyl]-3,8,12-triazatricyclo[7.4.0.0²,⁷]trideca-1(13),2(7),3,5,9,11-hexaen-10-yl}propan-2-ol

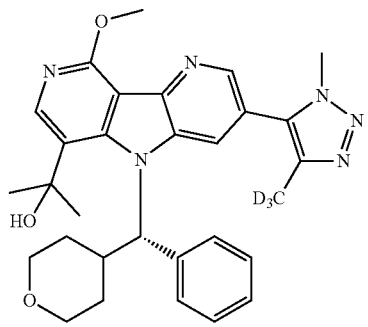 [SMILES: [2H]C([2H])([2H])c1nnn(C)c1-c1cnc2c3c(OC)ncc(C(C)(C)O)c3n([C@H](c3ccccc3)C3CCOCC3)c2c1]

Step 1: Methyl 13-methoxy-5-[4-(²H₃)methyl-1-methyl-1H-1,2,3-triazol-5-yl]-8-[(S)-oxan-4-yl(phenyl)methyl]-3,8,12-triazatricyclo[7.4.0.0²,⁷]trideca-1(9),2,4,6,10,12-hexaene-10-carboxylate A 2-5 mL microwave vial was charged with 4-(²H₃)methyl-1-methyl-5-(tributylstannyl)-1H-1,2,3-triazole (286 mg, 0.735 mmol) and diluted with DMF (2449 μL). (S)-methyl 3-bromo-9-methoxy-5-(phenyl(tetrahydro-2H-pyran-4-yl)methyl)-5H-pyrrolo[3,2-b:4,5-c']dipyridine-6-carboxylate (250 mg, 0.490 mmol) was added followed by triethylamine (102 μL, 0.735 mmol), copper(I) iodide (14.0 mg, 0.073 mmol) and tetrakis(triphenylphosphine)palladium(0) (42.5 mg, 0.037 mmol). The vial was sealed and degassed by bubbling through argon while sonicating for 2 min. The vial was then placed into a reaction block preheated to 80° C. After 1 h, the mixture was allowed to cool to room temperature and diluted with ethyl acetate and water. The biphasic mixture was filtered through a pad of Celite and transferred to a separatory funnel where the layers were separated. The organic was washed with water (×2) and brine (×2). The combined aqueous was back extracted with ethyl acetate (×2) and discarded. The combined organics were washed again with brine (×1), dried over magnesium sulfate, concentrated under reduced pressure, and purified by flash chromatography: (24 g ISCO RediSep Rf, loaded on dry column in DCM, dried under a stream of nitrogen and eluted with methanol in DCM 0% [75 mL], 0-5% [402 mL], 5% [150 mL]). The product containing fractions were collected to give impure product as a white solid. The white solid was repurified by flash chromatography: (24 g ISCO RediSep Rf, Rf loaded on dry column in DCM, dried under a stream of nitrogen and eluted with methanol in DCM 0% [150 mL], 0-3% [250 mL], 3% [500 mL]). The product containing fractions were collected to give the title compound (188 mg, 0.355 mmol, 72.5% yield) as a white solid. $^1$H NMR (400 MHz, CDCl₃) δ 8.87 (s, 1H), 8.63 (d, J=1.8 Hz, 1H), 7.57 (d, J=7.8 Hz, 2H), 7.52 (d, J=2.0 Hz, 1H), 7.43-7.36 (m, 2H), 7.32 (s, 1H), 6.72-6.63 (m, 1H), 4.41-4.38 (m, 3H), 4.06 (s, 3H), 4.07-4.02 (m, 1H), 3.82-3.76 (m, 1H), 3.73 (s, 3H), 3.53 (td, J=11.9, 1.8 Hz, 1H), 3.24 (td, J=11.9, 2.1 Hz, 1H), 2.99-2.84 (m, 1H), 2.11 (d, J=14.6 Hz, 1H), 1.69-1.56 (m, 1H), 1.39 (qd, J=12.5, 4.1 Hz, 1H), 0.52 (d, J=12.3 Hz, 1H). LC/MS (530, [M+H]⁺). LCMS: Rt=0.90 min; (ES): m/z (M+H)⁺ 530: (Column: Waters Acquity UPLC BEH C18, 2.1×50 mm, 1.7 μm particles; Mobile Phase A: water/0.05% TFA; Mobile Phase B: ACN/0.05% TFA; Gradient: 2-98% B over 1 min, then a 0.5-min hold at 98% B; Flow: 0.8 mL/min; Detection: UV=220 nm).

Step 2: 2-{13-Methoxy-5-[4-(²H₃)methyl-1-methyl-1H-1,2,3-triazol-5-yl]-8-[(S)-oxan-4-yl(phenyl)methyl]-3,8,12-triazatricyclo[7.4.0.0²,⁷]trideca-1(13),2(7),3,5,9,11-hexaen-10-yl}propan-2-ol The magnesiate reagent was prepared as follows:
To a 20 mL scintillation vial containing 2.0 mL of THF at dry ice/acetone bath temperature was added 252 μL of methylmagnesium bromide (3.0 M in diethyl ether) followed by 945 μL of methyllithium (1.6 M in diethyl ether). The effective concentration of this reagent based on Grignard would be 0.24 M. This mixture was stirred for 45 min then 190 μL (1.2 equivalent) of this reagent was added via plastic syringe to a solution of methyl 13-methoxy-5-[4-(²H₃)methyl-1-methyl-1H-1,2,3-triazol-5-yl]-8-[(S)-oxan-4-yl(phenyl)methyl]-3,8,12-triazatricyclo[7.4.0.0²,⁷]trideca-1(9),2,4,6,10,12-hexaene-10-carboxylate (20 mg, 0.038 mmol) in 0.5 mL of THF, also at dry ice/acetone bath temperature. After 2 h the dry ice/acetone bath was replaced with an ice/water bath. After 1 h at this temperature, an additional 300 μL (1.9 equivalent) of the magnesiate reagent was added. After 1 additional h, LC/MS showed conversion of starting material and formation of a ~1:1 mixture of desired product (530, [M+H]⁺) to ketone intermediate (514, [M+H]⁺). The mixture was briefly cooled in a dry ice acetone bath and quenched with saturated aqueous ammonium chloride. The mixture was diluted with ethyl acetate and allowed to warm/stir until it was a biphasic liquid. The aqueous portion was further extracted with ethyl acetate and the combined organics were washed with brine, dried over MgSO₄, filtered and concentrated to give 17.5 mg of an off-white solid. The crude material was purified via preparative LC/MS as two equivalent injections in 0.5 mL of methanol with the following conditions: Column: XBridge C18, 30×100 mm, 5-μm particles; Mobile Phase A: 5:95 ACN: water with 10 mM NH₄OAc; Mobile Phase B: 95:5 ACN: water with 10 mM NH₄OAc; 30% B for 30 min; Flow: 30 mL/min; 254 nm detection. The product containing fractions (Rt=8.30 min) gave the title compound (8.0 mg, 39%) as a white solid. The estimated purity by HPLC analysis was 97%. ¹H NMR (400 MHz, CDCl₃) δ 8.61 (d, J=2.0 Hz, 1H), 8.36 (s, 1H), 7.43-7.29 (m, 6H), 7.24 (d, J=2.0 Hz, 1H), 4.35 (s, 3H), 4.04 (dd, J=11.8, 3.0 Hz, 1H), 3.70 (dd, J=11.2, 3.6 Hz, 1H), 3.64 (s, 3H), 3.54 (td, J=11.9, 1.8 Hz, 1H), 3.18 (td, J=12.0, 1.9 Hz, 1H), 2.97-2.83 (m, 1H), 2.25 (d, J=17.1 Hz, 2H), 2.04 (s, 3H), 1.83 (s, 3H), 1.52-1.40 (m, J=12.7, 12.7, 4.5 Hz, 2H), 0.32 (d, J=13.1 Hz, 1H). LC/MS (530, [M+H]⁺). LCMS: Rt=1.259 min; (ES): m/z (M+H)⁺ 530: (Column: Waters Acquity UPLC BEH C18, 2.1×50 mm, 1.7 μm particles; Mobile Phase A: water/0.05% TFA; Mobile Phase B: ACN/0.05% TFA; Gradient: 2-98% B over 1 min, then a 0.5-min hold at 98% B; Flow: 0.8 mL/min; Detection: UV=220 nm). HPLC Rt=12.43 min (Column: Xbridge C18 3.5 μm, 3.0×150 mm; Mobile Phase A: 10 mM ammonium bicarbonate (pH=9.5)/95% H₂O/5% methanol; Mobile Phase B: 10 mM ammonium bicarbonate (pH=9.5)/5% H₂O/95% methanol; Gradient 10-100% B over 15 min; Flow: 1 mL/min; Detection: UV at 220 nm and 254 nM). HPLC Rt=13.42 min (Column: Xbridge Phenyl 3.5 μm, 3.0×150 mm; Mobile Phase A: 10 mM ammonium bicarbonate (pH=9.5)/95% H₂O/5% methanol; Mobile Phase B: 10 mM ammonium bicarbonate (pH=9.5)/5% H₂O/95% methanol; Gradient 10-100% B over 15 min; Flow: 1 mL/min; Detection: UV at 220 nm and 254 nM).

Example 139

{13-methoxy-5-[4-(²H₃)methyl-1-methyl-1H-1,2,3-triazol-5-yl]-8-[(S)-oxan-4-yl(phenyl)methyl]-3,8,12-triazatricyclo[7.4.0.0²,⁷]trideca-1(9),2,4,6,10,12-hexaen-10-yl}methanol

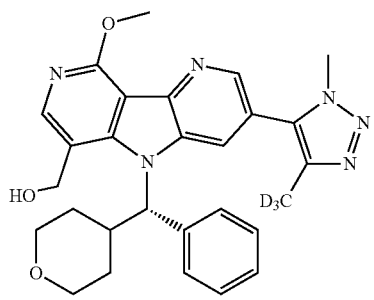 [SMILES: [2H]C([2H])([2H])c1nnn(C)c1-c1cnc2c3c(OC)ncc(CO)c3n([C@H](c3ccccc3)C3CCOCC3)c2c1]

A solution of methyl 13-methoxy-5-[4-(²H₃)methyl-1-methyl-1H-1,2,3-triazol-5-yl]-8-[(S)-oxan-4-yl(phenyl)methyl]-3,8,12-triazatricyclo[7.4.0.0²,⁷]trideca-1(9),2,4,6,10,12-hexaene-10-carboxylate (22 mg, 0.042 mmol) in THF (0.5 mL) was cooled in an ice water bath and lithium aluminum hydride 2.0 M in THF (0.042 mL, 0.083 mmol) was added. After 10 min, the mixture was quenched with one drop of water and two drops of 15% aqueous NaOH, diluted with ethyl acetate and stirred for 5 min then excess solid sodium sulfate was added. The mixture was filtered and concentrated to give 21.7 mg of an off-white solid. This material was purified on SiO₂ (4 g) loaded on dry column in DCM and eluted using DCM (51 mL), 20% acetone/DCM (50 mL), 30% acetone/DCM (100 mL), 50% acetone/DCM (50 mL), acetone (~50 mL). The product containing fractions gave 18.2 mg of a clear film. This material was 94% pure by 1H NMR. It was further purified via preparative LC/MS with the following conditions: Column: XBridge C18, 19×200 mm, 5-μm particles; Mobile Phase A: 5:95 ACN: water with 10-mM NH₄OAc; Mobile Phase B: 95:5 ACN: water with 10-mM NH₄OAc; Gradient: 15-55% B over 15 min, then a 5-min hold at 100% B; Flow: 20 mL/min. Fractions containing the desired product were combined and dried via centrifugal evaporation to give the title compound (16.4 mg, 79%). The estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.5-min hold at 100% B; Flow: 1.0 mL/min; Detection: UV at 220 nm. Injection 2 conditions: Column: Waters BEH C18, 2.0×50 mm, 1.7-μm particles; Mobile Phase A: 5:95 methanol:water with 10 mM NH₄OAc; Mobile Phase B: 95:5 methanol:water with 10 mM NH₄OAc; Temperature: 50° C.; Gradient: 0-100% B over 3 min, then a 0.5-min hold at 100% B; Flow: 0.5 mL/min; Detection: UV at 220 nm. $^1$H NMR (500 MHz, DMSO-$d_6$) δ 8.59 (s, 1H), 8.17 (s, 1H), 8.01 (s, 1H), 7.70 (d, J=7.7 Hz, 2H), 7.38-7.31 (m, 2H), 7.29-7.23 (m, 1H), 6.37 (d, J=10.6 Hz, 1H), 5.02 (s, 2H), 4.12 (s, 3H), 3.88 (br. s., 1H), 3.83 (s, 3H), 3.70 (d, J=10.3 Hz, 1H), 3.55-3.41 (m, 2H), 3.22 (t, J=11.4 Hz, 1H), 1.96-1.88 (m, 3H), 1.91 (s, 1H), 1.58-1.39 (m, 2H), 0.64 (d, J=11.7 Hz, 1H). LCMS: Rt=1.33 min; (ES): m/z (M+H)$^+$ 502: (Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm).

Example 140

Methyl 5-(dimethyl-1,2-oxazol-4-yl)-13-methoxy-8-[(S)-oxan-4-yl(phenyl)methyl]-3,8,12-triazatricyclo[7.4.0.0$^{2,7}$]trideca-1(13),2(7),3,5,9,11-hexaene-10-carboxylate

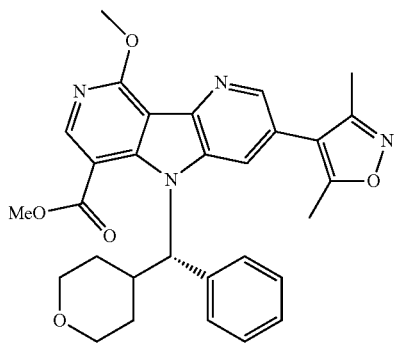 [SMILES: COC(=O)c1cnc(OC)c2c3ncc(-c4c(C)noc4C)cc3n([C@H](c3ccccc3)C3CCOCC3)c12]

A mixture of (S)-methyl 3-bromo-9-methoxy-5-(phenyl(tetrahydro-2H-pyran-4-yl)methyl)-5H-pyrrolo[3,2-b:4,5-c']dipyridine-6-carboxylate (42.9 mg, 0.084 mmol), (3,5-dimethylisoxazol-4-yl)boronic acid (17.8 mg, 0.126 mmol), PdCl$_2$(dppf)-CH$_2$Cl$_2$ (6.9 mg, 8.41 μmol), tripotassium phosphate, 2M aq (0.126 mL, 0.252 mmol) and THF (1 mL) in a 2 dram pressure rated vial was degassed by bubbling through argon while sonicating for 1-2 min. The vial was sealed and heated to 80° C. After 1 h, the mixture was cooled, diluted with water and extracted into ethyl acetate. The combined organics were washed with brine, dried over MgSO$_4$, filtered and concentrated to give a crude solid brown residue. This material was purified on SiO$_2$ (4 g) loaded on dry column in DCM and eluted using DCM (51 mL), 20-40% acetone/DCM. The product containing fractions gave 34.5 mg of a light brown solid. A portion of this material (13 mg) was precipitated from methanol to give the title compound (2.3 mg) as a white solid. The estimated purity by HPLC was 100%. $^1$H NMR (400 MHz, CDCl$_3$) δ 8.83 (s, 1H), 8.58 (d, J=1.5 Hz, 1H), 7.59 (d, J=7.5 Hz, 2H), 7.46-7.43 (m, 1H), 7.41-7.35 (m, 2H), 7.33-7.28 (m, 1H), 6.61 (d, J=10.5 Hz, 1H), 4.40-4.32 (m, 3H), 4.07-4.03 (m, 3H), 4.04-3.98 (m, 1H), 3.77 (dd, J=11.2, 2.6 Hz, 1H), 3.58-3.48 (m, 1H), 3.23 (td, J=11.8, 1.8 Hz, 1H), 2.92 (d, J=10.8 Hz, 1H), 2.25 (s, 3H), 2.15-2.09 (m, 1H), 2.09 (s, 3H), 1.67-1.53 (m, 1H), 1.35 (qd, J=12.3, 4.4 Hz, 1H), 0.47 (d, J=13.1 Hz, 1H). LCMS: Rt=1.232 min; (ES): m/z (M+H)$^+$ 527: (Column: Waters Acquity UPLC BEH C18, 2.1×50 mm, 1.7 μm particles; Mobile Phase A: water/0.05% TFA; Mobile Phase B: ACN/0.05% TFA; Gradient: 2-98% B over 1 min, then a 0.5-min hold at 98% B; Flow: 0.8 mL/min; Detection: UV=220 nm. HPLC Rt=14.32 min (Column: Xbridge C18 3.5 μm, 3.0×150 mm; Mobile Phase A: 10 mM ammonium bicarbonate (pH=9.5)/95% H$_2$O/5% methanol; Mobile Phase B: 10 mM ammonium bicarbonate (pH=9.5)/5% H$_2$O/95% methanol; Gradient 10-100% B over 15 min; Flow: 1 mL/min; Detection: UV at 220 nm and 254 nM). HPLC Rt=15.36 min (Column: Xbridge Phenyl 3.5 μm, 3.0×150 mm; Mobile Phase A: 10 mM ammonium bicarbonate (pH=9.5)/95% H$_2$O/5% methanol; Mobile Phase B: 10 mM ammonium bicarbonate (pH=9.5)/5% H$_2$O/95% methanol; Gradient 10-100% B over 15 min; Flow: 1 mL/min; Detection: UV at 220 nm and 254 nM).

Example 141

2-[5-(Dimethyl-1,2-oxazol-4-yl)-13-methoxy-8-[(S)-oxan-4-yl(phenyl)methyl]-3,8,12-triazatricyclo[7.4.0.0$^{2,7}$]trideca-1(9),2,4,6,10,12-hexaen-10-yl]propan-2-ol

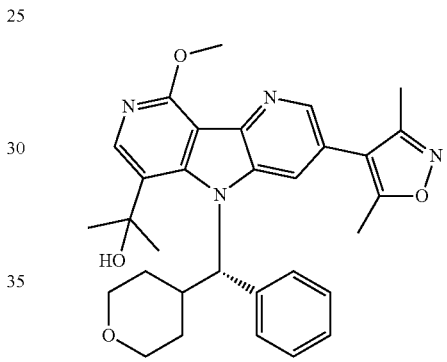

The magnesiate reagent was prepared as follows:
To a 20 mL scintillation vial containing 2.0 mL of THF at dry ice/acetone bath temperature was added 252 μL of methylmagnesium bromide (3.0 M in diethyl ether) followed by 945 μL of methyllithium (1.6 M in diethyl ether). The effective concentration of this reagent based on Grignard would be 0.24 M. This mixture was stirred for 45 min then 1.0 mL (5.0 equivalent) of this reagent was added via plastic syringe to a solution of (S)-methyl 3-(3,5-dimethylisoxazol-4-yl)-9-methoxy-5-(phenyl(tetrahydro-2H-pyran-4-yl)methyl)-5H-pyrrolo[3,2-b:4,5-c']dipyridine-6-carboxylate (26 mg, 0.049 mmol) in 1.0 mL of THF, also at dry ice/acetone bath temperature. After 30 min the mixture was again briefly cooled in the dry ice/acetone bath and 300 μL of the magnesiate reagent was added. The vial was transferred to the ice water bath. After 2.5 h the mixture was quenched with saturated aqueous ammonium chloride then warmed to room temperature, diluted with brine and extracted into ethyl acetate (3×). The combined organics were washed with brine, dried over MgSO$_4$, filtered and concentrated to give 24.2 mg of a yellow film. Column: XBridge C18, 30×100 mm, 5-μm particles; Mobile Phase A: 5:95 ACN: water with 10 mM NH$_4$OAc; Mobile Phase B: 95:5 ACN: water with 10 mM NH$_4$OAc; 33% B for 30 min; Flow: 30 mL/min; 254 nm detection. The product containing fractions (Rt=16.5 min) were combined to give the title compound (5.3 mg, 20%) as a white solid. The estimated purity by HPLC was 98%. $^1$H NMR (400 MHz, CDCl$_3$) δ

8.57 (d, J=1.8 Hz, 1H), 8.33 (s, 1H), 7.44-7.39 (m, 2H), 7.35 (t, J=7.4 Hz, 2H), 7.32-7.29 (m, 1H), 7.18 (d, J=1.8 Hz, 1H), 4.34 (s, 3H), 4.04 (dd, J=10.8, 3.0 Hz, 1H), 3.69 (dd, J=11.9, 3.6 Hz, 1H), 3.58-3.48 (m, 1H), 3.18 (td, J=12.0, 1.9 Hz, 1H), 2.96-2.83 (m, 1H), 2.25 (br. s., 1H), 2.19 (s, 3H), 2.03 (s, 3H), 2.05-2.00 (m, 1H), 2.00 (s, 3H), 1.81 (s, 3H), 1.48-1.37 (m, 1H), 0.30 (d, J=13.8 Hz, 2H). LCMS: Rt=1.03 min; (ES): m/z (M+H)$^+$ 527: (Column: Waters Acquity UPLC BEH C18, 2.1×50 mm, 1.7 μm particles; Mobile Phase A: water/0.05% TFA; Mobile Phase B: ACN/0.05% TFA; Gradient: 2-98% B over 1 min, then a 0.5-min hold at 98% B; Flow: 0.8 mL/min; Detection: UV=220 nm). HPLC Rt=12.05 min (Waters Xbridge C18 5 μm, 4.6×50 mm; Mobile Phase A: 95% water/5% ACN with 10 mM NH$_4$OAc; Mobile Phase B: 5% water/95% ACN with 10 mM NH$_4$OAc; Gradient 0-100% B over 15 min, Flow: 0.5 mL/min; Detection: UV=254 nm).

Example 142

2-[5-(Dimethyl-1H-1,2,3-triazol-5-yl)-13-methoxy-8-[(S)-oxan-4-yl(phenyl)methyl]-3,8,12-triazatricyclo[7.4.0.0$^{2,7}$]trideca-1(9),2,4,6,10,12-hexaen-10-yl]propan-2-ol

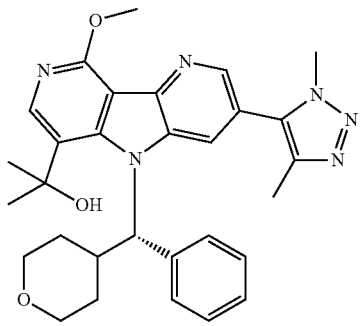 [SMILES: COc1ncc(C(C)(C)O)c2c1c1ncc(-c3c(C)nnn3C)cc1n2[C@H](c1ccccc1)C1CCOCC1]

A mixture of cerium (III) chloride (30.9 mg, 0.125 mmol) and (S)-methyl 3-(1,4-dimethyl-1H-1,2,3-triazol-5-yl)-9-methoxy-5-(phenyl(tetrahydro-2H-pyran-4-yl)methyl)-5H-pyrrolo[3,2-b:4,5-c']dipyridine-6-carboxylate (11 mg, 0.021 mmol) was suspended in THF (500 μL) and stirred for 1 h then cooled in an ice water bath and methylmagnesium bromide (3.0 M in diethyl ether, 42 μL, 0.125 mmol) was added. After five min the cooling bath was removed. After 2 h the mixture was cooled briefly in an ice-water bath and quenched with saturated aqueous ammonium chloride solution then extracted into ethyl acetate. The combined organics were washed with brine, dried over MgSO$_4$, filtered and concentrated to give 11.6 mg of a white residue. The crude material was purified by preparative HPLC in two equivalent 0.5 mL methanol injections: Column: XBridge C18, 30×100 mm, 5-μm particles; Mobile Phase A: 5:95 ACN:water with 10 mM NH$_4$OAc; Mobile Phase B: 95:5 ACN:water with 10 mM NH$_4$OAc; 30% B over 20 min; Flow: 30 mL/min; 254 nm detection. The product containing fractions gave the title compound (10 mg, 89%) as a white solid. The estimated purity of this material by $^1$HNMR and HPLC was determined to be >98%. $^1$H NMR (400 MHz, CDCl$_3$) δ 8.60 (d, J=1.8 Hz, 1H), 8.36 (s, 1H), 7.42-7.29 (m, 6H), 7.22 (d, J=1.8 Hz, 1H), 4.33 (s, 3H), 4.03 (dd, J=11.4, 2.9 Hz, 1H), 3.67 (br. s., 1H), 3.62 (s, 3H), 3.54 (t, J=11.3 Hz, 1H), 3.17 (t, J=11.2 Hz, 1H), 2.89 (d, J=9.0 Hz, 1H), 2.25 (d, J=14.3 Hz, 1H), 2.11 (s, 3H), 2.03 (s, 3H), 2.08-1.93 (m, 1H), 1.81 (s, 3H), 1.45 (qd, J=12.6, 4.4 Hz, 1H), 0.28 (d, J=12.8 Hz, 1H). LCMS: Rt=1.020 min; (ES): m/z (M+H)$^+$ 527: (Waters Acquity SDS; Column Type: ACQUITY UPLC® BEH C18 1.7 μm 2.1×50 mm; Run Time: 2.20 min; 0-100% B; Solvent A: 100% water/0.05% TFA; Solvent B: 100% ACN w/0.05% TFA; Detection: UV=220 nm). HPLC Rt=12.62 min (Column: Xbridge C18 3.5 μm, 3.0×150 mm; Mobile Phase A: 10 mM ammonium bicarbonate (pH=9.5)/95% H$_2$O/5% methanol; Mobile Phase B: 10 mM ammonium bicarbonate (pH=9.5)/5% H$_2$O/95% methanol; Gradient 10-100% B over 15 min; Flow: 1 mL/min; Detection: UV at 220 nm and 254 nM). HPLC Rt=13.58 min (Column: Xbridge Phenyl 3.5 μm, 3.0×150 mm; Mobile Phase A: 10 mM ammonium bicarbonate (pH=9.5)/95% H$_2$O/5% methanol; Mobile Phase B: 10 mM ammonium bicarbonate (pH=9.5)/5% H$_2$O/95% methanol; Gradient 10-100% B over 15 min; Flow: 1 mL/min; Detection: UV at 220 nm and 254 nM).

Example 143

5-(Dimethyl-1H-1,2,3-triazol-5-yl)-8-[(S)-oxan-4-yl(phenyl)methyl]-3,8,10,12-tetraazatricyclo[7.4.0.0$^{2,7}$]trideca-1(9),2(7),3,5,10,12-hexaene-11-carbonitrile

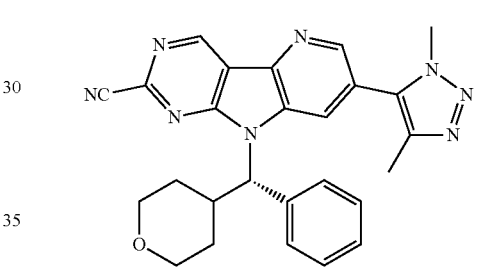

Step 1: 5-(5-Bromo-3-nitropyridin-2-yl)pyrimidine-2-carbonitrile

To a 250 mL round bottom flask was added 5-(4,4,5,5-tetramethyl-1,3,2-dioxaborolan-2-yl)pyrimidine-2-carbonitrile (0.65 g, 2.81 mmol), 2,5-dibromo-3-nitropyridine (0.793 g, 2.81 mmol) and 50 mL of THF. To this mixture was added 2M aqueous tripotassium phosphate (2.81 ml, 5.63 mmol) and PdCl$_2$(dppf) CH$_2$Cl$_2$ (0.230 g, 0.281 mmol). The resulting solution was degassed by bubbling through argon gas while sonicating for 1 min. The flask was sealed and heated in an oil bath at 65° C. overnight. The reaction mixture was concentrated to give a black residue. This material was purified on SiO$_2$ (40 g) loaded on dry column in DCM and eluted using hexane (51 mL), 20% EtOAc/hexane (252 mL), 20 to 50% EtOAc/hexane (357 mL, linear gradient). The product fractions gave the title compound (251 mg, 29%) as a white fluffy solid. $^1$H NMR (400 MHz, CDCl$_3$) δ 9.08 (d, J=2.0 Hz, 1H), 9.01 (s, 2H), 8.64 (d, J=2.0 Hz, 1H). LC/MS (306, [M+H]$^+$). LCMS: Rt=1.28 min; (ES): m/z (M+H)$^+$ 306: (Waters Acquity SDS; Column Type: ACQUITY UPLC® BEH C18 1.7 μm 2.1×50 mm; Run Time: 2.20 min; 0-100% B; Solvent A: 100% water/0.05% TFA; Solvent B: 100% ACN w/0.05% TFA; Flow: 0.8 mL/min; Detection: UV=220 nm).

Step 2: 7-Bromo-9H-pyrido[2',3':4,5]pyrrolo[2,3-d]pyrimidine-2-carbonitrile

A mixture of 5-(5-bromo-3-nitropyridin-2-yl)pyrimidine-2-carbonitrile (251 mg, 0.82 mmol) and 1,2-bis(diphenylphosphino)ethane (490 mg, 1.23 mmol) in 1,2-dichlorobenzene (328 μL) in a 20 mL pressure rated vial was heated to 160° C. After 35 min the mixture was cooled, diluted with diethyl ether and a brown solid was collected by filtration. The filtrate was concentrated under high vacuum and triturated with DCM. A yellow solid was collected by filtration to give the title compound (42.6 mg, 18%). The mother liquor was purified on $SiO_2$ (12 g) loaded on dry column in DCM and eluted using 0 to 100% EtOAc/hexane (880 mL, linear gradient). The product containing fractions gave an addition crop of impure title compound (27.7 mg, 12%) as a yellow solid. $^1$H NMR (400 MHz, $CD_3OD$) δ 9.58 (s, 1H), 8.77 (d, J=2.0 Hz, 1H), 8.32 (d, J=2.0 Hz, 1H). LCMS: Rt=0.77 min; (ES): m/z $(M+H)^+$ 276: (Column: Waters Acquity UPLC BEH C18, 2.1×50 mm, 1.7 μm particles; Mobile Phase A: water/0.05% TFA; Mobile Phase B: ACN/0.05% TFA; Gradient: 2-98% B over 1 min, then a 0.5-min hold at 98% B; Flow: 0.8 mL/min; Detection: UV=220 nm).

Step 3: (S)-7-Bromo-9-(phenyl(tetrahydro-2H-pyran-4-yl)methyl)-9H-pyrido[2',3':4,5]pyrrolo[2,3-d]pyrimidine-2-carbonitrile A mixture of (R)-phenyl(tetrahydro-2H-pyran-4-yl)methanol (59.3 mg, 0.309 mmol), 7-bromo-9H-pyrido[2',3':4,5]pyrrolo[2,3-d]pyrimidine-2-carbonitrile (42.3 mg, 0.154 mmol), and triphenylphosphine (81 mg, 0.309 mmol) in dichloromethane (2.0 mL) was cooled in an ice water bath and diisopropylazodicarboxylate (0.060 mL, 0.309 mmol) was added. After 10 min the cooling bath was removed. After 17 h, the crude reaction mixture was purified on $SiO_2$ (12 g) loaded on dry column in DCM and eluted using hexane (54 mL), 20% EtOAc/hexane (255 mL), 20 to 50% EtOAc/hexane (429 mL, linear gradient) to give 118 mg of a yellow film. A second purification was performed on this material: $SiO_2$ (12 g) loaded on dry column in DCM and eluted using hexane (51 mL), 25% EtOAc/hexane (252 mL), 25 to 65% EtOAc/hexane (429 mL, linear gradient) to give the title compound (86 mg, 124%) as an impure yellow foam. This material was used as is. LCMS: Rt=1.06 min; (ES): m/z $(M+H)^+$ 450: (Column: Waters Acquity UPLC BEH C18, 2.1×50 mm, 1.7 μm particles; Mobile Phase A: water/0.05% TFA; Mobile Phase B: ACN/0.05% TFA; Gradient: 2-98% B over 1 min, then a 0.5-min hold at 98% B; Flow: 0.8 mL/min; Detection: UV=220 nm).

Step 4: 5-(Dimethyl-1H-1,2,3-triazol-5-yl)-8-[(S)-oxan-4-yl(phenyl)methyl]-3,8,10,12-tetraazatricyclo[7.4.0.0²,⁷]trideca-1(9),2(7),3,5,10,12-hexaene-11-carbonitrile A mixture of (S)-7-bromo-9-(phenyl(tetrahydro-2H-pyran-4-yl)methyl)-9H-pyrido[2',3':4,5]pyrrolo[2,3-d]pyrimidine-2-carbonitrile (86 mg, 0.192 mmol), $Pd(Ph_3P)_4$ (11.1 mg, 9.59 μmol), copper(I) iodide (3.7 mg, 0.019 mmol), 1,4-dimethyl-5-(tributylstannyl)-1H-1,2,3-triazole (89 mg, 0.23 mmol) and triethylamine (40 μL, 0.288 mmol) in DMF (959 μL) in a 5 mL pressure rated vial was degassed by bubbling through argon while sonicating for 2-3 min. The vial was sealed and heated to 100° C. After 2 h, the reaction was removed from heat and let stand at room temperature overnight. The mixture was diluted with ethyl acetate and washed with water. The aqueous portion was extracted twice with ethyl acetate and the combined organics were washed twice with brine, dried over $MgSO_4$, filtered and concentrated to give 140 mg of a light brown oil. Approximately 30 mg of this material was purified via preparative LC/MS with the following conditions: Column: XBridge C18, 19×200 mm, 5-μm particles; Mobile Phase A: 5:95 ACN: water with 10-mM $NH_4OAc$; Mobile Phase B: 95:5 ACN: water with 10-mM $NH_4OAc$; Gradient: 25-65% B over 15 min, then a 5-min hold at 100% B; Flow: 20 mL/min. Fractions containing the desired product were combined and dried via centrifugal evaporation to give the title compound (6.0 mg, 31%). The estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM $NH_4OAc$; Mobile Phase B: 95:5 ACN:water with 10 mM $NH_4OAc$; Temperature: 50° C.; Gradient: 0% B, 0-100% B over 3 min, then a 0.5-min hold at 100% B; Flow: 1 mL/min; Detection: UV at 220 nm. Injection 2 conditions: Column: Waters BEH C18, 2.0×50 mm, 1.7-μm particles; Mobile Phase A: 5:95 methanol:water with 10 mM $NH_4OAc$; Mobile Phase B: 95:5 methanol:water with 10 mM $NH_4OAc$; Temperature: 50° C.; Gradient: 0% B, 0-100% B over 3 min, then a 0.5-min hold at 100% B; Flow: 0.5 mL/min; Detection: UV at 220 nm. $^1$H NMR (500 MHz, DMSO-$d_6$) δ 9.74 (s, 1H), 8.86 (s, 1H), 8.78 (br. s., 1H), 7.79 (d, J=7.3 Hz, 2H), 7.39-7.32 (m, 2H), 7.31-7.26 (m, 1H), 5.94 (d, J=11.0 Hz, 1H), 4.04 (s, 3H), 3.93-3.85 (m, 1H), 3.75 (d, J=10.3 Hz, 1H), 3.60 (d, J=9.9 Hz, 1H), 3.46-3.41 (m, 1H), 3.27 (t, J=11.4 Hz, 1H), 2.31 (s, 3H), 1.53 (d, J=11.7 Hz, 1H), 1.48-1.36 (m, 1H), 1.32-1.21 (m, 1H), 1.16 (d, J=12.5 Hz, 1H). LC/MS (465, $[M+H]^+$). LCMS: Rt=1.67 min; (ES): m/z $(M+H)^+$ 465: (Column: Waters BEH C18, 2.0×50 mm, 1.7 μm particles; Mobile Phase A: 5:95 ACN:water with 10 mM $NH_4OAc$; Mobile Phase B: 95:5 ACN:water with 10 mM $NH_4OAc$; Temperature: 50° C.; Gradient: 0% B, 0-100% B over 3 min, then a 0.5-min hold at 100% B; Flow: 1 mL/min; Detection: UV at 220 nm).

Example 144

5-(Dimethyl-1,2-oxazol-4-yl)-11-methanesulfonyl-8-[(S)-oxan-4-yl(phenyl)methyl]-3,8,10-triazatricyclo[7.4.0.0²,⁷]trideca-1(13),2(7),3,5,9,11-hexaene

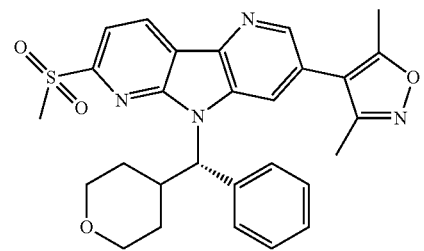 [SMILES: Cc1noc(C)c1-c1cnc2c3ccc(S(C)(=O)=O)nc3n([C@H](c3ccccc3)C3CCOCC3)c2c1]

Step 1: 5-Bromo-6'-(methylsulfonyl)-3-nitro-2,3'-bipyridine (6-(methylsulfonyl)pyridin-3-yl)boronic acid (1 g, 4.97 mmol), 2,5-dibromo-3-nitropyridine (1.402 g, 4.97 mmol), potassium carbonate (2.063 g, 14.9 mmol) and $PdCl_2$(dppf)-$CH_2Cl_2$Adduct (0.406 g, 0.497 mmol) were taken up in 50 mL of dioxane. 2 mL of water was added. The reaction mixture was bubbled in argon for 5 min while sonicating. The flask was capped and heated at 80° C. for 3 h. Concentrated and took up thick black residue in methylene chloride and purified on a 120 g ISCO (silica gel) column, eluting with 5% EtOAc/methylene chloride to 80% EtOAc/methylene chloride over 1200 mL. Concentrated fractions containing product to afford 0.43 g of the title compound (24%). LC/MS: RT=0.96 min (Column: Waters Acquity SDS; Mobile Phase A: 100% Water, 0.1% TFA; Mobile Phase B: 100% ACN, 0.1% TFA; Temperature 50° C.; Gradient 2% B to 98% B over 2.2 min; Flow 0.8 mL/min; Detection: UV at 220 nm). $^1$H NMR (400 MHz, DMSO-d$_6$) δ 9.25 (d, J=2.3 Hz, 1H), 9.01 (d, J=2.0 Hz, 1H), 8.99 (dd, J=2.3, 0.8 Hz, 1H), 8.41-8.34 (m, 1H), 8.21 (dd, J=8.2, 0.9 Hz, 1H), 3.39 (s, 3H).

Step 2: 3-Bromo-7-(methylsulfonyl)-5H-pyrrolo[2,3-b:4,5-b']dipyridine

A 100 mL round bottomed flask was charged with 5-bromo-6'-(methylsulfonyl)-3-nitro-2,3'-bipyridine (0.43 g, 1.20 mmol), triphenylphosphine (0.787 g, 3.00 mmol) and 1,2-dichlorobenzene (50 mL). Placed the flask in an oil bath, capped flask with a condenser and heated to 170° C. for 1½ h. Removed volatiles under a stream of nitrogen overnight, then on a rotary evaporator hooked up to a vacuum pump. Took up residue in methylene chloride and purified on an 80 g ISCO column, eluting with methylene chloride to 40% EtOAc/methylene chloride over 300 mL, then 40% EtOAc/methylene chloride to 80% EtOAc/methylene chloride over 600 mL. Fractions containing the first major eluting peak were combined to afford 0.1 g of the title compound (26%). LC/MS: RT=0.88 min. (Column: Waters Acquity SDS; Mobile Phase A: 100% Water, 0.1% TFA; Mobile Phase B: 100% ACN, 0.1% TFA; Temperature 50° C.; Gradient 2% B to 98% B over 2.2 min; Flow 0.8 mL/min; Detection: UV at 220 nm). $^1$H NMR (400 MHz, DMSO-d$_6$) δ 12.79 (br. s., 1H), 9.02-8.83 (m, 1H), 8.74 (d, J=11.0 Hz, 1H), 8.30 (d, J=10.8 Hz, 1H), 8.00 (t, J=10.3 Hz, 1H), 3.41 (br. s., 3H).

Step 3: (S)-3-Bromo-7-(methylsulfonyl)-5-(phenyl(tetrahydro-2H-pyran-4-yl)methyl)-5H-pyrrolo[2,3-b:4,5-b']dipyridine Suspended 3-bromo-7-(methylsulfonyl)-5H-pyrrolo[2,3-b:4,5-b']dipyridine (0.10 g, 0.307 mmol), (R)-phenyl(tetrahydro-2H-pyran-4-yl)methanol (0.088 g, 0.460 mmol) and triphenylphosphine (0.121 g, 0.460 mmol) in 20 mL of THF. Cooled in an ice bath and added DIAD (0.089 ml, 0.460 mmol) drop wise via a 21½ gauge needle at the rate of 1 drop every 5 seconds. Stirred for 15 min following complete addition of DIAD, removed bath and stirred for 1 h. Concentrated under nitrogen overnight. Took up residue up in methylene chloride and purified on a 24 g ISCO column, eluting with 5% EtOAc/methylene chloride to 80% EtOAc/methylene chloride over 800 mL. Combined fractions containing the title to afford 101 mg. LC/MS was consistent with title compound, contaminated with 3-bromo-7-(methylsulfonyl)-5H-pyrrolo[2,3-b:4,5-b']dipyridine. Used material directly in subsequent reaction.

Step 4: 5-(Dimethyl-1,2-oxazol-4-yl)-11-methanesulfonyl-8-[(S)-oxan-4-yl(phenyl)methyl]-3,8,10-triazatricyclo[7.4.0.0$^{2,7}$]trideca-1(13),2(7),3,5,9,11-hexaene Dissolved (S)-3-bromo-7-(methylsulfonyl)-5-(phenyl(tetrahydro-2H-pyran-4-yl)methyl)-5H-pyrrolo[2,3-b:4,5-b']dipyridine (30 mg, 0.060 mmol) in 1.5 mL of dioxane and (3,5-dimethylisoxazol-4-yl)boronic acid (12.7 mg, 0.090 mmol) and 0.2 mL of water. Potassium carbonate was added (24.9 mg, 0.180 mmol) and PdCl$_2$(dppf)-CH$_2$Cl$_2$ adduct (3.4 mg, 4.20 µmol) and bubbled in argon while sonicating for 5 min. Capped vial and heated at 100° C. for 50 min. The crude material was purified via preparative LC/MS with the following conditions: Column: XBridge C18, 19×200 mm, 5-µm particles; Mobile Phase A: 5:95 ACN: water with 10-mM NH$_4$OAc; Mobile Phase B: 95:5 ACN: water with 10-mM NH$_4$OAc; Gradient: 30-70% B over 30 min, then a 5-min hold at 100% B; Flow: 20 mL/min. Fractions containing the desired product were combined and dried via centrifugal evaporation. The yield of the product was 6.4 mg (21%), and its estimated purity by LCMS analysis was 100%. Two analytical LC/MS injections were used to determine the final purity. Injection 1 conditions: Column: Waters BEH C18, 2.0×50 mm, 1.7-µm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. RT=1.79 min. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. RT=2.50 min. $^1$H NMR (500 MHz, DMSO-d$_6$) δ 8.92 (d, J=8.1 Hz, 1H), 8.67 (s, 1H), 8.58 (br. s., 1H), 8.02 (d, J=8.1 Hz, 1H), 7.82 (d, J=7.3 Hz, 2H), 7.37-7.29 (m, 2H), 7.28-7.15 (m, 1H), 5.93 (d, J=8.8 Hz, 1H), 3.95-3.85 (m, 1H), 3.76 (d, J=10.3 Hz, 1H), 3.70 (d, J=10.6 Hz, 1H), 3.36 (br. s., 3H), 3.25 (t, J=11.4 Hz, 1H), 2.53 (s, 3H), 2.35 (s, 3H), 1.59-1.39 (m, 2H), 1.35-1.22 (m, 1H), 1.15 (d, J=11.7 Hz, 1H).

Example 145

5-(Dimethyl-1H-1,2,3-triazol-5-yl)-11-methanesulfonyl-8-[(S)-oxan-4-yl(phenyl)methyl]-3,8,10-triazatricyclo[7.4.0.0$^{2,7}$]trideca-1(13),2(7),3,5,9,11-hexaene

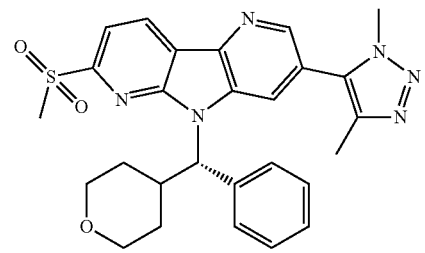 [SMILES: Cc1nnn(C)c1-c1cnc2c3ccc(S(C)(=O)=O)nc3n([C@H](c3ccccc3)C3CCOCC3)c2c1]

(S)-3-bromo-7-(methylsulfonyl)-5-(phenyl(tetrahydro-2H-pyran-4-yl)methyl)-5H-pyrrolo[2,3-b:4,5-b']dipyridine (30 mg, 0.060 mmol) was dissolved in 1.5 mL of NMP and added 1,4-dimethyl-1H-1,2,3-triazole (9.3 mg, 0.096 mmol). Tetramethylammonium acetate (12.0 mg, 0.090 mmol) and bis(triphenylphosphine)palladium(II) chloride (3.0 mg, 4.20 µmol) were added. Argon was bubbled through the mixture while sonicating for 5 min. The vial was capped and heated at 100° C. for 33 h, then cooled and the contents of the vial were filtered. The crude material was purified via preparative LC/MS with the following conditions: Column: XBridge C18, 19×200 mm, 5-µm particles; Mobile Phase A: 5:95 methanol: water with 10-mM NH$_4$OAc; Mobile Phase B: 95:5 methanol: water with 10-mM ammoniumacetate; Gradient: 45-85% B over 15 min, then a 5-min hold at 100% B; Flow: 20 mL/min. Fractions containing the desired product were combined and dried via centrifugal evaporation. The yield of the product was 2.8 mg (9%), and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. RT=2.27, M+H=517. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. RT=2.27, M+H=517. $^1$H NMR (500 MHz, DMSO-d$_6$) δ 8.96 (d, J=8.1 Hz, 1H), 8.76 (s, 2H), 8.05 (d, J=8.1 Hz, 1H), 7.83 (d, J=7.7 Hz, 2H), 7.33 (t, J=7.5 Hz, 2H), 7.26 (t, J=7.3 Hz, 1H), 5.93 (br. s., 1H), 4.07 (s, 3H), 3.95-3.83 (m, 1H), 3.82-3.60 (m, 2H), 3.47-3.36 (m, 1H), 3.31-3.19 (m, 1H), 2.34 (s, 3H), 1.59-1.49 (m, 1H), 1.49-1.38 (m, 1H), 1.38-1.22 (m, 1H), 1.16 (d, J=12.1 Hz, 1H).

Example 146

5-(1,4-Dimethyl-1H-pyrazol-5-yl)-11-methanesulfonyl-8-[(S)-oxan-4-yl(phenyl)methyl]-3,8,10-triazatricyclo[7.4.0.0$^{2,7}$]trideca-1(13),2(7),3,5,9,11-hexaene

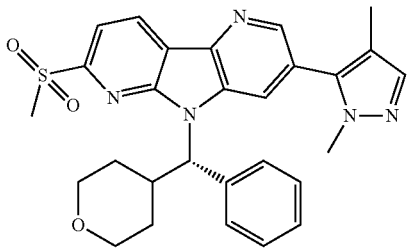 [SMILES: Cc1cnn(C)c1-c1cnc2c3ccc(S(C)(=O)=O)nc3n([C@H](c3ccccc3)C3CCOCC3)c2c1]

Dissolved (S)-3-bromo-7-(methylsulfonyl)-5-(phenyl(tetrahydro-2H-pyran-4-yl)methyl)-5H-pyrrolo[2,3-b:4,5-b']dipyridine (30 mg, 0.060 mmol) in 1.5 mL of dioxane and 1,4-dimethyl-5-(4,4,5,5-tetramethyl-1,3,2-dioxaborolan-2-yl)-1H-pyrazole (20.0 mg, 0.090 mmol) and 0.2 mL of water. Potassium carbonate (24.9 mg, 0.180 mmol) and PdCl$_2$(dppf)-CH$_2$Cl$_2$ adduct (3.4 mg, 4.20 μmol) were added and bubbled in argon while sonicating for 5 min. Capped vial and heated at 100° C. for 50 min and filtered. The crude material was purified via preparative LC/MS with the following conditions: Column: XBridge C18, 19×200 mm, 5-μm particles; Mobile Phase A: 5:95 ACN: water with 10-mM NH$_4$OAc; Mobile Phase B: 95:5 ACN: water with 10-mM NH$_4$OAc; Gradient: 20-60% B over 30 min, then a 5-min hold at 100% B; Flow: 20 mL/min. Fractions containing the desired product were combined and dried via centrifugal evaporation. The yield of the product was 6.3 mg (20%), and its estimated purity by LCMS analysis was 99%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. RT=1.75 min, M+H=516. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. RT=2.52 min, M+H=516. $^1$H NMR (500 MHz, DMSO-d$_6$) δ 8.94 (d, J=7.7 Hz, 1H), 8.73-8.64 (m, 2H), 8.04 (d, J=7.7 Hz, 1H), 7.83 (d, J=7.7 Hz, 2H), 7.47 (s, 1H), 7.36-7.28 (m, 2H), 7.28-7.19 (m, 1H), 5.94 (d, J=11.4 Hz, 1H), 3.94-3.85 (m, 1H), 3.80-3.65 (m, 2H), 3.52 (s, 3H), 3.48-3.35 (m, 2H), 3.25 (t, J=10.8 Hz, 1H), 2.07 (s, 3H), 1.50 (br. s., 1H), 1.44 (d, J=12.1 Hz, 1H), 1.36-1.21 (m, 1H), 1.17 (d, J=12.8 Hz, 1H).

Example 147

11-(Dimethyl-1,2-oxazol-4-yl)-5-(dimethyl-1H-1,2,3-triazol-5-yl)-8-[(S)-oxan-4-yl(phenyl)methyl]-3,8,10-triazatricyclo[7.4.0.0$^{2,7}$]trideca-1(13),2(7),3,5,9,11-hexaene

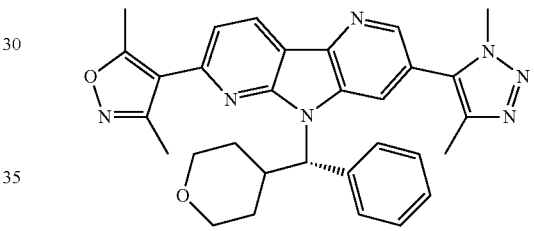

Dissolved (S)-7-chloro-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridine (47.3 mg, 0.1 mmol) and (3,5-dimethylisoxazol-4-yl)boronic acid (28.2 mg, 0.200 mmol) in 1.7 mL of dioxane. Added PdCl$_2$(dppf)-CH$_2$Cl$_2$Adduct (8.2 mg, 10.0 μmol) and 0.3 mL of sodium carbonate (300 μl, 0.300 mmol). Bubbled in argon for 2 min while sonicating. The vial was capped and heated at 100° C. for 4 h, the heating was discontinued and stirred for 3 days. The crude material was purified via preparative LC/MS with the following conditions: Column: XBridge C18, 19×200 mm, 5-μm particles; Mobile Phase A: 5:95 ACN: water with 0.1% trifluoroacetic acid; Mobile Phase B: 95:5 ACN: water with 0.1% trifluoroacetic acid; Gradient: 40-80% B over 35 min, then a 5-min hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol: water with 10-mM NH$_4$OAc; Mobile Phase B: 95:5 methanol: water with 10-mM NH$_4$OAc; Gradient: 45-85% B over 20 min, then a 5-min hold at 100% B; Flow: 20 mL/min. Fractions containing the desired product were combined and dried via centrifugal evaporation. The yield of the product was 3.6 mg (6.7%), and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 ACN:

water with 10 mM NH$_4$OAc; Mobile Phase B: 95:5 ACN: water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. RT=1.84 min, M+H=534. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. RT=2.82 min, M+H=534. $^1$H NMR (500 MHz, DMSO-d$_6$) δ 8.72 (d, J=8.1 Hz, 1H), 8.63 (s, 1H), 8.52 (br. s., 1H), 7.76 (d, J=7.3 Hz, 2H), 7.62 (d, J=7.7 Hz, 1H), 7.32 (t, J=7.5 Hz, 2H), 7.24 (t, J=7.3 Hz, 1H), 6.06 (br. s., 1H), 4.02 (s, 3H), 3.94-3.86 (m, 1H), 3.75 (d, J=9.2 Hz, 1H), 3.64 (br. s., 1H), 3.25 (t, J=11.2 Hz, 1H), 2.79 (s, 3H), 2.62 (s, 3H), 2.31 (s, 3H), 1.62 (br. s., 1H), 1.51-1.36 (m, 1H), 1.36-1.20 (m, 1H), 1.15 (br. s., 1H)

Example 148

5-(Dimethyl-1H-1,2,3-triazol-5-yl)-11-(1,4-dimethyl-1H-pyrazol-5-yl)-8-[(S)-oxan-4-yl(phenyl)methyl]-3,8,10-triazatricyclo[7.4.0.0$^{2,7}$]trideca-1(13),2(7),3,5,9,11-hexaene

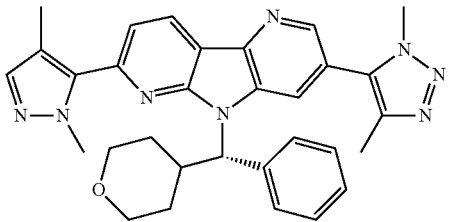 [SMILES: Cc1cnn(C)c1-c1ccc2c3ncc(-c4c(C)nnn4C)cc3n([C@H](c3ccccc3)C3CCOCC3)c2n1]

Dissolved (S)-7-chloro-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridine (47.3 mg, 0.1 mmol) and (1,4-dimethyl-1H-pyrazol-5-yl)boronic acid (28.0 mg, 0.200 mmol) in 1.7 mL of dioxane. Added PdCl$_2$(dppf)-CH$_2$Cl$_2$Adduct (8.2 mg, 10.0 μmol) and 0.3 mL of a 1M aqueous solution of sodium carbonate (300 μl, 0.300 mmol). Bubbled in argon for 2 min while sonicating. Heated in an oil bath at 100° C. for 4 h. The crude material was purified via preparative LC/MS with the following conditions: Column: XBridge C18, 19×200 mm, 5-μm particles; Mobile Phase A: 5:95 ACN: water with 10-mM NH$_4$OAc; Mobile Phase B: 95:5 ACN: water with 10-mM NH$_4$OAc; Gradient: 30-70% B over 20 min, then a 5-min hold at 100% B; Flow: 20 mL/min. Fractions containing the desired product were combined and dried via centrifugal evaporation. The yield of the product was 13.6 mg (25%), and its estimated purity by LCMS analysis was 97%. Two analytical LC/MS injections were used to determine the final purity. Injection 1 conditions: Column: Waters BEH C18, 2.0×50 mm, 1.7-μm particles; Mobile Phase A: 5:95ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. RT=1.78 min, M+H=533. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. RT=2.80 min, M+H=533. $^1$H NMR (500 MHz, DMSO-d$_6$) δ 8.70 (d, J=8.1 Hz, 1H), 8.64 (s, 1H), 8.54 (br. s., 1H), 7.81 (d, J=8.1 Hz, 1H), 7.76 (d, J=7.3 Hz, 2H), 7.32 (t, J=7.5 Hz, 2H), 7.24 (t, J=7.2 Hz, 1H), 6.80 (s, 1H), 6.04 (br. s., 1H), 4.36 (s, 3H), 4.03 (s, 3H), 3.90 (d, J=11.4 Hz, 1H), 3.75 (d, J=9.2 Hz, 1H), 3.65 (br. s., 1H), 3.25 (t, J=11.4 Hz, 1H), 2.31 (s, 3H), 2.26 (s, 3H), 1.62 (br. s., 1H), 1.52-1.37 (m, 1H), 1.37-1.24 (m, 1H), 1.19 (br. s., 1H).

Example 149

5-(Dimethyl-1H-1,2,3-triazol-5-yl)-8-[(S)-oxan-4-yl(phenyl)methyl]-11-[1-(propan-2-yl)-1H-pyrazol-4-yl]-3,8,10-triazatricyclo[7.4.0.0$^{2,7}$]trideca-1(13),2(7),3,5,9,11-hexaene

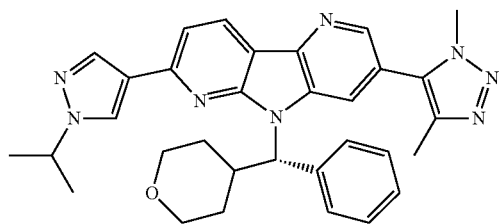 [SMILES: Cc1nnn(C)c1-c1cnc2c3ccc(-c4cnn(C(C)C)c4)nc3n([C@H](c3ccccc3)C3CCOCC3)c2c1]

Dissolved (S)-7-chloro-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridine (47.3 mg, 0.1 mmol) and 1-isopropyl-4-(4,4,5,5-tetramethyl-1,3,2-dioxaborolan-2-yl)-1H-pyrazole (47.2 mg, 0.200 mmol) in 1.7 mL of dioxane. Added PdCl$_2$(dppf)-CH$_2$Cl$_2$Adduct (8.2 mg, 10.0 μmol) and 0.3 mL of sodium carbonate (300 μl, 0.300 mmol). Bubbled in argon for 2 min while sonicating. Heated in the microwave at 100° C. for 2 h. The crude material was purified via preparative LC/MS with the following conditions: Column: XBridge C18, 19×200 mm, 5-μm particles; Mobile Phase A: 5:95 ACN: water with 10-mM NH$_4$OAc; Mobile Phase B: 95:5 ACN: water with 10-mM NH$_4$OAc; Gradient: 20-100% B over 15 min, then a 5-min hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol: water with 10-mM NH$_4$OAc; Mobile Phase B: 95:5 methanol: water with 10-mM NH$_4$OAc; Gradient: 45-85% B over 20 min, then a 5-min hold at 100% B; Flow: 20 mL/min. Fractions containing the desired product were combined and dried via centrifugal evaporation. The yield of the product was 21.1 mg (38%), and its estimated purity by LCMS analysis was 99%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. RT=1.82 min, M+H=547. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. RT=2.83 min, M+H=547. $^1$H NMR (500 MHz, DMSO-d$_6$) δ 8.61 (s, 1H), 8.58-8.54 (m, 2H), 8.52 (br. s., 1H), 8.28 (s, 1H), 7.84 (d, J=7.7 Hz, 2H), 7.71 (d, J=8.1 Hz, 1H), 7.31 (t, J=7.5 Hz, 2H), 7.23 (t, J=7.5 Hz, 1H), 5.92 (br. s., 1H), 4.66 (dt, J=13.4, 6.5 Hz, 1H), 4.03 (s, 3H), 3.91 (d, J=11.4 Hz, 1H), 3.77 (d, J=10.6 Hz, 2H), 3.33-3.22 (m, 1H), 2.31 (s, 3H), 1.53 (d, J=6.6 Hz, 7H), 1.44 (d, J=11.7 Hz, 1H), 1.37-1.25 (m, 1H), 1.25-1.16 (m, 1H).

Example 150

11-(1-Cyclopropyl-1H-pyrazol-4-yl)-5-(dimethyl-1H-1,2,3-triazol-5-yl)-8-[(S)-oxan-4-yl(phenyl)methyl]-3,8,10-triazatricyclo[7.4.0.0$^{2,7}$]trideca-1(13),2(7),3,5,9,11-hexaene

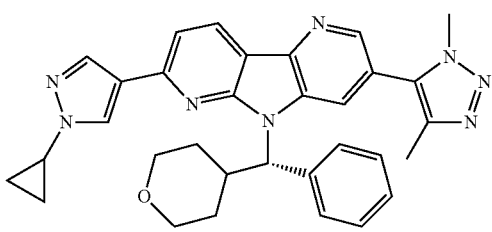 [SMILES: Cc1nnn(C)c1-c1cnc2c3ccc(-c4cnn(C5CC5)c4)nc3n([C@H](c3ccccc3)C3CCOCC3)c2c1]

Dissolved (S)-7-chloro-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridine (47.3 mg, 0.1 mmol) and 1-cyclopropyl-4-(4,4,5,5-tetramethyl-1,3,2-dioxaborolan-2-yl)-1H-pyrazole (46.8 mg, 0.200 mmol) in 1.7 mL of dioxane. Added PdCl$_2$(dppf)-CH$_2$Cl$_2$Adduct (8.2 mg, 10.0 μmol) and 0.3 mL of sodium carbonate (300 μl, 0.300 mmol). Bubbled in argon for 2 min while sonicating. Heated at 100° C. for 2 h. The crude material was purified via preparative LC/MS with the following conditions: Column: XBridge C18, 19×200 mm, 5-μm particles; Mobile Phase A: 5:95 ACN: water with 0.1% trifluoroacetic acid; Mobile Phase B: 95:5 ACN: water with 0.1% trifluoroacetic acid; Gradient: 35-75% B over 20 min, then a 5-min hold at 100% B; Flow: 20 mL/min. Fractions containing the desired product were combined and dried via centrifugal evaporation. The yield of the product was 34.0 mg (61%), and its estimated purity by LCMS analysis was 98%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.5-min hold at 100% B; Flow: 1.0 mL/min; Detection: UV at 220 nm. RT=1.81 min, M+H=545. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0-100% B over 3 min, then a 0.5-min hold at 100% B; Flow: 0.5 mL/min; Detection: UV at 220 nm. RT=3.15 min, M+H=545. H NMR (500 MHz, DMSO-d$_6$) δ 8.63 (s, 1H), 8.58-8.53 (m, 2H), 8.51 (br. s., 1H), 8.26 (s, 1H), 7.84 (d, J=7.7 Hz, 2H), 7.70 (d, J=8.1 Hz, 1H), 7.31 (t, J=7.5 Hz, 2H), 7.22 (t, J=7.2 Hz, 1H), 5.93 (br. s., 1H), 4.03 (s, 3H), 3.90 (dd, J=7.5, 3.5 Hz, 2H), 3.76 (d, J=10.6 Hz, 2H), 3.26 (t, J=11.4 Hz, 1H), 2.30 (s, 3H), 1.56 (d, J=10.6 Hz, 1H), 1.51-1.38 (m, 1H), 1.36-1.24 (m, 1H), 1.24-1.14 (m, 3H), 1.14-0.95 (m, 3H).

Example 151

11-(4-Cyclopropylpiperazin-1-yl)-5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaene

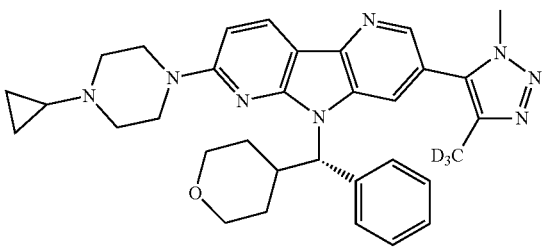 [SMILES: [2H]C([2H])([2H])c1nnn(C)c1-c1cnc2c3ccc(N4CCN(C5CC5)CC4)nc3n([C@H](c3ccccc3)C3CCOCC3)c2c1]

Dissolved 11-chloro-5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaene (30 mg, 0.063 mmol) in 1.5 mL of DMSO. Added 1-cyclopropylpiperazine, 2 HCl (125 mg, 0.630 mmol) and TEA (264 μl, 1.89 mmol). Capped vial and heated overnight at 100° C. The crude material was purified via preparative LC/MS with the following conditions: Column: XBridge C18, 19×200 mm, 5-μm particles; Mobile Phase A: 5:95 methanol: water with 10-mM NH$_4$OAc; Mobile Phase B: 95:5 methanol: water with 10-mM NH$_4$OAc; Gradient: 60-100% B over 20 min, then a 5-min hold at 100% B; Flow: 20 mL/min. Fractions containing the desired product were combined and dried via centrifugal evaporation. The yield of the product was 16.7 mg (46%), and its estimated purity by LCMS analysis was 99%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.5-min hold at 100% B; Flow: 1.0 mL/min; Detection: UV at 220 nm. RT=2.00 min, M+H=566. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0-100% B over 3 min, then a 0.5-min hold at 100% B; Flow: 0.5 mL/min; Detection: UV at 220 nm. RT=3.47 min, M+H=566. $^1$H NMR (500 MHz, DMSO-d$_6$) δ 8.40 (s, 1H), 8.32 (br. s., 1H), 8.26 (d, J=8.8 Hz, 1H), 7.77 (d, J=7.7 Hz, 2H), 7.34-7.28 (m, 2H), 7.25-7.19 (m, 1H), 6.90 (d, J=8.8 Hz, 1H), 5.72 (br. s., 1H), 4.01 (s, 3H), 3.88 (d, J=11.4 Hz, 1H), 3.80 (br. s., 1H), 3.65 (br. s., 1H), 3.25 (br. s., 1H), 2.74 (d, J=2.9 Hz, 4H), 1.72 (br. s., 1H), 1.46 (br. s., 1H), 1.43-1.32 (m, 1H), 1.25 (br. s., 2H).

Example 152

11-(4-tert-Butylpiperazin-1-yl)-5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaene

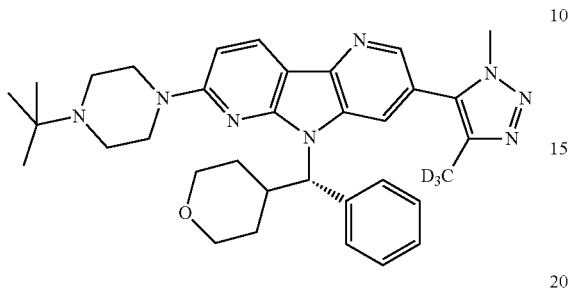

Dissolved 11-chloro-5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaene (30 mg, 0.063 mmol) in 1 mL of DMSO. Added 1-(tert-butyl)piperazine (90 mg, 0.630 mmol) and 1-(tert-butyl)piperazine (90 mg, 0.630 mmol). Capped vial and heated for 2 h at 100° C. The crude material was purified via preparative LC/MS with the following conditions: Column: XBridge C18, 19×200 mm, 5-μm particles; Mobile Phase A: 5:95 ACN: water with 0.1% trifluoroacetic acid; Mobile Phase B: 95:5 ACN: water with 0.1% trifluoroacetic acid; Gradient: 15-55% B over 15 min, then a 5-min hold at 100% B; Flow: 20 mL/min. Fractions containing the desired product were combined and dried via centrifugal evaporation. The yield of the product was 17.9 mg (46%), and its estimated purity by LCMS analysis was 95%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. RT=1.74 min, M+H=582. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. RT=2.76 min, M+H=582. $^1$H NMR (500 MHz, DMSO-d$_6$) δ 8.46 (s, 1H), 8.44-8.34 (m, 2H), 7.95 (s, 1H), 7.77 (d, J=7.7 Hz, 2H), 7.35-7.27 (m, 3H), 7.27-7.21 (m, 1H), 7.18 (s, 1H), 7.08 (s, 1H), 7.02 (d, J=8.8 Hz, 1H), 5.76 (br. s., 1H), 4.80-4.68 (m, 2H), 4.01 (s, 3H), 3.89 (d, J=11.0 Hz, 1H), 3.78 (d, J=11.4 Hz, 3H), 3.63 (br. s., 1H), 3.51 (br. s., 2H), 3.47-3.35 (m, 3H), 3.35-3.19 (m, 3H), 2.56 (t, J=5.5 Hz, 1H), 1.49 (br. s., 1H), 1.42 (s, 9H), 1.32-1.17 (m, 2H).

Example 153

5-[4-($^2$H$_3$)Methyl-1-methyl-1H-1,2,3-triazol-5-yl]-8-[(S)-oxan-4-yl(phenyl)methyl]-11-[4-(propan-2-yl)piperazin-1-yl]-3,8,10-triazatricyclo[7.4.0.0$^{2,7}$]trideca-1(9),2(7),3,5,10,12-hexaene

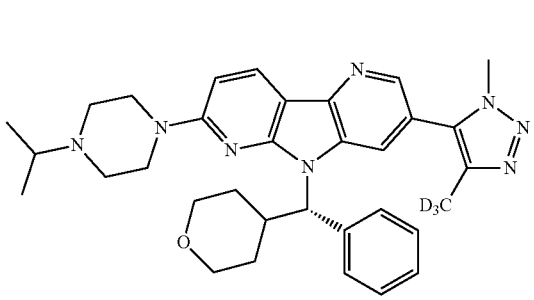 [SMILES: [2H]C([2H])([2H])c1nnn(C)c1-c1cnc2c3ccc(N4CCN(C(C)C)CC4)nc3n([C@H](c3ccccc3)C3CCOCC3)c2c1]

Dissolved 11-chloro-5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaene (30 mg, 0.063 mmol) in 1 mL of DMSO. Added 1-isopropylpiperazine (81 mg, 0.630 mmol). Capped vial and heated at 100° C. for 4½ h. The crude material was purified via preparative LC/MS with the following conditions: Column: XBridge C18, 19×200 mm, 5-μm particles; Mobile Phase A: 5:95 ACN: water with 0.1% trifluoroacetic acid; Mobile Phase B: 95:5 ACN: water with 0.1% trifluoroacetic acid; Gradient: 10-50% B over 15 min, then a 5-min hold at 100% B; Flow: 20 mL/min. Fractions containing the desired product were combined and dried via centrifugal evaporation. The yield of the product was 42.2 mg (82%), and its estimated purity by LCMS analysis was 97%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. RT=1.71 min, M+H=568. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. RT=2.75 min, M+H=568. $^1$H NMR (500 MHz, DMSO-d$_6$) δ 8.46 (s, 1H), 8.45-8.35 (m, 2H), 7.76 (d, J=7.7 Hz, 2H), 7.36-7.27 (m, 3H), 7.27-7.21 (m, 1H), 7.03 (d, J=8.8 Hz, 1H), 5.77 (br. s., 1H), 4.76 (br. s., 2H), 4.01 (s, 3H), 3.89 (d, J=11.4 Hz, 1H), 3.78 (d, J=10.3 Hz, 1H), 3.67 (br. s., 2H), 3.65-3.57 (m, 2H), 3.45-3.33 (m, 3H), 3.33-3.19 (m, 3H), 1.50 (br. s., 1H), 1.46-1.37 (m, 1H), 1.35 (d, J=6.6 Hz, 6H), 1.30-1.16 (m, 2H).

Example 154

5-[4-($^2$H$_3$)Methyl-1-methyl-1H-1,2,3-triazol-5-yl]-8-[(S)-oxan-4-yl(phenyl)methyl]-11-[4-(2,2,2-trifluoroethyl)piperazin-1-yl]-3,8,10-triazatricyclo[7.4.0.0$^{2,7}$]trideca-1(9),2(7),3,5,10,12-hexaene

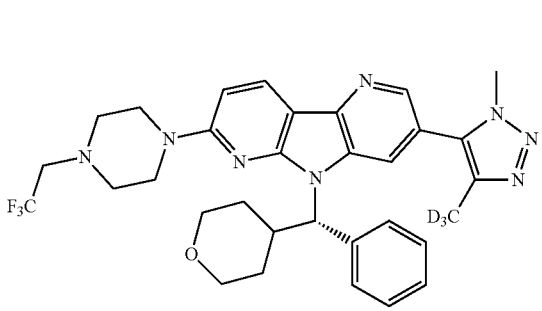 [SMILES: [2H]C([2H])([2H])c1nnn(C)c1-c1cnc2c3ccc(N4CCN(CC(F)(F)F)CC4)nc3n([C@H](c3ccccc3)C3CCOCC3)c2c1]

Dissolved 11-chloro-5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaene (30 mg, 0.063 mmol) in 2 of mL of DMSO. Added 1-(2,2,2-trifluoroethyl)piperazine, 2 HCl (152 mg, 0.630 mmol). Capped vial and heated at 100° C. overnight. The crude material was purified via preparative LC/MS with the following conditions: Column: XBridge C18, 19×200 mm, 5-μm particles; Mobile Phase A: 5:95 ACN: water with 10-mM NH$_4$OAc; Mobile Phase B: 95:5 ACN: water with 10-mM NH$_4$OAc; Gradient: 40-80% B over 20 min, then a 5-min hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 ACN: water with 0.1% trifluoroacetic acid; Mobile Phase B: 95:5 ACN: water with 0.1% trifluoroacetic acid; Gradient: 25-65% B over 15 min, then a 5-min hold at 100% B; Flow: 20 mL/min. Fractions containing the desired product were combined and dried via centrifugal evaporation. The yield of the product was 15.2 mg, and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. RT=2.10 min, M+H=608. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. RT=2.98 min, M+H=608. $^1$H NMR (500 MHz, DMSO-d$_6$) δ 8.52-8.41 (m, 2H), 8.31 (d, J=8.8 Hz, 1H), 7.77 (d, J=7.3 Hz, 2H), 7.35-7.28 (m, 2H), 7.27-7.21 (m, 2H), 6.96 (d, J=9.2 Hz, 1H), 5.74 (br. s., 1H), 4.01 (s, 3H), 3.88 (br. s., 1H), 3.79 (d, J=11.7 Hz, 1H), 3.63 (br. s., 1H), 3.44-3.22 (m, 4H), 2.85 (br. s., 4H), 2.56 (t, J=5.5 Hz, 1H), 1.46 (br. s., 1H), 1.38 (d, J=12.1 Hz, 1H), 1.24 (br. s., 2H).

Example 155

5,11-Bis(dimethyl-1H-1,2,3-triazol-5-yl)-8-[(S)-oxan-4-yl(phenyl)methyl]-3,8,10,12-tetraazatricyclo[7.4.0.0$^{2,7}$]trideca-1(9),2(7),3,5,10,12-hexaene

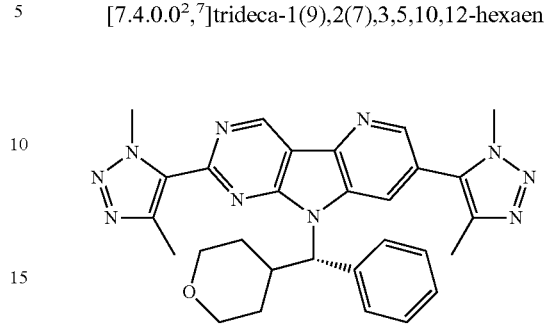

Step 1: 5-(5-Bromo-3-nitropyridin-2-yl)-2-chloropyrimidine

In a 250 mL thick-walled flask was added (2-chloropyrimidin-5-yl)boronic acid (1 g, 6.32 mmol), 2,5-dibromo-3-nitropyridine (1.780 g, 6.32 mmol) in 90 mL of THF. Added tripotassium phosphate (2.68 g, 12.6 mmol) and PdCl$_2$(dppf)-CH$_2$Cl$_2$Adduct (0.103 g, 0.126 mmol). Bubbled in argon through the mixture while sonicating for 1 min. Capped flask and heated in an oil bath at 65° C. overnight. Concentrated to afford a brown solid. The crude material was purified on a 120 g ISCO column, eluting with 20% EtOAc/hexanes to 50% EtOAc/hexanes over 20 column volumes. The fractions containing the title compound were concentrated to afford 0.72 g (36% yield) of a yellow solid. $^1$H NMR (400 MHz, CDCl$_3$) δ 9.04 (d, J=2.0 Hz, 1H), 8.83 (s, 2H), 8.58 (d, J=2.0 Hz, 1H).

Step 2: 7-Bromo-2-chloro-9H-pyrido[2',3':4,5]pyrrolo[2,3-d]pyrimidine

Suspended 5-(5-bromo-3-nitropyridin-2-yl)-2-chloropyrimidine (0.76 g, 2.41 mmol) and DPPE (1.440 g, 3.61 mmol) in 15 mL of 1,2-dichlorobenzene. Placed vial in an oil bath at 160° C. and heated for 30 min after complete dissolution of reactants. Cooled vial and removed volatiles on rotary evaporator hooked up to high vacuum pump. The crude material was purified on an 80 g ISCO column, eluting with 5% EtOAc/hexanes to 90% EtOAc/hexanes over 25 column volumes. Concentrated fractions containing the title compound to afford 0.41 g (58% yield). $^1$H NMR (400 MHz, DMSO-d$_6$) δ 13.00 (br. s., 1H), 9.43 (s, 1H), 8.73 (s, 1H), 8.28 (d, J=1.7 Hz, 1H).

Step 3: (S)-7-Bromo-2-chloro-9-(phenyl(tetrahydro-2H-pyran-4-yl)methyl)-9H-pyrido[2',3':4,5]pyrrolo[2,3-d]pyrimidine Dissolved (R)-phenyl(tetrahydro-2H-pyran-4-yl)methanol (0.556 g, 2.89 mmol) and 7-bromo-2-chloro-9H-pyrido[2',3':4,5]pyrrolo[2,3-d]pyrimidine (0.41 g, 1.45 mmol) in 5 mL of methylene chloride. Added triphenylphosphine (0.759 g, 2.89 mmol) and cooled vial in an ice bath. Added DIAD (0.562 ml, 2.89 mmol), capped vial and allowed bath to melt and stirred overnight. Purified on a 40 g ISCO column, eluting with 10% EtOAc/hexanes to 50% EtOAc/hexanes over 600 mL. Concentrated fractions containing the title compound to afford 1.2 g of a yellow oil. The material was further purified on a 40 g ISCO column, eluting with 0% EtOAc/hexanes to 20% EtOAc/hexanes over 20 column volumes. Concentration of the major peak afforded 0.67 g of the title compound which still contained impurities as determined by 1H NMR. Material was used directly in subsequent reactions. $^1$H NMR (400 MHz, CDCl$_3$) δ 9.39 (s, 1H), 8.69 (d, J=2.0 Hz, 1H), 8.07 (d, J=1.7 Hz, 1H), 7.63 (d, J=7.3 Hz, 2H), 7.43-7.31 (m, 14H), 6.34 (br. s., 3H), 4.05 (dd, J=11.2, 4.9 Hz, 3H), 3.92 (d, J=11.5 Hz, 4H), 3.50-3.38 (m, 4H), 3.38-3.23 (m, 3H), 1.54-1.44 (m, 4H), 1.23-1.10 (m, 5H), 0.95-0.85 (m, 2H)

Step 4: 5,11-Bis(dimethyl-1H-1,2,3-triazol-5-yl)-8-[(S)-oxan-4-yl(phenyl)methyl]-3,8,10,12-tetraazatricyclo[7.4.0.0$^{2,7}$]trideca-1(9),2(7),3,5,10,12-hexaene Dissolved (S)-7-bromo-2-chloro-9-(phenyl(tetrahydro-2H-pyran-4-yl)methyl)-9H-pyrido[2',3':4,5]pyrrolo[2,3-d]pyrimidine (325 mg, 0.710 mmol) and 1,4-dimethyl-5-(tributylstannyl)-1H-1,2,3-triazole (274 mg, 0.710 mmol) in 4 mL of DMF. Added copper iodide (27.0 mg, 0.142 mmol), Et$_3$N (148 µl, 1.07 mmol) and tetrakis (82 mg, 0.071 mmol). Bubbled in argon for 30 seconds while sonicating. Capped vial and placed in an oil bath at 100° C. and heated for 3 h. The crude material was purified via preparative LC/MS with the following conditions: Column: XBridge C18, 19×200 mm, 5-µm particles; Mobile Phase A: 5:95 methanol: water with 0.1% trifluoroacetic acid; Mobile Phase B: 95:5 methanol: water with 0.1% trifluoroacetic acid; Gradient: 50-100% B over 20 min, then a 5-min hold at 100% B; Flow: 20 mL/min. Fractions containing the desired product were combined and dried via centrifugal evaporation. The yield of the product was 2.3 mg (0.5%), and its estimated purity by LCMS analysis was 86%. Two analytical LC/MS injections were used to determine the final purity. Injection 1 conditions: Column: Waters BEH C18, 2.0×50 mm, 1.7-µm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.5-min hold at 100% B; Flow: 1.0 mL/min; Detection: UV at 220 nm. RT=1.73 min, M+H=535. Injection 2 conditions: Column: Waters BEH C18, 2.0×50 mm, 1.7-µm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0-100% B over 3 min, then a 0.5-min hold at 100% B; Flow: 0.5 mL/min; Detection: UV at 220 nm. RT=3.32 min, M+H=535. $^1$H NMR (500 MHz, DMSO-d$_6$) δ 9.73 (s, 1H), 8.76 (s, 1H), 8.66 (br. s., 1H), 7.79 (d, J=7.3 Hz, 2H), 7.38-7.30 (m, 3H), 7.29-7.19 (m, 2H), 5.98 (br. s., 1H), 4.54 (s, 3H), 4.04 (s, 3H), 3.95-3.85 (m, 1H), 3.76 (d, J=11.7 Hz, 1H), 3.67 (br. s., 1H), 3.27 (t, J=11.0 Hz, 1H), 2.78 (s, 3H), 2.31 (s, 3H), 1.58 (br. s., 1H), 1.50-1.38 (m, 1H), 1.37-1.22 (m, 1H), 1.22-1.07 (m, 1H).

Example 156

5-(Dimethyl-1H-1,2,3-triazol-5-yl)-11-[4-($^2$H$_3$)methylpiperazin-1-yl]-8-[(S)-oxan-4-yl(phenyl)methyl]-3,8,10,12-tetraazatricyclo[7.4.0.0$^{2,7}$]trideca-1(9),2(7),3,5,10,12-hexaene

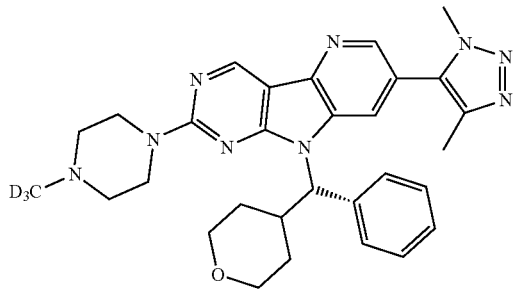

Step 1: 5-Bromo-11-[4-($^2$H$_3$)methylpiperazin-1-yl]-8-[(S)-oxan-4-yl(phenyl)methyl]-3,8,10,12-tetraazatricyclo[7.4.0.0$^{2,7}$]trideca-1(9),2(7),3,5,10,12-hexaene Dissolved (S)-7-bromo-2-chloro-9-(phenyl(tetrahydro-2H-pyran-4-yl)methyl)-9H-pyrido[2',3':4,5]pyrrolo[2,3-d]pyrimidine (30 mg, 0.066 mmol) in 1 mL of DMSO. Added 4-($^2$H$_3$)methylpiperazine 2 HCl (57.7 mg, 0.328 mmol). Capped vial and heated at 100° C. for 1 h. Partitioned reaction between EtOAc and water. Washed organic layer with brine, dried over MgSO$_4$, filtered and stripped to afford 37 mg of the title compound as a yellow-red oil. LC/MS and 1H NMR were consistent with impure product. Used material directly in subsequent reaction. LC/MS: RT=0.93, M+H=524, purity=69%. (Column: Waters Acquity SDS; Mobile Phase A: 100% Water, 0.1% TFA; Mobile Phase B: 100% ACN, 0.1% TFA; Temperature 50° C.; Gradient 2% B to 98% B over 2.2 min; Flow 0.8 mL/min; Detection: UV at 220 nm).

Step 2: 5-(Dimethyl-1H-1,2,3-triazol-5-yl)-1-[4-($^2$H$_3$)methylpiperazin-1-yl]-8-[(S)-oxan-4-yl(phenyl)methyl]-3,8,10,12-tetraazatricyclo[7.4.0.0$^{2,7}$]trideca-1(9),2(7),3,5,10,12-hexaene Dissolved 5-bromo-11-[4-($^2$H$_3$)methylpiperazin-1-yl]-8-[(S)-oxan-4-yl(phenyl)methyl]-3,8,10,12-tetraazatricyclo[7.4.0.0$^{2,7}$]trideca-1(9),2(7),3,5,10,12-hexaene and 1,4-dimethyl-5-(tributylstannyl)-1H-1,2,3-triazole (54.5 mg, 0.141 mmol) in 2 mL of DMF. Added copper(I) iodide (2.69 mg, 0.014 mmol), Et$_3$N (30 µl, 0.212 mmol) and tetrakis (8.15 mg, 7.05 µmol). Bubbled in argon for 30 seconds while sonicating. Capped vial and placed in an oil bath at 100° C. and heated overnight. The crude material was purified via preparative LC/MS with the following conditions: Column: XBridge C18, 19×200 mm, 5-µm particles; Mobile Phase A: 5:95 methanol: water with 0.1% trifluoroacetic acid; Mobile Phase B: 95:5 methanol: water with 0.1% trifluoroacetic acid; Gradient: 30-100% B over 20 min, then a 5-min hold at 100% B; Flow: 20 mL/min. Fractions containing the desired product were combined and dried via centrifugal evaporation. The material was further purified via preparative LC/MS with the following conditions: Column:

XBridge C18, 19×200 mm, 5-μm particles; Mobile Phase A: 5:95 ACN: water with 10-mM NH₄OAc; Mobile Phase B: 95:5 ACN: water with 10-mM NH₄OAc; Gradient: 20-60% B over 20 min, then a 5-min hold at 100% B; Flow: 20 mL/min. Fractions containing the desired product were combined and dried via centrifugal evaporation. The yield of the product was 1.5 mg (3.8%), and its estimated purity by LCMS analysis was 96%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0% B, 0-100% B over 3 min, then a 0.5-min hold at 100% B; Flow: 1 mL/min; Detection: UV at 220 nm. RT=1.52 min, M+H=541. Injection 2 conditions: Column: Waters BEH C18, 2.0×50 mm, 1.7-μm particles; Mobile Phase A: 5:95 methanol:water with 10 mM NH₄OAc; Mobile Phase B: 95:5 methanol:water with 10 mM NH₄OAc; Temperature: 50° C.; Gradient: 0% B, 0-100% B over 3 min, then a 0.5-min hold at 100% B; Flow: 0.5 mL/min; Detection: UV at 220 nm. RT=2.60 min, M+H=541. ¹H NMR (500 MHz, DMSO-d₆) δ 9.10 (s, 1H), 8.46 (s, 1H), 8.36 (br. s., 1H), 7.76 (d, J=7.7 Hz, 2H), 7.33 (t, J=7.5 Hz, 2H), 7.25 (t, J=7.3 Hz, 1H), 5.64 (br. s., 1H), 4.03-3.92 (m, 8H), 3.87 (d, J=10.3 Hz, 1H), 3.80 (d, J=11.7 Hz, 1H), 3.59 (br. s., 1H), 3.29-3.20 (m, 1H), 2.28 (s, 3H), 1.43 (br. s., 1H), 1.37 (d, J=12.5 Hz, 1H), 1.30-1.19 (m, 5H)

Example 157

11-(4-Cyclopropylpiperazin-1-yl)-5-(dimethyl-1H-1,2,3-triazol-5-yl)-8-[(S)-oxan-4-yl(phenyl)methyl]-3,8,10,12-tetraazatricyclo[7.4.0.0²,⁷]trideca-1(9),2(7),3,5,10,12-hexaene

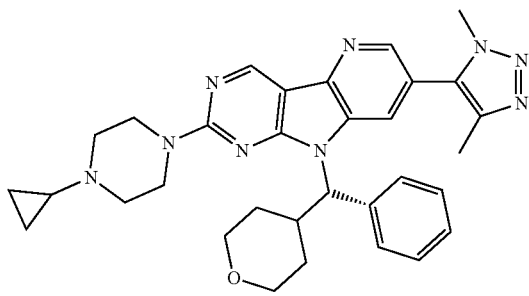

Step 1: (S)-7-Bromo-2-(4-cyclopropylpiperazin-1-yl)-9-(phenyl(tetrahydro-2H-pyran-4-yl)methyl)-9H-pyrido[2',3':4,5]pyrrolo[2,3-d]pyrimidine Dissolved (S)-7-bromo-2-chloro-9-(phenyl(tetrahydro-2H-pyran-4-yl)methyl)-9H-pyrido[2',3':4,5]pyrrolo[2,3-d]pyrimidine (34 mg, 0.074 mmol) in 1 mL of DMSO. Added 1-cyclopropylpiperazine, 2 HCl (73.9 mg, 0.371 mmol). Capped vial and heated at 100° C. for 1 h. Partitioned reaction between EtOAc and water. Washed organic layer with brine, dried over MgSO₄, filtered and stripped to afford 37 mg of the title compound as a yellow-red oil. LC/MS using method A indicted impurities were present; RT=1.0 min, M+H=547. The material was used directly in the subsequent reaction.

Step 2: 11-(4-Cyclopropylpiperazin-1-yl)-5-(dimethyl-1H-1,2,3-triazol-5-yl)-8-[(S)-oxan-4-yl(phenyl)methyl]-3,8,10,12-tetraazatricyclo[7.4.0.0²,⁷]trideca-1(9),2(7),3,5,10,12-hexaene Dissolved (S)-7-bromo-2-(4-cyclopropylpiperazin-1-yl)-9-(phenyl(tetrahydro-2H-pyran-4-yl)methyl)-9H-pyrido[2',3':4,5]pyrrolo[2,3-d]pyrimidine (37 mg, 0.068 mmol) and 1,4-dimethyl-5-(tributylstannyl)-1H-1,2,3-triazole (52.2 mg, 0.135 mmol) in 2 mL of DMF. Added copper (I) iodide (2.6 mg, 0.014 mmol), Et₃N (28 μl, 0.203 mmol) and tetrakis (7.8 mg, 6.76 μmol). Bubbled in argon for 30 seconds while sonicating. Capped vial and placed in an oil bath at 100° C. and heated overnight. The crude material was purified via preparative LC/MS with the following conditions: Column: XBridge C18, 19×200 mm, 5-μm particles; Mobile Phase A: 5:95 ACN: water with 10-mM NH₄OAc; Mobile Phase B: 95:5 ACN: water with 10-mM NH₄OAc; Gradient: 40-80% B over 20 min, then a 5-min hold at 100% B; Flow: 20 mL/min. Fractions containing the desired product were combined and dried via centrifugal evaporation. The yield of the product was 1.9 mg, and its estimated purity by LCMS analysis was 97%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0% B, 0-100% B over 3 min, then a 0.5-min hold at 100% B; Flow: 1 mL/min; Detection: UV at 220 nm. RT=1.96 min, M+H=564. Injection 2 conditions: Column: Waters BEH C18, 2.0×50 mm, 1.7-μm particles; Mobile Phase A: 5:95 methanol:water with 10 mM NH₄OAc; Mobile Phase B: 95:5 methanol:water with 10 mM NH₄OAc; Temperature: 50° C.; Gradient: 0% B, 0-100% B over 3 min, then a 0.5-min hold at 100% B; Flow: 0.5 mL/min, Detection: UV at 220 nm. RT=2.96 min, M+H=564. ¹H NMR (500 MHz, DMSO-d₆) δ 9.11 (s, 1H), 8.47 (br. s., 1H), 8.36 (br. s., 1H), 7.76 (d, J=7.7 Hz, 2H), 7.33 (t, J=7.3 Hz, 2H), 7.25 (t, J=7.3 Hz, 1H), 5.63 (br. s., 1H), 4.00 (s, 3H), 3.95 (br. s., 4H), 3.88 (d, J=12.1 Hz, 1H), 3.81 (d, J=11.4 Hz, 1H), 3.59 (br. s., 1H), 3.30-3.22 (m, 1H), 2.28 (s, 3H), 1.71 (br. s., 1H), 1.43 (br. s., 1H), 1.41-1.32 (m, 1H), 1.28 (br. s., 2H).

Example 158

(2R,6R)-4-[5-(4-Methoxy-1-methyl-1H-1,2,3-triazol-5-yl)-8-[(S)-oxan-4-yl(phenyl)methyl]-3,8,10,12-tetraazatricyclo[7.4.0.0²,⁷]trideca-1(9),2(7),3,5,10,12-hexaen-11-yl]-2,6-dimethyl-1λ⁶,4-thiomorpholine-1,1-dione

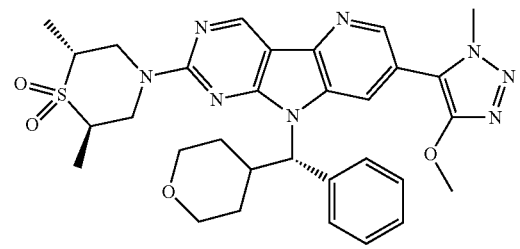 [SMILES: COc1nnn(C)c1-c1cnc2c3cnc(N4C[C@@H](C)S(=O)(=O)[C@H](C)C4)nc3n([C@H](c3ccccc3)C3CCOCC3)c2c1]

Step 1: (2R,6R)-4-(7-Bromo-9-((S)-phenyl(tetrahydro-2H-pyran-4-yl)methyl)-9H-pyrido[2',3':4,5]pyrrolo[2,3-d]pyrimidin-2-yl)-2,6-dimethylthiomorpholine 1,1-dioxide Dissolved (S)-7-bromo-2-chloro-9-(phenyl(tetrahydro-2H-pyran-4-yl)methyl)-9H-pyrido[2',3':4,5]pyrrolo[2,3-d]pyrimidine (34 mg, 0.074 mmol) in 1 mL of DMSO. Added (2R,6R)-2,6-dimethylthiomorpholine 1,1-dioxide, HCl (44.2 mg, 0.221 mmol). Capped vial and heated at 100° C. for 1 h. Partitioned reaction between EtOAc and water. Washed organic layer with brine, dried over MgSO$_4$, filtered and stripped to afford 40 mg of the title compound as a reddish brown oil. LC/MS indicated that impurities were present; RT=1.29 min, M+H=584, M+3H=586 (Column: Waters Acquity SDS; Mobile Phase A: 100% Water, 0.1% TFA; Mobile Phase B: 100% ACN, 0.1% TFA; Temperature 50° C.; Gradient 2% B to 98% B over 2.2 min; Flow 0.8 mL/min; Detection: UV at 220 nm). Material was used directly in the subsequent reaction.

Step 2: (2R,6R)-4-[5-(4-Methoxy-1-methyl-1H-1,2,3-triazol-5-yl)-8-[(S)-oxan-4-yl(phenyl)methyl]-3,8,10,12-tetraazatricyclo[7.4.0.0$^{2,7}$]trideca-1(9),2(7),3,5,10,12-hexaen-11-yl]-2,6-dimethyl-1λ$^6$,4-thiomorpholine-1,1-dione In a 20 mL, thick walled vial containing (2R,6R)-4-(7-bromo-9-((S)-phenyl(tetrahydro-2H-pyran-4-yl)methyl)-9H-pyrido[2',3':4,5]pyrrolo[2,3-d]pyrimidin-2-yl)-2,6-dimethylthiomorpholine 1,1-dioxide (8 mg, 0.014 mmol) was added 4-methoxy-1-((trimethylsilyl)methyl)-1H-1,2,3-triazole (5.1 mg, 0.027 mmol). Added 1.5 mL of DMF, tetramethylammonium acetate (7.3 mg, 0.055 mmol) and bis(triphenylphosphine)palladium (II) chloride (0.961 mg, 1.37 μmol). Bubbled argon through the mixture for 1 min while sonicating. Capped vial and heated at 100° C. for 15 h. The crude material was purified via preparative LC/MS with the following conditions: Column: XBridge C18, 19×200 mm, 5-μm particles; Mobile Phase A: 5:95 methanol: water with 10-mM NH$_4$OAc; Mobile Phase B: 95:5 methanol: water with 10-mM NH$_4$OAc; Gradient: 40-100% B over 20 min, then a 5-min hold at 100% B; Flow: 20 mL/min. Fractions containing the desired product were combined and dried via centrifugal evaporation. The yield of the product was 0.9 mg (11%), and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.5-min hold at 100% B; Flow: 1.0 mL/min; Detection: UV at 220 nm. RT=1.97 min, M+H=617. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0-100% B over 3 min, then a 0.5-min hold at 100% B; Flow: 0.5 mL/min; Detection: UV at 220 nm. RT=2.68 min, M+H=617. $^1$H NMR (500 MHz, DMSO-d$_6$) δ 9.18 (s, 1H), 8.52 (s, 1H), 8.42 (br. s., 1H), 7.74 (d, J=7.3 Hz, 3H), 7.34 (t, J=7.5 Hz, 2H), 7.27 (t, J=7.5 Hz, 1H), 5.68 (br. s., 1H), 5.13 (d, J=13.2 Hz, 2H), 4.08 (s, 3H), 4.01 (s, 3H), 3.90 (s, 3H), 3.80 (d, J=9.9 Hz, 1H), 3.41-3.31 (m, 5H), 3.24 (br. s., 1H), 1.42 (br. s., 3H), 1.33 (br. s., 8H), 1.23 (br. s., 3H).

Example 159

2-{8-[(S)-(4-Fluorophenyl)(oxan-4-yl)methyl]-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaen-11-yl}propan-2-ol

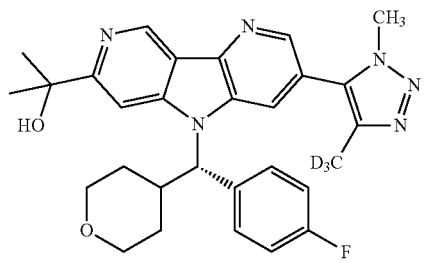 [SMILES: [2H]C([2H])([2H])c1nnn(C)c1-c1cnc2c3cnc(C(C)(C)O)cc3n([C@H](c3ccc(F)cc3)C3CCOCC3)c2c1]

Step 1: 4-($^2$H$_3$)Methyl-1-((trimethylsilyl)methyl)-1H-1,2,3-triazole

A solution of sodium ascorbate (344 mg, 1.74 mmol) in water (2170 μL) was added to a stirred solution of trimethyl ($^2$H$_3$-prop-1-yn-1-yl)silane (prepared according to PCT Int. Appl., 2007112352, 4 Oct. 2007, 200 mg, 1.74 mmol) and (azidomethyl)trimethylsilane (294 mg, 1.91 mmol) in t-BuOH (4340 μL) at ambient temperature. Copper (II) sulfate pentahydrate (87.0 mg, 0.347 mmol) in water (2170 μL) was subsequently added in a drop wise fashion. The reaction was stirred at ambient temperature for 16 h before it was diluted with water (10 mL) and ethyl acetate (20 mL). The 2 layers were separated, and the aqueous layer was washed with additional ethyl acetate (2×20 mL). The combined organics were dried over sodium sulfate, the solids were filtered away, and the volatiles were removed under reduced pressure. The crude material was purified using silica gel column chromatography with a gradient of ethyl acetate in hexanes (0-60%). 4-($^2$H$_3$)Methyl-1-((trimethylsilyl)methyl)-1H-1,2,3-triazole (125 mg, 0.725 mmol, 42%) was isolated as a colorless oil. $^1$H NMR (500 MHz, CDCl$_3$) δ 7.16 (br. s., 1H), 3.89 (s, 2H), 0.15 (s, 9H); LC/MS (M+H)=173.2; LC/MS RT=1.20 min (Column: Phenomenex Luna 30×2.0 mm 3 u; Mobile Phase A: 10:90 ACN:water with 0.1% TFA; Mobile Phase B: 90:10 ACN:water with 0.1% TFA; Temperature: 40° C.; Gradient: 0-100% B over 2 min; Flow: 1 mL/min).

Step 2: 4-($^2$H$_3$)Methyl-1-methyl-1H-1,2,3-triazole

TBAF (60.9 ml, 60.9 mmol) was added drop wise to a stirred solution of 4-($^2$H$_3$)methyl-1-((trimethylsilyl)methyl)-1H-1,2,3-triazole (prepared in route to methyl 3-[4-($^2$H$_3$)methyl-1-methyl-1H-1,2,3-triazol-5-yl]-5-[(S)-oxan-4-yl(phenyl)methyl]-5H-pyrido[3,2-b]indole-7-carboxylate, 8.75 g, 50.8 mmol) and water (1.83 mL, 102 mmol) in THF (203 mL) at 0° C. The reaction was stirred at that temperature for 1 h before it was removed from the cold bath and allowed to warm to ambient temperature. The reaction mixture was stirred at ambient temperature for 16 h. The volatiles were removed from the aqueous layer under reduced pressure. The resulting oil was purified using silica gel column chromatography with a gradient of methanol in ethyl acetate (0-20%). 1-Methyl-4-($^2$H$_3$)methyl-1H-1,2,3-triazole (4.67 g, 46.6 mmol, 92%) was isolated as a yellow oil. $^1$H NMR (500 MHz, DMSO-d$_6$) δ 7.76 (s, 1H), 3.98 (s, 3H); LC/MS (M+H)=101.2; LC/MS RT=0.57 min (Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min).

Step 3: 4-($^2$H$_3$)Methyl-1-methyl-5-(tributylstannyl)-1H-1,2,3-triazole n-BuLi (9.59 mL, 24.0 mmol) in hexanes was added drop wise to a stirred solution of 1-methyl-4-($^2$H$_3$)methyl-1H-1,2,3-triazole (2.00 g, 20.0 mmol) in THF (49.9 mL) at −78° C. under N$_2$ (g). A white precipitate formed upon addition. The reaction was stirred at that temperature for 30 min before tributyltin chloride (5.96 mL, 22.0 mmol) was added drop wise. The reaction was stirred for an additional 10 min before the cold bath was removed, and the reaction was allowed to warm to ambient temperature over 30 min. The reaction mixture was quenched with saturated aqueous ammonium chloride (20 mL) and diluted with 10% aqueous LiCl (20 mL). The layers were separated and the aqueous layer was washed with diethyl ether (3×30 mL). The combined organics were dried over sodium sulfate, the solids were filtered away, and the volatiles were removed under reduced pressure. The crude material was purified using silica gel column chromatography with a gradient of ethyl acetate in hexanes (0-50%). 1-Methyl-5-(tributylstannyl)-4-($^2$H$_3$)methyl-1H-1,2,3-triazole (6.02 g, 15.5 mmol, 77%) was isolated as a colorless oil. $^1$H NMR (500 MHz, DMSO-d$_6$) δ 3.97 (s, 3H), 1.62-1.39 (m, 6H), 1.35-1.25 (m, 6H), 1.24-1.10 (m, 6H), 0.91-0.83 (m, 9H).

Step 4: 11-Chloro-5-[4-($^2$H$_3$)methyl-1-methyl-1H-1,2,3-triazol-5-yl]-3,8,12-triazatricyclo[7.4.0.0$^2$,$^7$]trideca-1(9),2(7),3,5,10,12-hexaene A solution of 3-bromo-7-chloro-5H-pyrrolo[3,2-b:4,5-c']dipyridine (110 mg, 0.389 mmol, 1-methyl-5-(tributylstannyl)-4-($^2$H$_3$)methyl-1H-1,2,3-triazole (167 mg, 0.428 mmol), tetrakis(triphenylphosphine)palladium(0) (45.0 mg, 0.039 mmol), copper (I) iodide (14.8 mg, 0.078 mmol), and triethylamine (65 μL, 0.334 mmol) in DMF (3.89 mL) was degassed using N$_2$ (g) for 3 min. The reaction mixture was then heated to 80° C. for 16 h. The volatiles were removed under reduced pressure, and the crude material was purified using silica gel column chromatography with a gradient of methanol in ethyl acetate (0-20%). 11-Chloro-5-[4-($^2$H$_3$)methyl-1-methyl-1H-1,2,3-triazol-5-yl]-3,8,12-triazatricyclo[7.4.0.0$^2$,$^7$]trideca-1(9),2(7),3,5,10,12-hexaene (68.4 mg, 0.227 mmol, 58%) was isolated as a white solid. $^1$H NMR (400 MHz, DMSO-d$_6$) δ 12.27 (s, 1H), 9.23 (s, 1H), 8.66 (d, J=1.8 Hz, 1H), 8.16 (d, J=1.8 Hz, 1H), 7.69 (s, 1H), 4.01 (s, 3H); LC/MS (M+H)=302.15; LC/MS RT=1.048 min (Column: Phenomenex Luna 30×2.0 mm 3 u; Mobile Phase A: 10:90 ACN:water with 0.1% TFA; Mobile Phase B: 90:10 ACN:water with 0.1% TFA; Temperature: 40° C.; Gradient: 0-100% B over 2 min; Flow: 1 mL/min).

Step 5: (R)-(4-Fluorophenyl)(oxan-4-yl)methyl methanesulfonate

Methanesulfonyl chloride (78 μL, 0.999 mmol) was added drop wise to a stirred solution of (R)-(4-fluorophenyl)(tetrahydro-2H-pyran-4-yl)methanol (140.0 mg, 0.666 mmol and Et$_3$N (186 μL, 1.33 mmol) in DCM (6.7 mL) at 0° C. under N$_2$ (g). The reaction was stirred for 15 min before the reaction vessel was removed from the cold bath, and the reaction mixture was allowed to warm to ambient temperature over 1 h. The reaction mixture was quenched with saturated aqueous NaHCO$_3$ (5 mL). The layers were separated, and the aqueous layer was washed with diethyl ether (2×7 mL). The combined organics were dried over sodium sulfate, the solids were filtered away, and the volatiles were removed under reduced pressure. The product was used without additional purification.

Step 6: 11-Chloro-8-[(S)-(4-fluorophenyl)(oxan-4-yl)methyl]-5-[4-($^2$H$_3$)methyl-1-methyl-1H-1,2,3-triazol-5-yl]-3,8,12-triazatricyclo[7.4.0.0$^2$,$^7$]trideca-1(9),2(7),3,5,10,12-hexaene 11-Chloro-5-[4-($^2$H$_3$)methyl-1-methyl-1H-1,2,3-triazol-5-yl]-3,8,12-triazatricyclo[7.4.0.0$^2$,$^7$]trideca-1(9),2(7),3,5,10,12-hexaene (65.0 mg, 0.215 mmol), (R)-(4-fluorophenyl)(oxan-4-yl)methyl methanesulfonate (186.0 mg, 0.646 mmol), and cesium carbonate (281 mg, 0.862 mmol) were stirred in DMF (1.1 mL) at 60° C. under N$_2$ (g) for 16 h. The volatiles were removed under reduced pressure, and the crude material was purified using silica gel column chromatography with a gradient of methanol in ethyl acetate (0-20%). Fractions containing the desired product were combined and dried via centrifugal evaporation to afford 11-chloro-8-[(S)-(4-fluorophenyl)(oxan-4-yl)methyl]-5-[4-($^2$H$_3$)methyl-1-methyl-1H-1,2,3-triazol-5-yl]-3,8,12-triazatricyclo[7.4.0.0$^2$,$^7$]trideca-1(9),2(7),3,5,10,12-hexaene (13.5 mg, 0.027 mmol, 13% yield). LC/MS (M+H)=494.25; LC/MS RT=1.492 min (Column: Phenomenex Luna 30×2.0 MM 3 u; Mobile Phase A: 10:90 ACN:water with 0.1% TFA; Mobile Phase B: 90:10 ACN:water with 0.1% TFA; Temperature: 40° C.; Gradient: 0-100% B over 2 min; Flow: 1 mL/min).

Step 7: 1-{8-[(S)-(4-Fluorophenyl)(oxan-4-yl)methyl]-5-[4-($^2$H$_3$)methyl-1-methyl-1H-1,2,3-triazol-5-yl]-3,8,12-triazatricyclo[7.4.0.0$^2$,$^7$]trideca-1(9),2(7),3,5,10,12-hexaen-11-yl}ethan-1-one 11-Chloro-8-[(S)-(4-fluorophenyl)(oxan-4-yl)methyl]-5-[4-($^2$H$_3$)methyl-1-methyl-1H-1,2,3-triazol-5-yl]-3,8,12-triazatricyclo[7.4.0.0$^2$,$^7$]trideca-1(9),2(7),3,5,10,12-hexaene (13.5 mg, 0.027 mmol), PdCl$_2$(dppf)-CH$_2$Cl$_2$ adduct (2.2 mg, 2.70 μmol), and tributyl(1-ethoxyvinyl)stannane (11 μL, 0.033 mmol) were degassed in dioxane (273 μL) with N$_2$ (g) for 3 min. The reaction vessel was then heated to 80° C. for 16 h. Concentrated aqueous HCl (1 mL) was added to the reaction mixture drop wise, and it was stirred for 1 h at ambient temperature. The reaction mixture was quenched with saturated aqueous sodium bicarbonate (7 mL) and diluted with ethyl acetate (10 mL). The layers were separated, and the aqueous layer was washed with ethyl acetate (2×10 mL). The combined organics were dried over sodium sulfate, the solids were filtered away, and the volatiles were removed under reduced pressure. The product was purified using reversed phase preparative HPLC (TFA/MeOH/water). 100% Product yield was assumed.

Step 8: 2-{8-[(S)-(4-Fluorophenyl)(oxan-4-yl)methyl]-5-[4-($^2$H$_3$)methyl-1-methyl-1H-1,2,3-triazol-5-yl]-3,8,12-triazatricyclo[7.4.0.0$^2$,$^7$]trideca-1(13),2(7),3,5,9,11-hexaen-11-yl}propan-2-ol Methylmagnesium bromide (3M in diethyl ether, 259 μL, 0.778 mmol) was added to a stirred solution of 1-{8-[(S)-

(4-fluorophenyl)(oxan-4-yl)methyl]-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10,12-hexaen-11-yl}ethan-1-one (13.0 mg, 0.026 mmol) in THF (259 μL) under N$_2$ (g) at −20° C. The reaction mixture was stirred at that temperature for 2 h. The reaction mixture was then quenched with saturated aqueous ammonium chloride (8 mL) and diluted with ethyl acetate (20 mL) while still at −20° C. The mixture was removed from the cold bath and allowed to warm to ambient temperature. The layers were separated, and the aqueous phase was washed with a second portion of ethyl acetate (20 mL). The combined organics were dried over sodium sulfate, the solids were filtered away, and the volatiles were removed under reduced pressure. The crude material was purified via preparative LC/MS with the following conditions: Column: XBridge C18, 19×200 mm, 5-μm particles; Mobile Phase A: 5:95 ACN: water with 10-mM NH$_4$OAc; Mobile Phase B: 95:5 ACN: water with 10 mM NH$_4$OAc; Gradient: 10-50% B over 30 min, then a 5-min hold at 100% B; Flow: 20 mL/min. Fractions containing the desired product were combined and dried via centrifugal evaporation to afford 2-{8-[(S)-(4-fluorophenyl)(oxan-4-yl)methyl]-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaen-11-yl}propan-2-ol (3.2 mg, 6.1 μmol, 23% yield). $^1$H NMR (500 MHz, DMSO-d$_6$) δ=9.34 (s, 1H), 8.61 (s, 1H), 8.48 (br. s., 1H), 8.27 (br. s, 1H), 7.77-7.68 (m, 2H), 7.19 (t, J=8.8 Hz, 2H), 5.84 (d, J=11.4 Hz, 1H), 4.01 (s, 3H), 3.93-3.87 (m, 1H), 3.76-3.72 (m, 2H), 3.29-3.22 (m, 1H), 3.17 (s, 1H), 1.69-1.63 (m, 1H), 1.60-1.51 (m, 7H), 1.31 (d, J=8.8 Hz, 1H), 0.99 (d, J=13.2 Hz, 1H); LC/MS (M+H)=518.30; LC/MS RT=1.128 min (Column: Phenomenex Luna 30×2.0 MM 3 u; Mobile Phase A: 10:90 ACN:water with 0.1% TFA; Mobile Phase B: 90:10 ACN:water with 0.1% TFA; Temperature: 40° C.; Gradient: 0-100% B over 2 min; Flow: 1 mL/min).

Example 160

8-[(S)-(4-Fluorophenyl)(oxan-4-yl)methyl]-5,11-bis[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene

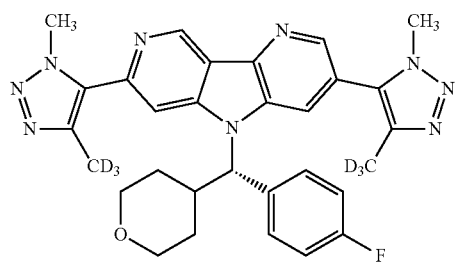 [SMILES: [2H]C([2H])([2H])c1nnn(C)c1-c1cnc2c3cnc(-c4c(C([2H])([2H])[2H])nnn4C)cc3n([C@H](c3ccc(F)cc3)C3CCOCC3)c2c1]

Step 1: 5-Bromo-11-chloro-8-[(S)-(4-fluorophenyl)(oxan-4-yl)methyl]-3,8,12-triazatricyclo[7.4.0.0$^{2,7}$]trideca-1(9),2(7),3,5,10,12-hexaene 3-Bromo-7-chloro-5H-pyrrolo[3,2-b:4,5-c']dipyridine (67.0 mg, 0.237 mmol), (R)-(4-fluorophenyl)(oxan-4-yl)methyl methanesulfonate (171.0 mg, 0.593 mmol, prepared in route to 2-{8-[(S)-(4-fluorophenyl)(oxan-4-yl)methyl]-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaen-11-yl}propan-2-ol), and cesium carbonate (309.0 mg, 0.949 mmol) were stirred in DMF (1.2 mL) at 60° C. under N$_2$ (g) for 16 h. The volatiles were removed under reduced pressure, and the crude material was purified using silica gel column chromatography with a gradient of ethyl acetate in hexanes (0-100%). Fractions containing the desired product were combined and dried via centrifugal evaporation to afford 5-bromo-11-chloro-8-[(S)-(4-fluorophenyl)(oxan-4-yl)methyl]-3,8,12-triazatricyclo[7.4.0.0$^{2,7}$]trideca-1(9),2(7),3,5,10,12-hexaene (113.0 mg, 0.237 mmol, 100% yield). LC/MS (M+H)=474.05; LC/MS RT=1.861 min (Column: Phenomenex Luna 30×2.0 MM 3 u; Mobile Phase A: 10:90 ACN:water with 0.1% TFA; Mobile Phase B: 90:10 ACN: water with 0.1% TFA; Temperature: 40° C.; Gradient: 0-100% B over 2 min; Flow: 1 mL/min).

Step 2: 8-[(S)-(4-Fluorophenyl)(oxan-4-yl)methyl]-5,11-bis[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene A solution of 5-bromo-11-chloro-8-[(S)-(4-fluorophenyl)(oxan-4-yl)methyl]-3,8,12-triazatricyclo[7.4.0.0$^{2,7}$]trideca-1(9),2(7),3,5,10,12-hexaene (110.0 mg, 0.232 mmol), 1-methyl-5-(tributylstannyl)-4-($^2$H$_3$)methyl-1H-1,2,3-triazole (99.0 mg, 0.255 mmol), tetrakis(triphenylphosphine)palladium(0) (26.8 mg, 0.023 mmol), copper (I) iodide (8.8 mg, 0.046 mmol), and triethylamine (39 μL, 0.278 mmol) in DMF (2.3 mL) was degassed using N$_2$ (g) for 3 min. The reaction mixture was then heated to 80° C. for 16 h. The volatiles were removed under reduced pressure, and the crude material was purified via preparative LC/MS with the following conditions: Column: XBridge C18, 19×200 mm, 5-μm particles; Mobile Phase A: 5:95 methanol: water with 10-mM NH$_4$OAc; Mobile Phase B: 95:5 ACN: water with 10 mM NH$_4$OAc; Gradient: 40-80% B over 20 min, then a 5-min hold at 100% B; Flow: 20 mL/min. Fractions containing the desired product were combined and dried via centrifugal evaporation to afford 8-[(S)-(4-fluorophenyl)(oxan-4-yl)methyl]-5,11-bis[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene (3.3 mg, 5.7 μmol, 3%) was isolated. $^1$H NMR (500 MHz, DMSO-d$_6$) δ 9.57 (s, 1H), 8.80-8.54 (m, 2H), 8.33 (br. s., 1H), 7.82-7.76 (m, 2H), 7.23-7.16 (m, 2H), 5.98 (d, J=11.0 Hz, 1H), 4.22 (s, 3H), 4.06 (br. s., 3H), 3.90 (d, J=9.5 Hz, 1H), 3.74 (d, J=9.2 Hz, 1H), 3.51-3.42 (m, 1H), 3.38 (d, J=4.4 Hz, 1H), 3.25 (t, J=11.7 Hz, 1H), 1.68 (d, J=12.1 Hz, 1H), 1.61-1.47 (m, 1H), 1.38-1.27 (m, 1H), 1.01 (d, J=12.5 Hz, 1H); LC/MS (M+H)=558.30; LC/MS RT=1.260 min (Column: Phenomenex Luna 30×2.0 mm 3 u; Mobile Phase A: 10:90 ACN:water with 0.1% TFA; Mobile Phase B: 90:10 ACN:water with 0.1% TFA; Temperature: 40° C.; Gradient: 0-100% B over 2 min; Flow: 1 mL/min).

Example 161

5-(Dimethyl-1H-1,2,3-triazol-5-yl)-8-[(S)-oxan-4-yl(phenyl)methyl]-11-(prop-1-en-2-yl)-3,8,10-triazatricyclo[7.4.0.0²,⁷]trideca-1(9),2(7),3,5,10,12-hexaene

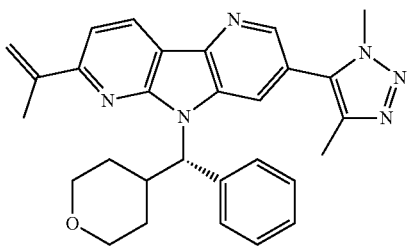 [SMILES: C=C(C)c1ccc2c3ncc(-c4c(C)nnn4C)cc3n([C@H](c3ccccc3)C3CCOCC3)c2n1]

Step 1:
5-(3,5-Dimethylisoxazol-4-yl)pyridin-3-amine

To a 20 mL scintillation vial was added (S)-3-bromo-7-chloro-5-(phenyl(tetrahydro-2H-pyran-4-yl)methyl)-5H-pyrrolo[2,3-b:4,5-b']dipyridine (0.223 mmol, 102 mg) 1,4-dimethyl-1H-1,2,3-triazole (0.223 mmol, 21.7 mg), Me₄NOAc (0.223 mmol, 29.7 mg) and PdCl₂(PPh₃)₂ (0.016 mmol, 11.0 mg) followed by the addition of 4 mL NMP. The air was replaced with argon. The sealed reaction vial was heated to 100° C. with stirring overnight. It was cooled to room temperature and diluted with EtOAc and washed twice with brine. The organic layer was dried over MgSO₄, and concentrated. It was subjected to purification on the ISCO, 24 g silica gel column, eluting with 50-100% EtOAc/hexanes, then 0-10% MeOH/EtOAc to obtain the title compound, 139 mg in 60% purity. A second ISCO was run using a 24 g silica gel column eluting with 0-100% (10% 2M NH₃ in EtOAc)/DCM to obtain the title compound (thick oil), 58 mg. LC/MS (M+H)=473.2 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Step 2: 5-(Dimethyl-1H-1,2,3-triazol-5-yl)-8-[(S)-oxan-4-yl(phenyl)methyl]-11-(prop-1-en-2-yl)-3,8,10-triazatricyclo[7.4.0.0²,⁷]trideca-1(9),2(7),3,5,10,12-hexaene (S)-7-Chloro-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridine (0.059 mmol, 28 mg) was weighed into a 50 mL round bottom flask, followed by the addition of 4,4,5,5-tetramethyl-2-(prop-1-en-2-yl)-1,3,2-dioxaborolane (0.074 mmol, 12.44 mg), then K₂CO₃ (0.148 mmol, 20.4 mg). To this was added 4 mL THF and 2 mL water, followed by the addition of Pd(PPh₃)₄ (2.37 μmol, 2.7 mg). The air was replaced with N₂, and the resulting mixture heated to 85° C. with stirring overnight. It was cooled to room temperature, diluted with EtOAc, washed with brine, dried over MgSO₄, and concentrated to obtain a crude mixture. The crude material was purified via preparative LC/MS with the following conditions: Column: XBridge C18, 19×200 mm, 5-μm particles; Mobile Phase A: 5:95 ACN: water with 10-mM NH₄OAc; Mobile Phase B: 95:5 ACN: water with 10-mM NH₄OAc; Gradient: 45-85% B over 15 min, then a 5-min hold at 100% B; Flow: 20 mL/min. Fractions containing the title compound were combined and dried via centrifugal evaporation. The yield of the product was 0.5 mg, and its estimated purity by LC/MS analysis was 100%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0% B, 0-100% B over 3 min, then a 0.5-min hold at 100% B; Flow: 1 mL/min; Detection: UV at 220 nm; RT=2.12 min, LC/MS (M+H)=479.5. Injection 2 conditions: Column: Waters BEH C18, 2.0×50 mm, 1.7-μm particles; Mobile Phase A: 5:95 methanol:water with 10 mM NH₄OAc; Mobile Phase B: 95:5 methanol:water with 10 mM NH₄OAc; Temperature: 50° C.; Gradient: 0% B, 0-100% B over 3 min, then a 0.5-min hold at 100% B; Flow: 0.5 mL/min; Detection: UV at 220 nm; RT=3.11 min, LC/MS (M+H)=479.5. ¹H NMR (500 MHz, DMSO-d₆) δ 8.59 (d, J=7.3 Hz, 3H), 7.83 (d, J=7.7 Hz, 2H), 7.76 (d, J=8.4 Hz, 1H), 7.35-7.28 (m, 2H), 7.26-7.19 (m, 1H), 6.22 (s, 1H), 5.85 (br. s., 1H), 5.56 (s, 1H), 4.05 (s, 3H), 3.92-3.88 (m, 1H), 3.77 (d, J=11.7 Hz, 2H), 3.25 (t, J=11.7 Hz, 1H), 2.40 (s, 3H), 2.32 (s, 3H), 1.48 (br. s., 1H), 1.46-1.37 (m, 1H), 1.28 (d, J=9.5 Hz, 1H), 1.25-1.17 (m, 2H). LC/MS (M+H)= 479.2 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 162

1-{5-[5-(Dimethyl-1H-1,2,3-triazol-5-yl)-8-[(S)-oxan-4-yl(phenyl)methyl]-3,8,10-triazatricyclo[7.4.0.0²,⁷]trideca-1(9),2(7),3,5,10,12-hexaen-11-yl]thiophen-2-yl}ethan-1-one

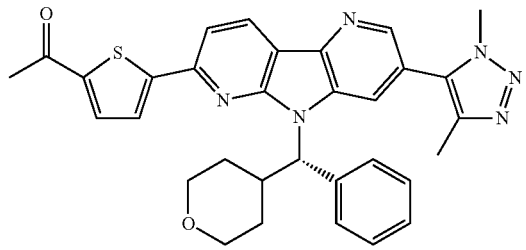 [SMILES: CC(=O)c1ccc(-c2ccc3c4ncc(-c5c(C)nnn5C)cc4n([C@H](c4ccccc4)C4CCOCC4)c3n2)s1]

Following a procedure analogous to the Suzuki coupling reaction described in the synthesis of 5-(dimethyl-1H-1,2,3-triazol-5-yl)-8-[(S)-oxan-4-yl(phenyl)methyl]-11-(prop-1-en-2-yl)-3,8,10-triazatricyclo[7.4.0.0²,⁷]trideca-1(9),2(7),3,5,10,12-hexaene, (S)-7-chloro-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridine and (5-acetylthiophene-2-yl)boronic acid were converted to the title compound in 23% yield. The estimated purity by LC/MS analysis was 97%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0% B, 0-100% B over 3 min, then a 0.5-min hold at 100% B; Flow: 1 mL/min; Detection: UV at 220 nm; RT=1.92 min, LCMS (M+H)=563.4. Injection 2 conditions: Column: Waters BEH C18, 2.0×50 mm, 1.7-μm particles;

Mobile Phase A: 5:95 methanol:water with 10 mM NH₄OAc; Mobile Phase B: 95:5 methanol:water with 10 mM NH₄OAc; Temperature: 50° C.; Gradient: 0% B, 0-100% B over 3 min, then a 0.5-min hold at 100% B; Flow: 0.5 mL/min; Detection: UV at 220 nm; RT=2.92 min, LCMS (M+H)=563.5. $^1$H NMR (500 MHz, DMSO-$d_6$) δ 8.70 (d, J=8.1 Hz, 1H), 8.64 (s, 2H), 8.13-8.08 (m, 2H), 8.06 (d, J=3.7 Hz, 1H), 7.88 (d, J=7.7 Hz, 2H), 7.31 (t, J=7.5 Hz, 2H), 7.24 (t, J=7.3 Hz, 1H), 5.83 (d, J=9.2 Hz, 1H), 4.09-4.02 (m, 3H), 3.98-3.91 (m, 1H), 3.78 (d, J=11.4 Hz, 1H), 3.40 (br. s., 2H), 3.32-3.23 (m, 1H), 2.63 (s, 3H), 2.33 (s, 3H), 1.56-1.39 (m, 2H), 1.37-1.19 (m, 2H); LC/MS (M+H)=563.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 163

5,11-Bis(dimethyl-1H-1,2,3-triazol-5-yl)-8-[(S)-oxan-4-yl(phenyl)methyl]-3,8,10-triazatricyclo[7.4.0.0²,⁷]trideca-1(9),2(7),3,5,10,12-hexaene

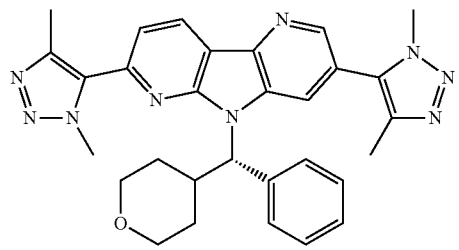 [SMILES: Cc1nnn(C)c1-c1cnc2c3ccc(-c4c(C)nnn4C)nc3n([C@H](c3ccccc3)C3CCOCC3)c2c1]

(S)-3-Bromo-7-chloro-5-(phenyl(tetrahydro-2H-pyran-4-yl)methyl)-5H-pyrrolo[2,3-b:4,5-b']dipyridine (300 mg, 0.657 mmol), 1,4-dimethyl-1H-1,2,3-triazole (77 mg, 0.788 mmol), Me₄NOAc (87 mg, 0.657 mmol), and PdCl₂(PPh₃)₂ (32.3 mg, 0.046 mmol) were weighed into a vial, and 12 mL NMP was added, and the air was replaced with argon. The sealed reaction vial was heated at 100° C. with stirring overnight. The next morning, LC/MS showed the mono-alkylated product as the major peak and a significant amount of the dialkylated product. It was cooled to room temperature and diluted with EtOAc and washed twice with brine. The organic layer was dried over MgSO₄, and concentrated to obtain a crude mixture. The crude material was purified via preparative LC/MS with the following conditions: Column: XBridge C18, 19×200 mm, 5-μm particles; Mobile Phase A: 5:95 ACN: water with 10-mM NH₄OAc; Mobile Phase B: 95:5 ACN: water with 10-mM NH₄OAc; Gradient: 20-60% B over 15 min, then a 5-min hold at 100% B; Flow: 20 mL/min. Fractions containing the title compound were combined and dried via centrifugal evaporation. Estimated purity by LC/MS analysis was 99%. An analytical LC/MS injection was used to determine the final purity. Conditions: Column: Waters BEH C18, 2.0×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0% B, 0-100% B over 3 min, then a 0.5-min hold at 100% B; Flow: 1 mL/min; Detection: UV at 220 nm; RT=1.51 min, LC/MS (M+H)=534.5. $^1$H NMR (500 MHz, DMSO-$d_6$) δ 8.82 (d, J=8.1 Hz, 1H), 8.67 (s, 1H), 8.57 (br. s., 1H), 7.77-7.71 (m, 3H), 7.35-7.29 (m, 2H), 7.27-7.21 (m, 1H), 6.06 (br. s., 1H), 4.38 (s, 3H), 4.03 (s, 3H), 3.90 (s, 1H), 3.74 (d, J=10.6 Hz, 1H), 3.62 (br. s., 1H), 3.40 (s, 1H), 3.24 (t, J=11.2 Hz, 1H), 2.54 (s, 3H), 2.31 (s, 3H), 1.62 (br. s., 1H), 1.51-1.39 (m, 1H), 1.35-1.21 (m, 1H), 1.14 (d, J=12.5 Hz, 1H); LC/MS (M+H)=534.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 164

5,11-Bis(dimethyl-1H-1,2,3-triazol-5-yl)-8-[(R)-oxan-4-yl(phenyl)methyl]-3,8,10-triazatricyclo[7.4.0.0²,⁷]trideca-1(9),2(7),3,5,10,12-hexaene

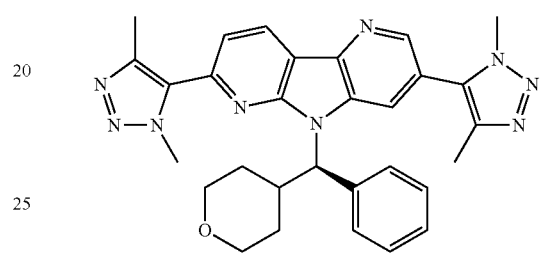

(R)-3-Bromo-7-chloro-5-(phenyl(tetrahydro-2H-pyran-4-yl)methyl)-5H-pyrrolo[2,3-b:4,5-b']dipyridine (30.0 mg, 0.066 mmol), 1,4-dimethyl-1H-1,2,3-triazole (25.5 mg, 0.263 mmol), Me₄NOAc (21.8 mg, 0.164 mmol), and PdCl₂(dppf)₂.DCM (3.8 mg, 4.60 μmol) were weighed into a 20 mL scintillation vial, and 3 mL DMF was added and the air was replaced with nitrogen. The reaction mixture was heated to 100° C. with stirring. After 1 h, it was cooled to room temperature, filtered, and concentrated. The crude material was purified via preparative LC/MS with the following conditions: Column: XBridge C18, 19×200 mm, 5-μm particles; Mobile Phase A: 5:95 ACN: water with 10-mM NH₄OAc; Mobile Phase B: 95:5 ACN: water with 10-mM NH₄OAc; Gradient: 20-60% B over 15 min, then a 5-min hold at 100% B; Flow: 20 mL/min. Fractions containing the desired product were combined and dried via centrifugal evaporation. The yield of the product was 4.2 mg, and its estimated purity by LC/MS analysis was 100%. Two analytical LC/MS injections were used to determine the final purity. Injection 1 conditions: Column: Waters BEH C18, 2.0×50 mm, 1.7-μm particles; Mobile Phase A: 5:95 ACN: water with 10 mM NH₄OAc; Mobile Phase B: 95:5 ACN: water with 10 mM NH₄OAc; Temperature: 50° C.; Gradient: 0% B, 0-100% B over 3 min, then a 0.5-min hold at 100% B; Flow: 1 mL/min; Detection: UV at 220 nm, RT=1.52 min, LC/MS (M+H)=534.5, LC/MS (M+H)=534.5. Injection 2 conditions: Column: Waters BEH C18, 2.0×50 mm, 1.7-μm particles; Mobile Phase A: 5:95 methanol:water with 10 mM NH₄OAc; Mobile Phase B: 95:5 methanol:water with 10 mM NH₄OAc; Temperature: 50° C.; Gradient: 0% B, 0-100% B over 3 min, then a 0.5-min hold at 100% B; Flow: 0.5 mL/min; Detection: UV at 220 nm. RT=2.50 min, LC/MS (M+H)=534.5. $^1$H NMR (500 MHz, DMSO-$d_6$) δ 8.82 (d, J=8.1 Hz, 1H), 8.67 (s, 1H), 8.58 (br. s., 1H), 7.74 (t, J=7.2 Hz, 3H), 7.36-7.28 (m, 2H), 7.28-7.20 (m, 1H), 6.07 (br. s., 1H), 4.39 (s, 3H), 4.03 (s, 3H), 3.89 (d, J=13.6 Hz, 1H), 3.75 (d, J=9.9 Hz, 1H), 3.61 (br. s., 1H), 3.43 (t, J=11.2 Hz, 1H), 3.24 (t, J=11.4 Hz, 1H), 2.55 (s, 3H), 2.31 (s, 3H), 1.62 (br. s., 1H), 1.51-1.39 (m, 1H), 1.29 (d, J=8.4

Hz, 1H), 1.15 (br. s., 1H); LC/MS (M+H)=534.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 165

5,11-Bis[4-($^2H_3$)methyl-1-methyl-1H-1,2,3-triazol-5-yl]-8-[(R)-oxan-4-yl(phenyl)methyl]-3,8,10-triazatricyclo[7.4.0.0$^{2,7}$]trideca-1(9),2(7),3,5,10,12-hexaene

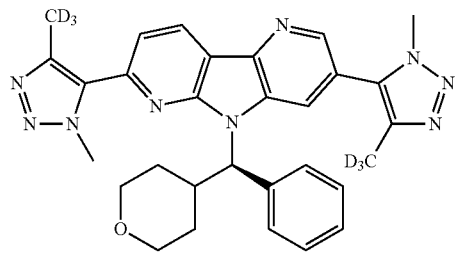 [SMILES: [2H]C([2H])([2H])c1nnn(C)c1-c1cnc2c3ccc(-c4c(C([2H])([2H])[2H])nnn4C)nc3n([C@@H](c3ccccc3)C3CCOCC3)c2c1]

Following a procedure analogous to the reaction described in the synthesis of 5,11-bis(dimethyl-1H-1,2,3-triazol-5-yl)-8-[(R)-oxan-4-yl(phenyl)methyl]-3,8,10-triazatricyclo[7.4.0.0$^{2,7}$]trideca-1(9),2(7),3,5,10,12-hexaene, the title compound was made from (R)-3-bromo-7-chloro-5-(phenyl(tetrahydro-2H-pyran-4-yl)methyl)-5H-pyrrolo[2,3-b:4,5-b']dipyridine and 4-($^2H_3$)methyl-1-methyl-1H-1,2,3-triazole in 39% yield. The estimated purity by LC/MS analysis was 100%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. RT=1.51 min, LC/MS (M+H)=540.5. Injection 2: conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. RT=2.51 min, LC/MS (M+H)=540.3. $^1$H NMR (500 MHz, DMSO-d$_6$) δ 8.82 (d, J=8.1 Hz, 1H), 8.67 (s, 1H), 8.58 (br. s., 1H), 7.74 (t, J=7.7 Hz, 3H), 7.32 (t, J=7.5 Hz, 2H), 7.24 (t, J=7.3 Hz, 1H), 6.06 (br. s., 1H), 4.39 (s, 3H), 4.03 (s, 3H), 3.89 (d, J=12.1 Hz, 1H), 3.75 (d, J=8.4 Hz, 1H), 3.61 (br. s., 1H), 3.49-3.40 (m, 1H), 3.24 (t, J=11.2 Hz, 1H), 1.62 (br. s., 1H), 1.51-1.38 (m, 1H), 1.36-1.21 (m, 1H), 1.15 (br. s., 1H); LC/MS (M+H)=540.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 166

5,11-Bis(4-methoxy-1-methyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaene

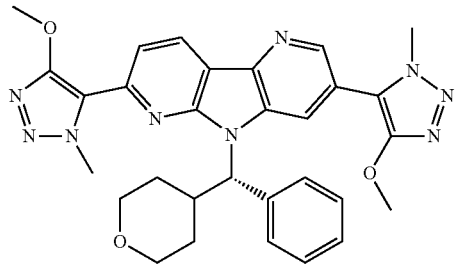 [SMILES: COc1nnn(C)c1-c1cnc2c3ccc(-c4c(OC)nnn4C)nc3n([C@H](c3ccccc3)C3CCOCC3)c2c1]

Following a procedure analogous to the reaction described in the synthesis of 5,11-bis(dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaene, 5-bromo-11-chloro-8-[(S)-oxan-4-yl(phenyl)methyl]-3,8,10-triazatricyclo[7.4.0.0$^{2,7}$]trideca-1(9),2(7),3,5,10,12-hexaene and 4-methoxy-1-[(trimethylsilyl)methyl]-1H-1,2,3-triazole were converted to the title compound in 29% yield. The crude material was purified via preparative LC/MS with the following conditions: Column: XBridge C18, 19×200 mm, 5-μm particles; Mobile Phase A: 5:95 methanol:water with 10-mM NH$_4$OAc; Mobile Phase B: 95:5 methanol:water with 10-mM NH$_4$OAc; Gradient: 60-100% B over 15 min, then a 5-min hold at 100% B; Flow: 20 mL/min. Fractions containing the title compound were combined and dried via centrifugal evaporation. The estimated purity by LC/MS analysis was 98%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. RT=1.74 min, LC/MS (M+H)=566.3. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. RT=2.78 min, LC/MS (M+H)=566.3. $^1$H NMR (500 MHz, DMSO-d$_6$) δ 8.76 (d, J=8.4 Hz, 1H), 8.65 (s, 1H), 8.49 (br. s., 1H), 7.90 (d, J=8.1 Hz, 1H), 7.74 (d, J=7.7 Hz, 2H), 7.34 (t, J=7.5 Hz, 2H), 7.26 (t, J=7.3 Hz, 1H), 6.07 (br. s., 1H), 4.59 (s, 3H), 4.16 (s, 3H), 4.08 (s, 3H), 4.03 (s, 3H), 3.90 (d, J=11.4 Hz, 1H), 3.73 (d, J=11.0 Hz, 1H), 3.55 (br. s., 1H), 3.41 (br. s., 4H), 3.25 (t, J=10.8 Hz, 1H), 1.66 (br. s., 1H), 1.52-1.41 (m, 1H), 1.29 (d, J=12.1 Hz, 1H), 1.12 (br. s., 1H); LC/MS (M+H)=566.2 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 167

11-Chloro-5-(4-methoxy-1-methyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaene

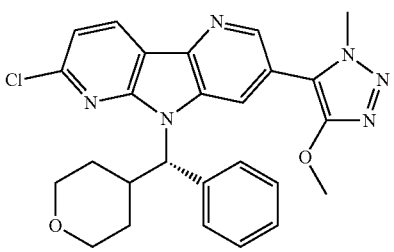 [SMILES: COc1nnn(C)c1-c1cnc2c3ccc(Cl)nc3n([C@H](c3ccccc3)C3CCOCC3)c2c1]

Following a procedure analogous to the reaction described in the synthesis of 5,11-bis(dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaene, 5-bromo-11-chloro-8-[(S)-oxan-4-yl(phenyl)methyl]-3,8,10-triazatricyclo[7.4.0.0$^{2,7}$]trideca-1(9),2(7),3,5,10,12-hexaene and 4-methoxy-1-[(trimethylsilyl)methyl]-1H-1,2,3-triazole were converted to the title compound in 54% yield. The crude material was purified via preparative LC/MS with the following conditions: Column: XBridge C18, 19×200 mm, 5-μm particles; Mobile Phase A: 5:95 methanol: water with 10-mM NH$_4$OAc; Mobile Phase B: 95:5 methanol: water with 10-mM NH$_4$OAc; Gradient: 50-100% B over 15 min, then a 5-min hold at 100% B; Flow: 20 mL/min. Fractions containing the title compound were combined and dried via centrifugal evaporation. The estimated purity by LC/MS analysis was 89%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. RT=1.52 min, LC/MS (M+H)=489.2. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. RT=3.02 min, LC/MS (M+H)=489.2. $^1$H NMR (500 MHz, DMSO-d$_6$) δ 8.71-8.64 (m, 1H), 8.60-8.55 (m, 1H), 8.52 (br. s., 1H), 8.41 (d, J=8.4 Hz, 1H), 7.76 (t, J=6.2 Hz, 2H), 7.41-7.21 (m, 4H), 5.87 (br. s., 1H), 4.10 (d, J=2.9 Hz, 3H), 4.03 (d, J=3.3 Hz, 3H), 3.89 (d, J=9.9 Hz, 1H), 3.80-3.71 (m, 1H), 3.68 (br. s., 1H), 3.56 (br. s., 1H), 3.29-3.22 (m, 1H), 1.56 (br. s., 1H), 1.51 (br. s., 1H), 1.42 (d, J=10.3 Hz, 1H), 1.29-1.21 (m, 1H), 1.17 (d, J=11.7 Hz, 1H), 1.08 (d, J=13.2 Hz, 1H); LC/MS (M+H)=489.2 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 168

5,11-Bis[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(9),2(7),3,5,10,12-hexaene

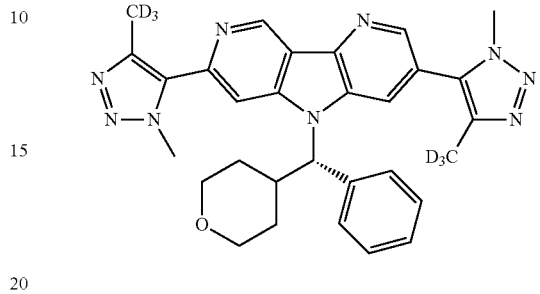

Following a procedure analogous to the reaction described in the synthesis of 5,11-bis(dimethyl-1H-1,2,3-triazol-5-yl)-8-[(R)-oxan-4-yl(phenyl)methyl]-3,8,10-triazatricyclo[7.4.0.0$^{2,7}$]trideca-1(9),2(7),3,5,10,12-hexaene, 5-bromo-11-chloro-8-[(S)-oxan-4-yl(phenyl)methyl]-3,8,12-triazatricyclo[7.4.0.0$^{2,7}$]trideca-1(9),2(7),3,5,10,12-hexaene and 4-($^2$H$_3$)methyl-1-methyl-1H-1,2,3-triazole were converted to the title compound in 3% yield. The crude material was purified via preparative LC/MS with the following conditions: Column: XBridge C18, 19×200 mm, 5-μm particles; Mobile Phase A: 5:95 ACN: water with 10-mM NH$_4$OAc; Mobile Phase B: 95:5 ACN: water with 10-mM NH$_4$OAc; Gradient: 10-50% B over 30 min, then a 5-min hold at 100% B; Flow: 20 mL/min. Fractions containing the title compound were combined and dried via centrifugal evaporation. The material was further purified via preparative LC/MS with the following conditions: Column: XBridge C18, 19×200 mm, 5-μm particles; Mobile Phase A: 5:95 methanol: water with 10-mM NH$_4$OAc; Mobile Phase B: 95:5 methanol: water with 10-mM NH$_4$OAc; Gradient: 40-80% B over 20 min, then a 5-min hold at 100% B; Flow: 20 mL/min. Fractions containing the title compound were combined and dried via centrifugal evaporation. The yield of the product was 0.8 mg, and its estimated purity by LC/MS analysis was 97%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. RT=1.44 min, LC/MS (M+H)=540.2. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. RT=2.75 min, LC/MS (M+H)=540.2. $^1$H NMR (500 MHz, DMSO-d$_6$) δ 9.57 (s, 1H), 8.72 (s, 1H), 8.66 (br. s., 1H), 8.31 (br. s., 1H), 7.73 (d, J=7.7 Hz, 2H), 7.40-7.34 (m, 2H), 7.32-7.25 (m, 1H), 5.97 (d, J=11.0 Hz, 1H), 4.22 (s, 3H), 4.05 (s, 3H), 3.90 (d, J=11.0 Hz, 1H), 3.74 (d, J=9.2 Hz, 1H), 3.51-3.44 (m, 2H), 3.26 (t, J=11.9 Hz, 1H), 1.71 (d, J=13.2 Hz, 1H), 1.60-1.50 (m, 1H), 1.39-1.27 (m, 1H), 1.01 (d, J=11.4 Hz, 1H); LC/MS (M+H)=540.3 [Column: Waters Aquity BEH C18 2.1×50 mm 1.7

Example 169

5-(Dimethyl-1H-1,2,3-triazol-5-yl)-8-[(S)-oxan-4-yl(phenyl)methyl]-3,8,10-triazatricyclo[7.4.0.0²,⁷]trideca-1(9),2(7),3,5,10,12-hexaene-11-carbonitrile

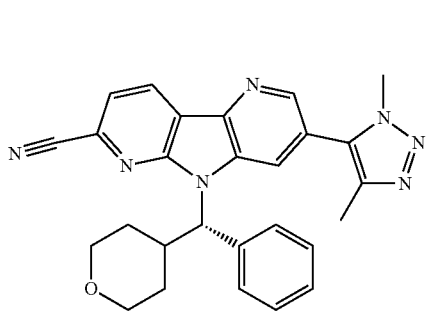 [SMILES: Cc1nnn(C)c1-c1cnc2c3ccc(C#N)nc3n([C@H](c3ccccc3)C3CCOCC3)c2c1]

To a microwave vial was added (S)-7-chloro-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridine (20.0 mg, 0.042 mmol), dicyanozinc (14.9 mg, 0.127 mmol), Pd(PPh$_3$)$_4$ (9.8 mg, 8.46 µmol) and NMP (1.5 mL). Argon was bubbled through and sealed under argon. It was subjected to heating in the microwave at 150° C. for ten min. It was filtered and the crude (filtrate) was purified via preparative LC/MS with the following conditions: Column: XBridge C18, 19×200 mm, 5-µm particles; Mobile Phase A: 5:95 ACN: water with 10-mM NH$_4$OAc; Mobile Phase B: 95:5 ACN: water with 10-mM NH$_4$OAc; Gradient: 40-80% B over 15 min, then a 5-min hold at 100% B; Flow: 20 mL/min. Fractions containing the title compound were combined and dried via centrifugal evaporation. The yield of the product was 10.3 mg (52%), and its estimated purity by LC/MS analysis was 99%. Two analytical LC/MS injections were used to determine the final purity. Injection 1 conditions: Column: Waters BEH C18, 2.0×50 mm, 1.7-µm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. RT=1.73 min, LC/MS (M+H)=464.4. Injection 2 conditions: Column: Waters BEH C18, 2.0×50 mm, 1.7-µm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. RT=2.66 min, LC/MS (M+H)=464.4; $^1$H NMR (500 MHz, DMSO-d$_6$) δ 8.88 (d, J=8.1 Hz, 1H), 8.75 (s, 1H), 8.69 (br. s., 1H), 8.02 (d, J=7.7 Hz, 1H), 7.79 (d, J=7.7 Hz, 2H), 7.38-7.31 (m, 2H), 7.30-7.24 (m, 1H), 5.95 (br. s., 1H), 4.04 (s, 3H), 3.92-3.85 (m, 1H), 3.75 (d, J=9.2 Hz, 1H), 3.63 (d, J=9.9 Hz, 1H), 3.47-3.40 (m, 1H), 3.30-3.22 (m, 1H), 2.32 (s, 3H), 1.55 (br. s., 1H), 1.48-1.37 (m, 1H), 1.34-1.22 (m, 1H), 1.11 (d, J=13.2 Hz, 1H); LC/MS (M+H)=464.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 170

5-(Dimethyl-1H-1,2,3-triazol-5-yl)-1-(1-ethoxyethenyl)-8-[(S)-oxan-4-yl(phenyl)methyl]-3,8,10-triazatricyclo[7.4.0.0²,⁷]trideca-1(9),2(7),3,5,10,12-hexaene

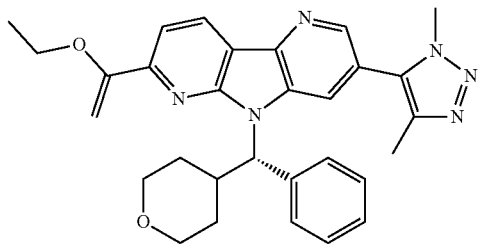 [SMILES: C=C(OCC)c1ccc2c3ncc(-c4c(C)nnn4C)cc3n([C@H](c3ccccc3)C3CCOCC3)c2n1]

To a 20 mL scintillation vial was added (S)-7-chloro-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridine (42 mg, 0.089 mmol), tributyl(1-ethoxyvinyl)stannane (35.3 mg, 0.098 mmol), and 2 mL of dioxane. This was followed by the addition of Pd(dppf)$_2$Cl$_2$.DCM (7.3 mg, 8.88 µmol) and the air was replaced with argon and the vial sealed under argon. It was heated to 100° C. with stirring overnight. It was cooled to room temperature, diluted with 2.5 mL of THF and filtered with a syringe filter, and the filtrate was concentrated on the rotary evaporator to a total of 0.5 mL. This material was purified via preparative LC/MS with the following conditions: Column: XBridge C18, 19×200 mm, 5-µm particles; Mobile Phase A: 5:95 ACN: water with 10-mM NH$_4$OAc; Mobile Phase B: 95:5 ACN: water with 10-mM NH$_4$OAc; Gradient: 50-90% B over 5 min, then a 15-min hold at 100% B; Flow: 20 mL/min. Fractions containing the title compound were combined and dried via centrifugal evaporation. The yield of the product was 69%, and its estimated purity by LC/MS analysis was 100%. Two analytical LC/MS injections were used to determine the final purity. Injection 1 conditions: Column: Waters BEH C18, 2.0×50 mm, 1.7-µm particles; Mobile Phase A: 5:95 ACN: water with 10 mM NH$_4$OAc; Mobile Phase B: 95:5 ACN: water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm, RT=2.20 min, LC/MS (M+H)=509.5. Injection 2 conditions: Column: Waters BEH C18, 2.0×50 mm, 1.7-µm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm, RT=3.11 min, LC/MS (M+H)=509.5. $^1$H NMR (500 MHz, DMSO-d$_6$) δ 8.65 (d, J=8.1 Hz, 1H), 8.62-8.56 (m, 2H), 7.82 (d, J=7.3 Hz, 2H), 7.73 (d, J=8.1 Hz, 1H), 7.34-7.28 (m, 2H), 7.26-7.20 (m, 1H), 5.85 (br. s., 1H), 5.73 (s, 1H), 4.66 (s, 1H), 4.10-4.02 (m, 5H), 3.90 (d, J=7.3 Hz, 1H), 3.77 (d, J=10.6 Hz, 2H), 3.43-3.38 (m, 4H), 3.28-3.20 (m, 1H), 2.34-2.29 (m, 3H), 1.54-1.37 (m, 5H), 1.33-1.24 (m, 1H), 1.24-1.17 (m, 1H); LC/MS (M+H)=509.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 171

1-[5-(Dimethyl-1H-1,2,3-triazol-5-yl)-8-[(S)-oxan-4-yl(phenyl)methyl]-3,8,10-triazatricyclo[7.4.0.0²,⁷]trideca-1(9),2(7),3,5,10,12-hexaen-11-yl]ethan-1-one

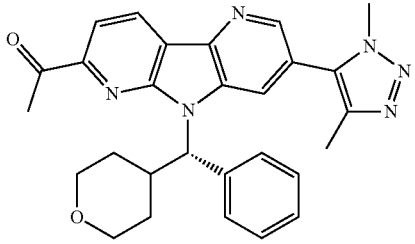 [SMILES: CC(=O)c1ccc2c3ncc(-c4c(C)nnn4C)cc3n([C@H](c3ccccc3)C3CCOCC3)c2n1]

To a 20 mL scintillation vial charged with 20 mg of 5-(dimethyl-1H-1,2,3-triazol-5-yl)-11-(1-ethoxyethenyl)-8-[(S)-oxan-4-yl(phenyl)methyl]-3,8,10-triazatricyclo[7.4.0.0²,⁷]trideca-1(9),2(7),3,5,10,12-hexaene dissolved in 5 mL THF was added 0.5 mL of 6N aq. HCl and stirred at room temperature. After 1.5 h, it was quenched with 5 mL of aq. K₂CO₃ (5% solution), and diluted with EtOAc. The organic layer was separated, washed with brine, dried over MgSO₄, filtered, and concentrated on the rotary evaporator to obtain a crude mixture. It was purified via preparative LC/MS with the following conditions: Column: XBridge C18, 19×200 mm, 5-µm particles; Mobile Phase A: 5:95 ACN: water with 10-mM NH₄OAc; Mobile Phase B: 95:5 ACN: water with 10-mM NH₄OAc; Gradient: 30-70% B over 30 min, then a 5-min hold at 100% B; Flow: 20 mL/min. Fractions containing the title product were combined and dried via centrifugal evaporation. The yield of the product was 88%, and its estimated purity by LC/MS analysis was 97%. Two analytical LC/MS injections were used to determine the final purity. Injection 1 conditions: Column: Waters BEH C18, 2.0×50 mm, 1.7-µm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.5-min hold at 100% B; Flow: 1.0 mL/min; Detection: UV at 220 nm, RT=1.85 min, LC/MS (M+H)=481.5. Injection 2 conditions: Column: Waters BEH C18, 2.0×50 mm, 1.7-µm particles; Mobile Phase A: 5:95 methanol:water with 10 mM NH₄OAc; Mobile Phase B: 95:5 methanol:water with 10 mM NH₄OAc; Temperature: 50° C.; Gradient: 0-100% B over 3 min, then a 0.5-min hold at 100% B; Flow: 0.5 mL/min; Detection: UV at 220 nm RT=3.19 min, LC/MS (M+H)=481.1. ¹H NMR (500 MHz, DMSO-d₆) δ 8.80 (d, J=7.7 Hz, 1H), 8.74-8.68 (m, 2H), 8.02 (d, J=8.1 Hz, 1H), 7.86 (d, J=7.3 Hz, 2H), 7.33 (t, J=7.3 Hz, 2H), 7.25 (t, J=7.3 Hz, 1H), 5.91 (br. s., 1H), 4.07 (s, 3H), 3.94-3.88 (m, 1H), 3.87-3.73 (m, 2H), 3.42-3.38 (m, 1H), 3.29 (t, J=11.2 Hz, 1H), 2.92 (s, 3H), 2.33 (s, 3H), 1.56-1.49 (m, 1H), 1.49-1.38 (m, 1H), 1.37-1.27 (m, 1H), 1.25-1.18 (m, 1H); LC/MS (M+H)=481.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 172

1-[5-(Dimethyl-1H-1,2,3-triazol-5-yl)-8-[(S)-oxan-4-yl(phenyl)methyl]-3,8,10-triazatricyclo[7.4.0.0²,⁷]trideca-1(9),2(7),3,5,10,12-hexaen-11-yl](1-²H)ethan-1-ol

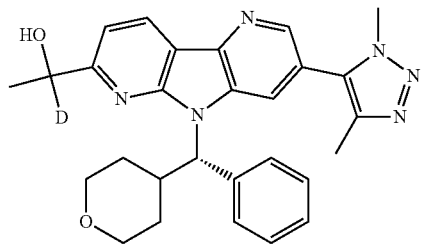 [SMILES: [2H]C(C)(O)c1ccc2c3ncc(-c4c(C)nnn4C)cc3n([C@H](c3ccccc3)C3CCOCC3)c2n1]

(S)-1-(3-(1,4-Dimethyl-1H-1,2,3-triazol-5-yl)-5-(phenyl(tetrahydro-2H-pyran-4-yl)methyl)-5H-pyrrolo[2,3-b:4,5-b']dipyridin-7-yl)ethanone (13.0 mg, 0.027 mmol) was dissolved in 5 mL of MeOH and stirred in an ice-bath. The NaBD₄ (1.4 mg, 0.032 mmol) was added and stirred for 10 min. The ice-bath was removed, and the reaction allowed to warm to room temperature with stirring. After 2 h, an additional 1 equivalent of the NaBD₄ was added and stirred. After 3 days, an additional 3 equivalents of the NaBD₄ was added and stirred. After 3 h, the reaction was quenched by diluting with 10 mL EtOAc, and washed with brine. The organic layer was dried over MgSO₄, filtered and concentrated to obtain a crude mixture. The crude mixture was dissolved in 1.5 mL MeOH and purified via preparative LC/MS with the following conditions: Column: XBridge C18, 19×200 mm, 5-µm particles; Mobile Phase A: 5:95 ACN: water with 10-mM NH₄OAc; Mobile Phase B: 95:5 ACN: water with 10-mM NH₄OAc; Gradient: 20-60% B over 15 min, then a 5-min hold at 100% B; Flow: 20 mL/min. Fractions containing the title compound were combined and dried via centrifugal evaporation. The yield of the product was 9.7 mg (72%), and its estimated purity by LC/MS analysis was 97%. Two analytical LC/MS injections were used to determine the final purity. Injection 1 conditions: Column: Waters BEH C18, 2.0×50 mm, 1.7-µm particles; Mobile Phase A: 5:95 ACN:water with 10 mM NH₄OAc; Mobile Phase B: 95:5 ACN:water with 10 mM NH₄OAc; Temperature: 50° C.; Gradient: 0% B, 0-100% B over 3 min, then a 0.5-min hold at 100% B; Flow: 1 mL/min; Detection: UV at 220 nm; RT=1.49 min,); LC/MS (M+H)=484.5. Injection 2 conditions: Column: Waters BEH C18, 2.0×50 mm, 1.7-µm particles; Mobile Phase A: 5:95 methanol:water with 10 mM NH₄OAc; Mobile Phase B: 95:5 methanol:water with 10 mM NH₄OAc; Temperature: 50° C.; Gradient: 0% B, 0-100% B over 3 min, then a 0.5-min hold at 100% B; Flow: 0.5 mL/min; Detection: UV at 220 nm, RT=2.45 min,); LC/MS (M+H)=484.5. ¹H NMR (500 MHz, DMSO-d₆) δ 8.66-8.45 (m, 3H), 7.84 (br. s., 2H), 7.58 (q, J=7.8 Hz, 1H), 7.31 (d, J=5.9 Hz, 2H), 7.28-7.17 (m, 2H), 5.88 (br. s., 1H), 4.04 (d, J=7.7 Hz, 3H), 2.89 (d, J=8.1 Hz, 2H), 2.74 (d, J=7.7 Hz, 2H), 2.32 (d, J=7.7 Hz, 3H), 1.91 (br. s., 2H), 1.57 (t, J=6.8 Hz, 3H), 1.51 (br. s., 1H), 1.39 (br. s., 1H), 1.25 (d, J=5.1 Hz, 1H), 1.13 (br. s., 1H); LC/MS (M+H)=484.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 173

1-[5-(Dimethyl-1H-1,2,3-triazol-5-yl)-8-[(S)-oxan-4-yl(phenyl)methyl]-3,8,10-triazatricyclo[7.4.0.0²,⁷]trideca-1(9),2(7),3,5,10,12-hexaen-11-yl]ethan-1-ol

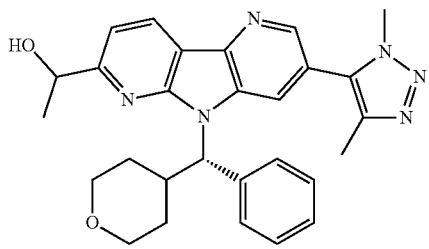 [SMILES: Cc1nnn(C)c1-c1cnc2c3ccc(C(C)O)nc3n([C@H](c3ccccc3)C3CCOCC3)c2c1]

(S)-1-(3-(1,4-Dimethyl-1H-1,2,3-triazol-5-yl)-5-(phenyl(tetrahydro-2H-pyran-4-yl)methyl)-5H-pyrrolo[2,3-b:4,5-b']dipyridin-7-yl)ethanone (15.0 mg, 0.031 mmol) was dissolved in 5 mL of MeOH and stirred in an ice-bath. The NaBH₄ (5.9 mg, 0.156 mmol) was added and stirred for 10 min. The ice-bath was removed and the reaction allowed to warm to room temperature with stirring. After 20 min, the reaction was quenched by diluting with 10 mL EtOAc, and washed with brine. The organic layer was dried over MgSO₄, filtered and concentrated to obtain a crude mixture. The crude mixture was dissolved in 1.5 mL MeOH and was purified via preparative LC/MS with the following conditions: Column: XBridge C18, 19×200 mm, 5-μm particles; Mobile Phase A: 5:95 ACN: water with 10-mM NH₄OAc; Mobile Phase B: 95:5 ACN: water with 10-mM NH₄OAc; Gradient: 25-65% B over 15 min, then a 5-min hold at 100% B; Flow: 20 mL/min. Fractions containing the title compound were combined and dried via centrifugal evaporation. The yield of the product was 12.5 mg (83%), and its estimated purity by LC/MS analysis was 98%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0% B, 0-100% B over 3 min, then a 0.5-min hold at 100% B; Flow: 1 mL/min; Detection: UV at 220 nm; RT=1.48 min, LC/MS (M+H)=483.5. Injection 2 conditions: Column: Waters BEH C18, 2.0×50 mm, 1.7-μm particles; Mobile Phase A: 5:95 methanol:water with 10 mM NH₄OAc; Mobile Phase B: 95:5 methanol:water with 10 mM NH₄OAc; Temperature: 50° C.; Gradient: 0% B, 0-100% B over 3 min, then a 0.5-min hold at 100% B; Flow: 0.5 mL/min; Detection: UV at 220 nm; RT=2.93 min, LC/MS (M+H)=483.5. ¹H NMR (500 MHz, DMSO-d₆) δ 8.63-8.51 (m, 3H), 7.84 (d, J=6.2 Hz, 2H), 7.58 (t, J=7.9 Hz, 1H), 7.35-7.26 (m, 2H), 7.26-7.19 (m, 1H), 5.87 (br. s., 1H), 5.03 (t, J=6.4 Hz, 1H), 4.04 (s, 3H), 3.76 (br. s., 2H), 3.38 (br. s., 2H), 3.25 (t, J=11.2 Hz, 1H), 2.90 (s, 2H), 2.74 (s, 2H), 2.32 (s, 3H), 1.91 (s, 3H), 1.50 (d, J=17.6 Hz, 1H), 1.44-1.33 (m, 1H), 1.26 (d, J=10.3 Hz, 1H), 1.13 (br. s., 1H); LC/MS (M+H)=483.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 174

2-[5-(Dimethyl-1H-1,2,3-triazol-5-yl)-8-[(S)-oxan-4-yl(phenyl)methyl]-3,8,10-triazatricyclo[7.4.0.0²,⁷]trideca-1(9),2(7),3,5,10,12-hexaen-11-yl]propan-2-ol

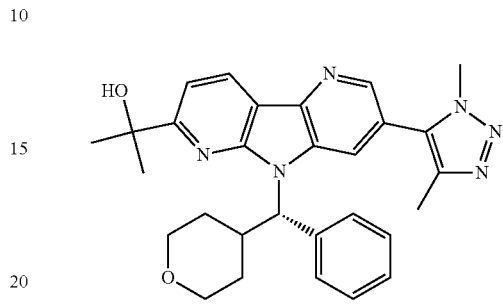

(S)-1-(3-(1,4-Dimethyl-1H-1,2,3-triazol-5-yl)-5-(phenyl(tetrahydro-2H-pyran-4-yl)methyl)-5H-pyrrolo[2,3-b:4,5-b']dipyridin-7-yl)ethanone (15.0 mg, 0.031 mmol) was dissolved in 5 mL of THF and stirred in an ice-bath. Methylmagnesium bromide (3M in diethyl ether, 0.156 mL, 0.468 mmol), was added and stirred. The ice-bath was removed, and the reaction allowed to warm to room temperature with stirring. After 10 min, the reaction was quenched by adding 1 mL acetone and diluting with 15 mL of EtOAc. It was washed with brine, and the organic layer was dried over MgSO₄, filtered and concentrated to obtain a crude mixture. The crude mixture was dissolved in 1.5 mL DMF. This was purified via preparative LC/MS with the following conditions: Column: XBridge C18, 19×200 mm, 5-μm particles; Mobile Phase A: 5:95 methanol: water with 10-mM NH₄OAc; Mobile Phase B: 95:5 methanol: water with 10-mM NH₄OAc; Gradient: 55-95% B over 15 min, then a 5-min hold at 100% B; Flow: 20 mL/min. Fractions containing the title compound were combined and dried via centrifugal evaporation. The yield of the product was 7.3 mg (47%), and its estimated purity by LC/MS analysis was 99%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0% B, 0-100% B over 3 min, then a 0.5-min hold at 100% B; Flow: 1 mL/min; Detection: UV at 220 nm, RT=1.64 min, LC/MS (M+H)=497.5; Injection 2 conditions: Column: Waters BEH C18, 2.0×50 mm, 1.7-μm particles; Mobile Phase A: 5:95 methanol:water with 10 mM NH₄OAc; Mobile Phase B: 95:5 methanol:water with 10 mM NH₄OAc; Temperature: 50° C.; Gradient: 0% B, 0-100% B over 3 min, then a 0.5-min hold at 100% B; Flow: 0.5 mL/min; Detection: UV at 220 nm; RT=2.96 min, LC/MS (M+H)=497.5. ¹H NMR (500 MHz, DMSO-d₆) δ 8.63-8.54 (m, 3H), 7.85 (d, J=7.7 Hz, 2H), 7.74 (d, J=8.1 Hz, 1H), 7.33-7.27 (m, 2H), 7.25-7.20 (m, 1H), 5.80 (br. s., 1H), 4.05 (s, 3H), 3.93-3.88 (m, 1H), 3.78 (d, J=10.3 Hz, 2H), 3.37 (s, 2H), 3.23 (t, J=11.2 Hz, 1H), 2.33 (s, 3H), 1.67 (s, 6H), 1.46 (br. s., 2H), 1.40 (d, J=8.8 Hz, 1H), 1.32-1.21 (m, 1H), 1.16 (d, J=12.1 Hz, 1H); LC/MS (M+H)=497.3 [Column: Waters Aquity BEH C18 2.1×50 mm 1.7 u; Mobile

Example 175

2-{5-[4-($^2$H$_3$)Methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaen-11-yl}propan-2-ol

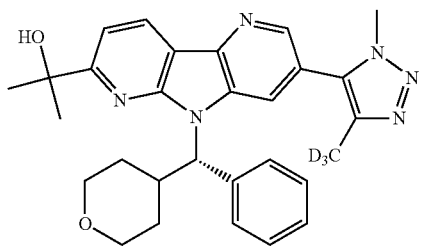 [SMILES: [2H]C([2H])([2H])c1nnn(C)c1-c1cnc2c3ccc(C(C)(C)O)nc3n([C@H](c3ccccc3)C3CCOCC3)c2c1]

Following a procedure analogous to the reaction described in the synthesis of 2-[5-(dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-11-yl]propan-2-ol, the title compound was synthesized in 26% yield from 1-{5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaen-11-yl}ethan-1-one and methylmagnesium bromide. The crude material was purified via preparative LC/MS with the following conditions: Column: XBridge C18, 19×200 mm, 5-µm particles; Mobile Phase A: 5:95 ACN: water with 10-mM NH$_4$OAc; Mobile Phase B: 95:5 ACN: water with 10-mM NH$_4$OAc; Gradient: 20-60% B over 20 min, then a 5-min hold at 100% B; Flow: 20 mL/min. Fractions containing the title compound were combined and dried via centrifugal evaporation. The yield of the product was 20.1 mg (26%), and its estimated purity by LC/MS analysis was 98%. Two analytical LC/MS injections were used to determine the final purity. Injection 1 conditions: Column: Waters BEH C18, 2.0×50 mm, 1.7-µm particles; Mobile Phase A: 5:95ACN: water with 10 mM NH$_4$OAc; Mobile Phase B: 95:5 ACN: water with 10 mM NH$_4$OAc; Temperature: 50° C.; Gradient: 0-100% B over 3 min, then a 0.5-min hold at 100% B; Flow: 1.0 mL/min; Detection: UV at 220 nm; RT=1.64 min, LC/MS (M+H)=500.0. Injection 2 conditions: Column: Waters BEH C18, 2.0×50 mm, 1.7-µm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0-100% B over 3 min, then a 0.5-min hold at 100% B; Flow: 0.5 mL/min; Detection: UV at 220 nm; RT=2.97 min, LC/MS (M+H) =500.1. $^1$H NMR (500 MHz, DMSO-d$_6$) δ 8.64-8.53 (m, 3H), 7.86 (d, J=7.7 Hz, 2H), 7.74 (d, J=8.1 Hz, 1H), 7.33-7.27 (m, 2H), 7.25-7.19 (m, 1H), 5.80 (br. s., 1H), 4.06 (s, 3H), 3.90 (d, J=10.3 Hz, 1H), 3.78 (d, J=10.6 Hz, 2H), 3.40-3.33 (m, 1H), 3.23 (t, J=11.6 Hz, 1H), 1.67 (s, 6H), 1.46 (br. s., 1H), 1.43-1.35 (m, 1H), 1.32-1.21 (m, 1H), 1.16 (d, J=12.1 Hz, 1H); LC/MS (M+H)=500.0 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 176

2-(5-{5-[4-($^2$H$_3$)Methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaen-11-yl}thiophen-2-yl)propan-2-ol

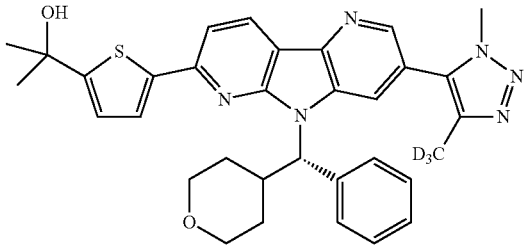 [SMILES: [2H]C([2H])([2H])c1nnn(C)c1-c1cnc2c3ccc(-c4ccc(C(C)(C)O)s4)nc3n([C@H](c3ccccc3)C3CCOCC3)c2c1]

Step 1: 1-(5-{5-[4-($^2$H$_3$)Methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaen-11-yl}thiophen-2-yl)ethan-1-one 11-Chloro-5-[4-($^2$H$_3$)methyl-1-methyl-1H-1,2,3-triazol-5-yl]-8-[(S)-oxan-4-yl(phenyl)methyl]-3,8,10-triazatricyclo [7.4.0.0$^{2,7}$]trideca-1(9),2(7),3,5,10,12-hexaene (0.168 mmol, 80 mg) was weighed into a microwave vial, followed by the addition of (5-acetylthiophene-2-yl)boronic acid (0.252 mmol, 42.9 mg), K$_2$CO$_3$ (0.420 mmol, 43.0 mg), Pd(PPh$_3$)$_4$ (0.017 mmol, 19.4 mg), 6 mL dioxane and 3 mL water. The air was replaced with N$_2$, and the resulting mixture heated in the microwave at 140° C. for 0.25 h. It was diluted with EtOAc, and washed with brine, dried over MgSO$_4$, and concentrated to obtain a crude mixture. This was purified on the ISCO with a 12 g silica gel column, eluting with 0-25% (10% 2N ammonia in EtOAc)/EtOAc to obtain 61 mg (52%) of the title compound. LC/MS (M+H)= 566.2 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Step 2: 2-(5-{5-[4-($^2$H$_3$)Methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaen-11-yl}thiophen-2-yl)propan-2-ol Following a procedure analogous to the reaction described in the synthesis of 2-[5-(dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-11-yl] propan-2-ol, the title compound was synthesized in 13% yield from 1-(5-{5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaen-11-yl}thiophen-2-yl)ethan-1-one and methylmagnesium bromide. The crude material was purified via preparative LC/MS with the following conditions: Column: XBridge C18, 19×200 mm, 5-µm particles; Mobile Phase A: 5:95 ACN: water with 10-mM NH$_4$OAc; Mobile Phase B: 95:5 ACN: water with 10-mM NH$_4$OAc; Gradient: 35-45% B over 15 min, then a 5-min hold at 100% B; Flow: 20 mL/min. Fractions containing the title compound were combined and dried via centrifugal evaporation. The estimated purity by LC/MS analysis was 99%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.5-min hold at 100% B; Flow: 1.0 mL/min; Detection: UV at 220 nm, RT=1.91 min, LC/MS (M+H)= 582.1. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0-100% B over 3 min, then a 0.5-min hold at 100% B; Flow: 0.5 mL/min; Detection: UV at 220 nm, RT=3.34 min, LC/MS (M+H)=582.1. $^1$H NMR (500 MHz, DMSO-d$_6$) δ 8.62-8.49 (m, 3H), 7.85 (d, J=7.7 Hz, 2H), 7.88 (d, J=8.1 Hz, 1H), 7.80 (d, J=4.0 Hz, 1H), 7.30 (t, J=7.5 Hz, 2H), 7.23 (t, J=7.3 Hz, 1H), 7.03 (d, J=3.7 Hz, 1H), 5.78 (br. s., 1H), 4.03 (s, 3H), 3.96-3.83 (m, 2H), 3.78 (d, J=10.6 Hz, 1H), 3.43-3.35 (m, 1H), 3.30 (t, J=10.8 Hz, 1H), 3.17 (d, J=4.8 Hz, 1H), 1.59 (s, 6H), 1.53-1.37 (m, 2H), 1.35-1.22 (m, 2H); LC/MS (M+H)=582.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 177

2-[5-(Dimethyl-1H-1,2,3-triazol-5-yl)-8-[(S)-oxan-4-yl(phenyl)methyl]-3,8,10-triazatricyclo[7.4.0.0$^{2,7}$] trideca-1(9),2(7),3,5,10,12-hexaen-11-yl](1,1,1-$^2$H$_3$) propan-2-ol

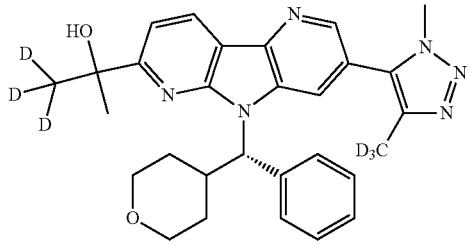 [SMILES: [2H]C([2H])([2H])c1nnn(C)c1-c1cnc2c3ccc(C(C)(O)C([2H])([2H])[2H])nc3n([C@H](c3ccccc3)C3CCOCC3)c2c1]

(S)-1-(3-(1,4-Dimethyl-1H-1,2,3-triazol-5-yl)-5-(phenyl (tetrahydro-2H-pyran-4-yl)methyl)-5H-pyrrolo[2,3-b:4,5-b']dipyridin-7-yl)ethanone (15.0 mg, 0.031 mmol) was dissolved in 5 mL of THF and stirred in an ice-bath. Methyllithium-D3 (3M in diethylether, 0.624 mL, 0.312 mmol) was added and stirred. The ice-bath was removed, and the reaction allowed to warm to room temperature with stirring. After 20 min, the reaction was quenched by adding 1 mL acetone and diluting with 15 mL of EtOAc. It was washed with brine, and the organic layer was dried over MgSO$_4$, filtered and concentrated to obtain a crude mixture. The crude was purified via preparative LC/MS with the following conditions: Column: XBridge C18, 19×200 mm, 5-μm particles; Mobile Phase A: 5:95 methanol: water with 10-mM NH$_4$OAc; Mobile Phase B: 95:5 methanol: water with 10-mM NH$_4$OAc; Gradient: 55-95% B over 15 min, then a 5-min hold at 100% B; Flow: 20 mL/min. Fractions containing the title compound were combined and dried via centrifugal evaporation. The yield of the product was 4.3 mg (28%), and its estimated purity by LC/MS analysis was 97%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm.; RT=1.66 min, LC/MS (M+H)=500.5. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm.; RT=2.65 min, LC/MS (M+H)=500.5. $^1$H NMR (500 MHz, DMSO-d$_6$) δ 8.63-8.54 (m, 3H), 7.85 (d, J=7.3 Hz, 2H), 7.74 (d, J=8.4 Hz, 1H), 7.34-7.27 (m, 2H), 7.26-7.21 (m, 1H), 5.80 (br. s., 1H), 4.05 (s, 3H), 3.92-3.87 (m, 1H), 3.78 (d, J=10.6 Hz, 1H), 3.41-3.34 (m, 3H), 3.23 (t, J=11.0 Hz, 1H), 2.33 (s, 3H), 1.67 (s, 3H), 1.46 (br. s., 1H), 1.40 (d, J=212.1 Hz, 1H), 1.31-1.21 (m, 1H), 1.16 (d, J=12.1 Hz, 1H); LC/MS (M+H)=500.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 178

5-(Dimethyl-1H-1,2,3-triazol-5-yl)-11-(morpholin-4-yl)-8-[(S)-oxan-4-yl(phenyl)methyl]-3,8,10-triazatricyclo[7.4.0.0$^{2,7}$]trideca-1(9),2(7),3,5,10,12-hexaene

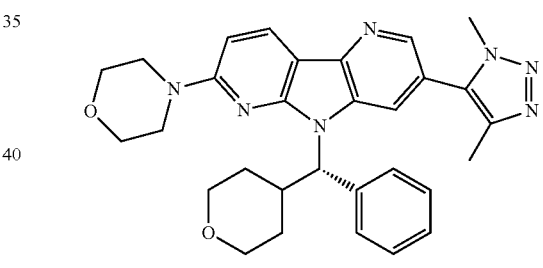

(S)-7-Chloro-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridine (25.0 mg, 0.053 mmol) was dissolved in 2 mL of morpholine and microwaved at 150° C. for 15 min. The contents of the reaction vial were concentrated on the rotary evaporator to obtain a crude mixture. The crude mixture was dissolved in 1.5 mL DMF, filtered, was purified via preparative LC/MS with the following conditions: Column: XBridge C18, 19×200 mm, 5-μm particles; Mobile Phase A: 5:95 ACN: water with 10-mM NH$_4$OAc; Mobile Phase B: 95:5 ACN: water with 10-mM NH$_4$OAc; Gradient: 30-70% B over 15 min, then a 5-min hold at 100% B; Flow: 20 mL/min. Fractions containing the desired product were combined and dried via centrifugal evaporation. The yield of the product was 17.6 mg (64%), and its estimated purity by LC/MS analysis was 100%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min;

Detection: UV at 220 nm; RT=1.67 min, LC/MS (M+H)= 524.5. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm; RT=2.67 min, LC/MS (M+H)=524.5. $^1$H NMR (500 MHz, DMSO-d$_6$) δ 8.41 (s, 1H), 8.37-8.26 (m, 2H), 7.77 (d, J=7.3 Hz, 2H), 7.35-7.27 (m, 2H), 7.26-7.19 (m, 1H), 6.90 (d, J=8.8 Hz, 1H), 5.73 (br. s., 1H), 4.00 (s, 3H), 3.91-3.70 (m, 10H), 3.63 (br. s., 1H), 3.39 (d, J=4.0 Hz, 1H), 3.26 (t, J=10.8 Hz, 1H), 2.29 (s, 3H), 1.48 (d, J=11.4 Hz, 1H), 1.43-1.33 (m, 1H), 1.28 (br. s., 1H), 1.24 (br. s., 1H); LC/MS (M+H)=524.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 179

1-[5-(Dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-11-yl]azetidin-3-ol

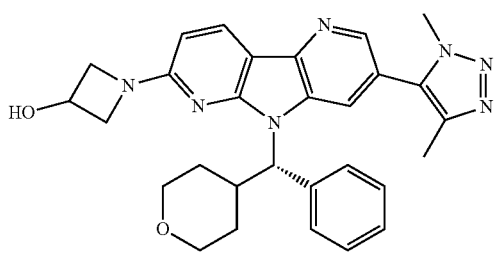 [SMILES: Cc1nnn(C)c1-c1cnc2c3ccc(N4CC(O)C4)nc3n([C@H](c3ccccc3)C3CCOCC3)c2c1]

Following a procedure analogous to the reaction described in the synthesis of 5-(dimethyl-1H-1,2,3-triazol-5-yl)-11-(morpholin-4-yl)-8-[(S)-oxan-4-yl(phenyl)methyl]-3,8,10-triazatricyclo[7.4.0.0$^{2,7}$]trideca-1(9),2(7),3,5,10,12-hexaene, the title compound was made in 25% yield from (S)-7-chloro-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridine and azetidin-3-ol hydrochloride. The crude material was purified via preparative LC/MS with the following conditions: Column: XBridge C18, 19×200 mm, 5-μm particles; Mobile Phase A: 5:95 ACN: water with 0.1% trifluoroacetic acid; Mobile Phase B: 95:5 ACN: water with 0.1% trifluoroacetic acid; Gradient: 10-50% B over 20 min, then a 5-min hold at 100% B; Flow: 20 mL/min. Fractions containing the title compound were combined and dried via centrifugal evaporation. The estimated purity by LC/MS analysis was 100%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm, RT=1.49 min, LC/MS (M+H)=510.5. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm, RT=2.51 min, LC/MS (M+H)=510.5. $^1$H NMR (500 MHz, DMSO-d$_6$) δ 8.45-8.35 (m, 2H), 8.25 (d, J=8.4 Hz, 1H), 7.81 (d, J=7.7 Hz, 2H), 7.35-7.28 (m, 2H), 7.26-7.20 (m, 1H), 6.41 (d, J=8.4 Hz, 1H), 5.66 (br. s., 1H), 4.72 (br. s., 1H), 4.45-4.37 (m, 2H), 4.00 (s, 3H), 3.93 (dd, J=8.8, 4.0 Hz, 2H), 3.87 (d, J=11.4 Hz, 1H), 3.79 (d, J=11.7 Hz, 1H), 3.69 (br. s., 1H), 3.36 (t, J=11.6 Hz, 1H), 3.27 (t, J=10.3 Hz, 1H), 2.29 (s, 3H), 1.43 (br. s., 1H), 1.39-1.32 (m, 1H), 1.23 (br. s., 2H); LC/MS (M+H)=510.2 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 180

1-[5-(Dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-11-yl]-4-methyl-piperidin-4-ol

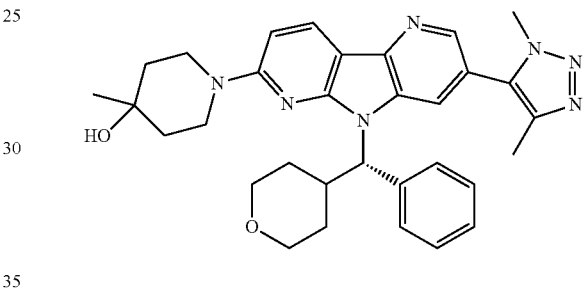

Following a procedure analogous to the reaction described in the synthesis of 5-(dimethyl-1H-1,2,3-triazol-5-yl)-11-(morpholin-4-yl)-8-[(S)-oxan-4-yl(phenyl)methyl]-3,8,10-triazatricyclo[7.4.0.0$^{2,7}$]trideca-1(9),2(7),3,5,10,12-hexaene, the title compound was made in 75% yield from 11-chloro-5-(dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaene and 4-methylpiperidin-4-ol. The crude material was purified via preparative LC/MS with the following conditions: Column: XBridge C18, 19×200 mm, 5-μm particles; Mobile Phase A: 5:95 ACN: water with 0.1% trifluoroacetic acid; Mobile Phase B: 95:5 ACN: water with 0.1% trifluoroacetic acid; Gradient: 10-60% B over 20 min, then a 5-min hold at 100% B; Flow: 20 mL/min. Fractions containing the title compound were combined and dried via centrifugal evaporation. The estimated purity by LC/MS analysis was 97%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.5-min hold at 100% B; Flow: 1.0 mL/min; Detection: UV at 220 nm, RT=1.62 min, LC/MS (M+H)=552.1. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0-100% B over 3 min, then a 0.5-min hold at 100% B; Flow: 0.5 mL/min; Detection: UV at 220 nm, RT=3.07 min, LC/MS (M+H) =552.1. $^1$H NMR (500 MHz, DMSO-d$_6$) δ 8.46-8.38 (m, 2H), 8.25 (d, J=8.8 Hz, 1H), 7.78 (d, J=7.3 Hz, 2H), 7.31 (t, J=7.5 Hz, 2H), 7.23 (t, J=7.3 Hz, 1H), 6.94 (d, J=8.8 Hz, 1H), 5.70 (br. s., 1H), 4.14 (d, J=9.2 Hz, 2H), 4.01 (s, 3H), 3.88 (d, J=10.3 Hz, 1H), 3.80 (d, J=10.6 Hz, 1H), 3.69-3.55 (m, 3H), 3.48 (br. s., 2H), 3.44 (br. s., 3H), 3.39-3.31 (m, 1H), 3.28-3.20 (m, 1H), 2.56 (t, J=5.5 Hz, 4H), 2.29 (s, 3H), 1.69-1.53 (m, 4H), 1.49-1.35 (m, 2H), 1.26 (br. s., 2H), 1.21 (s, 3H); LC/MS (M+H)=552.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 181

5-(Dimethyl-1H-1,2,3-triazol-5-yl)-N,N-dimethyl-8-[(S)-oxan-4-yl(phenyl)methyl]-3,8,10-triazatricyclo[7.4.0.0$^{2,7}$]trideca-1(9),2(7),3,5,10,12-hexaen-11-amine

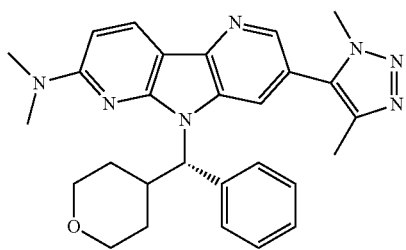 [SMILES: Cc1nnn(C)c1-c1cnc2c3ccc(N(C)C)nc3n([C@H](c3ccccc3)C3CCOCC3)c2c1]

The title compound was a side product obtained (in 37% yield) during the synthesis of 1-[5-(dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-11-yl]azetidin-3-ol. The crude material was purified via preparative LC/MS with the following conditions: Column: XBridge C18, 19×200 mm, 5-μm particles; Mobile Phase A: 5:95 ACN: water with 0.1% trifluoroacetic acid; Mobile Phase B: 95:5 ACN: water with 0.1% trifluoroacetic acid; Gradient: 10-50% B over 20 min, then a 5-min hold at 100% B; Flow: 20 mL/min. Fractions containing the title compound were combined and dried via centrifugal evaporation. The estimated purity by LC/MS analysis was 95%. Two analytical LC/MS injections were used to determine the final purity. Injection 1 conditions: Column: Waters BEH C18, 2.0×50 mm, 1.7-μm particles; Mobile Phase A: 5:95 ACN: water with 10 mM NH$_4$OAc; Mobile Phase B: 95:5 ACN: water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm, RT=1.81 min, LC/MS (M+H)=482.5. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm; RT=2.83 min, LC/MS (M+H)=482.5. $^1$H NMR (500 MHz, DMSO-d$_6$) δ 8.49-8.44 (m, 2H), 8.29 (d, J=9.2 Hz, 1H), 7.79 (d, J=7.3 Hz, 2H), 7.33-7.29 (m, 2H), 7.25-7.20 (m, 1H), 6.78 (d, J=8.8 Hz, 1H), 5.71 (br. s., 1H), 4.00 (s, 3H), 3.87 (d, J=12.1 Hz, 1H), 3.78 (d, J=10.6 Hz, 1H), 3.65 (s, 7H), 3.36 (t, J=11.0 Hz, 1H), 2.96-2.86 (m, 1H), 2.53-2.42 (m, 1H), 2.28 (s, 3H), 1.44 (br. s., 1H), 1.37 (d, J=8.4 Hz, 1H), 1.25 (br. s., 2H); LC/MS (M+H)=482.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 182

4-[5-(Dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-11-yl]-1,4-thiomorpholine-1,1-dione

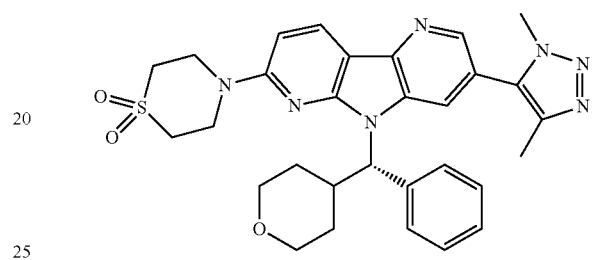

(S)-7-Chloro-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridine (40.0 mg, 0.085 mmol) and thiomorpholine 1,1-dioxide (45.7 mg, 0.338 mmol) and triethylamine (94 μl, 0.677 mmol) were dissolved in 1.5 mL of DMSO and microwaved at 175° C. for 2 h. The solids were filtered and the crude (filtrate) was purified via preparative LC/MS with the following conditions: Column: XBridge C18, 19×200 mm, 5-μm particles; Mobile Phase A: 5:95 ACN: water with 10-mM NH$_4$OAc; Mobile Phase B: 95:5 ACN: water with 10-mM NH$_4$OAc; Gradient: 20-60% B over 15 min, then a 5-min hold at 100% B; Flow: 20 mL/min. Fractions containing the title compound were combined and dried via centrifugal evaporation. The yield of the product was 15.8 mg (32%), and its estimated purity by LC/MS analysis was 99%. Injection conditions: Column: Waters BEH C18, 2.0×50 mm, 1.7-μm particles; Mobile Phase A: 5:95 methanol: water with 10 mM NH$_4$OAc; Mobile Phase B: 95:5 methanol:water with 10 mM NH$_4$OAc; Temperature: 50° C.; Gradient: 0-100% B over 3 min, then a 0.5-min hold at 100% B; Flow: 0.5 mL/min; Detection: UV at 220 nm, RT=2.74 min, LC/MS (M+H)=572.5. $^1$H NMR (500 MHz, DMSO-d$_6$) δ 8.43 (s, 1H), 8.37 (d, J=8.8 Hz, 1H), 7.94 (s, 1H), 7.73 (d, J=7.3 Hz, 2H), 7.34-7.28 (m, 2H), 7.26-7.20 (m, 1H), 7.05 (d, J=8.8 Hz, 1H), 5.73 (br. s., 1H), 4.37-4.25 (m, 4H), 4.01 (s, 3H), 3.87 (d, J=11.4 Hz, 1H), 3.77 (d, J=12.1 Hz, 1H), 3.56 (d, J=13.2 Hz, 1H), 3.48 (br. s., 4H), 3.41 (t, J=11.4 Hz, 1H), 3.25-3.21 (m, 1H), 2.29 (s, 3H), 1.49 (br. s., 1H), 1.45-1.35 (m, 1H), 1.29-1.16 (m, 2H); LC/MS (M+H)=572.2 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 183

8-{5-[4-($^2H_3$)Methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaen-11-yl}-8-azabicyclo[3.2.1]octan-3-ol

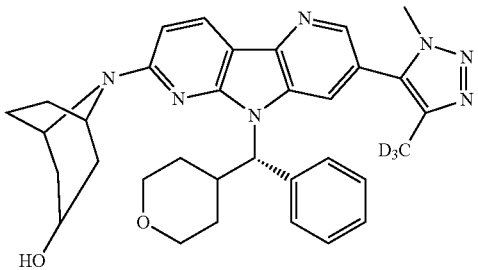 [SMILES: [2H]C([2H])([2H])c1nnn(C)c1-c1cnc2c3ccc(N4C5CCC4CC(O)C5)nc3n([C@H](c3ccccc3)C3CCOCC3)c2c1]

Following a procedure analogous to the reaction described in the synthesis of 4-[5-(dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-11-yl]-1λ$^6$,4-thiomorpholine-1,1-dione, the title compound was obtained in 22% yield from 11-chloro-5-(dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaene and 8-azabicyclo[3.2.1]octan-3-ol. The crude material was purified via preparative LC/MS with the following conditions: Column: XBridge C18, 19×200 mm, 5-μm particles; Mobile Phase A: 5:95 methanol: water with 10-mM NH$_4$OAc; Mobile Phase B: 95:5 methanol: water with 10-mM NH$_4$OAc; Gradient: 45-85% B over 20 min, then a 5-min hold at 100% B; Flow: 20 mL/min. Fractions containing the title compound were combined and dried via centrifugal evaporation. The yield of the product was 10.6 mg, and its estimated purity by LC/MS analysis was 100%. An analytical LC/MS injection was used to determine the final purity. Injection conditions: Column: Waters BEH C18, 2.0×50 mm, 1.7-μm particles; Mobile Phase A: 5:95 ACN: water with 10 mM NH$_4$OAc; Mobile Phase B: 95:5 ACN: water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm; RT=1.42 min, LC/MS (M+H)=567.6. $^1$H NMR (500 MHz, DMSO-d$_6$) δ 8.36 (s, 1H), 8.32 (br. s., 1H), 8.22 (d, J=8.8 Hz, 1H), 7.95 (s, 1H), 7.80 (d, J=7.7 Hz, 2H), 7.33-7.28 (m, 2H), 7.25-7.19 (m, 1H), 6.73 (d, J=8.8 Hz, 1H), 5.64 (br. s., 1H), 4.71 (br. s., 1H), 4.01 (s, 3H), 3.94-3.84 (m, 2H), 3.79 (d, J=11.0 Hz, 1H), 3.66 (br. s., 1H), 3.46 (br. s., 1H), 3.35 (t, J=11.6 Hz, 1H), 3.27-3.20 (m, 1H), 2.40 (d, J=7.0 Hz, 2H), 2.10 (br. s., 2H), 2.06 (br. s., 3H), 1.79 (d, J=14.3 Hz, 2H), 1.44 (br. s., 1H), 1.36 (d, J=11.7 Hz, 1H), 1.24 (br. s., 2H); LC/MS (M+H)=567.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 184

11-{8-Azabicyclo[3.2.1]octan-8-yl}-5-[4-($^2H_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaene

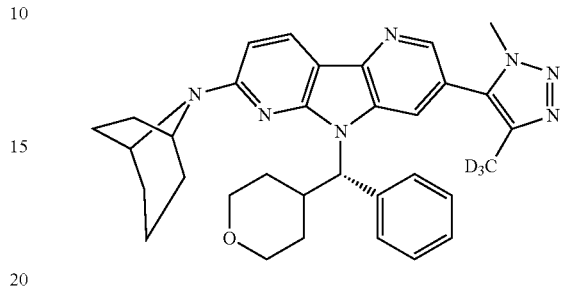

Following a procedure analogous to the reaction described in the synthesis of 4-[5-(dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-11-yl]-1λ$^6$,4-thiomorpholine-1,1-dione, the title compound was obtained in 14% yield from 11-chloro-5-[4-($^2H_3$)methyl-1-methyl-1H-1,2,3-triazol-5-yl]-8-[(S)-oxan-4-yl(phenyl)methyl]-3,8,10-triazatricyclo-[7.4.0.0$^{2,7}$]trideca-1(9),2(7),3,5,10,12-hexaene and 8-azabicyclo[3.2.1]octane hydrochloride. The crude material was purified via preparative LC/MS with the following conditions: Column: waters Xbridge c-18, 19×200 mm, 5-μm particles; Mobile Phase A: 5:95 ACN: water with 10-mM NH$_4$OAc; Mobile Phase B: 95:5 ACN: water with 10-mM NH$_4$OAc; Gradient: 30-70% B over 15 min, then a 5-min hold at 100% B; Flow: 20 mL/min. Fractions containing the title compound were combined and dried via centrifugal evaporation. The estimated purity by LC/MS analysis was 99%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm; RT=1.28 min, LC/MS (M+H)=551.3. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm; RT=3.21 min, LC/MS (M+H)=551.3. $^1$H NMR (500 MHz, DMSO-d$_6$) δ 8.37 (s, 1H), 8.32 (br. s., 1H), 8.23 (d, J=8.8 Hz, 1H), 7.81 (d, J=7.7 Hz, 2H), 7.30 (t, J=7.5 Hz, 2H), 7.22 (t, J=7.3 Hz, 1H), 6.74 (d, J=8.8 Hz, 1H), 5.64 (br. s., 1H), 4.72 (br. s., 2H), 4.01 (s, 3H), 3.87 (d, J=11.4 Hz, 1H), 3.79 (d, J=11.0 Hz, 1H), 3.67 (br. s., 1H), 3.38-3.31 (m, 1H), 3.28-3.19 (m, 1H), 2.12 (br. s., 2H), 1.94 (d, J=7.3 Hz, 3H), 1.86 (br. s., 2H), 1.53 (br. s., 3H), 1.43 (br. s., 1H), 1.40-1.32 (m, 1H), 1.25 (br. s., 2H); LC/MS (M+H)=551.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 185

4-{5-[4-($^2$H$_3$)Methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaen-11-yl}-1λ$^6$,4-thiomorpholine-1,1-dione

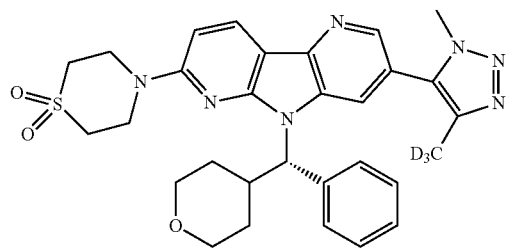 [SMILES: [2H]C([2H])([2H])c1nnn(C)c1-c1cnc2c3ccc(N4CCS(=O)(=O)CC4)nc3n([C@H](c3ccccc3)C3CCOCC3)c2c1]

Following a procedure analogous to the reaction described in the synthesis of 4-[5-(dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-11-yl]-1λ$^6$,4-thiomorpholine-1,1-dione, the title compound was obtained in 28% yield from 11-chloro-5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaene and thiomorpholine 1,1-dioxide. The solids were filtered, and the crude filtrate was purified via preparative LC/MS with the following conditions: Column: XBridge C18, 19×200 mm, 5-µm particles; Mobile Phase A: 5:95 methanol: water with 10-mM NH$_4$OAc; Mobile Phase B: 95:5 methanol: water with 10-mM NH$_4$OAc; Gradient: 45-85% B over 15 min, then a 5-min hold at 100% B; Flow: 20 mL/min. Fractions containing the title compound were combined and dried via centrifugal evaporation. The estimated purity by LC/MS analysis was 100%. Two analytical LC/MS injections were used to determine the final purity. Injection 1 conditions: Column: Waters BEH C18, 2.0×50 mm, 1.7-µm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm; RT=1.45 min, LC/MS (M+H)=575.3. Injection 2 conditions: Column: Waters BEH C18, 2.0×50 mm, 1.7-µm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm, RT=3.09 min, LC/MS (M+H)=575.3. $^1$H NMR (500 MHz, DMSO-d$_6$) δ 8.44 (s, 1H), 8.42-8.34 (m, 2H), 7.74 (d, J=7.3 Hz, 2H), 7.31 (t, J=7.5 Hz, 2H), 7.23 (t, J=7.3 Hz, 1H), 7.06 (d, J=8.8 Hz, 1H), 5.73 (br. s., 1H), 4.37-4.25 (m, 4H), 4.01 (s, 3H), 3.87 (d, J=9.2 Hz, 1H), 3.77 (d, J=11.0 Hz, 1H), 3.56 (br. s., 1H), 3.42-3.38 (m, 1H), 3.31-3.21 (m, 5H), 1.50 (d, J=12.1 Hz, 1H), 1.44-1.37 (m, 1H), 1.28-1.20 (m, 2H); LC/MS (M+H)=575.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 186

4-(1-{5-[4-($^2$H$_3$)Methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaen-11-yl}azetidin-3-yl)-1λ$^6$,4-thiomorpholine-1,1-dione

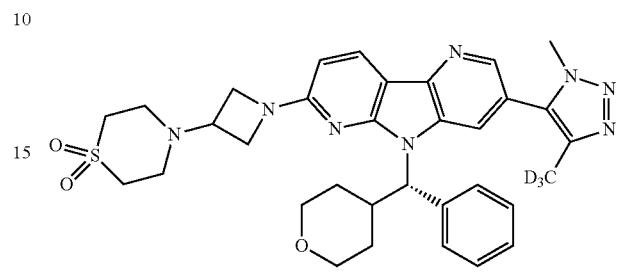

Following a procedure analogous to the reaction described in the synthesis of 4-[5-(dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-11-yl]-1λ$^6$,4-thiomorpholine-1,1-dione, the title compound was obtained in 19% yield from 11-chloro-5-[4-($^2$H$_3$)methyl-1-methyl-1H-1,2,3-triazol-5-yl]-8-[(S)-oxan-4-yl(phenyl)methyl]-3,8,10-triazatricyclo-[7.4.0.0$^{2,7}$]trideca-1(9),2(7),3,5,10,12-hexaene and 4-(azetidin-3-yl)-1λ$^6$-thiomorpholine-1,1-dione hydrochloride. The solids were filtered, and the crude was purified via preparative LC/MS with the following conditions: Column: XBridge Phenyl, 19×200 mm, 5-µm particles; Mobile Phase A: 5:95 ACN: water with 10-mM NH$_4$OAc; Mobile Phase B: 95:5 ACN: water with 10-mM NH$_4$OAc; Gradient: 20-60% B over 20 min, then a 5-min hold at 100% B; Flow: 20 mL/min. Fractions containing the title compound were combined and dried via centrifugal evaporation. The material was further purified via preparative LC/MS with the following conditions: Column: XBridge Phenyl, 19×200 mm, 5-µm particles; Mobile Phase A: 5:95 methanol: water with 10-mM NH$_4$OAc; Mobile Phase B: 95:5 methanol: water with 10-mM NH$_4$OAc; Gradient: 35-75% B over 20 min, then a 5-min hold at 100% B; Flow: 20 mL/min. Fractions containing the title compound were combined and dried via centrifugal evaporation. The estimated purity by LC/MS analysis was 98%. Two analytical LC/MS injections were used to determine the final purity. Injection 1 conditions: Column: Waters BEH C18, 2.0×50 mm, 1.7-µm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm, RT=1.49 min, LC/MS (M+H)=630.7. Injection 2 conditions: Column: Waters BEH C18, 2.0×50 mm, 1.7-µm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. RT=2.44 min, LC/MS (M+H)=630.7. $^1$H NMR (500 MHz, DMSO-d$_6$) δ 8.38 (br. s., 1H), 8.31 (br. s., 1H), 8.26 (br. s., 1H), 7.79 (br. s., 2H), 7.31 (br. s., 2H), 7.24 (br. s., 1H), 6.39 (br. s., 1H), 5.68 (br. s., 1H), 4.27 (br. s., 2H), 4.00 (br. s., 5H), 3.89 (br. s., 4H), 3.78 (br. s., 1H), 3.67 (br. s., 2H), 3.27 (br. s., 2H), 3.18 (br. s., 5H), 2.93 (br. s., 5H), 1.46 (br. s., 1H), 1.35 (br.

s., 3H), 0.82 (br. s., 1H); LC/MS (M+H)=630.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 187

N-[(2,4-Dimethoxyphenyl)methyl]-5-(dimethyl-1H-1,2,3-triazol-5-yl)-8-[(S)-oxan-4-yl(phenyl)methyl]-3,8,10-triazatricyclo[7.4.0.0²,⁷]trideca-1(9),2(7),3,5,10,12-hexaen-11-amine

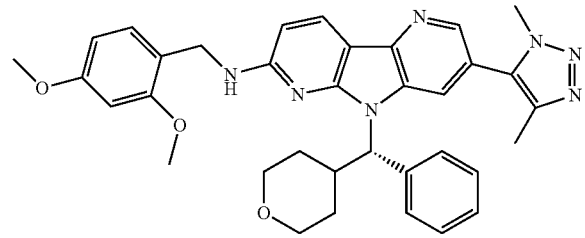 [SMILES: COc1ccc(CNc2ccc3c4ncc(-c5c(C)nnn5C)cc4n([C@H](c4ccccc4)C4CCOCC4)c3n2)c(OC)c1]

(S)-7-Chloro-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridine (120 mg, 0.254 mmol), (2,4-dimethoxyphenyl)-methanamine (424 mg, 2.54 mmol) and triethylamine (0.4 mL) were weighed into a vial and microwaved at 175° C. for 1.5 h. The reaction mixture was loaded directly onto a 24 g silica gel column, and subjected to purification on the ISCO. Elution the first 4 min with only DCM, then followed by 0-5% (10% 2M NH3/MeOH)/EtOAc to obtain 96% yield of the title compound. The final purity was determined by LC/MS: Injection conditions: Column: Waters BEH C18, 2.0×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.5-min hold at 100% B; Flow: 1.0 mL/min; Detection: UV at 220 nm, RT=1.98 min, LC/MS (M+H)=604.3. ¹H NMR (500 MHz, DMSO-d₆) δ 8.33 (s, 1H), 8.28 (br. s., 1H), 8.12 (d, J=8.4 Hz, 1H), 7.80 (t, J=5.5 Hz, 1H), 7.63 (d, J=4.4 Hz, 2H), 7.28-7.13 (m, 4H), 6.67-6.59 (m, 2H), 6.52 (dd, J=8.4, 1.8 Hz, 1H), 5.54 (br. s., 1H), 4.73-4.52 (m, 2H), 3.99 (s, 3H), 3.88-3.78 (m, 4H), 3.67 (d, J=10.3 Hz, 1H), 3.53-3.38 (m, 5H), 3.26-3.13 (m, 1H), 3.04 (t, J=11.0 Hz, 1H), 2.28 (s, 3H), 1.40-1.20 (m, 2H), 1.16-1.00 (m, 2H); LC/MS (M+H)=604.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 188

5-(Dimethyl-1H-1,2,3-triazol-5-yl)-11-(4-methanesulfonylpiperazin-1-yl)-8-[(S)-oxan-4-yl(phenyl)methyl]-3,8,10-triazatricyclo[7.4.0.0²,⁷]trideca-1(9),2(7),3,5,10,12-hexaene

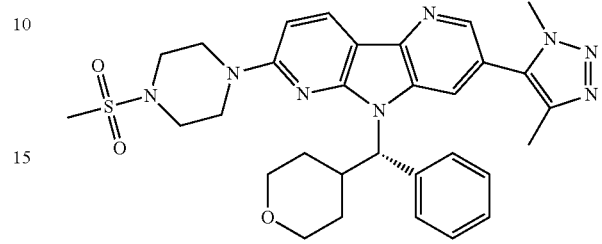

Following a procedure analogous to the reaction described in the synthesis of 4-[5-(dimethyl-1H-1,2,3-triazol-5-yl)-8-[(S)-oxan-4-yl(phenyl)methyl]-3,8,10-triazatricyclo[7.4.0.0²,⁷]trideca-1(9),2(7),3,5,10,12-hexaen-11-yl]-1λ⁶,4-thiomorpholine-1,1-dione, the title compound was obtained in 21% yield from and 1-(methylsulfonyl)piperazine. It was filtered and the crude (filtrate) was purified via preparative LC/MS with the following conditions: Column: XBridge C18, 19×mm, 5-μm particles; Mobile Phase A: 5:95 ACN: water with 10-mM NH₄OAc; Mobile Phase B: 95:5 ACN: water with 10-mM NH₄OAc; Gradient: 20-60% B over 20 min, then a 5-min hold at 100% B; Flow: 20 mL/min. Fractions containing the title compound were combined and dried via centrifugal evaporation. The estimated purity by LC/MS analysis was 98%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0% B, 0-100% B over 3 min, then a 0.5-min hold at 100% B; Flow: 1 mL/min; Detection: UV at 220 nm, RT=1.57 min, LC/MS (M+H)= 601.6. Injection 2 conditions: Column: Waters BEH C18, 2.0×50 mm, 1.7-μm particles; Mobile Phase A: 5:95 methanol:water with 10 mM NH₄OAc; Mobile Phase B: 95:5 methanol:water with 10 mM NH₄OAc; Temperature: 50° C.; Gradient: 0% B, 0-100% B over 3 min, then a 0.5-min hold at 100% B; Flow: 0.5 mL/min; Detection: UV at 220 nm, RT=2.47 min, LC/MS (M+H)=601.7. ¹H NMR (500 MHz, DMSO-d₆) δ 8.42 (s, 1H), 8.37-8.29 (m, 2H), 7.76 (d, J=7.3 Hz, 2H), 7.31 (t, J=7.5 Hz, 2H), 7.23 (t, J=7.3 Hz, 1H), 6.96 (d, J=8.8 Hz, 1H), 5.73 (br. s., 1H), 4.01 (s, 3H), 3.96-3.90 (m, 4H), 3.88 (d, J=9.9 Hz, 1H), 3.78 (d, J=10.6 Hz, 1H), 3.62 (br. s., 1H), 3.46-3.40 (m, 1H), 3.38-3.30 (m, 4H), 3.28 (t, J=12.1 Hz, 1H), 2.96 (s, 3H), 2.29 (s, 3H), 1.48 (br. s., 1H), 1.39 (d, J=10.3 Hz, 1H), 1.28 (br. s., 1H), 1.24 (br. s., 2H); LC/MS (M+H)=601.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 189

N-(2-Methanesulfonylethyl)-5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaen-11-amine

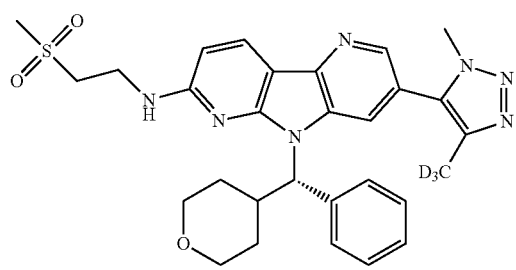 [SMILES: [2H]C([2H])([2H])c1nnn(C)c1-c1cnc2c3ccc(NCCS(C)(=O)=O)nc3n([C@H](c3ccccc3)C3CCOCC3)c2c1]

A microwaveable vial was charged with 11-chloro-5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaene (18.0 mg, 0.038 mmol), Xantphos (1.3 mg, 2.27 µmol), Cs$_2$CO$_3$ (24.6 mg, 0.076 mmol), Pd(OAc)$_2$ (0.4 mg, 1.9 µmol) and dioxane (2 mL). The air was replaced with argon. It was microwaved for 0.25 hr at 140° C. It was filtered and the crude material (filtrate) was purified via preparative LC/MS with the following conditions: Column: XBridge C18, 19×200 mm, 5-µm particles; Mobile Phase A: 5:95 ACN: water with 10-mM NH$_4$OAc; Mobile Phase B: 95:5 ACN: water with 10-mM NH$_4$OAc; Gradient: 15-55% B over 15 min, then a 5-min hold at 100% B; Flow: 20 mL/min. Fractions containing the title compound were combined and dried via centrifugal evaporation. The yield of the product was 1.3 mg, and its estimated purity by LC/MS analysis was 100%. Two analytical LC/MS injections were used to determine the final purity. Injection 1 conditions: Column: Waters BEH C18, 2.0×50 mm, 1.7-µm particles; Mobile Phase A: 5:95 ACN: water with 10 mM NH$_4$OAc; Mobile Phase B: 95:5 ACN: water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm, RT=1.39 min, LC/MS (M+H)=563.6. Injection 2 conditions: Column: Waters BEH C18, 2.0×50 mm, 1.7-µm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm, RT=2.26 min, LC/MS (M+H)=563.6. $^1$H NMR (500 MHz, DMSO-d$_6$) δ 8.38 (s, 1H), 8.35 (br. s., 1H), 8.15 (d, J=8.4 Hz, 1H), 7.81 (d, J=7.3 Hz, 2H), 7.70-7.64 (m, 1H), 7.31 (t, J=7.3 Hz, 2H), 7.23 (t, J=7.3 Hz, 1H), 6.57 (d, J=8.4 Hz, 1H), 5.72 (br. s., 1H), 4.01 (s, 3H), 3.96-3.92 (m, 1H), 3.86 (d, J=9.9 Hz, 1H), 3.78 (d, J=11.0 Hz, 1H), 3.69 (br. s., 1H), 3.57 (t, J=7.0 Hz, 2H), 3.35-3.28 (m, 3H), 3.09 (s, 3H), 1.90 (s, 3H), 1.47 (br. s., 1H), 1.38 (d, J=8.8 Hz, 1H), 1.30-1.20 (m, 2H); LC/MS (M+H)=563.2 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 190

4-[5-(Dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-11-yl]-2,6-dimethyl-1λ$^6$,4-thiomorpholine-1,1-dione, Diastereomer A

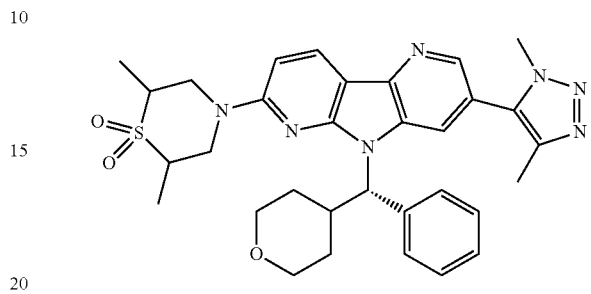

Following a procedure analogous to the reaction described in the synthesis of 4-[5-(dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-11-yl]-1λ$^6$,4-thiomorpholine-1,1-dione, the title compound (one of two diastereomers) was obtained in 2.5% yield from 11-chloro-5-(dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaene and 2,6-dimethylthiomorpholine 1,1-dioxide hydrochloride. The crude material was purified via preparative LC/MS with the following conditions: Column: XBridge C18, 19×200 mm, 5-µm particles; Mobile Phase A: 5:95 ACN: water with 10-mM NH$_4$OAc; Mobile Phase B: 95:5 ACN: water with 10-mM NH$_4$OAc; Gradient: 10-100% B over 25 min, then a 5-min hold at 100% B; Flow: 20 mL/min. Fractions containing the mixture of diastereomers were combined and dried via centrifugal evaporation. The material was further purified via preparative LC/MS with the following conditions: Column: XBridge Phenyl, 19×200 mm, 5-µm particles; Mobile Phase A: 5:95 methanol: water with 10-mM NH$_4$OAc; Mobile Phase B: 95:5 methanol: water with 10-mM NH$_4$OAc; Gradient: 40-80% B over 20 min, then a 5-min hold at 100% B; Flow: 20 mL/min. Fractions containing the mixture of diastereomers were combined and dried via centrifugal evaporation. The material was further purified through chiral separation. Column: ChiralPak AD-H, 21×250 mm, 5 µm; Mobile Phase: 20% EtOH/80% CO$_2$; Pressure: 150 bar, Temperature: 35° C.; Flow Rate: 40 mL/min; UV: 365 nm; Injection: 0.35 mL; Fraction Collection: Peak 1: 8.80'-11.25', Peak 2: 13.50'-16.00'. The yield of the products was 2.5% for one diastereomer (the title compound), and 9.5% for the other diastereomer. Absolute stereochemistry was not determined. The purity was 100% for both diastereomers. Two analytical LC/MS injections were used to determine the final purity. Injection 1 conditions: Column: Waters BEH C18, 2.0×50 mm, 1.7-µm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm; RT=1.62 min, LC/MS (M+H)=600.8. Injection 2 conditions: Column: Waters BEH C18, 2.0×50 mm, 1.7-µm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm, RT=2.56 min, LC/MS (M+H)=600.7. $^1$H NMR (500 MHz, DMSO-$d_6$) δ 8.42 (s, 1H), 8.38-8.30 (m, 2H), 7.74 (d, J=7.7 Hz, 2H), 7.35-7.28 (m, 2H), 7.27-7.20 (m, 1H), 7.08 (dd, J=8.6, 4.6 Hz, 1H), 5.76 (br. s., 1H), 4.34-4.23 (m, 2H), 4.03-3.96 (m, 3H), 3.92-3.85 (m, 1H), 3.76 (br. s., 1H), 3.56 (br. s., 1H), 3.25 (br. s., 1H), 2.31-2.25 (m, 3H), 1.53 (br. s., 1H), 1.41 (d, J=9.5 Hz, 1H), 1.31 (t, J=6.2 Hz, 6H), 1.23 (br. s., 1H), 1.17 (br. s., 1H); LC/MS (M+H)=600.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 191

4-[5-(Dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-11-yl]-2,6-dimethyl-1λ$^6$,4-thiomorpholine-1,1-dione Diastereomer B

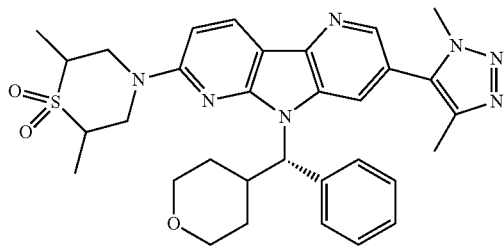 [SMILES: Cc1nnn(C)c1-c1cnc2c3ccc(N4CC(C)S(=O)(=O)C(C)C4)nc3n([C@H](c3ccccc3)C3CCOCC3)c2c1]

The title compound was the diastereomer obtained in 9.5% yield alongside the synthesis of 4-[5-(dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-11-yl]-2,6-dimethyl-1λ$^6$,4-thiomorpholine-1,1-dione, diastereomer A. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm; RT=1.62 min, LC/MS (M+H)=600.8. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm, RT=1.57 min, LC/MS (M+H)=600.7. $^1$H NMR (500 MHz, DMSO-$d_6$) δ 8.44 (s, 1H), 8.41-8.33 (m, 2H), 7.75 (d, J=7.3 Hz, 2H), 7.31 (t, J=7.5 Hz, 2H), 7.24 (t, J=7.0 Hz, 1H), 7.13 (d, J=8.8 Hz, 1H), 5.73 (br. s., 1H), 4.90 (d, J=8.8 Hz, 1H), 4.82 (d, J=11.0 Hz, 1H), 4.01 (s, 3H), 3.89 (d, J=7.3 Hz, 1H), 3.79 (d, J=10.3 Hz, 1H), 3.58 (br. s., 1H), 3.49-3.42 (m, 4H), 3.23 (br. s., 1H), 2.30 (s, 3H), 1.49 (br. s., 1H), 1.42 (d, J=9.5 Hz, 1H), 1.39-1.33 (m, 6H), 1.25 (br. s., 2H).

Example 192

5-(Dimethyl-1H-1,2,3-triazol-5-yl)-11-(4-methanesulfonylpiperidin-1-yl)-8-[(S)-oxan-4-yl(phenyl)methyl]-3,8,10-triazatricyclo[7.4.0.0$^{2,7}$]trideca-1(9),2(7),3,5,10,12-hexaene

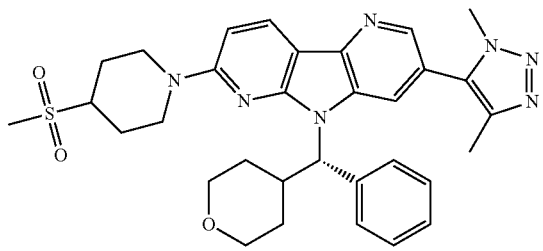 [SMILES: Cc1nnn(C)c1-c1cnc2c3ccc(N4CCC(S(C)(=O)=O)CC4)nc3n([C@H](c3ccccc3)C3CCOCC3)c2c1]

Following a procedure analogous to the reaction described in the synthesis of 5-(dimethyl-1H-1,2,3-triazol-5-yl)-11-(morpholin-4-yl)-8-[(S)-oxan-4-yl(phenyl)methyl]-3,8,10-triazatricyclo[7.4.0.0$^{2,7}$]trideca-1(9),2(7),3,5,10,12-hexaene, the title compound was made in 39% yield from 11-chloro-5-(dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaene and 4-(methylsulfonyl)piperidine. The crude material was purified via preparative LC/MS with the following conditions: Column: XBridge C18, 19×200 mm, 5-μm particles; Mobile Phase A: 5:95 ACN: water with 10-mM NH$_4$OAc; Mobile Phase B: 95:5 ACN: water with 10-mM NH$_4$OAc; Gradient: 25-65% B over 15 min, then a 5-min hold at 100% B; Flow: 20 mL/min. Fractions containing the title compound were combined and dried via centrifugal evaporation. The estimated purity by LC/MS analysis was 97%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm, RT=1.48 min, LC/MS (M+H)=600.5. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection, RT=2.38 min, LC/MS (M+H)=600.6. $^1$H NMR (500 MHz, DMSO-$d_6$) δ 8.40 (s, 1H), 8.34 (br. s., 1H), 8.29 (d, J=8.8 Hz, 1H), 7.77 (d, J=7.7 Hz, 2H), 7.33-7.26 (m, 2H), 7.25-7.20 (m, 1H), 6.96 (d, J=9.2 Hz, 1H), 5.69 (br. s., 1H), 4.74 (br. s., 2H), 4.00 (s, 3H), 3.88 (d, J=12.5 Hz, 1H), 3.78 (d, J=11.7 Hz, 1H), 3.63 (br. s., 1H), 3.26 (t, J=10.6 Hz, 1H), 3.18 (t, J=12.3 Hz, 2H), 2.98 (s, 3H), 2.29 (s, 3H), 2.21 (d, J=12.1 Hz, 2H), 1.69 (d, J=12.8 Hz, 2H), 1.51-1.33 (m, 2H), 1.24 (br. s., 2H); LC/MS (M+H)=600.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 193

2,6-Dimethyl-4-{5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaen-11-yl}-1λ$^6$,4-thiomorpholine-1,1-dione

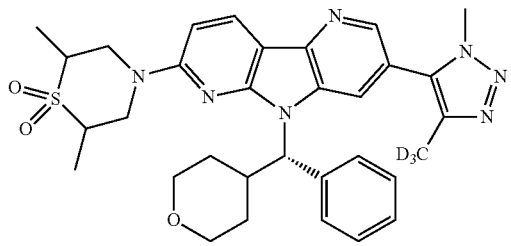 [SMILES: [2H]C([2H])([2H])c1nnn(C)c1-c1cnc2c3ccc(N4CC(C)S(=O)(=O)C(C)C4)nc3n([C@H](c3ccccc3)C3CCOCC3)c2c1]

Following a procedure analogous to the reaction described in the synthesis of 4-[5-(dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-11-yl]-1λ$^6$,4-thiomorpholine-1,1-dione, the title compound was obtained in 27% yield from 11-chloro-5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaene and 2,6-dimethylthiomorpholine 1,1-dioxide. The crude material was purified via preparative LC/MS with the following conditions: Column: XBridge C18, 19×200 mm, 5-μm particles; Mobile Phase A: 5:95 ACN: water with 10-mM NH$_4$OAc; Mobile Phase B: 95:5 ACN: water with 10-mM NH$_4$OAc; Gradient: 25-65% B over 15 min, then a 5-min hold at 100% B; Flow: 20 mL/min. Fractions containing the title compound were combined and dried via centrifugal evaporation. The estimated purity by LC/MS analysis was 98%. The absolute configuration of the methyl groups was not determined. Two analytical LC/MS injections were used to determine the final purity. Injection 1 conditions: Column: Waters BEH C18, 2.0×50 mm, 1.7-μm particles; Mobile Phase A: 5:95 ACN: water with 10 mM NH$_4$OAc; Mobile Phase B: 95:5 ACN: water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm, RT=1.63 min, LC/MS (M+H)=603.3. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm, RT=2.57 min, LC/MS (M+H)=603.3. $^1$H NMR (500 MHz, DMSO-d$_6$) δ 8.44 (s, 1H), 8.37 (d, J=8.8 Hz, 1H), 7.95 (s, 1H), 7.75 (d, J=7.7 Hz, 2H), 7.31 (t, J=7.5 Hz, 2H), 7.24 (t, J=7.3 Hz, 1H), 7.13 (d, J=8.8 Hz, 1H), 5.74 (br. s., 1H), 4.90 (d, J=9.5 Hz, 1H), 4.82 (d, J=12.5 Hz, 1H), 4.02 (s, 3H), 3.90 (d, J=11.4 Hz, 1H), 3.79 (d, J=11.7 Hz, 1H), 3.57 (br. s., 1H), 3.42 (s, 1H), 3.38-3.28 (m, 6H), 3.27-3.19 (m, 1H), 1.49 (br. s., 1H), 1.47-1.39 (m, 1H), 1.38-1.33 (m, 6H), 1.25 (br. s., 2H). LC/MS (M+H)=603.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 194

5-(Dimethyl-1H-1,2,3-triazol-5-yl)-11-(methylsulfanyl)-8-[(S)-oxan-4-yl(phenyl)methyl]-3,8,10-triazatricyclo[7.4.0.0$^{2,7}$]trideca-1(9),2(7),3,5,10,12-hexaene

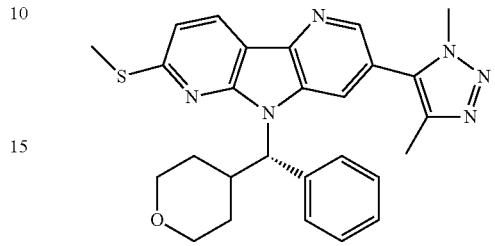

To a microwave vial was added (S)-7-chloro-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridine (11.0 mg, 0.023 mmol), followed by sodium methanethiolate (2.4 mg, 0.035 mmol). To these were added DMF (1.5 mL) and the resulting mixture heated in the microwave at 125° C. for 10 min. It was quenched by adding one drop of water and stirred for a few min at room temperature. It was then filtered and the filtrate (crude) was purified via preparative LC/MS with the following conditions: Column: XBridge C18, 19×200 mm, 5-μm particles; Mobile Phase A: 5:95 ACN: water with 10-mM NH$_4$OAc; Mobile Phase B: 95:5 ACN: water with 10-mM NH$_4$OAc; Gradient: 45-85% B over 15 min, then a 5-min hold at 100% B; Flow: 20 mL/min. Fractions containing the title compound were combined and dried via centrifugal evaporation. The yield of the product was 42%, and its estimated purity by LC/MS analysis was 100%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm, RT=1.82 min, LC/MS (M+H)=485.2. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm, RT=3.01 min, LC/MS (M+H)=485.4. $^1$H NMR (500 MHz, DMSO-d$_6$) δ 8.61-8.51 (m, 2H), 8.43 (d, J=8.1 Hz, 1H), 7.79 (d, J=7.3 Hz, 2H), 7.38-7.29 (m, 3H), 7.25 (d, J=7.0 Hz, 1H), 5.84 (br. s., 1H), 4.04 (s, 3H), 3.89 (d, J=11.7 Hz, 1H), 3.78 (d, J=10.6 Hz, 1H), 3.72 (br. s., 1H), 3.42-3.33 (m, 2H), 3.28 (t, J=11.9 Hz, 1H), 2.80 (s, 3H), 2.31 (s, 3H), 1.49 (br. s., 1H), 1.47-1.37 (m, 1H), 1.33-1.18 (m, 2H). LC/MS (M+H)=485.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 195

5-(Dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaene-11-sulfonamide

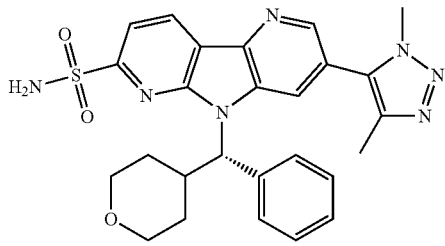 [SMILES: Cc1nnn(C)c1-c1cnc2c3ccc(S(N)(=O)=O)nc3n([C@H](c3ccccc3)C3CCOCC3)c2c1]

To (S)-7-chloro-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridine (25.0 mg, 0.053 mmol) dissolved in 1.5 mL DSMO was added Na$_2$S/9H$_2$O (0.264 mmol). The resulting mixture was heated to 170° C. for 20 min in the microwave. The reaction mixture was diluted with brine and extracted three times with 10% MeOH/EtOAc. The combined organic layer was concentrated on the rotary evaporator, and dissolved in 10 mL of MeCN. The contents of a separate vial containing 0.6 mL of 30% hydrogen peroxide, 20 mL of MeCN and 0.14 mL of thionyl chloride was slowly added, then stirred for 4 min at room temperature. Then 1 mL of 28% ammonium hydroxide was added and cooled to 0° C. To this mixture was added 2 drops of pyridine, and then the ice-bath was removed. The resulting reaction mixture was stirred for 0.5 hr. The reaction was quenched by adding 5 mL of 1M HCl, and then neutralized with dil. K$_2$CO$_3$. EtOAc was used to extract the products, and the organic layer was concentrated on the rotary evaporator. The residue was dissolved in 2 mL of dioxane, filtered and purified via preparative LC/MS with the following conditions: Column: XBridge C18, 19×200 mm, 5-μm particles; Mobile Phase A: 5:95 methanol:water with 10-mM NH$_4$OAc; Mobile Phase B: 95:5 methanol:water with 10-mM NH$_4$OAc; Gradient: 40-80% B over 15 min, then a 5-min hold at 100% B; Flow: 20 mL/min. Fractions containing the title compound were combined and dried via centrifugal evaporation. The yield of the product was 2.5 mg, and its estimated purity by LC/MS analysis was 100%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm, RT=1.31 min, LC/MS (M+H)=518.5. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm, RT=2.30 min, LC/MS (M+H)=518.4. $^1$H NMR (500 MHz, DMSO-d$_6$) δ 8.87 (d, J=8.1 Hz, 1H), 8.74-8.64 (m, 2H), 7.96 (d, J=7.7 Hz, 1H), 7.90 (d, J=7.3 Hz, 2H), 7.80 (s, 2H), 7.31 (t, J=7.2 Hz, 2H), 7.25 (t, J=7.2 Hz, 1H), 5.98 (br. s., 1H), 4.06 (s, 3H), 3.88 (d, J=10.6 Hz, 1H), 3.83 (br. s., 1H), 3.73 (d, J=10.6 Hz, 1H), 3.47 (t, J=11.4 Hz, 1H), 3.39 (d, J=1.1 Hz, 1H), 3.32-3.24 (m, 1H), 2.33 (s, 3H), 1.52 (br. s., 1H), 1.47-1.37 (m, 1H), 1.30 (d, J=8.4 Hz, 1H), 1.12 (d, J=11.4 Hz, 1H). LC/MS (M+H)=518.2 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 196

5-(Dimethyl-1H-1,2,3-triazol-5-yl)-8-[(S)-oxan-4-yl(phenyl)methyl]-11-(pyrrolidine-1-sulfonyl)-3,8,10-triazatricyclo[7.4.0.0$^{2,7}$]trideca-1(9),2(7),3,5,10,12-hexaene

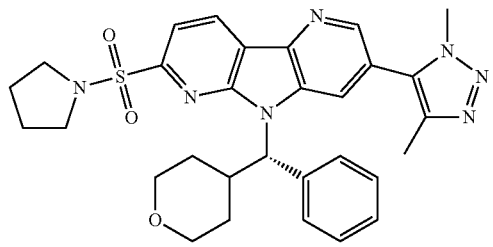 [SMILES: Cc1nnn(C)c1-c1cnc2c3ccc(S(=O)(=O)N4CCCC4)nc3n([C@H](c3ccccc3)C3CCOCC3)c2c1]

Following a procedure analogous to the reaction described in the synthesis of 5-(dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaene-11-sulfonamide, the title compound was obtained in 13% yield from 11-chloro-5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaene and pyrrolidine. The crude material was purified via preparative LC/MS with the following conditions: Column: XBridge C18, 19×200 mm, 5-μm particles; Mobile Phase A: 5:95 ACN:water with 10-mM NH$_4$OAc; Mobile Phase B: 95:5 ACN:water with 10-mM NH$_4$OAc; Gradient: 30-70% B over 15 min, then a 5-min hold at 100% B; Flow: 20 mL/min. Fractions containing the title compound were combined and dried via centrifugal evaporation. The estimated purity by LC/MS analysis was 95%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm, RT=1.75 min, LC/MS (M+H)=572.5. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm, RT=2.59 min, LC/MS (M+H)=572.5. $^1$H NMR (500 MHz, DMSO-d$_6$) δ 8.92 (d, J=7.7 Hz, 1H), 8.76-8.67 (m, 2H), 7.96 (d, J=7.7 Hz, 1H), 7.81 (d, J=7.3 Hz, 2H), 7.36-7.30 (m, 2H), 7.29-7.21 (m, 1H), 5.89 (d, J=8.8 Hz, 1H), 4.05 (s, 3H), 3.90 (d, J=5.5 Hz, 1H), 3.77 (d, J=12.1 Hz, 1H), 3.66 (d, J=10.3 Hz, 1H), 3.59-3.46 (m, 4H), 3.39 (s, 1H), 3.21 (t, J=11.4 Hz, 1H), 2.33 (s, 3H), 1.76 (br. s., 4H), 1.53 (br. s., 1H), 1.47-1.35 (m, 1H), 1.33-1.21 (m, 1H), 1.16 (d, J=10.6 Hz, 1H). LC/MS (M+H)=572.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 197

5-(Dimethyl-1H-1,2,3-triazol-5-yl)-11-(morpholine-4-sulfonyl)-8-[(S)-oxan-4-yl(phenyl)methyl]-3,8,10-triazatricyclo[7.4.0.0$^{2,7}$]trideca-1(9),2(7),3,5,10,12-hexaene

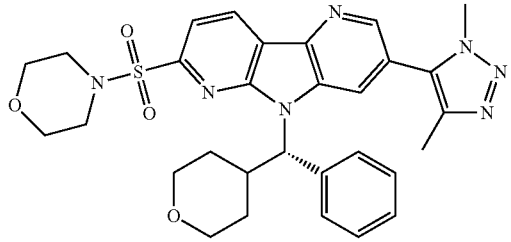 [SMILES: Cc1nnn(C)c1-c1cnc2c3ccc(S(=O)(=O)N4CCOCC4)nc3n([C@H](c3ccccc3)C3CCOCC3)c2c1]

Following a procedure analogous to the reaction described in the synthesis of 5-(dimethyl-1H-1,2,3-triazol-5-yl)-8-[(S)-oxan-4-yl(phenyl)methyl]-3,8,10-triazatricyclo [7.4.0.0$^{2,7}$]trideca-1(9),2(7),3,5,10,12-hexaene-11-sulfonamide, the title compound was obtained in 8% yield from 11-chloro-5-[4-($^2$H$_3$)methyl-1-methyl-1H-1,2,3-triazol-5-yl]-8-[(S)-oxan-4-yl(phenyl)methyl]-3,8,10-triazatricyclo [7.4.0.0$^{2,7}$]trideca-1(9),2(7),3,5,10,12-hexaene and morpholine. The crude material was purified via preparative LC/MS with the following conditions: Column: XBridge C18, 19×200 mm, 5-μm particles; Mobile Phase A: 5:95 ACN: water with 10-mM NH$_4$OAc; Mobile Phase B: 95:5 ACN: water with 10-mM NH$_4$OAc; Gradient: 20-60% B over 15 min, then a 5-min hold at 100% B; Flow: 20 mL/min. Fractions containing the title compound were combined and dried via centrifugal evaporation. The estimated purity by LC/MS analysis was 96%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm, RT=1.61 min, LC/MS (M+H)= 588.5. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm, RT=2.50 min, LC/MS (M+H)=588.5. $^1$H NMR (500 MHz, DMSO-d$_6$) δ 8.94 (d, J=8.1 Hz, 1H), 8.82-8.74 (m, 2H), 7.95 (d, J=8.1 Hz, 1H), 7.86 (d, J=7.3 Hz, 2H), 7.35-7.30 (m, 2H), 7.29-7.23 (m, 1H), 5.87 (d, J=10.3 Hz, 1H), 4.08 (s, 3H), 3.93-3.86 (m, 1H), 3.77 (d, J=12.8 Hz, 1H), 3.71 (t, J=4.4 Hz, 5H), 3.42-3.19 (m, 6H), 2.35 (s, 3H), 1.51 (d, J=12.5 Hz, 1H), 1.46-1.36 (m, 1H), 1.29 (d, J=8.1 Hz, 1H), 1.17 (d, J=12.5 Hz, 1H). LC/MS (M+H)=588.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 198

5-(Dimethyl-1H-1,2,3-triazol-5-yl)-11-[(4-methyl-piperazin-1-yl)sulfonyl]-8-[(S)-oxan-4-yl(phenyl) methyl]-3,8,10-triazatricyclo[7.4.0.0$^{2,7}$]trideca-1(9),2(7),3,5,10,12-hexaene

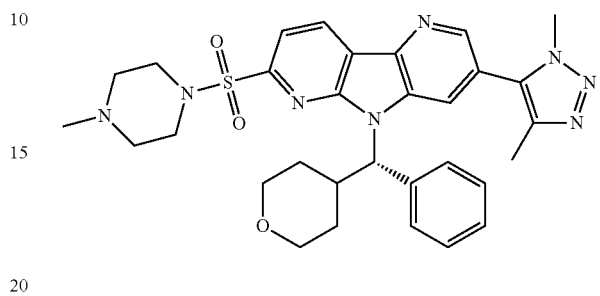

Following a procedure analogous to the reaction described in the synthesis of 5-(dimethyl-1H-1,2,3-triazol-5-yl)-8-[(S)-oxan-4-yl(phenyl)methyl]-3,8,10-triazatricyclo [7.4.0.0$^{2,7}$]trideca-1(9),2(7),3,5,10,12-hexaene-11-sulfonamide, the title compound was obtained in 7% yield from 11-chloro-5-[4-($^2$H$_3$)methyl-1-methyl-1H-1,2,3-triazol-5-yl]-8-[(S)-oxan-4-yl(phenyl)methyl]-3,8,10-triazatricyclo [7.4.0.0$^{2,7}$]trideca-1(9),2(7),3,5,10,12-hexaene and 1-methylpiperazine. The crude material was purified via preparative LC/MS with the following conditions: Column: XBridge C18, 19×200 mm, 5-μm particles; Mobile Phase A: 5:95 ACN: water with 10-mM NH$_4$OAc; Mobile Phase B: 95:5 ACN: water with 10-mM NH$_4$OAc; Gradient: 20-60% B over 25 min, then a 5-min hold at 100% B; Flow: 20 mL/min. Fractions containing the title compound were combined and dried via centrifugal evaporation. The estimated purity by LC/MS analysis was 97%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm, RT=1.56 min, LC/MS (M+H)= 601.5. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm, RT=2.51 min, LC/MS (M+H)=601.5. $^1$H NMR (500 MHz, DMSO-d$_6$) δ 8.93 (d, J=8.1 Hz, 1H), 8.81-8.73 (m, 2H), 7.94 (d, J=8.1 Hz, 1H), 7.87 (d, J=7.3 Hz, 2H), 7.32 (t, J=7.5 Hz, 2H), 7.26 (t, J=7.0 Hz, 1H), 5.86 (d, J=10.3 Hz, 1H), 4.08 (s, 3H), 3.93-3.85 (m, 2H), 3.76 (d, J=9.9 Hz, 1H), 3.71 (br. s., 1H), 3.44-3.29 (m, 4H), 3.25 (t, J=11.2 Hz, 1H), 2.43 (br. s., 4H), 2.34 (s, 3H), 2.18 (s, 3H), 1.49 (br. s., 1H), 1.45-1.35 (m, 1H), 1.34-1.22 (m, 1H), 1.15 (d, J=11.7 Hz, 1H). LC/MS (M+H)=601.4 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 199

5-(Dimethyl-1H-1,2,3-triazol-5-yl)-N-methyl-8-[(S)-oxan-4-yl(phenyl)methyl]-3,8,10-triazatricyclo[7.4.0.0²,⁷]trideca-1(9),2(7),3,5,10,12-hexaene-11-sulfonamide

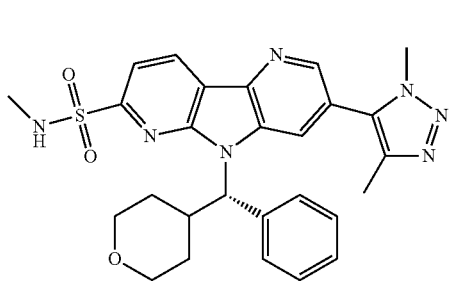 [SMILES: CNS(=O)(=O)c1ccc2c3ncc(-c4c(C)nnn4C)cc3n([C@H](c3ccccc3)C3CCOCC3)c2n1]

Following a procedure analogous to the reaction described in the synthesis of 5-(dimethyl-1H-1,2,3-triazol-5-yl)-8-[(S)-oxan-4-yl(phenyl)methyl]-3,8,10-triazatricyclo[7.4.0.0²,⁷]trideca-1(9),2(7),3,5,10,12-hexaene-11-sulfonamide, the title compound was obtained in 21% yield from 11-chloro-5-[4-(²H₃)methyl-1-methyl-1H-1,2,3-triazol-5-yl]-8-[(S)-oxan-4-yl(phenyl)methyl]-3,8,10-triazatricyclo[7.4.0.0²,⁷]trideca-1(9),2(7),3,5,10,12-hexaene and methanamine. The crude material was purified via preparative LC/MS with the following conditions: Column: XBridge C18, 19×200 mm, 5-μm particles; Mobile Phase A: 5:95 ACN: water with 10-mM NH₄OAc; Mobile Phase B: 95:5 ACN: water with 10-mM NH₄OAc; Gradient: 20-60% B over 15 min, then a 5-min hold at 100% B; Flow: 20 mL/min. Fractions containing the title compound were combined and dried via centrifugal evaporation. The estimated purity by LC/MS analysis was 93%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0% B, 0-100% B over 3 min, then a 0.5-min hold at 100% B; Flow: 1 mL/min; Detection: UV at 220 nm, RT=1.47 min, LC/MS (M+H)=532.2. Injection 2 conditions: Column: Waters BEH C18, 2.0×50 mm, 1.7-μm particles; Mobile Phase A: 5:95 methanol:water with 10 mM NH₄OAc; Mobile Phase B: 95:5 methanol:water with 10 mM NH₄OAc; Temperature: 50° C.; Gradient: 0% B, 0-100% B over 3 min, then a 0.5-min hold at 100% B; Flow: 0.5 mL/min; Detection: UV at 220 nm, RT=2.29 min, LC/MS (M+H)=532.2. ¹H NMR (500 MHz, DMSO-d₆) δ 8.89 (d, J=8.1 Hz, 1H), 8.72 (s, 2H), 7.96 (s, 1H), 7.88 (d, J=7.3 Hz, 2H), 7.35-7.29 (m, 2H), 7.27-7.22 (m, 1H), 5.91 (br. s., 1H), 4.06 (s, 3H), 3.81-3.71 (m, 2H), 3.33 (br. s., 1H), 3.26 (t, J=11.2 Hz, 1H), 2.71 (s, 3H), 2.33 (s, 3H), 1.98 (br. s., 1H), 1.94 (br. s., 1H), 1.51 (br. s., 1H), 1.44-1.37 (m, 1H), 1.26 (dd, J=19.1, 10.6 Hz, 2H). LC/MS (M+H)=532.1 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 200

5-(Dimethyl-1H-1,2,3-triazol-5-yl)-11-methanesulfinyl-8-[(S)-oxan-4-yl(phenyl)methyl]-3,8,10-triazatricyclo[7.4.0.0²,⁷]trideca-1(9),2(7),3,5,10,12-hexaene

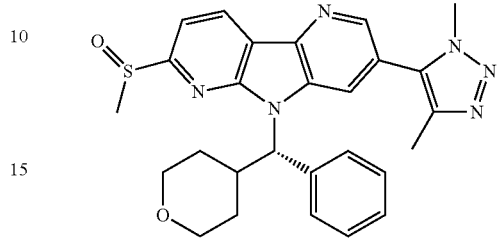

To a microwave vial was added (S)-7-chloro-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridine (43.0 mg, 0.091 mmol), followed by sodium methanethiolate (9.6 mg, 0.136 mmol) and DMF (1.5 mL). The resulting mixture was heated in the microwave at 125° C. for 10 min. It was quenched by adding one drop of water and stirred for five min at room temperature. It was diluted with 10% MeOH/EtOAc and washed with brine. The organic layer was concentrated and then 10 mL of methanol/water, 1:1 ratio was added and stirred at room temperature. To this stirring solution was added FeCl₃ (2.9 mg, 0.018 mmol) followed by 30% water solution of H₂O₂ (15.5 mg, 0.455 mmol). After 4 h, it was diluted with 10% MeOH/EtOAC and washed with brine. The organic layer was concentrated, dissolved in 2 mL of MeOH. This crude material was purified via preparative LC/MS with the following conditions: Column: XBridge C18, 19×200 mm, 5-μm particles; Mobile Phase A: 5:95 ACN: water with 10-mM NH₄OAc; Mobile Phase B: 95:5 ACN: water with 10-mM NH₄OAc; Gradient: 20-60% B over 15 min, then a 5-min hold at 100% B; Flow: 20 mL/min. Fractions containing the title compound were combined and dried via centrifugal evaporation. The estimated purity by LC/MS analysis was 97%. Two analytical LC/MS injections were used to determine the final purity. Injection 1 conditions: Column: Waters BEH C18, 2.0×50 mm, 1.7-μm particles; Mobile Phase A: 5:95 ACN: water with 10 mM NH₄OAc; Mobile Phase B: 95:5 ACN: water with 10 mM NH₄OAc; Temperature: 50° C.; Gradient: 0% B, 0-100% B over 3 min, then a 0.5-min hold at 100% B; Flow: 1 mL/min; Detection: UV at 220 nm, RT=1.33 min, LC/MS (M+H)=501.4. Injection 2 conditions: Column: Waters BEH C18, 2.0×50 mm, 1.7-μm particles; Mobile Phase A: 5:95 methanol:water with 10 mM NH₄OAc; Mobile Phase B: 95:5 methanol:water with 10 mM NH₄OAc; Temperature: 50° C.; Gradient: 0% B, 0-100% B over 3 min, then a 0.5-min hold at 100% B; Flow: 0.5 mL/min; Detection: UV at 220 nm, RT=2.46 min, LC/MS (M+H)=501.4. ¹H NMR (500 MHz, DMSO-d₆) δ 8.92 (dd, J=7.9, 4.6 Hz, 1H), 8.73-8.63 (m, 2H), 7.92 (dd, J=7.9, 5.7 Hz, 1H), 7.78 (t, J=6.6 Hz, 2H), 7.32 (dd, J=7.3, 3.7 Hz, 2H), 7.26 (d, J=8.1 Hz, 1H), 5.91 (br. s., 1H), 4.06 (s, 3H), 3.75 (br. s., 1H), 3.65 (d, J=16.9 Hz, 1H), 3.37 (d, J=15.0 Hz, 2H), 3.24 (t, J=11.6 Hz, 1H), 3.03 (s, 2H), 2.98 (s, 2H), 2.33 (s, 3H), 1.57 (d, J=12.5 Hz, 1H), 1.51-1.36 (m, 2H), 1.34-1.21 (m, 1H), 1.16 (d, J=13.2 Hz, 1H), 1.13-1.02 (m, 1H). LC/MS (M+H)=501.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 201

11-Methanesulfonyl-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(9),2(7),3,5,10,12-hexaene

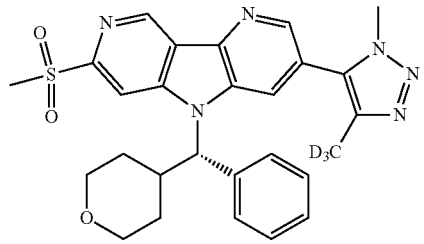 [SMILES: [2H]C([2H])([2H])c1nnn(C)c1-c1cnc2c3cnc(S(C)(=O)=O)cc3n([C@H](c3ccccc3)C3CCOCC3)c2c1]

11-Chloro-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(9),2(7),3,5,10,12-hexaene (60 mg, 0.126 mmol), sodium methanesulfinate (15.4 mg, 0.151 mmol), bis((trifluoromethyl)sulfonyl)copper (6.2 mg, 0.019 mmol) and N1,N2-dimethylethane-1,2-diamine (3.3 mg, 0.038 mmol) were weighed into a vial, and then 3 mL DMSO was added and sealed under nitrogen. The reaction vial was heated to 100° C. and held at that temperature for 24 h. It was cooled to room temperature, diluted with 10% MeOH/EtOAc, and washed twice with brine. The organic layer was dried over MgSO$_4$, and concentrated to obtain a crude mixture. This was taken up in 2 mL DMF and purified via preparative LC/MS with the following conditions: Column: XBridge C18, 19×200 mm, 5-µm particles; Mobile Phase A: 5:95 ACN: water with 10-mM NH$_4$OAc; Mobile Phase B: 95:5 ACN: water with 10-mM NH$_4$OAc; Gradient: 20-60% B over 15 min, then a 5-min hold at 100% B; Flow: 20 mL/min. Fractions containing the title compound were combined and dried via centrifugal evaporation. The yield of the product was 16%, and its estimated purity by LC/MS analysis was 100%. Two analytical LC/MS injections were used to determine the final purity. Injection 1 conditions: Column: Waters BEH C18, 2.0×50 mm, 1.7-µm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.5-min hold at 100% B; Flow: 1.0 mL/min; Detection: UV at 220 nm, RT=1.38 min, LC/MS (M+H)=520.0. Injection 2 conditions: Column: Waters BEH C18, 2.0×50 mm, 1.7-µm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0-100% B over 3 min, then a 0.5-min hold at 100% B; Flow: 0.5 mL/min; Detection: UV at 220 nm, RT=2.50 min, LC/MS (M+H)=520.0. $^1$H NMR (500 MHz, DMSO-d$_6$) δ 9.59 (s, 1H), 8.93 (br. s., 1H), 8.78 (s, 1H), 8.63 (br. s., 1H), 7.69 (d, J=7.3 Hz, 2H), 7.40-7.33 (m, 2H), 7.32-7.26 (m, 1H), 6.16 (d, J=11.0 Hz, 1H), 4.01 (s, 3H), 3.90 (d, J=9.2 Hz, 1H), 3.73 (d, J=9.9 Hz, 1H), 3.52-3.46 (m, 1H), 3.44 (s, 3H), 3.25 (t, J=11.6 Hz, 1H), 1.75-1.59 (m, 2H), 1.36 (d, J=8.1 Hz, 1H), 0.92 (d, J=12.1 Hz, 1H). LC/MS (M+H)=520.2 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 202

1-{5-[4-($^2$H$_3$)Methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaen-11-yl}ethan-1-one

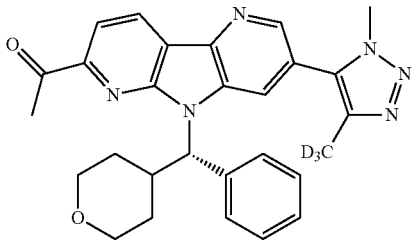 [SMILES: [2H]C([2H])([2H])c1nnn(C)c1-c1cnc2c3ccc(C(C)=O)nc3n([C@H](c3ccccc3)C3CCOCC3)c2c1]

Following a procedure analogous to the reaction described in the synthesis of 1-[5-(dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-11-yl]ethan-1-one, the title compound was obtained in 89% yield from 11-chloro-5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaene and tributyl(1-ethoxyvinyl)stannane. The crude mixture was purified using a 24 g silica gel column on a Biotage, eluting with 5-100% EtOAc/hexanes. The estimated purity by LC/MS analysis was 95%. Two analytical LC/MS injections were used to determine the final purity. Injection 1 conditions: Column: Waters BEH C18, 2.0×50 mm, 1.7-µm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.5-min hold at 100% B; Flow: 1.0 mL/min; Detection: UV at 220 nm, RT=1.78 min, LC/MS (M+H)=484.1. Injection 2 conditions: Column: Waters BEH C18, 2.0×50 mm, 1.7-µm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0-100% B over 3 min, then a 0.5-min hold at 100% B; Flow: 0.5 mL/min; Detection: UV at 220 nm, RT=3.09 min, LC/MS (M+H)=484.0. $^1$H NMR (500 MHz, DMSO-d$_6$) δ 8.79 (d, J=7.7 Hz, 1H), 8.75-8.68 (m, 2H), 8.02 (d, J=8.1 Hz, 1H), 7.87 (d, J=7.7 Hz, 2H), 7.34 (t, J=7.5 Hz, 2H), 7.25 (t, J=7.2 Hz, 1H), 5.93 (br. s., 1H), 4.08 (s, 3H), 3.91 (d, J=9.9 Hz, 1H), 3.77 (d, J=11.7 Hz, 1H), 3.46-3.38 (m, 1H), 3.35 (d, J=4.8 Hz, 1H), 3.30 (t, J=11.2 Hz, 1H), 2.93 (s, 3H), 1.53 (d, J=11.0 Hz, 1H), 1.49-1.39 (m, 1H), 1.38-1.27 (m, 1H), 1.22 (d, J=12.1 Hz, 1H). LC/MS (M+H)=484.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 203

11-(3,6-Dihydro-2H-thiopyran-4-yl)-5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaene

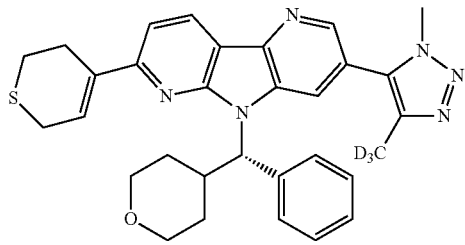 [SMILES: [2H]C([2H])([2H])c1nnn(C)c1-c1cnc2c3ccc(C4=CCSCC4)nc3n([C@H](c3ccccc3)C3CCOCC3)c2c1]

11-Chloro-5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaene (200 mg, 0.420 mmol) was weighed into a 50 mL round bottom flask, followed by the addition of 2-(3,6-dihydro-2H-thiopyran-4-yl)-4,4,5,5-tetramethyl-1,3,2-dioxaborolane (114 mg, 0.504 mmol), PdCl$_2$(dppf)$_2$.DCM (34.4 mg, 0.042 mmol), bis(di-tert-butyl(4-dimethylaminophenyl)phosphine)dichloropalladium(II) (8.9 mg, 0.013 mmol), and triethylamine (0.585 mL, 4.20 mmol). The air was replaced with N$_2$, and the resulting mixture heated to 85° C. with stirring, for 4 h. It was cooled to room temperature, diluted with EtOAc, washed with brine, dried over MgSO$_4$, and concentrated to obtain a crude mixture. This was subjected to a 40 g silica gel column chromatography on a Biotage eluting with 0-10% (10% 2M NH$_3$ in MeOH/EtOAc)/EtOAc to obtain 227 mg (71%) of the title compound. $^1$H NMR (500 MHz, DMSO-d$_6$) δ 8.64-8.48 (m, 3H), 7.78 (d, J=7.3 Hz, 2H), 7.31 (t, J=7.3 Hz, 2H), 7.26-7.15 (m, 2H), 5.86 (br. s., 1H), 4.03 (s, 3H), 3.89 (d, J=8.8 Hz, 1H), 3.76 (d, J=9.9 Hz, 2H), 3.35-3.49 (m, 4H), 3.25 (t, J=11.0 Hz, 1H), 2.99 (d, J=5.5 Hz, 3H), 1.50 (br. s., 2H), 1.41 (d, J=10.3 Hz, 1H), 1.28-1.18 (m, 2H). LC/MS (M+H)=540.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 204

4-{5-[4-($^2$H$_3$)Methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaen-11-yl}-3,6-dihydro-2H-1λ$^6$-thiopyran-1,1-dione 11-(3,6-Dihydro-2H-thiopyran-4-yl)-5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaene (93 mg, 0.172 mmol), was dissolved DCM (25 mL) and cooled to −78° C. under nitrogen. The solid 3-chlorobenzoperoxoic acid (77 mg, 0.345 mmol) was added and stirred. After 0.5 hr, the cooling bath was removed, and the reaction allowed to warm to room temperature. After 2 hr, the reaction was quenched by adding saturated aq. Na$_2$S$_2$O$_3$. The DCM was removed on the rotary evaporator, and the residue diluted and stirred with 10% MeOH/EtOAc. The organic layer was separated and redissolved in 2 mL of MeOH, filtered and purified via preparative LC/MS with the following conditions: Column: XBridge C18, 19×200 mm, 5-μm particles; Mobile Phase A: 5:95 methanol: water with 10-mM NH$_4$OAc; Mobile Phase B: 95:5 methanol: water with 10-mM NH$_4$OAc; Gradient: 45-90% B over 20 min, then a 5-min hold at 100% B; Flow: 20 mL/min. Fractions containing the title compound were combined and dried via centrifugal evaporation. The yield of the product was 59%, and its estimated purity by LC/MS analysis was 100%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm, RT=1.46 min, LC/MS (M+H)=572.3. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm, RT=2.34 min, LC/MS (M+H)=572.3. $^1$H NMR (500 MHz, DMSO-d$_6$) δ 8.65-8.59 (m, 2H), 8.56 (br. s., 1H), 7.75 (d, J=8.1 Hz, 1H), 7.79 (d, J=7.7 Hz, 2H), 7.32 (t, J=7.5 Hz, 2H), 7.24 (t, J=7.3 Hz, 1H), 6.94 (br. s., 1H), 5.92 (br. s., 1H), 4.10 (br. s., 2H), 4.04 (s, 3H), 3.90 (d, J=10.6 Hz, 1H), 3.76 (d, J=11.4 Hz, 2H), 3.56-3.50 (m, 2H), 3.49-3.40 (m, 2H), 3.37 (s, 1H), 3.27 (t, J=11.7 Hz, 1H), 1.53 (br. s., 1H), 1.48-1.37 (m, 1H), 1.34-1.23 (m, 1H), 1.18 (d, J=11.4 Hz, 1H); LC/MS (M+H)=572.2 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 205

4-{5-[4-($^2$H$_3$)Methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaen-11-yl}-1λ$^6$-thiane-1,1-dione

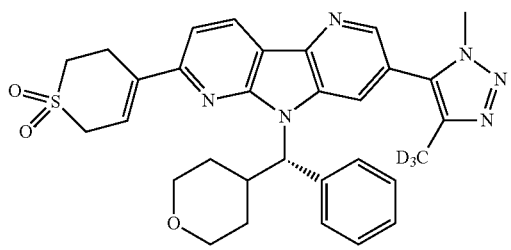 [SMILES: [2H]C([2H])([2H])c1nnn(C)c1-c1cnc2c3ccc(C4=CCS(=O)(=O)CC4)nc3n([C@H](c3ccccc3)C3CCOCC3)c2c1]

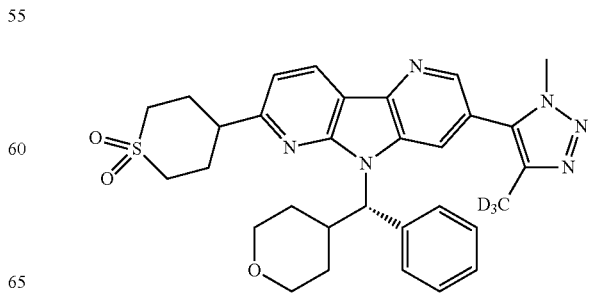

A 200 mL round bottom flask containing a solution of 4-{5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaen-11-yl}-3,6-dihydro-2H-1λ$^6$-thiopyran-1,1-dione (25 mg, 0.044 mmol) in 20 mL methanol and Pd/C (0.9 mg, 4.4 µmol) was stirred under hydrogen at room temperature. After 2 h, the reaction mixture was filtered through Celite and concentrated. The crude was dissolved in 2 mL MeOH and purified via preparative LC/MS with the following conditions: Column: XBridge C18, 19×200 mm, 5-µm particles; Mobile Phase A: 5:95 ACN: water with 10-mM NH$_4$OAc; Mobile Phase B: 95:5 ACN: water with 10-mM NH$_4$OAc; Gradient: 20-60% B over 15 min, then a 5-min hold at 100% B; Flow: 20 mL/min. Fractions containing the title compound were combined and dried via centrifugal evaporation. The yield of the product was 20%, and its estimated purity by LC/MS analysis was 96%. Two analytical LC/MS injections were used to determine the final purity. Injection 1 conditions: Column: Waters BEH C18, 2.0×50 mm, 1.7-µm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.5-min hold at 100% B; Flow: 1.0 mL/min; Detection: UV at 220 nm, RT=1.54 min, LC/MS (M+H)=574.3. Injection 2 conditions: Column: Waters BEH C18, 2.0×50 mm, 1.7-µm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0-100% B over 3 min, then a 0.5-min hold at 100% B; Flow: 0.5 mL/min; Detection: UV at 220 nm, RT=2.77 min, LC/MS (M+H)=574.3. $^1$H NMR (500 MHz, DMSO-d$_6$) δ 8.63-8.52 (m, 3H), 7.82 (d, J=7.7 Hz, 2H), 7.36 (d, J=8.1 Hz, 1H), 7.33-7.27 (m, 2H), 7.26-7.20 (m, 1H), 5.82 (br. s., 1H), 4.03 (s, 3H), 3.89 (s, 1H), 3.77 (d, J=10.3 Hz, 2H), 3.50-3.33 (m, 4H), 3.25 (br. s., 1H), 2.49-2.42 (m, 2H), 2.41-2.33 (m, 2H), 1.49 (d, J=11.7 Hz, 1H), 1.45-1.35 (m, 1H), 1.32-1.22 (m, 1H), 1.15 (d, J=12.1 Hz, 1H); LC/MS (M+H)=574.2 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 206

Propan-2-yl N-[5-(dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-11-yl]carbamate

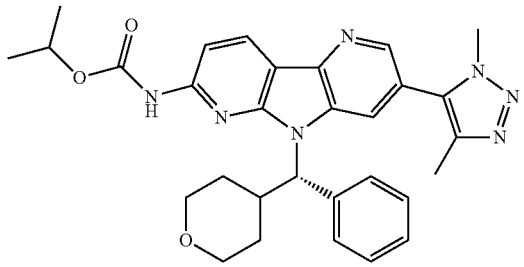 [SMILES: Cc1nnn(C)c1-c1cnc2c3ccc(NC(=O)OC(C)C)nc3n([C@H](c3ccccc3)C3CCOCC3)c2c1]

Step 1: (S)-3-(1,4-Dimethyl-1H-1,2,3-triazol-5-yl)-5-(phenyl(tetrahydro-2H-pyran-4-yl)methyl)-5H-pyrrolo[2,3-b:4,5-b']dipyridin-7-amine To round bottom flask containing (S)—N-(2,4-dimethoxybenzyl)-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridin-7-amine (95 mg, 0.157 mmol) dissolved in DCM (5 mL) was added TFA (1.58 mL, 2.36 mmol), and the resulting mixture stirred at room temperature. After 0.5 h, LC/MS indicated the reaction had gone to completion. The reaction mixture was concentrated on the rotary evaporator, and 10 mL water was added and stirred. The organic side product was extracted with diethyl ether, and then the pH of the aqueous layer was adjusted to ca. 9 with 1N NaOH solution. Extraction of the aqueous layer with 5% MeOH/EtOAc afforded the title compound in 94% after removing the solvents. LC/MS (M+H)=454.2 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Step 2: Propan-2-yl N-[5-(dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,1,12-hexaen-11-yl]carbamate To (S)-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridin-7-amine (22.0 mg, 0.049 mmol) suspended in DCM (4 mL) was added isopropyl carbonochloridate (0.146 mL, 0.146 mmol), followed by triethylamine (0.169 ml, 1.21 mmol) and the resulting mixture stirred at room temperature. After 1 h, it was diluted with 15 mL 5% MeOH/EtOAc, washed with brine, and the organic layer was concentrated to dryness. It was redissolved in 2 mL of methanol, filtered and purified via preparative LC/MS with the following conditions: Column: XBridge C18, 19×200 mm, 5-µm particles; Mobile Phase A: 5:95 ACN: water with 10-mM NH$_4$OAc; Mobile Phase B: 95:5 ACN: water with 10-mM NH$_4$OAc; Gradient: 35-75% B over 20 min, then a 5-min hold at 100% B; Flow: 20 mL/min. Fractions containing the title compound were combined and dried via centrifugal evaporation. The yield of the product was 8.8 mg, and its estimated purity by LC/MS analysis was 99%. Two analytical LC/MS injections were used to determine the final purity. Injection 1 conditions: Column: Waters BEH C18, 2.0×50 mm, 1.7-µm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm; RT=1.90 min, LC/MS (M+H)=540.7. Injection 2 conditions: Column: Waters BEH C18, 2.0×50 mm, 1.7-µm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm, RT=2.88 min, LC/MS (M+H)=540.6. $^1$H NMR (500 MHz, DMSO-d$_6$) δ 8.57-8.47 (m, 3H), 7.96-7.86 (m, 3H), 7.30 (t, J=7.3 Hz, 2H), 7.22 (t, J=7.2 Hz, 1H), 5.68 (br. s., 1H), 5.02 (dt, J=12.6, 6.4 Hz, 1H), 4.03 (s, 3H), 3.89 (d, J=13.9 Hz, 2H), 3.75 (d, J=10.6 Hz, 1H), 3.31 (br. s., 1H), 2.31 (s, 3H), 1.43 (br. s., 1H), 1.34 (d, J=6.2 Hz, 6H), 1.31-1.13 (m, 3H); LC/MS (M+H)=540.3 [Column: Waters Aquity BEH C18 2.1×50 mm 1.7 u;

Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 207

N-[5-(Dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-11-yl]-2,2-dimethylpropanamide

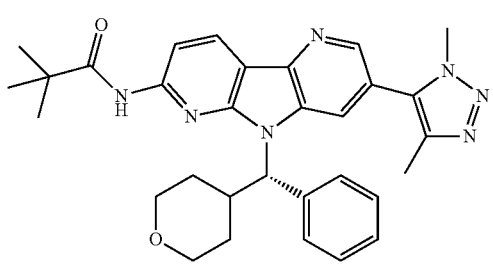 [SMILES: Cc1nnn(C)c1-c1cnc2c3ccc(NC(=O)C(C)(C)C)nc3n([C@H](c3ccccc3)C3CCOCC3)c2c1]

To (S)-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridin-7-amine (20.0 mg, 0.044 mmol) suspended in 1,4-dioxane (4 mL) was added pivaloyl chloride (16.0 mg, 0.132 mmol), followed by triethylamine (0.153 ml, 1.102 mmol) and the resulting mixture stirred at room temperature. After 0.5 h, it was diluted with 15 mL 5% MeOH/EtOAc, washed with brine, and the organic layer was concentrated to dryness. It was redissolved in 2 mL of methanol filtered and was purified via preparative LC/MS with the following conditions: Column: XBridge C18, 19×200 mm, 5-μm particles; Mobile Phase A: 5:95 ACN: water with 10-mM NH$_4$OAc; Mobile Phase B: 95:5 ACN: water with 10-mM NH$_4$OAc; Gradient: 25-65% B over 30 min, then a 5-min hold at 100% B; Flow: 20 mL/min.

Fractions containing the title compound were combined and dried via centrifugal evaporation. The yield of the product was 26%, and its estimated purity by LC/MS analysis was 97%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.5-min hold at 100% B; Flow: 1.0 mL/min; Detection: UV at 220 nm, RT=1.90 min, LC/MS (M+H)=538.2. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0-100% B over 3 min, then a 0.5-min hold at 100% B; Flow: 0.5 mL/min; Detection: UV at 220 nm; RT=2.09 min, LC/MS (M+H)=538.2. $^1$H NMR (500 MHz, DMSO-d$_6$) δ 9.91 (br. s., 1H), 8.59-8.52 (m, 2H), 8.42 (br. s., 1H), 8.13 (d, J=8.4 Hz, 1H), 7.86 (d, J=7.3 Hz, 2H), 7.32 (t, J=7.5 Hz, 2H), 7.24 (t, J=7.2 Hz, 1H), 5.98 (br. s., 1H), 4.00 (s, 3H), 3.93-3.87 (m, 1H), 3.76 (d, J=9.2 Hz, 2H), 3.45 (t, J=11.4 Hz, 1H), 3.28 (t, J=11.9 Hz, 1H), 2.29 (s, 3H), 1.60 (br. s., 1H), 1.37 (s, 10H), 1.32-1.22 (m, 1H), 1.11 (d, J=12.5 Hz, 1H); LC/MS (M+H)=538.1 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 208

N-[5-(Dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-11-yl]methanesulfonamide

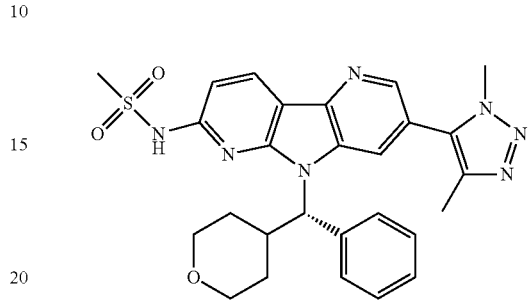

Following a procedure analogous to the reaction described in the synthesis of N-[5-(dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-11-yl]-2,2-dimethylpropanamide, the title compound was obtained in 13% yield from (S)-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridin-7-amine and methanesulfonyl chloride. The crude material was purified via preparative LC/MS with the following conditions: Column: XBridge C18, 19×200 mm, 5-μm particles; Mobile Phase A: 5:95 ACN: water with 10-mM NH$_4$OAc; Mobile Phase B: 95:5 ACN: water with 10-mM NH$_4$OAc; Gradient: 10-50% B over 30 min, then a 5-min hold at 100% B; Flow: 20 mL/min. Fractions containing the title compound were combined and dried via centrifugal evaporation. The yield of the product was 13% mg, and its estimated purity by LC/MS analysis was 93%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm; RT=1.56 min, LC/MS (M+H)=532.1. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm.; RT=2.99 min, LC/MS (M+H)=532.1. $^1$H NMR (500 MHz, DMSO-d$_6$) δ 8.52-8.47 (m, 2H), 8.45 (d, J=8.4 Hz, 1H), 7.93-7.85 (m, J=7.3 Hz, 2H), 7.31-7.26 (m, 2H), 7.25-7.19 (m, 1H), 6.86 (d, J=8.1 Hz, 1H), 5.74 (br. s., 1H), 4.03 (s, 3H), 3.91-3.85 (m, 1H), 3.75 (d, J=11.7 Hz, 2H), 3.51 (s, 3H), 3.36 (d, J=19.8 Hz, 2H), 3.32-3.26 (m, 1H), 2.31 (s, 3H), 1.45 (br. s., 1H), 1.35 (d, J=11.4 Hz, 1H), 1.24 (br. s., 2H); LC/MS (M+H)=532.1 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 209

4-[5-(Dimethyl-1,2-oxazol-4-yl)-8-[(S)-oxan-4-yl(phenyl)methyl]-3,8,10-triazatricyclo[7.4.0.0²,⁷]trideca-1(9),2(7),3,5,10,12-hexaen-11-yl]-1λ⁶,4-thiomorpholine-1,1-dione

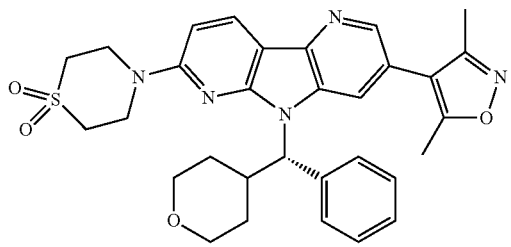 [SMILES: Cc1noc(C)c1-c1cnc2c3ccc(N4CCS(=O)(=O)CC4)nc3n([C@H](c3ccccc3)C3CCOCC3)c2c1]

Step 1: (S)-4-(3-Bromo-5-(phenyl(tetrahydro-2H-pyran-4-yl)methyl)-5H-pyrrolo[2,3-b:4,5-b']dipyridin-7-yl)thiomorpholine 1,1-dioxide (S)-3-Bromo-7-chloro-5-(phenyl(tetrahydro-2H-pyran-4-yl)methyl)-5H-pyrrolo[2,3-b:4,5-b']dipyridine (150 mg, 0.328 mmol), thiomorpholine 1,1-dioxide (311 mg, 2.30 mmol) and the triethylamine (0.365 mL, 2.63 mmol) were dissolved in 1.2 mL of DMSO and microwaved at 175° C. for 2 h. It was diluted with 1% MeOH/EtOAc and washed twice with brine. The organic layer was dried over MgSO₄ and concentrated to obtain 181 mg of crude. The crude material was purified via preparative LC/MS with the following conditions: Column: XBridge C18, 19×200 mm, 5-μm particles; Mobile Phase A: 5:95 ACN: water with 10-mM NH₄OAc; Mobile Phase B: 95:5 ACN: water with 10-mM NH₄OAc; Gradient: 40-80% B over 15 min, then a 5-min hold at 100% B; Flow: 20 mL/min. Fractions containing the title compound were combined and dried via centrifugal evaporation. The yield of the product was 76%. ¹H NMR (500 MHz, DMSO-d₆) δ 8.62 (br. s., 1H), 8.43 (s, 1H), 8.30 (d, J=8.4 Hz, 1H), 7.73 (d, J=7.3 Hz, 2H), 7.32 (t, J=7.5 Hz, 2H), 7.24 (t, J=7.3 Hz, 1H), 7.03 (d, J=8.8 Hz, 1H), 5.61 (br. s., 1H), 4.28 (br. s., 4H), 3.90-3.82 (m, 1H), 3.76 (d, J=10.3 Hz, 1H), 3.53 (br. s., 1H), 3.30-3.16 (m, 6H), 1.50-1.38 (m, 2H), 1.24 (d, J=7.3 Hz, 1H), 1.13 (d, J=11.0 Hz, 1H); LC/MS (M+H)=555.0 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Step 2: 4-[5-(Dimethyl-1,2-oxazol-4-yl)-8-[(S)-oxan-4-yl(phenyl)methyl]-3,8,10-triazatricyclo[7.4.0.0²,⁷]trideca-1(9),2(7),3,5,10,12-hexaen-11-yl]-1λ⁶,4-thiomorpholine-1,1-dione (S)-4-(3-Bromo-5-(phenyl(tetrahydro-2H-pyran-4-yl)methyl)-5H-pyrrolo[2,3-b:4,5-b']dipyridin-7-yl)thiomorpholine 1,1-dioxide (30.0 mg, 0.054 mmol), (3,5-dimethylisoxazol-4-yl)boronic acid (11.4 mg, 0.081 mmol), K₂CO₃ (14.9 mg, 0.108 mmol), and PdCl₂(dppf)₂·DCM (4.4 mg, 5.40 μmol) were dissolved in 3:1 dioxane/water and microwaved at 140° C. for 0.25 h. It was diluted with 1% MeOH/EtOAc and washed twice with brine. The organic layer was dried over MgSO₄ and concentrated to obtain a crude sample. This was dissolved in 2 mL of methanol and was purified via preparative LC/MS with the following conditions: Column: XBridge C18, 19×200 mm, 5-μm particles; Mobile Phase A: 5:95 ACN: water with 0.1% trifluoroacetic acid; Mobile Phase B: 95:5 ACN: water with 0.1% trifluoroacetic acid; Gradient: 20-60% B over 15 min, then a 5-min hold at 100% B; Flow: 20 mL/min. Fractions containing the title compound were combined and dried via centrifugal evaporation. The yield of the product was 32%, and its estimated purity by LC/MS analysis was 100%. Two analytical LC/MS injections were used to determine the final purity. Injection 1 conditions: Column: Waters BEH C18, 2.0×50 mm, 1.7-μm particles; Mobile Phase A: 5:95 ACN: water with 10 mM NH₄OAc; Mobile Phase B: 95:5 ACN: water with 10 mM NH₄OAc; Temperature: 50° C.; Gradient: 0% B, 0-100% B over 3 min, then a 0.5-min hold at 100% B; Flow: 1 mL/min; Detection: UV at 220 nm RT=1.73 min, LC/MS (M+H)=572.2. Injection 2 conditions: Column: Waters BEH C18, 2.0×50 mm, 1.7-μm particles; Mobile Phase A: 5:95 methanol:water with 10 mM NH₄OAc; Mobile Phase B: 95:5 methanol:water with 10 mM NH₄OAc; Temperature: 50° C.; Gradient: 0% B, 0-100% B over 3 min, then a 0.5-min hold at 100% B; Flow: 0.5 mL/min; Detection: UV at 220 nm RT=2.57 min, LC/MS (M+H)=572.6. ¹H NMR (500 MHz, DMSO-d₆) δ 8.42 (s, 1H), 8.37 (s, 1H), 7.74 (d, J=7.3 Hz, 2H), 7.36-7.29 (m, 2H), 7.28-7.20 (m, 2H), 7.08 (d, J=8.8 Hz, 1H), 5.76 (br. s., 1H), 4.31 (br. s., 4H), 3.92-3.84 (m, 1H), 3.77 (d, J=7.0 Hz, 1H), 3.58 (br. s., 1H), 3.49-3.40 (m, 4H), 3.28-3.21 (m, 2H), 2.48 (s, 3H), 2.31 (s, 3H), 1.49 (br. s., 1H), 1.42 (d, J=9.2 Hz, 1H), 1.29-1.14 (m, 2H); LC/MS (M+H)=572.2 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 210

4-[5-(Dimethyl-1H-1,2,3-triazol-5-yl)-8-[(S)-oxan-4-yl(phenyl)methyl]-3,8,10-triazatricyclo[7.4.0.0²,⁷]trideca-1(9),2(7),3,5,10,12-hexaen-11-yl]-3-methyl-1λ⁶,4-thiomorpholine-1,1-dione

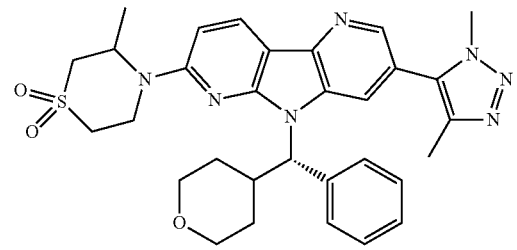 [SMILES: Cc1nnn(C)c1-c1cnc2c3ccc(N4CCS(=O)(=O)CC4C)nc3n([C@H](c3ccccc3)C3CCOCC3)c2c1]

(S)-7-Chloro-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridine (20.00 mg, 0.042 mmol), 3-methylthiomorpholine 1,1-dioxide (12.6 mg, 0.085 mmol), RuPhos (1.6 mg, 3.38 μmol), Pd(OAc)₂ (0.5 mg, 2.11 μmol) and Cs₂CO₃ (55.1 mg, 0.169 mmol) were dissolved in 1.5 mL of dioxane and heated at 110° C. for 1 h in the microwave. It was filtered and the crude filtrate was purified via preparative LC/MS with the following conditions: Column: XBridge C18, 19×mm, 5-μm particles; Mobile Phase A: 5:95 ACN: water with 10-mM NH₄OAc; Mobile Phase B:

95:5 ACN: water with 10-mM NH₄OAc; Gradient: 20-60% B over 20 min, then a 5-min hold at 100% B; Flow: 20 mL/min. Fractions containing the title compound were combined and dried via centrifugal evaporation. The material was further purified via preparative LC/MS with the following conditions: Column: Waters CSH C18, 19×mm, 5-μm particles; Mobile Phase A: 5:95 ACN: water with 10-mM NH₄OAc; Mobile Phase B: 95:5 ACN: water with 10-mM NH₄OAc; Gradient: 20-60% B over 20 min, then a 5-min hold at 100% B; Flow: 20 mL/min. Fractions containing the desired product were combined and dried via centrifugal evaporation. The yield of the product was 18%, and its estimated purity by LC/MS analysis was 100%. Two analytical LC/MS injections were used to determine the final purity. Injection 1 conditions: Column: Waters BEH C18, 2.0×50 mm, 1.7-μm particles; Mobile Phase A: 5:95 ACN: water with 10 mM NH₄OAc; Mobile Phase B: 95:5 ACN: water with 10 mM NH₄OAc; Temperature: 50° C.; Gradient: 0% B, 0-100% B over 3 min, then a 0.5-min hold at 100% B; Flow: 1 mL/min; Detection: UV at 220 nm; RT=1.54 min, LC/MS (M+H)=586.7. Injection 2 conditions: Column: Waters BEH C18, 2.0×50 mm, 1.7-μm particles; Mobile Phase A: 5:95 methanol:water with 10 mM NH₄OAc; Mobile Phase B: 95:5 methanol:water with 10 mM NH₄OAc; Temperature: 50° C.; Gradient: 0% B, 0-100% B over 3 min, then a 0.5-min hold at 100% B; Flow: 0.5 mL/min; Detection: UV at 220 nm; RT=2.43 min, LC/MS (M+H)=586.7. ¹H NMR (500 MHz, DMSO-d₆) δ 8.47 (s, 1H), 8.37 (d, J=8.8 Hz, 1H), 7.73 (d, J=7.7 Hz, 2H), 7.31 (t, J=7.3 Hz, 2H), 7.24 (t, J=7.2 Hz, 1H), 7.17 (s, 1H), 7.05 (d, J=9.2 Hz, 1H), 5.74 (br. s., 1H), 5.45 (br. s., 1H), 4.89 (d, J=13.2 Hz, 1H), 4.01 (d, J=2.9 Hz, 3H), 3.90-3.79 (m, 2H), 3.77 (br. s., 1H), 3.48 (dd, J=13.8, 5.3 Hz, 1H), 3.43-3.32 (m, 3H), 3.32-3.20 (m, 2H), 2.29 (d, J=2.6 Hz, 3H), 1.56 (d, J=6.6 Hz, 3H), 1.51 (br. s., 1H), 1.41 (d, J=5.1 Hz, 1H), 1.32-1.14 (m, 2H); LC/MS (M+H)=586.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 211

4-[5-(Dimethyl-1H-1,2,3-triazol-5-yl)-8-[(S)-oxan-4-yl(phenyl)methyl]-3,8,10-triazatricyclo[7.4.0.0²,⁷]trideca-1(9),2(7),3,5,10,12-hexaen-11-yl]-6-methyl-1λ⁶,4-thiazepane-1,1-dione

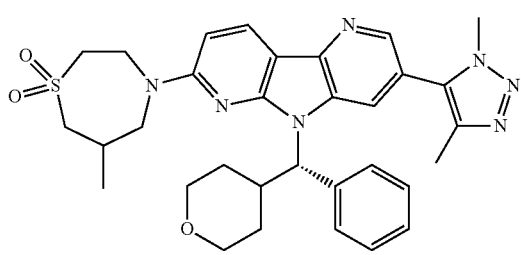 [SMILES: Cc1nnn(C)c1-c1cnc2c3ccc(N4CCS(=O)(=O)CC(C)C4)nc3n([C@H](c3ccccc3)C3CCOCC3)c2c1]

Following a procedure analogous to the reaction described in the synthesis of 4-[5-(dimethyl-1H-1,2,3-triazol-5-yl)-8-[(S)-oxan-4-yl(phenyl)methyl]-3,8,10-triazatricyclo[7.4.0.0²,⁷]trideca-1(9),2(7),3,5,10,12-hexaen-11-yl]-3-methyl-1λ⁶,4-thiomorpholine-1,1-dione, the title compound was obtained in 21% yield from (S)-7-chloro-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridine and 6-methyl-1,4-thiazepane 1,1-dioxide The crude material was purified via preparative LC/MS with the following conditions: Column: XBridge C18, 19×mm, 5-μm particles; Mobile Phase A: 5:95 ACN: water with 10-mM NH₄OAc; Mobile Phase B: 95:5 ACN: water with 10-mM NH₄OAc; Gradient: 20-60% B over 20 min, then a 5-min hold at 100% B; Flow: 20 mL/min. Fractions containing the title compound were combined and dried via centrifugal evaporation. The estimated purity by LC/MS analysis was 100%. Two analytical LC/MS injections were used to determine the final purity. Injection 1 conditions: Column: Waters BEH C18, 2.0×50 mm, 1.7-μm particles; Mobile Phase A: 5:95 ACN: water with 10 mM NH₄OAc; Mobile Phase B: 95:5 ACN: water with 10 mM NH₄OAc; Temperature: 50° C.; Gradient: 0% B, 0-100% B over 3 min, then a 0.5-min hold at 100% B; Flow: 1 mL/min; Detection: UV at 220 nm; RT=1.57 min, LC/MS (M+H)=600.7. Injection 2 conditions: Column: Waters BEH C18, 2.0×50 mm, 1.7-μm particles; Mobile Phase A: 5:95 methanol:water with 10 mM NH₄OAc; Mobile Phase B: 95:5 methanol:water with 10 mM NH₄OAc; Temperature: 50° C.; Gradient: 0% B, 0-100% B over 3 min, then a 0.5-min hold at 100% B; Flow: 0.5 mL/min; Detection: UV at 220 nm; RT=2.46 min, LC/MS (M+H)=600.7. ¹H NMR (500 MHz, DMSO-d₆) δ 8.40 (s, 1H), 8.30 (d, J=8.8 Hz, 2H), 7.77 (d, J=7.0 Hz, 2H), 7.30 (t, J=7.0 Hz, 2H), 7.23 (t, J=7.2 Hz, 1H), 6.81 (d, J=8.8 Hz, 1H), 5.70 (br. s., 1H), 4.45 (br. s., 1H), 4.24 (br. s., 1H), 4.00 (s, 3H), 3.93-3.85 (m, 3H), 3.77 (br. s., 1H), 3.71 (d, J=19.4 Hz, 2H), 3.59 (br. s., 1H), 3.36 (br. s., 1H), 3.32-3.15 (m, 3H), 2.60 (br. s., 1H), 2.29 (s, 3H), 1.47 (br. s., 1H), 1.40 (br. s., 1H), 1.24 (d, J=13.6 Hz, 2H), 1.17 (t, J=6.1 Hz, 3H); LC/MS (M+H)=600.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 212

4-{5-[4-(²H₃)Methyl-1-methyl-1H-1,2,3-triazol-5-yl]-8-[(S)-oxan-4-yl(phenyl)methyl]-3,8,10-triazatricyclo[7.4.0.0²,⁷]trideca-1(9),2(7),3,5,10,12-hexaen-11-yl}piperazine-2,6-dione

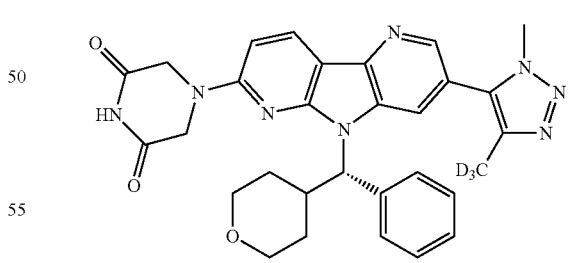

Following a procedure analogous to the reaction described in the synthesis of 4-[5-(dimethyl-1H-1,2,3-triazol-5-yl)-8-[(S)-oxan-4-yl(phenyl)methyl]-3,8,10-triazatricyclo[7.4.0.0²,⁷]trideca-1(9),2(7),3,5,10,12-hexaen-11-yl]-3-methyl-1λ⁶,4-thiomorpholine-1,1-dione, the title compound was obtained in 27% yield from 11-chloro-5-[4-(²H₃)methyl-1-methyl-1H-1,2,3-triazol-5-yl]-8-[(S)-oxan-4-yl(phenyl)methyl]-3,8,10-triazatricyclo[7.4.0.0²,⁷]trideca-1(9),2(7),3,5,10,12-hexaene and piperazine-2,6-dione.

The crude material was purified via preparative LC/MS with the following conditions: Column: XBridge C18, 19×200 mm, 5-μm particles; Mobile Phase A: 5:95 methanol: water with 10-mM NH$_4$OAc; Mobile Phase B: 95:5 methanol: water with 10-mM NH$_4$OAc; Gradient: 30-100% B over 20 min, then a 5-min hold at 100% B; Flow: 20 mL/min. Fractions containing the title compound were combined and dried via centrifugal evaporation. The material was further purified via preparative LC/MS with the following conditions: Column: XBridge C18, 19×200 mm, 5-μm particles; Mobile Phase A: 5:95 ACN: water with 10-mM NH$_4$OAc; Mobile Phase B: 95:5 ACN: water with 10-mM NH$_4$OAc; Gradient: 15-55% B over 20 min, then a 5-min hold at 100% B; Flow: 20 mL/min. Fractions containing the title compound were combined and dried via centrifugal evaporation. The estimated purity by LC/MS analysis was 98%. Two analytical LC/MS injections were used to determine the final purity. Injection 1 conditions: Column: Waters BEH C18, 2.0×50 mm, 1.7-μm particles; Mobile Phase A: 5:95 ACN: water with 10 mM NH$_4$OAc; Mobile Phase B: 95:5 ACN: water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm; RT=1.40 min, LC/MS (M+H)=554.6. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm; RT=2.30 min, LC/MS (M+H)=554.7. $^1$H NMR (500 MHz, DMSO-d$_6$) δ 8.48-8.39 (m, 2H), 8.34 (d, J=9.2 Hz, 1H), 7.76 (d, J=7.0 Hz, 1H), 7.69 (br. s., 1H), 7.34-7.27 (m, 3H), 7.23 (d, J=6.6 Hz, 1H), 5.71 (br. s., 1H), 4.65 (d, J=3.7 Hz, 1H), 4.59-4.54 (m, 1H), 4.26 (br. s., 1H), 4.00 (d, J=11.7 Hz, 3H), 3.90 (s, 2H), 3.77 (d, J=11.7 Hz, 2H), 3.72 (s, 2H), 3.65 (br. s., 1H), 3.35-3.26 (m, 1H), 1.47 (br. s., 1H), 1.44-1.28 (m, 2H), 1.24 (br. s., 2H); LC/MS (M+H)=554.2 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 213

4-[5-(Dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-11-yl]-2-methyl-1λ$^6$,4-thiomorpholine-1,1-dione

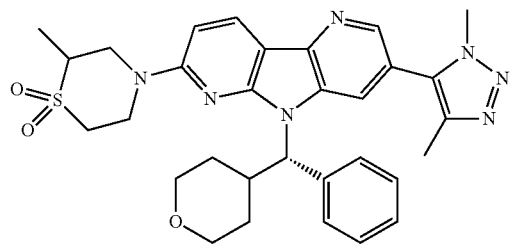 [SMILES: Cc1nnn(C)c1-c1cnc2c3ccc(N4CCS(=O)(=O)C(C)C4)nc3n([C@H](c3ccccc3)C3CCOCC3)c2c1]

Following a procedure analogous to the reaction described in the synthesis of 4-[5-(dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-11-yl]-3-methyl-1λ$^6$,4-thiomorpholine-1,1-dione, the title compound was obtained in 18% yield from (S)-7-chloro-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridine and 2-methylthiomorpholine 1,1-dioxide. The crude material was purified via preparative LC/MS with the following conditions: Column: XBridge C18, 19×200 mm, 5-μm particles; Mobile Phase A: 5:95 methanol: water with 10-mM NH$_4$OAc; Mobile Phase B: 95:5 methanol: water with 10-mM NH$_4$OAc; Gradient: 40-100% B over 20 min, then a 5-min hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 ACN: water with 10-mM NH$_4$OAc; Mobile Phase B: 95:5 ACN: water with 10-mM NH$_4$OAc; Gradient: 30-70% B over 20 min, then a 5-min hold at 100% B; Flow: 20 mL/min. Fractions containing the title compound were combined and dried via centrifugal evaporation. The yield estimated purity by LC/MS analysis was 97%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm; RT=1.62 min, LC/MS (M+H)=586.2 Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm; RT=2.45 min, LC/MS (M+H)=586.7. $^1$H NMR (500 MHz, DMSO-d$_6$) δ 8.46-8.32 (m, 3H), 7.74 (d, J=6.6 Hz, 2H), 7.31 (d, J=4.4 Hz, 2H), 7.24 (d, J=7.7 Hz, 1H), 7.12-7.05 (m, 1H), 5.73 (br. s., 1H), 4.91-4.77 (m, 1H), 4.72-4.57 (m, 1H), 4.01 (d, J=5.1 Hz, 3H), 3.90 (s, 2H), 3.77 (d, J=10.6 Hz, 2H), 3.56 (d, J=10.3 Hz, 2H), 3.35-3.19 (m, 3H), 2.29 (d, J=4.4 Hz, 3H), 1.50 (br. s., 1H), 1.41 (br. s., 1H), 1.31 (d, J=4.4 Hz, 3H), 1.24 (br. s., 2H); LC/MS (M+H)=586.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 214

5-[5-(Dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-11-yl]-2λ$^6$-thia-5-azabicyclo[2.2.1]heptane-2,2-dione

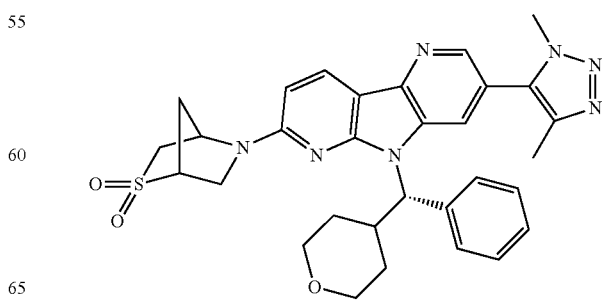

Following a procedure analogous to the reaction described in the synthesis of 4-[5-(dimethyl-1H-1,2,3-triazol-5-yl)-8-[(S)-oxan-4-yl(phenyl)methyl]-3,8,10-triazatricyclo[7.4.0.0²,⁷]trideca-1(9),2(7),3,5,10,12-hexaen-11-yl]-3-methyl-1λ⁶,4-thiomorpholine-1,1-dione, the title compound was obtained in 18% yield from (S)-7-chloro-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridine and (1R,4R)-2-thia-5-azabicyclo[2.2.1]heptane 2,2-dioxide hydrobromide. The crude material was purified via preparative LC/MS with the following conditions: Column: XBridge C18, 19×200 mm, 5-μm particles; Mobile Phase A: 5:95 ACN: water with 10-mM NH₄OAc; Mobile Phase B: 95:5 ACN: water with 10-mM NH₄OAc; Gradient: 25-65% B over 15 min, then a 5-min hold at 100% B; Flow: 20 mL/min. Fractions containing the title compound were combined and dried via centrifugal evaporation. The estimated purity by LC/MS analysis was 98%. Two analytical LC/MS injections were used to determine the final purity. Injection 1 conditions: Column: Waters BEH C18, 2.0×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.5-min hold at 100% B; Flow: 1.0 mL/min; Detection: UV at 220 nm; RT=1.56 min, LC/MS (M+H)=584.7. Injection 2 conditions: Column: Waters BEH C18, 2.0×50 mm, 1.7-μm particles; Mobile Phase A: 5:95 methanol:water with 10 mM NH₄OAc; Mobile Phase B: 95:5 methanol:water with 10 mM NH₄OAc; Temperature: 50° C.; Gradient: 0-100% B over 3 min, then a 0.5-min hold at 100% B; Flow: 0.5 mL/min; Detection: UV at 220 nm; RT=2.79 min, LC/MS (M+H)=584.1. ¹H NMR (500 MHz, DMSO-d₆) δ 8.44-8.36 (m, 2H), 8.33 (d, J=8.8 Hz, 1H), 7.77 (d, J=7.7 Hz, 2H), 7.32 (t, J=7.5 Hz, 2H), 7.24 (t, J=7.3 Hz, 1H), 6.64 (d, J=8.4 Hz, 1H), 5.69 (br. s., 1H), 5.24 (br. s., 1H), 4.19 (br. s., 1H), 4.02 (s, 3H), 3.94-3.85 (m, 2H), 3.76 (d, J=9.9 Hz, 1H), 3.65 (br. s., 1H), 3.46 (s, 4H), 3.41-3.37 (m, 1H), 3.31-3.16 (m, 2H), 2.74-2.67 (m, 1H), 2.66-2.60 (m, 1H), 2.30 (s, 3H), 1.48 (br. s., 1H), 1.43-1.32 (m, 1H), 1.24 (d, J=9.2 Hz, 1H), 1.17 (br. s., 1H); LC/MS (M+H)=584.2 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 215

Diethyl (2-{[5-(dimethyl-1H-1,2,3-triazol-5-yl)-8-[(S)-oxan-4-yl(phenyl)methyl]-3,8,10-triazatricyclo[7.4.0.0²,⁷]trideca-1(9),2(7),3,5,10,12-hexaen-11-yl]amino}ethyl)phosphonate

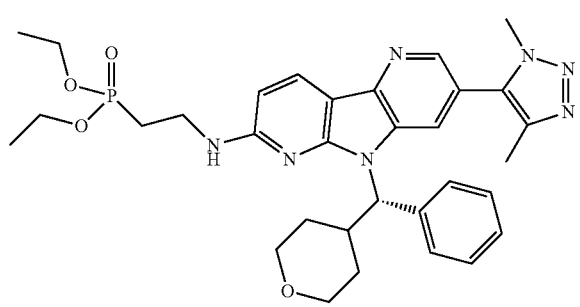 [SMILES: CCOP(=O)(CCNc1ccc2c3ncc(-c4c(C)nnn4C)cc3n([C@H](c3ccccc3)C3CCOCC3)c2n1)OCC]

Following a procedure analogous to the reaction described in the synthesis of 4-[5-(dimethyl-1H-1,2,3-triazol-5-yl)-8-[(S)-oxan-4-yl(phenyl)methyl]-3,8,10-triazatricyclo[7.4.0.0²,⁷]trideca-1(9),2(7),3,5,10,12-hexaen-11-yl]-3-methyl-1λ⁶,4-thiomorpholine-1,1-dione, the title compound was obtained in 31% yield from (S)-7-chloro-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridine and diethyl (2-aminoethyl)phosphonate, oxalic acid salt. The crude material was purified via preparative LC/MS with the following conditions: Column: XBridge C18, 19×200 mm, 5-μm particles; Mobile Phase A: 5:95 ACN: water with 10-mM NH₄OAc; Mobile Phase B: 95:5 ACN: water with 10-mM NH₄OAc; Gradient: 15-55% B over 30 min, then a 5-min hold at 100% B; Flow: 20 mL/min. Fractions containing the title compound were combined and dried via centrifugal evaporation. The estimated purity by LC/MS analysis was 96%. An analytical LC/MS injection was used to determine the final purity. Injection Conditions: Column: Waters BEH C18, 2.0×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.5-min hold at 100% B; Flow: 1.0 mL/min; Detection: UV at 220 nm; RT=1.44 min, LC/MS (M+H)=618.1. ¹H NMR (500 MHz, DMSO-d₆) δ 8.38-8.31 (m, 2H), 8.12 (d, J=8.4 Hz, 1H), 7.84 (d, J=7.3 Hz, 2H), 7.59 (br. s., 1H), 7.31 (t, J=7.5 Hz, 2H), 7.23 (t, J=7.2 Hz, 1H), 6.51 (d, J=8.4 Hz, 1H), 5.68 (br. s., 1H), 4.09-4.02 (m, 4H), 4.01 (s, 3H), 3.87 (d, J=8.1 Hz, 1H), 3.78 (d, J=12.1 Hz, 2H), 3.69 (br. s., 2H), 3.44 (d, J=10.3 Hz, 2H), 3.30 (t, J=11.2 Hz, 2H), 2.33 (br. s., 1H), 2.30 (s, 3H), 1.46 (br. s., 1H), 1.43-1.33 (m, 1H), 1.28-1.19 (m, 8H); LC/MS (M+H)=618.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 216

4-[5-(Dimethyl-1H-1,2,3-triazol-5-yl)-8-[(S)-oxan-4-yl(phenyl)methyl]-3,8,12-triazatricyclo[7.4.0.0²,⁷]trideca-1(9),2(7),3,5,10,12-hexaen-11-yl]-1λ⁶,4-thiomorpholine-1,1-dione

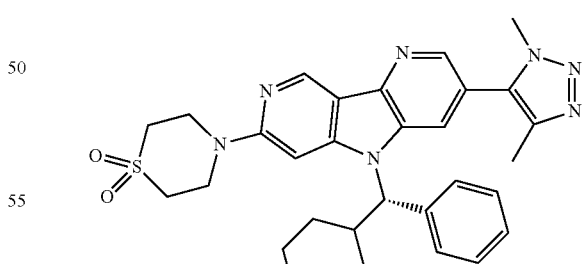

To (S)-7-chloro-3-(1,4-dimethyl-1H-1,2,3-triazol-5-yl)-5-(phenyl(tetrahydro-2H-pyran-4-yl)methyl)-5H-pyrrolo[3,2-b:4,5-c']dipyridine (12 mg, 0.025 mmol) in a microwaveable vial was added thiomorpholine 1,1-dioxide (3.4 mg, 0.025 mmol), RuPhos (1.1 mg, 2.54 μmol), Pd(OAc)₂ (0.570 mg, 2.54 μmol), K₃PO₄ (33.0 mg, 0.101 mmol) followed by dioxane (2 mL). The vial was sealed under argon and microwaved for 0.5 hr at 130° C. It was filtered and the crude (filtrate) was purified via preparative LC/MS with the following conditions: Column: XBridge C18, 19×200 mm, 5-μm particles; Mobile Phase A: 5:95 ACN: water with 10-mM NH₄OAc; Mobile Phase B: 95:5 ACN: water with 10-mM NH₄OAc; Gradient: 15-55% B over 30 min, then a 5-min hold at 100% B; Flow: 20 mL/min. Fractions containing the title compound were combined and dried via centrifugal evaporation. The yield of the product was 3.5%, and its estimated purity by LC/MS analysis was 100%. Two analytical LC/MS injections were used to determine the final purity. Injection 1 conditions: Column: Waters BEH C18, 2.0×50 mm, 1.7-μm particles; Mobile Phase A: 5:95 ACN: water with 10 mM NH₄OAc; Mobile Phase B: 95:5 ACN: water with 10 mM NH₄OAc; Temperature: 50° C.; Gradient: 0-100% B over 3 min, then a 0.5-min hold at 100% B; Flow: 1.0 mL/min; Detection: UV at 220 nm; RT=1.45 min, LC/MS (M+H)=572.2. Injection 2 conditions: Column: Waters BEH C18, 2.0×50 mm, 1.7-μm particles; Mobile Phase A: 5:95 methanol:water with 10 mM NH₄OAc; Mobile Phase B: 95:5 methanol:water with 10 mM NH₄OAc; Temperature: 50° C.; Gradient: 0-100% B over 3 min, then a 0.5-min hold at 100% B; Flow: 0.5 mL/min; Detection: UV at 220 nm; RT=2.68 min, LC/MS (M+H)= 572.2. ¹H NMR (500 MHz, DMSO-d₆) δ 9.01 (s, 1H), 8.43 (s, 1H), 7.68 (d, J=7.7 Hz, 3H), 7.34 (d, J=7.7 Hz, 3H), 7.27 (s, 1H), 5.75 (s, 1H), 4.28 (br. s., 4H), 3.95 (br. s., 3H), 3.89 (br. s., 2H), 3.20 (br. s., 4H), 2.25 (s, 3H), 1.70 (d, J=10.6 Hz, 2H), 1.53 (d, J=16.5 Hz, 2H), 1.37 (s, 1H); LC/MS (M+H)= 572.1 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 217

4-[5-(Dimethyl-1H-1,2,3-triazol-5-yl)-8-[(S)-oxan-4-yl(phenyl)methyl]-3,8,10-triazatricyclo[7.4.0.0²,⁷]trideca-1(9),2(7),3,5,10,12-hexaen-11-yl]-2-methyl-1λ⁶,4-thiomorpholine-1,1-dione, Diastereomer A

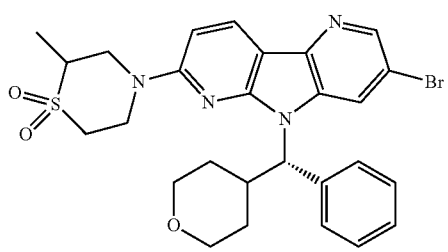 [SMILES: CC1CN(c2ccc3c4ncc(Br)cc4n([C@H](c4ccccc4)C4CCOCC4)c3n2)CCS1(=O)=O]

Step 1 A: tert-Butyl thiomorpholine-4-carboxylate 1,1-dioxide

Thiomorpholine 1,1-dioxide (2.00 g, 14.8 mmol) was dissolved in THF (20 mL) at 0° C. Di-tert-butyl dicarbonate (3.55 g, 16.3 mmol) was added, followed by triethylamine (4.12 mL, 29.6 mmol). The resulting mixture was stirred at room temperature overnight. It was diluted with EtOAc and washed with brine. The organic layer was dried over MgSO₄ and concentrated. The crude residue obtained was subjected to purification on the ISCO using an 80 g column and eluting with 0-70% EtOAc/hexanes (5% KMnO₄ aq. was used in staining the TLC plates). The appropriate fractions were combined and concentrated to obtain (3.46 g, 99%) of the title compound. ¹H NMR (400 MHz, CDCl₃) δ 4.00-3.89 (m, 4H), 3.06-2.97 (m, 4H), 1.51 (s, 10H)

Step 1 B: tert-Butyl 2-methylthiomorpholine-4-carboxylate 1,1-dioxide

A solution of tert-butyl thiomorpholine-4-carboxylate 1,1-dioxide (1.000 g, 4.25 mmol) in THF (25 mL) was cooled to −78° C. with stirring. Lithium diisopropyl amine (2.125 mL, 4.25 mmol) was slowly added, and the resulting mixture stirred for 0.5 h at −78° C. Iodomethane (0.905 g, 6.37 mmol) was added and allowed stir for 1 h. The cooling bath was removed, and the reaction allowed to warm to room temperature and stirred overnight. The reaction was quenched with brine and diluted with EtOAc. The layers were separated, and the aq. layer extracted once with EtOAc. The combined organic layer was dried over Na₂SO₄ and filtered. It was concentrated to obtain a crude mixture. The crude mixture was subjected to purification on a Biotage eluting with 5-100% EtOAc/hexanes to obtain (85%, 0.898 g, white solid) of the title compound. ¹H NMR (400 MHz, CDCl₃) δ 4.30-4.21 (m, 1H), 4.00-3.90 (m, 2H), 3.12-2.97 (m, 4H), 1.52-1.48 (m, 9H), 1.39-1.36 (m, 3H)

Step 1 C: Chiral Separation

Racemic tert-butyl 2-methylthiomorpholine-4-carboxylate 1,1-dioxide was subjected to chiral separation to obtain the individual enantiomers. Column: ChiralPak AD-H, 30×250 mm, 5 μm; Mobile Phase: 20% MeOH/80% CO₂; Pressure: 100 bar; Temperature: 40° C.; Flow Rate: 70 mL/min; UV: 205 nm; Injection: 0.35 mL (~20 mg/mL); Fraction Collection: Peak 1: 3.30'-3.75', Peak 2: 4.30'-5.00'. Absolute stereochemistry was not determined. Peak 1 was designated enantiomer A and Peak 2 was designated enantiomer B.

Step 1 D: 2-Methylthiomorpholine 1,1-dioxide hydrochloride, enantiomer A and 2-methylthiomorpholine 1,1-dioxide hydrochloride, enantiomer B To 26 mg (0.104 mmol) of each of the enantiomers A and B-tert-butyl 2-methylthiomorpholine-4-carboxylate 1,1-dioxide dissolved in 2 mL dioxane was added 4M HCl in dioxane (1.043 mL, 4.17 mmol) and stirred for 10 min at room temperature. The title compounds were obtained in 100% yields by concentrating the reaction mixtures of each.

Step 2: 4-[5-(Dimethyl-1H-1,2,3-triazol-5-yl)-8-[(S)-oxan-4-yl(phenyl)methyl]-3,8,10-triazatricyclo [7.4.0.0²,⁷]trideca-1(9),2(7),3,5,10,12-hexaen-11-yl]-2-methyl-1λ⁶,4-thiomorpholine-1,1-dione, Diastereomer A (S)-7-Chloro-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridine (25.0 mg, 0.053 mmol), 2-methylthiomorpholine 1,1-dioxide hydrochloride, enantiomer A (24.5 mg, 0.132 mmol), RuPhos (2.0 mg, 4.23 μmol), Pd(OAc)₂ (0.95 mg, 4.23 μmol) and K₃PO₄ (44.8 mg, 0.211 mmol) were dissolved in 2 mL of dioxane and heated at 120° C. for 0.5 h in the microwave. The reaction mixture was concentrated on the rotary evaporator, dissolved in 2 mL methanol, filtered and (filtrate) crude material was purified via preparative LC/MS with the following conditions: Column: XBridge C18, 19×200 mm, 5-μm particles; Mobile Phase A: 5:95 ACN: water with 10-mM NH₄OAc; Mobile Phase B: 95:5 ACN: water with 10-mM NH₄OAc; Gradient: 20-60% B over 20 min, then a 5-min hold at 100% B; Flow: 20 mL/min. Fractions containing the title compound were combined and dried via centrifugal evaporation. The material was further purified via preparative LC/MS with the following conditions: Column: XBridge C18, 19×200 mm, 5-μm particles; Mobile Phase A: 5:95 ACN: water with 0.1% trifluoroacetic acid; Mobile Phase B: 95:5 ACN: water with 0.1% trifluoroacetic acid; Gradient: 15-55% B over 20 min, then a 5-min hold at 100% B; Flow: 20 mL/min. Fractions containing the title compound were combined and dried via centrifugal evaporation. The yield of the product was 13%, and its estimated purity by LC/MS analysis was 92%. Two analytical LC/MS injections were used to determine the final purity. Injection 1 conditions: Column: Waters Acquity UPLC BEH C18, 2.1×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75-min hold at 100% B; Flow: 1.0 mL/min; Detection: UV at 220 nm. RT=1.81 min, LC/MS (M+H)=586.1. Injection 2 conditions: Column: Waters Acquity UPLC BEH C18, 2.1×50 mm, 1.7-μm particles; Mobile Phase A: 5:95 ACN:water with 0.1% trifluoroacetic acid; Mobile Phase B: 95:5 ACN: water with 0.1% trifluoroacetic acid; Temperature: 50° C.; Gradient: 0-100% B over 3 min, then a 0.75-min hold at 100% B; Flow: 1.0 mL/min; Detection: UV at 220 nm. RT=1.45 min, LC/MS (M+H)=586.2. ¹H NMR (500 MHz, DMSO-d₆) δ 8.47 (br. s., 2H), 8.36 (d, J=8.8 Hz, 1H), 7.75 (d, J=7.7 Hz, 2H), 7.32 (t, J=7.5 Hz, 2H), 7.24 (t, J=7.0 Hz, 1H), 7.11 (d, J=8.8 Hz, 1H), 5.75 (br. s., 1H), 4.84 (d, J=16.1 Hz, 1H), 4.69 (d, J=14.3 Hz, 1H), 4.02 (s, 3H), 3.89 (d, J=12.1 Hz, 1H), 3.85-3.74 (m, 2H), 3.64 (br. s., 1H), 3.62-3.52 (m, 2H), 3.49-3.29 (m, 3H), 3.23 (br. s., 2H), 2.31 (s, 3H), 1.50 (br. s., 1H), 1.47-1.37 (m, 1H), 1.32 (d, J=7.0 Hz, 3H), 1.29-1.15 (m, 2H); LC/MS (M+H)=586.0 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 218

4-[5-(Dimethyl-1H-1,2,3-triazol-5-yl)-8-[(S)-oxan-4-yl(phenyl)methyl]-3,8,10-triazatricyclo[7.4.0.0²,⁷]trideca-1(9),2(7),3,5,10,12-hexaen-11-yl]-2-methyl-1λ⁶,4-thiomorpholine-1,1-dione, diastereomer B

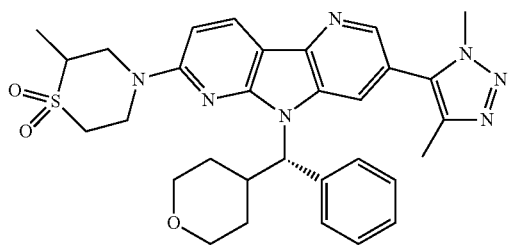 [SMILES: Cc1nnn(C)c1-c1cnc2c3ccc(N4CCS(=O)(=O)C(C)C4)nc3n([C@H](c3ccccc3)C3CCOCC3)c2c1]

Following a procedure analogous to the reaction described in the synthesis of 4-[5-(dimethyl-1H-1,2,3-triazol-5-yl)-8-[(S)-oxan-4-yl(phenyl)methyl]-3,8,10-triazatricyclo[7.4.0.0²,⁷]trideca-1(9),2(7),3,5,10,12-hexaen-11-yl]-2-methyl-1λ⁶,4-thiomorpholine-1,1-dione, diastereomer A, the title compound was obtained in 31% yield from 7-chloro-3-(1,4-dimethyl-1H-1,2,3-triazol-5-yl)-5-(phenyl (tetrahydro-2H-pyran-4-yl)methyl)-5H-pyrrolo[2,3-b:4,5-b']dipyridine and 2-methylthiomorpholine 1,1-dioxide hydrochloride, enantiomer B. Analytical LC/MS Injection 1 conditions; Column: Waters Acquity UPLC BEH C18, 2.1×50 mm, 1.7-μm particles; Mobile Phase A: 5:95 ACN:water with 10 mM NH₄OAc; Mobile Phase B: 95:5 ACN:water with 10 mM NH₄OAc; Temperature: 50° C.; Gradient: 0-100% B over 3 min, then a 0.75-min hold at 100% B; Flow: 1.0 mL/min; Detection: UV at 220 nm. RT=1.96 min, LC/MS (M+H)=586.1. Analytical LC/MS Injection 2 conditions; Column: Waters Acquity UPLC BEH C18, 2.1×50 mm, 1.7-μm particles; Mobile Phase A: 5:95 ACN:water with 0.1% trifluoroacetic acid; Mobile Phase B: 95:5 ACN: water with 0.1% trifluoroacetic acid; Temperature: 50° C.; Gradient: 0-100% B over 3 min, then a 0.75-min hold at 100% B; Flow: 1.0 mL/min; Detection: UV at 220 nm. RT=1.47 min, LC/MS (M+H)=586.1. ¹H NMR (500 MHz, DMSO-d₆) δ 8.47 (br. s., 1H), 8.43 (br. s., 1H), 8.37 (d, J=8.8 Hz, 1H), 7.75 (d, J=7.3 Hz, 2H), 7.35-7.29 (m, 2H), 7.26-7.21 (m, 1H), 7.12 (d, J=8.8 Hz, 1H), 5.75 (br. s., 1H), 4.88 (d, J=16.1 Hz, 1H), 4.64 (d, J=13.9 Hz, 1H), 4.01 (s, 3H), 3.90-3.85 (m, 1H), 3.84-3.74 (m, 2H), 3.64-3.50 (m, 4H), 3.50-3.37 (m, 3H), 3.36-3.21 (m, 3H), 2.29 (s, 3H), 1.49 (br. s., 1H), 1.46-1.35 (m, 1H), 1.32 (d, J=6.6 Hz, 3H), 1.25 (br. s., 2H); LC/MS (M+H)=586.1.

Example 219

(2-{[5-(Dimethyl-1H-1,2,3-triazol-5-yl)-8-[(S)-oxan-4-yl(phenyl)methyl]-3,8,10-triazatricyclo[7.4.0.0²,⁷]trideca-1(9),2(7),3,5,10,12-hexaen-11-yl]amino}ethyl)phosphonic acid

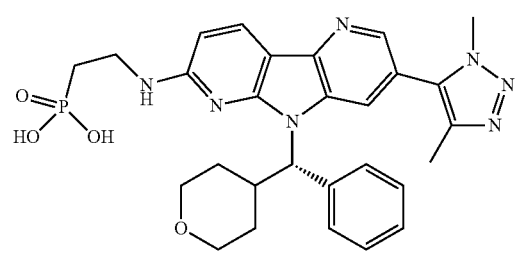 [SMILES: Cc1nnn(C)c1-c1cnc2c3ccc(NCCP(=O)(O)O)nc3n([C@H](c3ccccc3)C3CCOCC3)c2c1]

To (S)-7-chloro-3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridine (40.0 mg, 0.085 mmol) in a microwaveable vial was added diethyl (2-aminoethyl) phosphonate (30.6 mg, 0.169 mmol), RuPhos (1.2 mg, 2.54 μmol), Pd(OAc)₂ (0.95 mg, 4.23 μmol), K₃PO₄ (108 mg, 0.507 mmol) and dioxane (2 mL). The resulting mixture was microwaved for 0.5 h at 120° C. LC/MS showed step 1 was successful (M+1=618). The reaction mixture was diluted with EtOAc and washed with brine. The organic layer was dried over MgSO₄, and concentrated. The residue was dissolved in DCM (5 mL) and cooled to 0° C. Bromotrimethylsilane (51.8 mg, 0.338 mmol) was added, the ice-bath was removed, and the resulting mixture was stirred overnight at room temperature. It was concentrated, and 20 mL solution of 10:1 methanol/water was added and stirred for 6 h. LC/MS suggested the desired product was made, but the mono-ethyl side product was the major product (vide infra). It was concentrated on the rotary evaporator, and the solid residue taken up into a 10:1 methanol/H$_2$O solution with a drop of TFA. It was filtered and the crude material (the filtrate) was purified via preparative LC/MS with the following conditions: Column: XBridge C18, 19×200 mm, 5-μm particles; Mobile Phase A: 5:95 methanol: water with 10-mM NH$_4$OAc; Mobile Phase B: 95:5 methanol: water with 10-mM NH$_4$OAc; Gradient: 40-85% B over 20 min, then a 5-min hold at 100% B; Flow: 20 mL/min. Fractions containing the title compound (as the NH$_4$OAc salt) were combined and dried via centrifugal evaporation. The yield of the product was 7%, and its estimated purity by LC/MS analysis was 95%. Two analytical LC/MS injections were used to determine the final purity. Injection 1 conditions: Column: Waters Acquity UPLC BEH C18, 2.1×50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75-min hold at 100% B; Flow: 1.0 mL/min; Detection: UV at 220 nm. RT=1.10 min, LC/MS (M+H)=562.0. Injection 2 conditions: Column: Waters Acquity UPLC BEH C18, 2.1×50 mm, 1.7-μm particles; Mobile Phase A: 5:95 ACN:water with 0.1% trifluoroacetic acid; Mobile Phase B: 95:5 ACN:water with 0.1% trifluoroacetic acid; Temperature: 50° C.; Gradient: 0-100% B over 3 min, then a 0.75-min hold at 100% B; Flow: 1.0 mL/min; Detection: UV at 220 nm. RT=1.13 min, LC/MS (M+H)=562.0. $^1$H NMR (500 MHz, DMSO-d$_6$) δ 8.39-8.31 (m, 2H), 8.05 (d, J=8.4 Hz, 1H), 7.85 (d, J=7.0 Hz, 2H), 7.30 (t, J=7.7 Hz, 3H), 7.18 (t, J=7.3 Hz, 1H), 6.46 (d, J=8.4 Hz, 1H), 5.64 (br. s., 1H), 4.01 (s, 3H), 3.82 (d, J=10.3 Hz, 2H), 3.73 (br. s., 2H), 3.51-3.45 (m, 2H), 3.32 (br. s., 2H), 2.30 (s, 4H), 1.98-1.84 (m, 4H), 1.47 (br. s., 1H), 1.34 (d, J=8.1 Hz, 1H), 1.22 (br. s., 2H); LC/MS (M+H)=562.3 [Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min].

Example 220

(2-{[5-(Dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-11-yl]amino}ethyl)(ethoxy)phosphinic acid

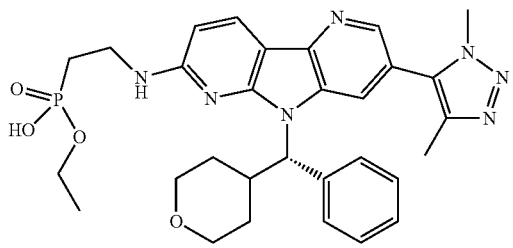 [SMILES: CCOP(=O)(O)CCNc1ccc2c3ncc(-c4c(C)nnn4C)cc3n([C@H](c3ccccc3)C3CCOCC3)c2n1]

The title compound was obtained in 26% yield during the synthesis and purification of (2-{[5-(dimethyl-1H-1,2,3-triazol-5-yl)-8-[(S)-oxan-4-yl(phenyl)methyl]-3,8,10-triazatricyclo[7.4.0.0$^{2,7}$]trideca 1(9),2(7),3,5,10,12-hexaen-11-yl]amino}ethyl)phosphonic acid. Analytical LC/MS Injection 1 conditions; Column: Waters Acquity UPLC BEH C18, 2.1× 50 mm, 1.7-μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 min, then a 0.75-min hold at 100% B; Flow: 1.0 mL/min; Detection: UV at 220 nm. RT=1.20 min, LC/MS (M+H)=590.0. Analytical LC/MS Injection 2 conditions; Column: Waters Acquity UPLC BEH C18, 2.1×50 mm, 1.7-μm particles; Mobile Phase A: 5:95 ACN:water with 0.1% trifluoroacetic acid; Mobile Phase B: 95:5 ACN:water with 0.1% trifluoroacetic acid; Temperature: 50° C.; Gradient: 0-100% B over 3 min, then a 0.75-min hold at 100% B; Flow: 1.0 mL/min; Detection: UV at 220 nm. RT=1.25 min, LC/MS (M+H)=590.0. $^1$H NMR (500 MHz, DMSO-d$_6$) δ 8.39-8.31 (m, 2H), 8.05 (d, J=8.4 Hz, 1H), 7.85 (d, J=7.0 Hz, 2H), 7.30 (t, J=7.7 Hz, 3H), 7.18 (t, J=7.3 Hz, 1H), 6.46 (d, J=8.4 Hz, 1H), 5.64 (br. s., 1H), 4.01 (s, 3H), 3.82 (d, J=10.3 Hz, 2H), 3.73 (br. s., 2H), 3.51-3.45 (m, 2H), 3.32 (br. s., 2H), 2.30 (s, 4H), 1.98-1.84 (m, 4H), 1.47 (br. s., 1H), 1.34 (d, J=8.1 Hz, 1H), 1.22 (br. s., 2H); HPLC, Injection 1 RT=1.20 min, Injection 2 RT=1.25 min; LC/MS (M+H)=590.3.

Example 221

5-(Dimethyl-1H-1,2,3-triazol-5-yl)-8-[(S)-(2-fluorophenyl)(oxan-4-yl)methyl]-11-methanesulfonyl-3,8,10-triazatricyclo[7.4.0.0$^{2,7}$]trideca-1(13),2(7),3,5,9,11-hexaene

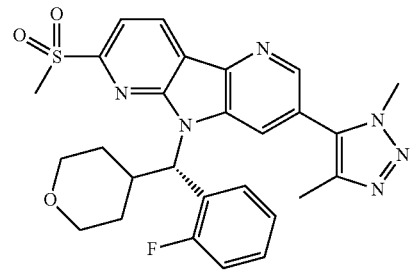 [SMILES: Cc1nnn(C)c1-c1cnc2c3ccc(S(C)(=O)=O)nc3n([C@H](c3ccccc3F)C3CCOCC3)c2c1]

Step 1: 2-(Methylsulfonyl)-5-(4,4,5,5-tetramethyl-1,3,2-dioxaborolan-2-yl)pyridine In a pressure vessel equipped with a magnetic stirring bar was added 4,4,4',4',5,5,5',5'-octamethyl-2,2'-bis(1,3,2-dioxaborolane) (1.291 g, 5.08 mmol) and 5-bromo-2-(methylsulfonyl)pyridine (1 g, 4.24 mmol). The solids were suspended in dioxane (15 mL) and DMSO (0.5 mL). Potassium acetate (0.831 g, 8.47 mmol) was added and the reaction mixture was degassed with argon with sonication for 5 min. PdCl$_2$(dppf)-CH$_2$Cl$_2$ adduct (0.173 g, 0.212 mmol) was added. The vessel was capped and heated within an oil bath for 3 h at 90° C. After 3 h, the reaction was cooled to room temperature while stirring. The reaction mixture was filtered, and the filtrate was concentrated. The aqueous layer was diluted with water and was extracted with ethyl acetate. Brine was used to help break up layers. The organic layer was dried over MgSO$_4$, filtered and concentrated under vacuum to give 1.56 g of a brown solid.

Step 2: 5-Bromo-6'-(methylsulfonyl)-3-nitro-2,3'-bipyridine

In a pressure vessel equipped with a magnetic stirring bar was added 2-(methylsulfonyl)-5-(4,4,5,5-tetramethyl-1,3,2- dioxaborolan-2-yl)pyridine (800 mg, 2.12 mmol) and 2,5-dibromo-3-nitropyridine (597 mg, 2.12 mmol). The solids were suspended in dioxane (25 mL) and water (8.33 mL). Potassium carbonate (879 mg, 6.36 mmol) and $PdCl_2(dppf)\cdot CH_2Cl_2$ adduct (138 mg, 0.170 mmol) were added. Argon was bubbled through the mixture while sonicating for 5 min. The vessel was capped and heated for 2 h at 90° C. The reaction vessel was cooled to room temperature. The reaction mixture was filtered and the filtrate was concentrated. The remaining aqueous layer was diluted with water and extracted with ethyl acetate. The organic layer was dried over $MgSO_4$, filtered and concentrated under vacuum to give a semi-solid. The material was taken up in DCM, and purified by silica gel chromatography (80 g ISCO silica column, eluting with 5-100% ethyl acetate/hexanes over 900 mL, TLC $R_f$=0.52 (50% ethyl acetate/hexanes). Like fractions were concentrated to give 470 mg (56%) of a yellow solid. LC/MS (M+H)=359.9. LC/MS purity: >91%; $R_t$=0.98 min. Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min.

Step 3: 3-Bromo-7-(methylsulfonyl)-5H-pyrrolo[3,2-b:4,5-c']dipyridine and 3-bromo-7-(methylsulfonyl)-5H-pyrrolo[2,3-b:4,5-b']dipyridine In a 50 mL round bottom flask equipped with a magnetic stirring bar was added 5-bromo-6'-(methylsulfonyl)-3-nitro-2,3'-bipyridine (300 mg, 0.838 mmol), and bis(diphenylphosphino)ethane (417 mg, 1.05 mmol). The solids were suspended in 1,2-dichlorobenzene (1414 µL). The reaction was heated to 1500 (oil bath) while stirring with the flask open to air. The reaction was allowed to continue for 0.75 h. The solvent was removed under a stream of nitrogen with heating. The black residue was taken up in methanol (with stirring) for purification by preparative HPLC: Conditions: 20-100% B; B solvent 90% methanol/0.1% TFA water, Phenomenex AXIA LUNA C18 30×100 mm, 10 micron, 30 mL/min flow rate, UV at 254 nm. Peak one: 100 mg (29%) $R_t$: 10.6 min; Peak two (23%) $R_t$: 11.5 min. Peak one: $^1H$ NMR (400 MHz, DMSO-$d_6$) δ 12.54 (s, 1H), 9.56 (s, 1H), 8.77 (d, J=2.0 Hz, 1H), 8.49 (d, J=2.0 Hz, 1H), 8.29 (d, J=0.8 Hz, 1H). Peak two: $^1H$ NMR (400 MHz, DMSO-$d_6$) δ 12.81 (s, 1H), 8.92 (d, J=8.0 Hz, 1H), 8.74 (d, J=2.0 Hz, 1H), 8.30 (d, J=2.0 Hz, 1H), 8.00 (d, J=7.8 Hz, 1H).

Step 4: (S)-3-Bromo-5-((2-fluorophenyl)(tetrahydro-2H-pyran-4-yl)methyl)-7-(methylsulfonyl)-5H-pyrrolo[2,3-b:4,5-b']dipyridine In a round bottom flask equipped with a magnetic stirring bar and cooled to 0° C. in an ice bath was added 3-bromo-7-(methylsulfonyl)-5H-pyrrolo[2,3-b:4,5-b']dipyridine (70 mg, 0.215 mmol), (R)-(2-fluorophenyl)(tetrahydro-2H-pyran-4-yl)methanol (67.7 mg, 0.322 mmol) and $Ph_3P$ (84 mg, 0.322 mmol). The solids were dissolved in THF (15 mL). DIAD (0.063 mL, 0.322 mmol) was added drop wise to this suspension over 15 min. The ice bath was removed and the reaction was allowed to warm to room temperature over 3 h. The reaction mixture was concentrated. The residue was dissolved in DMF, filtered and purified by preparative HPLC: Conditions: 20-100% B; B solvent 90% methanol/0.1% TFA water, Phenomenex AXIA LUNA C18 30×100 mm, 10 micron, 30 mL/min flow rate, UV at 254 nm. Desired product peak eluted at $R_t$: 16.1 min. Like fractions were concentrated to give 60 mg (46%) of yellow oil. Purified material at >85% purity. LC/MS (M+H)=520.1; HPLC conditions: $R_t$=3.25 min (Phenomenex LUNA C18 2×50 mm (4 min grad) eluting with 5-95% aq ACN containing 10 mM $NH_4OAc$, 0.8 mL/min, monitoring at 254 nm); Temperature: 40° C.).

Step 5: 5-(Dimethyl-1H-1,2,3-triazol-5-yl)-8-[(S)-(2-fluorophenyl)(oxan-4-yl)methyl]-11-methanesulfonyl-3,8,10-triazatricyclo[7.4.0.0$^{2,7}$]trideca-1(13),2(7),3,5,9,11-hexaene In a pressure vessel equipped with a magnetic stirring bar, was added (S)-3-bromo-5-((2-fluorophenyl)(tetrahydro-2H-pyran-4-yl)methyl)-7-(methylsulfonyl)-5H-pyrrolo[2,3-b:4,5-b']dipyridine (50 mg, 0.096 mmol), 1,4-dimethyl-1H-1,2,3-triazole (14.1 mg, 0.145 mmol) and NMP (1.5 mL). Tetramethylammonium acetate (19.3 mg, 0.145 mmol) and bis(triphenylphosphine) palladium(II) chloride (4.7 mg, 6.75 µmol) was added. Argon was bubbled into the mixture with sonication for 5 min. The vessel was capped and placed into a preheated oil bath at 100° C. and the reaction mixture was stirred overnight. The reaction mixture was filtered, and the solids were washed with DCM. The filtrate was concentrated under vacuum. The remaining oil was diluted with DMF and was filtered to remove solids. The mixture was purified by preparative HPLC: Column: Waters XBridge C18, 19×200 mm, 5-µm particles; Mobile Phase A: 5:95 methanol: water with 10 mM $NH_4OAc$; Mobile Phase B: 95:5 methanol: water with 10 mM $NH_4OAc$; Gradient: 35-75% B over 30 min, then a 5-min hold at 100% B; Flow: 20 mL/min. Fractions containing the desired product were combined and dried via centrifugal evaporation to give 1.4 mg (3%) of the title compound with an average purity by LC/MS analysis was 96%. Two analytical LC/MS injections were used to determine the final purity. Injection 1 conditions: Column: Waters BEH C18, 2.0×50 mm, 1.7 µm particles; Mobile Phase A: 5:95 ACN:water with 10 mM $NH_4OAc$; Mobile Phase B: 95:5 ACN:water with 10 mM $NH_4OAc$; Temperature: 50° C.; Gradient: 0% B, 0-100% B over 3 min, then a 0.5-min hold at 100% B; Flow: 1 mL/min; Detection: UV at 220 nm. $R_t$=1.48 min; LC/MS (M+H)=535.3. Injection 2 conditions: Column: Waters BEH C18, 2.0×50 mm, 1.7-µm particles; Mobile Phase A: 5:95 methanol:water with 10 mM $NH_4OAc$; Mobile Phase B: 95:5 methanol:water with 10 mM $NH_4OAc$; Temperature: 50° C.; Gradient: 0% B, 0-100% B over 3 min, then a 0.5-min hold at 100% B; Flow: 0.5 mL/min; Detection: UV at 220 nm. $R_t$=2.29 min; LC/MS (M+H)=535.3. $^1H$ NMR (500 MHz, DMSO-$d_6$) δ 8.95 (d, J=8.1 Hz, 1H), 8.82-8.75 (m, 1H), 8.70 (br. s., 1H), 8.26 (t, J=7.0 Hz, 1H), 8.01 (d, J=8.1 Hz, 1H), 7.34 (d, J=5.9 Hz, 1H), 7.31-7.25 (m, 1H), 7.16-7.09 (m, 1H), 6.25 (br. s., 1H), 4.07 (s, 3H), 3.93-3.85 (m, 2H), 3.74 (d, J=12.1 Hz, 1H), 3.62 (d, J=10.3 Hz, 1H), 3.37 (d, J=8.8 Hz, 1H), 3.27-3.19 (m, 2H), 2.35 (s, 3H), 1.72-1.60 (m, 3H), 1.56-1.46 (m, 1H), 0.98 (d, J=13.2 Hz, 1H). LC/MS (M+H)=535.3; HPLC conditions: $R_t$=2.56 min (Phenomenex LUNA C18 2×50 mm (4 min grad) eluting with 5-95% aq ACN containing 10 mM $NH_4OAc$, 0.8 mL/min, monitoring at 254 nm); Temperature: 40° C.).

Example 222

5-(Dimethyl-1,2-oxazol-4-yl)-8-[(S)-(2-fluorophenyl)(oxan-4-yl)methyl]-11-methanesulfonyl-3,8,10-triazatricyclo[7.4.0.0$^{2,7}$]trideca-1(13),2(7),3,5,9,11-hexaene

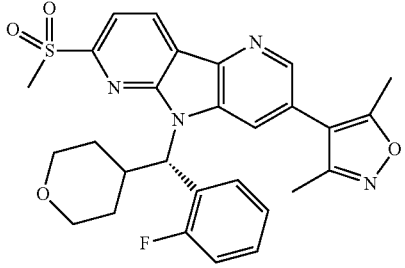 [SMILES: Cc1noc(C)c1-c1cnc2c3ccc(S(C)(=O)=O)nc3n([C@H](c3ccccc3F)C3CCOCC3)c2c1]

In a small pressure vessel equipped with a magnetic stirring bar was added (S)-3-bromo-5-((2-fluorophenyl)(tetrahydro-2H-pyran-4-yl)methyl)-7-(methylsulfonyl)-5H-pyrrolo[2,3-b:4,5-b']dipyridine (50 mg, 0.096 mmol) and (3,5-dimethylisoxazol-4-yl)boronic acid (20.4 mg, 0.145 mmol). The solids were suspended in dioxane (3 mL) and water (1 mL). Potassium carbonate (40.0 mg, 0.289 mmol) and PdCl$_2$(dppf)-CH$_2$Cl$_2$ adduct (6.3 mg, 7.72 µmol) were added. Argon was bubbled through the mixture while sonicating for 5 min. The vessel was capped and heated for 2 h at 90° C. The reaction mixture was filtered and the filtrate was taken up in water and ethyl acetate. The organic layer was dried over MgSO$_4$, filtered and concentrated to give oil. The oil was diluted with DMF then filtered to be purified by preparative HPLC: Column: Waters XBridge C18, 19×200 mm, 5-µm particles; Mobile Phase A: 5:95 methanol: water with 10 mM NH$_4$OAc; Mobile Phase B: 95:5 methanol: water with 10 mM NH$_4$OAc; Gradient: 35-75% B over 15 min, then a 5-min hold at 100% B; Flow: 20 mL/min. The material was re-purified via preparative LC/MS with the following conditions: Column: Waters XBridge C18, 19×200 mm, 5-µm particles; Mobile Phase A: 5:95 methanol: water with 10 mM NH$_4$OAc; Mobile Phase B: 95:5 methanol: water with 10 mM NH$_4$OAc; Gradient: 50-90% B over 20 min, then a 5-min hold at 100% B; Flow: 20 mL/min. Fractions containing the desired product were combined and dried via centrifugal evaporation to give 9.1 mg (17%) of the title compound with an average purity by LC/MS analysis was >99%. Two analytical LC/MS injections were used to determine the final purity. Injection 1 conditions: Column: Waters BEH C18, 2.0×50 mm, 1.7 µm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_t$=1.75 min; LC/MS (M+H)=535.1. Injection 2 conditions: Column: Waters BEH C18, 2.0×50 mm, 1.7-µm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_t$=2.52 min; LC/MS (M+H)=535.2. $^1$H NMR (500 MHz, DMSO-d$_6$) δ 8.90 (d, J=8.1 Hz, 1H), 8.68 (s, 1H), 8.52 (br. s., 1H), 8.25 (t, J=7.3 Hz, 1H), 7.99 (d, J=8.1 Hz, 1H), 7.34 (q, J=6.6 Hz, 1H), 7.31-7.23 (m, 1H), 7.18-7.07 (m, 1H), 6.21 (br. s., 1H), 3.97-3.85 (m, 1H), 3.74 (d, J=9.5 Hz, 1H), 3.62 (d, J=10.6 Hz, 1H), 3.39 (d, J=3.7 Hz, 3H), 3.27-3.13 (m, 2H), 2.51 (br. s., 3H), 2.35 (s, 3H), 1.66 (d, J=12.8 Hz, 1H), 1.58-1.45 (m, 1H), 1.43-1.28 (m, 1H), 0.96 (d, J=12.1 Hz, 1H). LC/MS (M+H)=535.3; HPLC conditions: R$_t$=2.60 min (Phenomenex LUNA C18 2×50 mm (4 min grad) eluting with 5-95% aq ACN containing 10 mM NH$_4$OAc, 0.8 mL/min, monitoring at 254 nm); Temperature: 40° C.).

Example 223

1-[5-(Dimethyl-1,2-oxazol-4-yl)-8-[(S)-(4-fluorophenyl)(oxan-4-yl)methyl]-3,8,12-triazatricyclo[7.4.0.0$^{2,7}$]trideca-1(13),2(7),3,5,9,11-hexaen-11-yl]($^2$H$_3$)ethan-1-one

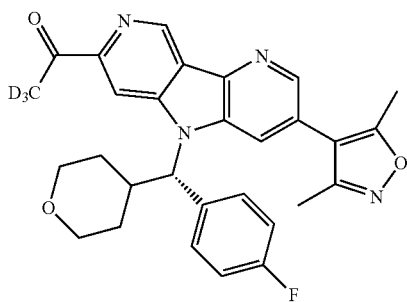 [SMILES: [2H]C([2H])([2H])C(=O)c1cc2c(cn1)c1ncc(-c3c(C)noc3C)cc1n2[C@H](c1ccc(F)cc1)C1CCOCC1]

In a small round bottom flask equipped with a magnetic stirring bar and cooled to −78° C. in an dry ice/acetone bath was added (S)-methyl 3-(3,5-dimethylisoxazol-4-yl)-5-((4-fluorophenyl)(tetrahydro-2H-pyran-4-yl)methyl)-5H-pyrrolo[3,2-b:4,5-c']dipyridine-7-carboxylate (50 mg, 0.087 mmol) and THF (10 mL). CD$_3$Li (1.75 mL, 0.875 mmol, 0.5M in diethyl ether, as a LiI complex) was added drop wise while at −78° C. After 2 h, the cooling bath was removed and the reaction mixture was warmed to room temperature. The reaction was quenched with methanol while stirring at room temperature. The solvents were removed under vacuum and the oil was taken up in methanol and filtered. The solution was purified by preparative HPLC: Column: Waters XBridge C18, 19×200 mm, 5-µm particles; Mobile Phase A: 5:95 methanol: water with 10 mM NH$_4$OAc; Mobile Phase B: 95:5 methanol: water with 10 mM NH$_4$OAc; Gradient: 10-80% B over 30 min, then a 5-min hold at 100% B; Flow: 20 mL/min. Fractions containing the desired product were combined and dried via centrifugal evaporation to give 1.6 mg (3%) of the title compound with an average purity by LC/MS analysis was 95%. Two analytical LC/MS injections were used to determine the final purity. Injection 1 conditions: Column: Waters BEH C18, 2.0×50 mm, 1.7 µm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_t$=1.25 min; LC/MS (M+H)=502.1. Injection 2 conditions: Column: Waters BEH C18, 2.0×50 mm, 1.7-µm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_t$=2.51 min; LC/MS (M+H)=502.1. $^1$H NMR (500 MHz, DMSO-d$_6$) δ 9.42 (s, 1H), 8.77 (br. s., 1H), 8.63 (s, 1H), 8.40

(br. s., 1H), 7.79-7.65 (m, 2H), 7.18 (t, J=8.6 Hz, 2H), 6.00 (d, J=11.0 Hz, 1H), 3.94-3.85 (m, 2H), 3.71 (d, J=9.2 Hz, 1H), 3.36 (br. s., 1H), 3.24 (t, J=11.4 Hz, 1H), 2.48 (s, 3H), 2.30 (s, 3H), 1.66 (br. s., 1H), 1.60 (d, J=11.0 Hz, 1H), 1.30 (d, J=8.1 Hz, 1H), 0.92 (d, J=13.2 Hz, 1H). LC/MS (M+H)= 502.1; HPLC conditions: $R_t$=3.46 min (Phenomenex LUNA C18 2×50 mm (4 min grad) eluting with 10-90% aq MeOH containing 0.1% TFA, 0.8 mL/min, monitoring at 254 nm); Temperature: 40° C.).

Example 224

2-[5-(Dimethyl-1,2-oxazol-4-yl)-8-[(S)-(4-fluorophenyl)(oxan-4-yl)methyl]-3,8,12-triazatricyclo[7.4.0.0$^{2,7}$]trideca-1(13),2(7),3,5,9,11-hexaen-11-yl]($^2H_6$)propan-2-ol

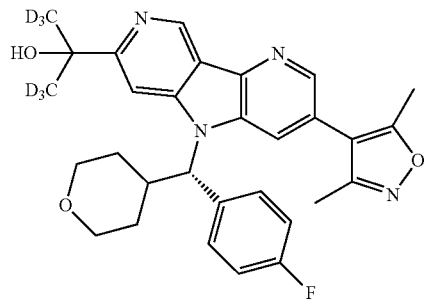 [SMILES: [2H]C([2H])([2H])C(O)(c1cc2c(cn1)c1ncc(-c3c(C)noc3C)cc1n2[C@H](c1ccc(F)cc1)C1CCOCC1)C([2H])([2H])[2H]]

In a small round bottom flask equipped with a magnetic stirring bar and cooled to −78° C. in an dry ice/acetone bath was added (S)-methyl 3-(3,5-dimethylisoxazol-4-yl)-5-((4-fluorophenyl)(tetrahydro-2H-pyran-4-yl)methyl)-5H-pyrrolo[3,2-b:4,5-c′]dipyridine-7-carboxylate (50 mg, 0.087 mmol) and THF (10 mL). CD$_3$Li (1.75 mL, 0.875 mmol, 0.5M in diethyl ether, as an LiI complex) was added drop wise while at −78° C. After 2 h, the cooling bath was removed and the reaction mixture was warmed to room temperature. The reaction was quenched with methanol while stirring at room temperature. The solvents were removed under vacuum and the residual oil was taken up in methanol and filtered. The solution was purified by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 10-80% B over 30 min, then a 5-min hold at 100% B; Flow: 20 mL/min. Fractions containing the desired product were combined and dried via centrifugal evaporation to give 22.3 mg (48%) of the title compound with an average purity by LC/MS analysis was 97%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. $R_t$=1.69 min; LC/MS (M+H)=521.3. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. $R_t$=2.97 min; LC/MS (M+H)=521.3. $^1$H NMR (500 MHz, DMSO-d$_6$) δ 9.30 (s, 1H), 8.52 (s, 1H), 8.30 (br. s., 1H), 8.24 (br. s., 1H), 7.72 (dd, J=8.1, 5.5 Hz, 2H), 7.18 (t, J=8.6 Hz, 2H), 5.83 (d, J=11.4 Hz, 1H), 3.96-3.83 (m, 1H), 3.74 (d, J=9.5 Hz, 1H), 3.47 (t, J=11.2 Hz, 2H), 3.37 (d, J=10.3 Hz, 1H), 3.26 (t, J=11.6 Hz, 1H), 2.47 (s, 3H), 2.29 (s, 3H), 1.73-1.63 (m, 1H), 1.63-1.49 (m, 1H), 1.37-1.23 (m, 1H), 0.97 (d, J=11.7 Hz, 1H). LC/MS (M+H)=521.2; HPLC conditions: $R_t$=3.13 min (Phenomenex LUNA C18 2×50 mm (4 min grad) eluting with 10-90% aq MeOH containing 0.1% TFA, 0.8 mL/min, monitoring at 254 nm); Temperature: 40° C.).

Example 225

2-{8-[(S)-(4-Fluorophenyl)(oxan-4-yl)methyl]-5-[5-($^2H_3$)methyl-3-methyl-1,2-oxazol-4-yl]-3,8,12-triazatricyclo[7.4.0.0$^{2,7}$]trideca-1(13),2(7),3,5,9,11-hexaen-11-yl}propan-2-ol

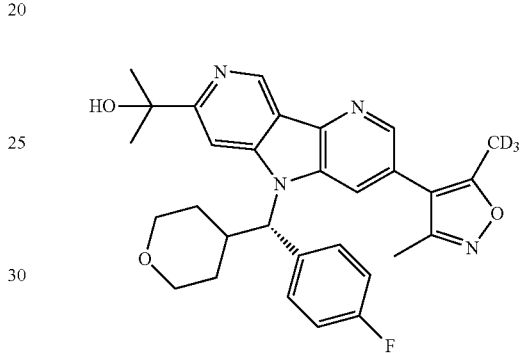

In a 20 mL pressure vial equipped with a magnetic stirring bar was added (S)-2-(3-(3,5-dimethylisoxazol-4-yl)-5-((4-fluorophenyl)(tetrahydro-2H-pyran-4-yl)methyl)-5H-pyrrolo[3,2-b:4,5-c′]dipyridin-7-yl)propan-2-ol (35 mg, 0.068 mmol) and CD$_3$OD (3 mL). Potassium t-butoxide (38.2 mg, 0.340 mmol) was added to the solution which dissolved at room temperature. The vial was placed into a preheated oil bath at 80° C. and was stirred overnight. The reaction mixture was concentrated. The residue was taken up in 2 mL of methanol and filtered for purification by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 30-70% B over 15 min, then a 5-min hold at 100% B; Flow: 20 mL/min. Fractions containing the desired product were combined and dried via centrifugal evaporation to give 16.8 mg (45%) of the title compound with an average purity by LC/MS analysis was 94%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. $R_t$=1.63 min; LC/MS (M+H)=576.6. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. $^1$H NMR (500 MHz, DMSO-d$_6$) δ 9.30 (s, 1H), 8.53 (s, 1H), 8.31 (br. s., 1H), 8.25

(br. s., 1H), 7.71 (dd, J=8.1, 5.5 Hz, 2H), 7.18 (t, J=8.8 Hz, 2H), 5.83 (d, J=11.4 Hz, 1H), 3.94-3.85 (m, 1H), 3.74 (d, J=9.5 Hz, 1H), 3.47 (t, J=11.0 Hz, 1H), 3.40 (d, J=5.1 Hz, 2H), 3.26 (t, J=11.7 Hz, 1H), 2.30 (s, 3H), 1.68 (d, J=12.5 Hz, 1H), 1.58 (d, J=9.2 Hz, 6H), 1.51 (d, J=13.2 Hz, 1H), 1.37-1.23 (m, 1H), 0.97 (d, J=13.2 Hz, 1H). LC/MS (M+H)= 576.6; HPLC conditions: $R_t$=2.76 min (Phenomenex LUNA C18 2×50 mm (4 min grad) eluting with 5-95% aq ACN containing 10 mM NH$_4$OAc, 0.8 mL/min, monitoring at 254 nm); Temperature: 40° C.).

Example 226

11-Chloro-5-(dimethyl-1H-1,2,3-triazol-5-yl)-8-[(S)-(2-fluorophenyl)(oxan-4-yl)methyl]-3,8,10-triazatricyclo[7.4.0.0$^{2,7}$]trideca-1(13),2(7),3,5,9,11-hexaene

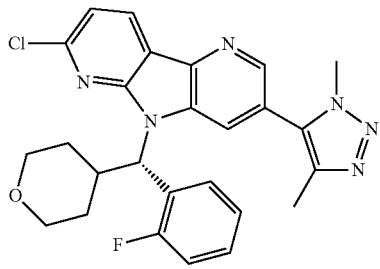 [SMILES: Cc1nnn(C)c1-c1cnc2c3ccc(Cl)nc3n([C@H](c3ccccc3F)C3CCOCC3)c2c1]

Step 1: 5-Bromo-6'-chloro-3-nitro-2,3'-bipyridine

In a 75 mL pressure flask equipped with a magnetic stirring bar was added (6-chloropyridin-3-yl)boronic acid (1 g, 6.35 mmol), 2,5-dibromo-3-nitropyridine (1.791 g, 6.35 mmol). The solids were suspended in THF (30 mL). The mixture was treated with PdCl$_2$(dppf)-CH$_2$Cl$_2$ adduct (0.259 g, 0.318 mmol) and K$_3$PO$_4$ (9.53 mL, 19.1 mmol) (25 g K$_3$PO$_4$/60 mL water=2M solution). Argon was bubbled through the mixture for 5 min while sonicating. The flask was capped and heated to 80° C. within a preheated oil bath for 2 h. The reaction vessel was cooled to room temperature. The reaction mixture was filtered, and the filtrate was concentrated to remove the organic solvent. The remaining aqueous layer was diluted with water and was extracted with ethyl acetate (emulsion formed, brine added). The organic layer was dried over MgSO$_4$, filtered and concentrated to give a solid. The material was taken up in DCM and ethyl acetate. The solution was purified by flash column chromatography (80 g silica gel ISCO, 0-50% ethyl acetate/hexanes over 600 mL total solvent, then 50-100% over 300 mL solvent; TLC Rf=0.88 (50% ethyl acetate/hexanes)). Like fractions were concentrated to give 660 mg (33%) of a pale yellow solid with 99% purity by LC/MS. LC/MS (M+H)= 315.9; HPLC conditions: $R_t$=3.43 min (Phenomenex LUNA C18 2×50 mm (4 min grad) eluting with 10-90% aq MeOH containing 0.1% TFA, 0.8 mL/min, monitoring at 254 nm); Temperature: 40° C.).

Step 2: 3-Bromo-7-chloro-5H-pyrrolo[2,3-b:4,5-b'] dipyridine and 3-bromo-7-chloro-5H-pyrrolo[3,2-b: 4,5-c']dipyridine In a round bottom flask equipped with a magnetic stirring bar was added 5-bromo-6'-chloro-3-nitro-2,3'-bipyridine (4.5 g, 14.3 mmol), and bis(diphenylphosphino)ethane (7.13 g, 17.9 mmol). The solids were suspended in 1,2-dichlorobenzene (16.1 ml, 143 mmol). The flask was flushed with nitrogen, and the reaction was heated to 150° C. (oil bath) with stirring. The reaction was allowed to continue for 1 h, open to air. Most of the solvent was removed by evaporation under a stream of nitrogen while heating to 100° C. The reaction mixture was diluted with 100 mL of dichloromethane and was stirred at room temperature overnight. A white precipitate formed and was removed by filtration, washing the solid with additional dichloromethane. This filtered material (2.08 g; 52%) was 3-bromo-7-chloro-5H-pyrrolo [3,2-b:4,5-c']dipyridine: $^1$H NMR (400 MHz, DMSO-d$_6$) δ 12.47 (br. s., 1H), 8.68-8.57 (m, 2H), 8.19 (d, J=1.8 Hz, 1H), 7.42 (d, J=8.3 Hz, 1H). The remaining filtrate which contains the other isomer plus multiple impurities was concentrated to remove remaining 1,2-dichlorobenzene. After solvent removal (nitrogen stream with heating at 100° C.), the oily residue was taken up in 50 mL of isopropyl acetate and stirred mixture at room temperature for several hours. A brown solid was filtered. The filtrate was concentrated under vacuum to give an oil. This oil was taken up in DCM and was transferred to the top of a 40 g ISCO silica gel column for purification. The material was eluted with 5-100% THF/ hexanes over 800 mL total volume. Like fractions (as identified by LC/MS; double spot by TLC ($R_f$=0.64/0.73 in 30% THF/hexanes)) were combined and concentrated under vacuum to give 600 mg (15%) of 3-bromo-7-chloro-5H-pyrrolo[2,3-b:4,5-b']dipyridine as an off-white solid. $^1$H NMR (400 MHz, CDCl$_3$) δ 1 capped 0.45 (br, s., 1H), 9.33 (s, 1H), 8.69 (d, J=1.8 Hz, 1H), 8.04 (d, J=1.8 Hz, 1H), 7.29 (s, 1H).

Step 3: (S)-3-Bromo-7-chloro-5-((2-fluorophenyl) (tetrahydro-2H-pyran-4-yl)methyl)-5H-pyrrolo[2,3-b:4,5-b']dipyridine In a round bottom flask equipped with a magnetic stirring bar and cooled to 0° C. in an ice bath was added 3-bromo-7-chloro-5H-pyrrolo[2,3-b:4,5-b']dipyridine (1000 mg, 1.77 mmol), (R)-(2-fluorophenyl)(tetrahydro-2H-pyran-4-yl) methanol (558 mg, 2.65 mmol) and Ph$_3$P (696 mg, 2.65 mmol). The solids were suspended in dichloromethane (40 mL). DIAD (0.516 mL, 2.65 mmol) was added drop wise to this suspension. The ice bath was removed and the reaction was allowed to warm to room temperature over 2 h. After 2 h at room temperature, a white precipitate that remained in the reaction mixture was filtered off. The filtrate was concentrated under vacuum to give a residue. The residue was taken up in DCM, and was transferred to the top of an 80 g ISCO silica gel column. The material was eluted with 0-100% ethyl acetate/hexane over 900 mL total volume of solvents. Like fractions ($R_f$=0.86 in 50% ethyl acetate/ hexane) were combined then concentrated under vacuum to give 660 mg (71%) of a white foam with >90% purity. LC/MS (M+H)=476.0; HPLC conditions: $R_t$=1.22 min. Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min.

Step 4: 11-Chloro-5-(dimethyl-1H-1,2,3-triazol-5-yl)-8-[(S)-(2-fluorophenyl)(oxan-4-yl)methyl]-3,8, 10-triazatricyclo[7.4.0.0$^{2,7}$]trideca-1(13),2(7),3,5,9, 11-hexaene In a 75 mL pressure vessel equipped with a magnetic stirring bar was added (S)-3-bromo-7-chloro-5-((2-fluorophenyl)(tetrahydro-2H-pyran-4-yl)methyl)-5H-pyrrolo[2,3-b:4,5-b']dipyridine (650 mg, 1.37 mmol), 1,4-dimethyl-1H-1,2,3-triazole (199 mg, 2.05 mmol) and NMP (10 mL). Tetramethyl NH$_4$OAc (274 mg, 2.05 mmol) and bis(triphenylphosphine) palladium(II) chloride (67.3 mg, 0.096 mmol) was added. Argon was bubbled into the mixture with sonication for 5 min, and then the vessel was capped and placed into a preheated oil bath at 100° C. The reaction mixture was stirred overnight. Solvent was removed under a stream of nitrogen while heating the vessel at 100° C. in an oil bath. The remaining residue was taken up DCM and was transferred to an 80 g ISCO silica gel column. The material was eluted with 0-75% of 10% 2M ammonia in methanol within ethyl acetate with the remainder hexanes, over 1 L of total volume. Like fractions (TLC R$_f$=0.58 in 50% of 10% 2M ammonia methanol within ethyl acetate/hexanes) were combined, concentrated under vacuum. The oil that remained was triturated with hexanes and resulting solid was filtered to give 197 mg (22%) of a >75% purity, yellow foam as the title compound. $^1$H NMR (500 MHz, DMSO-d$_6$) δ 8.71-8.62 (m, 2H), 8.21 (t, J=7.3 Hz, 1H), 7.46 (d, J=8.1 Hz, 1H), 7.41-7.24 (m, 2H), 7.12 (t, J=9.4 Hz, 1H), 6.18 (br. s., 1H), 4.01 (br. s., 3H), 3.93-3.82 (m, 2H), 3.74 (d, J=9.9 Hz, 1H), 3.53 (d, J=8.8 Hz, 1H), 3.49-3.36 (m, 1H), 3.30-3.12 (m, 1H), 2.29 (s, 3H), 1.66 (d, J=11.7 Hz, 1H), 1.53-1.39 (m, 1H), 1.39-1.26 (m, 1H), 0.96 (d, J=12.5 Hz, 1H). LC/MS (M+H)=491.4; HPLC conditions: R$_t$=3.30 min (Phenomenex LUNA C18 2×50 mm (4 min grad) eluting with 5-95% aq ACN containing 10 mM NH$_4$OAc, 0.8 mL/min, monitoring at 254 nm); Temperature: 40° C.).

Example 227

5,11-Bis(dimethyl-1H-1,2,3-triazol-5-yl)-8-[(S)-(2-fluorophenyl)(oxan-4-yl)methyl]-3,8,10-triazatricyclo[7.4.0.0$^{2,7}$]trideca-1(13),2(7),3,5,9,11-hexaene

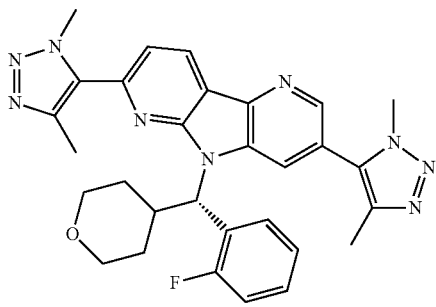 [SMILES: Cc1nnn(C)c1-c1cnc2c3ccc(-c4c(C)nnn4C)nc3n([C@H](c3ccccc3F)C3CCOCC3)c2c1]

In a 75 mL pressure vessel equipped with a magnetic stirring bar, was added (S)-3-bromo-7-chloro-5-((2-fluorophenyl)(tetrahydro-2H-pyran-4-yl)methyl)-5H-pyrrolo[2,3-b:4,5-b']dipyridine (650 mg, 1.37 mmol), 1,4-dimethyl-1H-1,2,3-triazole (199 mg, 2.05 mmol) and NMP (10 mL). Tetramethyl NH$_4$OAc (274 mg, 2.05 mmol) and bis(triphenylphosphine) palladium(II) chloride (67.3 mg, 0.096 mmol) was added. Argon was bubbled into the mixture with sonication for 5 min, then the vessel was capped and placed into a preheated oil bath at 100° C. The reaction mixture was stirred overnight. Most of the solvent was removed under a stream of nitrogen while heating for several hours in an oil bath set at 100° C. The remaining mixture was taken up in 2 mL of DMF then filtered for purification by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 10-80% B over 30 min, then a 5-min hold at 100% B; Flow: 20 mL/min. Fractions containing the desired product were combined and dried via centrifugal evaporation to give 4.7 mg (0.6%) of the title compound with an average purity by LC/MS analysis was >99%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_t$=1.50 min; LC/MS (M+H)=552.5. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_t$=2.51 min; LC/MS (M+H)=552.5. $^1$H NMR (500 MHz, DMSO-d$_6$) δ 8.81 (d, J=8.1 Hz, 1H), 8.68 (s, 1H), 8.46 (br. s., 1H), 8.20 (br. s., 1H), 7.71 (d, J=8.1 Hz, 1H), 7.34 (d, J=5.5 Hz, 1H), 7.29 (d, J=7.7 Hz, 1H), 7.17-7.04 (m, 1H), 6.36 (br. s., 1H), 4.34 (br. s., 3H), 4.00 (br. s., 3H), 3.93-3.83 (m, 1H), 3.72 (d, J=9.5 Hz, 1H), 3.47-3.38 (m, 4H), 3.27-3.15 (m, 1H), 2.29 (br. s., 3H), 1.72 (d, J=11.7 Hz, 1H), 1.58-1.42 (m, 1H), 1.33 (d, J=12.1 Hz, 1H), 0.98 (d, J=13.2 Hz, 1H). LC/MS (M+H)=552.5; HPLC conditions: R$_t$=2.57 min (Phenomenex LUNA C18 2×50 mm (4 min grad) eluting with 5-95% aq ACN containing 10 mM NH$_4$OAc, 0.8 mL/min, monitoring at 254 nm); Temperature: 40° C.).

Example 228

5-(Dimethyl-1H-1,2,3-triazol-5-yl)-8-[(S)-(2-fluorophenyl)(oxan-4-yl)methyl]-N-methyl-N-[2-(methylamino)ethyl]-3,8,10-triazatricyclo[7.4.0.0$^{2,7}$]trideca-1(13),2(7),3,5,9,11-hexaen-11-amine

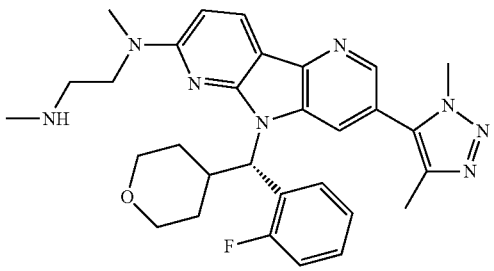 [SMILES: CNCCN(C)c1ccc2c3ncc(-c4c(C)nnn4C)cc3n([C@H](c3ccccc3F)C3CCOCC3)c2n1]

In a pressure vessel equipped with a magnetic stirring bar, was added (S)-7-chloro-3-(1,4-dimethyl-TH-1,2,3-triazol-5-yl)-5-((2-fluorophenyl)(tetrahydro-2H-pyran-4-yl)methyl)-5H-pyrrolo[2,3-b:4,5-b']dipyridine (60 mg, 0.122 mmol), sodium methanesulfinate (37.4 mg, 0.367 mmol), and copper(II)trifluoromethanesulfonate (6.6 mg, 0.018 mmol) and DMSO (1.5 mL). N,N'-dimethylethylenediamine (4 μl, 0.037 mmol) was added and the vial was purged with nitrogen. The vessel was capped and placed into a preheated oil bath at 100° C. The reaction was allowed to stir 5 h. Solids within the reaction mixture were removed by filtration and the filtrate was purified by preparative HPLC:

Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 10-60% B over 35 min, then a 5-min hold at 100% B; Flow: 20 mL/min. Fractions containing the desired product were combined and dried via centrifugal evaporation to give 25.7 mg (38%) of the title compound with an average purity by LC/MS analysis was >99%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_t$=1.20 min; LC/MS (M+H)=543.5. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_t$=2.15 min; LC/MS (M+H)=543.5. $^1$H NMR (500 MHz, DMSO-d$_6$) δ 8.39 (s, 1H), 8.27-8.11 (m, 3H), 7.32 (d, J=6.6 Hz, 1H), 7.28-7.20 (m, 1H), 7.12 (t, J=9.5 Hz, 1H), 6.66 (d, J=8.8 Hz, 1H), 6.00 (br. s., 1H), 4.01 (s, 3H), 3.94-3.80 (m, 2H), 3.77 (d, J=8.1 Hz, 2H), 3.58 (br. s., 1H), 3.49-3.33 (m, 4H), 3.29-3.22 (m, 1H), 3.18 (s, 2H), 2.85 (br. s., 2H), 2.40 (s, 3H), 2.30 (s, 3H), 1.96 (br. s., 3H), 1.60 (d, J=12.1 Hz, 1H), 1.42 (d, J=11.7 Hz, 1H), 1.38-1.26 (m, 1H), 1.03 (d, J=11.4 Hz, 1H). LC/MS (M+H)=543.6; HPLC conditions: R$_t$=2.36 min (Phenomenex LUNA C18 2×50 mm (4 min grad) eluting with 5-95% aq ACN containing 10 mM NH$_4$OAc, 0.8 mL/min, monitoring at 254 nm); Temperature: 40° C.).

Example 229

5-(Dimethyl-1H-1,2,3-triazol-5-yl)-8-[(S)-(2-fluorophenyl)(oxan-4-yl)methyl]-11-(1-methyl-1H-pyrazol-5-yl)-3,8,10-triazatricyclo[7.4.0.0$^{2,7}$]trideca-1(13),2(7),3,5,9,11-hexaene

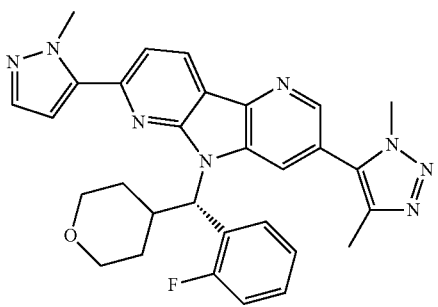 [SMILES: Cc1nnn(C)c1-c1cnc2c3ccc(-c4ccnn4C)nc3n([C@H](c3ccccc3F)C3CCOCC3)c2c1]

In a pressure vessel equipped with a magnetic stirring bar was added (S)-7-chloro-3-(1,4-dimethyl-1H-1,2,3-triazol-5-yl)-5-((2-fluorophenyl)(tetrahydro-2H-pyran-4-yl)methyl)-5H-pyrrolo[2,3-b:4,5-b']dipyridine (30 mg, 0.061 mmol), 1-methyl-5-(4,4,5,5-tetramethyl-1,3,2-dioxaborolan-2-yl)-1H-pyrazole (19.1 mg, 0.092 mmol), dioxane (2 mL) and water (1 mL). Potassium carbonate (21.1 mg, 0.153 mmol) and Pd(Ph$_3$P)$_4$ (5.30 mg, 4.58 μmol) was added. Nitrogen was bubbled into the mixture for 5 min, then the vessel was capped and placed into a preheated oil bath at 100° C. The reaction mixture was stirred 4 h. Solids within the reaction mixture were filtered and the filtrate was purified by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 15-55% B over 35 min, then a 5-min hold at 100% B; Flow: 20 mL/min. Fractions containing the desired product were combined and dried via centrifugal evaporation to give 18.0 mg (55%) of the title compound with an average purity by LC/MS analysis was >99%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_t$=1.65 min; LC/MS (M+H)=537.5. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_t$=2.67 min; LC/MS (M+H)=537.5. $^1$H NMR (500 MHz, DMSO-d$_6$) δ 8.71 (d, J=8.1 Hz, 1H), 8.65 (s, 1H), 8.41 (br. s., 1H), 8.23 (br. s., 1H), 7.85 (d, J=8.1 Hz, 1H), 7.59 (s, 1H), 7.40-7.25 (m, 2H), 7.12 (t, J=9.4 Hz, 1H), 7.00 (br. s., 1H), 6.39 (br. s., 1H), 4.40 (br. s., 3H), 3.99 (br. s., 3H), 3.94-3.85 (m, 1H), 3.73 (d, J=8.1 Hz, 1H), 3.54 (br. s., 1H), 3.28-3.12 (m, 1H), 2.28 (br. s., 3H), 1.73 (br. s., 1H), 1.47 (d, J=12.5 Hz, 1H), 1.35 (d, J=7.7 Hz, 1H), 1.00 (d, J=11.0 Hz, 1H). LC/MS (M+H)=537.5; HPLC conditions: R$_t$=2.78 min (Phenomenex LUNA C18 2×50 mm (4 min grad) eluting with 5-95% aq ACN containing 10 mM NH$_4$OAc, 0.8 mL/min, monitoring at 254 nm); Temperature: 40° C.).

Example 230

5-(Dimethyl-1H-1,2,3-triazol-5-yl)-8-[(S)-(2-fluorophenyl)(oxan-4-yl)methyl]-11-(1-methyl-1,2,3,6-tetrahydropyridin-4-yl)-3,8,10-triazatricyclo[7.4.0.0$^{2,7}$]trideca-1(13),2(7),3,5,9,11-hexaene

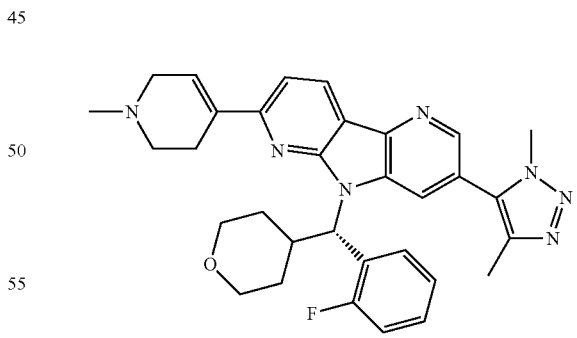

In a microwave pressure vessel equipped with a magnetic stirring bar was added (S)-7-chloro-3-(1,4-dimethyl-H-1,2,3-triazol-5-yl)-5-((2-fluorophenyl)(tetrahydro-2H-pyran-4-yl)methyl)-5H-pyrrolo[2,3-b:4,5-b']dipyridine (30 mg, 0.061 mmol), 1-methyl-4-(4,4,5,5-tetramethyl-1,3,2-dioxaborolan-2-yl)-1,2,3,6-tetrahydropyridine (20.45 mg, 0.092 mmol), dioxane (2 mL) and water (1 mL). Potassium carbonate (21.1 mg, 0.153 mmol) and Pd(Ph$_3$P)$_4$ (5.3 mg, 4.58 μmol) was added. Argon was bubbled into the mixture for 5 min, then the vessel was capped and placed into a preheated oil bath at 100° C. The reaction mixture was stirred for 4 h. Solids in the reaction mixture were filtered, and the filtrate was purified by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 10-50% B over 30 min, then a 5-min hold at 100% B; Flow: 20 mL/min. Fractions containing the desired product were combined and dried via centrifugal evaporation to give 27.3 mg (79%) of the title compound with an average purity by LC/MS analysis was 97%. Two analytical LC/MS injections were used to determine the final purity. Injection 1 conditions: Column: Waters BEH C18, 2.0×50 mm, 1.7 μm particles; Mobile Phase A: 5:95 ACN: water with 10 mM NH$_4$OAc; Mobile Phase B: 95:5 ACN: water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_f$=1.34 min; LC/MS (M+H)=552.5. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_f$=2.77 min; LC/MS (M+H)=552.5. $^1$H NMR (500 MHz, DMSO-d$_6$) δ 8.60 (s, 1H), 8.54 (d, J=8.1 Hz, 1H), 8.47 (br. s., 1H), 8.22 (t, J=7.5 Hz, 1H), 7.64 (d, J=8.4 Hz, 1H), 7.32 (d, J=6.6 Hz, 1H), 7.28-7.21 (m, 1H), 7.12 (t, J=9.4 Hz, 1H), 6.96 (br. s., 1H), 6.17 (br. s., 1H), 4.04 (s, 3H), 3.94-3.85 (m, 1H), 3.74 (d, J=9.9 Hz, 1H), 3.65 (br. s., 1H), 3.47-3.41 (m, 1H), 3.26-3.19 (m, 1H), 3.17 (br. s., 2H), 2.80 (d, J=18.3 Hz, 2H), 2.69 (d, J=5.5 Hz, 2H), 2.32 (s, 3H), 2.35 (s, 3H), 1.87 (s, 1H), 1.63 (d, J=11.7 Hz, 1H), 1.53-1.41 (m, 1H), 1.35 (d, J=7.7 Hz, 1H), 1.00 (d, J=13.2 Hz, 1H). LC/MS (M+H)=552.6; HPLC conditions: R$_f$=2.45 min (Phenomenex LUNA C18 2×50 mm (4 min grad) eluting with 5-95% aq ACN containing 10 mM NH$_4$OAc, 0.8 mL/min, monitoring at 254 nm); Temperature: 40° C.).

Example 231

5-(Dimethyl-1H-1,2,3-triazol-5-yl)-8-[(S)-(2-fluorophenyl)(oxan-4-yl)methyl]-11-(4-methylpiperazin-1-yl)-3,8,10-triazatricyclo[7.4.0.0$^{2,7}$]trideca-1(13),2(7),3,5,9,11-hexaene

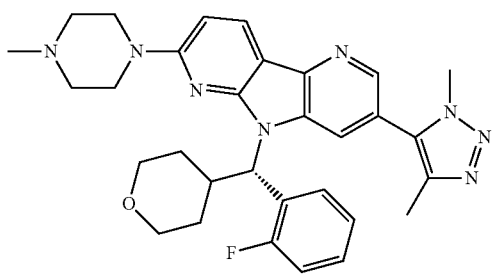 [SMILES: Cc1nnn(C)c1-c1cnc2c3ccc(N4CCN(C)CC4)nc3n([C@H](c3ccccc3F)C3CCOCC3)c2c1]

In a pressure vessel equipped with a magnetic stirring bar was added (S)-7-chloro-3-(1,4-dimethyl-1H-1,2,3-triazol-5-yl)-5-((2-fluorophenyl)(tetrahydro-2H-pyran-4-yl)methyl)-5H-pyrrolo[2,3-b:4,5-b']dipyridine (20 mg, 0.041 mmol), and 1-methylpiperazine (1 mL, 0.041 mmol). The vessel was capped and placed into a preheated oil bath at 100° C. The reaction mixture was stirred for 1 h. Solids in the reaction mixture were filtered and the filtrate was purified by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 25-65% B over 15 min, then a 5-min hold at 100% B; Flow: 20 mL/min. Fractions containing the desired product were combined and dried via centrifugal evaporation to give 13.6 mg (58%) of the title compound with an average purity by LC/MS analysis was 97%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_f$=1.41 min.; LC/MS (M+H)=555.5; Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_f$=2.81 min.; LC/MS (M+H)=555.5. $^1$H NMR (500 MHz, DMSO-d$_6$) δ 8.42 (s, 1H), 8.25 (d, J=8.8 Hz, 2H), 8.14 (t, J=7.9 Hz, 1H), 7.37-7.28 (m, 1H), 7.28-7.19 (m, 1H), 7.12 (t, J=9.2 Hz, 1H), 6.87 (d, J=8.8 Hz, 1H), 6.02 (br. s., 1H), 4.01 (s, 3H), 3.95-3.85 (m, 1H), 3.55 (br. s., 1H), 3.42 (d, J=10.6 Hz, 2H), 3.22 (t, J=11.6 Hz, 1H), 2.30 (s, 3H), 2.26 (s, 3H), 1.91 (s, 2H), 1.60 (d, J=13.2 Hz, 1H), 1.49-1.39 (m, 1H), 1.33 (d, J=8.1 Hz, 1H), 1.05 (d, J=13.6 Hz, 1H). LC/MS (M+H)=555.3; HPLC conditions: R$_f$=0.70 min. Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min.

Example 232

8-[(S)-(2-Fluorophenyl)(oxan-4-yl)methyl]-5,11-bis[4-($^2$H$_3$)methyl-1-methyl-1H-1,2,3-triazol-5-yl]-3,8,10-triazatricyclo[7.4.0.0$^{2,7}$]trideca-1(13),2(7),3,5,9,11-hexaene

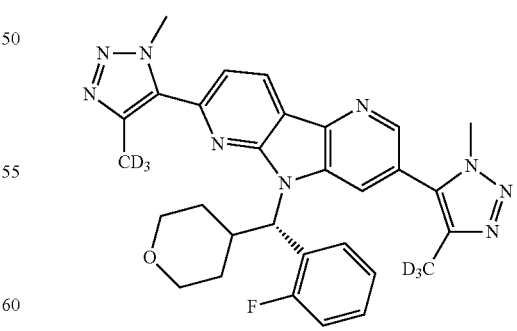

In a pressure vessel equipped with a magnetic stirring bar was added (S)-3-bromo-7-chloro-5-((2-fluorophenyl)(tetrahydro-2H-pyran-4-yl)methyl)-5H-pyrrolo[2,3-b:4,5-b']dipyridine (35 mg, 0.074 mmol), ($^2$H$_3$)methyl-1-methyl-1H-1,2,3-triazol (16.2 mg, 0.162 mmol) and NMP (1 mL).

Tetramethylammonium acetate (14.7 mg, 0.111 mmol) and bis(triphenylphosphine) palladium(II) chloride (3.62 mg, 5.16 µmol) was added. Argon was bubbled into the mixture with sonication for 5 min, then the vessel was capped and placed into a preheated oil bath at 100° C. The reaction mixture was stirred overnight. Solids in the reaction mixture were filtered, and the filtrate was purified by preparative HPLC: Column: Waters XBridge C18, 19×200 mm, 5-µm particles; Mobile Phase A: 5:95 methanol: water with 10 mM NH$_4$OAc; Mobile Phase B: 95:5 methanol: water with 10 mM NH$_4$OAc; Gradient: 15-80% B over 30 min, then a 5-min hold at 100% B; Flow: 20 mL/min. Fractions containing the desired product were combined and dried via centrifugal evaporation to give 14.0 mg (34%) of the title compound with an average purity by LC/MS analysis was >99%. Two analytical LC/MS injections were used to determine the final purity. Injection 1 conditions: Column: Waters BEH C18, 2.0×50 mm, 1.7 µm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. $R_t$=1.52 min.; LC/MS (M+H)=558.5. Injection 2 conditions: Column: Waters BEH C18, 2.0×50 mm, 1.7-µm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. $R_t$=2.51 min.; LC/MS (M+H)=558.5. $^1$H NMR (500 MHz, DMSO-d$_6$) δ 8.81 (d, J=8.1 Hz, 1H), 8.68 (s, 1H), 8.45 (br. s., 1H), 8.21 (br. s., 1H), 7.71 (d, J=8.1 Hz, 1H), 7.34 (d, J=5.1 Hz, 1H), 7.29 (d, J=8.1 Hz, 1H), 7.16-7.05 (m, 1H), 6.37 (br. s., 1H), 4.35 (br. s., 3H), 4.00 (br. s., 3H), 3.93-3.84 (m, 1H), 3.73 (d, J=9.9 Hz, 1H), 3.54 (br. s., 1H), 3.48-3.35 (m, 4H), 3.21 (t, J=11.9 Hz, 1H), 1.71 (br. s., 1H), 1.48 (d, J=8.4 Hz, 1H), 1.40-1.27 (m, 1H), 0.98 (d, J=12.5 Hz, 1H). LC/MS (M+H)=558.4; HPLC conditions: $R_t$=3.60 min. (Phenomenex LUNA C18 2×50 mm (4 min grad) eluting with 10-90% aq MeOH over 4 min containing 0.1% TFA, 0.8 mL/min, monitoring at 254 nm); Temperature: 40° C.).

Example 233

11-Chloro-8-[(S)-(2-fluorophenyl)(oxan-4-yl)methyl]-5-[4-($^2$H$_3$)methyl-1-methyl-1H-1,2,3-triazol-5-yl]-3,8,10-triazatricyclo[7.4.0.0$^{2,7}$]trideca-1(13),2(7),3,5,9,11-hexaene

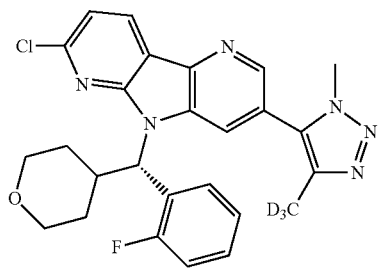 [SMILES: [2H]C([2H])([2H])c1nnn(C)c1-c1cnc2c3ccc(Cl)nc3n([C@H](c3ccccc3F)C3CCOCC3)c2c1]

In a pressure vessel equipped with a magnetic stirring bar was added (S)-3-bromo-7-chloro-5-((2-fluorophenyl)(tetrahydro-2H-pyran-4-yl)methyl)-5H-pyrrolo[2,3-b:4,5-b']dipyridine (35 mg, 0.074 mmol), ($^2$H$_3$)methyl-1-methyl-1H-1,2,3-triazol (16.2 mg, 0.162 mmol) and NMP (1 mL). Tetramethylammonium acetate (14.7 mg, 0.111 mmol) and bis(triphenylphosphine) palladium(II) chloride (3.6 mg, 5.16 µmol) was added. Argon was bubbled into the mixture with sonication for 5 min, then the vessel was capped and placed into a preheated oil bath at 100° C. The reaction mixture was stirred overnight. Solids in the reaction mixture were filtered and the filtrate was purified by preparative HPLC: Column: Waters XBridge C18, 19×200 mm, 5-µm particles; Mobile Phase A: 5:95 methanol: water with 10 mM NH$_4$OAc; Mobile Phase B: 95:5 methanol: water with 10 mM NH$_4$OAc; Gradient: 15-80% B over 30 min, then a 5-min hold at 100% B; Flow: 20 mL/min. Fractions containing the desired product were combined and dried via centrifugal evaporation to give 7.2 mg (20%) of the title compound with an average purity by LC/MS analysis was >99%. Two analytical LC/MS injections were used to determine the final purity. Injection 1 conditions: Column: Waters BEH C18, 2.0×50 mm, 1.7 µm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. $R_t$=1.89 min.; LC/MS (M+H)=494.4. Injection 2 conditions: Column: Waters BEH C18, 2.0×50 mm, 1.7-µm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. $R_t$=2.90 min.; LC/MS (M+H)=494.4. $^1$H NMR (500 MHz, DMSO-d$_6$) δ 8.71-8.64 (m, 2H), 8.51 (br. s., 1H), 8.22 (t, J=7.5 Hz, 1H), 7.47 (d, J=8.1 Hz, 1H), 7.41-7.25 (m, 2H), 7.12 (t, J=9.5 Hz, 1H), 6.17 (d, J=8.4 Hz, 1H), 4.01 (s, 3H), 3.89 (d, J=13.6 Hz, 1H), 3.75 (d, J=9.2 Hz, 1H), 3.53 (d, J=9.9 Hz, 1H), 3.49-3.41 (m, 1H), 3.23 (t, J=11.9 Hz, 1H), 1.67 (d, J=13.6 Hz, 1H), 1.46 (d, J=12.1 Hz, 1H), 1.35 (d, J=7.7 Hz, 1H), 0.97 (d, J=13.2 Hz, 1H). LC/MS (M+H)=494.2; HPLC conditions: $R_t$=4.08 min. (Phenomenex LUNA C18 2×50 mm (4 min grad) eluting with 10-90% aq MeOH containing 0.1% TFA, 0.8 mL/min, monitoring at 254 nm); Temperature: 40° C.).

Example 234

8-[(S)-(2-Fluorophenyl)(oxan-4-yl)methyl]-5-[4-($^2$H$_3$)methyl-1-methyl-1H-1,2,3-triazol-5-yl]-11-(4-methylpiperazin-1-yl)-3,8,10-triazatricyclo[7.4.0.0$^{2,7}$]trideca-1(13),2(7),3,5,9,11-hexaene

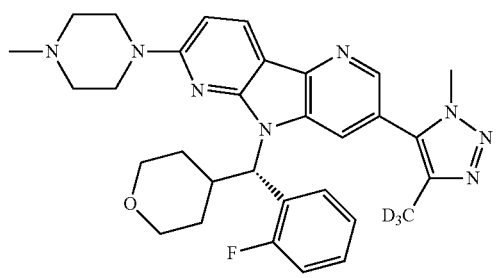 [SMILES: [2H]C([2H])([2H])c1nnn(C)c1-c1cnc2c3ccc(N4CCN(C)CC4)nc3n([C@H](c3ccccc3F)C3CCOCC3)c2c1]

In a pressure vessel equipped with a magnetic stirring bar was added 11-chloro-8-[(S)-(2-fluorophenyl)(oxan-4-yl)methyl]-5-[4-($^2$H$_3$)methyl-1-methyl-1H-1,2,3-triazol-5-yl]-

3,8,10-triazatricyclo[7.4.0.0²,⁷]trideca-1(13),2(7),3,5,9,11-hexaene (15 mg, 0.030 mmol), and 1-methylpiperazine (0.5 mL, 0.030 mmol) then the vessel was capped and placed into a preheated oil bath at 100° C. The reaction mixture was stirred for 1 h. Remaining 1-methylpiperazine was removed under a stream of nitrogen while heating. The residue was taken up the oil in methanol, filtered and the filtrate was purified by preparative HPLC: Column: Waters XBridge C18, 19×200 mm, 5-μm particles; Mobile Phase A: 5:95 methanol: water with 10 mM NH₄OAc; Mobile Phase B: 95:5 methanol: water with 10 mM NH₄OAc; Gradient: 20-60% B over 15 min, then a 5-min hold at 100% B; Flow: 20 mL/min. Fractions containing the desired product were combined and dried via centrifugal evaporation to give 15.1 mg (87%) of the title compound with an average purity by LC/MS analysis was 98%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH₄OAc; Mobile Phase B: 95:5 ACN:water with 10 mM NH₄OAc; Temperature: 50° C.; Gradient: 0% B, 0-100% B over 3 min, then a 0.5-min hold at 100% B; Flow: 1 mL/min; Detection: UV at 220 nm. $R_t$=1.38 min.; LC/MS (M+H)= 558.5. Injection 2 conditions: Column: Waters BEH C18, 2.0×50 mm, 1.7-μm particles; Mobile Phase A: 5:95 methanol:water with 10 mM NH₄OAc; Mobile Phase B: 95:5 methanol:water with 10 mM NH₄OAc; Temperature: 50° C.; Gradient: 0% B, 0-100% B over 3 min, then a 0.5-min hold at 100% B; Flow: 0.5 mL/min; Detection: UV at 220 nm. $R_t$=2.58 min.; LC/MS (M+H)=558.6. ¹H NMR (500 MHz, DMSO-d₆) δ 8.42 (s, 1H), 8.25 (d, J=8.4 Hz, 2H), 8.14 (t, J=7.7 Hz, 1H), 7.36-7.29 (m, 1H), 7.28-7.19 (m, 1H), 7.16-7.06 (m, 1H), 6.87 (d, J=9.2 Hz, 1H), 6.02 (br. s., 1H), 4.01 (s, 4H), 3.88 (d, J=12.1 Hz, 1H), 3.53 (br. s., 1H), 3.40 (br. s., 2H), 3.36 (br. s., 2H), 3.28-3.16 (m, 1H), 2.26 (s, 4H), 1.59 (d, J=12.5 Hz, 1H), 1.50-1.39 (m, 1H), 1.33 (d, J=12.8 Hz, 1H), 1.05 (d, J=10.3 Hz, 1H). LC/MS (M+H)=558.4; HPLC conditions: $R_t$=0.68 min. (Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min).

Example 235

8-[(S)-(2-Fluorophenyl)(oxan-4-yl)methyl]-11-methanesulfonyl-5-[4-(²H₃)methyl-1-methyl-1H-1,2,3-triazol-5-yl]-3,8,10-triazatricyclo[7.4.0.0²,⁷]trideca-1(13),2(7),3,5,9,11-hexaene

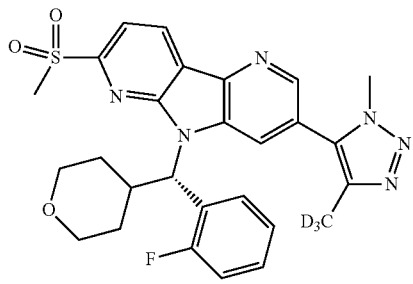 [SMILES: [2H]C([2H])([2H])c1nnn(C)c1-c1cnc2c3ccc(S(C)(=O)=O)nc3n([C@H](c3ccccc3F)C3CCOCC3)c2c1]

In a pressure vessel equipped with a magnetic stirring bar was added (S)-3-bromo-7-chloro-5-((2-fluorophenyl)(tetrahydro-2H-pyran-4-yl)methyl)-5H-pyrrolo[2,3-b:4,5-b'] dipyridine (50 mg, 0.101 mmol), sodium methanesulfinate (31.0 mg, 0.304 mmol), and copper(II)trifluoromethanesulfonate (5.5 mg, 0.015 mmol). The solids were dissolved in DMSO (1.5 mL). N,N'-dimethylethylenediamine (3 μl, 0.030 mmol) was added and the vial was purged with argon, then capped and placed into a preheated oil bath at 100° C. The reaction was allowed to stir 4 h. Solids in the reaction mixture were filtered and the filtrate was purified by preparative HPLC: Column: Waters XBridge C18, 19×200 mm, 5-μm particles; Mobile Phase A: 5:95 methanol: water with 10 mM NH₄OAc; Mobile Phase B: 95:5 methanol: water with 10 mM NH₄OAc; Gradient: 45-85% B over 20 min, then a 5-min hold at 100% B; Flow: 20 mL/min. Fractions containing the desired product were combined and dried via centrifugal evaporation to give 24.8 mg (43%) of the title compound with an average purity by LC/MS analysis was 95%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH₄OAc; Mobile Phase B: 95:5 ACN:water with 10 mM NH₄OAc; Temperature: 50° C.; Gradient: 0% B, 0-100% B over 3 min, then a 0.5-min hold at 100% B; Flow: 1 mL/min; Detection: UV at 220 nm. $R_t$=2.11 min.; LC/MS (M+H)=538.4. Injection 2 conditions: Column: Waters BEH C18, 2.0×50 mm, 1.7-μm particles; Mobile Phase A: 5:95 methanol:water with 10 mM NH₄OAc; Mobile Phase B: 95:5 methanol:water with 10 mM NH₄OAc; Temperature: 50° C.; Gradient: 0% B, 0-100% B over 3 min, then a 0.5-min hold at 100% B; Flow: 0.5 mL/min; Detection: UV at 220 nm. $R_t$=2.34 min. ¹H NMR (500 MHz, DMSO-d₆) δ 8.95 (d, J=7.7 Hz, 1H), 8.77 (s, 1H), 8.69 (br. s., 1H), 8.25 (t, J=7.7 Hz, 1H), 8.02 (d, J=8.1 Hz, 1H), 7.34 (q, J=6.8 Hz, 1H), 7.31-7.23 (m, 1H), 7.13 (t, J=9.4 Hz, 1H), 6.24 (br. s., 1H), 4.06 (s, 3H), 3.90 (d, J=11.0 Hz, 1H), 3.74 (d, J=8.8 Hz, 1H), 3.62 (d, J=9.2 Hz, 1H), 3.49-3.45 (m, 1H), 3.42 (br. s., 3H), 3.22 (t, J=11.7 Hz, 1H), 1.67 (d, J=12.1 Hz, 1H), 1.56-1.44 (m, 1H), 1.44-1.30 (m, 1H), 0.98 (d, J=12.5 Hz, 1H). LC/MS (M+H)= 538.2; HPLC conditions: $R_t$=0.87 min.; LC/MS (M+H)= 538.4, (Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min).

Example 236

8-[(S)-(2-Fluorophenyl)(oxan-4-yl)methyl]-N-methyl-5-[4-(²H₃)methyl-1-methyl-1H-1,2,3-triazol-5-yl]-N-[2-(methylamino)ethyl]-3,8,10-triazatricyclo[7.4.0.0²,⁷]trideca-1(13),2(7),3,5,9,11-hexaen-11-amine

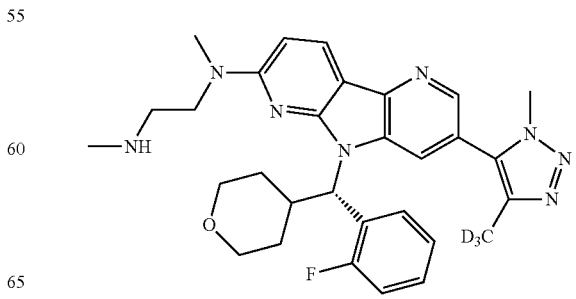

In a pressure vessel equipped with a magnetic stirring bar was added (S)-3-bromo-7-chloro-5-((2-fluorophenyl)(tetrahydro-2H-pyran-4-yl)methyl)-5H-pyrrolo-[2,3-b:4,5-b'] dipyridine (50 mg, 0.101 mmol), sodium methanesulfinate (31.0 mg, 0.304 mmol), and copper(II)trifluoromethanesulfonate (5.5 mg, 0.015 mmol). The solids were dissolved in DMSO (1.5 mL). N,N'-dimethylethylenediamine (3 µl, 0.030 mmol) was added and the vial was purged with argon, then capped and placed into a preheated oil bath at 100° C. The reaction was allowed to stir 4 h. Solids in the reaction mixture were filtered and the filtrate was purified by preparative HPLC: Column: XBridge C18, 19×200 mm, 5-µm particles; Mobile Phase A: 5:95 methanol: water with 10 mM $NH_4OAc$; Mobile Phase B: 95:5 methanol: water with 10 mM $NH_4OAc$; Gradient: 45-85% B over 20 min, then a 5-min hold at 100% B; Flow: 20 mL/min. Fractions containing the desired product were combined and dried via centrifugal evaporation to give 24.8 mg (43%) of the title compound with an average purity by LC/MS analysis was 95%. Two analytical LC/MS injections were used to determine the final purity. Injection 1 conditions: Column: Waters BEH C18, 2.0×50 mm, 1.7 µm particles; Mobile Phase A: 5:95 ACN:water with 10 mM $NH_4OAc$; Mobile Phase B: 95:5 ACN:water with 10 mM $NH_4OAc$; Temperature: 50° C.; Gradient: 0% B, 0-100% B over 3 min, then a 0.5-min hold at 100% B; Flow: 1 mL/min; Detection: UV at 220 nm. $R_t$=1.99 min.; LC/MS (M+H)=546.5. Injection 2 conditions: Column: Waters BEH C18, 2.0×50 mm, 1.7-µm particles; Mobile Phase A: 5:95 methanol:water with 10 mM $NH_4OAc$; Mobile Phase B: 95:5 methanol:water with 10 mM $NH_4OAc$; Temperature: 50° C.; Gradient: 0% B, 0-100% B over 3 min, then a 0.5-min hold at 100% B; Flow: 0.5 mL/min; Detection: UV at 220 nm. $R_t$=2.19 min.; LC/MS (M+H)=546.5. $^1$H NMR (500 MHz, DMSO-$d_6$) δ 8.39 (s, 1H), 8.25-8.13 (m, 3H), 7.37-7.29 (m, 1H), 7.25 (t, J=7.3 Hz, 1H), 7.17-7.06 (m, 1H), 6.66 (d, J=8.8 Hz, 1H), 6.01 (br. s., 1H), 4.00 (s, 3H), 3.92-3.81 (m, 2H), 3.76 (d, J=8.1 Hz, 2H), 3.28-3.14 (m, 4H), 2.89 (s, 2H), 2.85 (br. s., 1H), 2.74 (s, 1H), 2.39 (br. s., 2H), 1.88 (br. s., 1H), 1.60 (d, J=13.6 Hz, 1H), 1.42 (d, J=8.8 Hz, 1H), 1.33 (d, J=8.8 Hz, 1H), 1.03 (d, J=8.8 Hz, 2H). LC/MS (M+H)=546.3; HPLC conditions: $R_t$=0.71 min. (Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min).

Example 237

11-[(2R,6S)-2,6-Dimethylmorpholin-4-yl]-8-[(S)-(2-fluorophenyl)(oxan-4-yl)methyl]-5-[4-($^2H_3$)methyl-1-methyl-1H-1,2,3-triazol-5-yl]-3,8,10-triazatricyclo[7.4.0.0$^{2,7}$]trideca-1(13),2(7),3,5,9,11-hexaene

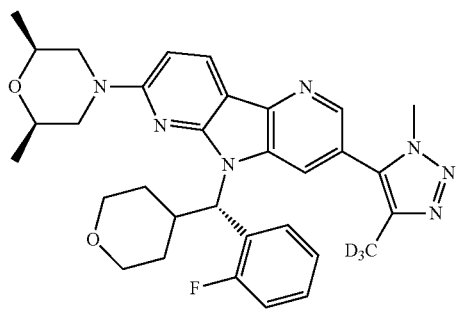 [SMILES: [2H]C([2H])([2H])c1nnn(C)c1-c1cnc2c3ccc(N4C[C@@H](C)O[C@@H](C)C4)nc3n([C@H](c3ccccc3F)C3CCOCC3)c2c1]

In a pressure vessel equipped with a magnetic stirring bar was added (S)-3-bromo-7-chloro-5-((2-fluorophenyl)(tetrahydro-2H-pyran-4-yl)methyl)-5H-pyrrolo[2,3-b:4,5-b'] dipyridine (30 mg, 0.061 mmol), and (2S,6R)-2,6-dimethylmorpholine (0.5 mL, 0.061 mmol). The vessel was capped and placed into a preheated oil bath at 100° C. The reaction mixture was stirred for 1 h. Remaining (2S,6R)-2,6-dimethylmorpholine (0.5 mL, 0.061 mmol) was removed under a stream of nitrogen while heating. The residue was taken up in methanol and was filtered. The filtrate was purified by preparative HPLC: Column: Waters XBridge C18, 19×200 mm, 5-µm particles; Mobile Phase A: 5:95 methanol: water with 10 mM $NH_4OAc$; Mobile Phase B: 95:5 methanol: water with 10 mM $NH_4OAc$; Gradient: 35-75% B over 20 min, then a 5-min hold at 100% B; Flow: 20 mL/min. Fractions containing the desired product were combined and dried via centrifugal evaporation to give 14.9 mg (42%) of the title compound with an average purity by LC/MS analysis was 99%. Two analytical LC/MS injections were used to determine the final purity. Injection 1 conditions: Column: Waters BEH C18, 2.0×50 mm, 1.7 µm particles; Mobile Phase A: 5:95 ACN:water with 10 mM $NH_4OAc$; Mobile Phase B: 95:5 ACN:water with 10 mM $NH_4OAc$; Temperature: 50° C.; Gradient: 0% B, 0-100% B over 3 min, then a 0.5-min hold at 100% B; Flow: 1 mL/min; Detection: UV at 220 nm. $R_t$=1.93 min.; LC/MS (M+H)=573.2. Injection 2 conditions: Column: Waters BEH C18, 2.0×50 mm, 1.7-µm particles; Mobile Phase A: 5:95 methanol:water with 10 mM $NH_4OAc$; Mobile Phase B: 95:5 methanol:water with 10 mM $NH_4OAc$; Temperature: 50° C.; Gradient: 0% B, 0-100% B over 3 min, then a 0.5-min hold at 100% B; Flow: 0.5 mL/min; Detection: UV at 220 nm. $R_t$=3.31 min.; LC/MS (M+H)=573.2. $^1$H NMR (500 MHz, DMSO-$d_6$) δ 8.43 (s, 1H), 8.27 (d, J=8.8 Hz, 2H), 8.09 (t, J=7.2 Hz, 1H), 7.38-7.28 (m, 1H), 7.28-7.20 (m, 1H), 7.13 (t, J=9.2 Hz, 1H), 6.89 (d, J=8.8 Hz, 1H), 6.02 (br. s., 1H), 4.40 (t, J=11.7 Hz, 2H), 4.01 (s, 3H), 3.90 (d, J=9.9 Hz, 1H), 3.77 (d, J=9.9 Hz, 1H), 3.67 (br. s., 2H), 3.52 (br. s., 1H), 3.46-3.37 (m, 1H), 3.28-3.10 (m, 1H), 2.71-2.57 (m, 2H), 1.60 (d, J=11.7 Hz, 1H), 1.45 (d, J=9.9 Hz, 1H), 1.33 (d, J=9.5 Hz, 1H), 1.25 (d, J=5.9 Hz, 6H), 1.06 (d, J=11.7 Hz, 1H). LC/MS (M+H)=573.4; HPLC conditions: $R_t$=0.94 min. (Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min).

Example 238

8-[(S)-(2-Fluorophenyl)(oxan-4-yl)methyl]-N,N-dimethyl-5-[4-($^2H_3$)methyl-1-methyl-1H-1,2,3-triazol-5-yl]-3,8,10-triazatricyclo[7.4.0.0$^{2,7}$]trideca-1(13),2(7),3,5,9,11-hexaen-11-amine

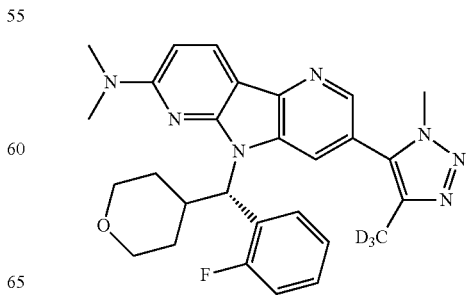

In a pressure vessel equipped with a magnetic stirring bar was added (S)-3-bromo-7-chloro-5-((2-fluorophenyl)(tetrahydro-2H-pyran-4-yl)methyl)-5H-pyrrolo[2,3-b:4,5-b'] dipyridine (26 mg, 0.053 mmol), and dimethylamine (5 mL, 10.0 mmol, 2M in THF). The vessel was capped and placed into a preheated oil bath at 100° C. The reaction mixture was stirred for 16 h. The remaining dimethylamine (5 mL, 10.0 mmol) was removed under a stream of nitrogen. The residue was taken up in methanol and DMF, then filtered. The filtrate was purified by preparative HPLC: Column: XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 40-80% B over 15 min, then a 5-min hold at 100% B; Flow: 20 mL/min. Fractions containing the desired product were combined and dried via centrifugal evaporation to give 11.1 mg (42%) of the title compound with an average purity by LC/MS analysis was 99%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. $R_t$=1.87 min.; LC/MS (M+H)= 503.2. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. $R_t$=3.24 min.; LC/MS (M+H)=503.2. $^1$H NMR (500 MHz, DMSO-d$_6$) δ 8.39 (s, 1H), 8.27-8.14 (m, 4H), 7.36-7.28 (m, 1H), 7.28-7.19 (m, 1H), 7.12 (t, J=9.4 Hz, 1H), 6.67 (d, J=8.8 Hz, 1H), 5.99 (br. s., 1H), 4.01 (s, 3H), 3.88 (d, J=10.3 Hz, 1H), 3.76 (d, J=9.5 Hz, 1H), 3.62 (br. s., 1H), 3.43-3.34 (m, 1H), 1.58 (d, J=13.6 Hz, 1H), 1.49-1.37 (m, 1H), 1.37-1.26 (m, 1H), 1.07 (d, J=11.7 Hz, 1H). LC/MS (M+H)= 503.2; HPLC conditions: $R_t$=1.02 min. (Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min).

Example 239

8-[(S)-(2-Fluorophenyl)(oxan-4-yl)methyl]-N-methyl-5-[4-($^2$H$_3$)methyl-1-methyl-1H-1,2,3-triazol-5-yl]-3,8,10-triazatricyclo[7.4.0.0$^{2,7}$]trideca-1(13),2(7),3,5,9,11-hexaen-11-amine

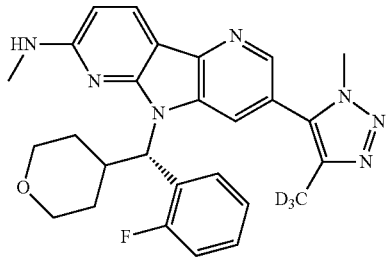 [SMILES: [2H]C([2H])([2H])c1nnn(C)c1-c1cnc2c3ccc(NC)nc3n([C@H](c3ccccc3F)C3CCOCC3)c2c1]

In a pressure vessel equipped with a magnetic stirring bar was added (S)-3-bromo-7-chloro-5-((2-fluorophenyl)(tetrahydro-2H-pyran-4-yl)methyl)-5H-pyrrolo[2,3-b:4,5-b'] dipyridine (26 mg, 0.053 mmol), and methanamine (1 mL, 0.053 mmol, 2M in methanol). The vessel was capped and placed into a preheated oil bath at 80° C. The reaction mixture was stirred for several days. Excess methanamine was removed under a stream of nitrogen while heating. The residue was taken up in methanol and filtered. The filtrate was purified by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 25-65% B over 15 min, then a 5-min hold at 100% B; Flow: 20 mL/min. Fractions containing the desired product were combined and dried via centrifugal evaporation to give 17.2 mg (66%) of the title compound with an average purity by LC/MS analysis was >99%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. $R_t$=1.66 min.; LC/MS (M+H)= 489.1. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. $R_t$=3.00 min.; LC/MS (M+H)=489.1. $^1$H NMR (500 MHz, DMSO-d$_6$) δ 8.37 (s, 1H), 8.29-8.16 (m, 2H), 8.09 (d, J=8.4 Hz, 1H), 7.38-7.28 (m, 2H), 7.28-7.20 (m, 1H), 7.12 (t, J=9.4 Hz, 1H), 6.48 (d, J=8.8 Hz, 1H), 5.98 (br. s., 1H), 4.00 (s, 3H), 3.94-3.82 (m, 1H), 3.77 (d, J=8.1 Hz, 1H), 3.65 (br. s., 1H), 3.24 (t, J=11.4 Hz, 1H), 3.00 (d, J=4.8 Hz, 3H), 1.56 (d, J=12.5 Hz, 1H), 1.49-1.27 (m, 2H), 1.07 (d, J=12.8 Hz, 1H). LC/MS (M+H)=489.2; HPLC conditions: $R_t$=0.82 min. (Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min).

Example 240

N-[5-(Dimethyl-1H-1,2,3-triazol-5-yl)-8-[(S)-(2-fluorophenyl)(oxan-4-yl)methyl]-3,8,10-triazatricyclo[7.4.0.0$^{2,7}$]trideca-1(13),2(7),3,5,9,11-hexaen-11-yl]methanesulfonamide

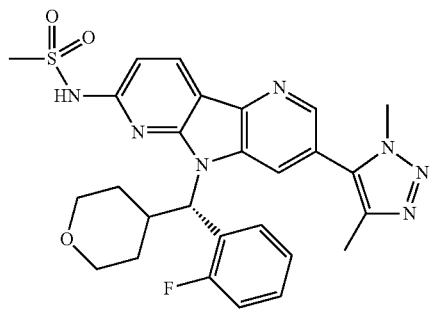 [SMILES: Cc1nnn(C)c1-c1cnc2c3ccc(NS(C)(=O)=O)nc3n([C@H](c3ccccc3F)C3CCOCC3)c2c1]

In a pressure vessel equipped with a magnetic stirring bar was added (S)-7-chloro-3-(1,4-dimethyl-1H-1,2,3-triazol-5-yl)-5-((2-fluorophenyl)(tetrahydro-2H-pyran-4-yl)methyl)-5H-pyrrolo[2,3-b:4,5-b']dipyridine (30 mg, 0.061 mmol), methanesulfonamide (8.72 mg, 0.092 mmol), cesium carbonate (39.8 mg, 0.122 mmol), Pd(OAc)$_2$ (0.4 mg, 1.83 μmol), and Xantphos (2.1 mg, 3.67 μmol). The solids were suspended in dioxane (2 mL). Argon was bubbled through the mixture for 5 min and then the vessel was placed into a preheated oil bath at 100° C. The reaction was heating for 16 h with stirring. The reaction mixture was filtered, and the filtrate was purified by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 20-60% B over 15 min, then a 5-min hold at 100% B; Flow: 20 mL/min. Fractions containing the desired product were combined and dried via centrifugal evaporation to give 26.8 mg (79%) of the title compound with an average purity by LC/MS analysis was >99%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. $R_t$=1.41 min.; LC/MS (M+H)=550.0. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. $R_t$=2.66 min.; LC/MS (M+H)=550.0. $^1$H NMR (500 MHz, DMSO-d$_6$) δ 8.52 (s, 1H), 8.45 (d, J=8.4 Hz, 1H), 8.40 (br. s., 1H), 8.34 (br. s., 1H), 7.32 (d, J=7.0 Hz, 1H), 7.22 (t, J=7.0 Hz, 1H), 7.12 (t, J=9.4 Hz, 1H), 6.85 (d, J=8.1 Hz, 1H), 6.04 (br. s., 1H), 4.01 (s, 3H), 3.89 (d, J=9.5 Hz, 1H), 3.74 (d, J=8.4 Hz, 1H), 3.67 (br. s., 1H), 3.51 (s, 1H), 3.46 (br. s., 2H), 3.28-3.15 (m, 1H), 2.34-2.23 (m, 3H), 1.56 (br. s., 1H), 1.48-1.31 (m, 2H), 1.24 (br. s., 1H), 1.16 (br. s., 1H), 1.03 (br. s., 3H). LC/MS (M+H)=550.1; HPLC conditions: $R_t$=0.82 min. (Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min).

Example 241

2-{8-[(S)-(2-Fluorophenyl)(oxan-4-yl)methyl]-5-[4-($^2$H$_3$)methyl-1-methyl-1H-1,2,3-triazol-5-yl]-3,8,10-triazatricyclo[7.4.0.0$^{2,7}$]trideca-1(13),2(7),3,5,9,11-hexaen-11-yl}propan-2-ol

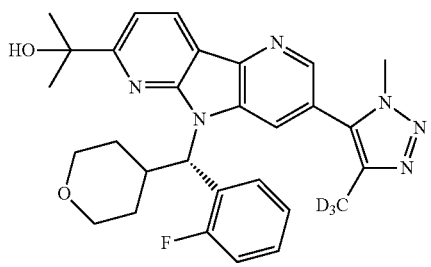 [SMILES: [2H]C([2H])([2H])c1nnn(C)c1-c1cnc2c3ccc(C(C)(C)O)nc3n([C@H](c3ccccc3F)C3CCOCC3)c2c1]

Step 1: 1-{8-[(S)-(2-Fluorophenyl)(oxan-4-yl)methyl]-5-[4-($^2$H$_3$)methyl-1-methyl-1H-1,2,3-triazol-5-yl]-3,8,10-triazatricyclo[7.4.0.0$^{2,7}$]trideca-1(13),2(7),3,5,9,11-hexaen-11-yl}ethan-1-one In a pressure vial equipped with a magnetic stirring bar was added 11-chloro-8-[(S)-(2-fluorophenyl)(oxan-4-yl)methyl]-5-[4-($^2$H$_3$)methyl-1-methyl-1H-1,2,3-triazol-5-yl]-3,8,10-triazatricyclo[7.4.0.0$^{2,7}$]trideca-1(13),2(7),3,5,9,11-hexaene (125 mg, 0.253 mmol), tributyl(1-ethoxyvinyl)stannane (101 mg, 0.278 mmol) and PdCl$_2$(dppf)-CH$_2$Cl$_2$ adduct (6.2 mg, 7.59 μmol). The solids were suspended in dioxane (2 mL). Argon was bubbled through the mixture for 5 min. The vessel was placed into a preheated oil bath at 100° C. The reaction was heated for 16 h with stirring. The vessel was cooled to room temperature. Intermediate LC/MS (M+H)=530.3; HPLC conditions: $R_t$=1.12 min. (Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min). The crude mixture was filtered and concentrated under vacuum. The residue was taken up in 10 mL of THF and was treated with 2 mL of 2M HCl solution while stirring at room temperature for 2 h. The solution was neutralized with aqueous K$_2$CO$_3$ solution and extracted with ethyl acetate. The organic layer was dried over MgSO$_4$, filtered and concentrated under vacuum to give 125 mg (84%) of a yellow residue. LC/MS (M+H)=502.5; HPLC conditions: $R_t$=2.92 min (Phenomenex LUNA C18 2×50 mm (4 min grad) eluting with 5-95% aq ACN containing 10 mM NH$_4$OAc, 0.8 mL/min, monitoring at 254 nm); Temperature: 40° C.).

Step 2: 2-{8-[(S)-(2-Fluorophenyl)(oxan-4-yl)methyl]-5-[4-($^2$H$_3$)methyl-1-methyl-1H-1,2,3-triazol-5-yl]-3,8,10-triazatricyclo[7.4.0.0$^{2,7}$]trideca-1(13),2(7),3,5,9,11-hexaen-11-yl}propan-2-ol In a round bottom flask equipped with a magnetic stirring bar and cooled to −10° C. in an ice/methanol bath was added 1-{8-[(S)-(2-fluorophenyl)(oxan-4-yl)methyl]-5-[4-($^2$H$_3$)methyl-1-methyl-1H-1,2,3-triazol-5-yl]-3,8,10-triazatricyclo[7.4.0.0$^{2,7}$]trideca-1(13),2(7),3,5,9,11-hexaen-11-yl}ethan-1-one (35 mg, 0.070 mmol) and dichloromethane (5 mL). MeMgBr (3M in diethyl ether, 0.233 mL, 0.698 mmol) was added drop wise to this suspension. The reaction was slowly warmed to room temperature for 1 h after removal of the cooling bath. The reaction was quenched with saturated NH$_4$Cl solution. The reaction mixture with transferred to a separatory funnel and was extracted with DCM. All organics were combined and were dried over MgSO$_4$, filtered and concentrated to give a yellow residue. The residue was dissolved in methanol and filtered. The filtrate was purified by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 35-75% B over 20 min, then a 5-min hold at 100% B; Flow: 20 mL/min. Fractions containing the desired product were combined and dried via centrifugal evaporation to give 24.8 mg (68%) of the title compound with an average purity by LC/MS analysis was >99%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. $R_t$=1.62 min.; LC/MS (M+H)=518.1. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. $R_t$=2.98 min.; LC/MS (M+H)=518.1. $^1$H NMR (500 MHz, DMSO-d$_6$) δ 8.63-8.54 (m, 2H), 8.49 (br. s., 1H), 8.24 (t, J=7.0 Hz, 1H), 7.71 (d, J=8.1 Hz, 1H), 7.31 (d, J=5.1 Hz, 1H), 7.26-7.18 (m, 1H), 7.12 (t, J=9.5 Hz, 1H), 6.14 (br. s., 1H), 4.05 (s, 3H), 3.90 (d, J=6.6 Hz, 1H), 3.81-3.66 (m, 2H), 3.44 (br. s., 1H), 3.24-3.11 (m, 2H), 1.65 (s, 3H), 1.58 (s, 4H), 1.46 (d, J=8.8 Hz, 1H), 1.34 (d, J=8.4 Hz, 1H), 0.96 (d, J=12.5 Hz, 1H). LC/MS (M+H)=518.3; HPLC conditions: $R_t$=0.89 min. (Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min).

Examples 242 and 243

1-Cyclopropyl-1-{8-[(S)-(2-fluorophenyl)(oxan-4-yl)methyl]-5-[4-($^2$H$_3$)methyl-1-methyl-1H-1,2,3-triazol-5-yl]-3,8,10-triazatricyclo[7.4.0.0$^{2,7}$]trideca-1(13),2(7),3,5,9,11-hexaen-11-yl}ethan-1-ol Example 242

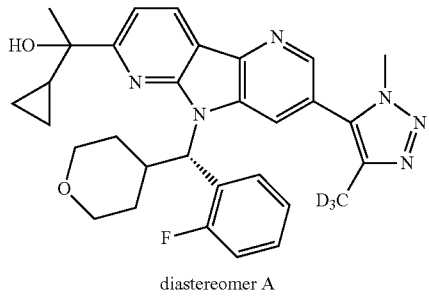

diastereomer A

Example 243

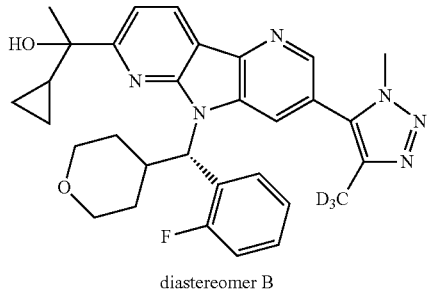

diastereomer B

In a round bottom flask equipped with a magnetic stirring bar and cooled to −78° C. in an dry ice/acetone bath was added 1-{8-[(S)-(2-fluorophenyl)(oxan-4-yl)methyl]-5-[4-($^2$H$_3$)methyl-1-methyl-1H-1,2,3-triazol-5-yl]-3,8,10-triazatricyclo[7.4.0.0$^{2,7}$]trideca-1(13),2(7),3,5,9,11-hexaen-11-yl}ethan-1-one (35 mg, 0.070 mmol) and THF (2 mL). Cyclopropylmagnesiumbromide (1.794 mL, 1.79 mmol, 1M in 2-methyltetrahydrofuran) was added drop wise to this suspension. The cooling bath was removed and the reaction was slowly allowed to warm to room temperature over 1 h. The reaction was quenched with saturated NH$_4$Cl solution. The reaction mixture with transferred to a separatory funnel and was extracted with DCM. All organics were combined and were dried over MgSO$_4$, filtered and concentrated to give a yellow residue. The residue was dissolve in methanol and filtered. The filtrate was purified by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 35-75% B over 20 min, then a 5-min hold at 100% B; Flow: 20 mL/min. Fractions containing the desired product were combined and dried via centrifugal evaporation to give 29 mg of a mixture of diastereomers. This material was subject to a chiral purification: Chiral SFC conditions: Phenomenex LUX Cellulose-2 preparative column, 20×250 mm, 5 μm; Mobile Phase: 35% methanol in CO$_2$, 130 bar; Temp: 35° C.; Flow rate: 45.0 mL/min. for 30 min.; UV monitored at 318 nm; Injection: 0.25 ml of ~10 mg/mL solution in MeOH (29 mg purified by stacked injection); $R_t$=isomer A: 21.6 min.; isomer B: 23.4 min. Fractions containing the desired products were combined and dried via evaporation to give 7.7 mg (8%) of the isomer A with an average purity by LC/MS analysis was >97%. Fractions containing the desired products were combined and dried via evaporation to give 10.7 mg (11%) of the isomer B with an average purity by LC/MS analysis was >99%. Isomer A: Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. $R_t$=1.77 min.; LC/MS (M+H)=544.2. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. $R_t$=2.81 min.; LC/MS (M+H)=544.2. Isomer B: Two analytical LC/MS injections were used to determine the final purity. Injection 1 conditions: Column: Waters BEH C18, 2.0×50 mm, 1.7 μm particles; Mobile Phase A: 5:95 ACN: water with 10 mM NH$_4$OAc; Mobile Phase B: 95:5 ACN: water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. $R_t$=1.79 min.; LC/MS (M+H)=544.2. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. $R_t$=2.84 min.; LC/MS (M+H)=544.2. Absolute stereochemistry not determined. Diastereomer A: $^1$H NMR (500 MHz, DMSO-d$_6$) δ 8.64-8.53 (m, 2H), 8.49 (br. s., 1H), 8.26 (t, J=7.3 Hz, 1H), 7.66 (d, J=8.1 Hz, 1H), 7.37-7.28 (m, 1H), 7.28-7.19 (m, 1H), 7.12 (t, J=9.4 Hz, 1H), 6.15 (br. s., 1H), 4.05 (s, 3H), 3.89 (d, J=9.9 Hz, 1H), 3.74 (d, J=9.5 Hz, 2H), 3.42-3.30 (m, 1H), 3.17 (t, J=11.4 Hz, 1H), 1.70-1.55 (m, 4H), 1.52-1.41 (m, 2H), 1.34 (d, J=8.4 Hz, 1H), 0.94 (d, J=12.5 Hz, 1H), 0.58-0.48 (m, 1H), 0.48-0.34 (m, 2H), 0.22 (d, J=8.4 Hz, 1H). Diastereomer B: $^1$H NMR (500 MHz, DMSO-d$_6$) δ 8.64-8.54 (m, 2H), 8.49 (br. s., 1H), 8.25 (t, J=7.2 Hz, 1H), 7.65 (d, J=8.1 Hz, 1H), 7.30 (d, J=6.2 Hz, 1H), 7.21 (t, J=7.3

Hz, 1H), 7.12 (t, J=9.2 Hz, 1H), 6.14 (br. s., 1H), 4.05 (s, 3H), 3.90 (d, J=10.3 Hz, 1H), 3.75 (d, J=12.1 Hz, 2H), 3.26-3.12 (m, 1H), 1.69 (s, 3H), 1.59 (br. s., 1H), 1.52-1.30 (m, 3H), 0.97 (d, J=12.1 Hz, 1H), 0.61-0.49 (m, 1H), 0.48-0.41 (m, 1H), 0.38 (d, J=4.8 Hz, 1H), 0.20-0.09 (m, 1H). LC/MS (M+H)=544.2; HPLC conditions: $R_t$=0.95 min. (Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min).

Example 244

8-[(S)-(2-Fluorophenyl)(oxan-4-yl)methyl]-5-[4-($^2H_3$)methyl-1-methyl-1H-1,2,3-triazol-5-yl]-11-(4-methylpiperazin-1-yl)-3,8,12-triazatricyclo[7.4.0.0$^{2,7}$]trideca-1(13),2(7),3,5,9,11-hexaene

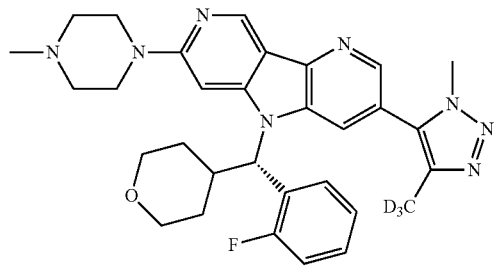 [SMILES: [2H]C([2H])([2H])c1nnn(C)c1-c1cnc2c3cnc(N4CCN(C)CC4)cc3n([C@H](c3ccccc3F)C3CCOCC3)c2c1]

In a pressure vessel equipped with a magnetic stirring bar was added 11-chloro-8-[(S)-(2-fluorophenyl)(oxan-4-yl)methyl]-5-[4-($^2H_3$)methyl-1-methyl-1H-1,2,3-triazol-5-yl]-3,8,12-triazatricyclo[7.4.0.0$^{2,7}$]trideca-1(13),2(7),3,5,9,11-hexaene (40 mg, 0.040 mmol), triethylamine (3 drops) and 1-methylpiperazine (1 mL, 0.040 mmol). The vessel was capped, placed into a preheated oil bath at 100° C. and stirred for 48 h. The reaction vessel was cooled and remaining 1-methylpiperazine was removed under a stream of nitrogen while heating. The residue was taken up in methanol and filtered. The filtrate was purified by preparative HPLC: Column: Waters XBridge C18, 19×200 mm, 5-µm particles; Mobile Phase A: 5:95 methanol: water with 10 mM NH$_4$OAc; Mobile Phase B: 95:5 methanol: water with 10 mM NH$_4$OAc; Gradient: 10-50% B over 15 min, then a 5-min hold at 100% B; Flow: 20 mL/min. Fractions containing the desired product were combined and dried via centrifugal evaporation to give 5.2 mg (23%) of the title compound with an average purity by LC/MS analysis was 98%. Two analytical LC/MS injections were used to determine the final purity. Injection 1 conditions: Column: Waters BEH C18, 2.0×50 mm, 1.7 µm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. $R_t$=1.20 min.; LC/MS (M+H)=558.3. Injection 2 conditions: Column: Waters BEH C18, 2.0×50 mm, 1.7-µm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. $R_t$=2.43 min.; LC/MS (M+H)=558.3. $^1$H NMR (500 MHz, DMSO-d$_6$) δ 8.95 (s, 1H), 8.42 (s, 1H), 8.23 (t, J=7.3 Hz, 2H), 7.43-7.26 (m, 3H), 7.20-7.05 (m, 2H), 5.94 (d, J=11.4 Hz, 1H), 3.95 (br. s., 3H), 3.89 (d, J=9.5 Hz, 2H), 3.74 (d, J=9.9 Hz, 2H), 3.66 (br. s., 4H), 3.54-3.45 (m, 1H), 3.37 (d, J=11.7 Hz, 1H), 3.29-3.15 (m, 1H), 2.47 (br. s., 3H), 2.26 (s, 3H), 1.74-1.67 (m, 1H), 1.67-1.51 (m, 1H), 1.40 (d, J=8.1 Hz, 1H), 0.88 (d, J=12.8 Hz, 1H). LC/MS (M+H)=558.4; HPLC conditions: $R_t$=2.85 min. Column: (Phenomenex LUNA C18 2×50 mm (4 min grad) eluting with 10-90% aq MeOH over 4 min containing 0.1% TFA, 0.8 mL/min, monitoring at 254 nm); Temperature: 40° C.).

Example 245

8-[(S)-(2-Fluorophenyl)(oxan-4-yl)methyl]-11-methanesulfonyl-5-[4-($^2H_3$)methyl-1-methyl-1H-1,2,3-triazol-5-yl]-3,8,12-triazatricyclo[7.4.0.0$^{2,7}$]trideca-1(13),2(7),3,5,9,11-hexaene

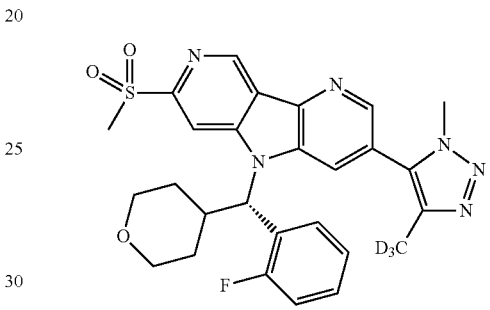

In a pressure vessel equipped with a magnetic stirring bar, was added 11-chloro-8-[(S)-(2-fluorophenyl)(oxan-4-yl)methyl]-5-[4-($^2H_3$)methyl-1-methyl-1H-1,2,3-triazol-5-yl]-3,8,12-triazatricyclo[7.4.0.0$^{2,7}$]trideca-1(13),2(7),3,5,9,11-hexaene (80 mg, 0.081 mmol), sodium methanesulfinate (24.8 mg, 0.243 mmol), and copper(II)trifluoromethanesulfonate (4.4 mg, 0.012 mmol). The solids were dissolved in DMSO (1.5 mL). N,N'-dimethylethylenediamine (1 drop) was added and the vial was purged with argon. The vessel was capped, placed into a preheated oil bath at 100° C. and stirred for 16 h. An additional 1 equivalent of sodium methanesulfinate, copper(II)trifluoromethanesulfonate and 2 equivalents of N,N'-dimethylethylenediamine was added. The reaction mixture was purged with argon, capped and re-heated to 100° C. for 4 h. Solids in the reaction mixture were filtered, and the filtrate was purified by preparative HPLC: Column: Waters XBridge C18, 19×200 mm, 5-µm particles; Mobile Phase A: 5:95 methanol: water with 10 mM NH$_4$OAc; Mobile Phase B: 95:5 methanol: water with 10 mM NH$_4$OAc; Gradient: 40-100% B over 20 min, then a 5-min hold at 100% B; Flow: 20 mL/min. Fractions containing the desired product were combined and dried via centrifugal evaporation to give 4.9 mg (11%) of the title compound with an average purity by LC/MS analysis was >99%. Two analytical LC/MS injections were used to determine the final purity. Injection 1 conditions: Column: Waters BEH C18, 2.0×50 mm, 1.7 µm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. $R_t$=1.32 min.; LC/MS (M+H)=538.3. Injection 2 conditions: Column: Waters BEH C18, 2.0×50 mm, 1.7-µm particles; Mobile Phase A: 5:95 methanol:water with 10 mM NH$_4$OAc; Mobile Phase B: 95:5 methanol:water with 10 mM NH₄OAc; Temperature: 50° C.; Gradient: 0% B, 0-100% B over 3 min, then a 0.5-min hold at 100% B; Flow: 0.5 mL/min; Detection: UV at 220 nm. R$_f$=2.18 min.; LC/MS (M+H)=538.3. ¹H NMR (500 MHz, DMSO-d₆) δ 9.59 (s, 1H), 8.79 (s, 2H), 8.54 (br. s., 1H), 8.34-8.21 (m, 1H), 7.46-7.29 (m, 3H), 7.14 (t, J=9.4 Hz, 1H), 6.33 (d, J=11.0 Hz, 1H), 3.98 (br. s., 3H), 3.90 (d, J=11.0 Hz, 1H), 3.72 (d, J=8.1 Hz, 1H), 3.49 (br. s., 2H), 3.41 (s, 2H), 3.21 (t, J=11.6 Hz, 1H), 1.73 (br. s., 2H), 1.42 (d, J=9.9 Hz, 1H), 0.78 (d, J=12.1 Hz, 1H). LC/MS (M+H)=538.3; HPLC conditions: R$_f$=3.32 min. Column: (Phenomenex LUNA C18 2×50 mm (4 min grad) eluting with 10-90% aq MeOH over 4 min containing 0.1% TFA, 0.8 mL/min, monitoring at 254 nm); Temperature: 40° C.).

Example 246

11-Chloro-8-[(3-fluoropyridin-2-yl)(oxan-4-yl)methyl]-5-[4-(²H₃)methyl-1-methyl-1H-1,2,3-triazol-5-yl]-3,8,10-triazatricyclo[7.4.0.0²,⁷]trideca-1(13),2(7),3,5,9,11-hexaene

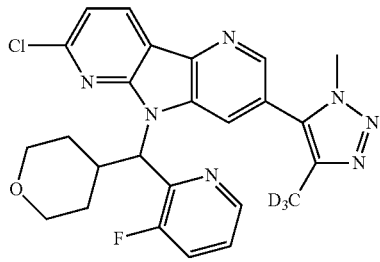 [SMILES: [2H]C([2H])([2H])c1nnn(C)c1-c1cnc2c3ccc(Cl)nc3n(C(c3ncccc3F)C3CCOCC3)c2c1]

In a pressure vessel equipped with a magnetic stirring bar was added 3-bromo-7-chloro-5-((3-fluoropyridin-2-yl)(tetrahydro-2H-pyran-4-yl)methyl)-5H-pyrrolo[2,3-b:4,5-b']dipyridine (70 mg, 0.147 mmol), (²H₃)methyl-1-methyl-1H-1,2,3-triazol (36.8 mg, 0.368 mmol) and NMP (1.5 mL). Tetramethylammonium acetate (29.4 mg, 0.221 mmol) and bis(triphenylphosphine) palladium(II) chloride (7.2 mg, 10.3 μmol) was added. Argon was bubbled into the mixture with sonication for 5 min. The vessel was capped, placed into a preheated oil bath at 100° C. and was stirred overnight. Solids in the reaction mixture were filtered and the filtrate was purified by preparative HPLC: Column: Waters XBridge C18, 19×200 mm, 5-μm particles; Mobile Phase A: 5:95 methanol: water with 10 mM NH₄OAc; Mobile Phase B: 95:5 methanol: water with 10 mM NH₄OAc; Gradient: 5-45% B over 30 min, then a 5-min hold at 100% B; Flow: 20 mL/min. Fractions containing the desired product were combined and dried via centrifugal evaporation to give 15.8 mg (20%) of the title compound with an average purity by LC/MS analysis was >91%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH₄OAc; Mobile Phase B: 95:5 ACN:water with 10 mM NH₄OAc; Temperature: 50° C.; Gradient: 0% B, 0-100% B over 3 min, then a 0.5-min hold at 100% B; Flow: 1 mL/min; Detection: UV at 220 nm. R$_f$=1.81 min.; LC/MS (M+H)=495.1. Injection 2 conditions: Column: Waters BEH C18, 2.0×50 mm, 1.7-μm particles; Mobile Phase A: 5:95 methanol:water with 10 mM NH₄OAc; Mobile Phase B: 95:5 methanol:water with 10 mM NH₄OAc; Temperature: 50° C.; Gradient: 0% B, 0-100% B over 3 min, then a 0.5-min hold at 100% B; Flow: 0.5 mL/min; Detection: UV at 220 nm. R$_f$=3.16 min.; LC/MS (M+H)=495.0. ¹H NMR (500 MHz, DMSO-d₆) δ 8.69 (d, J=5.9 Hz, 2H), 8.57 (br. s., 2H), 7.73 (t, J=9.4 Hz, 1H), 7.50 (d, J=8.1 Hz, 2H), 6.49 (d, J=11.0 Hz, 1H), 4.09-3.97 (m, 3H), 3.89-3.77 (m, 1H), 3.69 (d, J=9.5 Hz, 1H), 3.45 (d, J=10.6 Hz, 1H), 3.42-3.30 (m, 1H), 3.27-3.10 (m, 1H), 1.59 (d, J=13.2 Hz, 1H), 1.51-1.34 (m, 1H), 1.31-1.14 (m, 1H), 0.85 (d, J=13.2 Hz, 1H). LC/MS (M+H)=495.1; HPLC conditions: R$_f$=0.96 min. (Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min).

Example 247 and 248

8-[(3-Fluoropyridin-2-yl)(oxan-4-yl)methyl]-5,11-bis[4-(²H₃)methyl-1-methyl-1H-1,2,3-triazol-5-yl]-3,8,10-triazatricyclo[7.4.0.0²,⁷]trideca-1(13),2(7),3,5,9,11-hexaene

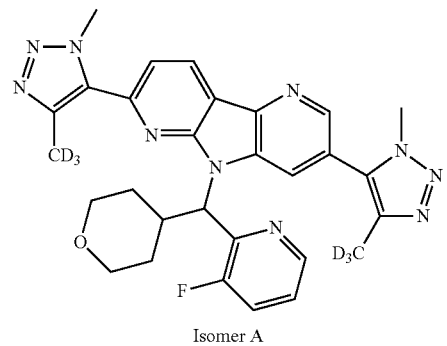

Isomer A

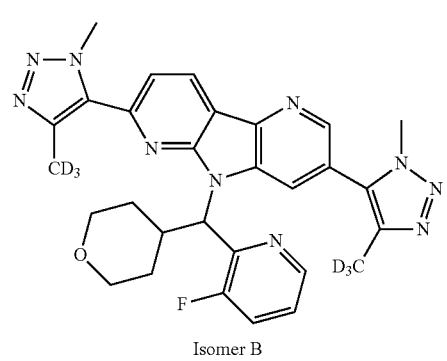

Isomer B

In a pressure vessel equipped with a magnetic stirring bar was added 3-bromo-7-chloro-5-((3-fluoropyridin-2-yl)(tetrahydro-2H-pyran-4-yl)methyl)-5H-pyrrolo[2,3-b:4,5-b']dipyridine (70 mg, 0.147 mmol), (²H₃)methyl-1-methyl-1H-1,2,3-triazol (36.8 mg, 0.368 mmol) and NMP (1.5 mL). Tetramethylammonium acetate (29.4 mg, 0.221 mmol) and bis(triphenylphosphine)palladium(II) chloride (7.2 mg, 10.3 μmol) was added. Argon was bubbled into the mixture with sonication for 5 min, then the vessel was capped, placed into a preheated oil bath at 100° C. and was stirred overnight. Solids in the reaction mixture were filtered, and the filtrate was purified by preparative HPLC: Column: Waters XBridge C18, 19×200 mm, 5-μm particles; Mobile Phase A:

5:95 methanol: water with 10 mM NH₄OAc; Mobile Phase B: 95:5 methanol: water with 10 mM NH₄OAc; Gradient: 5-45% B over 30 min, then a 5-min hold at 100% B; Flow: 20 mL/min. Fractions containing the desired product were combined and dried via centrifugal evaporation to give 15 mg of a mixture of enantiomers. This material was subject to a chiral purification: Chiral SFC conditions: Chiralcel OJ-H preparative column, 20×250 mm, 5 µm; Mobile Phase: 20% methanol in $CO_2$, 150 bar; Temp: 35° C.; Flow rate: 70.0 mL/min. for 14 min.; UV monitored at 334 nm; Injection: 0.35 ml of ~4 mg/mL solution in MeOH (15 mg purified by stacked injection); $R_f$=isomer A: 7.0 min.; isomer B: 10.5 min. Fractions containing the desired products were combined and dried via evaporation to give 6.0 mg (7%) of the isomer A with an average purity by LC/MS analysis was >99%. Fractions containing the desired products were combined and dried via evaporation to give 6.6 mg (8%) of the isomer B with an average purity by LC/MS analysis was 99%. Isomer A: Two analytical LC/MS injections were used to determine the final purity. Injection 1 conditions: Column: Waters BEH C18, 2.0×50 mm, 1.7 µm particles; Mobile Phase A: 5:95 ACN:water with 10 mM NH₄OAc; Mobile Phase B: 95:5 ACN:water with 10 mM NH₄OAc; Temperature: 50° C.; Gradient: 0% B, 0-100% B over 3 min, then a 0.5-min hold at 100% B; Flow: 1 mL/min; Detection: UV at 220 nm. $R_f$=1.40 min.; LC/MS (M+H)=559.3. Injection 2 conditions: Column: Waters BEH C18, 2.0×50 mm, 1.7-µm particles; Mobile Phase A: 5:95 methanol:water with 10 mM NH₄OAc; Mobile Phase B: 95:5 methanol:water with 10 mM NH₄OAc; Temperature: 50° C.; Gradient: 0% B, 0-100% B over 3 min, then a 0.5-min hold at 100% B; Flow: 0.5 mL/min; Detection: UV at 220 nm. $R_f$=2.39 min.; LC/MS (M+H)=559.3. Isomer B: Two analytical LC/MS injections were used to determine the final purity. Injection 1 conditions: Column: Waters BEH C18, 2.0×50 mm, 1.7 µm particles; Mobile Phase A: 5:95 ACN:water with 10 mM NH₄OAc; Mobile Phase B: 95:5 ACN:water with 10 mM NH₄OAc; Temperature: 50° C.; Gradient: 0% B, 0-100% B over 3 min, then a 0.5-min hold at 100% B; Flow: 1 mL/min; Detection: UV at 220 nm. $R_f$=1.37 min.; LC/MS (M+H)=559.3. Injection 2 conditions: Column: Waters BEH C18, 2.0×50 mm, 1.7-µm particles; Mobile Phase A: 5:95 methanol:water with 10 mM NH₄OAc; Mobile Phase B: 95:5 methanol:water with 10 mM NH₄OAc; Temperature: 50° C.; Gradient: 0% B, 0-100% B over 3 min, then a 0.5-min hold at 100% B; Flow: 0.5 mL/min; Detection: UV at 220 nm. $R_f$=2.39 min.; LC/MS (M+H)=559.3. ¹H NMR (500 MHz, DMSO-d₆) δ 8.82 (d, J=8.1 Hz, 1H), 8.70 (s, 1H), 8.65 (s, 1H), 8.58 (d, J=4.0 Hz, 1H), 7.78-7.68 (m, 2H), 7.55-7.43 (m, 1H), 6.67 (br. s., 1H), 4.39 (s, 3H), 4.05 (s, 3H), 3.83 (d, J=9.5 Hz, 1H), 3.66 (d, J=10.3 Hz, 1H), 3.38-3.31 (m, 2H), 3.20 (t, J=11.7 Hz, 1H), 1.58 (br. s., 1H), 1.45 (d, J=12.5 Hz, 1H), 1.22 (br. s., 1H), 0.84 (d, J=13.2 Hz, 1H). LC/MS (M+H)=559.3; HPLC conditions: $R_f$=0.82 min. (Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min).

Example 249

5-[4-(²H₃)Methyl-1-methyl-1H-1,2,3-triazol-5-yl]-11-[4-(²H₃)methylpiperazin-1-yl]-8-[(S)-oxan-4-yl(phenyl)methyl]-3,8,10-triazatricyclo[7.4.0.0²,⁷]trideca-1(13),2(7),3,5,9,11-hexaene

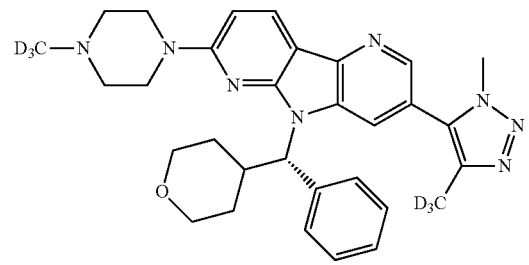 [SMILES: [2H]C([2H])([2H])c1nnn(C)c1-c1cnc2c3ccc(N4CCN(C([2H])([2H])[2H])CC4)nc3n([C@H](c3ccccc3)C3CCOCC3)c2c1]

In a pressure vessel equipped with a magnetic stirring bar, was added 11-chloro-5-[4-(²H₃)methyl-1-methyl-1H-1,2,3-triazol-5-yl]-8-[(S)-oxan-4-yl(phenyl)methyl]-3,8,10-triazatricyclo[7.4.0.0²,⁷]trideca-1(13),2(7),3,5,9,11-hexaene (30 mg, 0.063 mmol), triethylamine (0.088 mL, 0.630 mmol) and 1-(²H₃)methylpiperazine hydrochloride (44.0 mg, 0.315 mmol). The solids were dissolved in DMSO (1.5 mL). The vessel was capped, placed into a preheated oil bath at 100° C. and stirred for 16 h. The vessel was cooled to room temperature. Solids in the reaction mixture were filtered, and the filtrate was purified by preparative HPLC: Column: Waters XBridge C18, 19×200 mm, 5-µm particles; Mobile Phase A: 5:95 methanol: water with 10 mM NH₄OAc; Mobile Phase B: 95:5 methanol: water with 10 mM NH₄OAc; Gradient: 15-55% B over 15 min, then a 5-min hold at 100% B; Flow: 20 mL/min. Fractions containing the desired product were combined and dried via centrifugal evaporation to give 15.3 mg (43%) of the title compound with an average purity by LC/MS analysis was 97%. Two analytical LC/MS injections were used to determine the final purity. Injection 1 conditions: Column: Waters BEH C18, 2.0×50 mm, 1.7 µm particles; Mobile Phase A: 5:95 ACN: water with 10 mM NH₄OAc; Mobile Phase B: 95:5 ACN: water with 10 mM NH₄OAc; Temperature: 50° C.; Gradient: 0% B, 0-100% B over 3 min, then a 0.5-min hold at 100% B; Flow: 1 mL/min; Detection: UV at 220 nm. $R_f$=1.51 min.; LC/MS (M+H)=543.4. Injection 2 conditions: Column: Waters BEH C18, 2.0×50 mm, 1.7-µm particles; Mobile Phase A: 5:95 methanol:water with 10 mM NH₄OAc; Mobile Phase B: 95:5 methanol:water with 10 mM NH₄OAc; Temperature: 50° C.; Gradient: 0% B, 0-100% B over 3 min, then a 0.5-min hold at 100% B; Flow: 0.5 mL/min; Detection: UV at 220 nm. $R_f$=2.57 min.; LC/MS (M+H)=543.4. ¹H NMR (500 MHz, DMSO-d₆) δ 8.40 (s, 1H), 8.31 (br. s., 1H), 8.27 (d, J=8.8 Hz, 1H), 7.77 (d, J=7.7 Hz, 2H), 7.30 (t, J=7.5 Hz, 2H), 7.22 (t, J=7.3 Hz, 1H), 6.90 (d, J=8.8 Hz, 1H), 5.70 (br. s., 1H), 4.00 (s, 3H), 3.88 (d, J=11.4 Hz, 1H), 3.79 (br. s., 5H), 3.63 (br. s., 1H), 3.31-3.21 (m, 1H), 3.18 (d, J=3.7 Hz, 5H), 1.46 (br. s., 1H), 1.44-1.31 (m, 1H), 1.25 (br. s., 2H). LC/MS (M+H)=543.4; HPLC conditions: $R_f$=0.66 min. (Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min).

Example 250

5-(Dimethyl-1H-1,2,3-triazol-5-yl)-8-[(S)-(2-fluorophenyl)(oxan-4-yl)methyl]-11-[4-($^2H_3$)methylpiperazin-1-yl]-3,8,10-triazatricyclo[7.4.0.0$^{2,7}$]trideca-1(13),2(7),3,5,9,11-hexaene

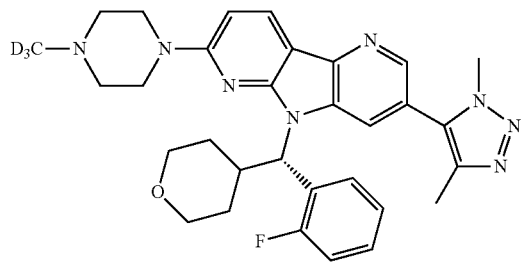 [SMILES: [2H]C([2H])([2H])N1CCN(c2ccc3c4ncc(-c5c(C)nnn5C)cc4n([C@H](c4ccccc4F)C4CCOCC4)c3n2)CC1]

Step 1: 1-($^2H_3$)Methylpiperazine hydrochloride t-Butyl piperazine-1-carboxylate (1 g, 5.37 mmol) was dissolved in THF (30 mL) within a round bottom flask equipped with a magnetic stirrer bar and cooled to 0° C. in an ice-water bath. 60% sodium hydride (0.258 g, 6.44 mmol.; in mineral oil) was added portion wise to the solution which was under a nitrogen atmosphere and vented. After 5 min, CD$_3$I (0.856 g, 5.91 mmol) was added to the mixture drop wise. The reaction was warmed to room temperature and stirred overnight. The reaction was quenched with water, transferred to a separatory funnel, and was extracted with ethyl acetate twice. The organic layers were combined, dried over MgSO$_4$, filtered, and concentrated under vacuum to give 1.45 g of a cloudy oil that partially solidified. At room temperature, 500 mg of this intermediate was suspended in 10 mL of 4M HCl in dioxane within a small round bottom flask containing a magnetic stirring bar. The mixture was stirred for 30 min. A thick solid formed almost immediately after HCl addition to the substrate. The dioxane was slowly removed under vacuum and then the remaining material was taken up in ethyl ether. The ether suspension was stirred for 15 min to break up and wash the solids. The ether was then removed under vacuum to give 400 mg of a pale yellow solid as an HCl salt.

Step 2: 5-(Dimethyl-1H-1,2,3-triazol-5-yl)-8-[(S)-(2-fluorophenyl)(oxan-4-yl)methyl]-11-[4-($^2H_3$)methylpiperazin-1-yl]-3,8,10-triazatricyclo[7.4.0.0$^{2,7}$]trideca-1(13),2(7),3,5,9,11-hexaene In pressure vessel equipped with a magnetic stirring bar was added (S)-7-chloro-3-(1,4-dimethyl-1H-1,2,3-triazol-5-yl)-5-((2-fluorophenyl)(tetrahydro-2H-pyran-4-yl)methyl)-5H-pyrrolo[2,3-b:4,5-b']dipyridine (14 mg, 0.029 mmol), triethylamine (0.032 mL, 0.228 mmol) and 1-($^2H_3$)methylpiperazine hydrochloride (15.9 mg, 0.114 mmol). The solids were dissolved in DMSO (1.5 mL). The vessel was capped, placed into a preheated oil bath at 100° C., and was stirred for 16 h overnight. The vessel was cooled to room temperature. Solids in the reaction mixture were filtered, and the filtrate was purified by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 15-55% B over 15 min, then a 5-min hold at 100% B; Flow: 20 mL/min. Fractions containing the desired product were combined and dried via centrifugal evaporation to give 14.6 mg (84%) of the title compound with an average purity by LC/MS analysis was >91%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_f$=1.50 min.; LC/MS (M+H)=558.3. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_f$=2.56 min.; LC/MS (M+H)=558.3. $^1$H NMR (500 MHz, DMSO-d$_6$) δ 8.40 (s, 1H), 8.29-8.19 (m, 2H), 8.12 (t, J=7.3 Hz, 1H), 7.36-7.27 (m, 1H), 7.27-7.18 (m, 1H), 7.11 (t, J=9.2 Hz, 1H), 6.86 (d, J=8.8 Hz, 1H), 6.00 (br. s., 1H), 3.99 (s, 3H), 3.87 (d, J=10.6 Hz, 1H), 3.74 (br. s., 4H), 3.45-3.34 (m, 1H), 3.22 (t, J=11.2 Hz, 1H), 3.17 (s, 3H), 2.48 (br. s., 3H), 2.28 (s, 3H), 1.59 (d, J=11.7 Hz, 1H), 1.42 (d, J=11.7 Hz, 1H), 1.32 (d, J=12.1 Hz, 1H), 1.03 (d, J=12.1 Hz, 1H). LC/MS (M+H)=558.3; HPLC conditions: R$_f$=0.65 min. (Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min).

Example 251

5-[4-($^2H_3$)Methyl-1-methyl-1H-1,2,3-triazol-5-yl]-8-[(S)-oxan-4-yl(phenyl)methyl]-11-(piperazin-1-yl)-3,8,10-triazatricyclo[7.4.0.0$^{2,7}$]trideca-1(13),2(7),3,5,9,11-hexaene

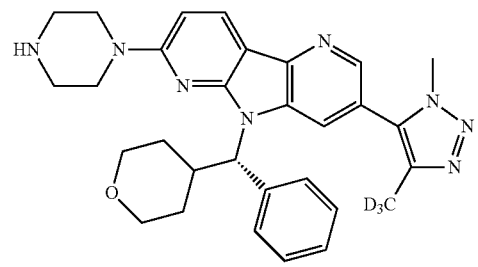 [SMILES: [2H]C([2H])([2H])c1nnn(C)c1-c1cnc2c3ccc(N4CCNCC4)nc3n([C@H](c3ccccc3)C3CCOCC3)c2c1]

In a pressure vessel equipped with a magnetic stirring bar was added 11-chloro-8-[((S)-phenyl)(oxan-4-yl)methyl]-5-[4-($^2H_3$)methyl-1-methyl-1H-1,2,3-triazol-5-yl]-3,8,10-triazatricyclo[7.4.0.0$^{2,7}$]trideca-1(13),2(7),3,5,9,11-hexaene (45 mg, 0.095 mmol), triethylamine (0.264 mL, 1.89 mmol) and 1-piperazine hydrochloride (99 mg, 0.473 mmol). The mixture was dissolved in DMSO (1.5 mL). The vessel was capped, placed into a preheated oil bath at 100° C. and was stirred for 16 h. The vessel was cooled to room temperature. Solids in the reaction mixture were filtered, and the filtrate was purified by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 10-60% B over 20 min, then a 5-min hold at 100% B; Flow: 20 mL/min. Fractions containing the desired product were combined and dried via centrifugal evaporation to give 24.7 mg (48%) of the title compound with an average purity by LC/MS analysis was >96%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_t$=1.18 min.; LC/MS (M+H)= 526.3. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_t$=2.14 min.; LC/MS (M+H)=526.3. $^1$H NMR (500 MHz, DMSO-d$_6$) δ 8.44-8.36 (m, 1H), 8.31 (br. s., 1H), 8.27-8.20 (m, 1H), 7.77 (d, J=7.3 Hz, 2H), 7.30 (t, J=7.5 Hz, 2H), 7.26-7.13 (m, 1H), 6.87 (d, J=9.2 Hz, 1H), 5.72 (br. s., 1H), 4.08-3.94 (m, 4H), 3.88 (d, J=10.6 Hz, 1H), 3.79 (d, J=11.0 Hz, 1H), 3.60 (br. s., 1H), 3.37 (t, J=11.0 Hz, 1H), 3.33-3.21 (m, 1H), 2.89 (s, 2H), 2.92 (s, 3H), 1.90 (br. s., 2H), 1.47 (br. s., 1H), 1.46-1.33 (m, 2H), 1.25 (br. s., 3H). LC/MS (M+H)= 526.3; HPLC conditions: R$_t$=2.77 min. (Column: Phenomenex LUNA C18 2×50 mm (4 min grad) eluting with 10-90% aq MeOH over 4 min containing 0.1% TFA, 0.8 mL/min, monitoring at 254 nm); Temperature: 40° C.).

Example 252

11-[(3R,5S)-3,5-Dimethylpiperazin-1-yl]-5-[4-($^2$H$_3$) methyl-1-methyl-1H-1,2,3-triazol-5-yl]-8-[(S)-oxan-4-yl(phenyl)methyl]-3,8,10-triazatricyclo[7.4.0.0$^{2,7}$] trideca-1(13),2(7),3,5,9,11-hexaene

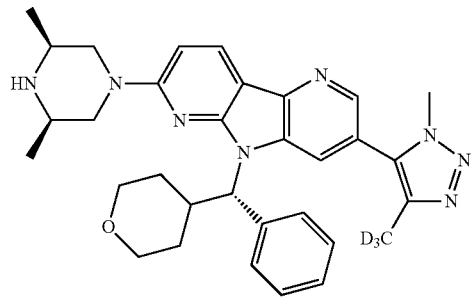 [SMILES: [2H]C([2H])([2H])c1nnn(C)c1-c1cnc2c3ccc(N4C[C@@H](C)N[C@@H](C)C4)nc3n([C@H](c3ccccc3)C3CCOCC3)c2c1]

In a pressure vessel equipped with a magnetic stirring bar was added 11-chloro-8-[((S)-phenyl)(oxan-4-yl)methyl]-5-[4-($^2$H$_3$)methyl-1-methyl-H-1,2,3-triazol-5-yl]-3,8,10-triazatricyclo[7.4.0.0$^{2,7}$]trideca-1(13),2(7),3,5,9,11-hexaene (45 mg, 0.095 mmol), triethylamine (0.132 mL, 0.945 mmol) and (2S,6R)-2,6-dimethylpiperazine (54.0 mg, 0.473 mmol). The solids were dissolved in DMSO (1.5 mL). The vessel was capped, placed into a preheated oil bath at 100° C. and the reaction mixture was stirred for 1 h. The vessel was cooled to room temperature. Solids in the reaction mixture were filtered, and the filtrate was purified by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 45-85% B over 15 min, then a 5-min hold at 100% B; Flow: 20 mL/min. Fractions containing the desired product were combined and dried via centrifugal evaporation to give 28.4 mg (52%) of the title compound with an average purity by LC/MS analysis was 95%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_t$=1.37 min.; LC/MS (M+H)=554.7. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_t$=2.36 min.; LC/MS (M+H)=554.7. $^1$H NMR (500 MHz, DMSO-d$_6$) δ 8.38 (s, 1H), 8.31 (s, 1H), 8.24 (d, J=8.8 Hz, 1H), 7.76 (d, J=7.7 Hz, 2H), 7.29 (t, J=7.5 Hz, 2H), 7.22 (t, J=7.3 Hz, 1H), 6.90 (d, J=8.8 Hz, 1H), 5.66 (d, J=8.8 Hz, 1H), 4.55-4.32 (m, 2H), 4.00 (s, 3H), 3.94-3.85 (m, 1H), 3.81 (d, J=11.0 Hz, 1H), 3.67 (br. s., 1H), 3.59 (d, J=13.9 Hz, 1H), 3.33 (t, J=11.0 Hz, 1H), 3.29-3.21 (m, 1H), 2.92-2.81 (m, 3H), 2.59 (t, J=11.6 Hz, 2H), 2.51 (br. s., 1H), 1.90 (s, 3H), 1.50-1.33 (m, 2H), 1.28 (br. s., 2H), 1.13 (dd, J=5.9, 2.2 Hz, 6H). LC/MS (M+H)=554.3; HPLC conditions: R$_t$=0.68 min: (Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min).

Example 253

8-[(S)-(2-Fluorophenyl)(oxan-4-yl)methyl]-5,11-bis (4-methoxy-1-methyl-1H-1,2,3-triazol-5-yl)-3,8,10-triazatricyclo[7.4.0.0$^{2,7}$]trideca-1(13),2(7),3,5,9,11-hexaene

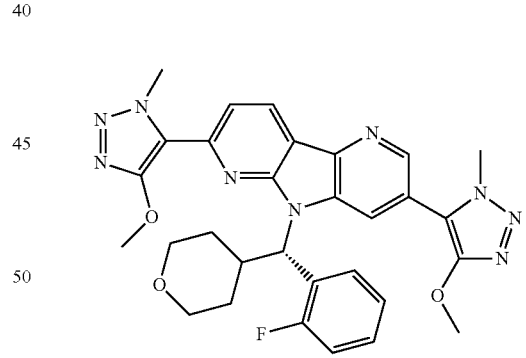

In a small pressure vessel already equipped with a magnetic stirring bar was added (S)-3-bromo-7-chloro-5-((2-fluorophenyl)(tetrahydro-2H-pyran-4-yl)methyl)-5H-pyrrolo[2,3-b:4,5-b']dipyridine (155 mg, 0.326 mmol), 4-methoxy-1-((trimethylsilyl)methyl)-1H-1,2,3-triazole (72.6 mg, 0.392 mmol) and NMP (2 mL). Tetramethylammonium acetate (54.4 mg, 0.408 mmol) and bis(triphenylphosphine) palladium(II) chloride (16.0 mg, 0.023 mmol) was added. Argon was bubbled into the mixture with sonication for 5 min, then the vessel was capped, placed into a preheated oil bath at 100° C., and the reaction mixture was stirred overnight. The vessel was cooled to room temperature, and the reaction mixture filtered. The filtrate was purified by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 20-60% B over 20 min, then a 5-min hold at 100% B; Flow: 20 mL/min. Fractions containing the desired product were combined and dried via centrifugal evaporation to give 18.0 mg (9%) of the title compound with an average purity by LC/MS analysis was >99%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_t$=1.74 min.; LC/MS (M+H)=584.7. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_t$=2.75 min.; LC/MS (M+H)=584.7. $^1$H NMR (500 MHz, DMSO-d$_6$) δ 8.75 (d, J=8.1 Hz, 1H), 8.67 (s, 1H), 8.39 (br. s., 1H), 8.21 (br. s., 1H), 7.88 (d, J=8.1 Hz, 1H), 7.45-7.26 (m, 2H), 7.19-7.07 (m, 1H), 6.39 (br. s., 1H), 4.56 (s, 3H), 4.15 (s, 3H), 4.10-3.98 (m, 6H), 3.90 (d, J=8.4 Hz, 1H), 3.71 (d, J=10.6 Hz, 1H), 3.53-3.43 (m, 2H), 3.27-3.13 (m, 1H), 1.73 (br. s., 1H), 1.58-1.42 (m, 1H), 1.32 (d, J=8.1 Hz, 1H), 0.94 (br. s., 1H). LC/MS (M+H)=584.3; HPLC conditions: R$_t$=0.97 min: (Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min).

Example 254

8-[(S)-(2-Fluorophenyl)(oxan-4-yl)methyl]-5-(4-methoxy-1-methyl-1H-1,2,3-triazol-5-yl)-11-(4-methylpiperazin-1-yl)-3,8,10-triazatricyclo[7.4.0.0$^{2,7}$]trideca-1(13),2(7),3,5,9,11-hexaene

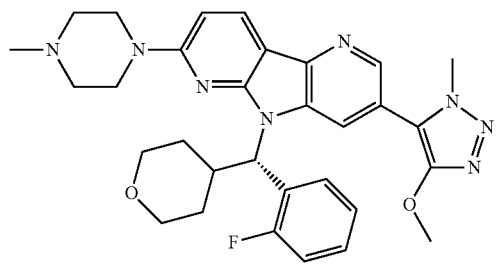 [SMILES: COc1nnn(C)c1-c1cnc2c3ccc(N4CCN(C)CC4)nc3n([C@H](c3ccccc3F)C3CCOCC3)c2c1]

In a 20 mL scintillation vial equipped with a magnetic stirring bar was added (S)-7-chloro-5-((2-fluorophenyl)(tetrahydro-2H-pyran-4-yl)methyl)-3-(4-methoxy-1-methyl-1H-1,2,3-triazol-5-yl)-5H-pyrrolo[2,3-b:4,5-b']dipyridine (30 mg, 0.059 mmol), triethylamine (0.082 mL, 0.592 mmol) and 1-methylpiperazine (29.6 mg, 0.296 mmol). The solids were dissolved in DMSO (1 mL). The vessel was capped, placed into a preheated aluminum block at 100° C. and the reaction mixture was stirred for 16 h. After cooling to room temperature. Solids in the reaction mixture were filtered, and the filtrate was purified by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 20-60% B over 20 min, then a 5-min hold at 100% B; Flow: 20 mL/min. Fractions containing the desired product were combined and dried via centrifugal evaporation to give 15.2 mg (44%) of the title compound with an average purity by LC/MS analysis was 98%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_t$=1.53 min.; LC/MS (M+H)=571.7. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_t$=2.65 min.; LC/MS (M+H)=571.7. $^1$H NMR (500 MHz, DMSO-d$_6$) δ 8.45 (s, 1H), 8.24 (d, J=8.4 Hz, 2H), 8.11 (t, J=7.5 Hz, 1H), 7.32 (d, J=6.6 Hz, 1H), 7.28-7.21 (m, 1H), 7.13 (t, J=9.2 Hz, 1H), 6.86 (d, J=8.8 Hz, 1H), 6.00 (br. s., 1H), 4.07 (s, 3H), 4.01 (s, 3H), 3.89 (d, J=15.8 Hz, 2H), 3.44 (d, J=14.3 Hz, 3H), 3.38 (br. s., 1H), 3.27-3.14 (m, 1H), 2.26 (s, 4H), 1.91 (s, 3H), 1.59 (d, J=12.1 Hz, 1H), 1.48-1.37 (m, 1H), 1.31 (d, J=12.1 Hz, 1H), 1.03 (d, J=13.2 Hz, 1H). LC/MS (M+H)=571.3; HPLC conditions: R$_t$=0.66 min: (Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min).

Example 255

8-[(S)-(2-Fluorophenyl)(oxan-4-yl)methyl]-5-(4-methoxy-1-methyl-1H-1,2,3-triazol-5-yl)-N-methyl-N-[2-(methylamino)ethyl]-3,8,10-triazatricyclo[7.4.0.0$^{2,7}$]trideca-1(13),2(7),3,5,9,11-hexaen-11-amine

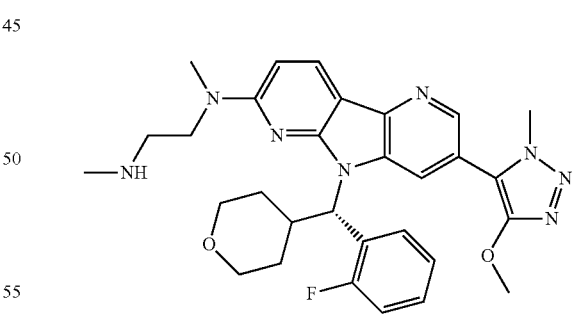

In a 20 mL scintillation vial equipped with a magnetic stirring bar was added (S)-7-chloro-5-((2-fluorophenyl)(tetrahydro-2H-pyran-4-yl)methyl)-3-(4-methoxy-1-methyl-1H-1,2,3-triazol-5-yl)-5H-pyrrolo[2,3-b:4,5-b']dipyridine (30 mg, 0.059 mmol), triethylamine (0.082 mL, 0.592 mmol) and N1,N2-dimethylethane-1,2-diamine (26.1 mg, 0.296 mmol). The solids were dissolved in DMSO (1 mL). The vessel was capped, placed into a preheated aluminum block at 100° C., and the reaction mixture was stirred for 16 h. The vessel was cooled to room temperature. Solids were removed by filtration and the filtrate was purified by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 15-55% B over 15 min, then a 5-min hold at 100% B; Flow: 20 mL/min. Fractions containing the desired product were combined and dried via centrifugal evaporation to give 17.1 mg (51%) of the title compound with an average purity by LC/MS analysis was >99%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. $R_t$=1.22 min.; LC/MS (M+H)=559.7. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. $R_t$=2.20 min.; LC/MS (M+H)=559.7. $^1$H NMR (500 MHz, DMSO-d$_6$) δ 8.42 (s, 1H), 8.22 (d, J=8.8 Hz, 2H), 8.16 (t, J=7.3 Hz, 1H), 7.38-7.30 (m, 1H), 7.30-7.20 (m, 1H), 7.13 (t, J=9.2 Hz, 1H), 6.66 (d, J=8.8 Hz, 1H), 6.02 (br. s., 1H), 4.06 (s, 3H), 4.00 (s, 3H), 3.94-3.80 (m, 2H), 3.76 (d, J=11.7 Hz, 2H), 3.49 (d, J=7.3 Hz, 3H), 3.40 (t, J=10.8 Hz, 1H), 3.31-3.20 (m, 1H), 2.89 (s, 2H), 2.41 (s, 3H), 1.89 (s, 3H), 1.60 (d, J=11.4 Hz, 1H), 1.42 (d, J=10.6 Hz, 1H), 1.31 (d, J=8.1 Hz, 1H), 1.00 (d, J=12.8 Hz, 1H). LC/MS (M+H)=559.3; HPLC conditions: $R_t$=0.65 min: (Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min).

Example 256

4-{8-[(S)-(2-Fluorophenyl)(oxan-4-yl)methyl]-5-(4-methoxy-1-methyl-1H-1,2,3-triazol-5-yl)-3,8,10-triazatricyclo[7.4.0.0$^{2,7}$]trideca-1(13),2(7),3,5,9,11-hexaen-11-yl}-1λ$^6$,4-thiomorpholine-1,1-dione

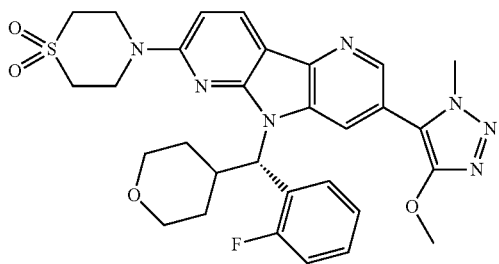 [SMILES: COc1nnn(C)c1-c1cnc2c3ccc(N4CCS(=O)(=O)CC4)nc3n([C@H](c3ccccc3F)C3CCOCC3)c2c1]

In a 20 mL scintillation vial equipped with a magnetic stirring bar was added (S)-7-chloro-5-((2-fluorophenyl)(tetrahydro-2H-pyran-4-yl)methyl)-3-(4-methoxy-1-methyl-1H-1,2,3-triazol-5-yl)-5H-pyrrolo[2,3-b:4,5-b']dipyridine (30 mg, 0.059 mmol), triethylamine (0.082 mL, 0.592 mmol) and thiomorpholine 1,1-dioxide (40.0 mg, 0.296 mmol). The mixture was dissolved in DMSO (1 mL). The vessel was capped, placed into a preheated aluminum block set at 100° C. and the reaction mixture was stirred for 16 h. The reaction mixture was transferred into microwave pressure vial, and was heated at 170° C. for 160 min. The vial was cooled to room temperature. Solids were filtered and the filtrate was purified by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 25-65% B over 15 min, then a 5-min hold at 100% B; Flow: 20 mL/min. Fractions containing the desired product were combined and dried via centrifugal evaporation to give 2.2 mg (6%) of the title compound with an average purity by LC/MS analysis was >99%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. $R_t$=1.51 min.; LC/MS (M+H)=606.2. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. $R_t$=2.42 min.; LC/MS (M+H)=606.2. $^1$H NMR (500 MHz, DMSO-d$_6$) δ 8.49 (s, 1H), 8.34 (d, J=8.4 Hz, 2H), 8.10 (t, J=7.5 Hz, 1H), 7.42-7.22 (m, 2H), 7.14 (t, J=9.5 Hz, 1H), 7.03 (d, J=8.8 Hz, 1H), 6.02 (br. s., 1H), 4.27 (br. s., 4H), 4.09 (s, 3H), 4.02 (s, 3H), 3.86 (d, J=9.5 Hz, 2H), 3.74 (d, J=10.6 Hz, 2H), 3.47-3.40 (m, 2H), 3.29-3.13 (m, 7H), 2.21-1.98 (m, 12H), 1.62 (d, J=13.2 Hz, 2H), 1.45 (d, J=8.4 Hz, 2H), 1.30 (d, J=12.8 Hz, 1H), 0.98 (d, J=12.1 Hz, 2H). LC/MS (M+H)=606.3; HPLC conditions: $R_t$=0.78 min: (Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min).

Example 257

N-[2-(Dimethylamino)ethyl]-N-ethyl-8-[(S)-(2-fluorophenyl)(oxan-4-yl)methyl]-5-(4-methoxy-1-methyl-1H-1,2,3-triazol-5-yl)-3,8,10-triazatricyclo[7.4.0.0$^{2,7}$]trideca-1(13),2(7),3,5,9,11-hexaen-11-amine

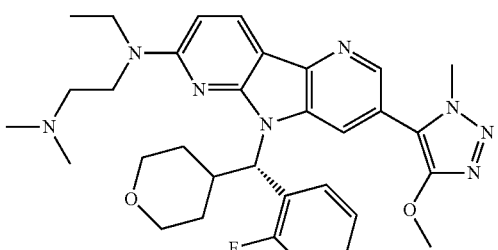

In a 20 mL scintillation vial equipped with a magnetic stirring bar was added (S)-7-chloro-5-((2-fluorophenyl)(tetrahydro-2H-pyran-4-yl)methyl)-3-(4-methoxy-1-methyl-1H-1,2,3-triazol-5-yl)-5H-pyrrolo[2,3-b:4,5-b']dipyridine (30 mg, 0.059 mmol), triethylamine (0.082 mL, 0.592 mmol) and N1-ethyl-N2,N2-dimethylethane-1,2-diamine (34.4 mg, 0.296 mmol). The mixture was dissolved in DMSO (1 mL). The vessel was capped, placed into a preheated aluminum block set at 100° C. and the reaction mixture was stirred for 48 h. The reaction vessel was cooled to room temperature. Solids in the reaction mixture were filtered, and the filtrate was purified by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 25-65% B over 15 min, then a 5-min hold at 100% B; Flow: 20 mL/min. Fractions containing the desired product were combined and dried via centrifugal evaporation to give 4.0 mg (11%) of the title compound with an average purity by LC/MS analysis was >99%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_t$=1.49 min.; LC/MS (M+H)=587.9. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_t$=2.63 min.; LC/MS (M+H)=587.9. $^1$H NMR (500 MHz, DMSO-d$_6$) δ 8.42 (s, 1H), 8.23-8.18 (m, 2H), 8.15 (t, J=8.1 Hz, 1H), 7.38-7.31 (m, 1H), 7.26 (t, J=7.2 Hz, 1H), 7.14 (t, J=9.4 Hz, 1H), 6.63 (d, J=8.8 Hz, 1H), 6.05 (br. s., 1H), 4.10-4.03 (m, 3H), 4.00 (s, 3H), 3.89 (d, J=12.1 Hz, 1H), 3.77 (br. s., 1H), 3.69-3.59 (m, 2H), 3.43-3.33 (m, 2H), 3.28-3.15 (m, 1H), 2.60 (d, J=7.0 Hz, 2H), 2.28 (s, 6H), 1.87 (s, 3H), 1.60 (br. s., 1H), 1.45-1.28 (m, 2H), 1.25 (t, J=7.0 Hz, 2H), 1.01 (d, J=10.3 Hz, 1H). LC/MS (M+H)=587.3; HPLC conditions: R$_t$=0.70 min: (Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min).

Example 258

11-(4-Cyclopropanecarbonylpiperazin-1-yl)-5-(dimethyl-1H-1,2,3-triazol-5-yl)-8-[(S)-(4-fluorophenyl)(oxan-4-yl)methyl]-3,8,10-triazatricyclo[7.4.0.0$^{2,7}$]trideca-1(13),2(7),3,5,9,11-hexaene

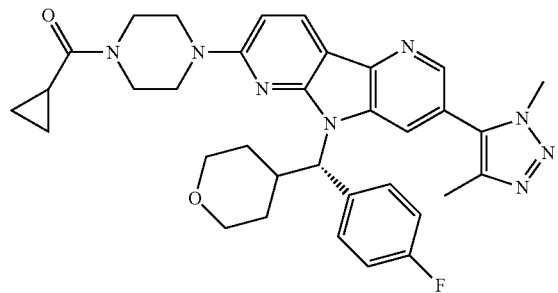 [SMILES: Cc1nnn(C)c1-c1cnc2c3ccc(N4CCN(C(=O)C5CC5)CC4)nc3n([C@H](c3ccc(F)cc3)C3CCOCC3)c2c1]

In a small pressure vessel equipped with a magnetic stirring bar was added (S)-7-chloro-3-(1,4-dimethyl-1H-1,2,3-triazol-5-yl)-5-((4-fluorophenyl)(tetrahydro-2H-pyran-4-yl)methyl)-5H-pyrrolo[2,3-b:4,5-b']dipyridine (25 mg, 0.051 mmol), cyclopropyl(piperazin-1-yl)methanone (9.8 mg, 0.064 mmol) and dioxane (2 mL). The solids were dissolved in dioxane (2 mL). Pd(OAc)$_2$ (0.343 mg, 1.53 μmol), RuPhos (1.4 mg, 3.06 μmol) and Cs$_2$CO$_3$ (24.9 mg, 0.076 mmol) was added. Argon was bubbled into the mixture with sonication for 5 min, then the vessel was capped, placed into a preheated oil bath at 100° C., and was stirred for 1.5 h. Solids were filtered and the filtrate was purified by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 40-100% B over 20 min, then a 5-min hold at 100% B; Flow: 20 mL/min. Fractions containing the desired product were combined and dried via centrifugal evaporation to give 5.3 mg (17%) of the title compound with an average purity by LC/MS analysis was >99%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_t$=1.67 min.; LC/MS (M+H)=609.8. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_t$=2.71 min.; LC/MS (M+H)=609.8. $^1$H NMR (500 MHz, DMSO-d$_6$) δ 8.40 (s, 1H), 8.37-8.26 (m, 2H), 7.88-7.75 (m, 2H), 7.15 (t, J=8.8 Hz, 2H), 6.91 (d, J=8.8 Hz, 1H), 5.72 (br. s., 1H), 4.01 (s, 3H), 3.94 (br. s., 2H), 3.92-3.83 (m, 3H), 3.78 (br. s., 3H), 3.71 (br. s., 2H), 3.60 (br. s., 1H), 3.40 (t, J=11.6 Hz, 1H), 3.25 (t, J=11.4 Hz, 1H), 2.29 (s, 3H), 2.07 (d, J=5.1 Hz, 1H), 1.44 (br. s., 1H), 1.39 (d, J=8.1 Hz, 1H), 1.33-1.15 (m, 2H), 0.85-0.69 (m, 4H). LC/MS (M+H)=609.4; HPLC conditions: R$_t$=3.59 min: (Column: Phenomenex LUNA C18 2×50 mm (4 min grad) eluting with 10-90% aq MeOH containing 0.1% TFA, 0.8 mL/min, monitoring at 254 nm); Temperature: 40° C.).

Example 259

11-Chloro-8-[(4,4-difluorocyclohexyl)(phenyl)methyl]-5-[4-($^2$H$_3$)methyl-1-methyl-1H-1,2,3-triazol-5-yl]-3,8,10-triazatricyclo[7.4.0.0$^{2,7}$]trideca-1(13),2(7),3,5,9,11-hexaene

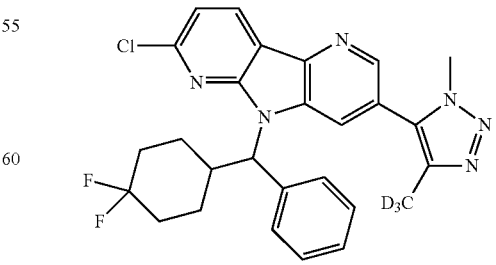

In a small pressure vessel equipped with a magnetic stirring bar was added 3-bromo-7-chloro-5-((4,4-difluorocyclohexyl)(phenyl)methyl)-5H-pyrrolo[2,3-b:4,5-b']
dipyridine (50 mg, 0.102 mmol), ($^2H_3$)methyl-1-methyl-1H-
1,2,3-triazol (20.4 mg, 0.204 mmol) and NMP (2 mL).
Tetramethylammonium acetate (17.0 mg, 0.127 mmol) and
bis(Ph$_3$P) palladium(II) chloride (5.0 mg, 7.13 µmol) was
added. Argon was bubbled into the mixture with sonication
for 5 min, then the vessel was capped and placed into a
preheated oil bath at 100° C. The reaction was heated and
stirred for 16 h. Solids were filtered and the filtrate was
purified by preparative HPLC: Column: Waters XBridge
C18, 19×200 mm, 5-µm particles; Mobile Phase A: 5:95
methanol: water with 10 mM NH$_4$OAc; Mobile Phase B:
95:5 methanol: water with 10 mM NH$_4$OAc; Gradient:
30-90% B over 20 min, then a 5-min hold at 100% B; Flow:
20 mL/min. Fractions containing the desired product were
combined and dried via centrifugal evaporation to give 13.5
mg (26%) of the title compound with an average purity by
LC/MS analysis was 98%. Two analytical LC/MS injections
were used to determine the final purity. Injection 1 condi-
tions: Column: Waters BEH C18, 2.0×50 mm, 1.7 µm
particles; Mobile Phase A: 5:95 ACN:water with 10 mM
NH$_4$OAc; Mobile Phase B: 95:5 ACN:water with 10 mM
NH$_4$OAc; Temperature: 50° C.; Gradient: 0% B, 0-100% B
over 3 min, then a 0.5-min hold at 100% B; Flow: 1 mL/min;
Detection: UV at 220 nm. R$_t$=2.28 min.; LC/MS (M+H)=
510.2. Injection 2 conditions: Column: Waters BEH C18,
2.0×50 mm, 1.7-µm particles; Mobile Phase A: 5:95 metha-
nol:water with 10 mM NH$_4$OAc; Mobile Phase B: 95:5
methanol:water with 10 mM NH$_4$OAc; Temperature: 50° C.;
Gradient: 0% B, 0-100% B over 3 min, then a 0.5-min hold
at 100% B; Flow: 0.5 mL/min; Detection: UV at 220 nm.
R$_t$=3.14 min.; LC/MS (M+H)=510.2. $^1$H NMR (500 MHz,
DMSO-d$_6$) δ 8.73-8.65 (m, 2H), 8.61 (br. s., 1H), 7.78 (d,
J=7.3 Hz, 2H), 7.51 (d, J=8.1 Hz, 1H), 7.35 (t, J=7.3 Hz,
2H), 7.26 (t, J=7.2 Hz, 1H), 5.92 (d, J=10.6 Hz, 1H), 4.03
(s, 3H), 3.55 (d, J=12.1 Hz, 1H), 3.36 (br. s., 1H), 2.08 (br.
s., 1H), 1.95 (br. s., 2H), 1.84-1.64 (m, 2H), 1.51-1.34 (m,
2H), 1.34-1.25 (m, 1H). LC/MS (M+H)=510.2; HPLC con-
ditions: R$_t$=1.14 min: (Column: Waters Aquity BEH C18
2.1×50 mm 1.7 u; Mobile Phase A: water with 0.05% TFA;
Mobile Phase B: ACN with 0.05% TFA; Temperature: 40°
C.; Gradient: 2-98% B over 1.5 min; Flow: 0.8 mL/min).

Examples 260 and 261

8-[(4,4-Difluorocyclohexyl)(phenyl)methyl]-5,11-bis
[4-($^2H_3$)methyl-1-methyl-H-1,2,3-triazol-5-yl]-3,8,
10-triazatricyclo[7.4.0.0$^{2,7}$]trideca-1(13),2(7),3,5,9,
11-hexaene Example 260

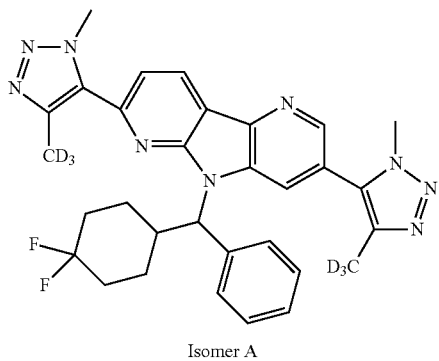

Isomer A

Example 261

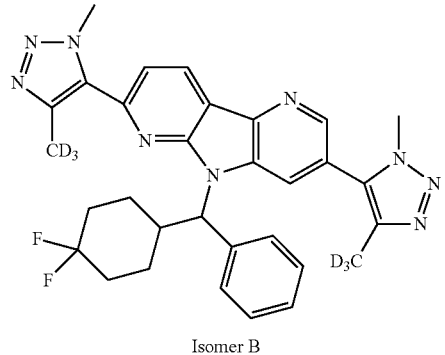

Isomer B

In a small pressure vessel equipped with a magnetic
stirring bar was added 3-bromo-7-chloro-5-((4,4-difluoro-
cyclohexyl)(phenyl)methyl)-5H-pyrrolo[2,3-b:4,5-b']
dipyridine (50 mg, 0.102 mmol), ($^2H_3$)methyl-1-methyl-1H-
1,2,3-triazol (20.4 mg, 0.204 mmol) and NMP (2 mL).
Tetramethylammonium acetate (17.0 mg, 0.127 mmol) and
bis(Ph$_3$P) palladium(II) chloride (5.0 mg, 7.13 µmol) was
added. Argon was bubbled into the mixture with sonication
for 5 min, then the vessel was capped and placed into a
preheated oil bath at 100° C. The reaction was heated and
stirred for 16 h. Solids were filtered and the filtrate was
purified by preparative HPLC: Column: Waters XBridge
C18, 19×200 mm, 5-µm particles; Mobile Phase A: 5:95
methanol: water with 10 mM NH$_4$OAc; Mobile Phase B:
95:5 methanol: water with 10 mM NH$_4$OAc; Gradient:
30-90% B over 20 min, then a 5-min hold at 100% B; Flow:
20 mL/min. Fractions containing the desired product were
combined and dried via centrifugal evaporation to give 19
mg of a mixture of enantiomers. This material was subject
to a chiral purification: Chiral SFC conditions: Chiralcel
OJ-H preparative column, 30×250 mm, 5 µm; Mobile Phase:
15% methanol in CO$_2$, 150 bar; Temp: 35° C.; Flow rate:
70.0 mL/min. for 25 min.; UV monitored at 254 nm;
Injection: 0.25 ml of ~9 mg/mL solution in MeOH (19 mg
purified by stacked injection); R$_t$=isomer A: 13.6 min.;
isomer B: 17.9 min. Fractions containing the desired prod-
ucts were combined and dried via evaporation to give 9.1 mg
(15%) of the isomer A with an average purity by LC/MS
analysis was >99%. Fractions containing the desired prod-
ucts were combined and dried via evaporation to give 8.6 mg
(15%) of the isomer B with an average purity by LC/MS
analysis was >99%. Isomer A: Two analytical LC/MS injec-
tions were used to determine the final purity. Injection 1
conditions: Column: Waters BEH C18, 2.0×50 mm, 1.7 µm
particles; Mobile Phase A: 5:95 ACN:water with 10 mM
NH$_4$OAc; Mobile Phase B: 95:5 ACN:water with 10 mM
NH$_4$OAc; Temperature: 50° C.; Gradient: 0% B, 0-100% B
over 3 min, then a 0.5-min hold at 100% B; Flow: 1 mL/min;
Detection: UV at 220 nm. R$_t$=1.79 min.; LC/MS (M+H)=
574.7. Injection 2 conditions: Column: Waters BEH C18,
2.0×50 mm, 1.7-µm particles; Mobile Phase A: 5:95 metha-
nol:water with 10 mM NH$_4$OAc; Mobile Phase B: 95:5
methanol:water with 10 mM NH$_4$OAc; Temperature: 50° C.;
Gradient: 0% B, 0-100% B over 3 min, then a 0.5-min hold
at 100% B; Flow: 0.5 mL/min; Detection: UV at 220 nm.
R$_t$=2.73 min.; LC/MS (M+H)=574.7. Isomer B: Two ana-
lytical LC/MS injections were used to determine the final
purity. Injection 1 conditions: Column: Waters BEH C18,
2.0×50 mm, 1.7 µm particles; Mobile Phase A: 5:95 ACN:

water with 10 mM NH$_4$OAc; Mobile Phase B: 95:5 ACN: water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_t$=1.79 min.; LC/MS (M+H)=574.7. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_t$=2.74 min.; LC/MS (M+H)=574.7. $^1$H NMR (500 MHz, DMSO-d$_6$) δ 8.82 (d, J=8.1 Hz, 1H), 8.67 (s, 1H), 8.54 (br. s., 1H), 7.73 (d, J=7.7 Hz, 3H), 7.38-7.29 (m, 2H), 7.29-7.20 (m, 1H), 6.10 (br. s., 1H), 4.36 (s, 3H), 4.03 (s, 3H), 3.53 (br. s., 1H), 2.07 (br. s., 1H), 1.94 (br. s., 2H), 1.82 (br. s., 1H), 1.68 (d, J=13.2 Hz, 1H), 1.52-1.41 (m, 1H), 1.37 (br. s., 1H), 1.30 (d, J=13.6 Hz, 1H). LC/MS (M+H)=574.3; HPLC conditions: R$_t$=0.93 min. (Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min).

Examples 262 and 263

8-[(4,4-Difluorocyclohexyl)(phenyl)methyl]-5,11-bis (dimethyl-1H-1,2,3-triazol-5-yl)-3,8,10-triazatricyclo[7.4.0.0$^{2,7}$]trideca-1(13),2(7),3,5,9,11-hexaene Example 262

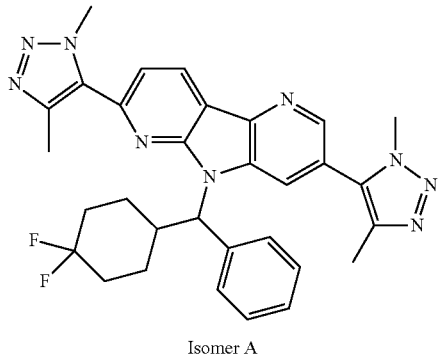

Isomer A

Example 263

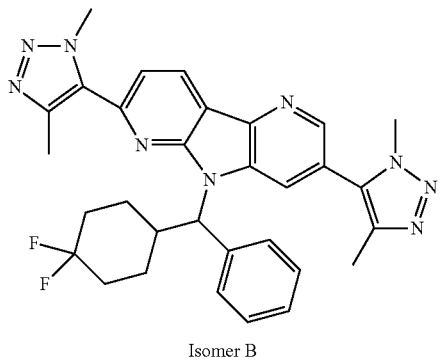

Isomer B

In a pressure vessel equipped with a magnetic stirring bar was added 3-bromo-7-chloro-5-((4,4-difluorocyclohexyl) (phenyl)methyl)-5H-pyrrolo[2,3-b:4,5-b']dipyridine (240 mg, 0.489 mmol), 1,4-dimethyl-1H-1,2,3-triazole (52.2 mg, 0.538 mmol) and DMF (5 mL). Tetramethylammonium acetate (98 mg, 0.734 mmol) and PdCl$_2$(dppf)-CH$_2$Cl$_2$ adduct (28.0 mg, 0.034 mmol) was added. Argon was bubbled into the mixture with sonication for 5 min, then the vessel was capped, placed into a preheated aluminum block set at 100° C. and was stirred for 16 h. Solids were filtered, and the filtrate was purified by preparative HPLC (20-100% B; B solvent 90% MeCN/0.1% TFA water, Phenomenex LUNA C18 30×100 mm, 10 micron, 30 mL/min flow rate, 254 nm UV; R$_t$=11.6 min.). Like fractions were concentrated and re-purified by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 40-80% B over 15 min, then a 5-min hold at 100% B; Flow: 20 mL/min. Fractions containing the desired product were combined and dried via centrifugal evaporation to give 18 mg of a mixture of enantiomers. This material was subject to a chiral purification: Chiral SFC conditions: Chiralcel OJ-H preparative column, 30×250 mm, 5 μm; Mobile Phase: 15% methanol in CO$_2$, 150 bar; Temp: 35° C.; Flow rate: 70.0 mL/min. for 25 min.; UV monitored at 254 nm; Injection: 0.25 ml of ~9 mg/mL solution in MeOH (18 mg purified by stacked injection); R$_t$=isomer A: 13.8 min.; isomer B: 18.3 min. Fractions containing the desired products were combined and dried via evaporation to give 6.9 mg (2%) of the isomer A with an average purity by LC/MS analysis was >99%. Fractions containing the desired products were combined and dried via evaporation to give 7.5 mg (3%) of the isomer B with an average purity by LC/MS analysis was >99%. Isomer A: Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_t$=1.76 min.; LC/MS (M+H)=568.7. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_t$=2.77 min.; LC/MS (M+H)=568.7. Isomer B: Two analytical LC/MS injections were used to determine the final purity. Injection 1 conditions: Column: Waters BEH C18, 2.0×50 mm, 1.7 μm particles; Mobile Phase A: 5:95 ACN: water with 10 mM NH$_4$OAc; Mobile Phase B: 95:5 ACN: water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_t$=1.86 min.; LC/MS (M+H)=568.7. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_t$=2.73 min.; LC/MS (M+H)=568.7. $^1$H NMR (500 MHz, DMSO-d$_6$) δ 8.82 (d, J=8.1 Hz, 1H), 8.67 (s, 1H), 8.54 (br. s., 1H), 7.73 (d, J=8.1 Hz, 3H), 7.32 (t, J=7.5 Hz, 2H), 7.25 (t, J=7.3 Hz, 1H), 6.09 (br. s., 1H), 4.36 (s, 3H), 4.02 (s, 3H), 3.52 (br. s., 1H), 2.30 (s, 3H), 2.07 (br. s., 1H), 1.92 (d, J=7.3 Hz, 1H), 1.82 (br. s., 1H), 1.73 (br. s., 1H), 1.66 (br. s., 1H), 1.45 (d, J=12.1 Hz, 1H), 1.37 (br. s., 1H), 1.30 (d, J=11.7 Hz, 1H). LC/MS (M+H)=568.2; HPLC conditions: R$_t$=0.93 min. (Column:

Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min).

Examples 264 and 265

8-[(4,4-Difluorocyclohexyl)(phenyl)methyl]-5-(dimethyl-1H-1,2,3-triazol-5-yl)-11-(4-methylpiperazin-1-yl)-3,8,10-triazatricyclo[7.4.0.0$^{2,7}$]trideca-1(13),2(7),3,5,9,11-hexaene Example 264

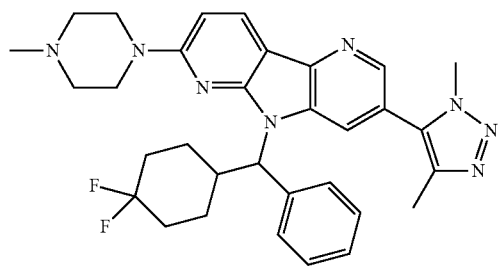

Isomer A

Example 265

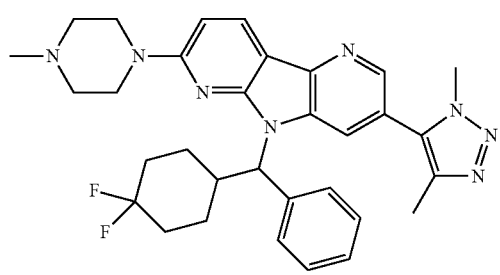

Isomer B

In a 20 mL scintillation vial equipped with a magnetic stirring bar was added 7-chloro-5-((4,4-difluorocyclohexyl)(phenyl)methyl)-3-(1,4-dimethyl-1H-1,2,3-triazol-5-yl)-5H-pyrrolo[2,3-b:4,5-b']dipyridine (40 mg, 0.079 mmol), triethylamine (0.110 mL, 0.789 mmol) and 1-methylpiperazine (39.5 mg, 0.394 mmol). The mixture was dissolved in DMSO (1 mL). The vessel was capped, placed into a preheated aluminum reaction block at 100° C., and the reaction mixture was stirred for 16 h. The vessel was cooled to room temperature. Solids were filtered, and the filtrate was purified by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 40-80% B over 15 min, then a 5-min hold at 100% B; Flow: 20 mL/min. Fractions containing the desired product were combined and dried via centrifugal evaporation to give a mixture of enantiomers. This material was subject to a chiral purification: Chiral HPLC conditions: Chiralpak AS preparative column, 21×250 mm, 10 μm; Mobile Phase: A: 0.1% diethylamine heptane; B: ethanol. Isocratic 8% B for 60 min. run time; Flow rate: 15.0 mL/min. for 60 min.; UV monitored at 254 nm; Injection: 0.25 mL; R$_t$=isomer A: 32.4 min.; isomer B: 41.8 min. Fractions containing the desired products were combined and dried via evaporation to give 6.0 mg (13%) of the isomer A with an average purity by LC/MS analysis was >99%. Fractions containing the desired products were combined and dried via evaporation to give 5.0 mg (11%) of the isomer B with an average purity by LC/MS analysis was >99%. Isomer A: Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_t$=1.71 min.; LC/MS (M+H)=571.1. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_t$=3.37 min.; LC/MS (M+H)=571.1. Isomer B: Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_t$=1.70 min.; LC/MS (M+H)=571.1. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_t$=3.37 min.; LC/MS (M+H)=571.1. $^1$H NMR (500 MHz, DMSO-d$_6$) δ 8.40 (s, 1H), 8.33 (br. s., 1H), 8.27 (d, J=8.8 Hz, 1H), 7.76 (d, J=7.3 Hz, 2H), 7.35-7.27 (m, 2H), 7.26-7.17 (m, 1H), 6.90 (d, J=9.2 Hz, 1H), 5.77 (br. s., 1H), 4.00 (s, 3H), 3.57 (br. s., 1H), 3.43 (d, J=7.7 Hz, 6H), 2.28 (d, J=8.4 Hz, 6H), 2.06 (br. s., 1H), 1.97 (br. s., 2H), 1.90 (br. s., 1H), 1.74 (br. s., 1H), 1.67 (s, 1H), 1.53-1.44 (m, 1H), 1.40 (d, J=11.7 Hz, 1H), 1.32-1.18 (m, 2H). LC/MS (M+H)=571.3; HPLC conditions: R$_t$=0.72 min. (Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min).

Examples 266 and 267

8-[(4,4-Difluorocyclohexyl)(phenyl)methyl]-5-(dimethyl-1H-1,2,3-triazol-5-yl)-N-methyl-N-[2-(methylamino)ethyl]-3,8,10-triazatricyclo[7.4.0.0$^{2,7}$]trideca-1(13),2(7),3,5,9,11-hexaen-11-amine Example 266

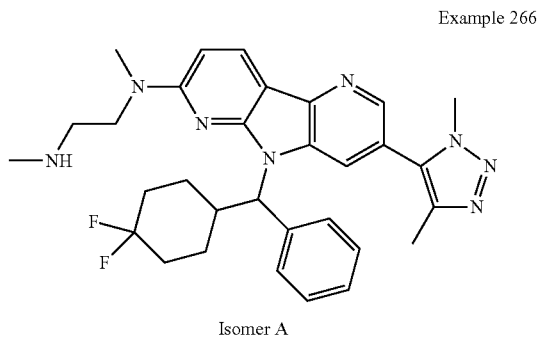

Isomer A

Example 267

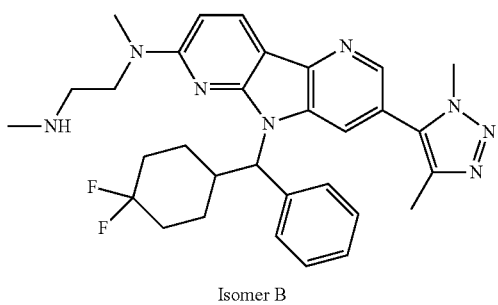

Isomer B

In a 20 mL scintillation vial equipped with a magnetic stirring bar was added 7-chloro-5-((4,4-difluorocyclohexyl)(phenyl)methyl)-3-(1,4-dimethyl-1H-1,2,3-triazol-5-yl)-5H-pyrrolo[2,3-b:4,5-b']dipyridine (40 mg, 0.079 mmol), triethylamine (0.110 mL, 0.789 mmol) and N1,N2-dimethylethane-1,2-diamine (34.8 mg, 0.394 mmol). The mixture was dissolved in DMSO (1 mL). The vessel was capped, placed into a preheated aluminum reaction block at 100° C., and the reaction mixture was stirred for 16 h. The vessel was cooled to room temperature. Solids were filtered, and the filtrate was purified by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 20-60% B over 15 min, then a 5-min hold at 100% B; Flow: 20 mL/min. Fractions containing the desired product were combined and dried via centrifugal evaporation to give 21 mg of a mixture of enantiomers. This material was subject to a chiral purification: Chiral SFC conditions: Lux Cellulose-1 preparative column, 20×250 mm, 5 μm; Mobile Phase: 15% methanol (0.1% diethylamine) in CO$_2$, 150 bar; Temp: 35° C.; Flow rate: 45.0 mL/min. for 25 min.; UV monitored at 254 nm; Injection: 0.25 ml of ~7 mg/mL solution in MeOH (21 mg purified by stacked injection); R$_t$=isomer A: 19.6 min.; isomer B: 21.3 min. Fractions containing the desired products were combined and dried via evaporation to give 11.5 mg (26%) of the isomer A with an average purity by LC/MS analysis was >99%. Fractions containing the desired products were combined and dried via evaporation to give 4.9 mg (11%) of the isomer B with an average purity by LC/MS analysis was >99%. Isomer A: Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_t$=1.50 min.; LC/MS (M+H)=559.1. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_t$=2.85 min.; LC/MS (M+H)=559.1. Isomer B: Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_t$=1.50 min.; LC/MS (M+H)=559.1. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_t$=2.85 min.; LC/MS (M+H)=559.1. $^1$H NMR (500 MHz, DMSO-d$_6$) δ 8.37 (s, 1H), 8.25 (d, J=8.8 Hz, 2H), 7.78 (d, J=7.0 Hz, 2H), 7.31 (t, J=7.3 Hz, 2H), 7.23 (t, J=7.3 Hz, 1H), 6.71 (d, J=8.8 Hz, 1H), 5.79 (br. s., 1H), 3.99 (s, 3H), 3.88 (d, J=14.3 Hz, 2H), 3.57 (br. s., 1H), 3.23 (s, 3H), 2.94 (t, J=6.4 Hz, 2H), 2.92-2.84 (m, 1H), 2.73 (s, 1H), 2.44 (s, 3H), 2.28 (s, 3H), 2.06 (br. s., 1H), 1.95 (br. s., 1H), 1.76 (br. s., 1H), 1.70 (br. s., 1H), 1.47-1.33 (m, 2H), 1.32-1.19 (m, 2H), 1.15 (t, J=7.2 Hz, 1H). LC/MS (M+H)=559.3; HPLC conditions: R$_t$=0.72 min. (Column: Waters Aquity BEH C18 2.1×50 mm 1.7 u; Mobile Phase A: water with 0.05% TFA; Mobile Phase B: ACN with 0.05% TFA; Temperature: 40° C.; Gradient: 2-98% B over 1.5 min; Flow: 0.8 mL/min).

Example 268

4-[5-(Dimethyl-1H-1,2,3-triazol-5-yl)-8-[(S)-(2-fluorophenyl)(oxan-4-yl)methyl]-3,8,10-triazatricyclo[7.4.0.0$^{2,7}$]trideca-1(13),2(7),3,5,9,11-hexaen-11-yl]-N,N-dimethylpiperazine-1-carboxamide

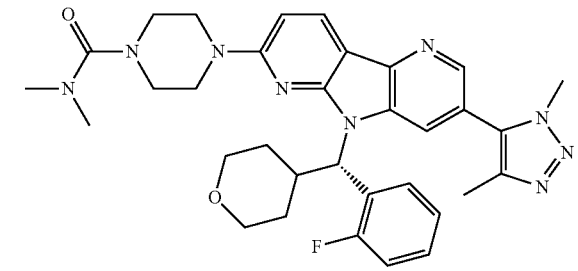

In a small pressure vessel equipped with a magnetic stirring bar was added (S)-7-chloro-3-(1,4-dimethyl-H-1,2,3-triazol-5-yl)-5-((2-fluorophenyl)(tetrahydro-2H-pyran-4-yl)methyl)-5H-pyrrolo[2,3-b:4,5-b']dipyridine (20 mg, 0.041 mmol), N,N-dimethylpiperazine-1-carboxamide (7.7 mg, 0.049 mmol) and dioxane (2 mL). Pd(OAc)$_2$ (0.3 mg, 1.22 μmol), RuPhos (1.1 mg, 2.44 μmol) and Cs$_2$CO$_3$ (19.9 mg, 0.061 mmol) was added. Argon was bubbled into the mixture with sonication for 5 min, the vessel was capped, placed into a preheated aluminum block at 100° C., and the reaction mixture was stirred for 48 h. Solids were filtered, and the filtrate was purified by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 25-65% B over 15 min, then a 5-min hold at 100% B; Flow: 20 mL/min. Fractions containing the desired product were combined and dried via centrifugal evaporation to give 3.3 mg (13%) of the title compound with an average purity by LC/MS analysis was 97%. Two analytical LC/MS injections were used to determine the final purity. Injection 1 conditions: Column: Waters BEH C18, 2.0×50 mm, 1.7 μm particles; Mobile Phase A: 5:95 ACN: water with 10 mM NH$_4$OAc; Mobile Phase B: 95:5 ACN:

water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_t$=1.75 min.; LC/MS (M+H)=612.2. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_t$=3.25 min.; LC/MS (M+H)=612.2. $^1$H NMR (500 MHz, DMSO-d$_6$) δ 8.42 (s, 1H), 8.27 (d, J=8.8 Hz, 2H), 8.15 (t, J=7.3 Hz, 1H), 7.37-7.28 (m, 1H), 7.28-7.22 (m, 1H), 7.11 (t, J=9.4 Hz, 1H), 6.87 (d, J=8.8 Hz, 1H), 6.02 (br. s., 1H), 4.00 (s, 3H), 3.94-3.84 (m, 2H), 3.55 (br. s., 1H), 3.43 (d, J=8.4 Hz, 6H), 3.32 (br. s., 4H), 3.27-3.15 (m, 1H), 2.83 (s, 6H), 2.29 (s, 3H), 1.61 (d, J=13.2 Hz, 1H), 1.50-1.39 (m, 1H), 1.38-1.24 (m, 1H), 1.03 (d, J=12.5 Hz, 1H). LC/MS (M+H)=612.3; HPLC conditions: R$_t$=3.35 min: Column: (Phenomenex LUNA C18 2×50 mm (4 min grad) eluting with 10-90% aq MeOH containing 0.1% TFA, 0.8 mL/min, monitoring at 254 nm); Temperature: 40° C.).

Example 269

4-[5-(Dimethyl-1H-1,2,3-triazol-5-yl)-8-[(S)-(2-fluorophenyl)(oxan-4-yl)methyl]-3,8,10-triazatricyclo[7.4.0.0$^{2,7}$]trideca-1(13),2(7),3,5,9,11-hexaen-11-yl]-N,N-dimethylpiperazine-1-sulfonamide

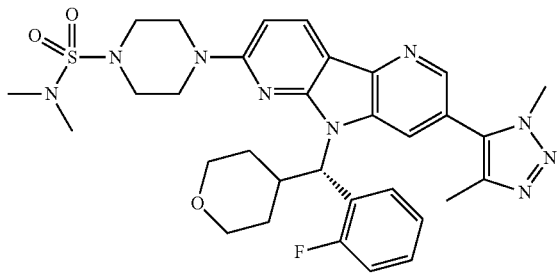 [SMILES: Cc1nnn(C)c1-c1cnc2c3ccc(N4CCN(S(=O)(=O)N(C)C)CC4)nc3n([C@H](c3ccccc3F)C3CCOCC3)c2c1]

In a small pressure vessel equipped with a magnetic stirring bar was added (S)-7-chloro-3-(1,4-dimethyl-H-1,2,3-triazol-5-yl)-5-((2-fluorophenyl)(tetrahydro-2H-pyran-4-yl)methyl)-5H-pyrrolo[2,3-b:4,5-b']dipyridine (20 mg, 0.041 mmol), N,N-dimethylpiperazine-1-sulfonamide (9.5 mg, 0.049 mmol) and dioxane (2 mL). Pd(OAc)$_2$ (0.3 mg, 1.22 μmol), RuPhos (1.1 mg, 2.44 μmol) and Cs$_2$CO$_3$ (19.9 mg, 0.061 mmol) was added. Argon was bubbled into the mixture with sonication for 5 min, then the vessel was capped and placed into a preheated aluminum block at 100° C., and the reaction mixture was stirred for 48 h. Solid were removed by filtration, and the filtrate was purified by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 35-75% B over 20 min, then a 5-min hold at 100% B; Flow: 20 mL/min. Fractions containing the desired product were combined and dried via centrifugal evaporation to give 2.7 mg (10%) of the title compound with an average purity by LC/MS analysis was 96%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_t$=1.85 min.; LC/MS (M+H)=648.1. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_t$=3.12 min.; LC/MS (M+H)=648.1. $^1$H NMR (500 MHz, DMSO-d$_6$) δ 8.44 (s, 1H), 8.30 (d, J=8.4 Hz, 2H), 8.15 (t, J=7.5 Hz, 1H), 7.32 (d, J=6.6 Hz, 1H), 7.28-7.20 (m, 1H), 7.11 (t, J=9.2 Hz, 1H), 6.90 (d, J=8.8 Hz, 1H), 6.02 (br. s., 1H), 4.01 (s, 3H), 3.90 (s, 2H), 3.87-3.79 (m, 4H), 3.75 (d, J=10.3 Hz, 1H), 3.53 (br. s., 1H), 3.49-3.43 (m, 3H), 3.34 (br. s., 2H), 3.28-3.15 (m, 1H), 2.87-2.77 (m, 6H), 2.30 (s, 3H), 1.62 (d, J=12.5 Hz, 1H), 1.45 (d, J=12.1 Hz, 1H), 1.33 (d, J=8.4 Hz, 1H), 1.10-0.96 (m, 1H). LC/MS (M+H)=648.3; HPLC conditions: R$_t$=3.52 min: Column: (Phenomenex LUNA C18 2×50 mm (4 min grad) eluting with 10-90% aq MeOH containing 0.1% TFA, 0.8 mL/min, monitoring at 254 nm); Temperature: 40° C.).

Example 270

5-(Dimethyl-1H-1,2,3-triazol-5-yl)-8-[(S)-(2-fluorophenyl)(oxan-4-yl)methyl]-11-[4-(1-methylpiperidin-4-yl)piperazin-1-yl]-3,8,10-triazatricyclo[7.4.0.0$^{2,7}$]trideca-1(13),2(7),3,5,9,11-hexaene

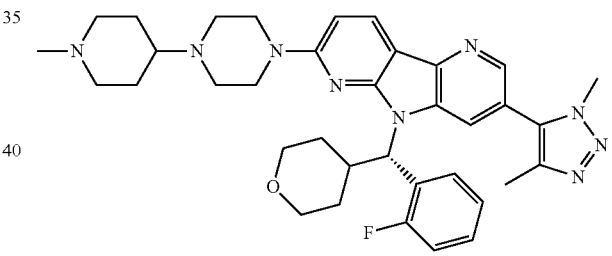

In a small microwave pressure vessel equipped with a magnetic stirring bar was added (S)-7-chloro-3-(1,4-dimethyl-1H-1,2,3-triazol-5-yl)-5-((2-fluorophenyl)(tetrahydro-2H-pyran-4-yl)methyl)-5H-pyrrolo[2,3-b:4,5-b']dipyridine (20 mg, 0.041 mmol), 1-(1-methylpiperidin-4-yl)piperazine (9.0 mg, 0.049 mmol) and dioxane (2 mL). Pd(OAc)$_2$ (0.3 mg, 1.22 μmol), RuPhos (1.1 mg, 2.44 μmol) and Cs$_2$CO$_3$ (19.9 mg, 0.061 mmol) was added. Argon was bubbled into the mixture with sonication for 5 min, then the vessel was capped, placed into a microwave reactor and heated to 120° C. with stirring for 0.25 h. Solids were filtered, and the filtrate was purified by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 30-100% B over 30 min, then a 5-min hold at 100% B; Flow: 20 mL/min. Fractions containing the desired product were combined and dried via centrifugal evaporation to give 11.5 mg (44%) of the title compound with an average purity by LC/MS analysis was >99%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH₄OAc; Mobile Phase B: 95:5 ACN:water with 10 mM NH₄OAc; Temperature: 50° C.; Gradient: 0% B, 0-100% B over 3 min, then a 0.5-min hold at 100% B; Flow: 1 mL/min; Detection: UV at 220 nm. $R_t$=1.37 min.; LC/MS (M+H)= 638.2. Injection 2 conditions: Column: Waters BEH C18, 2.0×50 mm, 1.7-μm particles; Mobile Phase A: 5:95 methanol:water with 10 mM NH₄OAc; Mobile Phase B: 95:5 methanol:water with 10 mM NH₄OAc; Temperature: 50° C.; Gradient: 0% B, 0-100% B over 3 min, then a 0.5-min hold at 100% B; Flow: 0.5 mL/min; Detection: UV at 220 nm. $R_t$=3.01 min.; LC/MS (M+H)=638.2. ¹H NMR (500 MHz, DMSO-d₆) δ 8.41 (s, 1H), 8.24 (d, J=8.1 Hz, 2H), 8.14 (t, J=7.3 Hz, 1H), 7.35-7.28 (m, 1H), 7.28-7.19 (m, 1H), 7.12 (t, J=9.4 Hz, 1H), 6.85 (d, J=8.8 Hz, 1H), 6.00 (br. s., 1H), 4.00 (s, 3H), 3.92-3.83 (m, 1H), 3.77 (br. s., 1H), 3.55 (br. s., 1H), 3.39 (br. s., 4H), 3.22 (t, J=11.6 Hz, 1H), 2.81 (d, J=11.0 Hz, 2H), 2.65 (br. s., 4H), 2.29 (s, 3H), 2.24-2.17 (m, 1H), 2.15 (s, 3H), 1.90-1.81 (m, 2H), 1.78 (d, J=11.0 Hz, 2H), 1.59 (d, J=12.1 Hz, 1H), 1.53-1.38 (m, 3H), 1.33 (d, J=8.8 Hz, 1H), 1.04 (d, J=12.1 Hz, 1H). LC/MS (M+H)=638.5; HPLC conditions: $R_t$=2.70 min: Column: (Phenomenex LUNA C18 2×50 mm (4 min grad) eluting with 10-90% aq MeOH containing 0.1% TFA, 0.8 mL/min, monitoring at 254 nm); Temperature: 40° C.).

Example 271

1-[5-(Dimethyl-1H-1,2,3-triazol-5-yl)-8-[(S)-(2-fluorophenyl)(oxan-4-yl)methyl]-3,8,10-triazatricyclo[7.4.0.0²,⁷]trideca-1(13),2(7),3,5,9,11-hexaen-11-yl]-N,N-dimethylpiperidine-4-carboxamide

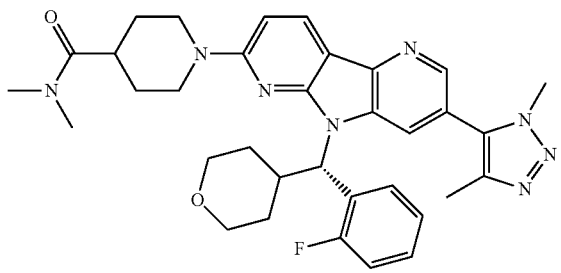 [SMILES: Cc1nnn(C)c1-c1cnc2c3ccc(N4CCC(C(=O)N(C)C)CC4)nc3n([C@H](c3ccccc3F)C3CCOCC3)c2c1]

In a small pressure vessel equipped with a magnetic stirring bar was added (S)-7-chloro-3-(1,4-dimethyl-H-1,2,3-triazol-5-yl)-5-((2-fluorophenyl)(tetrahydro-2H-pyran-4-yl)methyl)-5H-pyrrolo[2,3-b:4,5-b']dipyridine (20 mg, 0.041 mmol), N,N-dimethylpiperidine-4-carboxamide (6.4 mg, 0.041 mmol) and THF (2 mL). RuPhos precatalyst (1.8 mg, 2.44 μmol), RuPhos (1.1 mg, 2.44 μmol) and sodium t-butoxide (11.7 mg, 0.122 mmol) was added. Argon was bubbled into the mixture with sonication for 5 min. The vessel was capped, placed into a preheated oil bath at 100° C., and the reaction mixture was stirred for 16 h. Solid were filtered, and the filtrate was purified by preparative HPLC: Column: Waters XBridge C18, 19×200 mm, 5-μm particles; Mobile Phase A: 5:95 methanol: water with 10 mM NH₄OAc; Mobile Phase B: 95:5 methanol: water with 10 mM NH₄OAc; Gradient: 20-60% B over 20 min, then a 5-min hold at 100% B; Flow: 20 mL/min. Fractions containing the desired product were combined and dried via centrifugal evaporation to give 13.7 mg (54%) of the title compound with an average purity by LC/MS analysis was 98%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH₄OAc; Mobile Phase B: 95:5 ACN:water with 10 mM NH₄OAc; Temperature: 50° C.; Gradient: 0% B, 0-100% B over 3 min, then a 0.5-min hold at 100% B; Flow: 1 mL/min; Detection: UV at 220 nm. $R_t$=1.71 min.; LC/MS (M+H)=611.1. Injection 2 conditions: Column: Waters BEH C18, 2.0×50 mm, 1.7-μm particles; Mobile Phase A: 5:95 methanol:water with 10 mM NH₄OAc; Mobile Phase B: 95:5 methanol:water with 10 mM NH₄OAc; Temperature: 50° C.; Gradient: 0% B, 0-100% B over 3 min, then a 0.5-min hold at 100% B; Flow: 0.5 mL/min; Detection: UV at 220 nm. $R_t$=3.50 min.; LC/MS (M+H)=611.1. ¹H NMR (500 MHz, DMSO-d₆) δ 8.41 (s, 1H), 8.24 (d, J=8.4 Hz, 2H), 8.14 (t, J=7.3 Hz, 1H), 7.32 (d, J=5.5 Hz, 1H), 7.28-7.18 (m, 1H), 7.12 (t, J=9.4 Hz, 1H), 6.87 (d, J=8.8 Hz, 1H), 6.00 (br. s., 1H), 4.57 (d, J=11.7 Hz, 2H), 4.00 (s, 3H), 3.91-3.83 (m, 1H), 3.76 (d, J=10.6 Hz, 1H), 3.55 (br. s., 1H), 3.22 (t, J=11.4 Hz, 1H), 3.19-3.12 (m, 3H), 3.10 (s, 3H), 3.08-2.98 (m, 1H), 2.83 (s, 3H), 2.29 (s, 3H), 1.80 (d, J=12.1 Hz, 2H), 1.59 (d, J=11.4 Hz, 3H), 1.42 (d, J=11.4 Hz, 1H), 1.33 (d, J=9.9 Hz, 1H), 1.05 (d, J=11.7 Hz, 1H). LC/MS (M+H)=611.4; HPLC conditions: $R_t$=3.28 min: Column: (Phenomenex LUNA C18 2×50 mm (4 min grad) eluting with 10-90% aq MeOH containing 0.1% TFA, 0.8 mL/min, monitoring at 254 nm); Temperature: 40° C.).

Example 272

2-{1-[5-(Dimethyl-1H-1,2,3-triazol-5-yl)-8-[(S)-(2-fluorophenyl)(oxan-4-yl)methyl]-3,8,10-triazatricyclo[7.4.0.0²,⁷]trideca-1(13),2(7),3,5,9,11-hexaen-11-yl]piperidin-4-yl}propan-2-ol

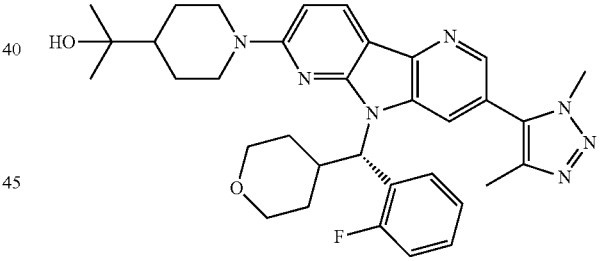

In a small microwave pressure vessel equipped with a magnetic stirring bar was added (S)-7-chloro-3-(1,4-dimethyl-1H-1,2,3-triazol-5-yl)-5-((2-fluorophenyl)(tetrahydro-2H-pyran-4-yl)methyl)-5H-pyrrolo[2,3-b:4,5-b']dipyridine (20 mg, 0.041 mmol), 2-(piperidin-4-yl)propan-2-ol (8.8 mg, 0.061 mmol) and THF (2 mL). RuPhos precatalyst (1.8 mg, 2.44 μmol), RuPhos (1.1 mg, 2.44 μmol) and sodium t-butoxide (11.7 mg, 0.122 mmol) was then added. Argon was bubbled into the mixture with sonication for 5 min. The vessel was capped, placed into a microwave reactor set at 100° C. and the reaction mixture was stirred for 0.25 h. Solids were removed by filtration, and the filtrate was purified by preparative HPLC: Column: Waters XBridge C18, 19×200 mm, 5-μm particles; Mobile Phase A: 5:95 methanol: water with 10 mM NH₄OAc; Mobile Phase B: 95:5 methanol: water with 10 mM NH₄OAc; Gradient: 40-80% B over 15 min, then a 5-min hold at 100% B; Flow: 20 mL/min. Fractions containing the desired product were combined and dried via centrifugal evaporation to give 7.3 mg (29%) of the title compound with an average purity by LC/MS analysis was 98%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_t$=1.75 min.; LC/MS (M+H)=598.3. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_t$=2.90 min.; LC/MS (M+H)=598.3. LC/MS (M+H)=598.4; HPLC conditions: R$_t$=3.55 min: Column: (Phenomenex LUNA C18 2×50 mm (4 min grad) eluting with 10-90% aq MeOH containing 0.1% TFA, 0.8 mL/min, monitoring at 254 nm); Temperature: 40° C.).

Example 273

1-[5-(Dimethyl-1H-1,2,3-triazol-5-yl)-8-[(S)-(2-fluorophenyl)(oxan-4-yl)methyl]-3,8,10-triazatricyclo[7.4.0.0$^{2,7}$]trideca-1(13),2(7),3,5,9,11-hexaen-11-yl]-2,2,6,6-tetramethylpiperidin-4-ol

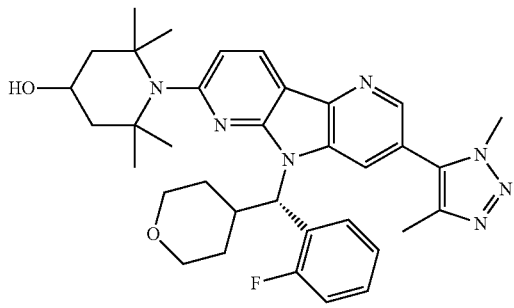 [SMILES: Cc1nnn(C)c1-c1cnc2c3ccc(N4C(C)(C)CC(O)CC4(C)C)nc3n([C@H](c3ccccc3F)C3CCOCC3)c2c1]

In a small microwave pressure vessel equipped with a magnetic stirring bar was added (S)-7-chloro-3-(1,4-dimethyl-1H-1,2,3-triazol-5-yl)-5-((2-fluorophenyl)(tetrahydro-2H-pyran-4-yl)methyl)-5H-pyrrolo[2,3-b:4,5-b']dipyridine (20 mg, 0.041 mmol), 2,2,6,6-tetramethylpiperidin-4-ol (9.6 mg, 0.061 mmol) and THF (2 mL). RuPhos precatalyst (1.8 mg, 2.44 μmol), RuPhos (1.1 mg, 2.44 μmol) and sodium t-butoxide (11.7 mg, 0.122 mmol) were added. Argon was bubbled into the mixture with sonication for 5 min. The vessel was capped, placed into a microwave reactor set at 100° C. and the reaction mixture was stirred for 0.25 h. Solids were filtered, and the filtrate was purified by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 20-60% B over 15 min, then a 5-min hold at 100% B; Flow: 20 mL/min. Fractions containing the desired product were combined and dried via centrifugal evaporation to give 0.5 mg (2%) of the title compound with an average purity by LC/MS analysis was >99%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_t$=1.39 min.; LC/MS (M+H)=612.4. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_t$=3.17 min.; LC/MS (M+H)=612.4. $^1$H NMR (500 MHz, DMSO-d$_6$) δ 8.53 (s, 1H), 8.46 (d, J=8.8 Hz, 1H), 8.26 (br. s., 1H), 7.35 (br. s., 1H), 7.25 (br. s., 1H), 7.16 (t, J=8.8 Hz, 1H), 6.76 (d, J=8.1 Hz, 1H), 5.70 (br. s., 1H), 4.00 (br. s., 3H), 3.90 (br. s., 1H), 3.79 (br. s., 1H), 3.55-3.45 (m, 4H), 3.22 (t, J=12.1 Hz, 1H), 2.29 (br. s., 3H), 2.18 (d, J=14.3 Hz, 2H), 1.36 (br. s., 9H), 1.24 (br. s., 1H), 1.16 (s, 6H), 1.05 (br. s., 1H). LC/MS (M+H)=612.4; HPLC conditions: R$_t$=3.47 min: Column: (Phenomenex LUNA C18 2×50 mm (4 min grad) eluting with 10-90% aq MeOH containing 0.1% TFA, 0.8 mL/min, monitoring at 254 nm); Temperature: 40° C.).

Example 274

1-[5-(Dimethyl-1H-1,2,3-triazol-5-yl)-8-[(S)-(2-fluorophenyl)(oxan-4-yl)methyl]-3,8,10-triazatricyclo[7.4.0.0$^{2,7}$]trideca-1(13),2(7),3,5,9,11-hexaen-11-yl]piperidine-4-carbonitrile

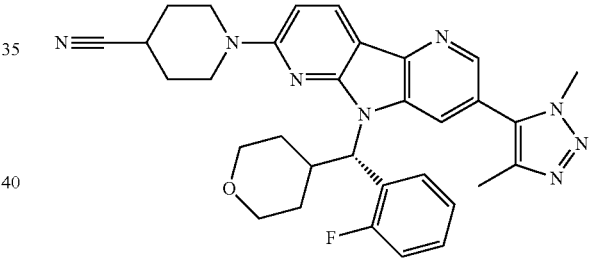

In a small pressure vial equipped with a magnetic stirring bar was added (S)-7-chloro-3-(1,4-dimethyl-1H-1,2,3-triazol-5-yl)-5-((2-fluorophenyl)(tetrahydro-2H-pyran-4-yl)methyl)-5H-pyrrolo[2,3-b:4,5-b']dipyridine (20 mg, 0.041 mmol), piperidine-4-carbonitrile (6.7 mg, 0.061 mmol) and THF (2 mL). RuPhos precatalyst (1.8 mg, 2.44 mol), RuPhos (1.1 mg, 2.44 μmol) and sodium t-butoxide (11.7 mg, 0.122 mmol) were added. Argon was bubbled into the mixture with sonication for 5 min. The vial was capped, placed into a preheated oil bath at 100° C. and the reaction mixture was stirred for 16 h. Solids were removed by filtration, and the filtrate was purified by preparative HPLC: Column: Water XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 35-75% B over 15 min, then a 5-min hold at 100% B; Flow: 20 mL/min. Fractions containing the desired product were combined and dried via centrifugal evaporation to give 5.0 mg (22%) of the title compound with an average purity by LC/MS analysis was >99%. Two analytical LC/MS injections were used to determine the final purity. Injection 1 conditions: Column: Waters BEH C18, 2.0×50 mm, 1.7 μm particles; Mobile Phase A:

5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_t$=1.74 min.; LC/MS (M+H)=565.2. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_t$=2.62 min.; LC/MS (M+H)=565.2. $^1$H NMR (500 MHz, DMSO-d$_6$) δ 8.43 (s, 1H), 8.26 (d, J=8.8 Hz, 2H), 8.14 (t, J=7.5 Hz, 1H), 7.39-7.28 (m, 1H), 7.28-7.20 (m, 1H), 7.13 (t, J=9.2 Hz, 1H), 6.90 (d, J=8.8 Hz, 1H), 6.03 (br. s., 1H), 4.06 (br. s., 2H), 4.01 (s, 3H), 3.92-3.84 (m, 1H), 3.76 (d, J=11.0 Hz, 1H), 3.63 (br. s., 2H), 3.55 (br. s., 1H), 3.47-3.39 (m, 1H), 3.22 (t, J=11.0 Hz, 2H), 2.30 (s, 3H), 2.03 (br. s., 2H), 1.81 (dd, J=18.5, 9.0 Hz, 2H), 1.61 (d, J=12.1 Hz, 1H), 1.45 (d, J=8.1 Hz, 1H), 1.33 (d, J=9.2 Hz, 1H), 1.03 (d, J=14.3 Hz, 1H). LC/MS (M+H)=565.3; HPLC conditions: R$_t$=3.38 min: Column: (Phenomenex LUNA C18 2×50 mm (4 min grad) eluting with 10-90% aq MeOH containing 0.1% TFA, 0.8 mL/min, monitoring at 254 nm; Temperature: 40° C.).

Example 275

N-[5-(Dimethyl-1H-1,2,3-triazol-5-yl)-8-[(S)-(2-fluorophenyl)(oxan-4-yl)methyl]-3,8,10-triazatricyclo[7.4.0.0$^{2,7}$]trideca-1(13),2(7),3,5,9,11-hexaen-11-yl]-2-methylpropanamide

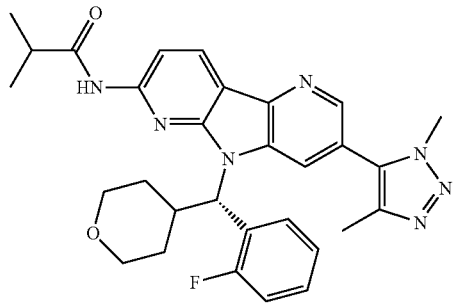 [SMILES: Cc1nnn(C)c1-c1cnc2c3ccc(NC(=O)C(C)C)nc3n([C@H](c3ccccc3F)C3CCOCC3)c2c1]

Step 1: (S)-3-(1,4-dimethyl-1H-1,2,3-triazol-5-yl)-5-((2-fluorophenyl)(tetrahydro-2H-pyran-4-yl)methyl)-5H-pyrrolo[2,3-b:4,5-b']dipyridin-7-amine In a small pressure vessel equipped with a magnetic stirring bar, was added (S)-7-chloro-3-(1,4-dimethyl-1H-1,2,3-triazol-5-yl)-5-((2-fluorophenyl)(tetrahydro-2H-pyran-4-yl)methyl)-5H-pyrrolo[2,3-b:4,5-b']dipyridine (20 mg, 0.041 mmol), 3-amino-3-methyltetrahydrothiophene 1,1-dioxide (9.1 mg, 0.061 mmol) and THF (2 mL). RuPhos precatalyst (1.8 mg, 2.44 μmol), RuPhos (1.1 mg, 2.44 μmol) and sodium t-butoxide (11.7 mg, 0.122 mmol) were added. Argon was bubbled into the mixture with sonication for 5 min. The vessel was capped, placed into a preheated oil bath at 100° C. and stirred for 16 h. The reaction vessel was cooled to room temperature. Solids were filtered and the filtrate was concentrated under vacuum to give 20 mg (78%) of a residue. LC/MS (M+H)=472.3; HPLC conditions: R$_t$=2.91 min: Column: (Phenomenex LUNA C18 2×50 mm (4 min grad) eluting with 10-90% aq MeOH containing 0.1% TFA, 0.8 mL/min, monitoring at 254 nm); Temperature: 40° C.).

Step 2: N-[5-(Dimethyl-1H-1,2,3-triazol-5-yl)-8-[(S)-(2-fluorophenyl)(oxan-4-yl)methyl]-3,8,10-triazatricyclo[7.4.0.0$^{2,7}$]trideca-1(13),2(7),3,5,9,11-hexaen-11-yl]-2-methylpropanamide In a 20 mL scintillation vial equipped with a magnetic stirring bar was added (S)-3-(1,4-dimethyl-1H-1,2,3-triazol-5-yl)-5-((2-fluorophenyl)(tetrahydro-2H-pyran-4-yl)methyl)-5H-pyrrolo[2,3-b:4,5-b']dipyridin-7-amine (10 mg, 0.021 mmol) in dichloromethane (1.5 mL). Triethylamine (9 μl, 0.064 mmol) and isobutyryl chloride (3.4 mg, 0.032 mmol) was added. The vial was capped, then stirred at 20° C. for 1 h. Dichloromethane was removed under vacuum and the remaining residue was taken up in methanol. Solids were filtered and the filtrate was purified by preparative HPLC: Column: Waters XBridge C18, 19×200 mm, 5-μm particles; Mobile Phase A: 5:95 methanol: water with 10 mM NH$_4$OAc; Mobile Phase B: 95:5 methanol: water with 10 mM NH$_4$OAc; Gradient: 55-95% B over 15 min, then a 5-min hold at 100% B; Flow: 20 mL/min. Fractions containing the desired product were combined and dried via centrifugal evaporation to give 4.7 mg (41%) of the title compound with an average purity by LC/MS analysis was >99%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0% B, 0-100% B over 3 min, then a 0.5-min hold at 100% B; Flow: 1 mL/min; Detection: UV at 220 nm. R$_t$=1.74 min.; LC/MS (M+H)=540.2. Injection 2 conditions: Column: Waters BEH C18, 2.0×50 mm, 1.7-μm particles; Mobile Phase A: 5:95 methanol:water with 10 mM NH$_4$OAc; Mobile Phase B: 95:5 methanol:water with 10 mM NH$_4$OAc; Temperature: 50° C.; Gradient: 0% B, 0-100% B over 3 min, then a 0.5-min hold at 100% B; Flow: 0.5 mL/min; Detection: UV at 220 nm. R$_t$=3.17 min.; LC/MS (M+H)=540.2. $^1$H NMR (500 MHz, DMSO-d$_6$) δ 10.66 (br. s., 1H), 8.55 (d, J=4.0 Hz, 2H), 8.43 (br. s., 1H), 8.34 (br. s., 1H), 8.19 (d, J=8.1 Hz, 1H), 7.40-7.21 (m, 2H), 7.11 (t, J=9.4 Hz, 1H), 6.15 (br. s., 1H), 3.99 (br. s., 3H), 3.91 (d, J=10.6 Hz, 1H), 3.75 (d, J=11.4 Hz, 1H), 3.25 (t, J=11.4 Hz, 1H), 3.00-2.91 (m, 1H), 2.28 (br. s., 3H), 1.64 (br. s., 1H), 1.52-1.32 (m, 2H), 1.27-1.09 (m, 6H), 0.99 (d, J=12.1 Hz, 1H). LC/MS (M+H)=540.3; HPLC conditions: R$_t$=3.84 min: Column: (Phenomenex LUNA C18 2×50 mm (4 min grad) eluting with 10-90% aq MeOH containing 0.1% TFA, 0.8 mL/min, monitoring at 254 nm; Temperature: 40° C.).

Example 276

N-[5-(Dimethyl-1H-1,2,3-triazol-5-yl)-8-[(S)-(2-fluorophenyl)(oxan-4-yl)methyl]-3,8,10-triazatricyclo[7.4.0.0²,⁷]trideca-1(13),2(7),3,5,9,11-hexaen-11-yl]cyclopropanecarboxamide

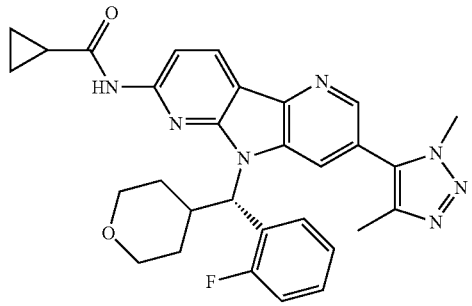 [SMILES: Cc1nnn(C)c1-c1cnc2c3ccc(NC(=O)C4CC4)nc3n([C@H](c3ccccc3F)C3CCOCC3)c2c1]

In a 20 mL scintillation vial equipped with a magnetic stirring bar was added (S)-3-(1,4-dimethyl-1H-1,2,3-triazol-5-yl)-5-((2-fluorophenyl)(tetrahydro-2H-pyran-4-yl)methyl)-5H-pyrrolo[2,3-b:4,5-b']dipyridin-7-amine (10 mg, 0.021 mmol) in dichloromethane (2 mL). Triethylamine (9 μl, 0.064 mmol) and cyclopropanecarbonyl chloride (3.3 mg, 0.032 mmol) was added. The vial was capped and stirred at 20° C. for 1 h. Dichloromethane was removed under vacuum and the residue was taken up in methanol. Solids were filtered and the filtrate was purified by preparative HPLC: Column: Waters XBridge C18, 19×200 mm, 5-μm particles; Mobile Phase A: 5:95 methanol: water with 10 mM NH₄OAc; Mobile Phase B: 95:5 methanol: water with 10 mM NH₄OAc; Gradient: 55-95% B over 15 min, then a 5-min hold at 100% B; Flow: 20 mL/min. Fractions containing the desired product were combined and dried via centrifugal evaporation to give 2.5 mg (21%) of the title compound with an average purity by LC/MS analysis was 97%. Two analytical LC/MS injections were used to determine the final purity. Injection 1 conditions: Column: Waters BEH C18, 2.0×50 mm, 1.7 μm particles; Mobile Phase A: 5:95 ACN:water with 10 mM NH₄OAc; Mobile Phase B: 95:5 ACN:water with 10 mM NH₄OAc; Temperature: 50° C.; Gradient: 0% B, 0-100% B over 3 min, then a 0.5-min hold at 100% B; Flow: 1 mL/min; Detection: UV at 220 nm. $R_t$=1.70 min.; LC/MS (M+H)=540.2. Injection 2 conditions: Column: Waters BEH C18, 2.0×50 mm, 1.7-μm particles; Mobile Phase A: 5:95 methanol:water with 10 mM NH₄OAc; Mobile Phase B: 95:5 methanol:water with 10 mM NH₄OAc; Temperature: 50° C.; Gradient: 0% B, 0-100% B over 3 min, then a 0.5-min hold at 100% B; Flow: 0.5 mL/min; Detection: UV at 220 nm. $R_t$=2.63 min.; LC/MS (M+H)=540.2. ¹H NMR (500 MHz, DMSO-d₆) δ 11.00 (br. s., 1H), 8.60-8.52 (m, 2H), 8.44 (br. s., 1H), 8.34 (br. s., 1H), 8.17 (d, J=8.4 Hz, 1H), 7.44-7.22 (m, 2H), 7.12 (t, J=9.4 Hz, 1H), 6.14 (br. s., 1H), 4.00 (br. s., 3H), 3.91 (d, J=10.3 Hz, 1H), 3.76 (d, J=9.5 Hz, 2H), 3.57-3.45 (m, 1H), 3.26 (t, J=11.0 Hz, 1H), 2.29 (br. s., 3H), 2.22-2.12 (m, 1H), 1.63 (br. s., 1H), 1.51-1.32 (m, 2H), 1.00 (d, J=11.7 Hz, 1H), 0.92 (d, J=5.9 Hz, 4H). LC/MS (M+H)=540.2; HPLC conditions: $R_t$=3.79 min: Column: (Phenomenex LUNA C18 2×50 mm (4 min grad) eluting with 10-90% aq MeOH containing 0.1% TFA, 0.8 mL/min, monitoring at 254 nm; Temperature: 40° C.).

Example 277

10-Methanesulfonyl-5-[4-(²H₃)methyl-1-methyl-1H-1,2,3-triazol-5-yl]-8-[(S)-oxan-4-yl(phenyl)methyl]-N-(2,2,2-trifluoroethyl)-3,8,12-triazatricyclo[7.4.0.0²,⁷]trideca-1(13),2(7),3,5,9,11-hexaen-13-amine

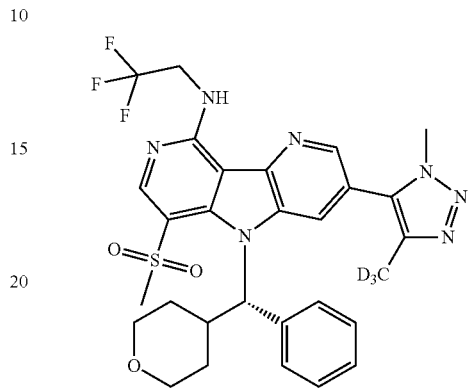

Step 1: 13-Chloro-10-methanesulfonyl-5-[4-(²H₃)methyl-1-methyl-1H-1,2,3-triazol-5-yl]-8-[(S)-oxan-4-yl(phenyl)methyl]-3,8,12-triazatricyclo[7.4.0.0²,⁷]trideca-1(13),2(7),3,5,9,11-hexaene A 100 mL round bottom flask was charged with 10-methanesulfonyl-13-methoxy-5-[4-(²H₃)methyl-1-methyl-1H-1,2,3-triazol-5-yl]-8-[(S)-oxan-4-yl(phenyl)methyl]-3,8,12-triazatricyclo[7.4.0.0²,⁷]trideca-1(13),2(7),3,5,9,11-hexaene (336 mg, 0.611 mmol) and DMF (6113 μL). To that solution was added POCl₃ (570 μL, 6.11 mmol). The vial was placed into an oil bath preheated to 80° C. and vented into a balloon partially filled with nitrogen. After 1.5 h, the mixture was poured onto ice and diluted with ethyl acetate. The reaction mixture was slowly quenched with solid sodium bicarbonate. The quenched solution was transferred to a separatory funnel and the layers were separated. The organic was washed with water (×2). The aqueous was extracted with ethyl acetate and discarded. The combined organics were washed with brine (×2), dried over magnesium sulfate, concentrated under reduced pressure, and purified by flash chromatography: (24 g ISCO RediSep Rf, acetone/DCM 0% [75 mL], 0-25% [250 mL], 25% [200 mL], 25-100% [400 mL]). The fractions were collected to give the title compound (282 mg, 83%). ¹H NMR (400 MHz, CDCl₃) δ 9.13 (s, 1H), 8.77 (d, J=1.8 Hz, 1H), 7.54 (d, J=1.8 Hz, 1H), 7.52-7.48 (m, 2H), 7.45-7.36 (m, 3H), 6.97 (d, J=10.0 Hz, 1H), 4.12-4.04 (m, 1H), 3.84-3.79 (m, 1H), 3.72 (s, 3H), 3.55 (td, J=11.8, 1.8 Hz, 1H), 3.48 (s, 3H), 3.23 (td, J=11.8, 1.8 Hz, 1H), 3.04-2.91 (m, 1H), 2.24-2.19 (m, 1H), 2.05-1.92 (m, 1H), 1.70-1.59 (m, 1H), 0.37 (d, J=14.3 Hz, 1H). LCMS: (M+H)⁺ 554.0.

Step 2: 10-Methanesulfonyl-5-[4-(²H₃)methyl-1-methyl-1H-1,2,3-triazol-5-yl]-8-[(S)-oxan-4-yl(phenyl)methyl]-N-(2,2,2-trifluoroethyl)-3,8,12-triazatricyclo[7.4.0.0²,⁷]trideca-1(13),2(7),3,5,9,11-hexaen-13-amine A 1-dram vial was charged with 13-chloro-10-methanesulfonyl-5-[4-(²H₃)methyl-1-methyl-1H-1,2,3-triazol-5-yl]-

8-[(S)-oxan-4-yl(phenyl)methyl]-3,8,12-triazatricyclo[7.4.0.0²,⁷]trideca-1(13),2(7),3,5,9,11-hexaene (66 mg, 0.119 mmol) and NMP (250 μL). To that solution was added 2,2,2-trifluoroethylamine (200 μL, 2.51 mmol). The vial was sealed and heated to 65° C. with stirring overnight. After 16 h, an additional 200 μL of amine was added and stirring continued for an additional 24 h. The crude mixture was cooled, filtered through a 0.45 syringe tip filter and purified directly by preparative HPLC: Column: Waters XBridge C18 100×30 mm 5 μm, Solvents: A:95:5water/acetonitrile; B:95:5 acetonitrile/water; Buffer: 10 mM ammonium acetate, % B gradient (time): 49% (11 min), Flow Rate: 30 mL/min, 4 injections monitored at 254 nm. The fractions containing product were concentrated under reduced pressure. The resulting solids were filtered through a plug of silica gel, eluting with 50% acetone in DCM. The isolated product was dissolved in 1 mL of ethanol and 1 mL of deionized water was added dropwise, slightly swirling the vial to give a white precipitate. The solids were sonicated for 2 min and collected by filtration to give the title compound (36.5 mg, 50%). LCMS: m/z (M+H)⁺ 617. ¹H NMR (400 MHz, CDCl₃) δ 8.98 (s, 1H), 8.50 (d, J=1.8 Hz, 1H), 8.31 (t, J=6.5 Hz, 1H), 7.50 (d, J=7.8 Hz, 2H), 7.43 (d, J=1.8 Hz, 1H), 7.42-7.30 (m, 3H), 6.92 (d, J=10.3 Hz, 1H), 4.67-4.52 (m, 2H), 4.11-4.03 (m, J=11.3 Hz, 1H), 3.83 (dd, J=11.7, 3.4 Hz, 1H), 3.73-3.70 (m, 3H), 3.59-3.48 (m, 1H), 3.35 (s, 3H), 3.30-3.19 (m, 1H), 2.94 (d, J=10.0 Hz, 1H), 2.23-2.11 (m, 1H), 1.93 (d, J=12.8 Hz, 1H), 1.73-1.60 (m, 1H), 0.48 (d, J=11.5 Hz, 1H).

Example 278

2-{10-Fluoro-5-[4-(²H₃)methyl-1-methyl-1H-1,2,3-triazol-5-yl]-8-[(S)-oxan-4-yl(phenyl)methyl]-3,8,12-triazatricyclo[7.4.0.0²,⁷]trideca-1(13),2(7),3,5,9,11-hexaen-11-yl}propan-2-ol

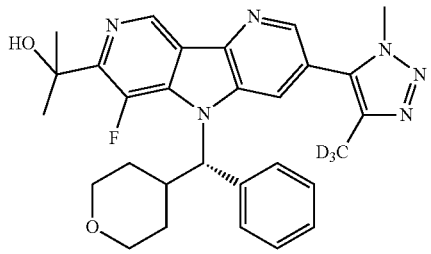 [SMILES: [2H]C([2H])([2H])c1nnn(C)c1-c1cnc2c3cnc(C(C)(C)O)c(F)c3n([C@H](c3ccccc3)C3CCOCC3)c2c1]

Step 1: Methyl 3-fluoro-5-(tetramethyl-1,3,2-dioxaborolan-2-yl)pyridine-2-carboxylate The title compound was prepared using methyl 5-bromo-3-fluoropicolinate according to the procedure described for methyl 5-(dimethyl-1H-1,2,3-triazol-5-yl)-13-methoxy-8-[(S)-oxan-4-yl(phenyl)methyl]-3,8,12-triazatricyclo[7.4.0.0², □]trideca-1(9),2,4,6,10,12-hexaene-10-carboxylate, step 1 (Example 135). The material was purified by flash chromatography: (40 g ISCO RediSep Rf, ethyl acetate/hexanes 0% [100 mL], 0-15% [150 mL], 15% [200 mL], 15-50% [400 mL]). The fractions containing product plus impurity were collected and concentrated under reduced pressure. This yellow oil was diluted with 10 mL of cold ether and hexanes was slowly added until a white solid formed. The solid was collected cold and washed with hexanes to give the title compound (1.38 g, 58%). ¹H NMR (400 MHz, CDCl₃) δ 8.82 (t, J=1.4 Hz, 1H), 7.91 (dd, J=10.5, 1.3 Hz, 1H), 4.03 (s, 3H), 1.38 (s, 12H).

Step 2: Methyl 5-(5-bromo-3-nitropyridin-2-yl)-3-fluoropyridine-2-carboxylate

The title compound was prepared using methyl 3-fluoro-5-(tetramethyl-1,3,2-dioxaborolan-2-yl)pyridine-2-carboxylate according to the procedure described for 5-(dimethyl-1H-1,2,3-triazol-5-yl)-13-fluoro-8-[(S)-oxan-4-yl(phenyl)methyl]-3,8,12-triazatricyclo[7.4.0.0²,⁷]trideca-1(13),2(7),3,5,9,11-hexaene, step 1 (Example 3). The material was purified by flash chromatography: (40 g ISCO RediSep Rf, ethyl acetate/DCM 0% [100 mL], 0-15% [750 mL]). The fractions containing product were concentrated under reduced pressure to give the title compound (764 mg, 43%). ¹H NMR (500 MHz, CDCl₃) δ 9.03 (d, J=2.0 Hz, 1H), 8.67 (dd, J=1.7, 1.1 Hz, 1H), 8.52 (d, J=2.0 Hz, 1H), 7.79 (dd, J=10.1, 1.8 Hz, 1H), 4.08 (s, 3H). LCMS: (M+H)⁺ 355.9.

Step 3: Methyl 5-bromo-12-fluoro-3,8,10-triazatricyclo[7.4.0.0²,⁷]trideca-1(9),2,4,6,10,12-hexaene-11-carboxylate and methyl 5-bromo-10-fluoro-3,8,12-triazatricyclo[7.4.0.0²,⁷]trideca-1(9),2,4,6,10,12-hexaene-1-carboxylate A 40 mL pressure vial was charged with methyl 5-(5-bromo-3-nitropyridin-2-yl)-3-fluoropyridine-2-carboxylate (764 mg, 2.15 mmol) and 1,2-bis(diphenylphosphino)ethane (1282 mg, 3.22 mmol). The mixture was suspended in 1,2-dichlorobenzene (5 mL) and placed in a reaction block preheated to 160° C. After 20 min, the mixture was concentrated under high vacuum pressure. The resultant black slurry was diluted with dichloromethane and sonicated for several minutes. A tan solid (212 mg) was collected by filtration as a 1:1 mixture of regioisomeric products (30% combined yield). This material was carried on as a mixture. LCMS: T_R=0.68 min; (ES): m/z (M+H)⁺ 325.9: Waters Acquity SDS; Column Type: ACQUITY UPLC® BEH C18 1.7 μm 2.1×50 mm; Run Time: 2.20 min; 0-100% B; Solvent A: water/0.05% TFA; Solvent B: acetonitrile/0.05% TFA; Flow: 0.8 mL/min; Detection: UV=254 nm.

Step 4: Methyl (S)-3-bromo-6-fluoro-5-(phenyl(tetrahydro-2H-pyran-4-yl)methyl)-5H-pyrrolo[3,2-b:4,5-c']dipyridine-7-carboxylate The title compound was prepared from methyl 5-bromo-12-fluoro-3,8,10-triazatricyclo[7.4.0.0²,⁷]trideca-1(9),2,4,6,10,12-hexaene-11-carboxylate and methyl 5-bromo-10-fluoro-3,8,12-triazatricyclo[7.4.0.0²,⁷]trideca-1(9),2,4,6,10,12-hexaene-1-carboxylate according to the procedure described for 13-methoxy-5-[4-(²H₃)methyl-1-methyl-1H-1,2,3-triazol-5-yl]-8-[(S)-oxan-4-yl(phenyl)methyl]-3,8,12-triazatricyclo[7.4.0.0²,⁷]trideca-1(13),2(7),3,5,9,11-hexaene, step 4 (Example 128). The material was purified by preparative HPLC: Column: Waters XBridge C18 100×30 mm 5 μm, Solvents: A:95:5 water/acetonitrile; B:95:5 acetonitrile/water; Buffer: 10 mM ammonium acetate, % B gradient (time): 0% (1 min), 0-100% (15 min), Flow Rate: 30 mL/min, 7 injections monitored at 254 nm. The fractions containing product were concentrated under reduced pressure. The resulting solids were filtered through a plug of silica gel, eluting the product with acetone to give the title compound (91 mg, 28%). ¹H NMR (400 MHz, CDCl₃) δ 9.42 (d, J=1.3 Hz, 1H), 8.70 (d, J=1.3 Hz, 1H), 8.06 (br. s., 1H), 7.50 (d, J=7.3 Hz, 2H), 7.43-7.37 (m, 2H), 7.36-7.33 (m, 1H), 6.07-5.91 (m, 1H), 4.10 (s, 3H), 4.05 (dd, J=11.9, 2.6 Hz, 1H), 3.89 (dd, J=11.8, 2.8 Hz, 1H), 3.56 (td, J=11.9, 2.0 Hz, 1H), 3.45-3.33 (m, 1H), 3.13-3.00 (m, 1H), 1.99 (d, J=13.6 Hz, 1H), 1.62-1.50 (m, 2H), 0.95 (d, J=12.5 Hz, 1H). LCMS: (M+H)+ 499.9.

Step 5: Methyl 10-fluoro-5-[4-($^{2}H_{3}$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene-11-carboxylate An oven dried 5 mL vial was charged with 4-($^{2}H_{3}$)methyl-1-methyl-5-(tributylstannyl)-1H-1,2,3-triazole (86 mg, 0.221 mmol) and diluted with DMF (1 mL). To that solution was added methyl (S)-3-bromo-6-fluoro-5-(phenyl(tetrahydro-2H-pyran-4-yl)methyl)-5H-pyrrolo[3,2-b:4,5-c']dipyridine-7-carboxylate (91.8 mg, 0.184 mmol), copper(I) iodide (5.3 mg, 0.028 mmol), triethylamine (0.039 mL, 0.276 mmol) and Pd(Ph$_{3}$P)$_{4}$ (16.0 mg, 0.014 mmol). The vial was sealed and degassed by bubbling with argon while sonicating for 2 min. The vial was placed into an oil bath preheated to 80° C. After 40 min, the mixture was cooled to room temperature and filtered through a pad of Celite and purified directly by preparative HPLC (Column: Waters XBridge C18 100×30 mm 5 μm, Solvents: A:95:5 water/acetonitrile; B:95:5 acetonitrile/water; Buffer: 10 mM ammonium acetate, % B gradient (time): 0% (1 min) 0-100% (15 min), 100% (4 min), Flow Rate: 30 mL/min, 2 injections monitored at 254 nm). The fractions containing product were concentrated under reduced pressure. The resulting solids were dissolved in DCM and filtered through a plug of silica gel, eluting the product with acetone to give 70.6 mg (74%). $^{1}$H NMR (400 MHz, CDCl$_{3}$) δ 9.51 (s, 1H), 8.62 (d, J=1.8 Hz, 1H), 7.69 (s, 1H), 7.54-7.46 (m, 2H), 7.44-7.32 (m, 3H), 6.21-6.06 (m, 1H), 4.14 (s, 3H), 4.10-4.03 (m, 1H), 3.94-3.87 (m, 1H), 3.85 (s, 3H), 3.61-3.50 (m, 1H), 3.41-3.29 (m, 1H), 3.14-2.96 (m, 1H), 2.10-2.04 (m, 1H), 1.66-1.50 (m, 2H), 0.99-0.93 (m, 1H). LCMS: (M+H)+ 518.1.

Step 6: 2-{10-Fluoro-5-[4-($^{2}H_{3}$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaen-11-yl}propan-2-ol The title compound was prepared from methyl 10-fluoro-5-[4-($^{2}H_{3}$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(9),2,4,6,10,12-hexaene-11-carboxylate according to the procedure described for 2-[5-(dimethyl-1H-1,2,3-triazol-5-yl)-13-methoxy-8-[(S)-oxan-4-yl(phenyl)methyl]-3,8,12-triazatricyclo[7.4.0.0$^{2,7}$]trideca-1(9),2,4,6,10,12-hexaen-10-yl]propan-2-ol (Example 142). This material was purified by preparative HPLC (Column: Waters XBridge C18 100×30 mm 5 um, Solvents: A:95:5water/acetonitrile; B:95:5 acetonitrile/water; Buffer: 10 mM ammonium acetate, % B gradient (time): 35% (15 min), Flow Rate: 30 mL/min, 2 injections monitored at 254 nm). The fractions containing product were concentrated under reduced pressure. The resulting solids were dissolved in DCM and filtered through a plug of silica gel, eluting the product with a 1:1 DCM/acetone solution to give the title compound (9 mg, 36%). $^{1}$H NMR (400 MHz, CDCl$_{3}$) δ 9.31 (d, J=1.8 Hz, 1H), 8.54 (d, J=1.5 Hz, 1H), 7.60 (d, J=1.5 Hz, 1H), 7.54-7.47 (m, 2H), 7.45-7.38 (m, 2H), 7.38-7.32 (m, 1H), 6.10-6.04 (m, 1H), 4.07 (dd, J=11.7, 2.6 Hz, 1H), 3.91 (dd, J=11.8, 2.8 Hz, 1H), 3.83 (s, 3H), 3.56 (td, J=11.9, 1.8 Hz, 1H), 3.36 (td, J=11.9, 1.9 Hz, 1H), 3.12-2.96 (m, 1H), 2.07 (d, J=13.6 Hz, 1H), 1.77 (dd, J=5.8, 1.3 Hz, 6H), 1.69-1.57 (m, 2H), 1.51 (qd, J=12.3, 4.1 Hz, 1H), 1.00 (d, J=12.8 Hz, 1H). LCMS: (M+H)+ 518.1.

Example 279

13-[(2,2-Difluorocyclopropyl)methoxy]-5-[4-($^{2}H_{3}$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(9),2(7),3,5,10,12-hexaene

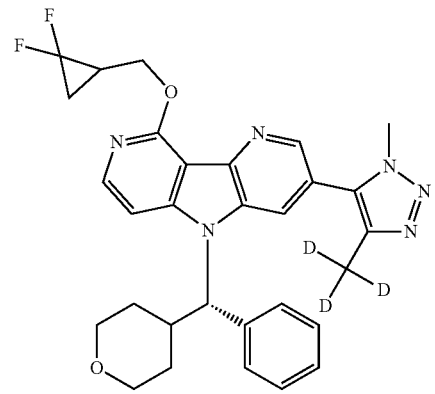 [SMILES: [2H]C([2H])([2H])c1nnn(C)c1-c1cnc2c3c(OCC4CC4(F)F)nccc3n([C@H](c3ccccc3)C3CCOCC3)c2c1]

The title compound was prepared using (2,2-difluorocyclopropyl)methanol according to the procedure described for 13-ethoxy-5-[4-($^{2}H_{3}$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene (Example 129). This material was purified by preparative HPLC; Column: Waters XBridge C18 100×30 mm 5 μm, Solvents: A:95:5 water/acetonitrile; B:95:5 acetonitrile/water; Buffer: 10 mM ammonium acetate, % B gradient (time): 45% (10 min), Flow Rate: 30 mL/min, 3 injections monitored @ 254 nm. The fractions containing product were concentrated under reduced pressure. The resulting solids were filtered through a plug of silica gel, eluting the product with 50% acetone to give the title compound (13.6 mg, 46%). $^{1}$H NMR (400 MHz, CDCl$_{3}$) δ 8.63 (d, J=1.8 Hz, 1H), 8.26 (d, J=6.0 Hz, 1H), 7.60 (s, 1H), 7.46-7.40 (m, 2H), 7.40-7.33 (m, 3H), 7.32-7.28 (m, 1H), 5.47 (d, J=10.5 Hz, 1H), 4.96-4.87 (m, 1H), 4.82-4.71 (m, 1H), 4.06 (dd, J=11.9, 2.6 Hz, 1H), 3.87 (s, 3H), 3.92-3.83 (m, 1H), 3.55 (td, J=11.8, 1.8 Hz, 1H), 3.41-3.31 (m, 1H), 3.15-3.01 (m, 1H), 2.46 (ddd, J=13.4, 11.3, 7.2 Hz, 1H), 2.03 (d, J=13.1 Hz, 1H), 1.66-1.46 (m, 3H), 1.45-1.33 (m, 1H), 1.08 (d, J=13.6 Hz, 1H). LCMS: (M+H)+ 548.2.

Example 280

13-Chloro-10-fluoro-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene

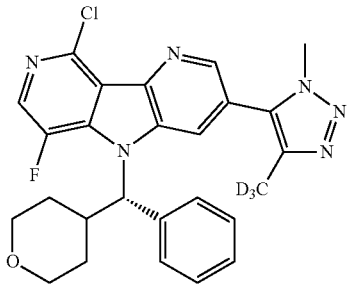 [SMILES: [2H]C([2H])([2H])c1nnn(C)c1-c1cnc2c3c(Cl)ncc(F)c3n([C@H](c3ccccc3)C3CCOCC3)c2c1]

Step 1: 2-Chloro-5-fluoro-3-(tetramethyl-1,3,2-dioxaborolan-2-yl)pyridine

The title compound was prepared using 3-bromo-2-chloro-5-fluoropyridine according to the procedure described for methyl 5-(dimethyl-1H-1,2,3-triazol-5-yl)-13-methoxy-8-[(S)-oxan-4-yl(phenyl)methyl]-3,8,12-triazatricyclo[7.4.0.0$^2$, □]trideca-1(9),2,4,6,10,12-hexaene-10-carboxylate, step 1 (Example 135). This material was purified by flash chromatography: (80 g ISCO RediSep Rf, dichloromethane/hexanes 0% (250 mL), 0-100% (1000 mL), 100% (250 mL) then 0-5% ethyl acetate in DCM (625 mL)). The fractions were collected to give the title compound (1.75 g, 74%). $^1$H NMR (400 MHz, CDCl$_3$) δ 8.28 (d, J=3.3 Hz, 1H), 7.75 (dd, J=7.9, 3.1 Hz, 1H), 1.39 (s, 12H).

Step 2: 3-(5-Bromo-3-nitropyridin-2-yl)-2-chloro-5-fluoropyridine

The title compound was prepared using 2-chloro-5-fluoro-3-(4,4,5,5-tetramethyl-1,3,2-dioxaborolan-2-yl)pyridine according to the procedure described for 5-(dimethyl-1H-1,2,3-triazol-5-yl)-13-fluoro-8-[(S)-oxan-4-yl(phenyl)methyl]-3,8,12-triazatricyclo[7.4.0.0$^{2,7}$]trideca-1(13),2(7),3,5,9,11-hexaene, step 1 (Example 3). This material was purified by flash chromatography: (40 g ISCO RediSep Rf, dichloromethane/hexanes 0% (102 mL), 10-100% (501 mL), 100% (501 mL)). The fractions were collected to give the title compound (717 mg, 35%). $^1$H NMR (400 MHz, CDCl$_3$) δ 9.02 (d, J=2.0 Hz, 1H), 8.67 (d, J=2.0 Hz, 1H), 8.44-8.34 (m, 1H), 7.59 (dd, J=7.5, 3.0 Hz, 1H). LCMS: (M+H)$^+$ 331/333.

Step 3: 5-Bromo-13-chloro-10-fluoro-3,8,12-triazatricyclo[7.4.0.0$^{2,7}$]trideca-1(9),2,4,6,10,12-hexaene The title compound was prepared using 3-(5-bromo-3-nitropyridin-2-yl)-2-chloro-5-fluoropyridine according to the procedure described for 5-(dimethyl-1H-1,2,3-triazol-5-yl)-13-fluoro-8-[(S)-oxan-4-yl(phenyl)methyl]-3,8,12-triazatricyclo[7.4.0.0$^{2,7}$]trideca-1(13),2(7),3,5,9,11-hexaene, step 2 (Example 3). This material was purified by flash chromatography: (40 g ISCO RediSep Rf, acetone/DCM 0% (102 mL), 10% (102 mL), 20% (501 mL), 20-50% (150 mL), 50% (150 mL), 50-70% (150 mL)). All fractions containing product were collected and concentrated under reduced pressure. The resulting solids were triturated with DCM to give a yellow solid. The solid was collected by filtration to give the title compound (98 mg, 15%). $^1$H NMR (400 MHz, DMSO-d$_6$) δ 13.10 (br. s., 1H), 8.78 (d, J=2.0 Hz, 1H), 8.43 (d, J=2.3 Hz, 1H), 8.27 (d, J=2.0 Hz, 1H).

Step 4: 13-Chloro-10-fluoro-5-[4-($^2$H)methyl-1-methyl-1H-1,2,3-triazol-5-yl]-3,8,12-triazatricyclo[7.4.0.0$^{2,7}$]trideca-1(9),2,4,6,10,12-hexaene The title compound was prepared using 4-($^2$H$_3$)methyl-1-methyl-5-(tributylstannyl)-1H-1,2,3-triazole and 5-bromo-13-chloro-10-fluoro-3,8,12-triazatricyclo[7.4.0.0$^{2,7}$]trideca-1(9),2,4,6,10,12-hexaene according to the procedure described for 5-(dimethyl-1H-1,2,3-triazol-5-yl)-13-fluoro-8-[(S)-oxan-4-yl(phenyl)methyl]-3,8,12-triazatricyclo[7.4.0.0$^{2,7}$]trideca-1(13),2(7),3,5,9,11-hexaene, step 3 (Example 3). This material was purified by flash chromatography: (24 g ISCO RediSep Rf, acetone/DCM 0% (102 mL), 0-25% (450 mL) 25% (351 mL)). The fractions were collected, concentrated under reduced pressure and the product was triturated with DCM to give the title compound (45.7 mg, 43%). $^1$H NMR (400 MHz, DMSO-d$_6$) δ 13.17 (br. s., 1H), 8.79 (d, J=1.8 Hz, 1H), 8.45 (d, J=2.5 Hz, 1H), 8.17 (d, J=1.8 Hz, 1H), 4.01 (s, 3H). LCMS: (M+H)$^+$ 320.

Step 5: 13-Chloro-10-fluoro-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene The title compound was prepared using 13-chloro-10-fluoro-5-[4-($^2$H$_3$)methyl-1-methyl-1H-1,2,3-triazol-5-yl]-3,8,12-triazatricyclo[7.4.0.0$^{2,7}$]trideca-1(9),2,4,6,10,12-hexaene according to the procedure described for 5-(dimethyl-1H-1,2,3-triazol-5-yl)-13-fluoro-8-[(S)-oxan-4-yl(phenyl)methyl]-3,8,12-triazatricyclo[7.4.0.0$^{2,7}$]trideca-1(13),2(7),3,5,9,11-hexaene, step 4 (Example 3). This material was purified by flash chromatography: (24 g ISCO RediSep Rf, acetone/DCM 0% (75 mL), 0-15% (150 mL), 15% (150 mL), 15-25% (150 mL), 25% (250 mL)). The fractions were collected to give the title compound (60 mg, 85%). $^1$H NMR (400 MHz, CDCl$_3$) δ 8.71 (d, J=1.8 Hz, 1H), 8.42 (d, J=4.3 Hz, 1H), 7.69 (s, 1H), 7.50-7.45 (m, 2H), 7.43-7.32 (m, 3H), 6.09-5.99 (m, 1H), 4.05 (dd, J=11.4, 2.1 Hz, 1H), 3.90 (dd, J=12.4, 3.1 Hz, 1H), 3.83 (s, 3H), 3.55 (td, J=11.9, 2.0 Hz, 1H), 3.36 (td, J=11.9, 1.9 Hz, 1H), 3.13-3.00 (m, 1H), 2.08 (br. s., 1H), 1.66-1.55 (m, 1H), 1.54-1.42 (m, 1H), 0.98 (d, J=13.1 Hz, 1H). LCMS: (M+H)$^+$ 494.

Examples 281 & 282

2-{8-[(4,4-Difluorocyclohexyl)(phenyl)methyl]-13-methoxy-5-[4-($^2$H$_3$)methyl-1-methyl-1H-1,2,3-triazol-5-yl]-3,8,12-triazatricyclo[7.4.0.0$^{2,7}$]trideca-1(9),2,4,6,10,12-hexaen-10-yl}propan-2-ol

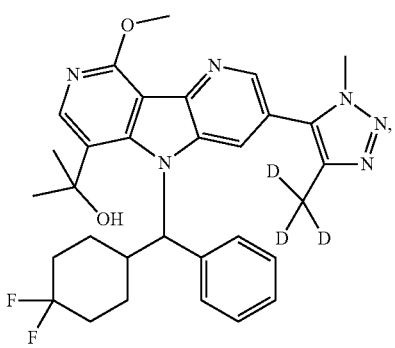

Example 281

Enantiomer 1

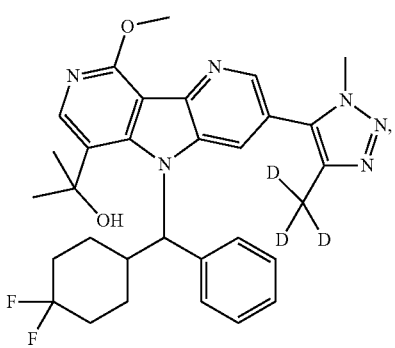

Example 282

Enantiomer 2

Step 1: Methyl 5-bromo-8-[(4,4-difluorocyclohexyl)(phenyl)methyl]-13-methoxy-3,8,12-triazatricyclo[7.4.0.0$^{2,7}$]trideca-1(9),2,4,6,10,12-hexaene-10-carboxylate The title compound was prepared using (4,4-difluorocyclohexyl)(phenyl)methanol and methyl 3-bromo-9-methoxy-5H-pyrrolo[3,2-b:4,5-c']dipyridine-6-carboxylate according to the procedure described for methyl 5-(dimethyl-1H-1,2,3-triazol-5-yl)-13-methoxy-8-[(S)-oxan-4-yl(phenyl)methyl]-3,8,12-triazatricyclo[7.4.0.0$^2$,☐]trideca-1(9),2,4,6,10,12-hexaene-10-carboxylate, step 4 (Example 135). This material was purified on SiO$_2$ (24 g), eluting with hexane (51 mL), 20% EtOAc/hexane (252 mL), 20 to 50% EtOAc/hexane (357 mL, linear gradient). The product containing fractions were collected to give the title compound (215 mg, 66%). $^1$H NMR (400 MHz, CDCl$_3$) δ 8.79 (s, 1H), 8.68 (d, J=0.8 Hz, 1H), 7.77 (d, J=1.8 Hz, 1H), 7.51 (d, J=7.5 Hz, 2H), 7.36 (t, J=7.3 Hz, 2H), 7.32-7.25 (m, 2H), 6.52 (d, J=10.8 Hz, 1H), 4.32 (s, 3H), 4.06-3.94 (m, 3H), 2.79 (q, J=10.7 Hz, 1H), 2.19 (d, J=12.3 Hz, 1H), 1.91-1.77 (m, 1H), 1.70-1.50 (m, 2H), 1.48-1.32 (m, 2H), 0.80 (d, J=12.3 Hz, 1H). LCMS: (M+H)$^+$ 544.10/546.10.

Step 2: Methyl 8-[(4,4-difluorocyclohexyl)(phenyl)methyl]-13-methoxy-5-[4-($^2$H$_3$)methyl-1-methyl-1H-1,2,3-triazol-5-yl]-3,8,12-triazatricyclo[7.4.0.0$^{2,7}$]trideca-1(9),2,4,6,10,12-hexaene-10-carboxylate The title compound was prepared from methyl 5-bromo-8-[(4,4-difluorocyclohexyl)(phenyl)methyl]-13-methoxy-3,8,12-triazatricyclo[7.4.0.0$^{2,7}$]trideca-1(9),2,4,6,10,12-hexaene-10-carboxylate and 4-($^2$H$_3$)methyl-1-methyl-5-(tributylstannyl)-1H-1,2,3-triazole according to the procedure described for methyl 5-(dimethyl-1H-1,2,3-triazol-5-yl)-13-methoxy-8-[(S)-oxan-4-yl(phenyl)methyl]-3,8,12-triazatricyclo[7.4.0.0$^2$, ☐]trideca-1(9),2,4,6,10,12-hexaene-10-carboxylate, step 5 (Example 135). This material was purified on SiO$_2$ (24 g), eluting with hexane (51 mL), 25% EtOAc/hexane (252 mL), DCM (100 mL), 25% acetone/DCM (300 mL), 50% acetone/DCM (150 mL). The product containing fractions gave the title compound (74.8 mg, 34%) which contained impurities but was used as is. $^1$H NMR (400 MHz, CDCl$_3$) δ 8.85 (s, 1H), 8.61 (d, J=1.3 Hz, 1H), 7.53 (d, J=7.0 Hz, 3H), 7.40-7.34 (m, 2H), 7.31 (d, J=7.3 Hz, 1H), 6.67 (d, J=10.0 Hz, 1H), 4.39-4.34 (m, 3H), 4.04 (s, 3H), 3.70 (d, J=2.0 Hz, 3H), 2.84 (br. s., 1H), 2.25 (d, J=13.6 Hz, 1H), 2.03-1.76 (m, 3H), 1.70-1.49 (m, 2H), 1.48-1.34 (m, 1H), 0.81 (d, J=12.3 Hz, 1H). LCMS: (M+H)$^+$ 564.25.

Step 3: 2-{8-[(4,4-Difluorocyclohexyl)(phenyl)methyl]-13-methoxy-5-[4-($^2$H$_3$)methyl-1-methyl-1H-1,2,3-triazol-5-yl]-3,8,12-triazatricyclo[7.4.0.0$^2$,$^7$]trideca-1(9),2,4,6,10,12-hexaen-10-yl}propan-2-ol The title compound was prepared from methyl 8-[(4,4-difluorocyclohexyl)(phenyl)methyl]-13-methoxy-5-[4-($^2$H$_3$)methyl-1-methyl-1H-1,2,3-triazol-5-yl]-3,8,12-triazatricyclo[7.4.0.0$^{2,7}$]trideca-1(9),2,4,6,10,12-hexaene-10-carboxylate according to the procedure described for 2-[5-(dimethyl-1H-1,2,3-triazol-5-yl)-13-methoxy-8-[(S)-oxan-4-yl(phenyl)methyl]-3,8,12-triazatricyclo[7.4.0.0$^2$,$^7$]trideca-1(9),2,4,6,10,12-hexaen-10-yl]propan-2-ol (Example 142). The crude material was purified by preparative HPLC (Waters X-Bridge C18, 30×100 mm S5; A=95% water, 5% acetonitrile, 10 mM ammonium acetate, B=5% water, 95% acetonitrile, 10 mM ammonium acetate; 40% B, 20 min, 30 mL/min, 254 nm detection). The product containing fractions were collected to give 39.6 mg of a white solid. The enantiomeric products were separated by chiral HPLC: Chiralcel OJ-H prep column, 30×250 mm, 5 μm; Mobile phase: 10% MeOH in CO$_2$, 150 bar, Temp: 35° C., Flow rate: 70 mL/min. for 19 min; UV monitored @ 252 nm. Injection: 0.25 mL of ~10 mg/mL in MeOH (40 mg purified by stacked injection). Peak 1 gave enantiomer 1 (17.1 mg, 22%). Peak 2 gave enantiomer 2 (18.8 mg, 25%). Enantiomer 1: (Chiral HPLC T$_R$=10.92 min): $^1$H NMR (400 MHz, CDCl$_3$) δ 8.61 (d, J=1.8 Hz, 1H), 8.37 (s, 1H), 7.40-7.30 (m, 5H), 7.25 (s, 1H), 7.17 (d, J=1.8 Hz, 1H), 4.35 (s, 3H), 3.60 (s, 3H), 2.80-2.65 (m, 1H), 2.46-2.35 (m, 1H), 2.25 (br. s., 2H), 2.04 (s, 3H), 1.96 (s, 1H), 1.84 (s, 4H), 1.45 (br. s., 2H), 0.91-0.78 (m, 1H), 0.61-0.50 (m, 1H). LCMS: (M+H)$^+$ 564.40.

Enantiomer 2 (Chiral HPLC T$_R$=14.05 min)$^1$H NMR (400 MHz, CDCl$_3$) δ 8.61 (d, J=1.8 Hz, 1H), 8.37 (s, 1H), 7.40-7.30 (m, 5H), 7.25 (s, 1H), 7.17 (d, J=1.8 Hz, 1H), 4.35 (s, 3H), 3.60 (s, 3H), 2.80-2.65 (m, 1H), 2.46-2.35 (m, 1H), 2.25 (br. s., 2H), 2.04 (s, 3H), 1.96 (s, 1H), 1.84 (s, 4H), 1.45 (br. s., 2H), 0.91-0.78 (m, 1H), 0.61-0.50 (m, 1H). LCMS: m/z (M+H)$^+$ 564.35.

Example 283

5-(Dimethyl-1H-1,2,3-triazol-5-yl)-11-methoxy-13-methyl-8-[(S)-oxan-4-yl(phenyl)methyl]-3,8,12-triazatricyclo[7.4.0.0²,⁷]trideca-1(9),2(7),3,5,10,12-hexaene

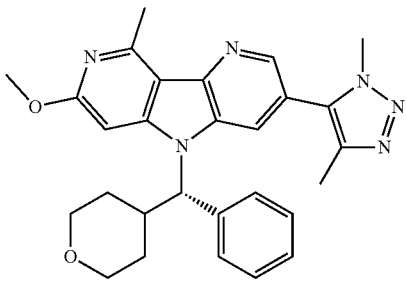 [SMILES: COc1cc2c(c(C)n1)c1ncc(-c3c(C)nnn3C)cc1n2[C@H](c1ccccc1)C1CCOCC1]

Step 1: 5-Bromo-2-(6-methoxy-2-methylpyridin-3-yl)-3-nitropyridine

The title compound was prepared using (6-methoxy-2-methylpyridin-3-yl)boronic acid according to the procedure described for 5-(dimethyl-1H-1,2,3-triazol-5-yl)-13-fluoro-8-[(S)-oxan-4-yl(phenyl)methyl]-3,8,12-triazatricyclo[7.4.0.0²,⁷]trideca-1(13),2(7),3,5,9,11-hexaene, step 1 (Example 3). This material was purified on SiO₂ (40 g), eluting with hexane (95 mL), 0 to 100% DCM/hexane (300 mL, linear gradient), 20% DCM (200 mL), 0 to 20% EtOAc/DCM (300 mL, linear gradient). The product containing fractions were collected to give the title compound (990 mg, 55.7%). ¹H NMR (400 MHz, CDCl₃) δ 8.95 (d, J=0.5 Hz, 1H), 8.48-8.40 (m, 1H), 7.43 (d, J=8.3 Hz, 1H), 6.66 (d, J=8.5 Hz, 1H), 3.97 (d, J=2.8 Hz, 3H), 2.28 (s, 3H). LCMS: (M+H)⁺ 324/326.

Step 2: 5-Bromo-11-methoxy-13-methyl-3,8,12-triazatricyclo[7.4.0.0²,⁷]trideca-1(13),2(7),3,5,9,11-hexaene The title compound was prepared using 5-bromo-2-(6-methoxy-2-methylpyridin-3-yl)-3-nitropyridine according to the procedure described for 5-(dimethyl-1H-1,2,3-triazol-5-yl)-13-fluoro-8-[(S)-oxan-4-yl(phenyl)methyl]-3,8,12-triazatricyclo[7.4.0.0²,⁷]trideca-1(13),2(7),3,5,9,11-hexaene, step 2 (Example 3). The mixture was cooled and concentrated to near dryness, then DCM was added. The title compound (228 mg, 26%) was collected by filtration as an off-white solid. The mother liquor was reconcentrated and this process was repeated. The residual mother liquor was purified on SiO₂ (24 g), eluting with DCM (200 mL), 5% acetone/DCM (200 mL), 10% acetone/DCM (200 mL). The product containing fractions were concentrated to give 363 mg (25.6%) of an off white solid that contained desired product, 1,2-bis(diphenylphosphino)ethane mono- and di-oxides. ¹H NMR (400 MHz, CDCl₃) δ 8.60 (d, J=2.0 Hz, 1H), 8.12-8.01 (m, 1H), 7.77 (d, J=1.8 Hz, 1H), 6.53 (s, 1H), 4.04 (s, 3H), 3.10 (s, 3H). LCMS: (M+H)⁺ 292.0.

Step 3: 5-Bromo-11-methoxy-13-methyl-8-[(S)-oxan-4-yl(phenyl)methyl]-3,8,12-triazatricyclo[7.4.0.0²,⁷]trideca-1(9),2(7),3,5,10,12-hexaene The title compound was prepared using 5-bromo-11-methoxy-13-methyl-3,8,12-triazatricyclo[7.4.0.0²,⁷]trideca-1(13),2(7),3,5,9,11-hexaene according to the procedure described for 5-(dimethyl-1H-1,2,3-triazol-5-yl)-13-fluoro-8-[(S)-oxan-4-yl(phenyl)methyl]-3,8,12-triazatricyclo[7.4.0.0²,⁷]trideca-1(13),2(7),3,5,9,11-hexaene, step 4 (Example 3). This material was purified on SiO₂ (24 g), eluting with hexane (51 mL), 20% EtOAc/hexane (396 mL), 20 to 100% EtOAc/hexane (645 mL, linear gradient). The product containing fractions were collected to give the title compound (180 mg, quant.). ¹H NMR (400 MHz, CDCl₃) δ 8.54 (d, J=1.8 Hz, 1H), 7.82 (d, J=1.8 Hz, 1H), 7.46-7.41 (m, 2H), 7.37-7.28 (m, 3H), 6.67 (s, 1H), 5.20 (d, J=10.8 Hz, 1H), 4.04 (s, 3H), 4.04-4.00 (m, 1H), 3.85 (d, J=8.5 Hz, 1H), 3.51 (td, J=11.8, 1.8 Hz, 1H), 3.37 (td, J=11.9, 1.8 Hz, 1H), 3.08-3.05 (m, 1H), 3.07 (s, 3H), 1.91 (d, J=13.1 Hz, 1H), 1.56-1.50 (m, 1H), 1.39-1.29 (m, J=13.2, 4.4 Hz, 1H), 1.11 (d, J=14.3 Hz, 1H). LCMS: (M+H)⁺ 466/468.

Step 4: 5-(Dimethyl-1H-1,2,3-triazol-5-yl)-11-methoxy-13-methyl-8-[(S)-oxan-4-yl(phenyl)methyl]-3,8,12-triazatricyclo[7.4.0.0²,⁷]trideca-1(9),2(7),3,5,10,12-hexaene The title compound was prepared using 5-bromo-11-methoxy-13-methyl-8-[(S)-oxan-4-yl(phenyl)methyl]-3,8,12-triazatricyclo[7.4.0.0²,⁷]trideca-1(9),2(7),3,5,10,12-hexaene and 1,4-dimethyl-5-(tributylstannyl)-1H-1,2,3-triazole according to the procedure described for 12-chloro-5-(dimethyl-1H-1,2,3-triazol-5-yl)-8-[(S)-(2-fluorophenyl)(oxan-4-yl)methyl]-3,8,11-triazatricyclo[7.4.0.0²,⁷]trideca-1(13),2(7),3,5,9,11-hexaene, step 4 (Example 4) (80° C., 16 h). This material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 50-100% B over 20 min, then a 5-min hold at 100% B; Flow: 20 mL/min. Fractions containing the desired product were combined and dried via centrifugal evaporation. The yield of the product was 25.5 mg (37%). ¹H NMR (500 MHz, DMSO-d₆) δ 8.56 (s, 1H), 7.66 (d, J=8.1 Hz, 2H), 7.38-7.31 (m, 3H), 7.29-7.23 (m, 2H), 5.73 (d, J=11.4 Hz, 1H), 4.02-3.95 (m, 6H), 3.88 (d, J=10.6 Hz, 1H), 3.73 (d, J=8.4 Hz, 1H), 3.46 (t, J=11.4 Hz, 1H), 3.34 (d, J=10.6 Hz, 1H), 3.28-3.23 (m, 1H), 3.02 (s, 3H), 2.29 (br. s., 3H), 1.67 (d, J=11.7 Hz, 1H), 1.53 (d, J=8.8 Hz, 1H), 1.29 (d, J=11.0 Hz, 1H), 1.01 (d, J=13.6 Hz, 1H). LCMS: (M+H)⁺ 483.

Example 284

2-{5-[4-(²H₃)Methyl-1-methyl-1H-1,2,3-triazol-5-yl]-8-[(S)-oxan-4-yl(phenyl)methyl]-3,8,12-triazatricyclo[7.4.0.0²,⁷]trideca-1(9),2(7),3,5,10,12-hexaen-11-yl}propan-2-ol

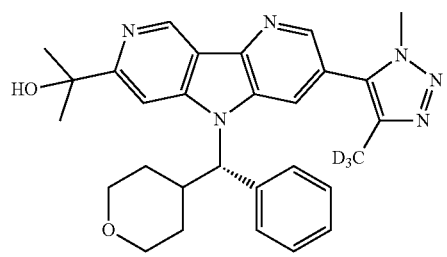 [SMILES: [2H]C([2H])([2H])c1nnn(C)c1-c1cnc2c3cnc(C(C)(C)O)cc3n([C@H](c3ccccc3)C3CCOCC3)c2c1]

Step 1: 2,4-Dichloro-5-(tetramethyl-1,3,2-dioxaborolan-2-yl)pyridine

A round bottom flask was charged with 5-bromo-2,4-dichloropyridine (10.0 g, 44.1 mmol), dioxane (300 mL), 4,4,4',4',5,5,5',5'-octamethyl-2,2'-bi(1,3,2-dioxaborolane) (16.79 g, 66.1 mmol), potassium acetate (12.98 g, 132 mmol) and PdCl$_2$(dppf)$_2$ dichlormethane adduct (1.800 g, 2.20 mmol). The mixture was degassed by bubbling argon through the solution for 2 min. This was heated for 2 h at 95° C. The solvent was evaporated and the crude material was directly used for the subsequent reaction.

Step 2: 5-(5-Bromo-3-nitropyridin-2-yl)-2,4-dichloropyridine

The title compound was prepared using 2,4-dichloro-5-(tetramethyl-1,3,2-dioxaborolan-2-yl)pyridine according to the procedure described for 5-(dimethyl-1H-1,2,3-triazol-5-yl)-13-fluoro-8-[(S)-oxan-4-yl(phenyl)methyl]-3,8,12-triazatricyclo[7.4.0.0$^{2,7}$]trideca-1(13),2(7),3,5,9,11-hexaene, step 1 (Example 3) with the following modification (65° C., 1.5 h). This material was purified using a 330 g silica gel column eluting with 2-50% [5% DCM/acetone]/hexanes to give the title compound (7.44 g, 48.4%). $^1$H NMR (400 MHz, CDCl$_3$) δ 9.05 (d, J=2.0 Hz, 1H), 8.68 (d, J=2.3 Hz, 1H), 8.47 (s, 1H), 7.52 (s, 1H). LCMS: (M+H)$^+$ 349.9.

Step 3: 5-Bromo-2-(4,6-dichloropyridin-3-yl)pyridin-3-amine

A 20 mL scintillation vial was charged with 5-(5-bromo-3-nitropyridin-2-yl)-2,4-dichloropyridine (113 mg, 0.324 mmol), Fe (54.3 mg, 0.971 mmol), CaCl$_2$ (35.9 mg, 0.324 mmol), EtOH (10 mL), and water (0.5 mL). Nitrogen was bubbled through the solution. The vial was sealed and heated to 65° C. After 2 h, the mixture was concentrated to dryness and the crude residue was purified on a 24 g SiO$_2$ column eluting with 0-50% of 10% (2N NH$_3$/MeOH in EtOAc)/DCM to give the title compound (83 mg, 80%). $^1$H NMR (400 MHz, CDCl$_3$) δ 8.44 (s, 1H), 8.21 (d, J=1.8 Hz, 1H), 7.56 (s, 1H), 7.31 (d, J=1.8 Hz, 1H), 3.72 (br. s., 2H). LCMS: (M+H)$^+$ 319.8.

Step 4: 5-Bromo-11-chloro-3,8,12-triazatricyclo[7.4.0.0$^{2,7}$]trideca-1(9),2(7),3,5,10,12-hexaene A 250 mL round bottom flask was charged with 5-bromo-2-(4,6-dichloropyridin-3-yl)pyridin-3-amine (2.00 g, 6.27 mmol) and THF (80 mL). This was stirred and cooled to 0° C. Sodium bis(trimethylsilyl)amide (1M in THF, 21.3 mL, 21.3 mmol) was added dropwise, and the solution stirred at 0° C. for 0.5 h. After 0.5 h, the ice-bath was removed. After 3 h, the reaction was quenched with saturated aqueous NH$_4$Cl. The mixture was diluted with EtOAc, and the organic layer was extracted, dried over MgSO$_4$, filtered and concentrated to afford a dark brown solid. This was subjected to purification on an 80 g silica gel column eluting with 0-10% acetone/DCM to obtain the title compound (761 mg, 43%). $^1$H NMR (400 MHz, DMSO-d$_6$) δ 12.15 (br. s., 1H), 9.18 (d, J=0.8 Hz, 1H), 8.65 (d, J=2.0 Hz, 1H), 8.29 (d, J=2.0 Hz, 1H), 7.68 (d, J=0.8 Hz, 1H). LCMS: (M+H)$^+$ 283.8.

Step 5: 5-Bromo-11-chloro-8-[(S)-oxan-4-yl(phenyl)methyl]-3,8,12-triazatricyclo[7.4.0.0$^{2,7}$]trideca-1(9),2(7),3,5,10,12-hexaene The title compound was prepared using 5-bromo-11-chloro-3,8,12-triazatricyclo[7.4.0.0$^{2,7}$]trideca-1(9),2(7),3,5,10,12-hexaene according to the procedure described for 5-(dimethyl-1H-1,2,3-triazol-5-yl)-13-fluoro-8-[(S)-oxan-4-yl(phenyl)methyl]-3,8,12-triazatricyclo[7.4.0.0$^{2,7}$]trideca-1(13),2(7),3,5,9,11-hexaene, step 4 (Example 3). This material was purified on an 80 g silica gel column eluting with 10-100% EtOAc/Hexanes to give the title compound (1.04 g, 69.9%). $^1$H NMR (400 MHz, DMSO-d$_6$) δ 9.17 (d, J=0.5 Hz, 1H), 8.82-8.76 (m, 1H), 8.67 (d, J=1.8 Hz, 1H), 8.29-8.20 (m, 1H), 7.68 (d, J=7.3 Hz, 2H), 7.41-7.34 (m, 2H), 7.32-7.25 (m, 1H), 5.83 (d, J=11.3 Hz, 1H), 3.89 (dd, J=11.3, 2.0 Hz, 1H), 3.73 (dd, J=11.3, 2.5 Hz, 1H), 3.55-3.48 (m, 1H), 3.46-3.36 (m, 1H), 3.30-3.26 (m, 1H), 1.71-1.63 (m, 1H), 1.61-1.47 (m, J=3.8 Hz, 1H), 1.36-1.24 (m, J=4.8 Hz, 1H), 0.91 (d, J=12.0 Hz, 1H). LCMS: (M+H)$^+$ 457.9.

Step 6: 11-Chloro-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(9),2(7),3,5,10,12-hexaene To a 2 dram pressure rated vial containing 5-bromo-11-chloro-8-[(S)-oxan-4-yl(phenyl)methyl]-3,8,12-triazatricyclo[7.4.0.0$^{2,7}$]trideca-1(9),2(7),3,5,10,12-hexaene (230 mg, 0.403 mmol), Pd(Ph$_3$P)$_4$ (34.9 mg, 0.030 mmol) and copper (I) iodide (11.51 mg, 0.060 mmol) was added 4-($^2$H$_3$)methyl-1-methyl-5-(tributylstannyl)-1H-1,2,3-triazole (157 mg, 0.403 mmol)-rinsed into vial via tared pipet with DMF (2.5 mL). To this solution was added TEA (0.084 mL, 0.604 mmol) and the mixture was degassed by bubbling with argon while sonicating for 1-2 min. The vial was sealed and heated to 80° C. After 16 h the mixture was cooled, filtered through celite using dichloromethane and concentrated under high vacuum to a brown oil. This material was purified on SiO$_2$ (12 g), eluting with acetone/dichlormethane (0-60%). The fractions were collected to give the title compound (110 mg, 57%). $^1$H NMR (400 MHz, chloroform-6) δ 9.38 (s, 1H), 8.54 (s, 1H), 7.71-7.62 (m, 2H), 7.48-7.31 (m, 5H), 5.42 (d, J=10.5 Hz, 1H), 4.10-4.01 (m, 1H), 3.89 (s, 3H), 3.94-3.84 (m, 1H), 3.63-3.48 (m, 1H), 3.38 (td, J=11.9, 1.9 Hz, 1H), 3.09 (d, J=8.8 Hz, 1H), 2.01 (d, J=13.6 Hz, 1H), 1.67-1.50 (m, 1H), 1.49-1.35 (m, 1H), 1.11 (d, J=12.5 Hz, 1H). LCMS: (M+H)+476.

Step 7: 5-[4-($^2$H$_3$)Methyl-1-methyl-1H-1,2,3-triazol-5-yl]-8-[(S)-oxan-4-yl(phenyl)methyl]-11-(prop-1-en-2-yl)-3,8,12-triazatricyclo[7.4.0.0$^{2,7}$]trideca-1(9),2(7),3,5,10,12-hexaene A 40 mL pressure rated vial was charged with 11-chloro-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(9),2(7),3,5,10,12-hexaene (212 mg, 0.445 mmol), Pd$_2$(dba)$_3$ (30.6 mg, 0.033 mmol), cesium carbonate (290 mg, 0.891 mmol) and 2.5 mL of dioxane. To this mixture was added isopropenylboronic acid pinacol ester (150 mg, 0.891 mmol) via tared syringe rinsing in with 1.0 mL of dioxane followed by tricyclohexylphosphine (1M in toluene, 67 µL, 0.067 mmol) via syringe (rinsed syringe into reaction mixture using 1.0 mL of dioxane). The vial was sealed and the reaction mixture was degassed using sonication while bubbling with argon for 2 min. The vial was placed in a reaction block preheated to 115° C. After 18 h, the mixture was cooled and concentrated. This material was purified on SiO$_2$ (24 g), eluting with DCM (51 mL), 20% acetone/DCM (300 mL), 20 to 100% acetone/DCM (456 mL, linear gradient). The product containing fractions gave the title compound (185.2 mg, 86%). $^1$H NMR (400 MHz, CDCl$_3$) δ

9.59 (d, J=0.8 Hz, 1H), 8.52 (d, J=1.8 Hz, 1H), 7.70 (s, 1H), 7.60 (d, J=1.5 Hz, 1H), 7.46-7.41 (m, 2H), 7.40-7.31 (m, 3H), 6.11 (s, 1H), 5.51 (d, J=10.5 Hz, 1H), 5.46 (t, J=1.5 Hz, 1H), 4.05 (d, J=3.0 Hz, 1H), 3.89 (s, 3H), 3.92-3.85 (m, 1H), 3.55 (td, J=11.9, 2.0 Hz, 1H), 3.36 (td, J=11.9, 2.0 Hz, 1H), 3.14-3.02 (m, 1H), 2.38 (s, 3H), 2.04 (d, J=12.8 Hz, 1H), 1.67-1.55 (m, 1H), 1.52-1.35 (m, J=12.4, 12.4, 4.3 Hz, 1H), 1.14 (d, J=12.5 Hz, 1H). LCMS: (M+H)$^+$ 482.3.

Step 8: 2-{5-[4-($^2$H$_3$)Methyl-1-methyl-1H-1,2,3-triazol-5-yl]-8-[(S)-oxan-4-yl(phenyl)methyl]-3,8,12-triazatricyclo[7.4.0.0$^2$,$^7$]trideca-1(9),2(7),3,5,10,12-hexaen-11-yl}propan-2-ol To a 20 mL scintillation vial containing 5-[4-($^2$H$_3$)methyl-1-methyl-1H-1,2,3-triazol-5-yl]-8-[(S)-oxan-4-yl(phenyl)methyl]-11-(prop-1-en-2-yl)-3,8,12-triazatricyclo[7.4.0.0$^2$,$^7$]trideca-1(9),2(7),3,5,10,12-hexaene (185.2 mg, 0.385 mmol) was added 2-propanol (3.2 mL) and DCM (0.6 mL). The flask was purged with oxygen and cooled in an ice water bath. Tris(2,2,6,6-tetramethyl-3,5-heptanedionato)manganese(III) (23.3 mg, 0.038 mmol) was added as a solid in one portion followed by phenylsilane (95 μL, 0.77 mmol) as a neat liquid. After stirring vigorously for 45 min under a balloon atmosphere of oxygen, the mixture was quenched with 20% aqueous sodium thiosulfate and extracted into ethyl acetate. The organics were washed with brine, dried over MgSO$_4$, filtered and concentrated to give 292 mg of a light brown clear residue. This material was purified on SiO$_2$ (12 g), eluting with DCM (51 mL), 30% acetone/DCM (200 mL), 50% acetone/DCM (200 mL), 70% acetone/DCM (300 mL). The product containing fractions gave 156 mg of a white film. This material was combined with 23.5 mg of product previously prepared identically and further purified by preparative HPLC in eight equivalent injections in 1.7 mL of methanol each: Column: XBridge phenyl, 30×100 mm, 5-μm particles; Mobile Phase A: 5:95 methanol: water with 10 mM ammonium bicarbonate; Mobile Phase B: 95:5 methanol: water with 10 mM ammonium bicarbonate; 20% B for 30 seconds, 45-70% B over 20 min; Flow: 50 mL/min; 254 nm detection. The combined fractions were concentrated and the white solid residue was partitioned between ethyl acetate and brine. The organic portion was dried over MgSO$_4$, filtered and concentrated to give the title compound (132 mg, 56%). $^1$H NMR (400 MHz, CDCl$_3$) δ 9.53 (s, 1H), 8.52 (s, 1H), 7.72 (br. s., 1H), 7.62 (br. s., 1H), 7.45-7.40 (m, 2H), 7.40-7.29 (m, 3H), 5.52 (d, J=10.5 Hz, 1H), 4.07 (d, J=8.5 Hz, 1H), 3.92-3.85 (m, 1H), 3.89 (s, 3H), 3.60-3.49 (m, 1H), 3.41-3.31 (m, 1H), 3.16-3.01 (m, 1H), 2.03 (d, J=13.6 Hz, 1H), 1.73 (s, 3H), 1.71 (s, 3H), 1.68-1.56 (m, 1H), 1.47-1.32 (m, 1H), 1.12 (d, J=13.3 Hz, 1H). LCMS: T$_R$=0.794 min; (ES): m/z (M+H)$^+$ 500.30: Waters Acquity SDS; Column Type: ACQUITY UPLC® BEH C18 1.7 μm 2.1×50 mm; Run Time: 2.20 min; 2-98% B; Solvent A: water/0.05% TFA; Solvent B: acetonitrile/0.05% TFA; Temperature: 40° C.; Flow: 0.8 mL/min; Detection: UV=220 nm. HPLC T$_R$=10.01 min; Column: Xbridge C18 3.5 μm, 3.0×150 mm; Mobile Phase A: 10 mM ammonium bicarbonate (pH=9.5)/95% H$_2$O/5% methanol; Mobile Phase B: 10 mM ammonium bicarbonate (pH=9.5)/5% H$_2$O/95% methanol; Gradient 40-80% B over 15 min; Flow: 1 mL/min; Detection: UV at 220 nm and 254 nM). HPLC T$_R$=12.07 min Column: Xbridge Phenyl 3.5 μm, 3.0×150 mm; Mobile Phase A: 10 mM ammonium bicarbonate (pH=9.5)/95% H$_2$O/5% methanol; Mobile Phase B: 10 mM ammonium bicarbonate (pH=9.5)/5% H$_2$O/95% methanol; Gradient 40-80% B over 15 min; Flow: 1 mL/min; Detection: UV at 220 nm and 254 nM).

Example 285

2-[5-(Dimethyl-1H-1,2,3-triazol-5-yl)-8-[(S)-oxan-4-yl(phenyl)methyl]-3,8,12-triazatricyclo[7.4.0.0$^2$,$^7$]trideca-1(9),2(7),3,5,10,12-hexaen-11-yl]propan-2-ol

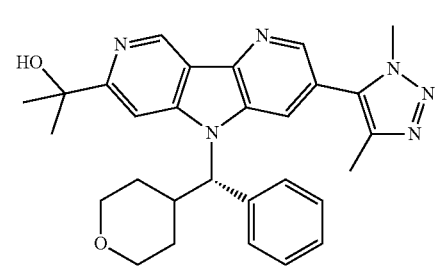 [SMILES: Cc1nnn(C)c1-c1cnc2c3cnc(C(C)(C)O)cc3n([C@H](c3ccccc3)C3CCOCC3)c2c1]

Prepared according to the procedure for 2-{5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^2$,$^7$]trideca-1(9),2(7),3,5,10,12-hexaen-11-yl}propan-2-ol using 4-($^2$H$_3$)methyl-1-methyl-5-(tributylstannyl)-1H-1,2,3-triazole. $^1$H NMR (400 MHz, CDCl$_3$) δ 9.54 (d, J=0.8 Hz, 1H), 8.54 (d, J=1.8 Hz, 1H), 7.71 (s, 1H), 7.60 (s, 1H), 7.46-7.29 (m, 5H), 5.53 (d, J=10.5 Hz, 1H), 4.08 (dd, J=11.4, 2.6 Hz, 1H), 3.89 (s, 3H), 3.94-3.85 (m, 1H), 3.56 (td, J=11.9, 1.8 Hz, 1H), 3.36 (td, J=11.9, 2.0 Hz, 1H), 3.08 (s, 1H), 2.29 (s, 3H), 2.08-2.03 (m, 1H), 1.74 (s, 3H), 1.72 (s, 3H), 1.69-1.56 (m, J=12.6, 12.6, 4.4 Hz, 1H), 1.47-1.34 (m, J=13.3, 4.5 Hz, 1H), 1.10 (d, J=13.3 Hz, 1H). LCMS: T$_R$=0.63 min; (ES): m/z (M+H)$^+$ 497.2: (Waters Acquity—Column: Waters Acquity UPLC BEH C18, 2.1×50 mm, 1.7 μm particles; Mobile Phase A: water/0.05% TFA; Mobile Phase B: acetonitrile/0.05% TFA; Gradient: 2-98% B over 1 min, then a 0.5-min hold at 98% B; Flow: 0.8 mL/min; Detection: UV=220 nm).

Example 286

10-Methanesulfonyl-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^2$,$^7$]trideca-1(13),2(7),3,5,9,11-hexaene

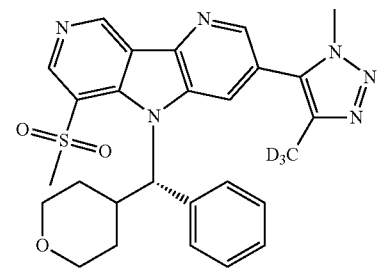 [SMILES: [2H]C([2H])([2H])c1nnn(C)c1-c1cnc2c3cncc(S(C)(=O)=O)c3n([C@H](c3ccccc3)C3CCOCC3)c2c1]

Step 1: 10-Methanesulfonyl-13-methoxy-5-[4-($^2$H$_3$)methyl-1-methyl-1H-1,2,3-triazol-5-yl]-3,8,12-triazatricyclo[7.4.0.0$^2$,$^7$]trideca-1(13),2(7),3,5,9,11-hexaene The title compound was prepared from 3-bromo-9-methoxy-6-(methylsulfonyl)-5H-pyrrolo[3,2-b:4,5-c']

dipyridine compound according to the procedure described for 13-methoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene, step 3 (Example 128). The crude reaction mixture was concentrated and the resulting solids were suspended in DCM and collected by filtration. The filter cake was washed with a small amount of DCM followed by several volumes of hexanes to give 155 mg of desired product. The supernatant was loaded directly onto the column and purified by flash chromatography: (24 g ISCO RediSep Rf, methanol/DCM 0% [75 mL], 0-4% [201 mL], 4% [201 mL], 4-10% [200 mL]). The fractions were collected to give the product as a tan solid. The solid was combined with the previous lot to give the title compound (771 mg, 62% yield). $^1$H NMR (400 MHz, CDCl$_3$) δ 9.93 (s, 1H), 8.75 (d, J=1.8 Hz, 1H), 8.72 (s, 1H), 7.85 (d, J=2.0 Hz, 1H), 4.41 (s, 3H), 4.05 (s, 3H), 3.27 (s, 3H). LCMS: T$_R$=0.60 min; (ES): m/z (M+H)$^+$ 376.0.

Step 2: 10-Methanesulfonyl-13-methoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene The title compound was prepared from 10-methanesulfonyl-13-methoxy-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene (250 mg, 0.666 mmol) according to the procedure described for 13-methoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene, step 4 (Example 128). The crude material was purified by flash chromatography (40 g ISCO RediSep Rf, acetone/DCM 0% [102 mL], 0-35% [400 mL], 35% [400 mL], 35-60% [600 mL]). The fractions were collected to give the title compound (336 mg, 0.611 mmol, 92% yield). $^1$H NMR (500 MHz, CDCl$_3$) δ 9.02 (s, 1H), 8.69 (d, J=1.8 Hz, 1H), 7.49 (d, J=7.9 Hz, 2H), 7.46 (d, J=1.8 Hz, 1H), 7.43-7.37 (m, 2H), 7.37-7.32 (m, 1H), 6.93 (d, J=9.9 Hz, 1H), 4.43 (s, 3H), 4.07 (dd, J=11.7, 2.7 Hz, 1H), 3.79 (dd, J=11.8, 3.1 Hz, 1H), 3.71 (s, 3H), 3.54 (t, J=11.9 Hz, 1H), 3.39 (s, 3H), 3.22 (td, J=11.9, 1.9 Hz, 1H), 3.00-2.90 (m, 1H), 2.19 (d, J=13.4 Hz, 1H), 2.02-1.91 (m, 1H), 1.67-1.58 (m, 1H), 0.37 (d, J=12.8 Hz, 1H); LCMS (M+H)=550.

Step 3: 13-Chloro-10-methanesulfonyl-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene The title compound was prepared using 10-methanesulfonyl-13-methoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene according to the procedure described for 8-[(4,4-difluorocyclohexyl)(phenyl)methyl]-5-(dimethyl-1H-1,2,3-triazol-5-yl)-10-methanesulfonyl-13-(propan-2-yloxy)-3,8,12-triazatricyclo[7.4.0.0$^{2,7}$]trideca-1(13),2(7),3,5,9,11-hexaene, step 3 (Example 118). This material was purified by flash chromatography: (24 g ISCO RediSep Rf, acetone/DCM 0% [75 mL], 0-25% [250 mL], 25% [200 mL], 25-100% [400 mL]). The fractions were collected to give the title compound (282 mg, 83%). $^1$H NMR (400 MHz, CDCl$_3$) δ 9.13 (s, 1H), 8.77 (d, J=1.8 Hz, 1H), 7.54 (d, J=1.8 Hz, 1H), 7.52-7.47 (m, 2H), 7.45-7.33 (m, 3H), 6.97 (d, J=10.0 Hz, 1H), 4.08 (dd, J=11.2, 3.6 Hz, 1H), 3.84-3.77 (m, 1H), 3.72 (s, 3H), 3.55 (td, J=11.8, 1.8 Hz, 1H), 3.48 (s, 3H), 3.28-3.18 (m, J=1.8 Hz, 1H), 3.05-2.89 (m, 1H), 2.23-2.19 (m, 1H), 2.04-1.91 (m, J=4.3 Hz, 1H), 1.70-1.59 (m, J=5.3 Hz, 1H), 0.37 (d, J=13.3 Hz, 1H). LCMS: (M+H)$^+$ 554.0.

Step 4: 10-Methanesulfonyl-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene To a suspension of 13-chloro-10-methanesulfonyl-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene (27 mg, 0.049 mmol) in methanol (0.5 mL) was added one drop of triethylamine and Pd/C 10%—small spatula tip, unmeasured. The reaction was conducted in a two dram vial. The vial was purged with hydrogen and held at a balloon atmosphere of hydrogen at room temperature with vigorous stirring. After 6.5 h, the mixture was filtered through celite using methanol and concentrated to give 31.2 mg of a yellow film. The crude material was purified by preparative HPLC as two roughly equivalent injections in 500 μL and 1 mL of methanol: Waters X-Bridge C18, 30×100 mm S5; A=95% water, 5% acetonitrile, 10 mM ammonium acetate, B=5% water, 95% acetonitrile, 10 mM ammonium acetate; 28% B, 30 min, 30 mL/min, 254 nm detection. The fractions were collected to give the title compound (17.9 mg, 69%). $^1$H NMR (400 MHz, CDCl$_3$) δ 9.86 (s, 1H), 9.35 (s, 1H), 8.62 (d, J=1.8 Hz, 1H), 7.57-7.47 (m, 3H), 7.40 (d, J=7.8 Hz, 3H), 6.98-6.91 (m, 1H), 4.14-4.02 (m, 1H), 3.85-3.76 (m, 1H), 3.73 (s, 3H), 3.60-3.51 (m, 1H), 3.48 (s, 3H), 3.29-3.18 (m, 1H), 3.07-2.88 (m, 1H), 2.25-2.12 (m, 1H), 2.01-1.88 (m, 1H), 1.73-1.60 (m, 1H), 0.46-0.31 (m, 1H). LCMS: (M+H)$^+$ 520.

Example 287

11-Methoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(9),2(7),3,5,10,12-hexaene

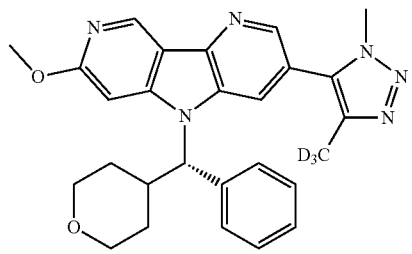 [SMILES: [2H]C([2H])([2H])c1nnn(C)c1-c1cnc2c3cnc(OC)cc3n([C@H](c3ccccc3)C3CCOCC3)c2c1]

A solution of sodium methoxide was prepared as follows: A vial containing 1.0 mL of dry methanol was cooled in an ice water bath and sodium (56.0 mg, 2.44 mmol) was added. The vial was stirred and briefly and intermittantly sonicated until the metal was consumed. In a separate 2 dram vial, 11-chloro-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(9),2(7),3,5,10,12-hexaene (27.3 mg, 0.057 mmol) was dissolved in 0.5 mL of dry methanol and cooled in an ice water bath. To this solution was added 0.5 mL of the sodium methoxide solution. The reaction vial was heated to 60° C. After 19 h an additional 300 μL of methanolic sodium methoxide solution was added and the temperature was increased to 80° C. After heating a further 22 h, the mixture was cooled and filtered through a plug of SiO₂ with DCM-10% MeOH/DCM to give 24 mg of a white solid. The crude material was purified by preparative HPLC as a single injection in 700 μL of methanol: Waters X-Bridge C18, 30×100 mm S5; A=95% water, 5% acetonitrile, 10 mM ammonium acetate, B=5% water, 95% acetonitrile, 10 mM ammonium acetate; 30% B, 30 min, 30 mL/min; 254 nm detection. The product containing fractions were combined, concentrated under high vacuum and passed through a pipet plug of SiO₂ with DCM then 5% MeOH/DCM to give the title compound (16.2 mg, 56.9%). $^1$H NMR (400 MHz, CDCl₃) δ 9.20 (s, 1H), 8.43 (d, J=1.8 Hz, 1H), 7.52 (d, J=1.8 Hz, 1H), 7.46-7.41 (m, 2H), 7.40-7.29 (m, 3H), 6.93 (s, 1H), 5.33 (d, J=11.0 Hz, 1H), 4.11 (s, 3H), 4.04 (dd, J=11.5, 2.8 Hz, 1H), 3.89 (s, 3H), 3.93-3.86 (m, 1H), 3.53 (td, J=11.9, 1.9 Hz, 1H), 3.38 (td, J=11.8, 2.0 Hz, 1H), 3.12-2.99 (m, 1H), 1.96 (d, J=13.6 Hz, 1H), 1.63-1.49 (m, J=13.3, 4.0 Hz, 1H), 1.48-1.35 (m, J=13.1, 4.5 Hz, 1H), 1.20 (d, J=12.5 Hz, 1H). LCMS: (M+H)⁺ 472.

Example 288

11-(Cyclopropylmethoxy)-5-[4-($^2$H₃)methyl-1-methyl-1H-1,2,3-triazol-5-yl]-8-[(S)-oxan-4-yl(phenyl)methyl]-3,8,12-triazatricyclo[7.4.0.0²,⁷]trideca-1(9),2(7),3,5,10,12-hexaene

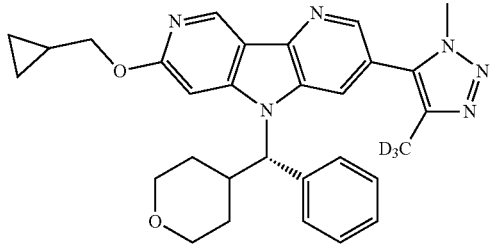 [SMILES: [2H]C([2H])([2H])c1nnn(C)c1-c1cnc2c3cnc(OCC4CC4)cc3n([C@H](c3ccccc3)C3CCOCC3)c2c1]

The title compound was prepared using 11-chloro-5-[4-($^2$H₃)methyl-1-methyl-1H-1,2,3-triazol-5-yl]-8-[(S)-oxan-4-yl(phenyl)methyl]-3,8,12-triazatricyclo[7.4.0.0²,⁷]trideca-1(9),2(7),3,5,10,12-hexaene according to the procedure described for 13-ethoxy-5-[4-($^2$H₃)methyl-1-methyl-1H-1,2,3-triazol-5-yl]-8-[(S)-oxan-4-yl(phenyl)methyl]-3,8,12-triazatricyclo[7.4.0.0²,⁷]trideca-1(13),2(7),3,5,9,11-hexaene, step 2 (Example 129). This material was purified via preparative HPLC as a single injection in 800 μL of methanol with the following conditions: Column: XBridge C18, 30×100 mm, 5-μm particles; Mobile Phase A: 5:95 acetonitrile: water with 10 mM ammonium acetate; Mobile Phase B: 95:5 acetonitrile: water with 10 mM ammonium acetate; 30% B over 30 min; Flow: 30 mL/min; 254 nm detection. The product containing fractions were combined and concentrated. The residue was taken up in dichloromethane and passed through a plug of silica gel eluting with 0-100% DCM/acetone to give the title compound (3.9 mg, 22%) in 96% purity along with an impure fraction (2.0 mg, 79% purity). $^1$H NMR (400 MHz, CDCl₃) δ 9.17 (d, J=0.5 Hz, 1H), 8.42 (d, J=1.8 Hz, 1H), 7.50 (d, J=1.8 Hz, 1H), 7.44 (d, J=7.0 Hz, 2H), 7.40-7.30 (m, 3H), 6.99 (s, 1H), 5.32 (d, J=10.8 Hz, 1H), 4.32 (d, J=6.5 Hz, 2H), 4.05 (d, J=9.0 Hz, 1H), 3.89 (s, 3H), 3.93-3.87 (m, 1H), 3.53 (td, J=11.9, 1.9 Hz, 1H), 3.38 (td, J=11.9, 1.9 Hz, 1H), 3.14-2.98 (m, J=11.1, 11.1, 11.1 Hz, 1H), 1.96 (d, J=13.1 Hz, 1H), 1.56 (td, J=12.5, 4.1 Hz, 1H), 1.47-1.36 (m, 2H), 1.20 (d, J=12.5 Hz, 1H), 0.75-0.66 (m, 2H), 0.49-0.41 (m, 2H). LCMS: (M+H)⁺ 512.

Examples 289 & 290

8-[(4,4-Difluorocyclohexyl)(phenyl)methyl]-5-(dimethyl-1H-1,2,3-triazol-5-yl)-10-methanesulfonyl-3,8,12-triazatricyclo[7.4.0.0²,⁷]trideca-1(13),2(7),3,5,9,11-hexaene

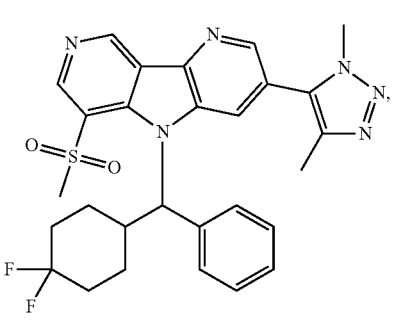

Enantiomer 1

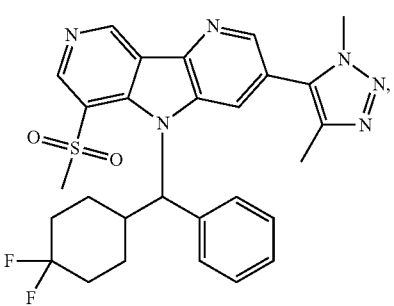

Enantiomer 2

Step 1: 5-(Dimethyl-1H-1,2,3-triazol-5-yl)-10-methanesulfonyl-13-methoxy-3,8,12-triazatricyclo[7.4.0.0²,⁷]trideca-1(13),2(7),3,5,9,11-hexaene The title compound was prepared from 3-bromo-9-methoxy-6-(methylsulfonyl)-5H-pyrrolo[3,2-b:4,5-c']dipyridine and 1,4-dimethyl-5-(tributylstannyl)-1H-1,2,3-triazole compound according to the procedure described for 13-methoxy-5-[4-($^2$H₃)methyl-1-methyl-1H-1,2,3-triazol-5-yl]-8-[(S)-oxan-4-yl(phenyl)methyl]-3,8,12-triazatricyclo[7.4.0.0²,⁷]trideca-1(13),2(7),3,5,9,11-hexaene, step 3 (Example 128). The crude mixture was concentrated and the resulting solids were suspended in DCM and collected by filtration. The filter cake was washed with a small amount of DCM followed by several volumes of hexanes to give 111 mg of desired product. The supernatant was loaded directly onto the column and purified by flash chromatography: (24 g ISCO RediSep Rf, methanol/DCM 0% [75 mL], 0-4% [201 mL], 4% [201 mL], 4-10% [200 mL]). The fractions were collected to give the product as a tan solid. The solid was combined with the previous lot to give the title compound (300 mg, 57%). $^1$H NMR (400 MHz, CDCl₃) δ 9.92 (s, 1H), 8.75 (d, J=2.0 Hz, 1H), 8.72 (s, 1H), 7.84 (d, J=1.8 Hz, 1H), 4.41 (s, 3H), 4.04 (s, 3H), 3.27 (s, 3H). LCMS: (M+H)⁺ 376.0.

Step 2: 8-[(4,4-Difluorocyclohexyl)(phenyl)methyl]-5-(dimethyl-1H-1,2,3-triazol-5-yl)-10-methanesulfonyl-13-methoxy-3,8,12-triazatricyclo[7.4.0.0²,⁷]trideca-1(13),2(7),3,5,9,11-hexaene The title compound was prepared using 5-(dimethyl-1H-1,2,3-triazol-5-yl)-10-methanesulfonyl-13-methoxy-3,8,12-triazatricyclo[7.4.0.0²,⁷]trideca-1(13),2(7),3,5,9,11-hexaene according to the procedure described for 13-methoxy-5-[4-(²H₃)methyl-1-methyl-1H-1,2,3-triazol-5-yl]-8-[(S)-oxan-4-yl(phenyl)methyl]-3,8,12-triazatricyclo[7.4.0.0²,⁷]trideca-1(13),2(7),3,5,9,11-hexaene, step 4 (Example 128). This material was purified by flash chromatography: (40 g ISCO RediSep Rf, acetone/DCM 0% [102 mL], 0-30% [400 mL], 30% [400 mL], 30-100% [400 mL]). The fractions were collected to give an additional 297 mg of desired product. The lots were combined to give the title compound (343 mg, 73%). ¹H NMR (400 MHz, CDCl₃) δ 9.00 (s, 1H), 8.69 (d, J=2.0 Hz, 1H), 7.51-7.46 (m, 2H), 7.44-7.34 (m, J=1.8 Hz, 4H), 6.92 (d, J=10.0 Hz, 1H), 4.43 (s, 3H), 3.68 (s, 3H), 3.42 (s, 3H), 2.85-2.73 (m, 1H), 2.41-2.30 (m, 1H), 2.28-2.18 (m, 1H), 2.14 (s, 3H), 1.99-1.85 (m, 3H), 1.72-1.60 (m, 1H), 1.52-1.42 (m, 1H), 0.59 (d, J=9.8 Hz, 1H). LCMS: (M+H)⁺ 581.0.

Step 3: 13-Chloro-8-[(4,4-difluorocyclohexyl)(phenyl)methyl]-5-(dimethyl-1H-1,2,3-triazol-5-yl)-10-methanesulfonyl-3,8,12-triazatricyclo[7.4.0.0²,⁷]trideca-1(13),2(7),3,5,9,11-hexaene The title compound was prepared using 8-[(4,4-difluorocyclohexyl)(phenyl) methyl]-5-(dimethyl-1H-1,2,3-triazol-5-yl)-10-methanesulfonyl-13-methoxy-3,8,12-triazatricyclo[7.4.0.0²,⁷]trideca-1(13),2(7),3,5,9,11-hexaene according to the procedure described for 8-[(4,4-difluorocyclohexyl)(phenyl)methyl]-5-(dimethyl-1H-1,2,3-triazol-5-yl)-10-methanesulfonyl-13-(propan-2-yloxy)-3,8,12-triazatricyclo[7.4.0.0²,⁷]trideca-1(13),2(7),3,5,9,11-hexaene, step 3 (Example 118). The crude material was triturated with DCM to give a white solid that was collected by filtration as desired product. The supernatant was concentrated and the trituration process was repeated three times to give a combined yield of 197 mg of pure product. The supernatant was purified by flash chromatography: (24 g ISCO RediSep Rf, ethylacetate/DCM 0% [102 mL], 0-30% [252 mL], 30% [300 mL], 30-100% [252 mL]). The combined lots gave the title compound (267 mg, 77%). ¹H NMR (400 MHz, CDCl₃) δ 9.10 (s, 1H), 8.77 (d, J=1.8 Hz, 1H), 7.52-7.35 (m, 7H), 6.96 (d, J=10.3 Hz, 1H), 3.70 (s, 3H), 3.50 (s, 3H), 2.86-2.70 (m, 1H), 2.42-2.32 (m, 1H), 2.29-2.20 (m, 1H), 2.15 (s, 3H), 2.03-1.89 (m, 4H), 1.72-1.61 (m, 1H). LCMS: (M+H)⁺ 585.0.

Step 4: 8-[(4,4-Difluorocyclohexyl)(phenyl)methyl]-5-(dimethyl-1H-1,2,3-triazol-5-yl)-10-methanesulfonyl-3,8,12-triazatricyclo[7.4.0.0²,⁷]trideca-1(13),2(7),3,5,9,11-hexaene To a 2 dram vial containing a suspension of 13-chloro-8-[(4,4-difluorocyclohexyl)(phenyl)methyl]-5-(dimethyl-1H-1,2,3-triazol-5-yl)-10-methanesulfonyl-3,8,12-triazatricyclo[7.4.0.0²,⁷]trideca-1(13),2(7),3,5,9,11-hexaene (21.5 mg, 0.037 mmol) in methanol (0.7 mL) was added one drop of triethylamine and Pd—C 10% (7.8 mg, 7.35 µmol). The vial was flushed with hydrogen gas and stirred under a balloon atmosphere of the same at room temperature. After 4 h, the mixture was filtered through a celite plug rinsing with 1:1 DCM/methanol to yield 24.6 mg of a yellow solid. This solid was triturated with DCM to give a racemic mixture of the title compounds (12.2 mg, 60%), as an off-white solid. The enantiomers were separated by chiral preparative HPLC: Chiralcel OJ-H prep column, 30×250 mm, 5 µm; Mobile phase: 30% MeOH in CO₂, 150 bar, 35° C.; Flow rate: 70 mL/min. for 14 min; UV monitored @ 220 nm; Injection: 0.35 mL of ~6 mg/mL in 1:1 MeOH:CHCl₃ (12 mg purified by stacked injection). Chiral SFC peak 1 ($T_R$=4.74 min); ¹H NMR (400 MHz, CDCl₃) δ 9.86 (s, 1H), 9.32 (s, 1H), 8.62 (d, J=1.8 Hz, 1H), 7.53-7.48 (m, 2H), 7.47 (d, J=1.5 Hz, 1H), 7.44-7.34 (m, 3H), 6.94 (d, J=10.0 Hz, 1H), 3.70 (s, 3H), 3.51 (s, 3H), 2.88-2.75 (m, 1H), 2.34 (br. s., 1H), 2.28-2.20 (m, 1H), 2.16 (s, 3H), 1.95 (d, J=2.8 Hz, 3H), 1.67 (d, J=12.0 Hz, 2H), 0.67-0.56 (m, 1H). LCMS: $T_R$=1.079 min; (ES): m/z (M+H)⁺ 551. Chiral SFC peak 2 ($T_R$=11.24 min); ¹H NMR (400 MHz, CDCl₃) δ 9.86 (s, 1H), 9.32 (s, 1H), 8.62 (d, J=1.8 Hz, 1H), 7.53-7.49 (m, 2H), 7.47 (d, J=1.8 Hz, 1H), 7.44-7.33 (m, 3H), 6.94 (d, J=10.0 Hz, 1H), 3.70 (s, 3H), 3.51 (s, 3H), 2.88-2.75 (m, 1H), 2.39-2.31 (m, 1H), 2.29-2.20 (m, 1H), 2.16 (s, 3H), 2.02-1.91 (m, 1H), 1.70-1.70 (m, 1H), 1.77-1.66 (m, J=15.1, 3.3 Hz, 2H), 0.68-0.57 (m, 1H). LCMS: (M+H)⁺ 551.

Example 291

2-{5-[4-(²H₃)Methyl-1-methyl-1H-1,2,3-triazol-5-yl]-8-[(S)-oxan-4-yl(phenyl)methyl]-3,8,12-triazatricyclo[7.4.0.0²,⁷]trideca-1(9),2,4,6,10,12-hexaen-10-yl}propan-2-ol

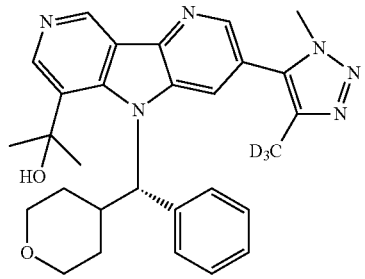 [SMILES: [2H]C([2H])([2H])c1nnn(C)c1-c1cnc2c3cncc(C(C)(C)O)c3n([C@H](c3ccccc3)C3CCOCC3)c2c1]

Step 1: 13-Chloro-5-[4-(²H₃)methyl-1-methyl-1H-1,2,3-triazol-5-yl]-8-[(S)-oxan-4-yl(phenyl)methyl]-10-(prop-1-en-2-yl)-3,8,12-triazatricyclo[7.4.0.0²,⁷]trideca-1(9),2,4,6,10,12-hexaene The title compound was prepared using 2-{13-methoxy-5-[4-(²H₃)methyl-1-methyl-1H-1,2,3-triazol-5-yl]-8-[(S)-oxan-4-yl(phenyl)methyl]-3,8,12-triazatricyclo[7.4.0.0²,⁷]trideca-1(9),2,4,6,10,12-hexaen-10-yl}propan-2-ol according to the procedure described for 8-[(4,4-difluorocyclohexyl)(phenyl)methyl]-5-(dimethyl-1H-1,2,3-triazol-5-yl)-10-methanesulfonyl-13-(propan-2-yloxy)-3,8,12-triazatricyclo[7.4.0.0²,⁷]trideca-1(13),2(7),3,5,9,11-hexaene, step 3 (Example 118). The mixture was worked up in the same way to give the title compound (13.4 mg, 61%). LCMS: $T_R$=1.182 min; (ES): m/z (M+H)⁺ 516.25: Waters Acquity SDS; Column Type: ACQUITY UPLC® BEH C18 1.7 μm 2.1×50 mm; Run Time: 2.20 min; 2-98% B; Solvent A: water/0.05% TFA; Solvent B: acetonitrile/0.05% TFA; Temperature: 40° C.; Flow: 0.8 mL/min; Detection: UV=220 nm.

Step 2: 2-{13-Chloro-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(9),2,4,6,10,12-hexaen-10-yl}propan-2-ol The title compound was prepared using 13-chloro-5-[4-($^2$H$_3$)methyl-1-methyl-1H-1,2,3-triazol-5-yl]-8-[(S)-oxan-4-yl(phenyl)methyl]-10-(prop-1-en-2-yl)-3,8,12-triazatricyclo[7.4.0.0$^{2,7}$]trideca-1(9),2,4,6,10,12-hexaene according to the procedure described for 5-[4-($^2$H$_3$)methyl-1-methyl-1H-1,2,3-triazol-5-yl]-8-[(S)-oxan-4-yl(phenyl)methyl]-11-(prop-1-en-2-yl)-3,8,12-triazatricyclo[7.4.0.0$^{2,7}$]trideca-1(9),2(7),3,5,10,12-hexaene. LCMS: $T_R$=1.027 min; (ES): m/z (M+H)⁺ 534.25: Waters Acquity SDS; Column Type: Acquity UPLC® BEH C18 1.7 μm 2.1×50 mm; Run Time: 2.20 min; 2-98% B; Solvent A: water/0.05% TFA; Solvent B: acetonitrile/0.05% TFA; Temperature: 40° C.; Flow: 0.8 mL/min; Detection: UV=220 nm.

Step 3: 2-{5-[4-($^2$H$_3$)Methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(9),2,4,6,10,12-hexaen-10-yl}propan-2-ol To a 2 dram vial containing 2-{13-chloro-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(9),2,4,6,10,12-hexaen-10-yl}propan-2-ol (13.4 mg, 0.025 mmol) in methanol (1.0 mL) was added Pd/C 10% (5.3 mg, 5.00 μmol) and triethylamine (2.5 mg, 0.025 mmol). The vial was purged with hydrogen and stirred vigorously under a balloon atmosphere of the same. After 4 h, the mixture was filtered through celite and concentrated. The crude material was purified via preparative HPLC (Column: XBridge C18, 30×100 mm, 5-μm particles; Mobile Phase A: 5:95 acetonitrile: water with 10 mM ammonium acetate; Mobile Phase B: 95:5 acetonitrile: water with 10 mM ammonium acetate; 20 to 70% B over 15 min; Flow: 30 mL/min; 254 nm detection). The fractions containing product were concentrated, dissolved in DCM, passed through a plug of silica gel with 5-10% methanol/DCM and concentrated to give the title compound (4.1 mg, 32%). ¹H NMR (400 MHz, CDCl₃) δ 9.64 (s, 1H), 8.78 (s, 1H), 8.51 (d, J=1.8 Hz, 1H), 7.44-7.28 (m, 6H), 7.25 (d, J=1.8 Hz, 1H), 4.05 (dd, J=11.4, 2.9 Hz, 1H), 3.71 (dd, J=11.7, 3.4 Hz, 1H), 3.65 (s, 3H), 3.60-3.52 (m, J=1.8 Hz, 1H), 3.20 (td, J=11.9, 1.8 Hz, 1H), 2.99-2.85 (m, 1H), 2.26 (d, J=13.3 Hz, 1H), 2.08 (s, 3H), 2.03 (s, 1H), 1.88 (s, 3H), 1.49 (qd, J=12.7, 4.8 Hz, 1H), 0.34 (d, J=13.1 Hz, 1H). LCMS: (M+H)⁺ 500.

Example 292

2-{13-Fluoro-5-[4-($^2$H$_3$)methyl-1-methyl-1H-1,2,3-triazol-5-yl]-8-[(S)-oxan-4-yl(phenyl)methyl]-3,8,11-triazatricyclo[7.4.0.0$^{2,7}$]trideca-1(13),2(7),3,5,9,11-hexaen-12-yl}propan-2-ol

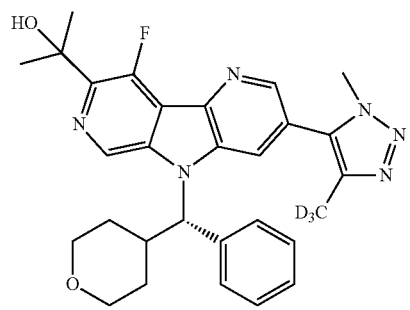 [SMILES: [2H]C([2H])([2H])c1nnn(C)c1-c1cnc2c3c(F)c(C(C)(C)O)ncc3n([C@H](c3ccccc3)C3CCOCC3)c2c1]

Step 1: 5-Bromo-2-(2-chloro-3-fluoropyridin-4-yl)-3-nitropyridine

The title compound was prepared from (2-chloro-3-fluoropyridin-4-yl)boronic acid according to the procedure described for 5-(dimethyl-1H-1,2,3-triazol-5-yl)-13-fluoro-8-[(S)-oxan-4-yl(phenyl)methyl]-3,8,12-triazatricyclo[7.4.0.0$^{2,7}$]trideca-1(13),2(7),3,5,9,11-hexaene, step 1 (Example 3). This material was purified on SiO₂ (120 g), eluting with hexane (100 mL), 30% DCM/hexane (750 mL), 30 to 100% DCM/hexane (1500 mL, linear gradient), DCM (700 mL). The product containing fractions were collected to give the title compound (1.22 g, 31%). ¹H NMR (400 MHz, CDCl₃) δ 9.07-9.01 (m, 1H), 8.65-8.60 (m, 1H), 8.41 (dd, J=5.0, 1.3 Hz, 1H), 7.52 (t, J=4.8 Hz, 1H). LCMS: (M+H)⁺ 333.

Step 2: 5-Bromo-12-chloro-13-fluoro-3,8,11-triazatricyclo[7.4.0.0$^{2,7}$]trideca-1(13),2(7),3,5,9,11-hexaene To a 40 mL pressure rated vial containing 5-bromo-2-(2-chloro-3-fluoropyridin-4-yl)-3-nitropyridine (1.22 g, 3.67 mmol) and 1,2-dichlorobenzene (15 mL) was added 1,2-bis(diphenylphosphino)ethane (3.65 g, 9.17 mmol). The vial was sealed and heated to 165° C. After 15 min the mixture was cooled and concentrated under high vacuum to give a dark residue. The crude material was purified on SiO₂ (12 g), eluting with hexane (51 mL), 20% EtOAc/hexane (252 mL), 20 to 50% EtOAc/hexane (357 mL, linear gradient). The product containing fractions were collected to give the title compound (131 mg, 12%). ¹H NMR (400 MHz, DMSO-d₆) δ 12.41 (br. s., 1H), 8.72 (d, J=2.0 Hz, 1H), 8.72 (d, J=1.3 Hz, 1H), 8.43 (d, J=2.3 Hz, 1H).

Step 3: 5-Bromo-12-chloro-13-fluoro-8-[(S)-oxan-4-yl(phenyl)methyl]-3,8,11-triazatricyclo[7.4.0.0$^{2,7}$]trideca-1(13),2(7),3,5,9,11-hexaene The title compound was prepared using 5-bromo-12-chloro-13-fluoro-3,8,11-triazatricyclo[7.4.0.0$^{2,7}$]trideca-1

(13),2(7),3,5,9,11-hexaene according to the procedure described for 13-methoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^2$,$^7$]trideca-1(13),2(7),3,5,9,11-hexaene, step 4 (Example 128). This material was purified on SiO$_2$ (24 g), eluting with hexane (51 mL), 0 to 100% EtOAc/hexane (825 mL, linear gradient). The product containing fractions were collected to give 243 mg of the title compound a yellow film. $^1$H NMR was consistent with desired plus impurities. This material was carried on as is. LCMS: T$_R$=1.10 min; (ES): m/z (M+H)$^+$ 475.6: (Waters Acquity—Column: Waters Acquity UPLC BEH C18, 2.1× 50 mm, 1.7 μm particles; Mobile Phase A: water/0.05% TFA; Mobile Phase B: acetonitrile/0.05% TFA; Gradient: 2-98% B over 1 min, then a 0.5-min hold at 98% B; Flow: 0.8 mL/min; Detection: UV=220 nm).

Step 4: 12-Chloro-13-fluoro-5-[4-($^2$H$_3$)methyl-1-methyl-1H-1,2,3-triazol-5-yl]-8-[(S)-oxan-4-yl(phenyl)methyl]-3,8,11-triazatricyclo[7.4.0.0$^2$,$^7$]trideca-1(13),2(7),3,5,9,11-hexaene The title compound was prepared using 5-bromo-12-chloro-13-fluoro-8-[(S)-oxan-4-yl(phenyl)methyl]-3,8,11-triazatricyclo[7.4.0.0$^2$,$^7$]trideca-1(13),2(7),3,5,9,11-hexaene and 4-($^2$H$_3$)methyl-1-methyl-5-(tributylstannyl)-1H-1,2,3-triazole according to the procedure described for 11-chloro-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^2$,$^7$]trideca-1(9),2(7),3,5,10,12-hexaene. This material was purified on SiO$_2$ (12 g), eluting with DCM (37 mL), 15% EtOAc/DCM (200 mL), 15 to 100% EtOAc/DCM (400 mL, linear gradient), EtOAc (100 mL). The product containing fractions were collected to give the title compound (55 mg, 42%). $^1$H NMR (400 MHz, CDCl$_3$) δ 8.82 (s, 1H), 8.67 (s, 1H), 7.81 (br. s., 1H), 7.48-7.33 (m, 5H), 5.54 (d, J=10.5 Hz, 1H), 4.09-4.02 (m, 1H), 3.94 (s, 3H), 3.90 (dd, J=12.0, 3.0 Hz, 1H), 3.55 (td, J=11.9, 1.8 Hz, 1H), 3.38 (td, J=11.9, 2.0 Hz, 1H), 3.12 (d, J=10.8 Hz, 1H), 1.99 (d, J=13.3 Hz, 1H), 1.66-1.52 (m, 1H), 1.43 (qd, J=12.3, 4.6 Hz, 1H), 1.15 (d, J=12.5 Hz, 1H). LCMS: (M+H)$^+$ 494.

Step 5: 1-{13-Fluoro-5-[4-($^2$H$_3$)methyl-1-methyl-1H-1,2,3-triazol-5-yl]-8-[(S)-oxan-4-yl(phenyl)methyl]-3,8,11-triazatricyclo[7.4.0.0$^2$,$^7$]trideca-1(13),2(7),3,5,9,11-hexaen-12-yl}ethan-1-one The title compound was prepared using 12-chloro-13-fluoro-5-[4-($^2$H$_3$)methyl-1-methyl-1H-1,2,3-triazol-5-yl]-8-[(S)-oxan-4-yl(phenyl)methyl]-3,8,11-triazatricyclo[7.4.0.0$^2$,$^7$]trideca-1(13),2(7),3,5,9,11-hexaene according to the procedure described for 5-(dimethyl-1H-1,2,3-triazol-5-yl)-11-(1-ethoxyethenyl)-8-[(S)-oxan-4-yl(phenyl)methyl]-3,8,10-triazatricyclo[7.4.0.0$^2$,$^7$]trideca-1(9),2(7),3,5,10,12-hexaene (Example 170). This material was purified on SiO$_2$ (4 g), eluting with DCM (60 mL), 10% acetone/DCM (100 mL), 20% acetone/DCM (50 mL), 30% acetone/DCM (50 mL), 50% acetone/DCM (50 mL). Fractions containing product were concentrated to give 24.9 mg (44.6%). $^1$H NMR (400 MHz, CDCl$_3$) δ 9.10 (d, J=1.8 Hz, 1H), 8.71 (d, J=1.8 Hz, 1H), 7.85 (d, J=1.8 Hz, 1H), 7.53-7.44 (m, 2H), 7.43-7.31 (m, 3H), 5.62 (d, J=10.5 Hz, 1H), 4.07 (dd, J=11.7, 2.9 Hz, 1H), 3.96-3.93 (m, 3H), 3.93-3.86 (m, 1H), 3.55 (td, J=11.9, 1.9 Hz, 1H), 3.39 (td, J=11.9, 2.0 Hz, 1H), 3.22-3.08 (m, 1H), 2.83 (s, 3H), 2.01 (d, J=13.1 Hz, 1H), 1.68-1.54 (m, 1H), 1.44 (qd, J=12.3, 4.3 Hz, 1H), 1.14 (d, J=12.3 Hz, 1H). LCMS: (M+H)$^+$ 502.

Step 6: 2-{13-Fluoro-5-[4-($^2$H$_3$)methyl-1-methyl-1H-1,2,3-triazol-5-yl]-8-[(S)-oxan-4-yl(phenyl)methyl]-3,8,11-triazatricyclo[7.4.0.0$^2$,$^7$]trideca-1(13),2(7),3,5,9,11-hexaen-12-yl}propan-2-ol The title compound was prepared using 1-{13-fluoro-5-[4-($^2$H$_3$)methyl-1-methyl-1H-1,2,3-triazol-5-yl]-8-[(S)-oxan-4-yl(phenyl)methyl]-3,8,11-triazatricyclo[7.4.0.0$^2$,$^7$]trideca-1(13),2(7),3,5,9,11-hexaen-12-yl}ethan-1-one according to the procedure described for 2-[5-(dimethyl-1H-1,2,3-triazol-5-yl)-13-methoxy-8-[(S)-oxan-4-yl(phenyl)methyl]-3,8,12-triazatricyclo[7.4.0.0$^2$,$^7$]trideca-1(9),2,4,6,10,12-hexaen-10-yl]propan-2-ol, (Example 142). This material was purified via preparative HPLC as three injections in 0.5 mL of methanol each with the following conditions: Column: XBridge C18, 30×100 mm, 5-μm particles; Mobile Phase A: 5:95 acetonitrile: water with 10 mM ammonium acetate; Mobile Phase B: 95:5 acetonitrile: water with 10 mM ammonium acetate; 29% B over 30 min, 100% B for 5 min; Flow: 30 mL/min; 254 nm detection. The product containing fractions were combined and concentrated to dryness under high vacuum. The resultant white residue was passed through a plug of silica gel using DCM then 10-50% acetone/DCM to give the title compound (9.4 mg, 36%). $^1$H NMR (400 MHz, CDCl$_3$) δ 8.95 (d, J=1.8 Hz, 1H), 8.65 (d, J=1.8 Hz, 1H), 7.77 (d, J=1.8 Hz, 1H), 7.49-7.43 (m, 3H), 7.42-7.32 (m, 3H), 7.21 (dd, J=6.0, 3.5 Hz, 1H), 5.58 (s, 1H), 5.53 (d, J=10.5 Hz, 1H), 4.07 (dd, J=11.5, 2.8 Hz, 1H), 3.95 (s, 3H), 3.91 (dd, J=12.2, 3.1 Hz, 1H), 3.55 (td, J=11.9, 1.9 Hz, 1H), 3.40 (td, J=11.9, 2.0 Hz, 1H), 3.20-3.06 (m, J=11.0 Hz, 1H), 1.99 (d, J=13.1 Hz, 1H), 1.74 (s, 6H), 1.66-1.54 (m, 1H), 1.51-1.38 (m, J=13.1, 4.3 Hz, 1H), 1.21 (d, J=12.5 Hz, 1H). LCMS: T$_R$=0.915 min; (ES): m/z (M+H)$^+$ 518: (Waters Acquity SDS; Column Type: ACQUITY UPLC® BEH C18 1.7 μm 2.1×50 mm; Run Time: 2.20 min; 0-100% B; Solvent A: 100% water/0.05% TFA; Solvent B: 100% ACN w/0.05% TFA; Detection: UV=220 nm).

Examples 293 & 294

2-{11-Chloro-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^2$,$^7$]trideca-1(13),2(7),3,5,9,11-hexaen-13-yl}propan-2-ol and 2-{13-chloro-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^2$,$^7$]trideca-1(13),2(7),3,5,9,11-hexaen-11-yl}propan-2-ol Example 293

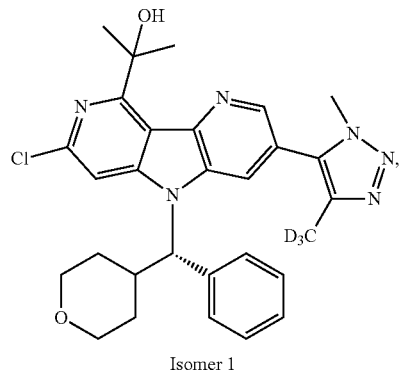

Isomer 1

Example 294

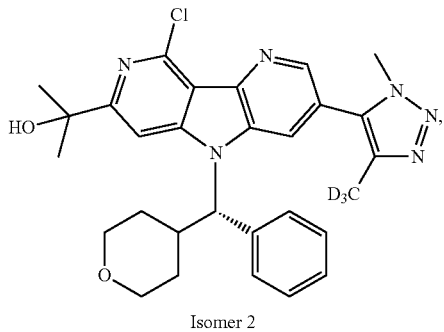

Isomer 2

Step 1: 5-Bromo-2-(2,6-dichloropyridin-3-yl)-3-nitropyridine

The title compound was prepared using (2,6-dichloropyridin-3-yl)boronic acid according to the procedure described for 5-(dimethyl-1H-1,2,3-triazol-5-yl)-13-fluoro-8-[(S)-oxan-4-yl(phenyl)methyl]-3,8,12-triazatricyclo[7.4.0.0$^{2,7}$]trideca-1(13),2(7),3,5,9,11-hexaene, step 1 (Example 3). This material was purified on SiO$_2$ (40 g), eluting with hexane (51 mL), 10% EtOAc/hexane (1000 mL), 10 to 100% EtOAc/hexane (850 mL, linear gradient). The product containing fractions were collected to give the title compound (891 mg, 56%). $^1$H NMR (400 MHz, CDCl$_3$) δ 9.01 (d, J=2.0 Hz, 1H), 8.66 (d, J=2.0 Hz, 1H), 7.87-7.72 (m, 1H), 7.47 (d, J=8.0 Hz, 1H). LCMS: (M+H)$^+$ 349.

Step 2: 5-Bromo-11,13-dichloro-3,8,12-triazatricyclo[7.4.0.0$^{2,7}$]trideca-1(13),2(7),3,5,9,11-hexaene The title compound was prepared using 5-bromo-2-(2,6-dichloropyridin-3-yl)-3-nitropyridine according to the procedure described for 5-(dimethyl-1H-1,2,3-triazol-5-yl)-13-fluoro-8-[(S)-oxan-4-yl(phenyl)methyl]-3,8,12-triazatricyclo[7.4.0.0$^{2,7}$]trideca-1(13),2(7),3,5,9,11-hexaene, step 2 (Example 3). $^1$H NMR (400 MHz, DMSO-d$_6$) δ 12.55-12.50 (m, 1H), 8.74 (d, J=2.0 Hz, 1H), 8.34 (d, J=2.0 Hz, 1H), 7.73 (s, 1H). LCMS: (M+H)$^+$ 317.8.

Step 3: 5-Bromo-11,13-dichloro-8-[(S)-oxan-4-yl(phenyl)methyl]-3,8,12-triazatricyclo[7.4.0.0$^{2,7}$]trideca-1(13),2(7),3,5,9,11-hexaene The title compound was prepared using 5-bromo-11,13-dichloro-3,8,12-triazatricyclo[7.4.0.0$^{2,7}$]trideca-1(13),2(7),3,5,9,11-hexaene according to the procedure described for 13-methoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene, step 4 (Example 128). This material was purified on SiO$_2$ (24 g), eluting with hexane (100 mL), 20% EtOAc/hexane (600 mL), 20 to 100% EtOAc/hexane (650 mL, linear gradient). LCMS: T$_R$=1.565 min; (ES): m/z (M+H)$^+$ 492.05: Waters Acquity SDS; Column Type: ACQUITY UPLC® BEH C18 1.7 μm 2.1×50 mm; Run Time: 2.20 min; 2-98% B; Solvent A: water/0.05% TFA; Solvent B: acetonitrile/0.05% TFA; Temperature: 40° C.; Flow: 0.8 mL/min; Detection: UV=220 nm.

Step 4: 11,13-Dichloro-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene The title compound was prepared from 5-bromo-11,13-dichloro-8-[(S)-oxan-4-yl(phenyl)methyl]-3,8,12-triazatricyclo[7.4.0.0$^{2,7}$]trideca-1(13),2(7),3,5,9,11-hexaene and 4-($^2$H$_3$)methyl-1-methyl-5-(tributylstannyl)-1H-1,2,3-triazole according to the procedure described for methyl 5-(dimethyl-1H-1,2,3-triazol-5-yl)-13-methoxy-8-[(S)-oxan-4-yl(phenyl)methyl]-3,8,12-triazatricyclo[7.4.0.0$^2$, □]trideca-1(9),2,4,6,10,12-hexaene-10-carboxylate, step 5 (Example 135). This material was purified on SiO$_2$ (12 g), eluting with DCM (37 mL), 15% EtOAc/DCM (252 mL), 15 to 100% EtOAc/DCM (400 mL, linear gradient), EtOAc (100 mL). The product containing fractions were collected to give the title compound (51.6 mg, 40%). $^1$H NMR (500 MHz, CDCl$_3$) δ 8.70 (d, J=1.7 Hz, 1H), 7.75-7.66 (m, 1H), 7.63-7.61 (m, 1H), 7.50-7.32 (m, 7H), 5.46 (d, J=10.5 Hz, 1H), 4.10-4.04 (m, 1H), 3.94-3.86 (m, 4H), 3.61-3.49 (m, 1H), 3.38 (td, J=11.9, 1.8 Hz, 1H), 3.09 (d, J=10.8 Hz, 1H), 1.66-1.55 (m, 1H), 1.41 (qd, J=12.3, 4.6 Hz, 1H), 1.07 (d, J=13.0 Hz, 1H). LCMS: (M+H)$^+$ 510.

Step 5: 1-{11-Chloro-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaen-13-yl}ethan-1-one and 1-{13-chloro-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaen-11-yl}ethan-1-one The title compounds were prepared using 11,13-dichloro-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene according to the procedure described for 5-(dimethyl-1H-1,2,3-triazol-5-yl)-11-(1-ethoxyethenyl)-8-[(S)-oxan-4-yl(phenyl)methyl]-3,8,10-triazatricyclo[7.4.0.0$^{2,7}$]trideca-1(9),2(7),3,5,10,12-hexaene (Example 170). This material was purified on SiO$_2$ (4 g), eluting with 10-30% acetone/DCM. The product containing fractions were collected to give the title compounds (45 mg, 86%). 1H NMR was consistent with a mixture of regioisomeric coupling products that were carried on as is.

Step 6: 2-{11-Chloro-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaen-13-yl}propan-2-ol and 2-{13-chloro-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaen-11-yl}propan-2-ol The title compounds were prepared using the product from step 5, this example according to the procedure described for 2-[5-(dimethyl-1H-1,2,3-triazol-5-yl)-13-methoxy-8-[(S)-oxan-4-yl(phenyl)methyl]-3,8,12-triazatricyclo[7.4.0.0$^{2,7}$]trideca-1(9),2,4,6,10,12-hexaen-10-yl]propan-2-ol, (Example 142). This material was purified on SiO$_2$ (4 g), eluting with DCM (30 mL), 5% acetone/DCM (50 mL), 10% acetone/DCM (50 mL), 20% acetone/DCM (50 mL), 50% acetone/DCM (50 mL). The collected fractions gave two lots (fractions A and B) of material that were enriched in the individual regioisomeric products. Fractions A and B were further independently purified by preparative HPLC (Column: XBridge C18, 30×100 mm, 5-μm particles; Mobile Phase A: 5:95 acetonitrile: water with 10 mM ammonium acetate; Mobile Phase B: 95:5 acetonitrile: water with 10 mM ammonium acetate; 35% B over 5 min then 35-100% B over 20 min, 100% B for 2 min; Flow: 30 mL/min; 254 nm detection).

2-{11-Chloro-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaen-13-yl}propan-2-ol (isomer 1, 4.8 mg) was isolated as a white solid: $^1$H NMR (400 MHz, CDCl$_3$) δ 8.50 (d, J=1.8 Hz, 1H), 7.67 (d, J=1.5 Hz, 1H), 7.56 (s, 1H), 7.48-7.31 (m, 5H), 5.47 (d, J=10.5 Hz, 1H), 4.07 (dd, J=11.7, 2.9 Hz, 1H), 3.90 (dd, J=11.7, 2.6 Hz, 1H), 3.87 (s, 3H), 3.55 (td, J=11.9, 1.9 Hz, 1H), 3.37 (td, J=11.9, 2.0 Hz, 1H), 3.15-2.99 (m, 1H), 2.07-2.00 (m, 1H), 1.83 (s, 3H), 1.81 (s, 3H), 1.67-1.53 (m, 1H), 1.48-1.35 (m, 1H), 1.10 (d, J=12.3 Hz, 1H). LCMS: T$_R$=0.97 min; (ES): m/z (M+H)$^+$ 534.0: Waters Acquity—Column: Waters Acquity UPLC BEH C18, 2.1×50 mm, 1.7 μm particles; Mobile Phase A: water/0.05% TFA; Mobile Phase B: acetonitrile/0.05% TFA; Temperature: 50° C.; Gradient: 2-98% B over 1 min, then a 0.5-min hold at 98% B; Flow: 0.8 mL/min; Detection: UV=220 nm.

2-{13-Chloro-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaen-1-yl}propan-2-ol (isomer 2, 25.4 mg) was isolated as a white solid: $^1$H NMR (400 MHz, CDCl$_3$) δ 8.68 (d, J=1.8 Hz, 1H), 7.72 (s, 1H), 7.62 (d, J=1.8 Hz, 1H), 7.44-7.32 (m, 5H), 5.55 (d, J=10.5 Hz, 1H), 4.11-4.04 (m, 1H), 3.88 (s, 3H), 3.92-3.86 (m, 1H), 3.58-3.52 (m, 1H), 3.36 (td, J=11.9, 2.0 Hz, 1H), 3.15-3.00 (m, 1H), 2.07 (d, J=13.6 Hz, 1H), 1.74 (s, 3H), 1.72 (s, 3H), 1.69-1.59 (m, J=4.3 Hz, 1H), 1.39 (qd, J=12.3, 4.1 Hz, 1H), 1.06 (d, J=13.3 Hz, 1H). LCMS: T$_R$=0.83 min; (ES): m/z (M+H)$^+$ 534.1: Waters Acquity—Column: Waters Acquity UPLC BEH C18, 2.1×50 mm, 1.7 μm particles; Mobile Phase A: water/0.05% TFA; Mobile Phase B: acetonitrile/0.05% TFA; Temperature: 50° C.; Gradient: 2-98% B over 1 min, then a 0.5-min hold at 98% B; Flow: 0.8 mL/min; Detection: UV=220 nm.

Example 295

5-[4-($^2$H$_3$)Methyl-1-methyl-1H-1,2,3-triazol-5-yl]-8-[(S)-oxan-4-yl(phenyl)methyl]-N-[2-(1H-1,2,3,4-tetrazol-5-yl)ethyl]-3,8,10-triazatricyclo[7.4.0.0$^{2,7}$]trideca-1(9),2(7),3,5,10,12-hexaen-11-amine

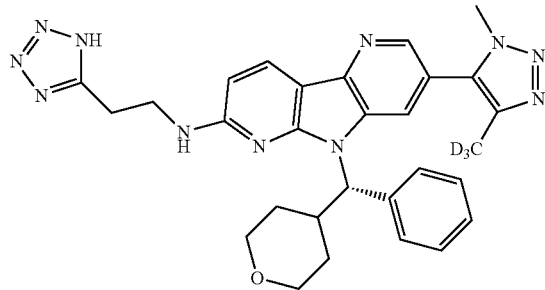 [SMILES: [2H]C([2H])([2H])c1nnn(C)c1-c1cnc2c3ccc(NCCc4nnn[nH]4)nc3n([C@H](c3ccccc3)C3CCOCC3)c2c1]

To 11-chloro-5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaene (13 mg, 0.027 mmol) in a microwaveable vial was added 2-(1H-tetrazol-5-yl)ethanamine hydrochloride (12.3 mg, 0.082 mmol), K$_3$PO$_4$ (89 mg, 0.273 mmol), and DMSO (1.5 mL). The vial was sealed under argon and heated in the microwave for 0.5 h at 180° C. It was filtered and the crude material purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55% B over 15 min, then a 5-min hold at 100% B; Flow: 20 mL/min. Fractions containing the desired product were combined and dried via centrifugal evaporation to give the product (56% yield). $^1$H NMR (500 MHz, DMSO-d$_6$) δ 8.36 (s, 1H), 8.32 (br. s., 1H), 8.10 (d, J=8.4 Hz, 1H), 7.96 (s, 1H), 7.84 (d, J=7.3 Hz, 2H), 7.57 (br. s., 1H), 7.30 (t, J=7.3 Hz, 2H), 7.22 (t, J=7.5 Hz, 1H), 6.52 (d, J=8.4 Hz, 1H), 5.68 (br. s., 1H), 4.01 (s, 3H), 3.98-3.91 (m, 1H), 3.83 (d, J=8.1 Hz, 2H), 3.76 (d, J=11.0 Hz, 2H), 3.36 (t, J=11.4 Hz, 1H), 3.28 (d, J=7.0 Hz, 2H), 1.92 (s, 3H), 1.44 (br. s., 1H), 1.36 (d, J=9.5 Hz, 1H), 1.25 (br. s., 2H); LCMS (M+1)=553; T$_R$=0.66 min [Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min].

Example 296

10,13-Dichloro-5-[4-($^2$H$_3$)methyl-1-methyl-1H-1,2,3-triazol-5-yl]-8-[(S)-oxan-4-yl(phenyl)methyl]-3,8,11-triazatricyclo[7.4.0.0$^{2,7}$]trideca-1(9),2(7),3,5,10,12-hexaene

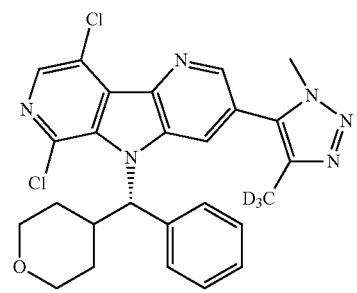 [SMILES: [2H]C([2H])([2H])c1nnn(C)c1-c1cnc2c3c(Cl)cnc(Cl)c3n([C@H](c3ccccc3)C3CCOCC3)c2c1]

Step 1: 5-Bromo-2',5'-dichloro-3-nitro-2,4'-bipyridine

To (2,5-dichloropyridin-4-yl)boronic acid (1.000 g, 5.21 mmol) and 2,5-dibromo-3-nitropyridine (1.470 g, 5.21 mmol) in a 100 mL round bottom flask was added THF (30 mL). To this was added a solution of K$_3$PO$_4$ (2.211 g, 10.4 mmol) in water (15 mL), followed by PdCl$_2$(dppf)$_2$.DCM (0.213 g, 0.261 mmol). The air was replaced with N$_2$ and the flask sealed. The resulting mixture was heated to 80° C. with stirring under refluxing conditions. After 2.5 h, it was cooled to room temperature, diluted with EtOAc and washed with brine. The organic layer was separated, dried over MgSO$_4$, filtered through a thin pad of silica gel (~1 inch) and concentrated on the rotavap. The residue obtained was purified by ISCO, 80 g column, eluting with 0-50% EtOAc/Hex to obtain 563 mg (31%). $^1$H NMR (500 MHz, CDCl$_3$)

δ 9.05 (d, J=2.1 Hz, 1H), 8.70 (d, J=2.0 Hz, 1H), 8.50-8.48 (m, 1H), 7.45 (d, J=0.5 Hz, 1H).

Step 2: 3-Bromo-6,9-dichloro-5H-pyrrolo[3,2-b:5,4-c']dipyridine

A mixture of 5-bromo-2',5'-dichloro-3-nitro-2,4'-bipyridine (535 mg, 1.53 mmol) and 1,2-bis(diphenylphosphino)ethane (764 mg, 1.92 mmol) in 1,2-dichlorobenzene (10 mL) was heated at 160° C. After 3 h, the reaction was cooled to room temperature and concentrated. The residue was purified on a 40 g silica gel column, eluting with 0-100% EtOAc/DCM to obtain 26% of the desired product. $^1$H NMR (400 MHz, Acetone) δ 8.80 (d, J=2.0 Hz, 1H), 8.35 (d, J=2.0 Hz, 1H), 8.29-8.26 (m, 1H).

Step 3: 5-Bromo-10,13-dichloro-8-[(S)-oxan-4-yl(phenyl)methyl]-3,8,11-triazatricyclo[7.4.0.0$^{2,7}$]trideca-1(9),2(7),3,5,10,12-hexaene A 50 mL round bottom flask was charged with 3-bromo-6,9-dichloro-5H-pyrrolo[3,2-b:5,4-c']dipyridine (120 mg, 0.379 mmol) and THF (5 mL). To this was added (R)-phenyl(tetrahydro-2H-pyran-4-yl)methanol (146 mg, 0.757 mmol), PPh$_3$ (199 mg, 0.757 mmol) and triethylamine (0.106 mL, 0.757 mmol). Di-tert-butyl azodicarboxylate (174 mg, 0.757 mmol) was added as a solid. The reaction allowed to stir overnight at room temperature. The reaction mixture was concentrated, loaded onto a 24 g silica gel column, and eluted with 2-70% EtOAc/Hex to obtain 365 mg of material. The material was repurified on a 24 g silica gel column eluting with 2-25% Acetone/Hexanes to obtain 131 mg (70%). $^1$H NMR (400 MHz, CDCl$_3$) δ 8.76 (d, J=1.8 Hz, 1H), 8.38-8.34 (m, 1H), 8.02-7.98 (m, 1H), 7.54 (d, J=7.5 Hz, 2H), 7.42 (t, J=7.4 Hz, 2H), 7.08 (d, J=11.0 Hz, 1H), 4.09 (dd, J=11.5, 2.5 Hz, 1H), 3.88 (dd, J=11.2, 3.1 Hz, 1H), 3.60 (td, J=11.9, 1.9 Hz, 1H), 3.36 (td, J=11.9, 2.0 Hz, 1H), 3.13-2.99 (m, 1H), 2.13 (d, J=14.1 Hz, 1H), 1.74-1.62 (m, 1H), 1.35-1.25 (m, 1H), 0.93-0.81 (m, 1H), 0.67 (d, J=13.6 Hz, 1H).

Step 4: 10,13-Dichloro-5-[4-($^2$H$_3$)methyl-1-methyl-1H-1,2,3-triazol-5-yl]-8-[(S)-oxan-4-yl(phenyl)methyl]-3,8,11-triazatricyclo[7.4.0.0$^{2,7}$]trideca-1(9),2(7),3,5,10,12-hexaene The (S)-3-bromo-6,9-dichloro-5-(phenyl(tetrahydro-2H-pyran-4-yl)methyl)-5H-pyrrolo[3,2-b:5,4-c']dipyridine (50.0 mg, 0.102 mmol), 4-($^2$H$_3$)methyl-1-methyl-5-(tributylstannyl)-1H-1,2,3-triazole (36.9 mg, 0.102 mmol), CuI (2.9 mg, 0.015 mmol), Pd(PPh$_3$)$_4$ (8.2 mg, 7.13 μmol), triethylamine (0.028 mL, 0.204 mmol) and DMF (2 mL) were weighed out into a 20 mL scintillation vial, and sealed under argon. The vial was place in a reaction block preheated to 100° C. After 7 h, the reaction was cooled to room temperature and filtered. The filtrate was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 45-85% B over 15 min, then a 5-min hold at 100% B; Flow: 20 mL/min. Fractions containing the desired product were combined and dried via centrifugal evaporation to obtain the desired product in 23% yield. $^1$H NMR (500 MHz, DMSO-d$_6$) δ 8.79 (s, 1H), 8.43 (s, 1H), 8.30 (s, 1H), 7.67 (d, J=7.3 Hz, 2H), 7.37 (t, J=7.3 Hz, 2H), 7.28 (t, J=7.3 Hz, 1H), 6.98 (d, J=11.4 Hz, 1H), 3.73 (d, J=10.3 Hz, 1H), 3.61-3.47 (m, 3H), 3.24 (t, J=11.7 Hz, 1H), 2.51 (br. s., 1H), 1.94 (d, J=13.2 Hz, 1H), 1.53-1.36 (m, 2H), 0.86 (d, J=11.4 Hz, 1H). LCMS (M+1)=510.

Example 297

1-{5-[4-($^2$H$_3$)Methyl-1-methyl-1H-1,2,3-triazol-5-yl]-8-[(S)-oxan-4-yl(phenyl)methyl]-3,8,11-triazatricyclo[7.4.0.0$^{2,7}$]trideca-1(9),2(7),3,5,10,12-hexaen-13-yl}ethan-1-one

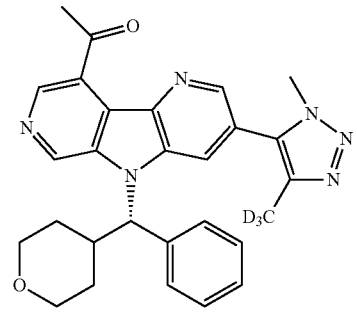 [SMILES: [2H]C([2H])([2H])c1nnn(C)c1-c1cnc2c3c(C(C)=O)cncc3n([C@H](c3ccccc3)C3CCOCC3)c2c1]

Step 1: 5-Bromo-3'-chloro-3-nitro-2,4'-bipyridine

Following a procedure analogous to the synthesis of 5-bromo-2',5'-dichloro-3-nitro-2,4'-bipyridine, the title compound was synthesized in 44% yield from (3-chloropyridin-4-yl)boronic acid. $^1$H NMR (400 MHz, CDCl$_3$) δ 9.05 (d, J=2.0 Hz, 1H), 8.72 (s, 1H), 8.71-8.67 (m, 2H), 7.41 (dd, J=5.0, 0.5 Hz, 1H)

Step 2: 3-Bromo-9-chloro-5H-pyrrolo[3,2-b:5,4-c']dipyridine

Following a procedure analogous to the synthesis of 3-bromo-6,9-dichloro-5H-pyrrolo[3,2-b:5,4-c']dipyridine, the title compound was synthesized in 38% yield from 5-bromo-3'-chloro-3-nitro-2,4'-bipyridine. LCMS (M+1)=282; T$_R$=0.65 min [Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min].

Step 3: (S)-3-Bromo-9-chloro-5-(phenyl(tetrahydro-2H-pyran-4-yl)methyl)-5H-pyrrolo[3,2-b:5,4-c']dipyridine Following a procedure analogous to the synthesis of 5-bromo-10,13-dichloro-8-[(S)-oxan-4-yl(phenyl)methyl]-3,8,11-triazatricyclo[7.4.0.0$^{2,7}$]trideca-1(9),2(7),3,5,10,12-hexaene, the title compound was synthesized in 60% yield from 3-bromo-9-chloro-5H-pyrrolo[3,2-b:5,4-c']dipyridine. LCMS (M+1)=456; T$_R$=0.97 min [Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min].

Step 4: 13-Chloro-5-[4-($^2$H$_3$)methyl-1-methyl-1H-1,2,3-triazol-5-yl]-8-[(S)-oxan-4-yl(phenyl)methyl]-3,8,11-triazatricyclo[7.4.0.0$^{2,7}$]trideca-1(9),2(7),3,5,10,12-hexaene (S)-3-Bromo-9-chloro-5-(phenyl(tetrahydro-2H-pyran-4-yl)methyl)-5H-pyrrolo[3,2-b:5,4-c']dipyridine (350 mg, 0.766 mmol), 4-($^2$H$_3$)methyl-1-methyl-5-(tributylstannyl)-1H-1,2,3-triazole (36.9 mg, 0.102 mmol), CuI (21.9 mg, 0.115 mmol), Pd(PPh$_3$)$_4$ (62.0 mg, 0.054 mmol), triethylamine (0.214 mL, 1.53 mmol) and DMF (15 mL) were weighed out into a 20 mL scintillation vial, and sealed under argon. The vial was place in a heating block preheated to 100° C. After 3 h, the reaction was cooled to room temperature, diluted with 5% MeOH/EtOAc, quenched with brine, and the organic layer was separated and concentrated. The crude mixture was purified by flash chromatography: (24 g ISCO RediSep 0-50% 10% (2M NH$_3$ in EtOAC)/EtOAc) to obtain (271 mg, 74% yield). $^1$H NMR (400 MHz, CDCl$_3$) δ 9.18 (s, 1H), 8.73 (d, J=1.8 Hz, 1H), 8.60 (s, 1H), 7.78 (d, J=1.8 Hz, 1H), 7.49-7.44 (m, 2H), 7.43-7.33 (m, 3H), 5.60 (d, J=10.5 Hz, 1H), 3.95 (s, 3H), 3.90 (dd, J=11.5, 3.0 Hz, 1H), 3.62-3.51 (m, 1H), 3.44-3.34 (m, 1H), 3.14 (q, J=11.1 Hz, 1H), 2.09-2.00 (m, 2H), 1.51-1.39 (m, 1H), 1.28 (t, J=7.2 Hz, 1H), 1.13 (d, J=13.1 Hz, 1H), 0.98-0.77 (m, 1H)

Step 5: 1-{5-[4-($^2$H$_3$)Methyl-1-methyl-1H-1,2,3-triazol-5-yl]-8-[(S)-oxan-4-yl(phenyl)methyl]-3,8,11-triazatricyclo[7.4.0.0$^{2,7}$]trideca-1(9),2(7),3,5,10,12-hexaen-13-yl}ethan-1-one A 20 mL scintillation vial was charged with 13-chloro-5-[4-($^2$H$_3$)methyl-1-methyl-1H-1,2,3-triazol-5-yl]-8-[(S)-oxan-4-yl(phenyl)methyl]-3,8,11-triazatricyclo[7.4.0.0$^{2,7}$]trideca-1(9),2(7),3,5,10,12-hexaene, tributyl(1-ethoxyvinyl)stannane (41.7 mg, 0.116 mmol), and dioxane (2 mL). This was followed by the addition of Pd(dppf)$_2$Cl$_2$.DCM (8.6 mg, 10.50 µmol) and the air was replaced with argon and the vial sealed under argon. It was heated to 100° C. with stirring overnight. The reaction was cooled to room temperature, diluted with 2.5 mL of THF and filtered with a syringe filter. About 0.5 mL of 6N HCl aq. and stirred. After 1.5 h, the reaction was neutralized with drops of aq. K$_2$CO$_3$ (10% solution), and diluted with EtOAc. The organic layer was separated, washed with brine, dried over MgSO$_4$, filtered, and concentrated on the rotavap to obtain a crude mixture. The crude material was purified via preparative LC/MS with the following conditions: Column: XBridge C18, 19×mm, 5-µm particles; Mobile Phase A: 5:95 acetonitrile: water with 10-mM ammonium acetate; Mobile Phase B: 95:5 acetonitrile: water with 10-mM ammonium acetate; Gradient: 15-60% B over 15 min, then a 5-min hold at 100% B; Flow: 20 mL/min. Fractions containing the desired product were combined and dried via centrifugal evaporation. The yield of the product was 21%. $^1$H NMR (500 MHz, DMSO-d$_6$) δ 9.73 (br. s., 1H), 8.76 (s, 1H), 8.50 (s, 1H), 7.74 (d, J=7.7 Hz, 2H), 7.39-7.33 (m, 2H), 7.31-7.24 (m, 1H), 6.05 (d, J=11.4 Hz, 1H), 4.06 (s, 3H), 3.94-3.86 (m, 1H), 3.73 (d, J=8.8 Hz, 1H), 3.50 (q, J=10.9 Hz, 2H), 3.38 (s, 1H), 3.29 (t, J=11.6 Hz, 1H), 3.01-2.96 (m, 3H), 1.73 (d, J=12.5 Hz, 1H), 1.63-1.51 (m, 1H), 1.34 (d, J=8.8 Hz, 1H), 0.97 (d, J=12.5 Hz, 1H).

Example 298

2-{5-[4-($^2$H$_3$)Methyl-1-methyl-1H-1,2,3-triazol-5-yl]-8-[(S)-oxan-4-yl(phenyl)methyl]-3,8,11-triazatricyclo[7.4.0.0$^{2,7}$]trideca-1(9),2(7),3,5,10,12-hexaen-13-yl}propan-2-ol

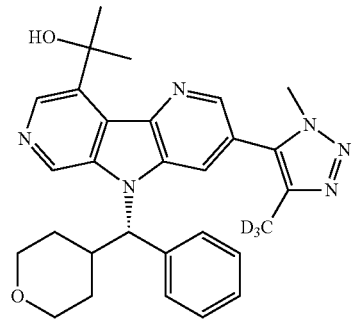 [SMILES: [2H]C([2H])([2H])c1nnn(C)c1-c1cnc2c3c(C(C)(C)O)cncc3n([C@H](c3ccccc3)C3CCOCC3)c2c1]

To 1-{5-[4-($^2$H$_3$)methyl-1-methyl-1H-1,2,3-triazol-5-yl]-8-[(S)-oxan-4-yl(phenyl)methyl]-3,8,11-triazatricyclo[7.4.0.0$^{2,7}$]trideca-1(9),2(7),3,5,10,12-hexaen-13-yl}ethan-1-one (20 mg, 0.041 mmol), dissolved in 3 mL THF at room temperature was added methyllithium (0.129 mL, 0.207 mmol). After 30 min of stirring, the reaction was quenched with 0.5 mL of acetone and concentrated. The crude material was purified via preparative LC/MS with the following conditions: Column: XBridge C18, 19×mm, 5-µm particles; Mobile Phase A: 5:95 acetonitrile: water with 10-mM ammonium acetate; Mobile Phase B: 95:5 acetonitrile: water with 10-mM ammonium acetate; Gradient: 15-55% B over 20 min, then a 5-min hold at 100% B; Flow: 20 mL/min. Fractions containing the desired product were combined and dried via centrifugal evaporation. The yield of the product was 4.0 mg. $^1$H NMR (500 MHz, DMSO-d$_6$) δ 8.79 (s, 1H), 8.54 (s, 1H), 7.96 (s, 2H), 7.73 (d, J=7.0 Hz, 2H), 7.35 (t, J=7.3 Hz, 2H), 7.27 (t, J=7.0 Hz, 1H), 6.03 (d, J=11.4 Hz, 1H), 4.08 (br. s., 3H), 3.94-3.88 (m, 2H), 3.72 (d, J=11.4 Hz, 2H), 3.32-3.24 (m, 1H), 3.17 (s, 1H), 1.77-1.73 (m, 6H), 1.71 (br. s., 1H), 1.57 (d, J=11.4 Hz, 1H), 1.33 (d, J=7.0 Hz, 1H), 0.95 (d, J=12.5 Hz, 1H). LCMS (M+1)=500, T$_R$=0.66 min [Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min].

Example 299

5-[4-($^2$H$_3$)Methyl-1-methyl-1H-1,2,3-triazol-5-yl]-8-[(S)-oxan-4-yl(phenyl)methyl]-3,8,11-triazatricyclo[7.4.0.0$^{2,7}$]trideca-1(9),2(7),3,5,10,12-hexaene

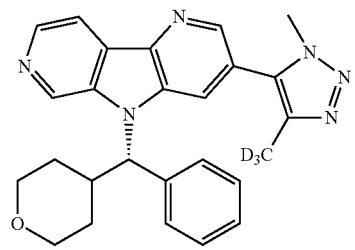 [SMILES: [2H]C([2H])([2H])c1nnn(C)c1-c1cnc2c3ccncc3n([C@H](c3ccccc3)C3CCOCC3)c2c1]

To a microwavable vial containing 13-chloro-5-[4-($^2$H$_3$)methyl-1-methyl-1H-1,2,3-triazol-5-yl]-8-[(S)-oxan-4-yl(phenyl)methyl]-3,8,11-triazatricyclo[7.4.0.0$^{2,7}$]trideca-1(9),2(7),3,5,10,12-hexaene (25 mg, 0.053 mmol), 2,2,2-trifluoroethanamine (13.0 mg, 0.131 mmol), sodium 2-methylpropan-2-olate (25.2 mg, 0.263 mmol), Pd(OAc)$_2$ (0.6 mg, 2.6 μmol), RuPhos (0.5 mg, 1.05 μmol) and dioxane (2 mL). The air was replaced with argon and the mixture heated at 120° C. for 50 min. The reaction mixture was filtered, and the crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-70% B over 25 min, then a 5-min hold at 100% B; Flow: 20 mL/min. Fractions containing the desired product were combined and dried via centrifugal evaporation. The yield of the product was 64%. $^1$H NMR (500 MHz, DMSO-d$_6$) δ 9.58 (br. s., 1H), 8.69 (s, 2H), 8.52 (d, J=5.1 Hz, 1H), 8.20 (d, J=5.1 Hz, 1H), 7.73 (d, J=7.7 Hz, 2H), 7.38-7.31 (m, 2H), 7.30-7.24 (m, 1H), 5.95 (d, J=11.0 Hz, 1H), 4.06 (s, 3H), 3.90 (d, J=11.7 Hz, 1H), 3.73 (d, J=8.8 Hz, 1H), 3.56-3.44 (m, 2H), 3.29 (t, J=11.6 Hz, 1H), 1.69 (d, J=12.5 Hz, 1H), 1.60-1.48 (m, 1H), 1.40-1.27 (m, 1H), 1.00 (d, J=12.5 Hz, 1H). LCMS (M+1)=442.

Example 300

13-Methoxy-5-[4-($^2$H$_3$)methyl-1-methyl-1H-1,2,3-triazol-5-yl]-8-[(S)-oxan-4-yl(phenyl)methyl]-3,8,11-triazatricyclo[7.4.0.0$^{2,7}$]trideca-1(9),2(7),3,5,10,12-hexaene

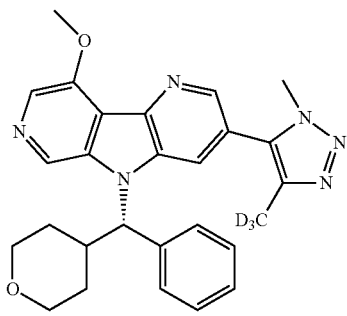 [SMILES: [2H]C([2H])([2H])c1nnn(C)c1-c1cnc2c3c(OC)cncc3n([C@H](c3ccccc3)C3CCOCC3)c2c1]

To a microwavable vial containing 13-chloro-5-[4-($^2$H$_3$)methyl-1-methyl-1H-1,2,3-triazol-5-yl]-8-[(S)-oxan-4-yl(phenyl)methyl]-3,8,11-triazatricyclo[7.4.0.0$^{2,7}$]trideca-1(9),2(7),3,5,10,12-hexaene (10 mg, 0.021 mmol), and sodium methanolate (22.7 mg, 0.105 mmol), and dioxane (1.5 mL). The air was replaced with nitrogen and the reaction heated at 120° C. for 10 min. The sample was quenched by addition of acetone and concentrated. It was then purified via preparative LC/MS with the following conditions: Column: XBridge C18, 19×mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 30 min, then a 5-min hold at 100% B; Flow: 20 mL/min. Fractions containing the desired product were combined and dried via centrifugal evaporation. The yield of the product was 36%. $^1$H NMR (500 MHz, DMSO-d$_6$) δ 9.21 (br. s., 1H), 8.67 (s, 2H), 8.25 (s, 1H), 7.70 (d, J=7.3 Hz, 2H), 7.37-7.31 (m, 2H), 7.30-7.24 (m, 1H), 5.92 (d, J=11.4 Hz, 1H), 4.12 (s, 3H), 4.04 (s, 2H), 3.91-3.87 (m, 1H), 3.73 (d, J=9.9 Hz, 1H), 3.52-3.41 (m, 2H), 3.36-3.32 (m, 3H), 3.28 (t, J=11.2 Hz, 1H), 3.18 (d, J=5.1 Hz, 1H), 1.92 (s, 2H), 1.70 (d, J=13.2 Hz, 1H), 1.62-1.49 (m, 1H), 1.31 (d, J=9.2 Hz, 1H), 0.96 (d, J=11.7 Hz, 1H). LCMS (M+1)=472; T$_R$=0.61 min [Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min].

Example 301

5-[4-($^2$H$_3$)Methyl-1-methyl-1H-1,2,3-triazol-5-yl]-8-[(S)-oxan-4-yl(phenyl)methyl]-13-(2,2,2-trifluoroethoxy)-3,8,11-triazatricyclo[7.4.0.0$^{2,7}$]trideca-1(9),2(7),3,5,10,12-hexaene

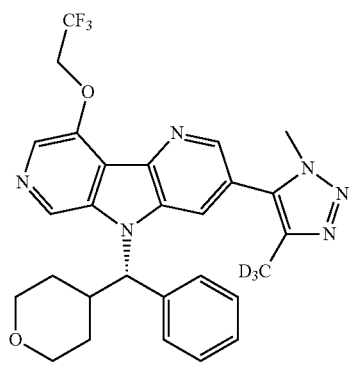 [SMILES: [2H]C([2H])([2H])c1nnn(C)c1-c1cnc2c3c(OCC(F)(F)F)cncc3n([C@H](c3ccccc3)C3CCOCC3)c2c1]

To a microwavable vial containing 13-methoxy-5-[4-($^2$H$_3$)methyl-1-methyl-1H-1,2,3-triazol-5-yl]-8-[(S)-oxan-4-yl(phenyl)methyl]-3,8,11-triazatricyclo[7.4.0.0$^{2,7}$]trideca-1(9),2(7),3,5,10,12-hexaene (11 mg, 0.023 mmol), and 2,2,2-trifluoroethanol (1.66 mL, 23.1 mmol), and dioxane (1.5 mL). The air was replaced with nitrogen and the reaction heated in the microwave at 120° C. for 0.5 h. LC/MS showed no product. To this was added 5 equivalents of K$_2$CO$_3$ and the reaction heated in the microwave at 185° C. for 1.5 h. The crude material was purified via preparative LC/MS with the following conditions: Column: XBridge C18, 19×mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 15 min, then a 5-min hold at 100% B; Flow: 20 mL/min. Fractions containing the desired product were combined and dried via centrifugal evaporation. The yield of the product was 41%. $^1$H NMR (500 MHz, DMSO-d$_6$) δ 9.32 (br. s., 1H), 8.76 (s, 1H), 8.34 (s, 1H), 7.96 (s, 1H), 7.71 (d, J=7.7 Hz, 2H), 7.38-7.32 (m, 2H), 7.30-7.24 (m, 1H), 5.97 (d, J=11.4 Hz, 1H), 5.21 (q, J=8.9 Hz, 2H), 4.05 (s, 3H), 3.91-3.86 (m, 1H), 3.73 (d, J=9.9 Hz, 1H), 3.52-3.44 (m, 3H), 3.32-3.24 (m, 2H), 1.91 (s, 9H), 1.71 (d, J=12.1 Hz, 1H), 1.61-1.49 (m, 1H), 1.39-1.26 (m, 1H). LCMS (M+1)=540; T$_R$=0.74 min [Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min].

Example 302

5-[4-($^2$H$_3$)Methyl-1-methyl-1H-1,2,3-triazol-5-yl]-8-[(S)-oxan-4-yl(phenyl)methyl]-N-(2,2,2-trifluoroethyl)-3,8,11-triazatricyclo[7.4.0.0$^{2,7}$]trideca-1(9),2(7),3,5,10,12-hexaen-13-amine

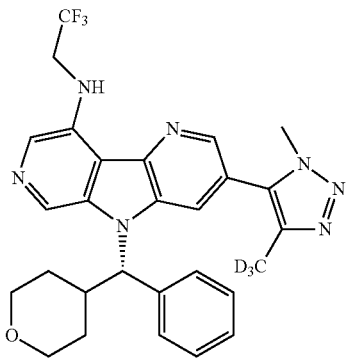 [SMILES: [2H]C([2H])([2H])c1nnn(C)c1-c1cnc2c3c(NCC(F)(F)F)cncc3n([C@H](c3ccccc3)C3CCOCC3)c2c1]

To a microwavable vial containing 13-methoxy-5-[4-($^2$H$_3$)methyl-1-methyl-1H-1,2,3-triazol-5-yl]-8-[(S)-oxan-4-yl(phenyl)methyl]-3,8,11-triazatricyclo[7.4.0.0$^{2,7}$]trideca-1(9),2(7),3,5,10,12-hexaene (11 mg, 0.023 mmol), and 2,2,2-trifluoroethanamine (229 mg, 2.311 mmol), in dioxane (1.5 mL) was added RuPhos (0.216 mg, 0.462 µmol) followed by Pd(OAc)$_2$ (0.2 mg, 0.69 µmol). The air was replaced with argon and the reaction heated in the microwave at 125° C. for 25 min. The reaction mixture was filtered. The filtrate was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 40-80% B over 15 min, then a 5-min hold at 100% B; Flow: 20 mL/min. Fractions containing the desired product were combined and dried via centrifugal evaporation. The yield of the product was 61%. $^1$H NMR (500 MHz, DMSO-d$_6$) δ 8.88 (br. s., 1H), 8.68-8.57 (m, 2H), 8.13 (s, 1H), 7.69 (d, J=7.7 Hz, 2H), 7.37-7.31 (m, 2H), 7.29-7.23 (m, 1H), 6.92 (t, J=7.0 Hz, 1H), 5.83 (d, J=11.4 Hz, 1H), 4.51-4.39 (m, 2H), 4.04 (s, 3H), 3.88 (d, J=9.2 Hz, 1H), 3.73 (d, J=9.2 Hz, 1H), 3.53-3.46 (m, 2H), 3.29 (t, J=11.7 Hz, 1H), 2.55 (s, 6H), 1.66 (d, J=12.5 Hz, 1H), 1.58-1.46 (m, 1H), 1.32 (d, J=12.1 Hz, 1H), 1.03 (d, J=14.3 Hz, 1H). LCMS (M+1)=539; T$_R$=0.72 min [Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min].

Examples 303 & 304

8-[(3-Fluoropyridin-2-yl)(oxan-4-yl)methyl]-5-[4-($^2$H$_3$)methyl-1-methyl-1H-1,2,3-triazol-5-yl]-N-(2,2,2-trifluoroethyl)-3,8,11-triazatricyclo[7.4.0.0$^{2,7}$]trideca-1(9),2(7),3,5,10,12-hexaen-13-amine

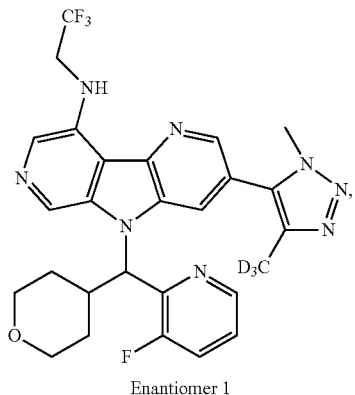

Example 303

Enantiomer 1

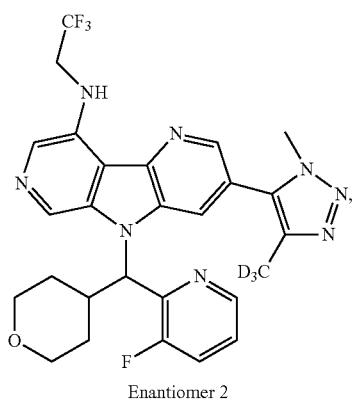

Example 304

Enantiomer 2

Step 1: 5-Bromo-3'-chloro-3-nitro-2,4'-bipyridine

Following a procedure analogous to the synthesis of 5-bromo-2',5'-dichloro-3-nitro-2,4'-bipyridine, the title compound was synthesized in 44% yield from (3-chloropyridin-4-yl)boronic acid. $^1$H NMR (400 MHz, CDCl$_3$) δ 9.05 (d, J=2.0 Hz, 1H), 8.72 (s, 1H), 8.71-8.67 (m, 2H), 7.41 (dd, J=5.0, 0.5 Hz, 1H).

Step 2: 3-Bromo-9-chloro-5H-pyrrolo[3,2-b:5,4-c'] dipyridine

Following a procedure analogous to the synthesis of 3-bromo-6,9-dichloro-5H-pyrrolo[3,2-b:5,4-c']dipyridine, the title compound was synthesized in 24% yield from 5-bromo-3'-chloro-3-nitro-2,4'-bipyridine. LCMS (M+1)= 282; T$_R$=0.69 min [Column: Waters Aquity BEH C18 2.1× 50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min].

Step 3: 5-Bromo-13-chloro-8-[(R)-(3-fluoropyridin-2-yl)(oxan-4-yl)methyl]-3,8,11-triazatricyclo[7.4.0.0$^{2,7}$]trideca-1(9),2(7),3,5,10,12-hexaene Following a procedure analogous to the synthesis of 5-bromo-10,13-dichloro-8-[(S)-oxan-4-yl(phenyl)methyl]-

3,8,11-triazatricyclo[7.4.0.0$^{2,7}$]trideca-1(9),2(7),3,5,10,12-hexaene, the title compound was synthesized in 35% yield from 3-bromo-9-chloro-5H-pyrrolo[3,2-b:5,4-c']dipyridine and (S)-(3-fluoropyridin-2-yl)(tetrahydro-2H-pyran-4-yl)methanol. LCMS (M+1)=475; T$_R$=0.92 min [Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min].

Step 4: 13-Chloro-8-[(R)-(3-fluoropyridin-2-yl)(oxan-4-yl)methyl]-5-[4-($^2$H$_3$)methyl-1-methyl-1H-1,2,3-triazol-5-yl]-3,8,11-triazatricyclo[7.4.0.0$^{2,7}$]trideca-1(9),2(7),3,5,10,12-hexaene (R)-3-Bromo-9-chloro-5-((3-fluoropyridin-2-yl)(tetrahydro-2H-pyran-4-yl)methyl)-5H-pyrrolo[3,2-b:5,4-c']dipyridine (100 mg, 0.210 mmol), 4-($^2$H$_3$)methyl-1-methyl-5-(tributylstannyl)-1H-1,2,3-triazole (36.9 mg, 0.102 mmol), CuI (6.0 mg, 0.032 mmol), Pd(PPh$_3$)$_4$ (17.0 mg, 0.015 mmol), triethylamine (0.059 mL, 0.420 mmol) and DMF (15 mL) were weighed out into a 20 mL scintillation vial, and sealed under argon. The vial was place into a reaction block preheated to 100° C. After 3 h, the reaction was cooled to room temperature, diluted with 5% MeOH/EtOAc, quenched with brine, and the organic layer was separated and concentrated. The crude mixture was purified by flash chromatography using 24 g silica gel column and eluting with 0-50% B/EtOAc to obtain (62.5%) 65 mg. [B=10% (2M NH3 in EtOAC)]. LCMS (M+1)=495; T$_R$=0.79 min [Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min].

Step 5: 8-[(3-Fluoropyridin-2-yl)(oxan-4-yl)methyl]-5-[4-($^2$H$_3$)methyl-1-methyl-1H-1,2,3-triazol-5-yl]-N-(2,2,2-trifluoroethyl)-3,8,11-triazatricyclo[7.4.0.0$^{2,7}$]trideca-1(9),2(7),3,5,10,12-hexaen-13-amine To a microwavable vial containing 13-chloro-8-[(R)-(3-fluoropyridin-2-yl)(oxan-4-yl)methyl]-5-[4-($^2$H$_3$)methyl-1-methyl-1H-1,2,3-triazol-5-yl]-3,8,11-triazatricyclo[7.4.0.0$^{2,7}$]trideca-1(9),2(7),3,5,10,12-hexaene (25 mg, 0.051 mmol) and 2,2,2-trifluoroethanamine (500 mg, 5.05 mmol), in dioxane (1.5 mL) was added RuPhos (0.471 mg, 1.01 µmol) followed by Pd(OAc)$_2$ (0.3 mg, 1.52 µmol). The air was replaced with argon and the reaction heated in the microwave at 125° C. for 25 min. The chiral center was epimerized as follows: The reaction was concentrated, and treated with MeOH (4 mL) and KotBu (60 mg). The resulting mixture was heated at 100° C. with stirring overnight. The reaction mixture was filtered and concentrated. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 25-65% B over 15 min, then a 5-min hold at 100% B; Flow: 20 mL/min. Fractions containing the desired product were combined and dried via centrifugal evaporation. The material was further purified through chiral separation using the following conditions: Column: Chiralpak AD 21×250 mm 5 u; Flow Rate: 15 ml/min; Collection Time: 10 to 40 min; Solvent A: 100% Heptane; Solvent B: 100% Ethanol; Vial: 20; Isocratic Collection By: UV; Start % B: 15; Wavelength: 254; Retention time of Enantiomer 1=12.72 min. Retention time of Enantiomer 2=17.59 min. The yield of Enantiomer 1 was 3.5 mg (12%) The yield of Enantiomer 2 was 4.1 mg (15%). $^1$H NMR (500 MHz, DMSO-d$_6$) δ 8.73 (s, 2H), 8.62 (d, J=4.4 Hz, 1H), 8.17 (br. s., 1H), 7.72 (t, J=9.0 Hz, 1H), 7.51 (dt, J=8.6, 4.5 Hz, 1H), 7.12-7.03 (m, 1H), 6.26 (d, J=11.4 Hz, 1H), 4.54-4.43 (m, 2H), 4.07 (s, 2H), 3.86 (d, J=10.6 Hz, 1H), 3.69 (d, J=9.5 Hz, 1H), 3.27-3.20 (m, 1H), 2.90 (s, 1H), 2.74 (s, 1H), 1.64 (br. s., 1H), 1.58 (dd, J=11.7, 4.0 Hz, 1H), 1.41-1.31 (m, 1H), 0.77 (d, J=12.5 Hz, 1H); LCMS (M+1)=558; T$_R$=0.69 min [Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min].

Example 305

11-Chloro-8-[(S)-(3-fluoropyridin-2-yl)(oxan-4-yl)methyl]-13-methoxy-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10,12-hexaene

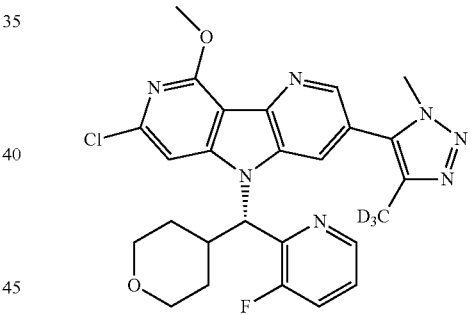

A round bottom flask was charged with 11-chloro-13-methoxy-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10,12-hexaene (450 mg, 1.36 mmol), (R)-(3-fluoropyridin-2-yl)(tetrahydro-2H-pyran-4-yl)methanol (372 mg, 1.76 mmol), PPh$_3$ (711 mg, 2.71 mmol), di-tert-butyl azodicarboxylate (625 mg, 2.71 mmol), and THF (5 mL). The air was replaced with argon and the reaction mixture stirred at room temperature. After 16 h, the reaction mixture was concentrated, loaded onto an 80 g silica gel column, and purified on the biotage eluting with 0-30% (10% 2M NH3 in MeOH in EtOAc)/EtOAc to obtain 372 mg (52%). $^1$H NMR (400 MHz, CD$_3$OD) δ 8.65-8.57 (m, 3H), 7.76 (s, 1H), 7.61 (ddd, J=9.9, 8.5, 1.3 Hz, 1H), 7.48 (dt, J=8.5, 4.4 Hz, 1H), 6.09 (d, J=11.3 Hz, 1H), 4.21 (s, 3H), 4.09 (s, 3H), 4.00-3.92 (m, 1H), 3.82 (dd, J=11.7, 3.1 Hz, 1H), 3.61-3.49 (m, 2H), 3.40-3.35 (m, 1H), 1.78 (d, J=12.8 Hz, 1H), 1.59 (qd, J=12.1, 4.6 Hz, 1H), 1.43 (qd, J=12.5, 4.3 Hz, 1H), 0.92-0.84 (m, 1H); LC/MS [M+H]$^+$=525.0.

Examples 306 & 307

2-({11-Chloro-13-methoxy-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10,12-hexaen-8-yl}(oxan-4-yl)methyl)pyridin-3-ol and 11-Chloro-8-[(3-fluoropyridin-2-yl)(oxan-4-yl)methyl]-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10-pentaen-13-one Example 306

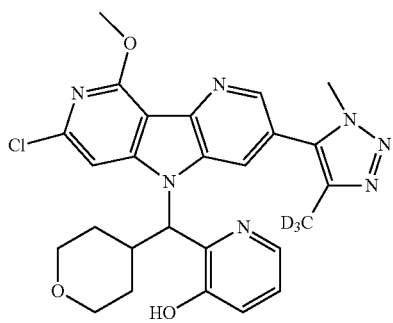 [SMILES: [2H]C([2H])([2H])c1nnn(C)c1-c1cnc2c3c(OC)nc(Cl)cc3n([C@H](c3ncccc3F)C3CCOCC3)c2c1]

Example 307

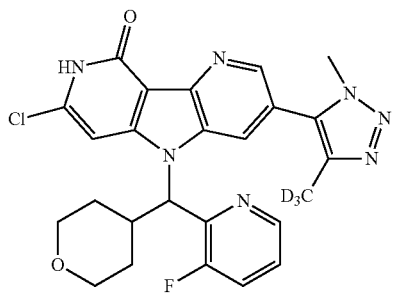

To 20 mg of 11-chloro-8-[(R)-(3-fluoropyridin-2-yl)(oxan-4-yl)methyl]-13-methoxy-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10,12-hexaene (0.038 mmol) dissolved in 3 mL of MeOH, in a scintillation vial was added KOtBu (8.6 mg, 0.076 mmol). The resulting mixture was heated to 80° C. with stirring overnight. The reaction mixture was filtered and concentrated. The crude material was purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 10-50% B over 30 min, then a 5-min hold at 100% B; Flow: 20 mL/min. Fractions containing the desired products were combined and dried via centrifugal evaporation. 2-({11-chloro-13-methoxy-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10,12-hexaen-8-yl}(oxan-4-yl)methyl)pyridin-3-ol (20% yield): $^1$H NMR (500 MHz, DMSO-d$_6$) δ 8.54 (br. s., 1H), 8.33 (br. s., 1H), 7.48-7.44 (m, 1H), 7.40 (br. s., 1H), 7.17 (br. s., 3H), 6.00 (br. s., 1H), 3.97 (br. s., 2H), 3.91 (m, 2H), 3.82 (d, J=11.7 Hz, 1H), 3.70 (d, J=9.5 Hz, 2H), 3.27-3.14 (m, 1H), 2.55 (s, 5H), 1.64 (br. s., 1H), 1.49 (d, J=11.7 Hz, 1H), 1.33 (br. s., 1H), 0.64 (d, J=11.7 Hz, 1H); LCMS (M+1)=523; T$_R$=0.65 min.

11-Chloro-8-[(3-fluoropyridin-2-yl)(oxan-4-yl)methyl]-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10-pentaen-13-one (49% yield): $^1$H NMR (500 MHz, DMSO-d$_6$) δ 8.63 (d, J=4.4 Hz, 1H), 8.58 (br. s., 1H), 7.75 (t, J=9.2 Hz, 1H), 7.54 (d, J=3.7 Hz, 1H), 7.13 (br. s., 1H), 6.12 (br. s., 1H), 4.00 (br. s., 2H), 3.90 (3, 2H), 3.84 (d, J=9.5 Hz, 1H), 3.72 (d, J=7.3 Hz, 1H), 3.18 (d, J=4.8 Hz, 1H), 2.55 (s, 3H), 1.60 (d, J=15.0 Hz, 2H), 1.33 (br. s., 1H), 0.72 (d, J=11.4 Hz, 1H); Method A retention time=1.26 min; Method B retention time=1.17 min. LC/MS [M+H]$^+$=511.0.

Example 308

1-{8-[(S)-(3-Fluoropyridin-2-yl)(oxan-4-yl)methyl]-13-methoxy-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10,12-hexaen-11-yl}ethan-1-one

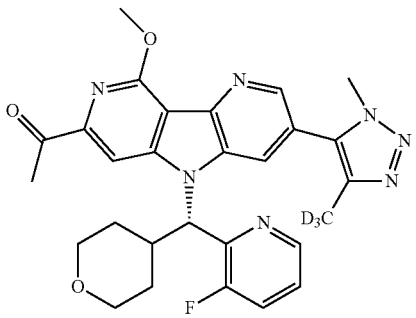 [SMILES: [2H]C([2H])([2H])c1nnn(C)c1-c1cnc2c3c(OC)nc(C(C)=O)cc3n([C@H](c3ncccc3F)C3CCOCC3)c2c1]

A 20 mL scintillation vial was charged with 11-chloro-8-[(S)-(3-fluoropyridin-2-yl)(oxan-4-yl)methyl]-13-methoxy-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10,12-hexaene (75 mg, 0.143 mmol), tributyl(1-ethoxyvinyl)stannane (56.8 mg, 0.157 mmol), and 2 mL of dioxane. This was followed by the addition of Pd(dppf)$_2$Cl$_2$-DCM (11.7 mg, 0.014 mmol) and the air was replaced with argon and the vial sealed under argon. It was heated to 100° C. with stirring overnight. The reaction was cooled to room temperature, diluted with 2.5 mL of THF and filtered with a syringe filter. To the filtrate in a 20 mL scintillation vial was added 2 mL of 1 N HCl aq. and stirred. After 1.5 h, the reaction was quenched with 5 mL of aq. K$_2$CO$_3$ (5% solution), and diluted with 5% MeOH/EtOAc solution. The organic layer was separated, washed with brine, dried over MgSO$_4$, filtered, and concentrated on the rotavap to obtain a crude mixture. It was purified using a 12 g silica gel column and eluting with 0-40% B/EtOAC [B=10% 2N ammonia/MeOH in EtOAC] to obtain 72% yield of the title compound. $^1$H NMR (500 MHz, DMSO-d$_6$) δ 8.75 (s, 1H), 8.63 (d, J=4.4 Hz, 1H), 8.36 (br. s., 1H), 7.96 (s, 1H), 7.71 (t, J=9.2 Hz, 1H), 7.51 (dt, J=8.5, 4.4 Hz, 1H), 6.34 (d, J=10.6 Hz, 1H), 4.21 (s, 3H), 4.06 (d, J=11.0 Hz, 1H), 3.67 (d, J=8.4 Hz, 1H), 3.47 (br. s., 1H), 3.25-3.14 (m, 1H), 2.76-2.72 (m, 3H), 1.67 (d, J=12.1 Hz, 2H), 1.37-1.28 (m, 1H), 0.66 (d, J=11.7 Hz, 1H); LC/MS [M+H]$^+$=533.1.

Example 309

2-{8-[(S)-(3-Fluoropyridin-2-yl)(oxan-4-yl)methyl]-13-methoxy-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10,12-hexaen-11-yl}propan-2-ol

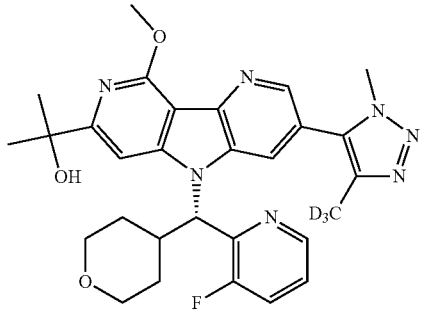 [SMILES: [2H]C([2H])([2H])c1nnn(C)c1-c1cnc2c3c(OC)nc(C(C)(C)O)cc3n([C@H](c3ncccc3F)C3CCOCC3)c2c1]

1-{8-[(S)-(3-Fluoropyridin-2-yl)(oxan-4-yl)methyl]-13-methoxy-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10,12-hexaen-11-yl}ethan-1-one (25.0 mg, 0.047 mmol) was dissolved in THF (5 mL) and CeCl$_3$ (23.1 mg, 0.094 mmol) was added. The resulting mixture was stirred at room temperature for one min followed by the addition of the methylmagnesium bromide (0.078 mL, 0.235 mmol) and then stirring for 10 min. The reaction was quenched by diluting with 10 mL EtOAc, and washed with brine. The organic layer was dried over MgSO$_4$, filtered and concentrated to obtain a crude mixture. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 15 min, then a 5-min hold at 100% B; Flow: 20 mL/min. Fractions containing the desired product were combined and dried via centrifugal evaporation. The yield of the product was 19.7 mg. $^1$H NMR (500 MHz, DMSO-d$_6$) δ 8.61 (br. s., 3H), 7.96 (s, 1H), 7.82 (br. s., 1H), 7.72 (t, J=9.4 Hz, 1H), 7.51 (dt, J=8.5, 4.4 Hz, 1H), 6.13 (br. s., 1H), 4.09 (s, 4H), 4.04 (br. s., 3H), 3.86 (d, J=8.8 Hz, 1H), 3.70 (d, J=8.1 Hz, 1H), 3.26-3.15 (m, 1H), 2.57-2.53 (m, 3H), 1.91 (s, 3H), 1.37-1.24 (m, 1H), 0.70 (d, J=12.5 Hz, 1H); LC/MS [M+H]$^+$= 549.1.

Example 310

1-{8-[(R)-(3-Fluoropyridin-2-yl)(oxan-4-yl)methyl]-13-methoxy-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10,12-hexaen-11-yl}ethan-1-one

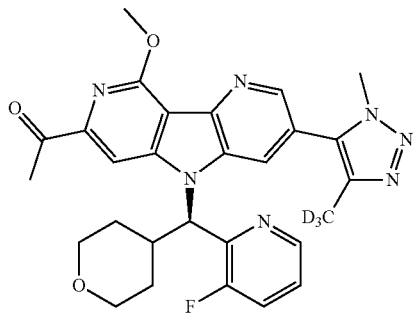 [SMILES: [2H]C([2H])([2H])c1nnn(C)c1-c1cnc2c3c(OC)nc(C(C)=O)cc3n([C@@H](c3ncccc3F)C3CCOCC3)c2c1]

The title compound was made by following a procedure analogous to the synthesis 1-{8-[(S)-(3-fluoropyridin-2-yl)(oxan-4-yl)methyl]-13-methoxy-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10,12-hexaen-11-yl}ethan-1-one. $^1$H NMR (500 MHz, DMSO-d$_6$) δ 8.74 (s, 1H), 8.63 (d, J=4.8 Hz, 2H), 7.96 (s, 1H), 7.71 (t, J=9.4 Hz, 1H), 7.51 (dt, J=8.5, 4.4 Hz, 1H), 6.34 (d, J=11.0 Hz, 1H), 4.20 (s, 4H), 4.06 (br. s., 2H), 3.86 (d, J=12.1 Hz, 1H), 3.67 (d, J=8.1 Hz, 1H), 3.25-3.15 (m, 1H), 2.90 (s, 4H), 2.77-2.69 (m, 6H), 1.65 (br. s., 3H), 1.33 (td, J=12.3, 7.7 Hz, 1H), 0.66 (d, J=13.2 Hz, 1H); LC/MS [M+H]$^+$=533.1.

Examples 311 & 312

2-{8-[(R)-(3-Fluoropyridin-2-yl)(oxan-4-yl)methyl]-13-methoxy-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10,12-hexaen-11-yl}propan-2-ol and 8-[(R)-(3-Fluoropyridin-2-yl)(oxan-4-yl)methyl]-11-(2-hydroxypropan-2-yl)-5-[4-($^2$H$_3$)methyl-1-methyl-1H-1,2,3-triazol-5-yl]-3,8,12-triazatricyclo[7.4.0.0$^2$,$^7$]trideca-1(9),2(7),3,5,10,12-hexaen-13-ol Example 311

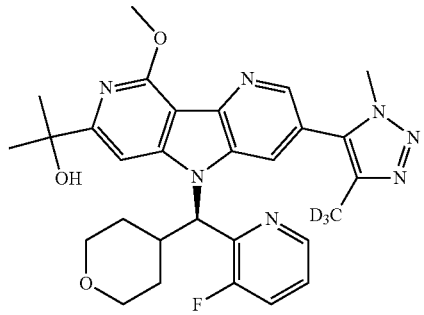

Example 312

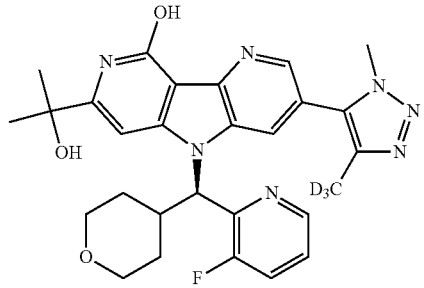

To a solution of 1-{8-[(R)-(3-fluoropyridin-2-yl)(oxan-4-yl)methyl]-13-methoxy-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10,12-hexaen-11-yl}ethan-1-one (20.0 mg, 0.038 mmol) THF (5 mL) was added CeCl$_3$ (46.3 mg, 0.188 mmol), and the resulting mixture stirred at room temperature. The methylmagnesium bromide (0.063 mL, 0.188 mmol) was added and stirred for 10 min at room temperature. The reaction was quenched by diluting with 10 mL EtOAc, and washed with brine. The organic layer was separated, dried over MgSO$_4$, filtered and concentrated. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-60% B over 20 min, then a 5-min hold at 100% B; Flow: 20 mL/min. Fractions containing the desired products were combined and dried via centrifugal evaporation. 2-{8-[(R)-(3-Fluoropyridin-2-yl)(oxan-4-yl)methyl]-13-methoxy-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10,12-hexaen-11-yl}propan-2-ol (16% yield): $^1$H NMR [Acetic acid salt] (500 MHz, DMSO-d$_6$) δ 8.61 (br. s., 2H), 7.96 (s, 1H), 7.82 (br. s., 1H), 7.72 (t, J=9.2 Hz, 1H), 7.51 (dt, J=8.5, 4.4 Hz, 1H), 6.13 (br. s., 1H), 4.09 (s, 3H), 4.04 (br. s., 3H), 3.86 (d, J=9.9 Hz, 1H), 3.70 (d, J=8.8 Hz, 1H), 3.25-3.17 (m, 1H), 2.55 (s, 3H), 1.90 (s, 3H), 1.69 (br. s., 1H), 1.58 (br. s., 1H), 1.30 (dd, J=12.3, 4.2 Hz, 1H), 0.71 (d, J=11.7 Hz, 1H); LC/MS [M+H]$^+$=549.1.

8-[(R)-(3-Fluoropyridin-2-yl)(oxan-4-yl)methyl]-11-(2-hydroxypropan-2-yl)-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10,12-hexaen-13-ol (69% yield): $^1$H NMR [Acetic acid salt] (500 MHz, DMSO-d$_6$) δ 8.61 (d, J=4.8 Hz, 1H), 8.53 (s, 1H), 7.96 (s, 1H), 7.74 (t, J=9.0 Hz, 1H), 7.52 (dt, J=8.3, 4.3 Hz, 1H), 7.08 (br. s., 1H), 6.08 (br. s., 1H), 4.00 (br. s., 3H), 3.86 (d, J=10.3 Hz, 1H), 3.73 (d, J=8.4 Hz, 1H), 3.29-3.16 (m, 1H), 2.74 (s, 2H), 2.55 (s, 4H), 1.90 (s, 3H), 1.66 (br. s., 1H), 1.33 (d, J=13.6 Hz, 1H); LC/MS [M+H]$^+$=535.1.

Example 313

8-[(S)-(3-Fluoropyridin-2-yl)(oxan-4-yl)methyl]-13-methoxy-N-methyl-5-[4-($^2$H$_3$)methyl-1-methyl-1H-1,2,3-triazol-5-yl]-N-[2-(methylamino)ethyl]-3,8,12-triazatricyclo[7.4.0.0$^{2,7}$]trideca-1(9),2(7),3,5,10,12-hexaen-11-amine

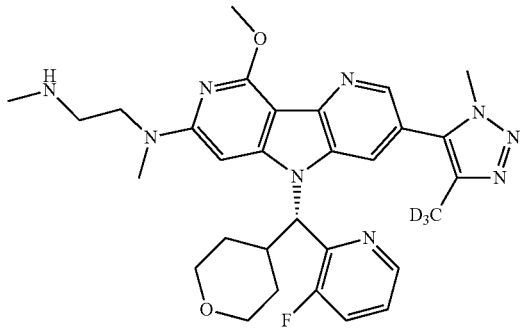 [SMILES: [2H]C([2H])([2H])c1nnn(C)c1-c1cnc2c3c(OC)nc(N(C)CCNC)cc3n([C@H](c3ncccc3F)C3CCOCC3)c2c1]

To 11-chloro-8-[(S)-(3-fluoropyridin-2-yl)(oxan-4-yl)methyl]-13-methoxy-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10,12-hexaene (15.0 mg, 0.029 mmol) in a microwaveable vial was added N1,N2-dimethylethane-1,2-diamine (252 mg, 2.86 mmol), followed by triethylamine (0.020 mL, 0.143 mmol). The resulting mixture was heated in the microwave for 0.5 h. The reaction mixture was filtered and concentrated. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 0-35% B over 25 min, then a 6-min hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile: water with 0.1% trifluoroacetic acid; Mobile Phase B: 95:5 acetonitrile: water with 0.1% trifluoroacetic acid; Gradient: 2-42% B over 20 min, then a 5-min hold at 100% B; Flow: 20 mL/min. Fractions containing the desired product were combined and dried via centrifugal evaporation. The yield of the product was 29%. $^1$H NMR (500 MHz, DMSO-d$_6$) δ 8.62 (br. s., 1H), 8.40 (br. s., 1H), 7.71 (t, J=9.2 Hz, 1H), 7.51 (dt, J=8.5, 4.4 Hz, 1H), 7.16 (br. s., 2H), 6.05 (d, J=11.4 Hz, 1H), 4.05 (s, 5H), 3.99-3.82 (m, 4H), 3.72 (d, J=9.5 Hz, 1H), 3.43-3.36 (m, 1H), 3.22 (d, J=10.6 Hz, 1H), 2.75 (s, 3H), 2.66 (s, 3H), 2.55 (s, 3H), 1.70 (br. s., 1H), 1.58 (d, J=7.3 Hz, 1H), 1.34 (br. s., 1H), 1.25 (d, J=3.3 Hz, 1H), 0.78 (d, J=11.7 Hz, 1H). LCMS (M+1)=577.

Example 314

11-Chloro-8-[(3-fluoropyridin-2-yl)(oxan-4-yl)methyl]-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10,12-hexaene

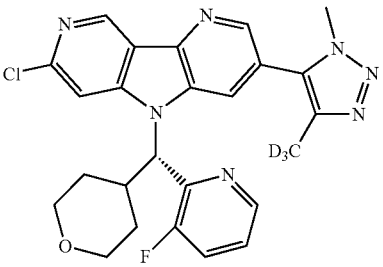 [SMILES: [2H]C([2H])([2H])c1nnn(C)c1-c1cnc2c3cnc(Cl)cc3n([C@H](c3ncccc3F)C3CCOCC3)c2c1]

Step 1: 5-Bromo-11-chloro-8-[(S)-(3-fluoropyridin-2-yl)(oxan-4-yl)methyl]-3,8,12-triazatricyclo[7.4.0.0$^{2,7}$]trideca-1(9),2(7),3,5,10,12-hexaene A 20 mL scintillation vial was charged with PPh$_3$ (111 mg, 0.425 mmol) and THF (8 mL). The vial was cooled in an ice water bath and di-tert-butyl azodicarboxylate (98 mg, 0.425 mmol) was added and stirred for 15 min. (R)-(3-Fluoropyridin-2-yl)(tetrahydro-2H-pyran-4-yl)methanol (90 mg, 0.425 mmol) was added and the resulting mixture stirred for another 15 min. Then 3-bromo-7-chloro-5H-pyrrolo[3,2-b:4,5-c']dipyridine (60.0 mg, 0.212 mmol) was added. The ice-water bath was removed after about 10 min. After 3 h, the reaction was concentrated on the rotavap, and purified on the biotage with an 24 g silica gel column and eluting with 10-100% EtOAc/Hexanes to obtain 70% of the title compound. LCMS (M+1)=476; T$_R$=0.98 min [Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min].

Step 2: 11-Chloro-8-[(3-fluoropyridin-2-yl)(oxan-4-yl)methyl]-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10,12-hexaene A 20 mL scintillation vial was charged with (S)-3-bromo-7-chloro-5-((3-fluoropyridin-2-yl)(tetrahydro-2H-pyran-4- yl)methyl)-5H-pyrrolo[3,2-b:4,5-c']dipyridine (60 mg, 0.126 mmol), 4-($^2$H$_3$)methyl-1-methyl-5-(tributylstannyl)-1H-1,2,3-triazole (49.1 mg, 0.126 mmol), CuI (3.6 mg, 0.019 mmol), triethylamine (25.5 mg, 0.252 mmol) and DMF (8 mL). Argon was bubbled through followed by the addition of Pd(PPh$_3$)$_4$ (10.2 mg, 8.83 µmol) and then heated at 100° C. After 1.5 h, the reaction mixture was concentrated and purified on a 12 g silica gel column, eluting with 0-50% (10% 2M NH$_3$ in MeOH in EtOAc)/EtOAc to obtain 53 mg (84% yield). $^1$H NMR (500 MHz, DMSO-d$_6$) δ 9.24 (s, 1H), 8.72 (s, 1H), 8.64 (d, J=4.8 Hz, 1H), 7.74 (t, J=9.2 Hz, 1H), 7.53 (dt, J=8.5, 4.4 Hz, 1H), 6.26 (d, J=11.0 Hz, 1H), 4.04 (br. s., 2H), 3.86 (d, J=11.4 Hz, 1H), 3.70 (d, J=9.2 Hz, 1H), 2.55 (br. s., 3H), 1.61 (br. s., 2H), 1.39 (d, J=9.9 Hz, 1H), 0.75 (d, J=11.4 Hz, 1H). LCMS (M+1)=495; T$_R$=0.83 min [Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min].

Examples 315-323

The compounds in Table 1 were prepared according to the procedures described for Example 314:

TABLE 1

| Example | R$_1$ | R$_2$ | HPLC T$_R$ (min)$^a$ | LC/MS (M + H) | Chiral Column T$_R$ (min)$^b$ |
|---|---|---|---|---|---|
| 315 | (tetrahydropyran-CH-(2-fluorophenyl), stereo) | 1-methyl-5-(D$_3$C)-1,2,3-triazol-4-yl | 1.660 | 494 | |
| 316 | (tetrahydropyran-CH-(3-fluoropyridin-2-yl), racemic) | 1,5-dimethyl-1,2,3-triazol-4-yl | 1.565 | 492 | |
| 317 | (tetrahydropyran-CH-(3-fluoropyridin-2-yl), Enantiomer 1) | 1,5-dimethyl-1,2,3-triazol-4-yl | 1.563 | 492 | 27.3 |
| 318 | (tetrahydropyran-CH-(3-fluoropyridin-2-yl), Enantiomer 2) | 1,5-dimethyl-1,2,3-triazol-4-yl | 1.565 | 492 | 33.7 |

TABLE 1-continued

| Example | R₁ | R₂ | HPLC T$_R$ (min)$^a$ | LC/MS (M + H) | Chiral Column T$_R$ (min)$^b$ |
|---|---|---|---|---|---|
| 319 | (tetrahydropyran-CH-(3-fluoropyridin-2-yl)), racemic | 1-methyl-5-(CD₃)-triazol-4-yl | 1.568 | 495 | |
| 320 | (tetrahydropyran-CH-(3-fluoropyridin-2-yl)), Enantiomer 1 | 1-methyl-5-(CD₃)-triazol-4-yl | 1.562 | 495 | 27.2 |
| 321 | (tetrahydropyran-CH-(3-fluoropyridin-2-yl)), Enantiomer 2 | 1-methyl-5-(CD₃)-triazol-4-yl | 1.550 | 495 | 33.5 |
| 322 | (tetrahydropyran-CH-(4-fluorophenyl)) | 1,5-dimethyl-triazol-4-yl | 1.726 | 491 | |
| 323 | (tetrahydropyran-CH-(5-chloropyridin-2-yl)) | 1,5-dimethyl-triazol-4-yl | 1.707 | 508 | |

$^a$HPLC Method for Table 1: Column: Waters Acquity UPLC BEH C18, 2.1 × 50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.0 mL/min; Detection: UV at 220 nm.

$^b$Chiral Separation Conditions: Column: Chiralpak AD 21 × 250 mm 5 u; Flow Rate: 15 mL/min; Collection Time: 22 to 49 min; Instrument: 49; Sample Tray: 4 mL vials Solvent A: 100% Heptane; Solvent B: 100% Ethanol; Vial: 20; Isocratic Collection By: UV; Start % B: 15 Wavelength: 254

Example 324

11-Chloro-5-(dimethyl-1,2-oxazol-4-yl)-8-[(3-fluoropyridin-2-yl)(oxan-4-yl)methyl]-3,8,12-triazatricyclo[7.4.0.0²,⁷]trideca-1(9),2(7),3,5,10,12-hexaene

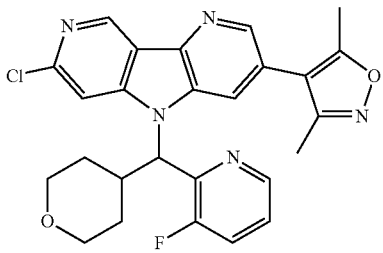 [SMILES: Cc1noc(C)c1-c1cnc2c3cnc(Cl)cc3n(C(c3ncccc3F)C3CCOCC3)c2c1]

Step 1: 3-Bromo-7-chloro-5-((3-fluoropyridin-2-yl)(tetrahydro-2H-pyran-4-yl)methyl)-5H-pyrrolo[3,2-b:4,5-c']dipyridine Following a procedure analogous to the synthesis of 5-bromo-10,13-dichloro-8-[(S)-oxan-4-yl(phenyl)methyl]-3,8,11-triazatricyclo[7.4.0.0²,⁷]trideca-1(9),2(7),3,5,10,12-hexaene, the title compound was synthesized in 95% yield from 3-bromo-7-chloro-5H-pyrrolo[3,2-b:4,5-c']dipyridine. LCMS (M+1)=475; $T_R$=0.98 min [Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min].

Step 2: 11-Chloro-5-(dimethyl-1,2-oxazol-4-yl)-8-[(3-fluoropyridin-2-yl)(oxan-4-yl)methyl]-3,8,12-triazatricyclo[7.4.0.0²,⁷]trideca-1(9),2(7),3,5,10,12-hexaene To 20 mL scintillation vial was added 3-bromo-7-chloro-5-((3-fluoropyridin-2-yl)(tetrahydro-2H-pyran-4-yl)methyl)-5H-pyrrolo[3,2-b:4,5-c']dipyridine (35 mg, 0.074 mmol), 3,5-dimethyl-4-(tributylstannyl)isoxazole (28.4 mg, 0.074 mmol), CuI (2.1 mg, 0.011 mmol), triethylamine (14.9 mg, 0.147 mmol) and DMF (2 mL). Argon was bubbled through followed by the addition of Pd(PPh₃)₄ (6.0 mg, 5.15 μmol) and then heated at 100° C. for 2 days. The reaction was concentrated, redissolved in 1 mL methanol and filtered. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55% B over 15 min, then a 5-min hold at 100% B; Flow: 20 mL/min. Fractions containing the desired product were combined and dried via centrifugal evaporation. The yield of the product was 12%. ¹H NMR (500 MHz, DMSO-d₆) δ 9.15 (s, 1H), 8.60-8.50 (m, 2H), 8.29 (br. s., 2H), 7.79-7.64 (m, 2H), 7.50 (dt, J=8.5, 4.4 Hz, 1H), 6.16 (d, J=11.0 Hz, 1H), 4.43-4.26 (m, 2H), 3.93-3.84 (m, 1H), 3.71 (d, J=8.1 Hz, 1H), 3.21 (t, J=11.4 Hz, 1H), 2.55 (s, 3H), 2.21 (s, 3H), 1.71-1.54 (m, 2H), 1.44-1.30 (m, 1H), 0.67 (d, J=12.8 Hz, 1H). LCMS (M+1)=492; $T_R$=0.84 min [Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min].

Examples 325-328

The compounds in Table 2 were prepared according to the procedures described for Example 324:

TABLE 2

| Example | R | HPLC $T_R$ (min)ᵃ | LC/MS (M + H) | Chiral Column $T_R$ (min)ᵇ |
|---|---|---|---|---|
| 325 | (tetrahydropyran-4-yl)(phenyl)methyl | 1.943 | 473 | |
| 326 | (tetrahydropyran-4-yl)(4-fluorophenyl)methyl | 1.899 | 491 | |

TABLE 2-continued

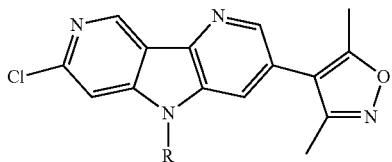

| Example | R | HPLC $T_R$ (min)[a] | LC/MS (M + H) | Chiral Column $T_R$ (min)[b] |
|---|---|---|---|---|
| 327 | Enantiomer 1 | 1.940 | 508 | 15.3 |
| 328 | Enantiomer 2 | 1.940 | 508 | 19.7 |

[a]HPLC Method for Table 2: Column: Waters Acquity UPLC BEH C18, 2.1 × 50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.0 mL/min; Detection: UV at 220 nm.
[b]Chiral Separation Conditions: Column: Chiralpak AD 21 × 250 mm 5 u, Isocratic Collection by UV, Start % B: 15 Wavelength: 254, Flow Rate: 15 mL/min, Solvent A: 100% Heptane, Solvent B: 100% Ethanol, Injection Vol: 250 uL, Collection Time: 12 to 28 min.

Example 329

5-(Dimethyl-1,2-oxazol-4-yl)-11-(1-ethoxyethenyl)-8-[(S)-(4-fluorophenyl)(oxan-4-yl)methyl]-3,8,12-triazatricyclo[7.4.0.0²,⁷]trideca-1(9),2(7),3,5,10,12-hexaene

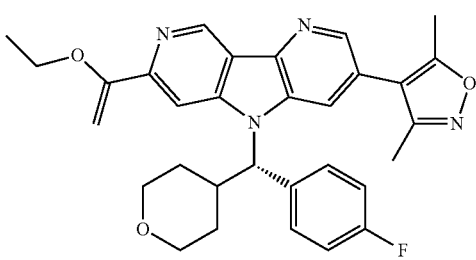 [SMILES: C=C(OCC)c1cc2c(cn1)c1ncc(-c3c(C)noc3C)cc1n2[C@H](c1ccc(F)cc1)C1CCOCC1]

A 20 mL scintillation vial was charged with (S)-4-(7-chloro-5-((4-fluorophenyl)(tetrahydro-2H-pyran-4-yl)methyl)-H-pyrrolo[3,2-b:4,5-c']dipyridin-3-yl)-3,5-dimethylisoxazole (75 mg, 0.153 mmol), tributyl(1-ethoxyvinyl)stannane (55.2 mg, 0.153 mmol), and dioxane (6 mL). This was followed by the addition of PdCl₂(dppf)₂-CH₂Cl₂ adduct (6.2 mg, 7.64 µmol) and the vial.sealed under argon. It was heated to 100° C. with stirring overnight. The reaction was cooled to room temperature, and concentrated on the rotavap. The crude material was purified on the biotage using a 12 g column and eluting with 0-15% (10% 2M NH₃ in MeOH in EtOAc)/EtOAc to obtain 47 mg of the desired product. ¹H NMR (500 MHz, DMSO-d₆) δ 9.34 (s, 1H), 8.57 (d, J=1.5 Hz, 1H), 8.37 (br. s., 1H), 8.11 (br. s., 1H), 7.67 (dd, J=8.6, 5.3 Hz, 2H), 7.19 (t, J=8.8 Hz, 2H), 5.90 (d, J=11.0 Hz, 1H), 5.55 (s, 1H), 4.53 (s, 1H), 4.09-3.99 (m, 2H), 3.94-3.85 (m, 1H), 3.73 (d, J=9.2 Hz, 1H), 3.44 (d, J=8.4 Hz, 1H), 3.30-3.20 (m, 1H), 2.48 (s, 3H), 2.30 (s, 3H), 1.72 (d, J=9.9 Hz, 1H), 1.59 (d, J=7.3 Hz, 1H), 1.49 (t, J=7.0 Hz, 3H), 1.32-1.22 (m, 1H), 0.93 (d, J=12.1 Hz, 1H). LCMS (M+1)=527; $T_R$=0.78 min [Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min].

Example 330

1-[5-(Dimethyl-1,2-oxazol-4-yl)-8-[(S)-(4-fluorophenyl)(oxan-4-yl)methyl]-3,8,12-triazatricyclo[7.4.0.0²,⁷]trideca-1(9),2(7),3,5,10,12-hexaen-11-yl]ethan-1-one

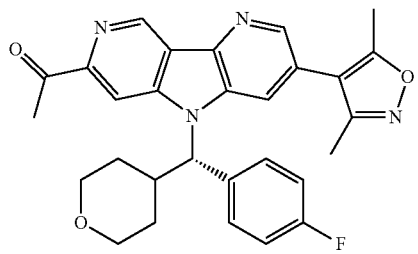 [SMILES: CC(=O)c1cc2c(cn1)c1ncc(-c3c(C)noc3C)cc1n2[C@H](c1ccc(F)cc1)C1CCOCC1]

To 20 mg of 5-(dimethyl-1,2-oxazol-4-yl)-11-(1-ethoxyethenyl)-8-[(S)-(4-fluorophenyl)(oxan-4-yl)methyl]-3,8,12-triazatricyclo[7.4.0.0²,⁷]trideca-1(9),2(7),3,5,10,12-hexaene dissolved in 5 mL of THF was added 1 mL of 3N HCl aq. and stirred. After 1.5 h, the reaction was quenched with 5 mL of aq. K$_2$CO$_3$ (5% solution), and diluted with EtOAc. The organic layer was separated, washed with brine, dried over MgSO$_4$, filtered, and concentrated on the rotavap to obtain a crude mixture. The crude mixture was loaded onto a 12 g silica gel column and purified on the biotage, eluting with 0-15% (10% 2M NH$_3$ in MeOH in EtOAc)/EtOAc to obtain 58% of the desired product. $^1$H NMR (500 MHz, DMSO-d$_6$) δ 9.52 (s, 1H), 8.71 (br. s., 1H), 8.66 (d, J=1.1 Hz, 1H), 8.42 (br. s., 1H), 7.72 (dd, J=8.8, 5.5 Hz, 2H), 7.18 (t, J=8.8 Hz, 2H), 6.05 (d, J=11.7 Hz, 1H), 3.94-3.85 (m, 1H), 3.71 (d, J=8.8 Hz, 1H), 3.55-3.39 (m, 1H), 3.23 (t, J=11.0 Hz, 1H), 2.78 (s, 3H), 2.48 (s, 3H), 2.30 (s, 3H), 1.71-1.65 (m, 1H), 1.61 (d, J=8.8 Hz, 1H), 1.37-1.25 (m, 1H), 0.90 (d, J=12.5 Hz, 1H). LCMS (M+1)=499; T$_R$=0.80 min [Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min].

Example 331

2-[5-(Dimethyl-1,2-oxazol-4-yl)-8-[(S)-(4-fluorophenyl)(oxan-4-yl)methyl]-3,8,12-triazatricyclo[7.4.0.0²,⁷]trideca-1(9),2(7),3,5,10,12-hexaen-11-yl]propan-2-ol

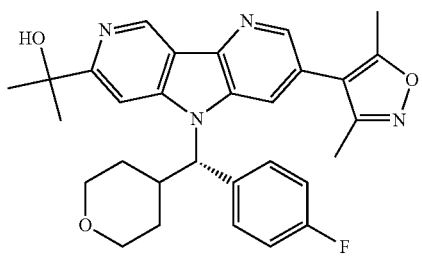 [SMILES: Cc1noc(C)c1-c1cnc2c3cnc(C(C)(C)O)cc3n([C@H](c3ccc(F)cc3)C3CCOCC3)c2c1]

To a solution of (S)-1-(3-(3,5-dimethylisoxazol-4-yl)-5-((4-fluorophenyl)(tetrahydro-2H-pyran-4-yl)methyl)-5H-pyrrolo[3,2-b:4,5-c']dipyridin-7-yl)ethanone (36 mg, 0.072 mmol) in THF (6 mL) at room temperature was added methylmagnesium bromide (86 mg, 0.722 mmol). The resulting mixture was stirred at room temperature overnight and quenched by addition of acetone (5 mL). The sample was concentrated and purified via preparative LC/MS with the following conditions: Column: waters xbridge c-18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 20-60% B over 20 min, then a 5-min hold at 100% B; Flow: 20 mL/min. Fractions containing the desired product were combined and dried via centrifugal evaporation. The yield of the product was 2.7 mg. $^1$H NMR (500 MHz, DMSO-d$_6$) δ 9.36 (s, 1H), 8.65 (s, 1H), 8.40 (br. s., 1H), 7.76 (dd, J=8.4, 5.5 Hz, 2H), 7.25-7.18 (m, 3H), 7.13 (s, 1H), 7.03 (s, 1H), 5.98 (d, J=10.3 Hz, 1H), 3.98-3.86 (m, 1H), 3.74 (d, J=8.8 Hz, 1H), 3.60-3.42 (m, 1H), 3.39-3.21 (m, 1H), 2.48 (s, 3H), 2.30 (s, 3H), 1.72 (br. s., 1H), 1.67 (br. s., 6H), 1.60-1.52 (m, 1H), 1.32 (d, J=12.1 Hz, 1H), 0.96 (d, J=11.7 Hz, 1H; LCMS (M+1)=515; T$_R$=0.71 min [Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min].

Examples 332-339

The compounds in Table 3 were prepared according to the procedures described for Example 331. Where incorporated, the 1,4-dimethyl-1H-1,2,3-triazole was installed by following a procedure analogous to the synthesis 10,13-dichloro-5-[4-($^2$H$_3$)methyl-1-methyl-1H-1,2,3-triazol-5-yl]-8-[(S)-oxan-4-yl(phenyl)methyl]-3,8,11-triazatricyclo[7.4.0.0²,⁷]trideca-1(9),2(7),3,5,10,12-hexaene.

TABLE 3

| Example | R$_1$ | R$_2$ | R$_3$ | HPLC T$_R$ (min)$^a$ | LC/MS (M + H) |
|---|---|---|---|---|---|
| 332 | HO—⫿ | (tetrahydropyran-CH-(2-fluorophenyl)) | (4-D$_3$C-1-methyl-1,2,3-triazol-5-yl) | 1.232 | 518 |

TABLE 3-continued

| Example | R₁ | R₂ | R₃ | HPLC T_R (min)^a | LC/MS (M + H) |
|---|---|---|---|---|---|
| 333 | acetyl | 4-(2-fluorophenyl)(tetrahydropyran-4-yl)methyl | 4-(CD₃)-1-methyl-1,2,3-triazol-5-yl | 1.617 | 502 |
| 334 | 2-hydroxypropan-2-yl | (3-fluoropyridin-2-yl)(tetrahydropyran-4-yl)methyl | 4-(CD₃)-1-methyl-1,2,3-triazol-5-yl | 1.454 | 519 |
| 335 | 2-hydroxypropan-2-yl | phenyl(tetrahydropyran-4-yl)methyl | 3,5-dimethylisoxazol-4-yl | 1.761 | 497 |
| 336 | 2-hydroxypropan-2-yl | (4-fluorophenyl)(tetrahydropyran-4-yl)methyl | 1,4-dimethyl-1,2,3-triazol-5-yl | 1.460 | 515 |
| 337 | acetyl | (4-fluorophenyl)(tetrahydropyran-4-yl)methyl | 1,4-dimethyl-1,2,3-triazol-5-yl | 1.618 | 499 |
| 338 | 2-hydroxypropan-2-yl | (3-fluoropyridin-2-yl)(tetrahydropyran-4-yl)methyl | 3,5-dimethylisoxazol-4-yl | 1.640 | 516 |

TABLE 3-continued

[Structure with R1, R2, R3 substituents on pyrrolodipyridine core]

| Example | R1 | R2 | R3 | HPLC T_R (min)[a] | LC/MS (M + H) |
|---|---|---|---|---|---|
| 339 | HO-C(CH3)2- | (S)-(oxan-4-yl)(3-fluoropyridin-2-yl)methyl | 1,4-dimethyl-1H-1,2,3-triazol-5-yl | 1.211 | 516 |

[a]HPLC Method: Column for Table 3: Waters Acquity UPLC BEH C18, 2.1 × 50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min, then a 0.75-min hold at 100% B; Flow: 1.0 5 mL/min; Detection: UV at 220 nm

Example 340

2-[5-(4-Ethyl-1-methyl-1H-1,2,3-triazol-5-yl)-8-[(S)-oxan-4-yl(phenyl)methyl]-3,8,12-triazatricyclo[7.4.0.0²,⁷]trideca-1(9),2(7),3,5,10,12-hexaen-11-yl]propan-2-ol

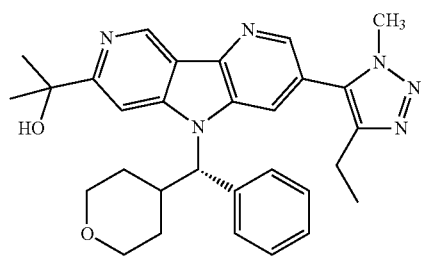 [SMILES: CCc1nnn(C)c1-c1cnc2c3cnc(C(C)(C)O)cc3n([C@H](c3ccccc3)C3CCOCC3)c2c1]

Step 1: (1-Methyl-1H-1,2,3-triazol-4-yl)methyl methanesulfonate

To a solution of (1-methyl-1H-1,2,3-triazol-4-yl)methanol (145 mg, 1.28 mmol) and triethylamine (0.45 mL, 3.2 mmol) in DCM (5 mL) at 0° C. was added methanesulfonyl chloride (0.150 mL, 1.92 mmol). The ice bath was removed and stirring continued for 30 min. The reaction was quenched by addition of saturated sodium bicarbonate. The reaction was diluted with ethyl acetate and the layers separated. The organics were dried over MgSO₄, filtered, and concentrated to give 240 mg (98%). It was used immediately in the next step without purification. ¹H NMR (500 MHz, CDCl₃) δ 7.75 (s, 1H), 5.39 (s, 2H), 4.15 (d, J=1.6 Hz, 3H), 3.06 (s, 3H).

Step 2. 4-Ethyl-1-methyl-1H-1,2,3-triazole

A dry flask was charged with copper(I) iodide (717 mg, 3.77 mmol) and flushed with nitrogen. To this was added THF (5 mL). The resulting suspension was vigorously stirred for 15 min, cooled to 0° C. and treated with methylmagnesium bromide (2.51 mL, 7.53 mmol). After stirring at 0° C. for 15 min, the heterogeneous mixture was treated with a solution of (1-methyl-1H-1,2,3-triazol-4-yl)methyl methanesulfonate (240 mg, 1.26 mmol) in THF (1 mL+1 mL rinse). After stirring for 30 min, the reaction was quenched by addition of saturated ammonium chloride and diluted with ethyl acetate. The layers were separated. The organics were washed with brine spiked with concentrated ammonium hydroxide in water and the layers separated. The organics were dried over MgSO₄, filtered, and concentrated to give 44 mg (32%). ¹H NMR (500 MHz, CDCl₃) δ 7.27 (s, 1H), 4.06 (s, 3H), 2.75 (qd, J=7.6, 0.6 Hz, 2H), 1.28 (t, J=7.6 Hz, 3H).

Step 3: (S)-7-Chloro-3-(4-ethyl-1-methyl-1H-1,2,3-triazol-5-yl)-5-(phenyl(tetrahydro-2H-pyran-4-yl)methyl)-5H-pyrrolo[3,2-b:4,5-c']dipyridine A vial was charged with 5-bromo-11-chloro-8-[(S)-oxan-4-yl(phenyl)methyl]-3,8,12-triazatricyclo[7.4.0.0²,⁷]trideca-1(9),2(7),3,5,10,12-hexaene (139 mg, 0.305 mmol), 4-ethyl-1-methyl-1H-1,2,3-triazole (44 mg, 0.396 mmol), tetramethylammonium acetate (122 mg, 0.914 mmol), and diacetoxypalladium (27.3 mg, 0.122 mmol). The vial was flushed with nitrogen. To this was added N-methylpyrrolidinone (2.0 mL) and the reaction vigorously stirred under a stream of nitrogen for 10 min. The vial was sealed, heated to 100° C., and held at that temperature overnight. The reaction was diluted with ethyl acetate, and washed twice with brine. The organic layer was dried over MgSO₄, concentrated, and purified by preparative HPLC (Column: Phenomenex Luna Axia; 30×100 mm; Mobile Phase A: 10:90 methanol:water with 0.1% TFA; Mobile Phase B: 90:10 methanol:water with 0.1% TFA; Gradient: 10-100% B over 15 min, then a 2-min hold at 100% B; Flow: 40 mL/min). Fractions containing the desired product were combined and concentrated. The resulting residue was suspended in ethyl acetate/saturated sodium bicarbonate and the layers separated. The organics were dried over MgSO₄, filtered, and concentrated to give 30 mg (20%). LC/MS (M+H)=487.25; LC/MS T_R=1.497 min (Column: Acquity BEH C18 21×50 mm 1.7 um; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 4: (S)-3-(4-Ethyl-1-methyl-1H-1,2,3-triazol-5-yl)-5-(phenyl(tetrahydro-2H-pyran-4-yl)methyl)-7-(prop-1-en-2-yl)-5H-pyrrolo[3,2-b:4,5-c']dipyridine A 1 dram vial was charged with (S)-7-chloro-3-(4-ethyl-1-methyl-1H-1,2,3-triazol-5-yl)-5-(phenyl(tetrahydro-2H-pyran-4-yl)methyl)-5H-pyrrolo[3,2-b:4,5-c']dipyridine (30 mg, 0.062 mmol), $Cs_2CO_3$ (40.1 mg, 0.123 mmol), and dioxane (616 μL). The resulting solution was purged with nitrogen for 15 min. To this mixture was added isopropenylboronic acid pinacol ester (23 μL, 0.12 mmol), tricyclohexylphosphine (1 M in toluene, 12 μL, 0.012 mmol), and $Pd_2(dba)_3$ (5.6 mg, 6.2 μmol). The vial was purged 5 min longer, sealed, and immersed in an oil bath preheated to 115° C. The reaction was stirred at that temperature overnight. The reaction was poured into EtOAc, washed with water, then brine, dried over $MgSO_4$, filtered, and concentrated. Column chromatography (0→100% acetone/DCM) gave 21 mg (69%). LC/MS (M+H)=493.20; LC/MS $T_R$=0.925 min (Column: Acquity BEH C18 21×50 mm 1.7 um; Mobile Phase A: water with 0.05% TFA; Mobile Phase B: acetonitrile with 0.05% TFA; Temperature: 40° C.; Gradient: 2-98% B over 1.5 min; Flow: 0.8 mL/min).

Step 5: 2-[5-(4-Ethyl-1-methyl-1H-1,2,3-triazol-5-yl)-8-[(S)-oxan-4-yl(phenyl)methyl]-3,8,12-triazatricyclo[7.4.0.0$^{2,7}$]trideca-1(9),2(7),3,5,10,12-hexaen-11-yl]propan-2-ol A vial was charged with (S)-3-(4-ethyl-1-methyl-1H-1,2,3-triazol-5-yl)-5-(phenyl(tetrahydro-2H-pyran-4-yl)methyl)-7-(prop-1-en-2-yl)-5H-pyrrolo[3,2-b:4,5-c']dipyridine (21 mg, 0.043 mmol), 2-propanol (0.5 mL), and DCM (0.1 mL). The resulting solution was placed in a 0° C. bath, treated with phenylsilane (10.5 μL, 0.085 mmol), purged with oxygen, and treated with tris(2,2,6,6-tetramethyl-3,5-heptanedionato)manganese(III) (2.6 mg, 4.3 μmol). The vial was purged with oxygen again and stirred under a balloon of oxygen for 30 min at 0° C. The reaction was quenched by addition of 20% aqueous sodium thiosulfate. After stirring for 5 min at 0° C., the reaction was diluted with ethyl acetate and the layers separated. The organics were concentrated and the resulting residue purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 15 min, then a 5-min hold at 100% B; Flow: 20 mL/min. Fractions containing the desired product were combined and dried via centrifugal evaporation to give 12.6 mg (57%). $^1$H NMR (500 MHz, DMSO-d$_6$) δ 9.34 (s, 1H), 8.56 (s, 1H), 8.44 (s, 1H), 8.25 (s, 1H), 7.66 (d, J=8.1 Hz, 2H), 7.38-7.32 (m, 2H), 7.31-7.25 (m, 1H), 5.80 (d, J=11.0 Hz, 1H), 3.97 (s, 3H), 3.91 (d, J=10.3 Hz, 1H), 3.76 (d, J=9.5 Hz, 1H), 3.53-3.25 (m, 2H), 2.65 (dquin, J=15.2, 7.6 Hz, 2H), 2.55 (s, 3H), 1.71 (d, J=12.1 Hz, 1H), 1.61 (s, 3H), 1.59 (s, 3H), 1.41-1.28 (m, 1H), 1.17 (t, J=7.5 Hz, 3H), 1.06 (d, J=12.5 Hz, 1H); LC/MS (M+H)=511.1.

Example 341

8-[(S)-(3-Fluoropyridin-2-yl)(oxan-4-yl)methyl]-10-methanesulfonyl-5-[4-($^2$H$_3$)methyl-1-methyl-1H-1,2,3-triazol-5-yl]-N-(2,2,2-trifluoroethyl)-3,8,12-triazatricyclo[7.4.0.0$^{2,7}$]trideca-1(13),2(7),3,5,9,11-hexaen-13-amine

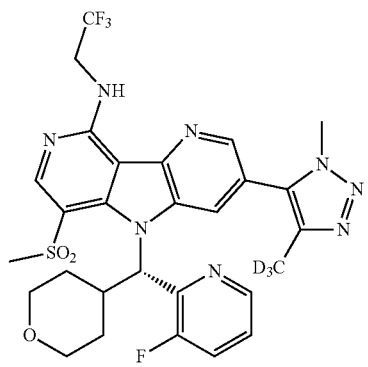 [SMILES: [2H]C([2H])([2H])c1nnn(C)c1-c1cnc2c3c(NCC(F)(F)F)ncc(S(C)(=O)=O)c3n([C@H](c3ncccc3F)C3CCOCC3)c2c1]

The title compound was prepared according to the procedure of 10-methanesulfonyl-5-[4-($^2$H$_3$)methyl-1-methyl-1H-1,2,3-triazol-5-yl]-8-[(S)-oxan-4-yl(phenyl)methyl]-N-(2,2,2-trifluoroethyl)-3,8,12-triazatricyclo[7.4.0.0$^{2,7}$]trideca-1(13),2(7),3,5,9,11-hexaen-13-amine, beginning with 8-[(3-fluoropyridin-2-yl)(oxan-4-yl)methyl]-10-methanesulfonyl-13-methoxy-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaene. $^1$H NMR (500 MHz, DMSO) δ 8.84 (s, 1H), 8.73 (d, J=1.5 Hz, 1H), 8.56 (d, J=4.4 Hz, 1H), 8.42 (t, J=6.6×2 Hz, 1H), 8.1 (d, J=1.5 Hz, 1H), 7.7 (m, 1H), 7.52 (m, 1H), 7.1 (d, J=9.5 Hz, 1H), 4.7 (m, 2H), 3.9 (s, 3H), 3.88 (d, J=11.7 Hz, 1H), 3.68 (d, J=6.6 Hz, 1H), 3.46 (brs, 1H), 3.36 (m, 2H), 2.55 (s, 3H), 1.79 (d, J=12.1 Hz, 1H), 1.66 (d, J=12.1 Hz, 2H), 0.53 (d, J=11.4 Hz, 1H); LCMS (M+H)=636.5.

Example 342

11-Methanesulfonyl-13-methoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene

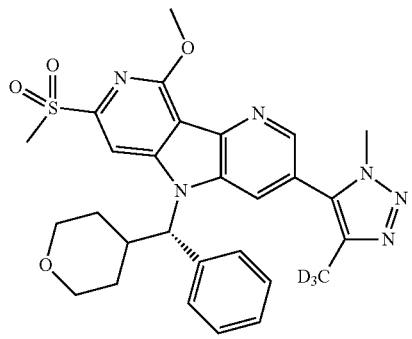 [SMILES: [2H]C([2H])([2H])c1nnn(C)c1-c1cnc2c3c(OC)nc(S(C)(=O)=O)cc3n([C@H](c3ccccc3)C3CCOCC3)c2c1]

Step 1: 5-Bromo-6'-chloro-2'-methoxy-3-nitro-2,3'-bipyridine

A 150 mL pressure flask was charged with (6-chloro-2-methoxypyridin-3-yl)boronic acid (2.5 g, 13.3 mmol) and 2,5-dibromo-3-nitropyridine (3.38 g, 12.01 mmol). The solids were suspended in THF (60 mL). The mixture was treated with $PdCl_2(dppf)\cdot CH_2Cl_2$ adduct (0.545 g, 0.667 mmol) and $K_3PO_4$ (2M, 20 mL, 40 mmol). Argon was bubbled through the mixture for 5 min while sonicating. The flask was capped and heated to 80° C. in a preheated oil bath. The reaction was cooled to room temperature. The reaction mixture was filtered and the filtrate was concentrated to remove THF. The remaining water layer was diluted further with water and was extracted with ethyl acetate. The organic layer was dried over $MgSO_4$, filtered and concentrated under vacuum to give a solid. The material was taken up in DCM and a minimum of ethyl acetate and purified by flash column chromatography (80 g ISCO column, 0-30% ethyl acetate/hexanes over 600 mL, then 50-100% over 300 mL). Like fractions were concentrated to give 4.5 g (78%). $^1$H NMR (400 MHz, $CDCl_3$) δ 8.94 (d, J=2.0 Hz, 1H), 8.44 (d, J=2.0 Hz, 1H), 7.97 (d, J=8.0 Hz, 1H), 7.14 (d, J=7.8 Hz, 1H), 3.89 (s, 3H). LC/MS (M+H)=345.95.

Step 2: 3-Bromo-7-chloro-9-methoxy-5H-pyrrolo[3,2-b:4,5-c']dipyridine

A round bottom flask was charged with 5-bromo-6'-chloro-2'-methoxy-3-nitro-2,3'-bipyridine (3 g, 8.71 mmol) and bis(diphenylphosphino)ethane (4.34 g, 10.9 mmol). The solids were suspended in 1,2-dichlorobenzene (9.80 mL). The flask was flushed with nitrogen. The reaction was heated to 150° C. in a preheated oil bath while stirring. After the reaction was complete by LCMS, the reaction was allowed to continue for 1 h open to air. The solvent was removed under a stream of nitrogen while heating to 100° C. 100 mL of DCM was added directly to the reaction mixture and was stirred at room temperature overnight. A white precipitate formed and was collected by filtration, washing with DCM to give 683 mg (23%). $^1$H NMR (400 MHz, DMSO-$d_6$) δ 12.18 (s, 1H), 8.61 (d, J=2.3 Hz, 1H), 8.22 (d, J=2.0 Hz, 1H), 7.30 (s, 1H), 4.09 (s, 3H). LC/MS (M+H)=313.95.

Step 3: (S)-3-Bromo-7-chloro-9-methoxy-5-(phenyl(tetrahydro-2H-pyran-4-yl)methyl)-5H-pyrrolo[3,2-b:4,5-c']dipyridine A round bottom flask was charged with 3-bromo-7-chloro-9-methoxy-5H-pyrrolo[3,2-b:4,5-c']dipyridine (380 mg, 1.22 mmol) and THF (15 mL). (R)-phenyl(tetrahydro-2H-pyran-4-yl)methanol (467 mg, 2.43 mmol), triphenylphosphine (638 mg, 2.43 mmol), and triethylamine (0.339 mL, 2.43 mmol) were added and the vial was cooled in an ice-water bath. Di-tert-butyl azodicarboxylate (560 mg, 2.43 mmol) was added dropwise and the reaction was stirred for 15 min at 0° C. before the ice bath was removed. The reaction was allowed to warm to room temperature and stir overnight. The reaction mixture was concentrated under vacuum. The residue was taken up in DCM and was transferred to the top of 24 g and 40 g ISCO FCC combined columns and then eluted with 0-100% ethyl acetate/hexanes over 900 mL of total solvent. Like fractions were combined and concentrated to give 650 mg (93%). $^1$H NMR (400 MHz, $CDCl_3$) δ 8.79 (d, J=1.8 Hz, 1H), 8.08 (d, J=1.8 Hz, 1H), 7.48-7.33 (m, 4H), 7.29 (s, 1H), 7.23 (s, 1H), 5.30 (d, J=11.0 Hz, 1H), 4.23 (s, 3H), 4.10 (dd, J=11.9, 2.9 Hz, 1H), 3.93 (dd, J=12.0, 3.3 Hz, 1H), 3.65-3.53 (m, 1H), 3.52-3.32 (m, 1H), 3.05 (dt, J=11.4, 3.6 Hz, 1H), 2.00 (d, J=13.1 Hz, 1H), 1.65-1.51 (m, 1H), 1.45-1.33 (m, 1H), 1.02 (d, J=13.3 Hz, 1H). LC/MS (M+H)=488.04.

Step 4: 11-Chloro-13-methoxy-5-[4-($^2H_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene A pressure vessel was charged with (S)-3-bromo-7-chloro-9-methoxy-5-(phenyl(tetrahydro-2H-pyran-4-yl)methyl)-5H-pyrrolo[3,2-b:4,5-c']dipyridine (100 mg, 0.205 mmol), 4-($^2H_3$)methyl-1-methyl-5-(tributylstannyl)-1H-1,2,3-triazole (84 mg, 0.216 mmol), and $(Ph_3P)_4Pd$ (23.7 mg, 0.021 mmol). The solids were suspended in DMF (2.5 mL). The reaction mixture was stirred and bubbled in argon for 5 min before copper (I) iodide (7.8 mg, 0.041 mmol) and triethylamine (0.043 mL, 0.308 mmol) were added. Argon was bubbled through the mixture again for 5 min and the vessel was placed in a preheated oil bath at 100° C. The reaction was allowed to continue heating for 16 h with stirring. The reaction was cooled to room temperature, filtered through a syringe filter, and diluted with excess water and ethyl acetate. The organic layer was removed and dried over $MgSO_4$, filtered and concentrated under vacuum. The residue was purified by preparative HPLC: (20-100% B; B solvent 90% $CH_3CN$/0.1% TFA water, Phenomenex AXIA LUNA C18 30×100 mm, 10 micron, 254 nm UV, 30 mL/min; $T_R$ 10.7 min. for the desired product). Like fractions were combined and concentrated under vacuum to give 70 mg (61%). $^1$H NMR (500 MHz, DMSO-$d_6$) δ 8.63 (d, J=1.5 Hz, 1H), 8.45 (br. s., 1H), 7.68 (d, J=7.3 Hz, 3H), 7.36 (t, J=7.6 Hz, 2H), 7.31-7.23 (m, 1H), 5.85 (d, J=11.1 Hz, 1H), 4.10 (s, 3H), 3.98 (s, 3H), 3.88 (d, J=11.0 Hz, 1H), 3.74 (d, J=12.1 Hz, 1H), 3.51-3.37 (m, 2H), 3.26 (t, J=11.5 Hz, 1H), 2.12-2.03 (m, 3H), 1.72-1.63 (m, 1H), 1.62-1.46 (m, 1H), 1.36-1.20 (m, 2H), 0.94 (d, J=12.2 Hz, 1H). LC/MS (M+H)=506.1.

Step 5: 11-Methanesulfonyl-13-methoxy-5-[4-($^2H_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene A pressure vessel was charged with 11-chloro-13-methoxy-5-[4-($^2H_3$)methyl-1-methyl-1H-1,2,3-triazol-5-yl]-8-[(S)-oxan-4-yl(phenyl)methyl]-3,8,12 triazatricyclo[7.4.0.0$^{2,7}$]trideca-1(13),2(7),3,5,9,11-hexaene (20 mg, 0.040 mmol), sodium methanesulfinate (12.1 mg, 0.119 mmol), and copper(II)trifluoromethanesulfonate (14.3 mg, 0.040 mmol). The solids were dissolved in DMSO (1 mL). N,N'-dimethylethylene diamine (0.013 mL, 0.119 mmol) was added. The vial was purged with argon, capped, and placed in a preheated oil bath at 100° C. The reaction was stirred for 4 h. Solids were removed by filtration, and the filtrate purified by preparative HPLC: Column: Water XBridge C18, 19×200 mm, 5-µm particles; Mobile Phase A: 5:95 methanol: water with 10 mM ammonium acetate; Mobile Phase B: 95:5 methanol: water with 10 mM ammonium acetate; Gradient: 10-50% B over 15 min, then a 5-min hold at 100% B; Flow: 20 mL/min. Fractions containing the desired product were combined and dried via centrifugal evaporation to give 4.9 mg (21%). $^1$H NMR (500 MHz, DMSO-$d_6$) δ 8.74 (s, 1H), 8.56 (br. s., 1H), 7.67 (d, J=7.7 Hz, 2H), 7.36 (t, J=7.2 Hz, 2H), 7.29 (t, J=7.9 Hz, 1H), 6.11 (d, J=11.7 Hz, 1H), 4.20 (s, 3H), 4.16-4.07 (m, 1H), 3.99 (s, 3H), 3.93-3.84 (m, 3H), 3.73 (d, J=9.2 Hz, 1H), 3.56-3.44 (m, 1H), 3.42 (s, 3H), 3.24 (t, J=11.7 Hz, 1H), 3.18 (d, J=5.1 Hz, 3H), 1.69 (br. s., 2H), 1.33 (d, J=9.5 Hz, 1H), 0.88 (d, J=13.6 Hz, 1H). LC/MS (M+H)=550.25.

Example 343

11-(4,4-Difluoropiperidin-1-yl)-13-methoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene

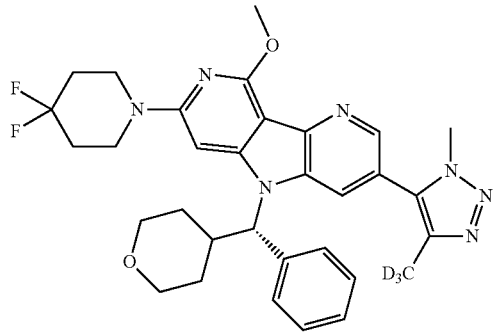 [SMILES: [2H]C([2H])([2H])c1nnn(C)c1-c1cnc2c3c(OC)nc(N4CCC(F)(F)CC4)cc3n([C@H](c3ccccc3)C3CCOCC3)c2c1]

A pressure vial was charged with 11-chloro-13-methoxy-5-[4-($^2$H$_3$)methyl-1-methyl-1H-1,2,3-triazol-5-yl]-8-[(S)-oxan-4-yl(phenyl)methyl]-3,8,12 triazatricyclo[7.4.0.0$^{2,7}$]trideca-1(13),2(7),3,5,9,11-hexaene (20 mg, 0.040 mmol), 4,4-difluoropiperidine HCl (9.3 mg, 0.059 mmol) and dioxane (2 mL). To this was added (2-dicyclohexylphosphino-2',6'-diisopropyl-1,1'-biphenyl)[2-(2-aminoethyl)phenyl]palladium(II) (1.7 mg, 2.4 µmol), Pd(OAc)$_2$ (0.5 mg, 2.4 µmol), RuPhos (1.1 mg, 2.4 µmol), and sodium t-butoxide (15.2 mg, 0.16 mmol). Argon was bubbled into the mixture with sonication for 5 min. The vial was capped and placed in a preheated oil bath at 100° C. The reaction mixture was stirred for 16 h. Solids were removed by filtration, and the filtrate purified by preparative HPLC: Column: Water XBridge C18, 19×200 mm, 5-µm particles; Mobile Phase A: 5:95 methanol: water with 10 mM ammonium acetate; Mobile Phase B: 95:5 methanol: water with 10 mM ammonium acetate; Gradient: 40-80% B over 16 min, then a 5-min hold at 100% B; Flow: 20 mL/min. Fractions containing the desired product were combined and dried via centrifugal evaporation to give 5.0 mg (21%). $^1$H NMR (500 MHz, DMSO-d$_6$) δ 8.37 (s, 1H), 8.11 (br. s., 1H), 7.67 (d, J=7.3 Hz, 2H), 7.34 (t, J=7.3 Hz, 2H), 7.30-7.20 (m, 1H), 5.73 (d, J=11.0 Hz, 1H), 4.03 (s, 3H), 3.98-3.83 (m, 9H), 3.75 (d, J=8.8 Hz, 1H), 3.47 (t, J=11.2 Hz, 1H), 3.26 (t, J=11.7 Hz, 1H), 3.17 (br. s., 1H), 2.10 (br. s., 4H), 1.70 (d, J=13.6 Hz, 1H), 1.55 (d, J=10.6 Hz, 1H), 1.33 (d, J=11.0 Hz, 1H), 1.00 (d, J=12.1 Hz, 1H). LC/MS (M+H)=591.34.

Example 344

2-{13-Methoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaen-11-yl}propan-2-ol

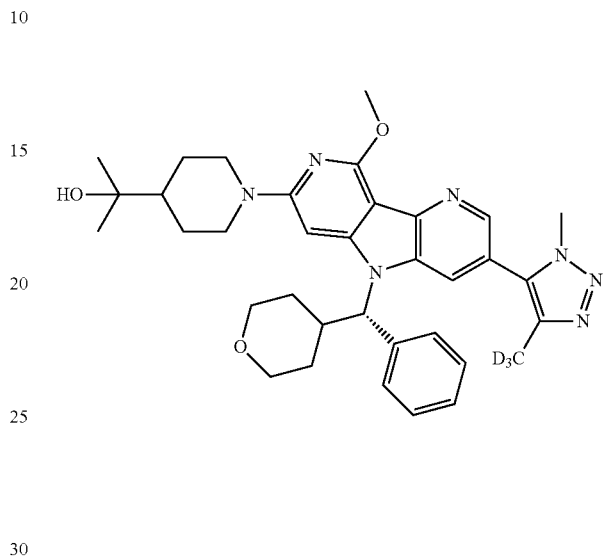

A 20 mL vial was charged with 11-chloro-13-methoxy-5-[4-($^2$H$_3$)methyl-1-methyl-1H-1,2,3-triazol-5-yl]-8-[(S)-oxan-4yl(phenyl)methyl]-3,8,12 triazatricyclo[7.4.0.0$^{2,7}$]trideca-1(13),2(7),3,5,9,11-hexaene (20 mg, 0.039 mmol), cerium (III) chloride (19.2 mg, 0.078 mmol), and THF (2 mL). The vial was cooled to 0° C. and methyl magnesium bromide (3M in diethyl ether, 0.13 mL, 0.39 mmol) was added. The reaction was stirred for 1 h while allowing it to warm to room temperature. After 1 h at room temperature, the mixture was quenched with saturated ammonium chloride solution and diluted with ethyl acetate. The mixture was transferred to a separatory funnel and the layers separated. Brine was added to break up the emulsion. The organic layer was dried over MgSO$_4$, filtered, and concentrated to give an off-white residue. Solids were removed by filtration, and the filtrate purified by preparative HPLC: Column: Water XBridge C18, 19×200 mm, 5-µm particles; Mobile Phase A: 5:95 methanol: water with 10 mM ammonium acetate; Mobile Phase B: 95:5 methanol: water with 10 mM ammonium acetate; Gradient: 25-65% B over 15 min, then a 5-min hold at 100% B; Flow: 20 mL/min. Fractions containing the desired product were combined and dried via centrifugal evaporation to give 14.9 mg (72%). $^1$H NMR (500 MHz, DMSO-d$_6$) δ 8.56 (d, J=1.8 Hz, 1H), 8.38 (br. s., 1H), 7.88 (br. s., 1H), 7.65 (d, J=7.7 Hz, 2H), 7.41-7.31 (m, 2H), 7.31-7.13 (m, 1H), 5.77 (d, J=11.4 Hz, 1H), 5.33 (s, 1H), 4.10 (s, 3H), 3.98 (s, 3H), 3.94-3.84 (m, 1H), 3.74 (d, J=10.3 Hz, 1H), 3.37 (d, J=4.4 Hz, 1H), 3.32-3.21 (m, 1H), 1.71 (d, J=13.2 Hz, 1H), 1.56 (s, 3H), 1.58 (s, 4H), 1.39-1.20 (m, 1H), 0.97 (d, J=12.1 Hz, 1H). LC/MS (M+H)=530.37.

Examples 345 & 346

2-{8-[(4,4-Difluorocyclohexyl)(phenyl)methyl]-13-methoxy-5-[4-($^2H_3$)methyl-1-methyl-1H-1,2,3-triazol-5-yl]-3,8,12-triazatricyclo[7.4.0.0$^{2,7}$]trideca-1(13),2(7),3,5,9,11-hexaen-11-yl}propan-2-ol Example 345

Enantiomer A

Example 346

Enantionmer B

Step 1: 11-Chloro-13-methoxy-5-[4-($^2H_3$)methyl-1-methyl-1H-1,2,3-triazol-5-yl]-3,8,12-triazatricyclo[7.4.0.0$^{2,7}$]trideca-1(9),2(7),3,5,10,12-hexaene 3-Bromo-7-chloro-9-methoxy-5H-pyrrolo[3,2-b:4,5-c']dipyridine (1.0 g, 3.2 mmol), 4-($^2H_3$)methyl-1-methyl-5-(tributylstannyl)-1H-1,2,3-triazole (36.9 mg, 0.102 mmol), CuI (0.091 g, 0.480 mmol), Pd(PPh$_3$)$_4$ (0.259 g, 0.224 mmol), triethylamine (0.892 mL, 6.40 mmol) and DMF (20 mL) were weighed into a 20 mL scintillation vial and sealed under argon. The vial was placed in a reaction block preheated to 100° C. and stirred for 16 h. The reaction was concentrated to dryness under vacuum with heating. The crude mixture was purified by flash chromatography: (40 g ISCO RediSep 0-40% 10% (2M NH$_3$ in EtOAc)/EtOAc) to obtain 734 mg (69%). $^1$H NMR (400 MHz, DMSO-d$_6$) δ 8.61 (d, J=1.8 Hz, 1H), 8.08 (d, J=2.0 Hz, 1H), 7.31 (s, 1H), 4.12 (s, 3H), 4.00 (s, 3H).

Step 2: 11-Chloro-8-[(4,4-difluorocyclohexyl)(phenyl)methyl]-13-methoxy-5-[4-($^2H_3$)methyl-1-methyl-1H-1,2,3-triazol-5-yl]-3,8,12-triazatricyclo[7.4.0.0$^{2,7}$]trideca-1(13),2(7),3,5,9,11-hexaene A 20 mL vial was charged with 11-chloro-13-methoxy-5-[4-($^2H_3$)methyl-1-methyl-1H-1,2,3-triazol-5-yl]-3,8,12-triazatricyclo[7.4.0.0$^{2,7}$]trideca-1(9),2(7),3,5,10,12-hexaene (150 mg, 0.452 mmol) and DCM (10 mL). (4,4-difluorocyclohexyl)(phenyl)methanol (205 mg, 0.904 mmol), Ph$_3$P (237 mg, 0.904 mmol), and triethylamine (0.126 mL, 0.904 mmol) were added and the vial cooled to 0° C. DIAD (0.088 mL, 0.452 mmol) was added. The reaction was stirred for 15 min at 0° C. and allowed to warm to room temperature overnight. The reaction mixture was concentrated under vacuum. This residue was taken up in DCM, transferred to the top of a 40 g ISCO silica column, and eluted with 0-100% B (B=10% 2M NH$_3$ in methanol in ethyl acetate)/hexanes over 750 mL of total solvent. Like fractions were combined and concentrated to give 100 mg (41%). LC/MS (M+H)=540.25; HPLC conditions: T$_R$=4.27 min.; purity 98%: Column: Phenomenex LUNA C18 2×50 mm (4 min grad) eluting with 10-90% aqueous methanol containing 0.1% TFA, 0.8 mL/min, monitoring at 254 nm); Temperature: 40° C.

Step 3: 1-{8-[(4,4-Difluorocyclohexyl)(phenyl)methyl]-13-methoxy-5-[4-($^2H_3$)methyl-1-methyl-1H-1,2,3-triazol-5-yl]-3,8,12-triazatricyclo[7.4.0.0$^{2,7}$]trideca-1(13),2(7),3,5,9,11-hexaen-11-yl}ethan-1-one A pressure vessel was charged with 11-chloro-8-[(4,4-difluorocyclohexyl)(phenyl)methyl]-13-methoxy-5-[4-($^2H_3$)methyl-1-methyl-1H-1,2,3-triazol-5-yl]-3,8,12-triazatricyclo[7.4.0.0$^{2,7}$]trideca-1(13),2(7),3,5,9,11-hexaene (50 mg, 0.093 mmol), tributyl(1-ethoxyvinyl)stannane (36.8 mg, 0.102 mmol), and PdCl$_2$(dppf)-CH$_2$Cl$_2$ adduct (7.6 mg, 9.3 µmol). The solids were suspended in dioxane (3 mL). Argon was bubbled through the mixture for 5 min. The vessel was placed in a preheated oil bath at 100° C. The reaction was allowed to continue heating for 16 h with stirring. The reaction was cooled to room temperature. The mixture was filtered through a syringe filter and concentrated under vacuum. The residue was taken up in 10 mL of THF and treated with 2 mL of 2M HCl solution while stirring for 2 h at room temperature. The solution was neutralized with aq. K$_2$CO$_3$ solution, extracted with ethyl acetate, dried over MgSO$_4$, filtered, and concentrated under vacuum. The material was taken up in DCM and purified by flash column chromatography (24+40 g ISCO columns, 0-50%, then 50-100% of B: 10% 2M ammonia in methanol in ethyl acetate/hexanes over 900 mL). Like fractions were concentrated to give 40 mg (39%). LC/MS (M+H)=548.30; HPLC conditions: T$_R$=4.15 min.; purity 99%: Column: Phenomenex LUNA C18 2×50 mm (4 min grad) eluting with 10-90% aqueous methanol containing 0.1% TFA, 0.8 mL/min, monitoring at 254 nm); Temperature: 40° C.

Step 4: 2-{8-[(4,4-Difluorocyclohexyl)(phenyl)methyl]-13-methoxy-5-[4-($^2H_3$)methyl-1-methyl-1H-1,2,3-triazol-5-yl]-3,8,12-triazatricyclo[7.4.0.0$^{2,7}$]trideca-1(13),2(7),3,5,9,11-hexaen-11-yl}propan-2-ol A 20 mL vial containing was charged with 1-{8-[(4,4-difluorocyclohexyl)(phenyl)methyl]-13-methoxy-5-[4-($^2H_3$)methyl-1-methyl-1H-1,2,3-triazol-5-yl]-3,8,12-triazatricyclo[7.4.0.0$^{2,7}$]trideca-1(13),2(7),3,5,9,11-hexaen-11-yl}ethan-1-one (40 mg, 0.073 mmol) and THF (3 mL). The vial was cooled to 0° C. and methyl magnesium bromide (3M in diethyl ether, 0.146 mL, 0.438 mmol) was added. The reaction was stirred for 1 h while allowing it to warm to room temperature. After 1 h at room temperature, the mixture was quenched with saturated ammonium chloride solution and diluted with ethyl acetate. The mixture was transferred to a separatory funnel and the layers separated. Brine was added to break up the emulsion. The organic layer was dried over MgSO$_4$, filtered, and concentrated under vacuum to give an off-white residue. Solids in the reaction mixture were filtered, and this material was subjected to chiral separation: Chiralcel OD preparative column, 21×250 mm, 10 μm; Mobile Phase: 15% ethanol/heptane over 32 min., Flow rate: 15.0 mL/min.; UV monitored at 254 nm; T$_R$=Enantiomer A: 14.7 min.; Enantiomer B: 21.1 min. Fractions containing the desired products were combined and dried via evaporation to give 9.1 mg (22%) of Enantiomer A and 12.1 mg (29%) of Enantiomer B. $^1$H NMR (500 MHz, DMSO-d$_6$) δ 8.57 (d, J=1.8 Hz, 1H), 8.39 (br. s., 1H), 7.90 (br. s., 1H), 7.65 (d, J=7.7 Hz, 2H), 7.43-7.31 (m, 2H), 7.31-7.21 (m, 1H), 5.82 (d, J=11.7 Hz, 1H), 5.30 (s, 1H), 4.10 (s, 3H), 4.00 (s, 3H), 2.16-2.03 (m, 2H), 2.03-1.84 (m, 3H), 1.83-1.67 (m, 1H), 1.58 (d, J=9.2 Hz, 8H), 1.39-1.17 (m, 2H). LC/MS (M+H)=564.33.

Example 347

12-Chloro-5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(13),2(7),3,5,9,11-hexaene

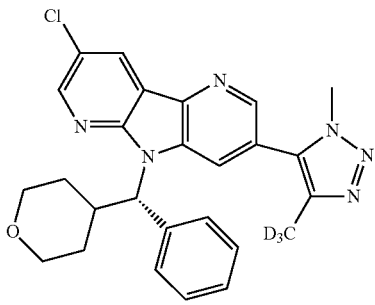 [SMILES: [2H]C([2H])([2H])c1nnn(C)c1-c1cnc2c3cc(Cl)cnc3n([C@H](c3ccccc3)C3CCOCC3)c2c1]

Step 1: 5-Bromo-5'-chloro-3-nitro-2,3'-bipyridine

A pressure flask was charged with (5-chloropyridin-3-yl)boronic acid (5 g, 31.8 mmol) and 2,5-dibromo-3-nitropyridine (8.06 g, 28.6 mmol). The solids were suspended in THF (100 mL). The mixture was treated with PdCl$_2$(dppf)-CH$_2$Cl$_2$ adduct (1.297 g, 1.589 mmol) and K$_3$PO$_4$ (2M, 47.7 mL, 95 mmol). Argon was bubbled through the mixture for 5 min while sonicating. The flask was capped and heated to 80° C. in a preheated oil bath for 2 h. The reaction was cooled to room temperature, filtered, and the filtrate was concentrated to remove THF. The remaining water layer was diluted further with water and extracted with ethyl acetate. The organic layer was dried over MgSO$_4$, filtered and concentrated under vacuum to give a solid. The material was triturated with ethanol and the remaining brown solid (6.8 g, 68%) dried under vacuum. LC/MS (M+H)=315.97; HPLC conditions: T$_R$=3.73 min.: Column: Phenomenex LUNA C18 2×50 mm (4 min grad) eluting with 10-90% aqueous methanol containing 0.1% TFA, 0.8 mL/min, monitoring at 254 nm); Temperature: 40° C.

Step 2: 3-Bromo-8-chloro-5H-pyrrolo[2,3-b:4,5-b']dipyridine

A round bottom flask was charged with 5-bromo-5'-chloro-3-nitro-2,3'-bipyridine (3 g, 9.54 mmol) and bis(diphenylphosphino)ethane (4.75 g, 11.9 mmol). The solids were suspended in 1,2-dichlorobenzene (10.7 mL). The flask was flushed with nitrogen. The reaction was heated to 150° C. in a preheated oil bath while stirring. After the reaction was complete by LCMS, the reaction was allowed to continue for 1 h open to air. The solvent was removed under a stream of nitrogen while heating to 100° C. The reaction mixture was diluted with 100 mL of DCM, stirred at 0° C., and allowed to warm to room temperature overnight. A white precipitate (175 mg, 6%) formed and was collected by filtration, washing with DCM. TLC: 30% B/hexanes (B: 10% 2 M NH$_3$ in methanol/EtOAc); Rf=0.40; other isomer Rf=0.67. LC/MS (M+H)=283.98; HPLC conditions: T$_R$=3.84 min.: Column: Phenomenex LUNA C18 2×50 mm (4 min grad) eluting with 10-90% aqueous methanol containing 0.1% TFA, 0.8 mL/min, monitoring at 254 nm); Temperature: 40° C.

Step 3: (S)-3-Bromo-8-chloro-5-(phenyl(tetrahydro-2H-pyran-4-yl)methyl)-5H-pyrrolo[2,3-b:4,5-b']dipyridine A 100 mL round bottom flask was charged with 3-bromo-8-chloro-5H-pyrrolo[2,3-b:4,5-b']dipyridine (425 mg, 1.50 mmol) and DCM (20 mL). (R)-phenyl(tetrahydro-2H-pyran-4-yl)methanol (578 mg, 3.01 mmol), Ph$_3$P (789 mg, 3.01 mmol), and triethylamine (0.419 mL, 3.01 mmol) were added and the vial cooled to 0° C. DIAD (0.585 mL, 3.01 mmol) was added and the reaction stirred for 15 min at 0° C. The reaction was allowed to warm to room temperature overnight. The reaction mixture was concentrated under vacuum. The residue was taken up in DCM and was transferred to the top of a 80 g ISCO silica column and was eluted with 0-100% ethyl acetate/hexanes over 900 mL of total solvent. Like fractions were combined (R$_f$ 0.67 in 50% EA/hexanes) and concentrated to give 560 mg (82%). LC/MS (M+H)=457.9; HPLC conditions: T$_R$=1.21 min.: Column: Phenomenex LUNA C18 2×50 mm (4 min grad) eluting with 10-90% aqueous methanol containing 0.1% TFA, 0.8 mL/min, monitoring at 254 nm); Temperature: 40° C.

Step 4: 12-Chloro-5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(13),2(7),3,5,9,11-hexaene A pressure vessel was charged with (S)-3-bromo-8-chloro-5-(phenyl(tetrahydro-2H-pyran-4-yl)methyl)-5H-pyrrolo[2,3-b:4,5-b']dipyridine (50 mg, 0.11 mmol), 4-($^2$H$_3$)methyl-1-methyl-5-(tributylstannyl)-1H-1,2,3-triazole (44.7 mg, 0.115 mmol), and (Ph$_3$P)$_4$Pd (12.7 mg, 11.0 μmol). The solids were suspended in DMF (2 mL) and stirred while bubbling argon for 5 min. To this was added copper(I) iodide (4.2 mg, 0.022 mmol) and triethylamine (0.031 mL, 0.22 mmol). Argon was bubbled through the mixture for 5 min and then the vessel placed in a preheated oil bath at 100° C. for 16 h. The reaction was cooled to room temperature. The mixture was filtered through a syringe filter then diluted with DMF for purification by preparative HPLC: (20-100% B; B solvent 90% CH$_3$CN/0.1% TFA water, Phenomenex AXIA LUNA C18 30×100 mm, 10 micron, 254 nm UV, 30 mL/min; T$_R$ 13.7 min.). Like fractions were combined then concentrated under vacuum to give 50 mg (91%). $^1$H NMR (400 MHz, DMSO-d$_6$) δ 8.79 (d, J=2.5 Hz, 1H), 8.74 (d, J=2.5 Hz, 1H), 8.67 (d, J=1.8 Hz, 1H), 8.62 (s, 1H), 7.80 (d, J=7.3 Hz, 2H), 7.37-7.29 (m, 2H), 7.29-7.17 (m, 1H), 5.92

(d, J=9.5 Hz, 1H), 4.04 (s, 3H), 3.88 (d, J=8.5 Hz, 1H), 3.80-3.57 (m, 2H), 3.45-3.35 (m, 1H), 1.60-1.49 (m, 1H), 1.46-1.35 (m, 1H), 1.32-1.22 (m, 1H), 1.21-1.04 (m, 2H). LC/MS (M+H)=476.31.

Example 348

Methyl 5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(13),2(7),3,5,9,11-hexaene-12-carboxylate

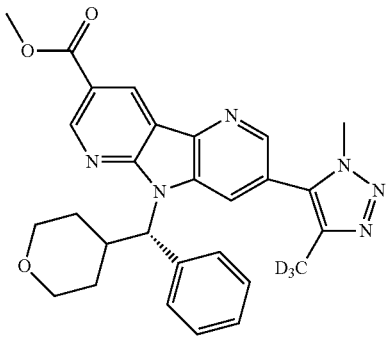 [SMILES: [2H]C([2H])([2H])c1nnn(C)c1-c1cnc2c3cc(C(=O)OC)cnc3n([C@H](c3ccccc3)C3CCOCC3)c2c1]

Step 1: Methyl 5-bromo-3-nitro-[2,3'-bipyridine]-5'-carboxylate

A pressure flask was charged with methyl 5-(4,4,5,5-tetramethyl-1,3,2-dioxaborolan-2-yl)nicotinate (1.4 g, 5.32 mmol) and 2,5-dibromo-3-nitropyridine (1.35 g, 4.79 mmol). The solids were suspended in THF (40 mL). The mixture was treated with PdCl$_2$(dppf)-CH$_2$Cl$_2$ adduct (0.217 g, 0.266 mmol) and K$_3$PO$_4$ (2 M, 8 mL, 16 mmol). Argon was bubbled through the mixture for 5 min with sonication. The flask was capped and placed in a preheated oil bath at 80° C. After 2 h, the vessel was cooled to room temperature and the reaction mixture was filtered. The filtrate was concentrated under vacuum to near dryness. The remaining water layer was diluted with water and was extracted with ethyl acetate. Brine was added and the organic layer was removed, dried over MgSO$_4$, filtered and concentrated under vacuum to give 2.14 g (95%). $^1$H NMR (400 MHz, CDCl$_3$) δ 9.35 (d, J=2.0 Hz, 1H), 9.02 (d, J=2.0 Hz, 1H), 8.94 (d, J=2.3 Hz, 1H), 8.57-8.43 (m, 2H), 4.01 (s, 3H). LC/MS (M+H)=348.10.

Step 2: Methyl 3-bromo-5H-pyrrolo[2,3-b:4,5-b']dipyridine-8-carboxylate

A round bottom flask was charged with methyl 5-bromo-3-nitro-[2,3'-bipyridine]-5'-carboxylate (450 mg, 1.33 mmol) and bis(diphenylphosphino)ethane (663 mg, 1.66 mmol). The solids were suspended in 1,2-dichlorobenzene (1.5 mL). The flask was flushed with nitrogen. The reaction was heated to 150° C. in a preheated oil bath while stirring. After the reaction was complete by LCMS, the reaction was allowed to continue for 1 h open to air. The solvent was removed under a stream of nitrogen while heating to 100° C. The reaction mixture was diluted with 75 mL of DCM and was stirred 0° C., then allowed to warm to room temperature overnight. A white precipitate formed and was collected by filtration, washing with DCM (150 mg; 31%). $^1$H NMR (500 MHz, DMSO-d$_6$) δ 12.69 (s, 1H), 9.14 (d, J=1.9 Hz, 1H), 8.98 (d, J=2.2 Hz, 1H), 8.69 (d, J=1.9 Hz, 1H), 8.22 (d, J=1.9 Hz, 1H), 3.94 (s, 3H). LC/MS (M+H)=308.05.

Step 3: (S)-Methyl 3-bromo-5-(phenyl(tetrahydro-2H-pyran-4-yl)methyl)-5H-pyrrolo[2,3-b:4,5-b']dipyridine-8-carboxylate A round bottom flask at 0° C. was charged with methyl 3-bromo-5H-pyrrolo[2,3-b:4,5-b']dipyridine-8-carboxylate (100 mg, 0.327 mmol), (R)-phenyl(tetrahydro-2H-pyran-4-yl)methanol (126 mg, 0.653 mmol), Ph$_3$P (171 mg, 0.653 mmol), and DCM (10 mL). DIAD (0.127 mL, 0.653 mmol) was added dropwise to the suspension. The reaction was allowed to warm to room temperature and was stirred for 16 h. The reaction mixture was concentrated under vacuum. The residue was taken up in a minimum of DCM, and transferred to the top of combined 24 g and 40 g ISCO silica columns. The material was eluted with 0-100% ethyl acetate/hexane over 1000 mL. Like fractions were combined and concentrated under vacuum to give 150 mg (95%). LC/MS (M+H)=480.20; HPLC conditions: T$_R$=4.27 min.: Column: Phenomenex C18 2×50 mm (4 min grad) eluting with 10-90% aqueous methanol containing 0.1% TFA, 0.8 mL/min, monitoring at 254 nm); Temperature: 40° C.

Step 4: Methyl 5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(13),2(7),3,5,9,11-hexaene-12-carboxylate A pressure vessel was charged with (S)-methyl 3-bromo-5-(phenyl(tetrahydro-2H-pyran-4-yl)methyl)-5H-pyrrolo[2,3-b:4,5-b']dipyridine-8-carboxylate (112 mg, 0.233 mmol), 4-($^2$H$_3$)methyl-1-methyl-5-(tributylstannyl)-1H-1,2,3-triazole (95 mg, 0.245 mmol), (Ph$_3$P)$_4$Pd (26.9 mg, 0.023 mmol). The solids were suspended in DMF (3 mL). The suspension was stirred and bubbled with argon for 5 min before copper (I) iodide (8.9 mg, 0.047 mmol) and triethylamine (0.049 mL, 0.350 mmol) were added. Argon was bubbled through the mixture for 5 min and then the vessel was placed in a preheated oil bath at 100° C. for 16 h. The reaction was cooled to room temperature and filtered through a syringe filter. The material was purified by preparative HPLC: (20-100% B; B solvent 90% CH$_3$CN/0.1% TFA water, Phenomenex AXIA LUNA C18 30×100 mm, 10 micron, 254 nm UV, 30 mL/min; T$_R$ 11.4 min.). Like fractions were combined then concentrated under vacuum to give 89 mg (65%). $^1$H NMR (500 MHz, DMSO-d$_6$) δ 9.29 (d, J=2.2 Hz, 1H), 9.05 (d, J=1.8 Hz, 1H), 8.72 (d, J=1.8 Hz, 1H), 8.66 (br. s., 1H), 7.82 (d, J=7.3 Hz, 2H), 7.39-7.29 (m, 2H), 7.29-7.18 (m, 1H), 6.00 (br. s., 1H), 4.04 (s, 3H), 3.96 (s, 3H), 3.93-3.80 (m, 1H), 3.74 (d, J=11.7 Hz, 2H), 1.77 (s, 1H), 1.54 (br. s., 1H), 1.41 (d, J=8.1 Hz, 1H), 1.34-1.17 (m, 1H), 1.12 (d, J=12.1 Hz, 1H). LC/MS (M+H)=500.40.

Example 349

2-{5-[4-($^2$H$_3$)Methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(13),2(7),3,5,9,11-hexaen-12-yl}propan-2-ol

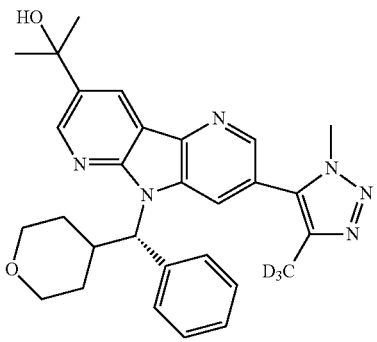 [SMILES: [2H]C([2H])([2H])c1nnn(C)c1-c1cnc2c3cc(C(C)(C)O)cnc3n([C@H](c3ccccc3)C3CCOCC3)c2c1]

A 20 mL vial was charged with methyl 5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(13),2(7),3,5,9,11-hexaene-12-carboxylate (45 mg, 0.090 mmol), and THF (3 mL). Methylmagnesium bromide (3 M in diethyl ether, 0.45 mL, 1.35 mmol) was added. After 1 h at room temperature, the reaction was quenched with saturated NH$_4$Cl solution while stirring at room temperature. Ethyl acetate was added and stirring continued. The mixture was transferred to a separatory funnel and the layers separated. Brine was added to break up the emulsion. The organic layer was dried over MgSO$_4$, filtered, and concentrated under vacuum to give a yellow residue. Solids were removed by filtration and the filtrate purified by preparative HPLC: Column: Water XBridge C18, 19×200 mm, 5-μm particles; Mobile Phase A: 5:95 methanol: water with 10 mM ammonium acetate; Mobile Phase B: 95:5 methanol: water with 10 mM ammonium acetate; Gradient: 25-65% B over 15 min, then a 5-min hold at 100% B; Flow: 20 mL/min. Fractions containing the desired product were combined and dried via centrifugal evaporation to give 21.0 mg (46%). $^1$H NMR (500 MHz, DMSO-d$_6$) δ 8.88 (d, J=1.8 Hz, 1H), 8.68 (d, J=2.2 Hz, 1H), 8.60 (s, 1H), 8.54 (br. s., 1H), 7.81 (d, J=8.1 Hz, 2H), 7.37-7.27 (m, 2H), 7.27-7.12 (m, 1H), 5.91 (br. s., 1H), 4.03 (s, 3H), 3.88 (d, J=11.4 Hz, 1H), 3.75 (d, J=10.6 Hz, 1H), 3.42 (br. s., 1H), 3.35-3.17 (m, 1H), 2.55 (s, 1H), 1.86 (s, 1H), 1.61 (s, 6H), 1.53 (br. s., 1H), 1.48-1.32 (m, 1H), 1.32-1.18 (m, 1H), 1.12 (d, J=12.5 Hz, 1H). LC/MS (M+H)=500.40.

Example 350

2-[5-(Dimethyl-1H-1,2,3-triazol-5-yl)-8-[(S)-oxan-4-yl(phenyl)methyl]-3,8,10-triazatricyclo[7.4.0.0$^{2,7}$]trideca-1(13),2(7),3,5,9,11-hexaen-12-yl]propan-2-ol

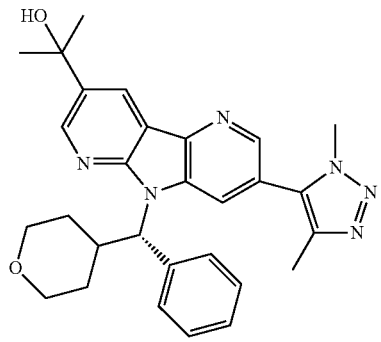 [SMILES: Cc1nnn(C)c1-c1cnc2c3cc(C(C)(C)O)cnc3n([C@H](c3ccccc3)C3CCOCC3)c2c1]

Step 1: (S)-Methyl 3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridine-8-carboxylate A pressure vessel was charged with (S)-methyl 3-bromo-5-(phenyl(tetrahydro-2H-pyran-4-yl)methyl)-5H-pyrrolo[2,3-b:4,5-b']dipyridine-8-carboxylate (126 mg, 0.262 mmol), 1,4-dimethyl-5-(tributylstannyl)-1H-1,2,3-triazole (106 mg, 0.275 mmol), and (Ph$_3$P)$_4$Pd (30.3 mg, 0.026 mmol). The solids were suspended in DMF (3 mL). The suspension was stirred and bubbled with argon for 5 min before copper(I) iodide (9.99 mg, 0.052 mmol) and triethylamine (0.055 mL, 0.393 mmol) were added. Argon was bubbled through the mixture for 5 min and then the vessel was placed in a preheated oil bath at 100° C. The reaction was allowed to continue heating for 16 h with stirring. The reaction was cooled to room temperature and filtered through a syringe filter. The material was purified by preparative HPLC: (20-100% B; B solvent 90% CH$_3$CN/0.1% TFA water, Phenomenex AXIA LUNA C18 30×100 mm, 10 micron, 254 nm UV, 30 mL/min; T$_R$ 11.5 min.). Like fractions were combined then concentrated under vacuum to give 135 mg (83%). LC/MS (M+H)=497.20; HPLC conditions: T$_R$=3.80 min.: Column: Phenomenex C18 2×50 mm (4 min grad) eluting with 10-90% aqueous methanol containing 0.1% TFA, 0.8 mL/min, monitoring at 254 nm); Temperature: 40° C.

Step 2: 2-[5-(Dimethyl-1H-1,2,3-triazol-5-yl)-8-[(S)-oxan-4-yl(phenyl)methyl]-3,8,10-triazatricyclo[7.4.0.0$^{2,7}$]trideca-1(13),2(7),3,5,9,11-hexaen-12-yl]propan-2-ol A 20 mL vial was charged with (S)-methyl 3-(1,4-dimethyl-1H-1,2,3-triazol-5-yl)-5-(phenyl(tetrahydro-2H-pyran-4-yl)methyl)-5H-pyrrolo[2,3-b:4,5-b']dipyridine-8-carboxylate (60 mg, 0.121 mmol), and THF (3 mL). Methylmagnesium bromide (3 M in diethyl ether, 0.60 mL, 1.8 mmol) was added. After 1 h at room temperature, the reaction was quenched with saturated NH$_4$Cl solution while stirring at room temperature. To this was added ethyl acetate with stirring. The mixture was transferred to a separatory funnel and the layers separated. Brine was added to break up the emulsion. The organic layer was dried over MgSO$_4$, filtered and concentrated under vacuum to give a yellow residue. The residue was dissolved in 2 mL of DMF. Solids were removed by filtration, and the filtrate purified by preparative HPLC: Column: Water XBridge C18, 19×200 mm, 5-μm particles; Mobile Phase A: 5:95 methanol: water with 10 mM ammonium acetate; Mobile Phase B: 95:5 methanol: water with 10 mM ammonium acetate; Gradient: 25-65% B over 15 min, then a 5-min hold at 100% B; Flow: 20 mL/min. Fractions containing the desired product were combined and dried via centrifugal evaporation to give 14.3 mg (24%). $^1$H NMR (500 MHz, DMSO-d$_6$) δ 8.89 (d, J=2.2 Hz, 1H), 8.68 (d, J=2.2 Hz, 1H), 8.60 (d, J=1.5 Hz, 1H), 8.55 (br. s., 1H), 7.81 (d, J=7.7 Hz, 2H), 7.36-7.28 (m, 2H), 7.28-7.17 (m, 1H), 5.92 (br. s., 1H), 4.03 (s, 3H), 3.88 (d, J=10.6 Hz, 1H), 3.75 (d, J=9.2 Hz, 2H), 3.37 (s, 1H), 3.26 (t, J=12.3 Hz, 1H), 2.31 (s, 3H), 1.61 (s, 6H), 1.53 (br. s., 1H), 1.45-1.34 (m, 1H), 1.34-1.18 (m, 1H), 1.13 (d, J=14.3 Hz, 1H). LC/MS (M+H)=497.25.

Example 351

2-[5-(Dimethyl-1,2-oxazol-4-yl)-8-[(S)-oxan-4-yl(phenyl)methyl]-3,8,10-triazatricyclo[7.4.0.0$^{2,7}$]trideca-1(13),2(7),3,5,9,11-hexaen-12-yl]propan-2-ol

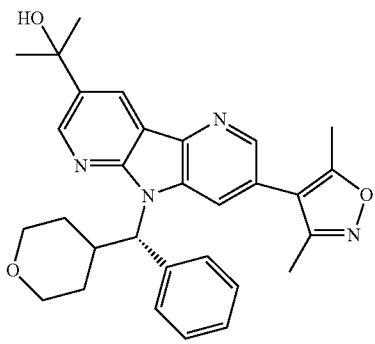 [SMILES: Cc1noc(C)c1-c1cnc2c3cc(C(C)(C)O)cnc3n([C@H](c3ccccc3)C3CCOCC3)c2c1]

Step 1: 3,5-Dimethyl-4-(tributylstannyl)isoxazole

A solution of 3,5-dimethylisoxazole (1.20 g, 12.4 mmol) in THF (25 mL) was cooled to −78° C. To this was added butyllithium (5.93 mL, 14.8 mmol) dropwise under nitrogen. This mixture was allowed to stir for 0.5 h. Tributylchlorostannane (4.15 g, 12.4 mmol) was then added, dropwise. The reaction was stirred at −78° C. for 10 min., the cooling bath was removed, and the reaction allowed to warm to room temperature over 1 h. The reaction was quenched with 15 mL saturated NH$_4$Cl solution, and then diluted with 15 mL 10% aq. LiCl. The layers were separated, and the aq. layer extracted with diethyl ether (3×20 mL). The combined organic layers were dried over Na$_2$SO$_4$ and filtered. The filtrate was concentrated and purified by flash column chromatography using 2-30% EtOAc/hexanes on an 80 g silica gel column to obtain 3.21 g (67%).

Step 2: (S)-Methyl 3-(3,5-dimethylisoxazol-4-yl)-5-(phenyl(tetrahydro-2H-pyran-4-yl)methyl)-5H-pyrrolo[2,3-b:4,5-b']dipyridine-8-carboxylate A 20 mL pressure vessel was charged with (S)-methyl 3-bromo-5-(phenyl(tetrahydro-2H-pyran-4-yl)methyl)-5H-pyrrolo[2,3-b:4,5-b']dipyridine-8-carboxylate (97 mg, 0.202 mmol), 3,5-dimethyl-4-(tributylstannyl)isoxazole (82 mg, 0.212 mmol), and (Ph$_3$P)$_4$Pd (23.3 mg, 0.020 mmol). The solids were suspended in DMF (3 mL). The suspension was stirred and bubbled with argon for 5 min before copper(I) iodide (7.7 mg, 0.040 mmol) and triethylamine (0.042 mL, 0.303 mmol) were added. Argon was bubbled through the mixture for 5 min and then the vessel was placed in a preheated oil bath at 100° C. The reaction was allowed to continue heating for 16 h with stirring. The reaction was cooled to room temperature and filtered through a syringe filter. The material was purified by preparative HPLC: (20-100% B; B solvent 90% CH$_3$CN/0.1% TFA water, Phenomenex AXIA LUNA C18 30×100 mm, 10 micron, 254 nm UV, 30 mL/min; T$_R$ 12.0 min.). Like fractions were combined then concentrated under vacuum to give 47 mg (47%). $^1$H NMR (400 MHz, DMSO-d$_6$) δ 9.22 (d, J=2.3 Hz, 1H), 8.98 (d, J=2.3 Hz, 1H), 8.58 (d, J=1.5 Hz, 1H), 8.52 (s, 1H), 7.77 (d, J=7.3 Hz, 2H), 7.35-7.23 (m, 3H), 5.91 (d, J=10.0 Hz, 1H), 3.95 (s, 3H), 3.89 (d, J=11.0 Hz, 1H), 3.74 (d, J=11.8 Hz, 1H), 3.42 (s, 1H), 3.26 (d, J=1.5 Hz, 1H), 2.11-2.07 (m, 6H), 1.59 (s, 1H), 1.51 (br. s., 1H), 1.45 (d, J=4.3 Hz, 1H), 1.36-1.27 (m, 1H), 1.07 (d, J=10.0 Hz, 1H), 0.89 (t, J=7.3 Hz, 1H). LC/MS (M+H)=497.25.

Step 3: 2-[5-(Dimethyl-1,2-oxazol-4-yl)-8-[(S)-oxan-4-yl(phenyl)methyl]-3,8,10-triazatricyclo[7.4.0.0$^{2,7}$]trideca-1(13),2(7),3,5,9,11-hexaen-12-yl]propan-2-ol A 20 mL vial was charged with (S)-methyl 3-(3,5-dimethylisoxazol-4-yl)-5-(phenyl(tetrahydro-2H-pyran-4-yl)methyl)-5H-pyrrolo[2,3-b:4,5-b']dipyridine-8-carboxylate (41 mg, 0.083 mmol), and THF (3 mL). Methylmagnesium bromide (3 M in diethyl ether, 0.41 mL, 1.23 mmol) was added. After 1 h at room temperature, the reaction was quenched with saturated NH$_4$Cl solution while stirring at room temperature. To this was added ethyl acetate with stirring. The mixture was transferred to a separatory funnel and the layers separated. Brine was added to break up the emulsion. The organic layer was dried over MgSO$_4$, filtered and concentrated under vacuum to give a yellow residue. The residue was dissolved in 2 mL of DMF. Solids were removed by filtration, and the filtrate purified by preparative HPLC: Column: Water XBridge C18, 19×200 mm, 5-μm particles; Mobile Phase A: 5:95 methanol: water with 10 mM ammonium acetate; Mobile Phase B: 95:5 methanol: water with 10 mM ammonium acetate; Gradient: 30-70% B over 20 min, then a 5-min hold at 100% B; Flow: 20 mL/min. Fractions containing the desired product were combined and dried via centrifugal evaporation to give 18.7 mg (45%). $^1$H NMR (500 MHz, DMSO-d$_6$) δ 8.80 (d, J=2.2 Hz, 1H), 8.60 (d, J=2.2 Hz, 1H), 8.44 (s, 1H), 8.37 (s, 1H), 7.75 (d, J=7.3 Hz, 2H), 7.35-7.27 (m, 2H), 7.27-7.14 (m, 1H), 5.80 (br. s., 1H), 4.34 (s, 2H), 3.88 (d, J=12.5 Hz, 1H), 3.74 (d, J=11.0 Hz, 1H), 3.37 (d, J=6.6 Hz, 1H), 3.31-3.17 (m, 1H), 2.55 (s, 6H), 1.59 (s, 6H), 1.51 (d, J=13.2 Hz, 1H), 1.47-1.35 (m, 1H), 1.31-1.15 (m, 1H), 1.08 (d, J=11.0 Hz, 1H). LC/MS (M+H)=497.1.

Example 352

2-{8-[(S)-(3-Fluoropyridin-2-yl)(oxan-4-yl)methyl]-5-[4-($^2$H$_3$)methyl-1-methyl-1H-1,2,3-triazol-5-yl]-3,8,10-triazatricyclo[7.4.0.0$^{2,7}$]trideca-1(13),2(7),3,5,9,11-hexaen-12-yl}propan-2-ol

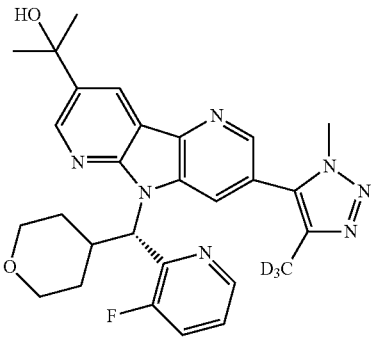 [SMILES: [2H]C([2H])([2H])c1nnn(C)c1-c1cnc2c3cc(C(C)(C)O)cnc3n([C@H](c3ncccc3F)C3CCOCC3)c2c1]

Step 1: (S)-Methyl 3-bromo-5-((3-fluoropyridin-2-yl)(tetrahydro-2H-pyran-4-yl)methyl)-5H-pyrrolo[2,3-b:4,5-b']dipyridine-8-carboxylate A round bottom flask at 0° C. was charged with methyl 3-bromo-5H-pyrrolo[2,3-b:4,5-b']dipyridine-8-carboxylate (159 mg, 0.519 mmol), (R)-(3-fluoropyridin-2-yl)(tetrahydro-2H-pyran-4-yl)methanol (219 mg, 1.04 mmol), Ph$_3$P (272 mg, 1.04 mmol), and DCM (10 mL). To this suspension was added DIAD (0.202 mL, 1.04 mmol) dropwise. The ice bath was removed and the reaction was allowed to warm to room temperature and was stirred for 16 h. The reaction mixture was concentrated under vacuum. The residue was taken up in a minimum of DCM, and transferred to the top of a 40 g ISCO silica gel column. The material was eluted with 0-100% ethyl acetate/hexanes over 1000 mL. Like fractions were combined and concentrated under vacuum to give 420 mg (81%). LC/MS (M+H)=499.10; HPLC conditions: T$_R$=4.31 min.: Column: Phenomenex C18 2×50 mm (4 min grad) eluting with 10-90% aqueous methanol containing 0.1% TFA, 0.8 mL/min, monitoring at 254 nm); Temperature: 40° C.

Step 2: Methyl 8-[(S)-(3-fluoropyridin-2-yl)(oxan-4-yl)methyl]-5-[4-($^2$H$_3$)methyl-1-methyl-1H-1,2,3-triazol-5-yl]-3,8,10-triazatricyclo[7.4.0.0$^{2,7}$]trideca-1(13),2(7),3,5,9,11-hexaene-12-carboxylate A pressure vessel was charged with (S)-methyl 3-bromo-5-((3-fluoropyridin-2-yl)(tetrahydro-2H-pyran-4-yl)methyl)-5H-pyrrolo[2,3-b:4,5-b']dipyridine-8-carboxylate (260 mg, 0.521 mmol), 4-($^2$H$_3$)methyl-1-methyl-5-(tributylstannyl)-1H-1,2,3-triazole (213 mg, 0.547 mmol), and (Ph$_3$P)$_4$Pd (60.2 mg, 0.052 mmol). The solids were suspended in DMF (4 mL). The suspension was stirred and bubbled with argon for 5 min before copper(I) iodide (19.8 mg, 0.104 mmol) and triethylamine (0.109 mL, 0.781 mmol) were added. Argon was bubbled through the mixture for 5 min and the vessel placed in a preheated oil bath at 100° C. After 16 h, the reaction was cooled to room temperature and filtered through a syringe filter. The material was purified by preparative HPLC: (20-100% B; B solvent 90% CH$_3$CN/0.1% TFA water, Phenomenex AXIA LUNA C18 30×100 mm, 10 micron, 254 nm UV, 30 mL/min; T$_R$ 9.6 min.). Like fractions were combined then concentrated under vacuum to give 180 mg (57%). LC/MS (M+H)=519.1.; T$_R$=0.85 min. Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min.

Step 3: 2-{8-[(S)-(3-Fluoropyridin-2-yl)(oxan-4-yl)methyl]-5-[4-($^2$H$_3$)methyl-1-methyl-1H-1,2,3-triazol-5-yl]-3,8,10-triazatricyclo[7.4.0.0$^{2,7}$]trideca-1(13),2(7),3,5,9,11-hexaen-12-yl}propan-2-ol A 50 mL round bottom flask was charged with methyl 8-[(S)-(3-fluoropyridin-2-yl)(oxan-4-yl)methyl]-5-[4-($^2$H$_3$)methyl-1-methyl-1H-1,2,3-triazol-5-yl]-3,8,10-triazatricyclo[7.4.0.0$^{2,7}$]trideca-1(13),2(7),3,5,9,11-hexaene-12-carboxylate (75 mg, 0.145 mmol) and THF (10 mL). Methylmagnesium bromide (3 M in diethyl ether, 0.72 mL, 2.16 mmol) was added. After 1 h at room temperature, the reaction was quenched with saturated NH$_4$Cl solution while stirring at room temperature. Ethyl acetate was added with stirring. The mixture was transferred to a separatory funnel and the layers separated. Brine was added to break up the emulsion. The organic layer was dried over MgSO$_4$, filtered and concentrated under vacuum to give a yellow residue. This residue was taken up in 2 mL of DMF. Solids were removed by filtration, and the filtrate purified by preparative HPLC: Column: Water XBridge C18, 19×200 mm, 5-μm particles; Mobile Phase A: 5:95 methanol: water with 10 mM ammonium acetate; Mobile Phase B: 95:5 methanol: water with 10 mM ammonium acetate; Gradient: 15-55% B over 20 min, then a 5-min hold at 100% B; Flow: 20 mL/min. Fractions containing the desired product were combined and dried via centrifugal evaporation to give 33.0 mg (44%). $^1$H NMR (500 MHz, DMSO-d$_6$) δ 8.85 (d, J=1.8 Hz, 1H), 8.68 (d, J=2.2 Hz, 1H), 8.63 (d, J=1.5 Hz, 1H), 8.60-8.52 (m, 2H), 7.71 (t, J=9.2 Hz, 1H), 7.48 (dt, J=8.5, 4.4 Hz, 1H), 6.66 (d, J=11.4 Hz, 1H), 5.37 (s, 1H), 4.04 (s, 3H), 3.84 (d, J=12.1 Hz, 1H), 3.68 (d, J=9.9 Hz, 1H), 3.21 (t, J=11.6 Hz, 1H), 1.66-1.54 (m, 8H), 1.43 (d, J=8.4 Hz, 1H), 1.23 (dd, J=12.3, 4.2 Hz, 1H), 0.83 (d, J=12.8 Hz, 1H). LC/MS (M+H)=519.30.

Examples 353 & 354

2-{8-[(5-Chloropyridin-2-yl)(oxan-4-yl)methyl]-5-[4-($^2$H$_3$)methyl-1-methyl-1H-1,2,3-triazol-5-yl]-3,8,10-triazatricyclo[7.4.0.0$^{2,7}$]trideca-1(13),2(7),3,5,9,11-hexaen-12-yl}propan-2-ol

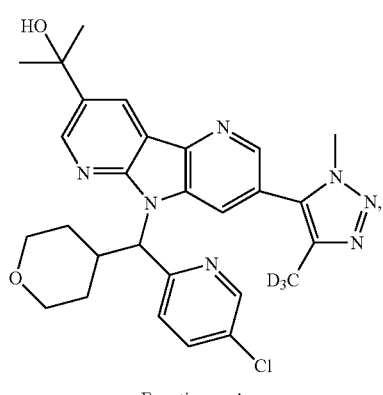

Example 353

Enantiomer A

Example 354

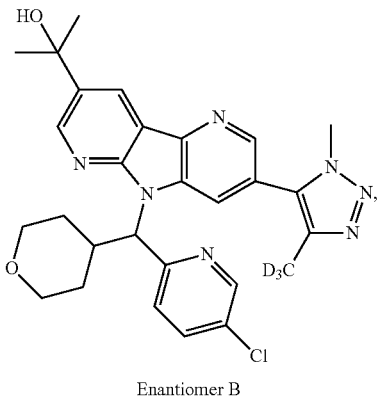

Enantiomer B

Step 1: Methyl 3-bromo-5-((5-chloropyridin-2-yl)(tetrahydro-2H-pyran-4-yl)methyl)-5H-pyrrolo[2,3-b:4,5-b']dipyridine-8-carboxylate A round bottom flask at 0° C. was charged with methyl 3-bromo-5H-pyrrolo[2,3-b:4,5-b']dipyridine-8-carboxylate (75 mg, 0.245 mmol), (5-chloropyridin-2-yl)(tetrahydro-2H-pyran-4-yl)methanol (112 mg, 0.490 mmol), Ph$_3$P (129 mg, 0.490 mmol), and DCM (5 mL). To this suspension was added DIAD (0.095 mL, 0.490 mmol) dropwise. The ice bath was removed and the reaction was allowed to warm to room temperature and was stirred for 16 h. The reaction mixture was concentrated under vacuum. The residue was taken up in a minimum of fresh DCM, and was transferred to the top of a 40 g ISCO silica gel column. The material was eluted with 0-100% ethyl acetate/hexanes over 1100 mL. Like fractions were combined and concentrated under vacuum to give 145 mg (57%). LC/MS (M+H)=516.8.; T$_R$=1.16 min. Column: Waters Aquity BEH C18 2.1×50 mm 1.7 u; Mobile Phase A: water with 0.05% TFA; Mobile Phase B: acetonitrile with 0.05% TFA; Temperature: 40° C.; Gradient: 2-98% B over 1.5 min; Flow: 0.8 mL/min.

Step 2: Methyl 8-[(5-chloropyridin-2-yl)(oxan-4-yl)methyl]-5-[4-($^2$H$_3$)methyl-1-methyl-1H-1,2,3-triazol-5-yl]-3,8,10-triazatricyclo[7.4.0.0$^{2,7}$]trideca-1(13),2(7),3,5,9,11-hexaene-12-carboxylate A pressure vessel was charged with methyl 3-bromo-5-((5-chloropyridin-2-yl)(tetrahydro-2H-pyran-4-yl)methyl)-5H-pyrrolo[2,3-b:4,5-b']dipyridine-8-carboxylate (126 mg, 0.244 mmol), 4-($^2$H$_3$)methyl-1-methyl-5-(tributylstannyl)-1H-1,2,3-triazole (100 mg, 0.257 mmol), (Ph$_3$P)$_4$Pd (28.2 mg, 0.024 mmol). The solids were suspended in DMF (2 mL). The suspension was stirred and bubbled with argon for 5 min before copper(I) iodide (9.3 mg, 0.049 mmol) and triethylamine (0.051 mL, 0.366 mmol) were added. Argon was bubbled through the mixture for 5 min and then the vessel was placed in a preheated oil bath at 100° C. The reaction was heated for 16 h with stirring. The reaction was cooled to room temperature and filtered through a syringe filter. The material was purified by preparative HPLC: (20-100% B; B solvent 90% CH$_3$CN/0.1% TFA water, Phenomenex AXIA LUNA C18 30×100 mm, 10 micron, 254 nm UV, 30 mL/min; T$_R$ 11.5 min.). Like fractions were combined then concentrated under vacuum to give 70 mg (43%). LC/MS (M+H)=535.25; HPLC conditions: T$_R$=2.25 min.; Column: Phenomenex C18 2×50 mm (4 min grad) eluting with 10-90% aqueous methanol containing 0.1% TFA, 0.8 mL/min, monitoring at 254 nm); Temperature: 40° C.

Step 3: 2-{8-[(5-Chloropyridin-2-yl)(oxan-4-yl)methyl]-5-[4-($^2$H$_3$)methyl-1-methyl-1H-1,2,3-triazol-5-yl]-3,8,10-triazatricyclo[7.4.0.0$^{2,7}$]trideca-1(13),2(7),3,5,9,11-hexaen-12-yl}propan-2-ol A 50 mL round bottom flask was charged with methyl 8-[(5-chloropyridin-2-yl)(oxan-4-yl)methyl]-5-[4-($^2$H$_3$)methyl-1-methyl-1H-1,2,3-triazol-5-yl]-3,8,10-triazatricyclo[7.4.0.0$^{2,7}$]trideca-1(13),2(7),3,5,9,11-hexaene-12-carboxylate (70 mg, 0.131 mmol) and THF (10 mL). Methylmagnesium bromide (3 M in diethyl ether, 0.65 mL, 1.95 mmol) was added. The reaction was stirred for 16 h at room temperature. The reaction was quenched with saturated NH$_4$Cl solution while stirring at room temperature. To this was added ethyl acetate with stirring. The mixture was transferred to a separatory funnel and the layers separated. Brine was added to break up the emulsion. The organic layer was dried over MgSO$_4$, filtered and concentrated under vacuum to give a yellow residue. This residue was taken up in DMF. Solids in the reaction mixture were filtered, and this material (8 mg) was subjected to chiral separation: Chiralcel OD preparative column, 21×250 mm, 10 μm; Mobile Phase: 15% ethanol/heptane over 42 min., Flow rate: 15.0 mL/min.; UV monitored at 254 nm; T$_R$=Enantiomer A: 22.5 min.; Enantiomer B: 30.1 min. Fractions containing the desired products were combined and dried via evaporation to give 2.5 mg (4%) of Enantiomer A and 2.6 mg (4%) of Enantiomer B. $^1$H NMR (500 MHz, DMSO-d$_6$) δ 8.85 (d, J=1.8 Hz, 1H), 8.69 (d, J=2.2 Hz, 1H), 8.67-8.60 (m, 2H), 8.55 (s, 1H), 7.91 (dd, J=8.4, 2.6 Hz, 1H), 7.69 (d, J=8.1 Hz, 1H), 6.25 (d, J=9.5 Hz, 1H), 4.06 (s, 3H), 3.85 (d, J=9.9 Hz, 1H), 3.70 (d, J=12.5 Hz, 1H), 3.23 (s, 1H), 1.66-1.58 (m, 7H), 1.58-1.52 (m, 1H), 1.52-1.41 (m, 1H), 1.30-1.13 (m, 2H), 0.96 (d, J=12.8 Hz, 1H). LC/MS (M+H)=535.1.

Examples 357 & 358

2-{5-[4-($^2$H$_3$)Methyl-1-methyl-1H-1,2,3-triazol-5-yl]-8-[1-(pyridin-2-yl)butyl]-3,8,12-triazatricyclo[7.4.0.0$^{2,7}$]trideca-1(13),2(7),3,5,9,11-hexaen-11-yl}propan-2-ol

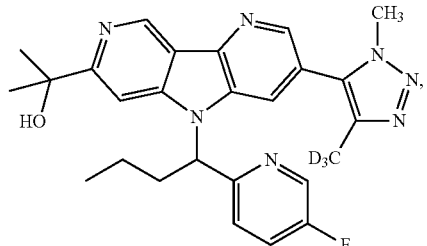

Example 357

Enantiomer A

Example 358

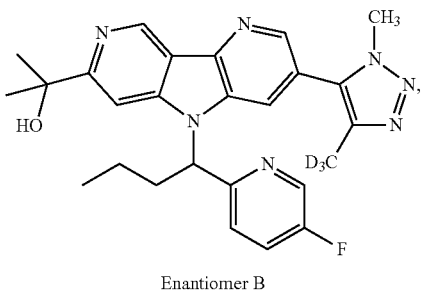

Enantiomer B

Step 1: 1-(5-Fluoropyridin-2-yl)butan-1-ol

1-Bromopropane (369 mg, 3.0 mmol) was added drop wise to a stirred suspension of magnesium (72.9 mg, 3.0 mmol) and one crystal of iodine in THF (2.6 mL) at ambient temperature. The reaction mixture was stirred for 1 h before it was cooled in an ice-water bath. 5-Fluoropicolinaldehyde (250 mg, 2.0 mmol) was added drop wise. The reaction mixture was then stirred for 1 h. The reaction mixture was quenched with saturated aqueous ammonium chloride (5 mL) and diluted with ethyl acetate (40 mL) and water (30 mL). The product was extracted into the organic phase before the layers were separated. The aqueous layer was extracted with a second portion of ethyl acetate (50 mL), and the combined organics were dried over sodium sulfate. The volatiles were removed under reduced pressure. The crude reaction material was purified using silica gel column chromatography with ethyl acetate in hexanes (0-100%). 1-(5-Fluoropyridin-2-yl)butan-1-ol (243 mg, 72% yield) was isolated as a pale-yellow oil. $^1$H NMR (500 MHz, DMSO-$d_6$) δ 8.46 (d, J=3.0 Hz, 1H), 7.74-7.62 (m, 1H), 7.53 (dd, J=8.7, 4.7 Hz, 1H), 5.35 (d, J=5.0 Hz, 1H), 4.67-4.48 (m, 1H), 1.76-1.62 (m, 1H), 1.62-1.52 (m, 1H), 1.43-1.25 (m, 2H), 0.91-0.79 (m, 3H); LC/MS (M+H)=170.05.

Step 2: 5-Bromo-11-chloro-8-[1-(5-fluoropyridin-2-yl)butyl]-3,8,12-triazatricyclo[7.4.0.0$^{2,7}$]trideca-1(9),2(7),3,5,10,12-hexaene Di-tert-butyl azodicarboxylate (163 mg, 0.71 mmol) in THF (3.5 mL) was added drop wise to a stirred solution of 5-bromo-11-chloro-3,8,12-triazatricyclo[7.4.0.0$^{2,7}$]trideca-1(9),2(7),3,5,10,12-hexaene (100 mg, 0.354 mmol), 1-(5-fluoropyridin-2-yl)butan-1-ol (120 mg, 0.71 mmol), triphenylphosphine (186 mg, 0.71 mmol), and Et$_3$N (99 µL, 0.71 mmol) in THF (3.5 mL) at 0° C. The reaction mixture was allowed to warm to ambient temperature over 10 min and stirred for an additional 72 h at that temperature. The crude reaction mixture was loaded onto a silica gel column and purified using ethyl acetate in hexanes (0-100%). 5-Bromo-11-chloro-8-[1-(5-fluoropyridin-2-yl)butyl]-3,8,12-triazatricyclo[7.4.0.0$^{2,7}$]trideca-1(9),2(7),3,5,10,12-hexaene (154 mg, quant.) was isolated as a white solid with a minor triphenylphosphine oxide contaminant. LC/MS (M+H) =433.0; LC/MS T$_R$=2.115 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min). The material was used without additional purification.

Step 3: 11-Chloro-8-[1-(5-fluoropyridin-2-yl)butyl]-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10,12-hexaene 5-Bromo-11-chloro-8-[1-(5-fluoropyridin-2-yl)butyl]-3,8,12-triazatricyclo[7.4.0.0$^{2,7}$]trideca-1(9),2(7),3,5,10,12-hexaene (154 mg, 0.36 mmol), 4-($^2$H$_3$)methyl-1-methyl-5-(tributylstannyl)-1H-1,2,3-triazole (207 mg, 0.53 mmol), Pd(PPh$_3$)$_4$(41.0 mg, 0.04 mmol), copper(I) iodide (13.5 mg, 0.07 mmol), and triethylamine (59 µL, 0.43 mmol) in DMF (1.7 mL) were degassed with N$_2$ (g) for 3 min. The reaction mixture was subsequently stirred at 100° C. for 16 h. The crude reaction mixture was subjected to silica gel column chromatography with ethyl acetate in hexanes (0-100%) followed by methanol in ethyl acetate (0-20%). 11-Chloro-8-[1-(5-fluoropyridin-2-yl)butyl]-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10,12-hexaene (133 mg, 83% yield) was isolated. LC/MS (M+H)=453.10; LC/MS T$_R$=1.170 min (Column: Waters Aquity C18 50×2.1 mm 1.7 u; Mobile Phase A: 100% water with 0.05% TFA; Mobile Phase B: 100% acetonitrile with 0.05% TFA; Temperature: 40° C.; Gradient: 2-98% B over 1.5 min; Flow: 0.8 mL/min).

Step 4: 1-{8-[1-(5-Fluoropyridin-2-yl)butyl]-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10,12-hexaen-11-yl}ethan-1-one 11-Chloro-8-[1-(5-fluoropyridin-2-yl)butyl]-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10,12-hexaene (130 mg, 0.29 mmol), tributyl(1-ethoxyvinyl)tin (207 mg, 0.57 mmol), Pd$_2$(dba)$_3$ (52.6 mg, 0.06 mmol), tricyclohexylphosphine (179 µL, 0.12 mmol, 20% wt in toluene), and cesium carbonate (187 mg, 0.57 mmol) in dioxane (2.9 mL) were degassed with N$_2$ (g) for 3 min. The reaction mixture was subsequently stirred at 115° C. for 16 h. 1N Aqueous HCl (2 mL) was added, and the reaction mixture was stirred for 20 min. The reaction mixture was quenched with 1.5 M aqueous monobasic potassium phosphate (5 mL), and the layers were separated. The aqueous layer was extracted with ethyl acetate (3×10 mL). The combined organics were dried over sodium sulfate. The solids were removed by filtration, and the volatiles were removed under reduced pressure. Crude 1-{8-[1-(5-fluoropyridin-2-yl)butyl]-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10,12-hexaen-11-yl}ethan-1-one was used without purification. LC/MS (M+H) =461.30; LC/MS T$_R$=1.437 min (Column: Phenomenex Luna 30×2.0 mm 3 u; Mobile Phase A: 10:90 acetonitrile: water with 0.1% TFA; Mobile Phase B: 90:10 acetonitrile: water with 0.1% TFA; Temperature: 40° C.; Gradient: 0-100% B over 2 min; Flow: 1 mL/min).

Step 5: 2-{5-[4-($^2$H$_3$)Methyl-1-methyl-1H-1,2,3-triazol-5-yl]-8-[1-(pyridin-2-yl)butyl]-3,8,12-triazatricyclo[7.4.0.0$^{2,7}$]trideca-1(13),2(7),3,5,9,11-hexaen-11-yl}propan-2-ol Methylmagnesium bromide (3M in diethyl ether, 2870 µL, 8.60 mmol) was added to a stirred solution of 1-{8-[1-(5-fluoropyridin-2-yl)butyl]-5-[4-($^2$H$_3$)methyl-1-methyl-1H-1,2,3-triazol-5-yl]-3,8,12-triazatricyclo[7.4.0.0$^{2,7}$]trideca-1(9),2(7),3,5,10,12-hexaen-11-yl}ethan-1-one (132 mg, 0.29 mmol) in THF (2.9 mL) under N$_2$ (g) at −20° C.

The reaction mixture was stirred at that temperature for 1 h. The reaction mixture was then quenched with saturated aqueous ammonium chloride (8 mL) and diluted with ethyl acetate (20 mL) while still at −20° C. The mixture was removed from the cold bath and allowed to warm to ambient temperature. The layers were separated, and the aqueous phase was extracted with a second portion of ethyl acetate (20 mL). The combined organics were dried over sodium sulfate, the solids were removed by filtration, and the volatiles were removed under reduced pressure. The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10 mM ammonium acetate; Gradient: 40-80% B over 20 min, then a 5-min hold at 100% B; Flow: 20 mL/min. Fractions containing the desired product were combined and dried via centrifugal evaporation to afford racemic 2-{5-[4-($^2$H$_3$)methyl-1-methyl-1H-1,2,3-triazol-5-yl]-8-[1-(pyridin-2-yl)butyl]-3,8,12-triazatricyclo[7.4.0.0$^{2,7}$]trideca-1(13),2(7),3,5,9,11-hexaen-11-yl}propan-2-ol. Enantiomers A and B were separated using chiral preparative HPLC (Column: Chiralpak AD 21×250 mm 5 u; Mobile Phase: 15% ethanol in heptane; Flow: 15 mL/min). The first eluting enantiomer (12.61 min) was defined as Enantiomer A (14.2 mg, 10% yield), and the second eluting enantiomer (17.56 min) was defined as Enantiomer B (12.4 mg, 9% yield). $^1$H NMR (500 MHz, DMSO-d$_6$) δ 9.37 (s, 1H), 8.65 (s, 1H), 8.58 (d, J=2.9 Hz, 1H), 8.29 (s, 1H), 7.98 (br. s., 1H), 7.72 (td, J=8.8, 2.9 Hz, 1H), 7.54 (dd, J=8.8, 4.4 Hz, 1H), 6.33-6.26 (m, 1H), 4.00 (s, 3H), 2.65-2.58 (m, 2H), 1.55 (s, 3H), 1.51 (s, 3H), 1.34-1.20 (m, 1H), 1.11-0.97 (m, 1H), 0.88 (t, J=7.2 Hz, 3H). LC/MS (M+H)=477.20.

Examples 359 & 360

2-{8-[1-(3-Fluoropyridin-2-yl)butyl]-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaen-11-yl}propan-2-ol Example 359

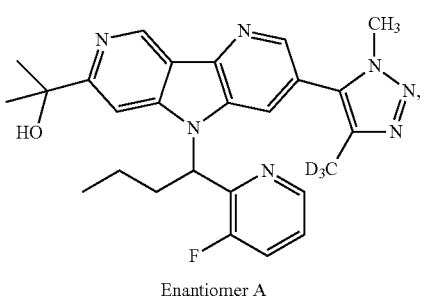

Enantiomer A

Example 360

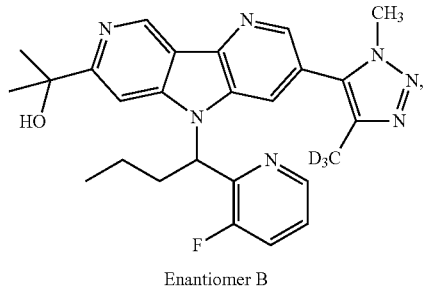

Enantiomer B

Enantiomers A and B of 2-{8-[1-(3-fluoropyridin-2-yl)butyl]-5-[4-($^2$H$_3$)methyl-1-methyl-1H-1,2,3-triazol-5-yl]-3,8,12-triazatricyclo[7.4.0.0$^{2,7}$]trideca-1(13),2(7),3,5,9,11-hexaen-11-yl}propan-2-ol were prepared according to the procedures described in route to 2-{5-[4-($^2$H$_3$)methyl-1-methyl-1H-1,2,3-triazol-5-yl]-8-[1-(pyridin-2-yl)butyl]-3,8,12-triazatricyclo[7.4.0.0$^{2,7}$]trideca-1(13),2(7),3,5,9,11-hexaen-11-yl}propan-2-ol. Enantiomers A and B were separated using chiral preparative SFC (Column: Lux Cellulose-2 21×250 mm 5 u; Mobile Phase: 25% ethanol in CO$_2$; Flow: 60 mL/min; Pressure: 100 bar; Temperature: 35° C.). The first eluting enantiomer (15.5 min) was defined as Enantiomer A (5.1 mg, 3% yield), and the second eluting enantiomer (23.0 min) was defined as Enantiomer B (5.2 mg, 3% yield). $^1$H NMR (500 MHz, DMSO-d$_6$) δ 9.35 (s, 1H), 8.66 (s, 1H), 8.58 (d, J=4.4 Hz, 1H), 8.35 (s, 1H), 8.05 (s, 1H), 7.69 (t, J=8.8 Hz, 1H), 7.54-7.49 (m, 1H), 6.54-6.47 (m, 1H), 4.02 (s, 3H), 2.74-2.63 (m, 1H), 1.55 (s, 3H), 1.50 (s, 3H), 1.36 (d, J=7.0 Hz, 2H), 1.07 (d, J=7.3 Hz, 2H), 0.89 (t, J=7.3 Hz, 3H). LC/MS (M+H)=477.25.

Example 361

2-{12-Fluoro-11-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaen-5-yl}propan-2-ol

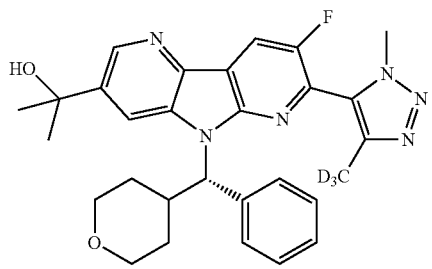 [SMILES: [2H]C([2H])([2H])c1nnn(C)c1-c1nc2c(cc1F)c1ncc(C(C)(C)O)cc1n2[C@H](c1ccccc1)C1CCOCC1]

Step 1: 5-Bromo-6'-chloro-5'-fluoro-3-nitro-2,3'-bipyridine

A flask was charged 2,5-dibromo-3-nitropyridine (1.608 g, 5.70 mmol) and (6-chloro-5-fluoropyridin-3-yl)boronic acid (1.0 g, 5.7 mmol). The flask was flushed with nitrogen for 30 min. To this was added tetrahydrofuran (17.5 mL), followed by 2M aqueous tripotassium phosphate (5.7 mL, 11.4 mmol). The resulting mixture was stirred while bubbling nitrogen through the mixture for 30 min. To this was added PdCl$_2$(dppf)$_2$.DCM (0.163 g, 0.200 mmol). The flask was sealed and immersed in a sand bath at 75° C. The reaction was held at that temperature for 2 h, then slowly cooled to ambient temperature. The reaction was poured into a stirred mixture of water and EtOAc. The layers were separated. The organics were washed twice more with water, then brine, and concentrated. Flash chromatography (0→20% EA/Hex) to gave 1.0 g (53%). LCMS (M+H)= 332.5, T$_R$=1.698 min (Column: Phenomenex LUNA C18, 30×2, 3 u; Mobile Phase A: 90:10 water:acetonitrile with 0.1% TFA; Mobile Phase B: 10:90 water:acetonitrile with 0.1% TFA; Temperature: 40° C.; Gradient: 0-100% B over 2 min, hold 1 min; Flow rate: 1 mL/min).

Step 2: 3-Bromo-7-chloro-8-fluoro-5H-pyrrolo[2,3-b:4,5-b']dipyridine

A 100 mL flask was charged with 5-bromo-6'-chloro-5'-fluoro-3-nitro-2,3'-bipyridine (1.0 g, 3.0 mmol) and 1,2-bis(diphenylphosphino)ethane (1.5 g, 3.8 mmol) and flushed with nitrogen. The solids were suspended in 1,2-dichlorobenzene (12 mL), and stirred under a stream of nitrogen for 15 min. The flask was sealed and immersed in a preheated oil bath at 165° C. for 3 h. The reaction was allowed to cool to room temperature and the precipitate collected by filtration. The mother liquor was discarded. The solid was stirred under DCM and collected by filtration to give 400 mg (44%). LCMS (M+H)=300.15, T$_R$=1.413 min (Column: Phenomenex LUNA C18, 2×30, 3 u; Mobile Phase A: 95:5 water: acetonitrile with 10 Mm Ammonium acetate; Mobile Phase B: 5:95 water:acetonitrile with 10 Mm Ammonium acetate; Temperature: 40° C.; Gradient: 0-100% B over 2 min, hold 1 min; Flow rate: 1 mL/min).

Step 3: (S)-3-Bromo-7-chloro-8-fluoro-5-(phenyl(tetrahydro-2H-pyran-4-yl)methyl)-5H-pyrrolo[2,3-b:4,5-b']dipyridine A dry vial was charged with 3-bromo-7-chloro-8-fluoro-5H-pyrrolo[2,3-b:4,5-b']dipyridine (385 mg, 1.28 mmol), triphenylphosphine (672 mg, 2.56 mmol) and (R)-phenyl(tetrahydro-2H-pyran-4-yl)methanol (493 mg, 2.56 mmol). The mixture was dissolved in THF (12 mL) and cooled to 0° C. Di-tert-butyl azodicarboxylate (590 mg, 2.56 mmol) in 0.5 mL THF was added dropwise. The reaction was allowed to gradually warm to room temperature overnight. The reaction was concentrated and purified by flash chromatography to give 840 mg (quant.) white foam solid which contained coupling byproducts. LCMS (M+H)=474.75, T$_R$=2.177 min (Column: Phenomenex LUNA C18, 2×30, 3 u; Mobile Phase A: 95:5 water:acetonitrile with 10 Mm Ammonium acetate; Mobile Phase B: 5:95 water:acetonitrile with 10 Mm Ammonium acetate; Temperature: 40° C.; Gradient: 0-100% B over 2 min, hold 1 min; Flow rate: 1 mL/min).

Step 4: (S)-1-(7-Chloro-8-fluoro-5-(phenyl(tetrahydro-2H-pyran-4-yl)methyl)-5H-pyrrolo[2,3-b:4,5-b']dipyridin-3-yl)ethan-1-one A flask was charged with (S)-3-bromo-7-chloro-8-fluoro-5-(phenyl(tetrahydro-2H-pyran-4-yl)methyl)-5H-pyrrolo[2,3-b:4,5-b']dipyridine (406 mg, 0.855 mmol) and DMF (8 mL). The solution was degassed with a stream of nitrogen and treated with tributyl(1-ethoxyvinyl)stannane (618 mg, 1.71 mmol), triethylamine (0.178 mL, 1.28 mmol), CuI (16.3 mg, 0.086 mmol), and Pd(PPh$_3$)$_4$ (49.4 mg, 0.043 mmol). The reaction was warmed to 100° C. with stirring. After 4.5 h, the reaction was cooled to room temperature, diluted with EtOAc, and washed with water and brine. The organic layer was concentrated. The residue was dissolved in 10 mL THF, treated with 5 mL 3M HCl, and stirred for 1 h at room temperature. The reaction was quenched with 15 mL of aq. K$_2$CO$_3$ (5% solution), and diluted with EtOAc. The organic layer was separated, washed with brine, dried over MgSO$_4$, filtered, and concentrated. The resulting residue was purified by flash chromatography (0→40% EA/Hex) to give 120 mg (32%). LCMS (M+H)=438.33, T$_R$=1.897 min (Column: Phenomenex LUNA C18, 2×30, 3 u; Mobile Phase A: 95:5 water:acetonitrile with 10 Mm Ammonium acetate; Mobile Phase B: 5:95 water:acetonitrile with 10 Mm Ammonium acetate; Temperature: 40° C.; Gradient: 0-100% B over 2 min, hold 1 min; Flow rate: 1 mL/min).

Step 5: (S)-2-(7-Chloro-8-fluoro-5-(phenyl(tetrahydro-2H-pyran-4-yl)methyl)-5H-pyrrolo[2,3-b:4,5-b']dipyridin-3-yl)propan-2-ol Methylmagnesium bromide (3M in diethyl ether, 2.3 mL, 6.9 mmol) was added to a stirred solution of (S)-1-(7-chloro-8-fluoro-5-(phenyl(tetrahydro-2H-pyran-4-yl)methyl)-5H-pyrrolo[2,3-b:4,5-b']dipyridin-3-yl)ethan-1-one (100 mg, 0.228 mmol) in THF (2.3 mL) under N$_2$ (g) at −20° C. The reaction was stirred at that temperature for 1 h. The reaction mixture was quenched with saturated aqueous ammonium chloride (6 mL) and diluted with ethyl acetate (14 mL) while still at −20° C. The mixture was allowed to warm to ambient temperature. The layers were separated and the aqueous phase was washed with a second portion of ethyl acetate (7 mL). The combined organics were concentrated. The resulting residue was purified by flash chromatography (~50% EA/Hex) to give 97 mg (94%). LCMS (M+H)=454.2, T$_R$=1.602 min (Column: Phenomenex LUNA C18, 30×2, 3 u; Mobile Phase A: 90:10 water:acetonitrile with 0.1% TFA; Mobile Phase B: 10:90 water:acetonitrile with 0.1% TFA; Temperature: 40° C.; Gradient: 0-100% B over 2 min, hold 1 min; Flow rate: 1 mL/min).

Step 6: 2-{12-Fluoro-11-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaen-5-yl}propan-2-ol A 2 mL microwave vial was charged with (S)-2-(7-Chloro-8-fluoro-5-(phenyl(tetrahydro-2H-pyran-4-yl)methyl)-5H-pyrrolo[2,3-b:4,5-b']dipyridin-3-yl)propan-2-ol (35.0 mg, 0.077 mmol), 4-($^2$H$_3$)methyl-1-((trimethylsilyl)methyl)-1H-1,2,3-triazole (39.9 mg, 0.231 mmol), tetramethylammonium acetate (12.3 mg, 0.093 mmol), and DMF (1.5 mL). The resulting mixture was degassed with a stream of N$_2$. To this was added PdCl$_2$(PPh$_3$)$_2$ (5.4 mg, 7.7 µmol). The vial was flushed with nitrogen and heated at 110° C. with stirring for 5 h. The reaction mixture was purified by preparative HPLC (Column: XBridge C18, 19×200 mm, 5-µm particles; Mobile Phase A: 5:95 acetonitrile: water with 0.1% trifluoroacetic acid; Mobile Phase B: 95:5 acetonitrile: water with 0.1% trifluoroacetic acid; Gradient: 20-80% B over 25 min, then a 5-min hold at 100% B; Flow: 20 mL/min) to give 20 mg (50% yield). $^1$H NMR (500 MHz, DMSO) δ 8.77 (s, 1H), 8.69 (d, J=9.54 Hz, 1H), 8.45 (s, 1H), 7.70 (m, 2H), 7.30 (m, 2H), 7.24 (m, 1H), 5.87 (m, 1H), 4.17

(s, 3H), 3.87 (m, 1H), 3.74 (m, 1H), 3.21 (m, 1H), 2.55 (m, 2H), 1.61 (s, 6H), 1.50 (m, 2H), 1.27 (m, 1H), 1.10 (m, 1H); LCMS (M+H)=517.6

Examples 362 & 363

2-{8-[(3-Fluoropyridin-2-yl)(oxan-4-yl)methyl]-11-[4-($^{2}H_{3}$)methyl-1-methyl-1H-1,2,3-triazol-5-yl]-3,8,10-triazatricyclo[7.4.0.0$^{2,7}$]trideca-1(9),2,4,6,10,12-hexaen-5-yl}propan-2-ol

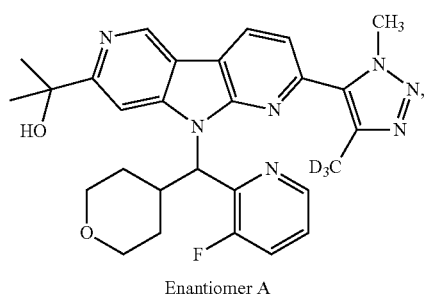

Example 362

Enantiomer A

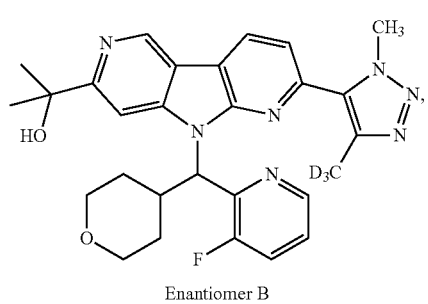

Example 363

Enantiomer B

Step 1: 5-Bromo-6'-chloro-3-nitro-2,3'-bipyridine

In a 75 mL pressure flask equipped with a magnetic stirring bar was added (6-chloropyridin-3-yl)boronic acid (1 g, 6.35 mmol), 2,5-dibromo-3-nitropyridine (1.791 g, 6.35 mmol). The solids were suspended in THF (30 mL). The mixture was treated with PdCl$_2$(dppf)-CH$_2$Cl$_2$ adduct (0.259 g, 0.318 mmol) and K$_3$PO$_4$ (9.53 mL, 19.06 mmol) (25 g K$_3$PO$_4$/60 mL water=2M solution). Argon was bubbled through the mixture for 5 min while sonicating. The flask was capped and heated to 80° C. within a preheated oil bath for 2 h. The reaction vessel was cooled to room temperature. The reaction mixture was filtered, and the filtrate was concentrated to remove the organic solvent. The remaining aqueous layer was diluted with water and was extracted with ethyl acetate (emulsion formed, brine added). The organic layer was dried over MgSO$_4$, filtered and concentrated to give a solid. The material was taken up in DCM and ethyl acetate. The solution was purified by flash column chromatography (80 g silica gel ISCO, 0-50% ethyl acetate/hexanes over 600 mL total solvent, then 50-100% over 300 mL solvent; TLC R$_f$=0.88 (50% ethyl acetate/hexanes)). Like fractions were concentrated to give 660 mg (33%) of a pale yellow solid with 99% purity by LC/MS. LC/MS (M+H)= 315.9; HPLC conditions: T$_R$=3.43 min (Phenomenex LUNA C18 2×50 mm (4 min grad) eluting with 10-90% aq MeOH containing 0.1% TFA, 0.8 mL/min, monitoring at 254 nm); Temperature: 40° C.).

Step 2: 3-Bromo-7-chloro-5H-pyrrolo[2,3-b:4,5-b']dipyridine and 3-bromo-7-chloro-5H-pyrrolo[3,2-b:4,5-c']dipyridine In a round bottom flask equipped with a magnetic stirring bar was added 5-bromo-6'-chloro-3-nitro-2,3'-bipyridine (4.5 g, 14.3 mmol), and bis(diphenylphosphino)ethane (7.13 g, 17.9 mmol). The solids were suspended in 1,2-dichlorobenzene (16.1 mL, 143 mmol). The flask was flushed with nitrogen, and the reaction was heated to 150° C. (oil bath) with stirring. The reaction was allowed to continue for 1 h, open to air. Most of the solvent was removed by evaporation under a stream of nitrogen while heating to 100° C. The reaction mixture was diluted with 100 mL of dichloromethane and was stirred at room temperature overnight. A white precipitate formed and was removed by filtration, washing the solid with additional dichloromethane. This filtered material (2.08 g; 52%) was 3-bromo-7-chloro-5H-pyrrolo[3,2-b:4,5-c']dipyridine: $^{1}$H NMR (400 MHz, DMSO-d$_6$) δ 12.47 (br. s., 1H), 8.68-8.57 (m, 2H), 8.19 (d, J=1.8 Hz, 1H), 7.42 (d, J=8.3 Hz, 1H). The remaining filtrate which contains the other isomer plus multiple impurities was concentrated to remove remaining 1,2-dichlorobenzene. After solvent removal (nitrogen stream with heating at 100° C.), the oily residue was taken up in 50 mL of isopropyl acetate and stirred mixture at room temperature for several h. A brown solid was filtered. The filtrate was concentrated under vacuum to give an oil. This oil was taken up in DCM and was transferred to the top of a 40 g ISCO silica gel column for purification. The material was eluted with 5-100% THF/hexanes over 800 mL total volume. Like fractions (as identified by LC/MS; double spot by TLC (R$_f$=0.64/0.73 in 30% THF/hexanes)) were combined and concentrated under vacuum to give 600 mg (15%) of 3-bromo-7-chloro-5H-pyrrolo[2,3-b:4,5-b']dipyridine as an off-white solid. $^{1}$H NMR (400 MHz, CDCl$_3$) δ 1 capped 0.45 (br, s., 1H), 9.33 (s, 1H), 8.69 (d, J=1.8 Hz, 1H), 8.04 (d, J=1.8 Hz, 1H), 7.29 (s, 1H).

Step 3: (3-Fluoropyridin-2-yl)(oxan-4-yl)methanol

4-Bromooxane (3.17 g, 19.2 mmol) was added drop wise to a stirred suspension of magnesium (466 mg, 19.2 mmol) and one crystal of iodine in THF (26 mL) at ambient temperature. The reaction mixture was stirred for 30 min before it was cooled to 0° C. 3-Fluoropicolinaldehyde (1.20 g, 9.59 mmol) was added drop wise. The reaction mixture was then stirred for 30 min. The reaction mixture was quenched with saturated aqueous ammonium chloride (40 mL) and diluted with ethyl acetate (100 mL) and water (30 mL). The product was extracted into the organic phase before the layers were separated. The aqueous layer was washed with a second portion of ethyl acetate (50 mL), and the combined organics were dried over sodium sulfate. The volatiles were removed under reduced pressure. The crude reaction material was purified using silica gel column chromatography. (3-Fluoropyridin-2-yl)(oxan-4-yl)methanol (1.47 g, 6.96 mmol, 73% yield) was isolated as a colorless oil. $^{1}$H NMR (400 MHz, CDCl$_3$) δ 8.40-8.45 (m, 1H), 7.40-7.46 (m, 1H), 7.27-7.33 (m, 1H), 4.83-4.88 (m, 1H), 4.00 (td, J=2.14, 11.37 Hz, 2H), 3.36 (ddt, J=2.20, 9.23, 11.77 Hz, 2H), 1.90-2.03 (m, 1H), 1.65-1.78 (m, 1H), 1.57 (dq, J=4.65, 12.47 Hz, 1H), 1.39-1.49 (m, 2H).

Step 4: 5-Bromo-11-chloro-8-[(3-fluoropyridin-2-yl) (oxan-4-yl)methyl]-3,8,10-triazatricyclo[7.4.0.0$^{2,7}$] trideca-1(9),2,4,6,10,12-hexaene Di-tert-butyl azodicarboxylate (245 mg, 1.06 mmol) in THF (7.0 mL) was added drop wise to a stirred solution of 3-bromo-7-chloro-5H-pyrrolo[2,3-b:4,5-b']dipyridine (200 mg, 0.71 mmol), (3-Fluoropyridin-2-yl)(oxan-4-yl)methanol (224 mg, 1.06 mmol), triphenylphosphine (279 mg, 1.06 mmol), and Et$_3$N (148 µL, 1.06 mmol) in THF (7.1 mL) at 0° C. The reaction mixture was allowed to warm to ambient temperature over 10 min and stirred for an additional 16 h at that temperature. The crude reaction mixture was loaded onto a silica gel column and purified using ethyl acetate in hexanes (0-100%). Racemic 5-bromo-11-chloro-8-[(3-fluoropyridin-2-yl)(oxan-4-yl)methyl]-3,8,10-triazatricyclo [7.4.0.0$^{2,7}$]trideca-1(9),2,4,6,10,12-hexaene (337 mg, 0.71 mmol, >100% yield) was isolated as a white solid with a minor triphenylphosphine oxide contaminant. LC/MS (M+H)=475.05; LC/MS T$_R$=2.052 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min). The material was used without additional purification.

Step 5: 2-{8-[(3-Fluoropyridin-2-yl)(oxan-4-yl) methyl]-11-[4-($^2$H$_3$)methyl-1-methyl-1H-1,2,3-triazol-5-yl]-3,8,10-triazatricyclo[7.4.0.0$^{2,7}$]trideca-1 (9),2,4,6,10,12-hexaen-5-yl}propan-2-ol 5-Bromo-11-chloro-8-[(3-fluoropyridin-2-yl)(oxan-4-yl) methyl]-3,8,10-triazatricyclo[7.4.0.0$^{2,7}$]trideca-1(9),2,4,6, 10,12-hexaene (337 mg, 0.71 mmol), tributyl(1-ethoxyvinyl)tin (512 mg, 1.42 mmol), tetrakis (82.0 mg, 0.07 mmol), copper(I) iodide (27.0 mg, 0.14 mmol), and triethylamine (128 µL, 0.92 mmol) in DMF (3.5 mL) were degassed with N$_2$ (g) for 3 min. The reaction mixture was subsequently stirred at 100° C. for 3 h. LC/MS showed conversion to the enol ether. 1N Aqueous HCl (2 mL) was added, and the reaction mixture was stirred for 20 min. The reaction mixture was quenched with 1.5 M aqueous monobasic potassium phosphate (5 mL), and the layers were separated. The aqueous layer was washed with ethyl acetate (3×10 mL). The combined organics were dried over sodium sulfate. The solids were filtered away, and the volatiles were removed under reduced pressure. The crude product was purified using silica gel column chromatography with ethyl acetate in hexanes (0-100%). 2-{8-[(3-Fluoropyridin-2-yl)(oxan-4-yl) methyl]-11-[4-($^2$H$_3$)methyl-1-methyl-1H-1,2,3-triazol-5-yl]-3,8,10-triazatricyclo[7.4.0.0$^{2,7}$]trideca-1(9),2,4,6,10,12-hexaen-5-yl}propan-2-ol (161 mg, 0.37 mmol, 52% yield) was isolated. LC/MS (M+H)=439.15; LC/MS T$_R$=1.701 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 6: 2-{8-[(3-fluoropyridin-2-yl)(oxan-4-yl) methyl]-11-[4-($^2$H$_3$)methyl-1-methyl-1H-1,2,3-triazol-5-yl]-3,8,10-triazatricyclo[7.4.0.0$^{2,7}$]trideca-1 (9),2,4,6,10,12-hexaen-5-yl}propan-2-ol 2-{8-[(3-Fluoropyridin-2-yl)(oxan-4-yl)methyl]-11-[4-($^2$H$_3$)methyl-1-methyl-1H-1,2,3-triazol-5-yl]-3,8,10-triazatricyclo[7.4.0.0$^{2,7}$]trideca-1(9),2,4,6,10,12-hexaen-5-yl}propan-2-ol (160 mg, 0.37 mmol), 4-($^2$H$_3$)methyl-1-methyl-5-(tributylstannyl)-1H-1,2,3-triazole (184 mg, 0.47 mmol), Pd$_2$(dba)$_3$ (66.8 mg, 0.07 mmol), tricyclohexylphosphine (227 µL, 0.15 mmol, 20% wt in toluene), and cesium carbonate (238 mg, 0.73 mmol) in dioxane (3.6 mL) were degassed with N$_2$ (g) for 3 min. The reaction mixture was subsequently stirred at 115° C. for 3 h. The volatiles were removed under reduced pressure, and the crude reaction mixture was taken into the next step without purification. 100% yield assumed. LC/MS (M+H)=503.30; LC/MS T$_R$=1.465 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 7: 2-{8-[(3-Fluoropyridin-2-yl)(oxan-4-yl) methyl]-11-[4-($^2$H$_3$)methyl-1-methyl-1H-1,2,3-triazol-5-yl]-3,8,10-triazatricyclo[7.4.0.0$^{2,7}$]trideca-1 (9),2,4,6,10,12-hexaen-5-yl}propan-2-ol Methylmagnesium bromide (3.58 mL, 10.8 mmol, 3 M) was added to a stirred solution of 2-{8-[(3-fluoropyridin-2-yl)(oxan-4-yl)methyl]-11-[4-($^2$H$_3$)methyl-1-methyl-1H-1,2, 3-triazol-5-yl]-3,8,10-triazatricyclo[7.4.0.0$^{2,7}$]trideca-1(9), 2,4,6,10,12-hexaen-5-yl}propan-2-ol (180 mg, 0.36 mmol) in THF (3.6 mL) under N$_2$ (g) at −20° C. The reaction mixture was stirred at that temperature for 1 h. The reaction mixture was then quenched with saturated aqueous ammonium chloride (8 mL) and diluted with ethyl acetate (20 mL) while still at −20° C. The mixture was removed from the cold bath and allowed to warm to ambient temperature. The layers were separated, and the aqueous phase was washed with a second portion of ethyl acetate (20 mL). The combined organics were dried over sodium sulfate, the solids were filtered away, and the volatiles were removed under reduced pressure. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10 mM ammonium acetate; Gradient: 5-45% B over 22 min, then a 5-min hold at 100% B; Flow: 20 mL/min. Fractions containing the desired product were combined and dried via centrifugal evaporation to afford racemic 2-{8-[(3-Fluoropyridin-2-yl)(oxan-4-yl)methyl]-11-[4-($^2$H$_3$)methyl-1-methyl-1H-1,2,3-triazol-5-yl]-3,8,10-triazatricyclo [7.4.0.0$^{2,7}$]trideca-1(9),2,4,6,10,12-hexaen-5-yl}propan-2-ol. Enantiomers A and B were separated using chiral preparatory HPLC (Column: Chiralpak AD 21×250 mm 5 u; Mobile Phase: 10% ethanol in heptane; Flow: 15 mL/min). The first eluting enantiomer (30 min) was defined as Enantiomer A (15.0 mg, 8% yield), and the second eluting enantiomer (35 min) was defined as Enantiomer B (16.0 mg, 8% yield). $^1$H NMR (500 MHz, DMSO-d$_6$) δ 8.74-8.68 (m, 2H), 8.60 (d, J=4.4 Hz, 1H), 8.50 (d, J=1.5 Hz, 1H), 7.70-7.63 (m, 2H), 7.51-7.46 (m, 1H), 6.59 (d, J=9.5 Hz, 1H), 5.37 (s, 1H), 4.37 (s, 3H), 3.87 (d, J=10.6 Hz, 1H), 3.69 (d, J=9.5 Hz, 1H), 3.54-3.29 (m, 2H), 3.23-3.11 (m, 1H), 1.72 (d, J=11.4 Hz, 1H), 1.57-1.51 (m, 6H), 1.47 (d, J=8.1 Hz, 1H), 1.29-1.18 (m, 1H), 0.77 (d, J=14.3 Hz, 1H); LC/MS T$_R$=1.220 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Example 364

2-{11-[4-($^2$H$_3$)Methyl-1-methyl-1H-1,2,3-triazol-5-yl]-8-[(S)-(oxan-4-yl)(phenyl)methyl]-3,8,12-triazatricyclo[7.4.0.0$^{2,7}$]trideca-1(9),2,4,6,10,12-hexaen-5-yl}propan-2-ol

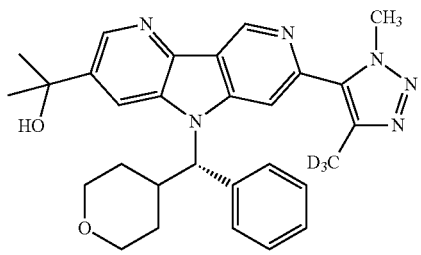

Step 1: 5-Bromo-11-chloro-8-[(S)-(oxan-4-yl)(phenyl)methyl]-3,8,12-triazatricyclo[7.4.0.0$^{2,7}$]trideca-1(9),2,4,6,10,12-hexaene Di-tert-butyl azodicarboxylate (97.0 mg, 419 μmol) in THF (2.8 mL) was added drop wise to a stirred solution of 3-bromo-7-chloro-5H-pyrrolo[3,2-b:4,5-c']dipyridine (prepared in route to 2-{8-[(3-fluoropyridin-2-yl)(oxan-4-yl)methyl]-11-[4-($^2$H$_3$)methyl-1-methyl-1H-1,2,3-triazol-5-yl]-3,8,10-triazatricyclo[7.4.0.0$^{2,7}$]trideca-1(9),2,4,6,10,12-hexaen-5-yl}propan-2-ol, 79.0 mg, 0.28 mmol), (S)-(oxan-4-yl)(phenyl)methanol (81.0 mg, 419 μmol), triphenylphosphine (110 mg, 419 μmol), and Et$_3$N (58.5 μL, 419 μmol) in THF (2.8 mL) at 0° C. The reaction mixture was allowed to warm to ambient temperature over 10 min and stirred for an additional 5 h at that temperature. The crude reaction mixture was loaded onto a silica gel column and purified using ethyl acetate in hexanes (0-100%). 5-Bromo-11-chloro-8-[(S)-(oxan-4-yl)(phenyl)methyl]-3,8,12-triazatricyclo[7.4.0.0$^{2,7}$]trideca-1(9),2,4,6,10,12-hexaene (24.4 mg, 19% yield) was isolated as a white solid. LC/MS (M+H)=456.10; LC/MS T$_R$=1.818 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 2: 1-{11-Chloro-8-[(S)-(oxan-4-yl)(phenyl)methyl]-3,8,12-triazatricyclo[7.4.0.0$^{2,7}$]trideca-1(9),2,4,6,10,12-hexaen-5-yl}ethan-1-one 5-Bromo-11-chloro-8-[(S)-(oxan-4-yl)(phenyl)methyl]-3,8,12-triazatricyclo[7.4.0.0$^{2,7}$]trideca-1(9),2,4,6,10,12-hexaene (35.0 mg, 0.08 mmol), tributyl(1-ethoxyvinyl)tin (55 mg, 0.15 mmol), tetrakis (8.9 mg, 8 μmol), copper(I) iodide (2.9 mg, 15 μmol), and triethylamine (14 μL, 0.10 mmol) in DMF (380 μL) were degassed with N$_2$ (g) for 3 min. The reaction mixture was subsequently stirred at 100° C. for 5 h. LC/MS showed conversion to the enol ether. 1N Aqueous HCl (2 mL) was added, and the reaction mixture was stirred for 20 min. The reaction mixture was quenched with 1.5 M aqueous monobasic potassium phosphate (5 mL), and the layers were separated. The aqueous layer was washed with ethyl acetate (3×10 mL). The combined organics were dried over sodium sulfate. The solids were filtered away, and the volatiles were removed under reduced pressure. The crude product was purified using silica gel column chromatography with ethyl acetate in hexanes (0-100%). 1-{11-Chloro-8-[(S)-(oxan-4-yl)(phenyl)methyl]-3,8,12-triazatricyclo[7.4.0.0$^{2,7}$]trideca-1(9),2,4,6,10,12-hexaen-5-yl}ethan-1-one (32.2 mg, 0.08 mmol, >100% yield) was isolated as a pale-yellow oil with some triphenylphosphine oxide impurity. LC/MS (M+H)=420.05; LC/MS T$_R$=1.602 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Step 3: 1-{11-[4-($^2$H$_3$)Methyl-1-methyl-1H-1,2,3-triazol-5-yl]-8-[(S)-(oxan-4-yl)(phenyl)methyl]-3,8,12-triazatricyclo[7.4.0.0$^{2,7}$]trideca-1(9),2,4,6,10,12-hexaen-5-yl}ethan-1-one 1-{11-Chloro-8-[(S)-(oxan-4-yl)(phenyl)methyl]-3,8,12-triazatricyclo[7.4.0.0$^{2,7}$]trideca-1(9),2,4,6,10,12-hexaen-5-yl}ethan-1-one (32.0 mg, 0.08 mmol), 4-($^2$H$_3$)methyl-1-methyl-5-(tributylstannyl)-1H-1,2,3-triazole (38.6 mg, 0.10 mmol), Pd$_2$(dba)$_3$ (14.0 mg, 15 μmol), tricyclohexylphosphine (47.5 μL, 0.03 mmol, 20% wt in toluene), and cesium carbonate (49.7 mg, 0.15 mmol) in dioxane (760 μL) were degassed with N$_2$ (g) for 3 min. The reaction mixture was subsequently stirred at 115° C. for 5 h. The volatiles were removed under reduced pressure, and the crude reaction mixture was taken into the next step without purification. 100% yield assumed.

Step 4: 2-{11-[4-($^2$H$_3$)Methyl-1-methyl-1H-1,2,3-triazol-5-yl]-8-[(S)-(oxan-4-yl)(phenyl)methyl]-3,8,12-triazatricyclo[7.4.0.0$^{2,7}$]trideca-1(9),2,4,6,10,12-hexaen-5-yl}propan-2-ol Methylmagnesium bromide (765 μL, 2.30 mmol, 3 M) was added to a stirred solution of 1-{11-[4-($^2$H$_3$)methyl-1-methyl-1H-1,2,3-triazol-5-yl]-8-[(S)-(oxan-4-yl)(phenyl)methyl]-3,8,12-triazatricyclo[7.4.0.0$^{2,7}$]trideca-1(9),2,4,6,10,12-hexaen-5-yl}ethan-1-one (37.0 mg, 0.08 mmol) in THF (765 μL) under N$_2$ (g) at −20° C. The reaction mixture was stirred at that temperature for 1 h. The reaction mixture was then quenched with saturated aqueous ammonium chloride (8 mL) and diluted with ethyl acetate (20 mL) while still at −20° C. The mixture was removed from the cold bath and allowed to warm to ambient temperature. The layers were separated, and the aqueous phase was washed with a second portion of ethyl acetate (20 mL). The combined organics were dried over sodium sulfate, the solids were filtered away, and the volatiles were removed under reduced pressure. The crude material was purified via preparative LC/MS with the following conditions: Column: XBridge C18, 19×200 mm, 5-μm particles; Mobile Phase A: 5:95 acetonitrile: water with 0.1% TFA; Mobile Phase B: 95:5 acetonitrile: water with 0.1% TFA; Gradient: 8-48% B over 20 min, then a 5-min hold at 100% B; Flow: 20 mL/min. Fractions containing the desired product were combined and dried via centrifugal evaporation to afford 2-{11-[4-($^2$H$_3$)methyl-1-methyl-1H-1,2,3-triazol-5-yl]-8-[(S)-(oxan-4-yl)(phenyl)methyl]-3,8,12-triazatricyclo[7.4.0.0$^{2,7}$]trideca-1(9),2,4,6,10,12-hexaen-5-yl}propan-2-ol (4.5 mg, 12% yield). $^1$H NMR (500 MHz, DMSO-d$_6$) δ 9.49 (s, 1H), 8.80 (s, 1H), 8.51 (br. s., 1H), 8.17 (br. s., 1H), 7.67 (d, J=7.70 Hz, 2H), 7.33-7.40 (m, 2H), 7.25-7.31 (m, 1H), 7.22 (s, 1H), 7.12 (s, 1H), 7.02 (s, 1H), 5.92 (d, J=11.00 Hz, 1H), 4.18 (s, 3H), 3.91 (d, J=5.14 Hz, 1H), 3.73 (d, J=9.54 Hz, 1H), 3.26 (t, J=11.00 Hz, 1H), 1.73 (d, J=12.84 Hz, 1H), 1.65-1.53 (m, 7H), 1.38-1.27 (m, 1H), 0.95 (d, J=12.10 Hz, 1H). LC/MS (M+H)=500.35; LC/MS T$_R$=1.188 min (Column: Phenomenex Luna 30×2.0 mm 3 u; Mobile Phase A: 10:90 acetonitrile:water with 0.1% TFA; Mobile Phase B: 90:10 acetonitrile:water with 0.1% TFA; Temperature: 40° C.; Gradient: 0-100% B over 2 min; Flow: 1 mL/min).

Examples 365-376

The compounds in Table 4 were prepared from commercially available starting materials or intermediates prepared according to analogous procedures described for 2-{8-[(3-fluoropyridin-2-yl)(oxan-4-yl)methyl]-11-[4-($^2$H$_3$)methyl-1-methyl-1H-1,2,3-triazol-5-yl]-3,8,10-triazatricyclo[7.4.0.0$^{2,7}$]trideca-1(9),2,4,6,10,12-hexaen-5-yl}propan-2-ol or 2-{11-[4-($^2$H$_3$)methyl-1-methyl-1H-1,2,3-triazol-5-yl]-8-[(S)-(oxan-4-yl)(phenyl)methyl]-3,8,10-triazatricyclo[7.4.0.0$^{2,7}$]trideca-1(9),2,4,6,10,12-hexaen-5-yl}propan-2-ol:

TABLE 4

| Example | Structure | HPLC T$_R$ (min) | LC/MS (M + H) | HPLC Method$^a$ |
|---|---|---|---|---|
| 365 | 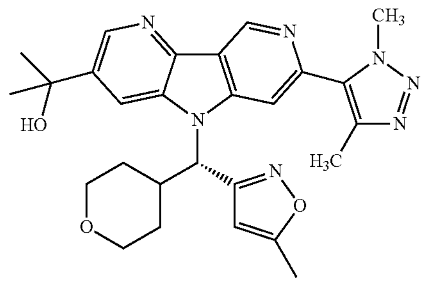 [SMILES: Cc1cc([C@H](C2CCOCC2)n2c3cc(-c4c(C)nnn4C)ncc3c3ncc(C(C)(C)O)cc32)no1] | 7.65 | 502.3 | A |
| 366 Enantiomer A | 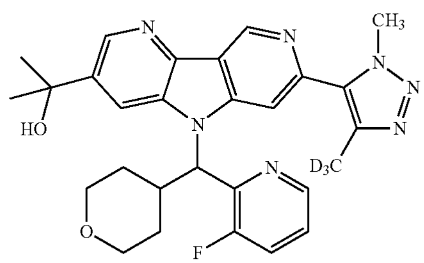 [SMILES: [2H]C([2H])([2H])c1nnn(C)c1-c1cc2c(cn1)c1ncc(C(C)(C)O)cc1n2C(c1ncccc1F)C1CCOCC1] | 20.17 | 519.3 | B |
| 367 Enantiomer B | 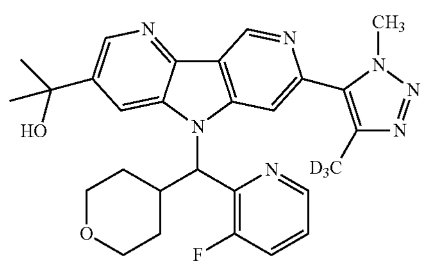 [SMILES: [2H]C([2H])([2H])c1nnn(C)c1-c1cc2c(cn1)c1ncc(C(C)(C)O)cc1n2C(c1ncccc1F)C1CCOCC1] | 26.30 | 519.3 | B |
| 368 | 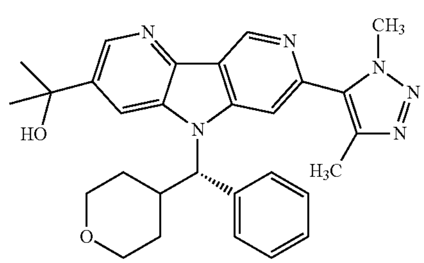 | 1.35 | 497.30 | C |

TABLE 4-continued

| Example | Structure | HPLC T$_R$ (min) | LC/MS (M + H) | HPLC Method$^a$ |
|---|---|---|---|---|
| 369 | 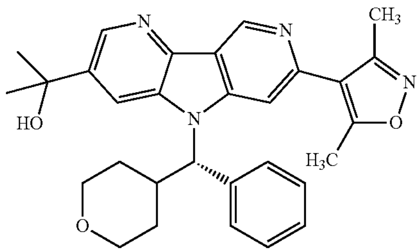 [SMILES: Cc1noc(C)c1-c1cc2c(cn1)c1ncc(C(C)(C)O)cc1n2[C@H](c1ccccc1)C1CCOCC1] | 1.39 | 497.25 | C |
| 370 Enantiomer A | 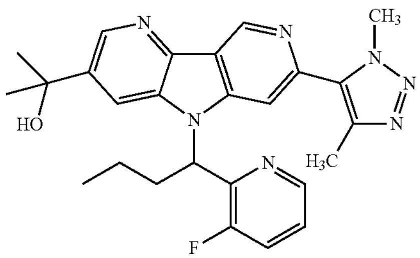 [SMILES: CCCC(c1ncccc1F)n1c2cc(-c3c(C)nnn3C)ncc2c2ncc(C(C)(C)O)cc21] | 20.17 | 474.10 | D |
| 371 Enantiomer B | 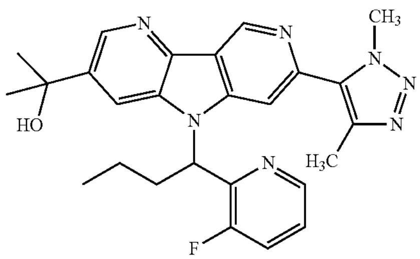 [SMILES: CCCC(c1ncccc1F)n1c2cc(-c3c(C)nnn3C)ncc2c2ncc(C(C)(C)O)cc21] | 22.90 | 474.10 | D |
| 372 | 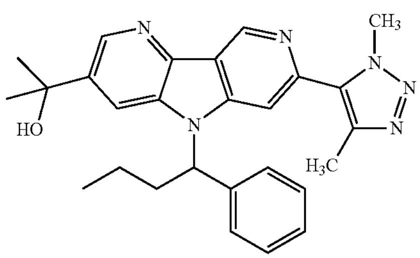 [SMILES: CCCC(c1ccccc1)n1c2cc(-c3c(C)nnn3C)ncc2c2ncc(C(C)(C)O)cc21] | 1.46 | 455.25 | C |
| 373 Enantiomer A | 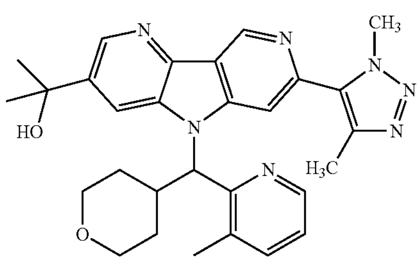 [SMILES: Cc1cccnc1C(C1CCOCC1)n1c2cc(-c3c(C)nnn3C)ncc2c2ncc(C(C)(C)O)cc21] | 10.14 | 512.30 | E |
| 374 Enantiomer B | 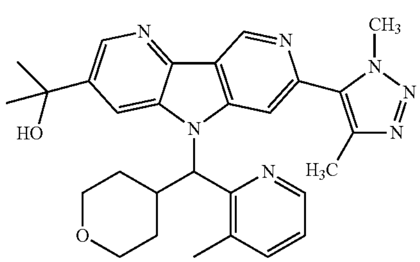 [SMILES: Cc1cccnc1C(C1CCOCC1)n1c2cc(-c3c(C)nnn3C)ncc2c2ncc(C(C)(C)O)cc21] | 17.66 | 512.30 | E |

TABLE 4-continued

| Example | Structure | HPLC T$_R$ (min) | LC/MS (M + H) | HPLC Method$^a$ |
|---|---|---|---|---|
| 375 Enantiomer A | 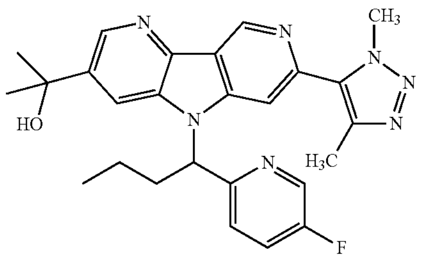 [SMILES: CCCC(c1ccc(F)cn1)n1c2cc(-c3c(C)nnn3C)ncc2c2ncc(C(C)(C)O)cc21] | 80.0 | 474.25 | F |
| 376 Enantiomer B | 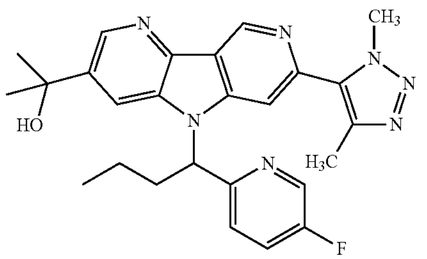 [SMILES: CCCC(c1ccc(F)cn1)n1c2cc(-c3c(C)nnn3C)ncc2c2ncc(C(C)(C)O)cc21] | 89.3 | 474.25 | F |

$^a$HPLC Conditions for Table 4: Method A: Column: Chiralcel OD 4.6 × 100 mm 5 u; Mobile Phase A: 100% heptane with 0.1% dimethylamine; Mobile Phase B: 100% ethanol; Gradient: 20% B; Flow: 2 mL/min. Method B: Column: Chiralcel OD 21 × 250 mm 10 u; Mobile Phase A: 100% heptane; Mobile Phase B: 100% ethanol; Gradient: 15% B; Flow: 15 mL/min. Method C: Column: Phenomenex 2 × 30 mm 3 u; Mobile Phase A: 90% water and 10% acetonitrile with 0.1% TFA; Mobile Phase B: 10% water and 90% acetonitrile with 0.1% TFA; Gradient: 0-100% B over 2 min; Flow: 1 mL/min. Method D: Column: Chiralpak AD 21 × 250 mm 5 u; Mobile Phase A: 100% heptane; Mobile Phase B: 100% ethanol; Gradient: 13% B; Flow: 15 mL/min. Method E: Column: Chiralcel OJ 21 × 250 mm 10 u; Mobile Phase A: heptane; Mobile Phase B: 100% ethanol; Gradient: 20% B; Flow: 15 mL/min. Method F: Column: Chiralpak AD 21 × 250 mm 5 u; Mobile Phase A: 100% heptane; Mobile Phase B: 100% ethanol; Gradient: 5% B; Flow: 15 mL/min.

Example 377

1-[11-(Dimethyl-1H-1,2,3-triazol-5-yl)-8-[(R)-oxan-4-yl(phenyl)methyl]-3,8,10-triazatricyclo[7.4.0.0$^{2,7}$]trideca-1(9),2(7),3,5,10,12-hexaen-5-yl]ethan-1-one

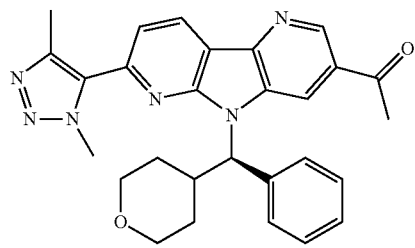 [SMILES: CC(=O)c1cnc2c3ccc(-c4c(C)nnn4C)nc3n([C@@H](c3ccccc3)C3CCOCC3)c2c1]

Step 1: 5-Bromo-11-chloro-8-[(R)-oxan-4-yl(phenyl)methyl]-3,8,10-triazatricyclo[7.4.0.0$^{2,7}$]trideca-1(9),2(7),3,5,10,12-hexaene To a suspension of 3-bromo-7-chloro-5H-pyrrolo[2,3-b:4,5-b']dipyridine (104 mg, 0.368 mmol) and (S)-phenyl(tetrahydro-2H-pyran-4-yl)methanol (92 mg, 0.479 mmol) in 4 mL of DCM was added triphenylphosphine (193 mg, 0.736 mmol). The resulting mixture was cooled to 0° C. To this was added DIAD (149 mg, 0.736 mmol). After 5 min, the ice bath was removed and stirring was continued at room temperature overnight. The reaction was concentrated and purified on the biotage using a 40 g column, eluting with 2-30% EtOAc/hexanes to obtain 91% yield of the desired product. LC/MS [M+H]$^+$=456 (triplet).

Step 2: 1-{11-Chloro-8-[(R)-oxan-4-yl(phenyl) methyl]-3,8,10-triazatricyclo[7.4.0.0$^{2,7}$]trideca-1(9), 2(7),3,5,10,12-hexaen-5-yl}ethan-1-one (R)-3-Bromo-7-chloro-5-(phenyl(tetrahydro-2H-pyran-4-yl)methyl)-5H-pyrrolo[2,3-b:4,5-b']dipyridine (93 mg, 0.204 mmol), tributyl(1-ethoxyvinyl)stannane (147 mg, 0.407 mmol), CuI (3.88 mg, 0.020 mmol), triethylamine (30.8 mg, 0.305 mmol), and Pd(PPh$_3$)$_4$ (11.8 mg, 10.2 μmol) were weighed into a 20 scintillation vial followed by the addition of DMF (2 mL). The air was replaced with argon, and the mixture heated to 100° C. with stirring. After 1 h, an additional portion of tributyl(1-ethoxyvinyl)stannane (147 mg, 0.407 mmol) was added and heating continued until the starting material was consumed. The reaction was cooled to room temperature, diluted with EtOAc, and washed with brine. The organic layer was concentrated, dissolved in 10 mL THF, and treated with 2 mL 3M HCl solution. After stirring for 1 h at room temperature, the reaction was quenched with 15 mL of aq. K$_2$CO$_3$ (5% solution) and diluted with EtOAc. The organic layer was separated, washed with brine, dried over MgSO$_4$, filtered, and concentrated. The crude mixture was subjected to a flash chromatography (24 g column), eluting with 5-100% EtOAc/hexanes to obtain the desired product in 61% yield. LC/MS [M+H]$^+$=420.

Step 3: 1-[11-(Dimethyl-1H-1,2,3-triazol-5-yl)-8-[(R)-oxan-4-yl(phenyl)methyl]-3,8,10-triazatricyclo[7.4.0.0$^{2,7}$]trideca-1(9),2(7),3,5,10,12-hexaen-5-yl] ethan-1-one (R)-1-(7-Chloro-5-(phenyl(tetrahydro-2H-pyran-4-yl) methyl)-5H-pyrrolo[2,3-b:4,5-b']dipyridin-3-yl)ethanone (30.0 mg, 0.071 mmol), 1,4-dimethyl-1H-1,2,3-triazole (10.4 mg, 0.107 mmol), tetramethylammonium acetate (11.4 mg, 0.086 mmol), and PdCl$_2$(PPh$_3$)$_2$(5.0 mg, 7.1 μmol) were weighed into a 20 mL scintillation vial. DMF (2 mL) was added and the air replaced with nitrogen. The reaction mixture was stirred at 100° C. overnight. The reaction was cooled to room temperature, diluted with EtOAc, and washed twice with brine. The organic layer was dried over MgSO$_4$ and concentrated. The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol: water with 10-mM ammonium acetate; Gradient: 50-90% B over 20 min, then a 5-min hold at 100% B; Flow: 20 mL/min. Fractions containing the desired product were combined and dried via centrifugal evaporation. The yield of the product was 84%. LC/MS [M+H]$^+$=481 $^1$H NMR (500 MHz, DMSO-d$_6$) δ 9.13 (s, 1H), 8.84 (d, J=8.1 Hz, 2H), 7.72 (d, J=8.1 Hz, 3H), 7.33-7.28 (m, 2H), 7.25-7.21 (m, 1H), 6.04 (br. s., 1H), 4.34 (s, 3H), 3.89 (d, J=10.3 Hz, 1H), 3.72 (d, J=9.2 Hz, 1H), 3.58 (br. s., 1H), 3.51 (s, 3H), 3.46-3.39 (m, 1H), 3.25-3.15 (m, 1H), 2.78 (s, 3H), 1.59 (br. s., 1H), 1.51 (d, J=8.8 Hz, 1H), 1.31 (d, J=10.3 Hz, 1H), 1.07 (d, J=14.3 Hz, 1H).

Example 378

2-[11-(Dimethyl-1H-1,2,3-triazol-5-yl)-8-[(R)-oxan-4-yl(phenyl)methyl]-3,8,10-triazatricyclo[7.4.0.0$^{2,7}$]trideca-1(9),2(7),3,5,10,12-hexaen-5-yl]propan-2-ol

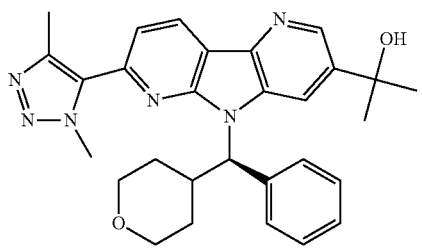 [SMILES: Cc1nnn(C)c1-c1ccc2c3ncc(C(C)(C)O)cc3n([C@@H](c3ccccc3)C3CCOCC3)c2n1]

(R)-1-(7-(1,4-Dimethyl-1H-1,2,3-triazol-5-yl)-5-(phenyl(tetrahydro-2H-pyran-4-yl)methyl)-5H-pyrrolo[2,3-b:4,5-b']dipyridin-3-yl)ethanone (18.0 mg, 0.037 mmol) was dissolved in 5 mL of THF and cooled to 0° C. To this methylmagnesium bromide (3M in diethyl ether, 0.187 mL, 0.562 mmol) was added. After 5 min, the ice bath was removed and the reaction stirred overnight. The reaction was quenched by addition of 1 mL acetone and diluted with 15 mL of EtOAc. It was washed with brine, and the organic layer was dried over MgSO$_4$, filtered and concentrated. The crude material was purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 20-60% B over 20 min, then a 5-min hold at 100% B; Flow: 20 mL/min. Fractions containing the desired product were combined and dried via centrifugal evaporation. The yield of the product was 69%. LC/MS [M+H]$^+$=497. $^1$H NMR (500 MHz, DMSO-d$_6$) δ 8.72 (d, J=7.7 Hz, 1H), 8.36 (br. s., 2H), 7.71-7.61 (m, 3H), 7.32-7.27 (m, 2H), 7.26-7.20 (m, 1H), 5.93 (br. s., 1H), 4.32 (s, 3H), 3.88 (d, J=9.9 Hz, 1H), 3.73 (d, J=8.4 Hz, 1H), 3.62 (s, 3H), 3.42 (t, J=11.4 Hz, 1H), 3.22 (t, J=11.6 Hz, 1H), 2.91-2.90 (m, 4H), 1.58 (br. s., 7H), 1.47 (d, J=12.1 Hz, 1H), 1.30-1.20 (m, 2H), 1.09 (br. s., 1H).

Examples 379 & 380

The compounds in Table 5 were prepared according to the procedures described for 2-[11-(dimethyl-1H-1,2,3-triazol-5-yl)-8-[(R)-oxan-4-yl(phenyl)methyl]-3,8,10-triazatricyclo[7.4.0.0$^{2,7}$]trideca-1(9),2(7),3,5,10,12-hexaen-5-yl]propan-2-ol:

TABLE 5

| Example | R | HPLC T$_R$ (min) | LC/MS (M + H) | HPLC Method[a] |
|---|---|---|---|---|
| 379 | ![ketone] | 1.657 | 481 | A |
| 380 | ![alcohol OH] | 1.530 | 497 | A |

[a]HPLC Method A conditions for Table 5: Column: Waters BEH C18, 2.0 × 50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.5-minute hold at 100% B; Flow: 1.0 mL/min; Detection: UV at 220 nm.

Example 381

4-[11-(Dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-5-yl]-1λ$^6$,4-thiomorpholine-1,1-dione

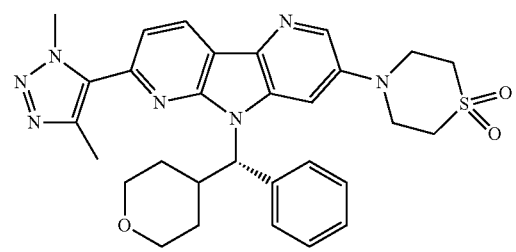 [SMILES: Cc1nnn(C)c1-c1ccc2c3ncc(N4CCS(=O)(=O)CC4)cc3n([C@H](c3ccccc3)C3CCOCC3)c2n1]

Step 1: (S)-4-(7-Chloro-5-(phenyl(tetrahydro-2H-pyran-4-yl)methyl)-5H-pyrrolo[2,3-b:4,5-b']dipyridin-3-yl)thiomorpholine 1,1-dioxide (S)-3-Bromo-7-chloro-5-(phenyl(tetrahydro-2H-pyran-4-yl)methyl)-5H-pyrrolo[2,3-b:4,5-b']dipyridine (60.0 mg, 0.131 mmol), thiomorpholine 1,1-dioxide (26.6 mg, 0.197 mmol), RuPhos (4.9 mg, 10.5 µmol), Pd(OAc)$_2$ (1.5 mg, 6.57 µmol), and Cs$_2$CO$_3$ (171 mg, 0.525 mmol) were dissolved in 2 mL of dioxane and heated at 115° C. for 1.5 h in the microwave. The sample was diluted with EtOAc, washed with brine, concentrated, and purified by flash chromatography (24 g silica gel column, eluting with 0-10% MeOH/EtOAc) to obtain 38% yield. LC/MS [M+H]$^+$=511. $^1$H NMR (500 MHz, DMSO-d$_6$) δ 8.46-8.39 (m, 2H), 7.88 (br. s., 1H), 7.78 (d, J=7.3 Hz, 2H), 7.38-7.29 (m, 3H), 7.27-7.23 (m, 1H), 5.70 (d, J=11.0 Hz, 1H), 4.01 (br. s., 4H), 3.89 (d, J=13.2 Hz, 1H), 3.76 (d, J=11.0 Hz, 1H), 3.60 (br. s., 1H), 3.54-3.47 (m, 1H), 3.41 (s, 2H), 3.24 (br. s., 4H), 1.53-1.36 (m, 2H), 1.33-1.23 (m, 1H), 1.08 (d, J=11.0 Hz, 1H).

Step 2: 4-[11-(Dimethyl-1H-1,2,3-triazol-5-yl)-8-[(S)-oxan-4-yl(phenyl)methyl]-3,8,10-triazatricyclo[7.4.0.0$^{2,7}$]trideca-1(9),2(7),3,5,10,12-hexaen-5-yl]-1λ$^6$,4-thiomorpholine-1,1-dione To a 20 mL scintillation vial was added (S)-4-(7-chloro-5-(phenyl(tetrahydro-2H-pyran-4-yl)methyl)-5H-pyrrolo[2,3-b:4,5-b']dipyridin-3-yl)thiomorpholine 1,1-dioxide (17 mg, 0.033 mmol), 1,4-dimethyl-5-(tributylstannyl)-1H-1,2,3-triazole (14.1 mg, 0.037 mmol), and 2 mL of dioxane. This was followed by the addition of Pd(dppf)$_2$Cl$_2$.DCM (2.7 mg, 3.3 µmol). The air was replaced with argon and the vial sealed. It was heated to 140° C. in the microwave, held at that temperature for 0.5 h, and filtered. The filtrate was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 40-100% B over 20 min, then a 5-min hold at 100% B; Flow: 20 mL/min. Fractions containing the desired product were combined and dried via centrifugal evaporation. The yield of the product was 35%. LC/MS [M+H]$^+$=572. $^1$H NMR (500 MHz, DMSO-d$_6$) δ 8.55 (d, J=8.1 Hz, 1H), 8.45 (s, 1H), 7.85 (br. s., 1H), 7.73 (d, J=7.3 Hz, 2H), 7.57 (d, J=8.1 Hz, 1H), 7.34-7.27 (m, 2H), 7.25-7.19 (m, 1H), 5.85 (br. s., 1H), 4.31 (s, 3H), 4.02 (br. s., 4H), 3.93-3.86 (m, 1H), 3.75 (d, J=9.2 Hz, 1H), 3.63 (br. s., 1H), 3.43 (d, J=11.4 Hz, 1H), 3.40-3.33 (m, 1H), 3.31-3.16 (m, 5H), 1.56 (br. s., 1H), 1.50-1.41 (m, 1H), 1.30 (d, J=11.4 Hz, 1H), 1.13 (d, J=11.4 Hz, 1H).

Evaluation of Biological Activity

Exemplary compounds were tested for inhibition of BRD2, BRD3, BRD4 and BRDT activity. Experimental procedures and results are provided below. Cloning, Expression, and Purification of Human Bromodomains for Thermal Shift Assays (TSA)

Recombinant DNA clones encoding bromodomains of human proteins were optimized for E. coli expression, chemically synthesizedd (GenScript, Piscataway N.J.), and inserted into a modified pET28 expression vector to construct tobacco vein mottling virus (TVMV) protease cleavable N-terminal hexahistidine fusions. The non-native amino acids (MGSSHHHHHHSSGETVRFQSM) (SEQ ID NO: 1) were immediately followed by bromodomain proteins with the amino acid residue sequences (followed by accessions referenced from and numbered according to the Uniprot Knowledgebase; Uniprot Consortium; www.uniprot.org) as follows:

CECR2(420-543), Q9BXF3-1; FALZ(2917-3037), Q12830-1; GCN5(731-837), Q92830-1; PCAF(715-831), Q92831-1; BRD2(24-472), P25440-1; BRD3(1-434), Q15059-1; BRD4(44-168), BRD4(333-460), BRD4(44-460), O60885-1; BRDT(1-383), Q58F21-1; BAZ1B(1340-1457), Q9UIG0-1; CREBBP(1081-1197), Q92793-1; EP300(1040-1161), Q09472-1; WDR9(1310-1430), Q9NSI6-1; ATAD2(981-1108), Q6PL18-1; BRD1(556-688), O95696-1; BRD7(129-236), Q9NPI1-1; BRD9(134-239), Q9H8M2-1; BRPF1(626-740), P55201-2; ATAD2B(952-1086), Q9ULI0-1; BAZ2B(2054-2168), Q9UIF8-1; SP140L(400-580), Q9H930-4; SP140(687-862), Q13342-1; TIF1(896-1014), O15164-1; TRIM28(619-805), Q13263-1; BRWD3(1295-1443), Q6RI45-1; TAF1(1377-1503), TAF1(1501-1635), P21675-1; TAF1L(1402-1522), TAF1L(1523-1654), Q8IZX4-1; ASH1L(2433-2564), Q9NR48-1; PB1(43-156), PB1(178-291), PB1(388-494), PB1(645-766), PB1(773-917), Q86U86-1; SMARCA2(1367-1511), P51531-1; SMARCA2-2(1367-1493), P51531-2.

The recombinant vectors were transformed into E. coli BL21 (DE3). The transformed cells were cultured in 1 L terrific broth in 2.5 L Thomson Ultra Yield shaker flasks at 37° C., 230 rpm and, at a cell density of OD600 nm=1.0, were induced with 0.5 mM IPTG and incubated in the shaker at 20° C. for 16-18 hours. The cell pellets were harvested by sedimentation and lysed by sonication in buffer containing 0.1 mg/ml lysozyme. Each sample was clarified by sedimentation, and the supernatant was loaded onto a HisTrap affinity column (GE Healthcare Life Sciences). The column was washed and then eluted with an imidazole gradient. The peak protein fractions containing the bromodomain protein were pooled, concentrated, and the protein was purified further by size exclusion chromatography on a Superdex 200 column (GE Healthcare Life Sciences) equilibrated with the final storage buffer (20 mM Tris-HCl pH 8.0, 200 mM NaCl, 5% glycerol, 2 mM DTT). The SEC peak fractions containing purified protein at 2-5 mg/ml were pooled, and the pool was divided into aliquots, flash frozen in liquid nitrogen, and store at −80° C.

Cloning, Expression, and Purification of Biotinylated Human Bromodomains for TR-FRET Assays Recombinant DNA clones encoding bromodomains of human BRD2, BRD3, BRD4 and BRDT were optimized for E. coli expression, chemically synthesized (GenScript, Piscataway N.J.), and inserted into a modified pET28 expression vector to construct tobacco vein mottling virus (TVMV) protease cleavable N-terminal hexahistidine fusions followed by a site specific biotinylation motif recognized by E. coli biotin ligase (BirA). The non-native amino acids (MGSSHHHHHHSSGETVRFQGLNDIFEAQKIEWHEDTGHM) (SEQ ID NO: 2) were immediately followed by bromodomain constructs of BRD4 with the amino acid residue sequences (followed by the BRD4 accession referenced from and numbered according to the Uniprot Knowledgebase; Uniprot Consortium; www.uniprot.org) as follows: BRD4(44-168), BRD4(333-460), BRD4 (44-460), BRD4(1-477), O60885-1.

Each of the recombinant vectors were co-transformed into E. coli BL21 STAR (DE3) together with a plasmid encoding BirA under chloramphenicol selection. The transformed cells were cultured at 37° C. in 2.5 L Thomson Ultra Yield shaker flasks containing 1 L M9-CAS medium (Teknova) supplemented with 40 µg/ml kanamycin, 35 µg/ml chloramphenicol, and 100 µM biotin. At a cell density corresponding to an OD600 nm=0.6, the cultures were induced with 0.5 mM IPTG and incubated in the shaker for an additional 20 hours at 20° C. The cell pellets were harvested by sedimentation and lysed by sonication in buffer containing 0.1 mg/ml lysozyme. Each sample was clarified by sedimentation, and the supernatant was loaded onto a HisTrap affinity column. The column was washed and then eluted with an imidazole gradient. The peak protein fractions containing the bromodomain protein were pooled and incubated for 18 hours at 4° C. with purified His-TVMV protease (1:15 mass ratio of TVMV:BRD4 protein). The sample was exchanged into low imidazole buffer and passed through a HisTrap column to capture the cleaved His-tag and His-TVMV enzyme. The protein in the HisTrap column flow through was further purified and exchanged into the final storage buffer (PBS pH 7.0, 5% Glycerol, 1 mM DTT) by size exclusion chromatography on a Superdex 200 column. To improve purity, the BRD4(1-477) and BRD4(44-460) proteins were subjected to an additional cation exchange chromatography purification step prior to size exclusion chromatography. Essentially quantitative mono-biotinylation (+226 Da) of each protein was confirmed by electrospray ionization mass spectrometry analysis on the final sample. The purified samples were divided into aliquots, flash frozen in liquid nitrogen, and stored at −80° C.

Time Resolved Fluorescence Resonance Energy Transfer (TR-FRET) Assay

The binding of compounds to bromodomain BRD4 (44-168), BRD4 (333-460), and BRD4 (1-477 or 44-460) was assessed using a time resolved fluorescent resonance energy transfer binding assay (1), that measures the binding of a fluorescently labeled probe molecule to the bromodomain protein. The bromodomain protein, fluorescent probe molecule (either a biotinylated histone peptide or a fluorescently labeled small molecule), and dose-responded test compound are incubated together to reach thermodynamic equilibrium. In the absence of a test compound, the bromodomain and small molecule are bound, resulting in a high fluorescent signal. In the presence of a sufficient concentration of inhibitor, this intercation is disrupted resulting in a lost of fluorescent resonance energy transfer.

All assay components were dissolved in buffer composition 20 mM Hepes pH 7.5, 150 mM NaCl, 5 mM DTT, 0.005% Tween 20, and 100 ug/ml BSA for BRD4 (1-477 and 44-460). The final concentrations of the bromodomain proteins are 1.6 nM BRD4(44-168), 1 nM BRD4(333-460), and 1 nM BRD4(1-477 or 44-460), and the fluorescent probe molecule is 100 nM, 50 nM, and 7.5 nM respectively. All proteins were biotinylated. A streptavidin labeled with terbium cryptate (Cisbio SA-Tb) was used as detection, and pre-mixed with the bromodomain protein at a final concentration of 0.2 nM. In some instances for BRD4 (44-460), anti-His terbium cryptate was used as a detection. 7.5 nl of dose-responded test compound or dmso vehicle (0.0375%) was pre-spotted in a black Corning 384 well plate and 10 ul each of bromodomain/detection reagent and fluorescent small molecule solution were added to the plate, and the reaction incubated for 60 min at room temperature. Plates were then read on EnVision plate reader, (λex=340 nm, acceptor λEm=520 nm, and donor λEm=615 nm, LANCE D400 mirror). Time resolved fluorescnce intensity measurements were made at both emissions, and the ratio of acceptor/donor was calculated and used for data analysis. All data was normalized to 16 high vehicle wells and 8 low reference control wells, and then a four parameter curve fit was applied:

$$Y=a+((b-a)/(1+(10x/10c)d)$$

Where 'a' is the minimum, 'b' is the Hill slope, 'c' is the IC50, and 'd' is the maximum.

Histone Peptide: Purchased from GenScript

H4K5K8K12K16
(SEQ ID NO: 3)
Biotin-AHA-SGRGK(Ac)GGK(Ac)GLGK(Ac)GGAK(Ac)RHRKV

The fluorescently labeled small molecule used was a BRD4 inhibitor known in the art 1. F. Degorce, A. Card, S. Soh, E. Trinquet, G. P. Knapik and B. Xie, HTRF: A technology tailored for drug discovery—a review of theoretical aspects and recent applications. Current Chemical Genomics (2009) 3, 22-32

Thermal Shift Assay

The effect of compound binding on the thermal stability of the bromodomains was measured using a BioRad CFX real time PCR instrument by monitoring the fluorescence enhancement of an external probe (SYPRO orange) as it binds preferentially to the unfolded protein. The unfolding reactions were carried out in a 384-well plate in a 4 uL volume with 2-8 uM of bromodomain protein, 1-2% (v/v) DMSO in buffer containing 10 mM Hepes, pH 7.4, 500 mM NaCl. SYPRO orange dye was added at a dilution of 1:500. Compound concentrations ranged from 1.6-100 uM. Unfolding reactions were monitored by first equilibrating the instrument at 25° C. for 2.4 sec, followed by ramping the temperature in 0.5° C. increments from 25 to 95° C. with 60 s equilibration prior to a read at each temperature. Excitation and emission filters for the SYPRO orange dye were set to FRET with the excitation range from 450-490 nm and the emission range from 560-580 nm. The midpoint temperature was determined by calculating the inflection point using the second derivative. The observed temperature shifts were recorded as the difference between the midpoint between a reference well containing protein with dmso but no ligand and a well containing protein with compound.

The thermal shift assay is a biophysical technique that compares the change in unfolding transition temperature of a protein obtained in the presence and absence of a ligand (1). Typically, a fluorescent dye is used to monitor the protein unfolding as the protein is heated. During the unfolding process, hydrophobic regions of the protein are exposed, resulting in an increase in the dye binding and an increase in fluorescence intensity. The midpoint of the protein unfolding transition is defined as the Tm. A ligand that binds to the protein causes an increase in the protein thermal stability, thus increasing the Tm, proportionally to both the ligand concentration and its binding affinity.

1. M. W. Pantoliano, E. C. Petrella, J. D. Kwasnoski, V. S. Lobanov, J. Myslik, E. Graf, T. Carver, E. Asel, B. A. Springer, P. Lane, F. R. Salemme, High-density miniaturized thermal shift assays as a general strategy for drug discovery. J. Biomol. Screen 6(2001) 429-440.
2. M. D. Cummings, M. A. Farnum, M. I. Nelen, Universal screening methods and application of ThermoFluor. J. Biomol. Screen 11 (2006) 854-863

MYC HCS Assay

Tumor cells in complete RPMI growth media (Gibco, 11875-085) supplemented with 10% FBS were harvested and plated into 384 black clear-bottom PDL cell culture plates in 30 ul media with 10,000 cells per well. After compound treatment at 37 C for 4 hrs, cells were fixed in 4% Formaldehyde at room temperature for 30 min and subsequently permeabilized. After washing and blocking, the plates were then incubated with anti-myc primary antibody 1:1000 (Cell Signaling Technology, 5605) at RT overnight. The following day, cells were washed and blocked before adding secondary antibody Alexa 488 Goat-anti Rabbit 1:2000 (Invitrogen, A11034) at RT in the dark for 1 hr. Cells were subsequently washed and scanned on the Cellomics ArrayScan with 10× objective lens.

MTS Cell Proliferation Assay

Tumor cells were plated at certain seeding densities in 384-well black clear bottom Matrix plates at 40 ul per well and incubated overnight at 37° C. in 5% $CO_2$ before assaying. On the next day, one set of cell plates (T0 plates) were used to determine time zero cell density, and 3-(4,5-dimethylthiazol-2-yl)-5-(3-carboxymethoxyphenyl)-2-(4-sulfophenyl)-2H-tetrazolium from the CellTiter 96 AQueous Non-Radioactive Cell proliferation Kit (Promega, G5440) was added at 4 µl/well into T0 plates followed by incubation at 37° C. in 5% $CO_2$ for three hours. Absorbance at 490 nm was measured on an Envision reader (Perkin Elmer, Boston, Mass.). On the same day, the remaining cell plates (T72 plates) were treated with compounds at 37° C. in 5% $CO_2$. After 72 hours, 4 ul MTS reagents were then added onto those cell plates. The plates were further incubated at 37° C. in 5% $CO_2$ for three hours and the absorbance values at A490 were measured on an Envision reader.

Human Tumor Xenograft Models in Mice

All rodents were obtained from Jackson Laboratory. (Bar Harbor, Me.), and maintained in an ammonia-free environment in a defined and pathogen-free colony. All mice were quarantined approximately 1 week prior to their use for tumor propagation and drug efficacy testing. Mice were fed food and water ad libitum. The animal care program of Bristol-Myers Squibb Pharmaceutical Research Institute is fully accredited by the American Association for Accreditation of Laboratory Animal Care (AAALAC). All experiments were performed in accordance with Bristol-Myers Squibb (BMS) animal test methods and guidelines.

Tumor xenografts were grown and maintained subcutaneously (SC) in NSG (NOD scid IL2 receptor gamma chain knockout) mice (Jackson Lab). Tumors were propagated as subcutaneous transplants using tumor fragments obtained from donor mice.

Preclinical Chemotherapy Trials

The required numbers of animals needed to detect a meaningful response were pooled at the start of the experiment and each was given bilateral subcutaneous implants of two tumor fragments (~20 mg) with a 13-gauge trocar. Tumors were allowed to grow to the pre-determined size window (tumors outside the range were excluded) and animals were evenly distributed to various treatment and control groups. There were typically 6-8 mice per treatment and control groups, consisting of 10-12 tumors. Treatment of each animal was based on individual body weight. Treated animals were checked daily for treatment related toxicity/mortality. Each group of animals was weighed before the initiation of treatment ($Wt_1$) and then again following the last treatment dose ($Wt_2$). The difference in body weight ($Wt_2-Wt_1$) provides a measure of treatment-related toxicity.

Tumor response was determined by measurement of tumors with a caliper twice a week, until the tumors reached a predetermined "target" size of 0.5 gm or 1 gm depending on the tumor type. Tumor weights (mg) were estimated from the formula:

$$\text{Tumor weight} = (\text{length} \times \text{width}^2) \div 2$$

Tumor response criteria are expressed in terms of tumor growth inhibition (% TGI). Tumor growth delay is defined as the difference in time (days) required for the treated tumors (T) to reach a predetermined target size compared to those of the control group (C). For this purpose, the tumor weight of a group is expressed as medium tumor weight (MTW).

Tumor growth inhibition is calculated as follows:

$$\% \text{ Tumor Growth Inhibition} = \frac{\left(1 - \frac{T_t}{T_0} * \frac{C_0}{C_t}\right)}{\left(1 - \frac{C_0}{C_t}\right)}$$

where,
$C_t$=Median control tumor size at end of treatment
$C_0$=Median control tumor size at treatment initiation
$T_t$=Median tumor size of treated group at end of treatment
$T_0$=Median tumor size of treated group at treatment initiation Activity is defined as the achievement of durable tumor growth inhibition of 50% or greater (i.e. TGI≥50%) for a period equivalent to at least 1 tumor volume doubling time and drug treatment must be for a period equivalent to at least 2 tumor volume doubling time.

Tumor response was also expressed in terms of tumor growth delay and expressed as log cell kill (LCK value), defined as the difference in time (days) required for the treated tumors (T) to reach a predetermined target size compared to those of the control group (C).

Whenever possible, antitumor activity was determined at a range of dose levels up to the maximum tolerated dose (MTD) which is defined as the dose level immediately below which excessive toxicity (i.e. more than one death) occurred. When death occurred, the day of death was recorded. Treated mice dying prior to having their tumors reach target size were considered to have died from drug toxicity. No control mice died bearing tumors less than target size. Treatment groups with more than one death caused by drug toxicity were considered to have had excessively toxic treatments and their data were not included in the evaluation of a compound's antitumor efficacy.

Potential drug toxicity interaction affecting treatment tolerability is an important consideration in combination chemotherapy trials. Interpretation of combination therapeutic results must be based on comparison of antitumor activity of the best possible response for the single agents versus the combination at comparably tolerated doses.

Therefore, therapeutic synergism was defined as a therapeutic effect achieved with a tolerated regimen of the combined agents that exceeded the optimal effect achieved at any tolerated dose of monotherapy. Statistical evaluations of data were performed using Gehan's generalized Wilcoxon test. Statistical significance was declared at $P<0.05$.

Drug Administration

For administration of BET inhibitors to rodents, compounds were dissolved in 90% PEG300/10% TPGS/10% Ethanol. BET inhibitors were typically administered orally on a schedule of QDx7 or QDx10 (5 day-on-2 day-off), although other schedules had also been evaluated and shown to be efficacious The activity data shown below is based on the use of one of the FRET assays described. Compounds with an $IC_{50}$ less than 1500 nM are shown with (+), compounds with an $IC_{50}$ less than 10 nM are shown with (++) and those with an $IC_{50}$ less than 1 nM are shown with (+++).

| Example # | FRET BRD4 $IC_{50}$ (nM) |
| --- | --- |
| Example 1 | ++ |

| Example # | FRET BRD4 IC$_{50}$ (nM) |
|---|---|
| Example 2 | ++ |
| Example 3 | ++ |
| Example 4 | ++ |
| Example 5 | ++ |
| Example 6 | +++ |
| Example 7 | ++ |
| Example 8 | ++ |
| Example 9 | ++ |
| Example 10 | ++ |
| Example 11 | ++ |
| Example 12 | ++ |
| Example 13 | +++ |
| Example 14 | ++ |
| Example 15 | + |
| Example 16 | ++ |
| Example 17 | ++ |
| Example 18 | ++ |
| Example 19 | ++ |
| Example 20 | ++ |
| Example 21 | + |
| Example 22 | ++ |
| Example 23 | + |
| Example 24 | ++ |
| Example 25 | ++ |
| Example 26 | ++ |
| Example 27 | ++ |
| Example 28 | ++ |
| Example 29 | +++ |
| Example 30 | +++ |
| Example 31 | ++ |
| Example 32 | ++ |
| Example 33 | +++ |
| Example 34 | ++ |
| Example 35 | ++ |
| Example 36 | ++ |
| Example 37 | ++ |
| Example 38 | ++ |
| Example 39 | ++ |
| Example 40 | +++ |
| Example 41 | +++ |
| Example 42 | ++ |
| Example 43 | +++ |
| Example 44 | ++ |
| Example 45 | +++ |
| Example 46 | ++ |
| Example 47 | +++ |
| Example 48 | +++ |
| Example 49 | +++ |
| Example 50 | +++ |
| Example 51 | +++ |
| Example 52 | +++ |
| Example 53 | +++ |
| Example 54 | ++ |
| Example 55 | +++ |
| Example 56 | +++ |
| Example 57 | +++ |
| Example 58 | +++ |
| Example 59 | +++ |
| Example 60 | +++ |
| Example 61 | +++ |
| Example 62 | +++ |
| Example 63 | +++ |
| Example 64 | +++ |
| Example 65 | + |
| Example 66 | ++ |
| Example 67 | + |
| Example 68 | +++ |
| Example 69 | + |
| Example 70 | +++ |
| Example 71 | + |
| Example 72 | ++ |
| Example 73 | + |
| Example 74 | ++ |
| Example 75 | + |
| Example 76 | +++ |
| Example 77 | +++ |
| Example 78 | +++ |
| Example 79 | +++ |
| Example 80 | +++ |
| Example 81 | +++ |
| Example 82 | + |
| Example 83 | +++ |
| Example 84 | + |
| Example 85 | +++ |
| Example 86 | ++ |
| Example 87 | + |
| Example 88 | ++ |
| Example 89 | + |
| Example 90 | ++ |
| Example 91 | + |
| Example 92 | ++ |
| Example 93 | ++ |
| Example 94 | ++ |
| Example 95 | ++ |
| Example 96 | + |
| Example 97 | +++ |
| Example 98 | ++ |
| Example 99 | +++ |
| Example 100 | ++ |
| Example 101 | ++ |
| Example 102 | ++ |
| Example 103 | ++ |
| Example 104 | ++ |
| Example 105 | ++ |
| Example 106 | ++ |
| Example 107 | ++ |
| Example 108 | ++ |
| Example 109 | ++ |
| Example 110 | ++ |
| Example 111 | ++ |
| Example 112 | +++ |
| Example 113 | +++ |
| Example 114 | ++ |
| Example 115 | +++ |
| Example 116 | +++ |
| Example 117 | ++ |
| Example 118 | ++ |
| Example 119 | + |
| Example 120 | ++ |
| Example 121 | + |
| Example 122 | ++ |
| Example 123 | + |
| Example 124 | ++ |
| Example 125 | + |
| Example 126 | ++ |
| Example 127 | + |
| Example 128 | ++ |
| Example 129 | +++ |
| Example 130 | +++ |
| Example 131 | ++ |
| Example 132 | +++ |
| Example 133 | +++ |
| Example 134 | +++ |
| Example 135 | +++ |
| Example 136 | ++ |
| Example 137 | ++ |
| Example 138 | ++ |
| Example 139 | ++ |
| Example 140 | +++ |
| Example 141 | ++ |
| Example 142 | ++ |
| Example 143 | + |
| Example 144 | ++ |
| Example 145 | ++ |
| Example 146 | + |
| Example 147 | ++ |
| Example 148 | ++ |
| Example 149 | ++ |
| Example 150 | +++ |
| Example 151 | ++ |

| Example # | FRET BRD4 IC$_{50}$ (nM) |
|---|---|
| Example 152 | ++ |
| Example 153 | ++ |
| Example 154 | ++ |
| Example 155 | ++ |
| Example 156 | ++ |
| Example 157 | ++ |
| Example 158 | ++ |
| Example 159 | + |
| Example 160 | ++ |
| Example 161 | ++ |
| Example 162 | ++ |
| Example 163 | +++ |
| Example 164 | ++ |
| Example 165 | ++ |
| Example 166 | ++ |
| Example 167 | + |
| Example 168 | +++ |
| Example 169 | ++ |
| Example 170 | ++ |
| Example 171 | ++ |
| Example 172 | ++ |
| Example 173 | ++ |
| Example 174 | +++ |
| Example 175 | ++ |
| Example 176 | ++ |
| Example 177 | +++ |
| Example 178 | +++ |
| Example 179 | +++ |
| Example 180 | +++ |
| Example 181 | +++ |
| Example 182 | +++ |
| Example 183 | ++ |
| Example 184 | ++ |
| Example 185 | ++ |
| Example 186 | ++ |
| Example 187 | ++ |
| Example 188 | +++ |
| Example 189 | +++ |
| Example 190 | +++ |
| Example 191 | +++ |
| Example 192 | +++ |
| Example 193 | +++ |
| Example 194 | ++ |
| Example 195 | ++ |
| Example 196 | ++ |
| Example 197 | ++ |
| Example 198 | ++ |
| Example 199 | ++ |
| Example 200 | ++ |
| Example 201 | ++ |
| Example 202 | ++ |
| Example 203 | ++ |
| Example 204 | ++ |
| Example 205 | ++ |
| Example 206 | ++ |
| Example 207 | ++ |
| Example 208 | ++ |
| Example 209 | ++ |
| Example 210 | ++ |
| Example 211 | ++ |
| Example 212 | ++ |
| Example 213 | +++ |
| Example 214 | +++ |
| Example 215 | ++ |
| Example 216 | NA |
| Example 217 | ++ |
| Example 218 | +++ |
| Example 219 | +++ |
| Example 220 | +++ |
| Example 221 | ++ |
| Example 222 | ++ |
| Example 223 | ++ |
| Example 224 | ++ |
| Example 225 | +++ |
| Example 226 | ++ |
| Example 227 | +++ |
| Example 228 | +++ |
| Example 229 | ++ |
| Example 230 | ++ |
| Example 231 | ++ |
| Example 232 | ++ |
| Example 233 | ++ |
| Example 234 | ++ |
| Example 235 | ++ |
| Example 236 | +++ |
| Example 237 | +++ |
| Example 238 | ++ |
| Example 239 | ++ |
| Example 240 | ++ |
| Example 241 | ++ |
| Example 242 | ++ |
| Example 243 | ++ |
| Example 244 | ++ |
| Example 245 | ++ |
| Example 246 | ++ |
| Example 247 | +++ |
| Example 248 | ++ |
| Example 249 | ++ |
| Example 250 | ++ |
| Example 251 | ++ |
| Example 252 | +++ |
| Example 253 | ++ |
| Example 254 | +++ |
| Example 255 | ++ |
| Example 256 | ++ |
| Example 257 | +++ |
| Example 258 | ++ |
| Example 259 | + |
| Example 260 | ++ |
| Example 261 | ++ |
| Example 262 | ++ |
| Example 263 | ++ |
| Example 264 | ++ |
| Example 265 | +++ |
| Example 266 | ++ |
| Example 267 | ++ |
| Example 268 | +++ |
| Example 269 | +++ |
| Example 270 | +++ |
| Example 271 | ++ |
| Example 272 | NA |
| Example 273 | NA |
| Example 274 | ++ |
| Example 275 | ++ |
| Example 276 | ++ |
| Example 277 | +++ |
| Example 278 | +++ |
| Example 279 | +++ |
| Example 280 | ++ |
| Example 281 | ++ |
| Example 282 | +++ |
| Example 283 | +++ |
| Example 284 | +++ |
| Example 285 | +++ |
| Example 286 | ++ |
| Example 287 | +++ |
| Example 288 | +++ |
| Example 289 | + |
| Example 290 | +++ |
| Example 291 | +++ |
| Example 292 | ++ |
| Example 293 | ++ |
| Example 294 | ++ |
| Example 295 | +++ |
| Example 296 | +++ |
| Example 297 | ++ |
| Example 298 | ++ |
| Example 299 | +++ |
| Example 300 | +++ |
| Example 301 | +++ |

| Example # | FRET BRD4 IC$_{50}$ (nM) |
|---|---|
| Example 302 | +++ |
| Example 303 | ++ |
| Example 304 | ++ |
| Example 305 | ++ |
| Example 306 | ++ |
| Example 307 | ++ |
| Example 308 | ++ |
| Example 309 | ++ |
| Example 310 | ++ |
| Example 311 | ++ |
| Example 312 | ++ |
| Example 313 | + |
| Example 314 | ++ |
| Example 315 | ++ |
| Example 316 | ++ |
| Example 317 | + |
| Example 318 | ++ |
| Example 319 | NA |
| Example 320 | + |
| Example 321 | ++ |
| Example 322 | ++ |
| Example 323 | ++ |
| Example 324 | + |
| Example 325 | NA |
| Example 326 | ++ |
| Example 327 | + |
| Example 328 | ++ |
| Example 329 | ++ |
| Example 330 | ++ |
| Example 331 | ++ |
| Example 332 | ++ |
| Example 333 | ++ |
| Example 334 | NA |
| Example 335 | ++ |
| Example 336 | ++ |
| Example 337 | ++ |
| Example 338 | ++ |
| Example 339 | ++ |
| Example 340 | ++ |
| Example 341 | +++ |
| Example 342 | ++ |
| Example 343 | +++ |
| Example 344 | ++ |
| Example 345 | +++ |
| Example 346 | +++ |
| Example 347 | + |
| Example 348 | ++ |
| Example 349 | +++ |
| Example 350 | ++ |
| Example 351 | + |
| Example 352 | ++ |
| Example 353 | NA |
| Example 354 | NA |
| Example 357 | ++ |
| Example 358 | ++ |
| Example 359 | ++ |
| Example 360 | ++ |
| Example 361 | ++ |
| Example 362 | ++ |
| Example 363 | +++ |
| Example 364 | ++ |
| Example 365 | ++ |
| Example 366 | ++ |
| Example 367 | ++ |
| Example 368 | ++ |
| Example 369 | ++ |
| Example 370 | ++ |
| Example 371 | ++ |
| Example 372 | + |
| Example 373 | + |
| Example 374 | ++ |
| Example 375 | + |
| Example 376 | ++ |
| Example 377 | ++ |
| Example 378 | ++ |
| Example 379 | +++ |
| Example 380 | ++ |
| Example 381 | ++ |

NA = Not Available

What is claimed is:

1. The compound of the formula

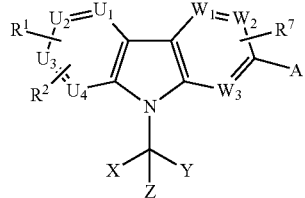

(I)

wherein

U$_1$, U$_2$, U$_3$ and U$_4$ are independently —N— or —CH—, provided that at least one of them is —N—;

W$_1$, W$_2$ and W$_3$ are independently —N— or —CH—, provided that at least one of them is —N—;

A is

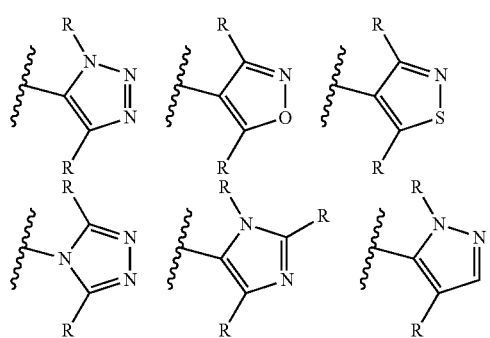

-continued

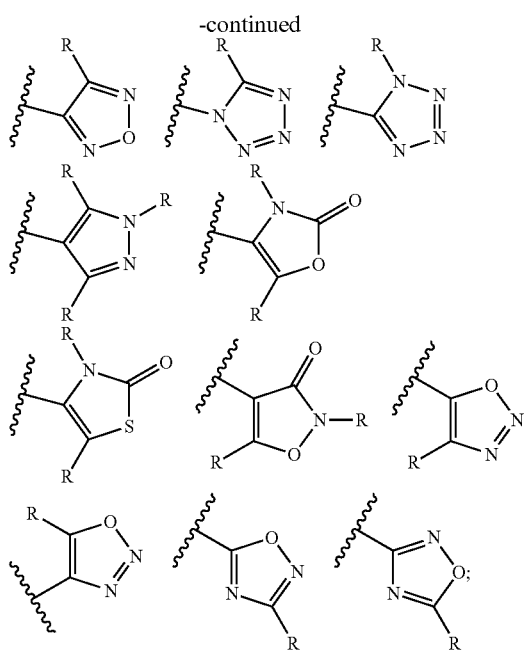

R is independently one or more hydrogen, CD$_3$, halogen, haloalkyl hydroxyalkyl, CN, (C$_1$-C$_6$)alkyl, (C$_1$-C$_6$) alkoxy, or (C$_3$-C$_6$)cycloalkyl;

X and Y are independently selected from hydrogen, optionally substituted (C$_1$-C$_6$)alkyl, optionally substituted (C$_3$-C$_8$)cycloalkyl, optionally substituted aryl, optionally substituted heteroaryl or optionally substituted heterocyclo, wherein the optional substituents in each case are independently alkyl, cycloalkyl, aryl or halo;

Z is hydrogen, halogen, —OH, (C$_1$-C$_6$)alkyl or (C$_1$-C$_6$)alkoxy;

R$^1$ is, independently at each occurrence, one or more hydrogen, halogen, —CN, —OR$^4$, —NR$^3$R$^4$, —CONR$^3$R$^4$, —COOH, —OCONR$^3$R$^4$, —NR$^6$OCOR$^3$, —NR$^6$CONR$^3$R$^4$, —NR$^6$SO$_2$NR$^3$R$^4$, —NR$^6$SO$_2$R$^4$, optionally substituted (C$_1$-C$_6$)alkyl, optionally substituted (C$_2$-C$_6$)alkenyl, optionally substituted (C$_2$-C$_6$)alkynyl, optionally substituted (C$_1$-C$_6$) alkoxy, optionally substituted (C$_3$-C$_8$)cycloalkyl, optionally substituted (C$_3$-C$_8$)cycloalkyl (C$_1$-C$_6$)alkyl, optionally substituted (C$_3$-C$_8$)cycloalkyl-CO—, optionally substituted (C$_3$-C$_8$)cycloalkyl-SO$_2$—, optionally substituted aryl (C$_1$-C$_6$)alkoxy, optionally substituted (C$_3$-C$_8$)cycloalkyl (C$_1$-C$_6$)alkoxy, optionally substituted heterocyclyl-CO—, optionally substituted 4-10 membered mono or azabicyclo heterocyclyl comprising carbon atoms and 1-4 heteroatoms selected from N, O, P(=O) and S(O)$_p$, optionally substituted (C$_1$-C$_6$)alkyl-SO$_2$—, —NR$^6$SO$_2$-optionally substituted (C$_1$-C$_6$)alkyl, —NR$^6$SO$_2$-optionally substituted heterocyclo, optionally substituted (C$_1$-C$_6$)alkyl-NR$^6$SO$_2$— or optionally substituted heterocyclo-NR$^6$SO$_2$—, wherein the optional substituents in each case are independently alkyl, cycloalkyl, aryl, 5-7 membered heterocyclyl comprising carbon atoms, and 1-4 heteroatoms selected from N and O; halo, haloalkyl, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, arylamino, thiol, alkylthio, arylthio, arylalkylthio, alkylthiono, arylthiono, arylalkylthiono, alkylsulfonyl, arylsulfonyl, arylalkylsulfonyl, —SO$_2$NH$_2$, nitro, cyano or carboxy;

p is 0, 1 or 2;

R$^2$ is hydrogen, halogen, —CN, OH, —CONR$^3$R$^4$, —NR$^6$COOR$^4$, —NR$^6$CONR$^3$R$^4$, —NR$^6$COR$^4$, —NR$^6$SO$_2$R$^5$, —SO$_2$NR$^3$R$^4$, —NR$^6$SO$_2$NR$^3$R$^4$, (C$_1$-C$_6$)alkyl, (C$_3$-C$_8$)cycloalkyl, (C$_1$-C$_6$) alkoxy, aryl, (C$_1$-C$_6$)alkyl-SO$_2$—, aryl-SO$_2$ or heterocyclo;

R$^3$ is hydrogen, (C$_1$-C$_6$)alkyl, (C$_3$-C$_8$)cycloalkyl, (C$_2$-C$_6$)alkenyl, (C$_2$-C$_6$)alkynyl, cyano(C$_1$-C$_6$)alkyl, hydroxy(C$_1$-C$_6$)alkyl, aryl, aryl(C$_1$-C$_6$)alkyl, aryloxy(C$_1$-C$_6$)alkyl, (C$_1$-C$_6$)alkyl-SO$_2$—, heterocyclyl or heterocyclyl(C$_1$-C$_6$)alkyl;

R$^4$ is hydrogen, (C$_1$-C$_6$)alkyl or (C$_3$-C$_8$)cycloalkyl;

R$^5$ is hydrogen, (C$_1$-C$_6$)alkyl, (C$_3$-C$_8$)cycloalkyl, (C$_2$-C$_6$)alkenyl, (C$_2$-C$_6$)alkynyl, cyano(C$_1$-C$_6$)alkyl, hydroxy(C$_1$-C$_6$)alkyl, aryl, aryl(C$_1$-C$_6$)alkyl, aryloxy(C$_1$-C$_6$)alkyl, (C$_1$-C$_6$)alkyl-SO$_2$—, heterocyclyl or heterocyclyl(C$_1$-C$_6$)alkyl;

R$^6$ is hydrogen or (C$_1$-C$_6$)alkyl;

R$^7$ is hydrogen, (C$_1$-C$_6$)alkyl, —OR$^4$, CN or halogen;

the term heterocyclo, heterocycle or heterocyclyl in each occurrence meaning a 4-10 membered mono or azabicyclo ring comprising carbon atoms and 1-4 heteroatoms selected from N, O, P(=O) and S(O)$_2$, or a pharmaceutically acceptable salt, tautomer or stereoisomer thereof.

2. A compound according to claim 1

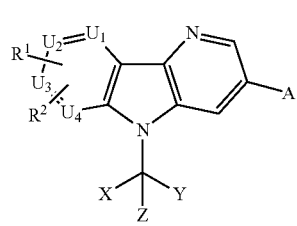

(I)

wherein:
U$_1$, U$_2$, U$_3$ and U$_4$ are independently —N— or —CH—, provided that at least one of them is —N—;
A is

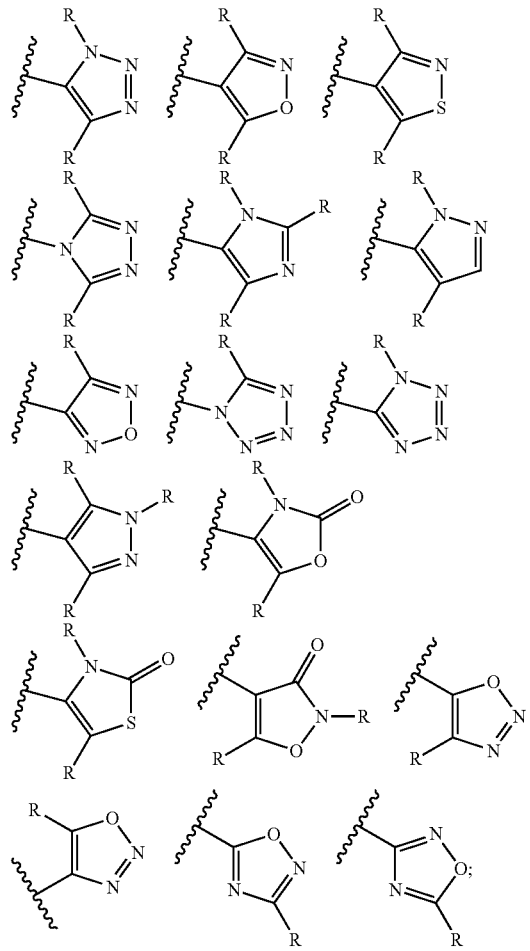

R is independently one or more hydrogen, CD$_3$, halogen, haloalkyl hydroxyalkyl, CN, (C$_1$-C$_6$)alkyl, (C$_1$-C$_6$) alkoxy, or (C$_3$-C$_6$)cycloalkyl;
X and Y are independently selected from hydrogen, optionally substituted (C$_1$-C$_6$)alkyl, optionally substituted (C$_3$-C$_8$)cycloalkyl, optionally substituted aryl, optionally substituted heteroaryl or optionally substituted heterocyclo, wherein the optional substituents in each case are independently alkyl, cycloalkyl, aryl or halo;
Z is hydrogen, halogen, —OH, (C$_1$-C$_6$)alkyl or (C$_1$-C$_6$)alkoxy;

R¹ is, independently at each occurrence, one or more hydrogen, halogen, —CN, —OR⁴, —NR³R⁴, —CONR³R⁴, —COOH, —OCONR³R⁴, —NR⁶OCOR³, —NR⁶CONR³R⁴, —NR⁶SO₂NR³R⁴, —NR⁶SO₂R⁴, optionally substituted (C₁-C₆)alkyl, optionally substituted (C₂-C₆)alkenyl, optionally substituted (C₂-C₆)alkynyl, optionally substituted (C₁-C₆) alkoxy, optionally substituted (C₃-C₈)cycloalkyl, optionally substituted (C₃-C₈)cycloalkyl (C₁-C₆)alkyl, optionally substituted (C₃-C₈)cycloalkyl-CO—, optionally substituted (C₃-C₈)cycloalkyl-SO₂—, optionally substituted aryl (C₁-C₆)alkoxy, optionally substituted (C₃-C₈)cycloalkyl (C₁-C₆)alkoxy, optionally substituted heterocyclyl-CO—, optionally substituted 4-10 membered mono or azabicyclo heterocyclyl comprising carbon atoms and 1-4 heteroatoms selected from N, O, P(═O) and S(O)ₚ, optionally substituted (C₁-C₆)alkyl-SO₂—, —NR⁶SO₂-optionally substituted (C₁-C₆)alkyl, —NR⁶SO₂-optionally substituted heterocyclo, optionally substituted (C₁-C₆)alkyl-NR⁶SO₂— or optionally substituted heterocyclo-NR⁶SO₂—, wherein the optional substituents in each case are independently alkyl, cycloalkyl, aryl, 5-7 membered heterocyclyl comprising carbon atoms, and 1-4 heteroatoms selected from N and O; halo, haloalkyl, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, arylamino, thiol, alkylthio, arylthio, arylalkylthio, alkylthiono, arylthiono, arylalkylthiono, alkylsulfonyl, arylsulfonyl, arylalkylsulfonyl, —SO₂NH₂, nitro, cyano or carboxy;

p is 0, 1 or 2;

R² is hydrogen, halogen, —CN, OH, —CONR³R⁴, —NR⁶COOR⁴, —NR⁶CONR³R⁴, —NR⁶COR⁴, —NR⁶SO₂R⁵, —SO₂NR³R⁴, —NR⁶SO₂NR³R⁴, (C₁-C₆)alkyl, (C₃-C₈)cycloalkyl, (C₁-C₆) alkoxy, aryl, (C₁-C₆)alkyl-SO₂—, aryl-SO₂ or heterocyclo;

R³ is hydrogen, (C₁-C₆)alkyl, (C₃-C₈)cycloalkyl, (C₂-C₆) alkenyl, (C₂-C₆)alkynyl, cyano(C₁-C₆)alkyl, hydroxy (C₁-C₆)alkyl, aryl, aryl(C₁-C₆)alkyl, aryloxy(C₁-C₆) alkyl, (C₁-C₆)alkyl-SO₂—, heterocyclyl or heterocyclyl(C₁-C₆)alkyl;

R⁴ is hydrogen, (C₁-C₆)alkyl or (C₃-C₈)cycloalkyl;

R⁵ is hydrogen, (C₁-C₆)alkyl, (C₃-C₈)cycloalkyl, (C₂-C₆) alkenyl, (C₂-C₆)alkynyl, cyano(C₁-C₆)alkyl, hydroxy (C₁-C₆)alkyl, aryl, aryl(C₁-C₆)alkyl, aryloxy(C₁-C₆) alkyl, (C₁-C₆)alkyl-SO₂—, heterocyclyl or heterocyclyl(C₁-C₆)alkyl;

R⁶ is hydrogen or (C₁-C₆)alkyl;

R⁷ is hydrogen, (C₁-C₆)alkyl, —OR⁴, CN or halogen;

the term heterocyclo, heterocycle or heterocyclyl in each occurrence meaning a 4-10 membered mono or azabicyclo ring comprising carbon atoms and 1-4 heteroatoms selected from N, O, P(═O) and S(O)₂, or a pharmaceutically acceptable salt, tautomer or stereoisomer thereof.

3. A compound according to claim 2 of formula (II)

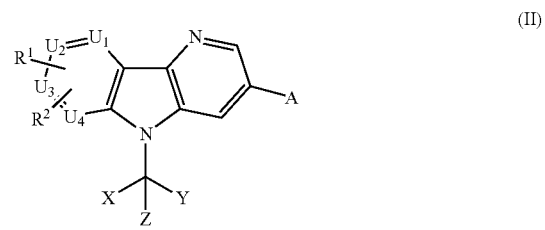

(II)

wherein:
U₁, U₂, U₃ and U₄ are independently —N— or —CH—, provided that at least one of them is —N—;
A is

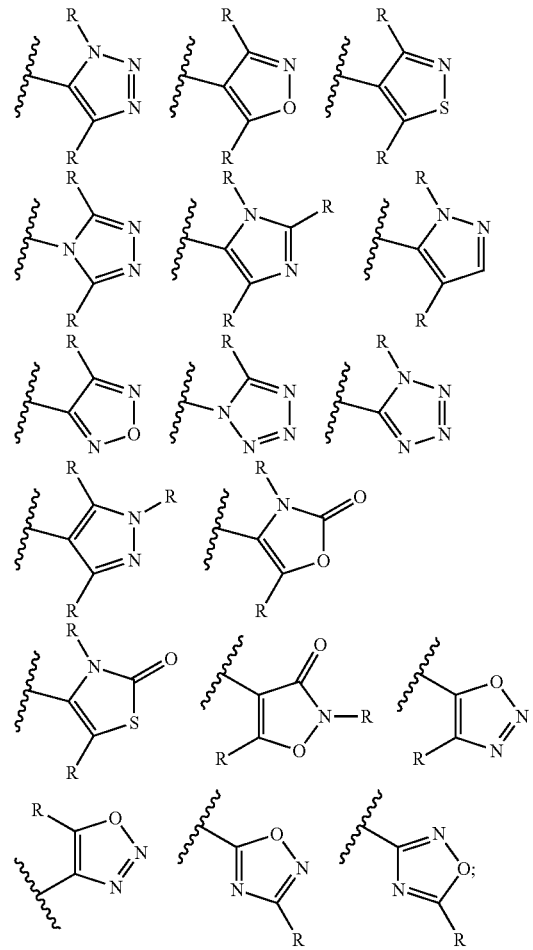

R is independently one or more hydrogen, CD₃, halogen, haloalkyl hydroxyalkyl, CN, (C₁-C₆)alkyl, (C₁-C₆) alkoxy, or (C₃-C₆)cycloalkyl;
X and Y are independently selected from hydrogen, optionally substituted (C₁-C₆)alkyl, optionally substituted (C₃-C₈)cycloalkyl, optionally substituted aryl, optionally substituted heteroaryl or optionally substituted heterocyclo, wherein the optional substituents in each case are independently alkyl, cycloalkyl, aryl or halo;
Z is hydrogen, halogen, —OH, (C₁-C₆)alkyl or (C₁-C₆) alkoxy;

R¹ is, independently at each occurrence, one or more hydrogen, halogen, —CN, —OR⁴, —NR³R⁴, —CONR³R⁴, —COOH, —OCONR³R⁴, —NR⁶OCOR³, —NR⁶CONR³R⁴, —NR⁶SO₂NR³R⁴, —NR⁶SO₂R⁴, optionally substituted (C₁-C₆)alkyl, optionally substituted (C₂-C₆)alkenyl, optionally substituted (C₂-C₆)alkynyl, optionally substituted (C₁-C₆) alkoxy, optionally substituted (C₃-C₈)cycloalkyl, optionally substituted (C₃-C₈)cycloalkyl (C₁-C₆)alkyl, optionally substituted (C₃-C₈)cycloalkyl-CO—, optionally substituted (C₃-C₈)cycloalkyl-SO₂—, optionally substituted aryl (C₁-C₆)alkoxy, optionally substituted (C₃-C₈)cycloalkyl (C₁-C₆)alkoxy, optionally substituted heterocyclyl-CO—, optionally substituted 4-10 membered mono or azabicyclo heterocyclyl comprising carbon atoms and 1-4 heteroatoms selected from N, O, P(═O) and S(O)ₚ, optionally substituted (C₁-C₆)alkyl-SO₂—, —NR⁶SO₂-optionally substituted (C₁-C₆)alkyl, —NR⁶SO₂-optionally substituted heterocyclo, optionally substituted (C₁-C₆)alkyl-NR⁶SO₂— or optionally substituted heterocyclo-NR⁶SO₂—, wherein the optional substituents in each case are independently alkyl, cycloalkyl, aryl, 5-7 membered heterocyclyl comprising carbon atoms, and 1-4 heteroatoms selected from N and O; halo, haloalkyl, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, arylamino, thiol, alkylthio, arylthio, arylalkylthio, alkylthiono, arylthiono, arylalkylthiono, alkylsulfonyl, arylsulfonyl, arylalkylsulfonyl, —SO₂NH₂, nitro, cyano or carboxy;

R² is hydrogen, halogen, —CN, OH, (C₁-C₆)alkyl, (C₃-C₈)cycloalkyl, (C₁-C₆) alkoxy, aryl, or heterocyclo;

R³ is hydrogen, (C₁-C₆)alkyl, (C₃-C₈)cycloalkyl, (C₂-C₆)alkenyl, (C₂-C₆)alkynyl, cyano(C₁-C₆)alkyl, hydroxy (C₁-C₆)alkyl, aryl, aryl(C₁-C₆)alkyl, aryloxy(C₁-C₆)alkyl, (C₁-C₆)alkyl-SO₂—, heterocyclyl or heterocyclyl(C₁-C₆)alkyl;

R⁴ is hydrogen, (C₁-C₆)alkyl or (C₃-C₈)cycloalkyl;

R⁶ is hydrogen or (C₁-C₆)alkyl;

the term heterocyclo, heterocycle or heterocyclyl in each occurrence meaning a 4-10 membered mono or azabicyclo ring comprising carbon atoms and 1-4 heteroatoms selected from N, O, P(═O) and S(O)₂, or a pharmaceutically acceptable salt, tautomer or stereoisomer thereof.

4. A compound according to claim 1 of the formula

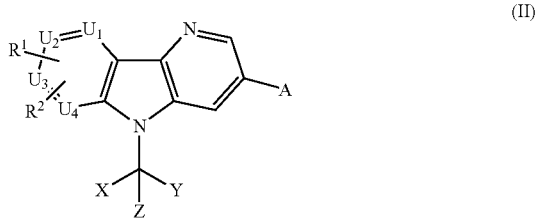

(II)

wherein
A is

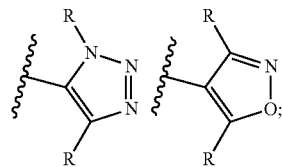

R is independently one or more hydrogen, CD₃, halogen, haloalkyl hydroxyalkyl, CN, (C₁-C₆)alkyl, (C₁-C₆) alkoxy, or (C₃-C₆)cycloalkyl;

X and Y are independently selected from hydrogen, optionally substituted (C₁-C₆)alkyl, optionally substituted (C₃-C₈)cycloalkyl, optionally substituted aryl, optionally substituted heteroaryl or optionally substituted heterocyclo, wherein the optional substituents in each case are independently alkyl, cycloalkyl, aryl or halo;

Z is hydrogen, halogen, —OH, (C₁-C₆)alkyl or (C₁-C₆) alkoxy;

R¹ is, independently at each occurrence, one or more hydrogen, halogen, —CN, —OR⁴, —NR³R⁴, —CONR³R⁴, —COOH, —OCONR³R⁴, —NR⁶OCOR³, —NR⁶CONR³R⁴, —NR⁶SO₂NR³R⁴, —NR⁶SO₂R⁴, optionally substituted (C₁-C₆)alkyl, optionally substituted (C₂-C₆)alkenyl, optionally substituted (C₂-C₆)alkynyl, optionally substituted (C₁-C₆) alkoxy, optionally substituted (C₃-C₈)cycloalkyl, optionally substituted (C₃-C₈)cycloalkyl (C₁-C₆)alkyl, optionally substituted (C₃-C₈)cycloalkyl-CO—, optionally substituted (C₃-C₈)cycloalkyl-SO₂—, optionally substituted aryl (C₁-C₆)alkoxy, optionally substituted (C₃-C₈)cycloalkyl (C₁-C₆)alkoxy, optionally substituted heterocyclyl-CO—, optionally substituted 4-10 membered mono or azabicyclo heterocyclyl comprising carbon atoms and 1-4 heteroatoms selected from N, O, P(═O) and S(O)ₚ, optionally substituted (C₁-C₆)alkyl-SO₂—, —NR⁶SO₂-optionally substituted (C₁-C₆)alkyl, —NR⁶SO₂-optionally substituted heterocyclo, optionally substituted (C₁-C₆)alkyl-NR⁶SO₂— or optionally substituted heterocyclo-NR⁶SO₂—, wherein the optional substituents in each case are independently alkyl, cycloalkyl, aryl, 5-7 membered heterocyclyl comprising carbon atoms, and 1-4 heteroatoms selected from N and O; halo, haloalkyl, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, arylamino, thiol, alkylthio, arylthio, arylalkylthio, alkylthiono, arylthiono, arylalkylthiono, alkylsulfonyl, arylsulfonyl, arylalkylsulfonyl, —SO₂NH₂, nitro, cyano or carboxy;

R² is hydrogen, halogen, —CN, OH, (C₁-C₆)alkyl, (C₃-C₈)cycloalkyl, (C₁-C₆) alkoxy, aryl, or heterocyclo;

R³ is hydrogen, (C₁-C₆)alkyl, (C₃-C₈)cycloalkyl, (C₂-C₆)alkenyl, (C₂-C₆)alkynyl, cyano(C₁-C₆)alkyl, hydroxy (C₁-C₆)alkyl, aryl, aryl(C₁-C₆)alkyl, aryloxy(C₁-C₆)alkyl, (C₁-C₆)alkyl-SO₂—, heterocyclyl or heterocyclyl(C₁-C₆)alkyl;

R⁴ is hydrogen, (C₁-C₆)alkyl or (C₃-C₈)cycloalkyl;

R⁶ is hydrogen or (C₁-C₆)alkyl;

the term heterocyclo, heterocycle or heterocyclyl in each occurrence meaning a 4-10 membered mono or azabicyclo ring comprising carbon atoms and 1-4 heteroatoms selected from N, O, P(═O) and S(O)₂, or a pharmaceutically acceptable salt, tautomer or stereoisomer thereof.

5. A compound according to claim 4 of the formula

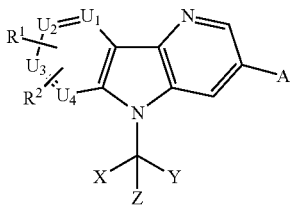

(II)

wherein:
A is

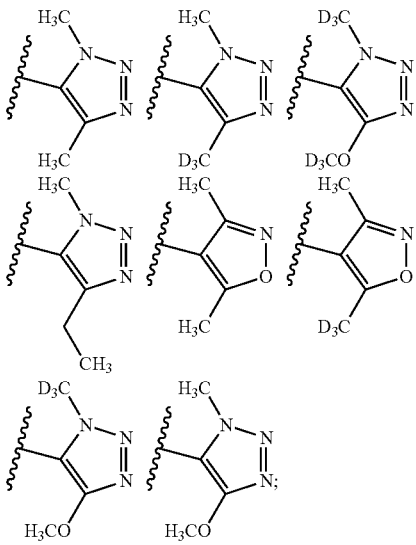

X and Y are independently selected from hydrogen, optionally substituted ($C_1$-$C_6$)alkyl, optionally substituted ($C_3$-$C_8$)cycloalkyl, optionally substituted aryl, optionally substituted heteroaryl or optionally substituted heterocyclo, wherein the optional substituents in each case are independently alkyl, cycloalkyl, aryl or halo;

Z is hydrogen, halogen, —OH, ($C_1$-$C_6$)alkyl or ($C_1$-$C_6$)alkoxy;

$R^1$ is, independently at each occurrence, one or more hydrogen, halogen, —CN, —$OR^4$, —$NR^3R^4$, —$CONR^3R^4$, —COOH, —$OCONR^3R^4$, —$NR^6OCOR^3$, —$NR^6CONR^3R^4$, —$NR^6SO_2NR^3R^4$, —$NR^6SO_2R^4$, optionally substituted ($C_1$-$C_6$)alkyl, optionally substituted ($C_2$-$C_6$)alkenyl, optionally substituted ($C_2$-$C_6$)alkynyl, optionally substituted ($C_1$-$C_6$)alkoxy, optionally substituted ($C_3$-$C_8$)cycloalkyl, optionally substituted ($C_3$-$C_8$)cycloalkyl ($C_1$-$C_6$)alkyl, optionally substituted ($C_3$-$C_8$)cycloalkyl-CO—, optionally substituted ($C_3$-$C_8$)cycloalkyl-$SO_2$—, optionally substituted aryl ($C_1$-$C_6$)alkoxy, optionally substituted ($C_3$-$C_8$)cycloalkyl ($C_1$-$C_6$)alkoxy, optionally substituted heterocyclyl-CO—, optionally substituted 4-10 membered mono or azabicyclo heterocyclyl comprising carbon atoms and 1-4 heteroatoms selected from N, O, P(=O) and S(O)$_p$, optionally substituted ($C_1$-$C_6$)alkyl-$SO_2$—, —$NR^6SO_2$-optionally substituted ($C_1$-$C_6$)alkyl, —$NR^6SO_2$-optionally substituted heterocyclo, optionally substituted ($C_1$-$C_6$) alkyl-$NR^6SO_2$— or optionally substituted heterocyclo-$NR^6SO_2$—, wherein the optional substituents in each case are independently alkyl, cycloalkyl, aryl, 5-7 membered heterocyclyl comprising carbon atoms, and 1-4 heteroatoms selected from N and O; halo, haloalkyl, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, arylamino, thiol, alkylthio, arylthio, arylalkylthio, alkylthiono, arylthiono, arylalkylthiono, alkylsulfonyl, arylsulfonyl, arylalkylsulfonyl, —$SO_2NH_2$, nitro, cyano or carboxy;

$R^2$ is hydrogen, halogen, —CN, OH, ($C_1$-$C_6$)alkyl, ($C_3$-$C_8$)cycloalkyl, ($C_1$-$C_6$) alkoxy, aryl, or heterocyclo;

$R^3$ is hydrogen, ($C_1$-$C_6$)alkyl, ($C_3$-$C_8$)cycloalkyl, ($C_2$-$C_6$)alkenyl, ($C_2$-$C_6$)alkynyl, cyano($C_1$-$C_6$)alkyl, hydroxy($C_1$-$C_6$)alkyl, aryl, aryl($C_1$-$C_6$)alkyl, aryloxy($C_1$-$C_6$)alkyl, ($C_1$-$C_6$)alkyl-$SO_2$—, heterocyclyl or heterocyclyl($C_1$-$C_6$)alkyl;

$R^4$ is hydrogen, ($C_1$-$C_6$)alkyl or ($C_3$-$C_8$)cycloalkyl;

$R^6$ is hydrogen or ($C_1$-$C_6$)alkyl;

the term heterocyclo, heterocycle or heterocyclyl in each occurrence meaning a 4-10 membered mono or azabicyclo ring comprising carbon atoms and 1-4 heteroatoms selected from N, O, P(=O) and S(O)$_2$, or a pharmaceutically acceptable salt, tautomer or stereoisomer thereof.

6. A compound according to claim 1 of the formula

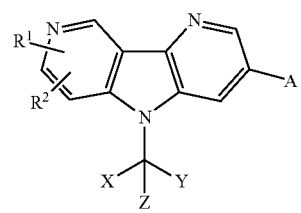

(III)

wherein:
A is

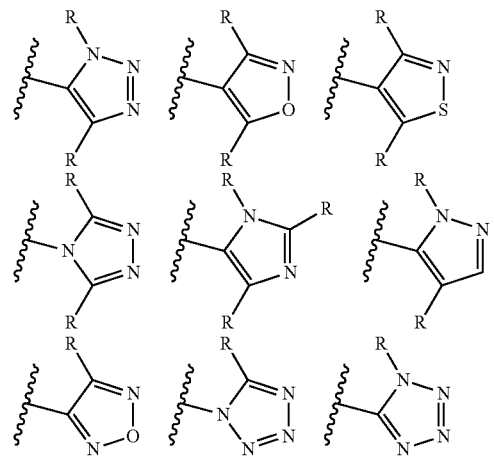

-continued

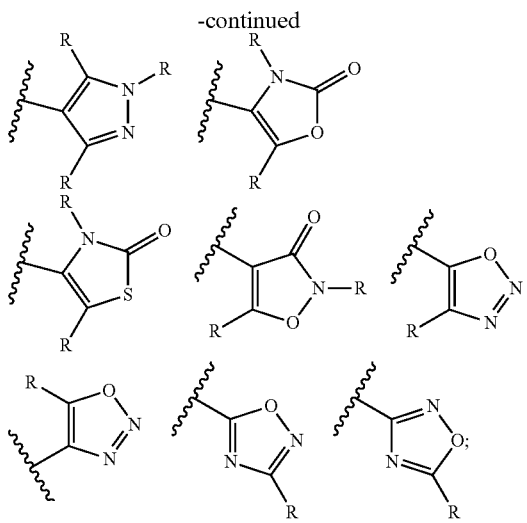

R is independently one or more hydrogen, CD₃, halogen, haloalkyl hydroxyalkyl, CN, $(C_1-C_6)$alkyl, $(C_1-C_6)$ alkoxy, or $(C_3-C_6)$cycloalkyl;

X and Y are independently selected from hydrogen, optionally substituted $(C_1-C_6)$alkyl, optionally substituted $(C_3-C_8)$cycloalkyl, optionally substituted aryl, optionally substituted heteroaryl or optionally substituted heterocyclo, wherein the optional substituents in each case are independently alkyl, cycloalkyl, aryl or halo;

Z is hydrogen, halogen, —OH, $(C_1-C_6)$alkyl or $(C_1-C_6)$ alkoxy;

R¹ is, independently at each occurrence, one or more hydrogen, halogen, —CN, —OR⁴, —NR³R⁴, —CONR³R⁴, —COOH, —OCONR³R⁴, —NR⁶OCOR³, —NR⁶CONR³R⁴, —NR⁶SO₂NR³R⁴, —NR⁶SO₂R⁴, optionally substituted $(C_1-C_6)$alkyl, optionally substituted $(C_2-C_6)$alkenyl, optionally substituted $(C_2-C_6)$alkynyl, optionally substituted $(C_1-C_6)$ alkoxy, optionally substituted $(C_3-C_8)$cycloalkyl, optionally substituted $(C_3-C_8)$cycloalkyl $(C_1-C_6)$alkyl, optionally substituted $(C_3-C_8)$cycloalkyl-CO—, optionally substituted $(C_3-C_8)$cycloalkyl-SO₂—, optionally substituted aryl $(C_1-C_6)$alkoxy, optionally substituted $(C_3-C_8)$cycloalkyl $(C_1-C_6)$alkoxy, optionally substituted heterocyclyl-CO—, optionally substituted 4-10 membered mono or azabicyclo heterocyclyl comprising carbon atoms and 1-4 heteroatoms selected from N, O, P(=O) and S(O)ₚ, optionally substituted $(C_1-C_6)$alkyl-SO₂—, —NR⁶SO₂-optionally substituted $(C_1-C_6)$alkyl, —NR⁶SO₂-optionally substituted heterocyclo, optionally substituted $(C_1-C_6)$alkyl-NR⁶SO₂— or optionally substituted heterocyclo-NR⁶SO₂—, wherein the optional substituents in each case are independently alkyl, cycloalkyl, aryl, 5-7 membered heterocyclyl comprising carbon atoms, and 1-4 heteroatoms selected from N and O; halo, haloalkyl, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, arylamino, thiol, alkylthio, arylthio, arylalkylthio, alkylthiono, arylthiono, arylalkylthiono, alkylsulfonyl, arylsulfonyl, arylalkylsulfonyl, —SO₂NH₂, nitro, cyano or carboxy;

R² is hydrogen, halogen, —CN, OH, —CONR³R⁴, —NR⁶COOR⁴, —NR⁶CONR³R⁴, —NR⁶COR⁴, —NR⁶SO₂R⁵, —SO₂NR³R⁴, —NR⁶SO₂NR³R⁴, $(C_1-C_6)$alkyl, $(C_3-C_8)$cycloalkyl, $(C_1-C_6)$ alkoxy, aryl, $(C_1-C_6)$alkyl-SO₂—, aryl-SO₂ or heterocyclo;

R³ is hydrogen, $(C_1-C_6)$alkyl, $(C_3-C_8)$cycloalkyl, $(C_2-C_6)$alkenyl, $(C_2-C_6)$alkynyl, cyano$(C_1-C_6)$alkyl, hydroxy$(C_1-C_6)$alkyl, aryl, aryl$(C_1-C_6)$alkyl, aryloxy$(C_1-C_6)$ alkyl, $(C_1-C_6)$alkyl-SO₂—, heterocyclyl or heterocyclyl$(C_1-C_6)$alkyl;

R⁴ is hydrogen, $(C_1-C_6)$alkyl or $(C_3-C_8)$cycloalkyl;

R⁵ is hydrogen, $(C_1-C_6)$alkyl, $(C_3-C_8)$cycloalkyl, $(C_2-C_6)$alkenyl, $(C_2-C_6)$alkynyl, cyano$(C_1-C_6)$alkyl, hydroxy$(C_1-C_6)$alkyl, aryl, aryl$(C_1-C_6)$alkyl, aryloxy$(C_1-C_6)$ alkyl, $(C_1-C_6)$alkyl-SO₂—, heterocyclyl or optionally substituted heterocyclyl$(C_1-C_6)$alkyl;

R⁶ is hydrogen or $(C_1-C_6)$alkyl;

the term heterocyclo, heterocycle or heterocyclyl in each occurrence meaning a 4-10 membered mono or azabicyclo ring comprising carbon atoms and 1-4 heteroatoms selected from N, O, P(=O) and S(O)₂, or a pharmaceutically acceptable salt, tautomer or stereoisomer thereof.

7. A compound according to claim 6 wherein A is

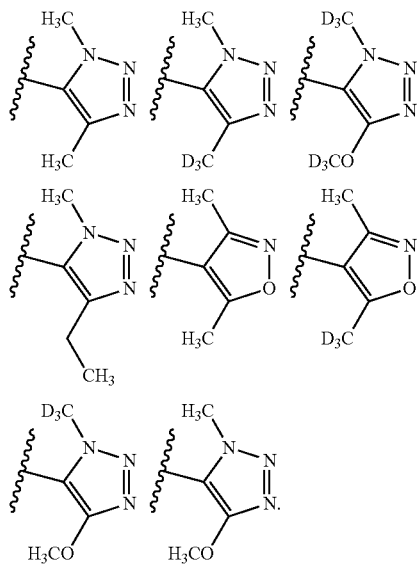

8. A compound according to claim 1 of the formula

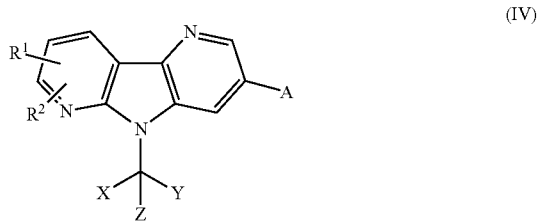

(IV)

wherein:

A is

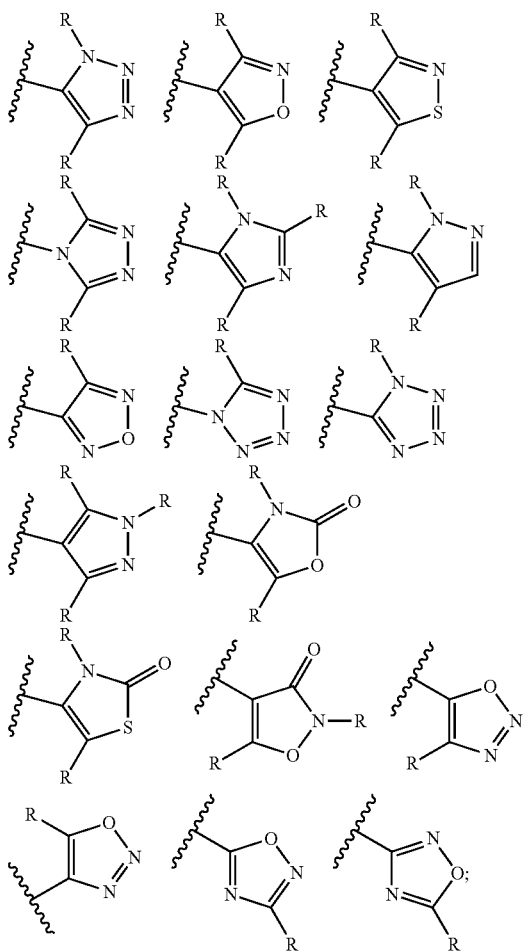

R is independently one or more hydrogen, $CD_3$, halogen, haloalkyl hydroxyalkyl, CN, $(C_1-C_6)$alkyl, $(C_1-C_6)$alkoxy, or $(C_3-C_6)$cycloalkyl;

X and Y are independently selected from hydrogen, optionally substituted $(C_1-C_6)$alkyl, optionally substituted $(C_3-C_8)$cycloalkyl, optionally substituted aryl, optionally substituted heteroaryl or optionally substituted heterocyclo, wherein the optional substituents in each case are independently alkyl, cycloalkyl, aryl or halo;

Z is hydrogen, halogen, —OH, $(C_1-C_6)$alkyl or $(C_1-C_6)$alkoxy;

$R^1$ is, independently at each occurrence, one or more hydrogen, halogen, —CN, —$OR^4$, —$NR^3R^4$, —$CONR^3R^4$, —COOH, —$OCONR^3R^4$, —$NR^6OCOR^3$, —$NR^6CONR^3R^4$, —$NR^6SO_2NR^3R^4$, —$NR^6SO_2R^4$, optionally substituted $(C_1-C_6)$alkyl, optionally substituted $(C_2-C_6)$alkenyl, optionally substituted $(C_2-C_6)$alkynyl, optionally substituted $(C_1-C_6)$alkoxy, optionally substituted $(C_3-C_8)$cycloalkyl, optionally substituted $(C_3-C_8)$cycloalkyl $(C_1-C_6)$alkyl, optionally substituted $(C_3-C_8)$cycloalkyl-CO—, optionally substituted $(C_3-C_8)$cycloalkyl-$SO_2$—, optionally substituted aryl $(C_1-C_6)$alkoxy, optionally substituted $(C_3-C_8)$cycloalkyl $(C_1-C_6)$alkoxy, optionally substituted heterocyclyl-CO—, optionally substituted 4-10 membered mono or azabicyclo heterocyclyl comprising carbon atoms and 1-4 heteroatoms selected from N, O, P(=O) and $S(O)_p$, optionally substituted $(C_1-C_6)$alkyl-$SO_2$—, —$NR^6SO_2$-optionally substituted $(C_1-C_6)$alkyl, —$NR^6SO_2$-optionally substituted heterocyclo, optionally substituted $(C_1-C_6)$alkyl-$NR^6SO_2$— or optionally substituted heterocyclo-$NR^6SO_2$—, wherein the optional substituents in each case are independently alkyl, cycloalkyl, aryl, 5-7 membered heterocyclyl comprising carbon atoms, and 1-4 heteroatoms selected from N and O; halo, haloalkyl, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, arylamino, thiol, alkylthio, arylthio, arylalkylthio, alkylthiono, arylthiono, arylalkylthiono, alkylsulfonyl, arylsulfonyl, arylalkylsulfonyl, —$SO_2NH_2$, nitro, cyano or carboxy;

$R^2$ is hydrogen, halogen, —CN, OH, —$CONR^3R^4$, —$NR^6COOR^4$, —$NR^6CONR^3R^4$, —$NR^6COR^4$, —$NR^6SO_2R^5$, —$SO_2NR^3R^4$, —$NR^6SO_2NR^3R^4$, $(C_1-C_6)$alkyl, $(C_3-C_8)$cycloalkyl, $(C_1-C_6)$ alkoxy, aryl, $(C_1-C_6)$alkyl-$SO_2$—, aryl-$SO_2$ or heterocyclo;

$R^3$ is hydrogen, $(C_1-C_6)$alkyl, $(C_3-C_8)$cycloalkyl, $(C_2-C_6)$ alkenyl, $(C_2-C_6)$alkynyl, cyano$(C_1-C_6)$alkyl, hydroxy $(C_1-C_6)$alkyl, aryl, aryl$(C_1-C_6)$alkyl, aryloxy$(C_1-C_6)$ alkyl, $(C_1-C_6)$alkyl-$SO_2$—, heterocyclyl or heterocyclyl$(C_1-C_6)$alkyl;

$R^4$ is hydrogen, $(C_1-C_6)$alkyl or $(C_3-C_8)$cycloalkyl;

$R^5$ is hydrogen, $(C_1-C_6)$alkyl, $(C_3-C_8)$cycloalkyl, $(C_2-C_6)$ alkenyl, $(C_2-C_6)$alkynyl, cyano$(C_1-C_6)$alkyl, hydroxy $(C_1-C_6)$alkyl, aryl, aryl$(C_1-C_6)$alkyl, aryloxy$(C_1-C_6)$ alkyl, $(C_1-C_6)$alkyl-$SO_2$—, heterocyclyl or heterocyclyl$(C_1-C_6)$alkyl;

$R^6$ is hydrogen or $(C_1-C_6)$alkyl;

the term heterocyclo, heterocycle or heterocyclyl in each occurrence meaning a 4-10 membered mono or azabicyclo ring comprising carbon atoms and 1-4 heteroatoms selected from N, O, P(=O) and $S(O)_2$, or a pharmaceutically acceptable salt, tautomer or stereoisomer thereof.

9. A compound according to claim 8 wherein

A is

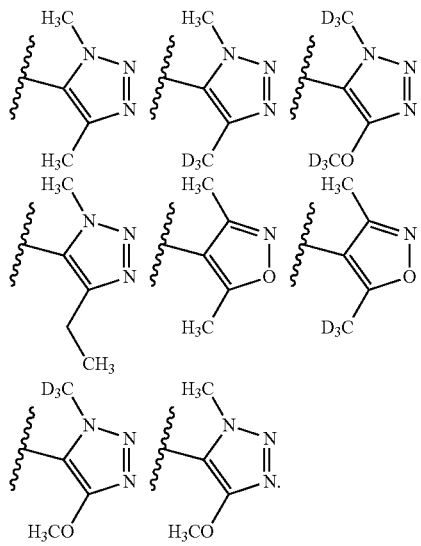

10. A compound according to claim 1 of the formula

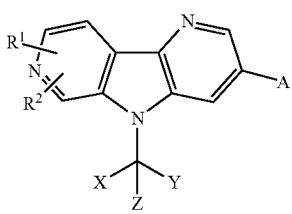

(V)

wherein:

A is

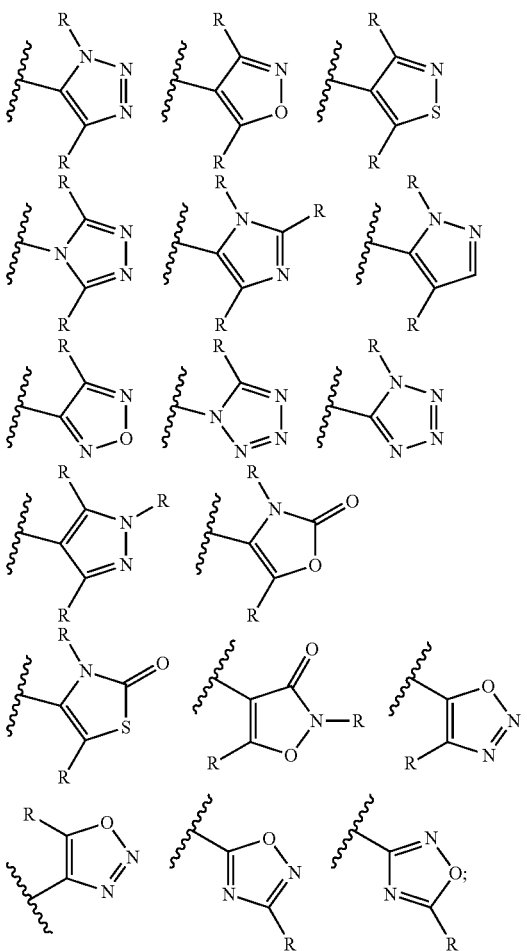

R is independently one or more hydrogen, CD$_3$, halogen, haloalkyl hydroxyalkyl, CN, (C$_1$-C$_6$)alkyl, (C$_1$-C$_6$)alkoxy, or (C$_3$-C$_6$)cycloalkyl;

X and Y are independently selected from hydrogen, optionally substituted (C$_1$-C$_6$)alkyl, optionally substituted (C$_3$-C$_8$)cycloalkyl, optionally substituted aryl, optionally substituted heteroaryl or optionally substituted heterocyclo, wherein the optional substituents in each case are independently alkyl, cycloalkyl, aryl or halo;

Z is hydrogen, halogen, —OH, (C$_1$-C$_6$)alkyl or (C$_1$-C$_6$)alkoxy;

R$^1$ is, independently at each occurrence, one or more hydrogen, halogen, —CN, —OR$^4$, —NR$^3$R$^4$, —CONR$^3$R$^4$, —COOH, —OCONR$^3$R$^4$, —NR$^6$OCOR$^3$, —NR$^6$CONR$^3$R$^4$, —NR$^6$SO$_2$NR$^3$R$^4$, —NR$^6$SO$_2$R$^4$, optionally substituted (C$_1$-C$_6$)alkyl, optionally substituted (C$_2$-C$_6$)alkenyl, optionally substituted (C$_2$-C$_6$)alkynyl, optionally substituted (C$_1$-C$_6$)alkoxy, optionally substituted (C$_3$-C$_8$)cycloalkyl, optionally substituted (C$_3$-C$_8$)cycloalkyl (C$_1$-C$_6$)alkyl, optionally substituted (C$_3$-C$_8$)cycloalkyl-CO—, optionally substituted (C$_3$-C$_8$)cycloalkyl-SO$_2$—, optionally substituted aryl (C$_1$-C$_6$)alkoxy, optionally substituted (C$_3$-C$_5$)cycloalkyl (C$_1$-C$_6$)alkoxy, optionally substituted heterocyclyl-CO—, optionally substituted 4-10 membered mono or azabicyclo heterocyclyl comprising carbon atoms and 1-4 heteroatoms selected from N, O, P(=O) and S(O)$_p$, optionally substituted (C$_1$-C$_6$)alkyl-SO$_2$—, —NR$^6$SO$_2$-optionally substituted (C$_1$-C$_6$)alkyl, —NR$^6$SO$_2$-optionally substituted heterocyclo, optionally substituted (C$_1$-C$_6$)alkyl-NR$^6$SO$_2$— or optionally substituted heterocyclo-NR$^6$SO$_2$—, wherein the optional substituents in each case are independently alkyl, cycloalkyl, aryl, 5-7 membered heterocyclyl comprising carbon atoms, and 1-4 heteroatoms selected from N and O; halo, haloalkyl, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, arylamino, thiol, alkylthio, arylthio, arylalkylthio, alkylthiono, arylthiono, arylalkylthiono, alkylsulfonyl, arylsulfonyl, arylalkylsulfonyl, —SO$_2$NH$_2$, nitro, cyano or carboxy;

R$^2$ is hydrogen, halogen, —CN, OH, —CONR$^3$R$^4$, —NR$^6$COOR$^4$, —NR$^6$CONR$^3$R$^4$, —NR$^6$COR$^4$, —NR$^6$SO$_2$R$^5$, —SO$_2$NR$^3$R$^4$, —NR$^6$SO$_2$NR$^3$R$^4$, (C$_1$-C$_6$)alkyl, (C$_3$-C$_8$)cycloalkyl, (C$_1$-C$_6$) alkoxy, aryl, (C$_1$-C$_6$)alkyl-SO$_2$—, aryl-SO$_2$ or heterocyclo;

R$^3$ is hydrogen, (C$_1$-C$_6$)alkyl, (C$_3$-C$_8$)cycloalkyl, (C$_2$-C$_6$)alkenyl, (C$_2$-C$_6$)alkynyl, cyano(C$_1$-C$_6$)alkyl, hydroxy (C$_1$-C$_6$)alkyl, aryl, aryl(C$_1$-C$_6$)alkyl, aryloxy(C$_1$-C$_6$) alkyl, (C$_1$-C$_6$)alkyl-SO$_2$—, heterocyclyl or heterocyclyl(C$_1$-C$_6$)alkyl;

R$^4$ is hydrogen, (C$_1$-C$_6$)alkyl or (C$_3$-C$_8$)cycloalkyl;

R$^5$ is hydrogen, (C$_1$-C$_6$)alkyl, (C$_3$-C$_8$)cycloalkyl, (C$_2$-C$_6$)alkenyl, (C$_2$-C$_6$)alkynyl, cyano(C$_1$-C$_6$)alkyl, hydroxy (C$_1$-C$_6$)alkyl, aryl, aryl(C$_1$-C$_6$)alkyl, aryloxy(C$_1$-C$_6$) alkyl, (C$_1$-C$_6$)alkyl-SO$_2$—, heterocyclyl or heterocyclyl(C$_1$-C$_6$)alkyl;

R$^6$ is hydrogen or (C$_1$-C$_6$)alkyl;

the term heterocyclo, heterocycle or heterocyclyl in each occurrence meaning a 4-10 membered mono or azabicyclo ring comprising carbon atoms and 1-4 heteroatoms selected from N, O, P(=O) and S(O)$_2$, or a pharmaceutically acceptable salt, tautomer or stereoisomer thereof.

11. A compound according to claim 10 wherein A is

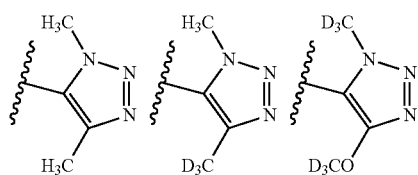

-continued

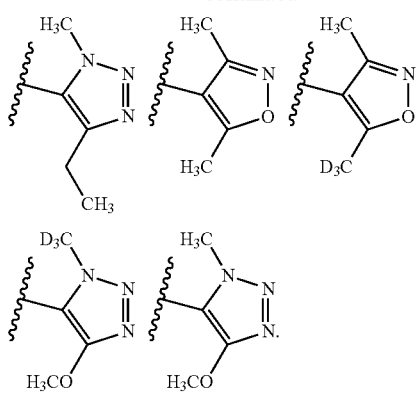

12. A compound according to claim 1 of the formula

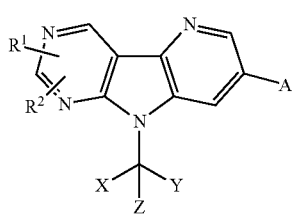

(VI)

wherein:

A is

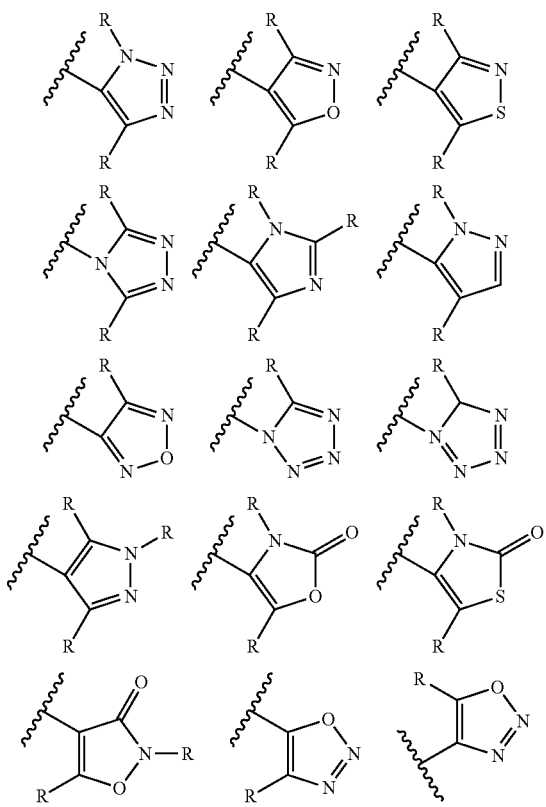

-continued

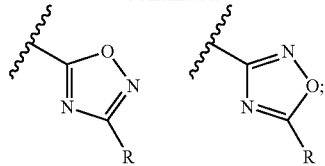

R is independently one or more hydrogen, $CD_3$, halogen, haloalkyl hydroxyalkyl, CN, $(C_1-C_6)$alkyl, $(C_1-C_6)$alkoxy, or $(C_3-C_6)$cycloalkyl;

X and Y are independently selected from hydrogen, optionally substituted $(C_1-C_6)$alkyl, optionally substituted $(C_3-C_8)$cycloalkyl, optionally substituted aryl, optionally substituted heteroaryl or optionally substituted heterocyclo, wherein the optional substituents in each case are independently alkyl, cycloalkyl, aryl or halo;

Z is hydrogen, halogen, —OH, $(C_1-C_6)$alkyl or $(C_1-C_6)$alkoxy;

$R^1$ is, independently at each occurrence, one or more hydrogen, halogen, —CN, —OR$^4$, —NR$^3$R$^4$, —CONR$^3$R$^4$, —COOH, —OCONR$^3$R$^4$, —NR$^6$OCOR$^3$, —NR$^6$CONR$^3$R$^4$, —NR$^6$SO$_2$NR$^3$R$^4$, —NR$^6$SO$_2$R$^4$, optionally substituted $(C_1-C_6)$alkyl, optionally substituted $(C_2-C_6)$alkenyl, optionally substituted $(C_2-C_6)$alkynyl, optionally substituted $(C_1-C_6)$alkoxy, optionally substituted $(C_3-C_8)$cycloalkyl, optionally substituted $(C_3-C_8)$cycloalkyl $(C_1-C_6)$alkyl, optionally substituted $(C_3-C_8)$cycloalkyl-CO—, optionally substituted $(C_3-C_8)$cycloalkyl-SO$_2$—, optionally substituted aryl $(C_1-C_6)$alkoxy, optionally substituted $(C_3-C_8)$cycloalkyl $(C_1-C_6)$alkoxy, optionally substituted heterocyclyl-CO—, optionally substituted 4-10 membered mono or azabicyclo heterocyclyl comprising carbon atoms and 1-4 heteroatoms selected from N, O, P(=O) and S(O)$_p$, optionally substituted $(C_1-C_6)$alkyl-SO$_2$—, —NR$^6$SO$_2$-optionally substituted $(C_1-C_6)$alkyl, —NR$^6$SO$_2$-optionally substituted heterocyclo, optionally substituted $(C_1-C_6)$alkyl-NR$^6$SO$_2$— or optionally substituted heterocyclo-NR$^6$ SO$_2$—, wherein the optional substituents in each case are independently alkyl, cycloalkyl, aryl, 5-7 membered heterocyclyl comprising carbon atoms, and 1-4 heteroatoms selected from N and O; halo, haloalkyl, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, arylamino, thiol, alkylthio, arylthio, arylalkylthio, alkylthiono, arylthiono, arylalkylthiono, alkylsulfonyl, arylsulfonyl, arylalkylsulfonyl, —SO$_2$NH$_2$, nitro, cyano or carboxy;

$R^2$ is hydrogen, halogen, —CN, OH, —CONR$^3$R$^4$, —NR$^6$COOR$^4$, —NR$^6$CONR$^3$R$^4$, —NR$^6$COR$^4$, —NR$^6$SO$_2$R$^5$, —SO$_2$NR$^3$R$^4$, —NR$^6$SO$_2$NR$^3$R$^4$, $(C_1-C_6)$alkyl, $(C_3-C_8)$cycloalkyl, $(C_1-C_6)$ alkoxy, aryl, $(C_1-C_6)$alkyl-SO$_2$—, aryl-SO$_2$ or heterocyclo;

$R^3$ is hydrogen, $(C_1-C_6)$alkyl, $(C_3-C_8)$cycloalkyl, $(C_2-C_6)$alkenyl, $(C_2-C_6)$alkynyl, cyano$(C_1-C_6)$alkyl, hydroxy $(C_1-C_6)$alkyl, aryl, aryl$(C_1-C_6)$alkyl, aryloxy$(C_1-C_6)$alkyl, $(C_1-C_6)$alkyl-SO$_2$—, heterocyclyl or heterocyclyl$(C_1-C_6)$alkyl;

$R^4$ is hydrogen, $(C_1-C_6)$alkyl or $(C_3-C_8)$cycloalkyl;

$R^5$ is hydrogen, $(C_1-C_6)$alkyl, $(C_3-C_8)$cycloalkyl, $(C_2-C_6)$alkenyl, $(C_2-C_6)$alkynyl, cyano$(C_1-C_6)$alkyl, hydroxy ($C_1$-$C_6$)alkyl, aryl, aryl($C_1$-$C_6$)alkyl, aryloxy($C_1$-$C_6$)alkyl, ($C_1$-$C_6$)alkyl-$SO_2$—, heterocyclyl or heterocyclyl($C_1$-$C_6$)alkyl;

$R^6$ is hydrogen or ($C_1$-$C_6$)alkyl;

the term heterocyclo, heterocycle or heterocyclyl in each occurrence meaning a 4-10 membered mono or azabicyclo ring comprising carbon atoms and 1-4 heteroatoms selected from N, O, P(=O) and $S(O)_2$, or a pharmaceutically acceptable salt, tautomer or stereoisomer thereof.

13. A compound according to claim 12 wherein A is

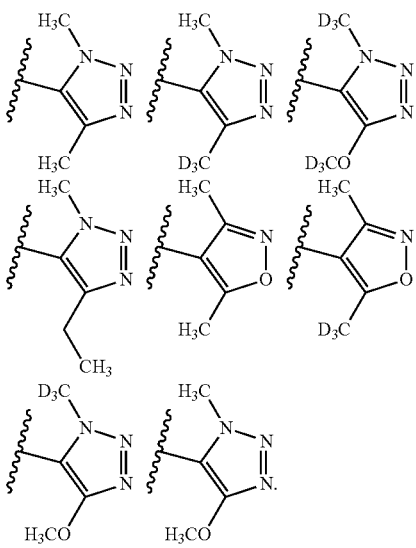

14. A compound according to claim 1 selected from the following:

5-(dimethyl-1H-1,2,3-triazol-5-yl)-10-methanesulfonyl-13-methoxy-8-[(S)-oxan-4-yl(phenyl)methyl]-3,8,12-triazatricyclo[7.4.0.0$^{2,7}$]trideca-1(13),2(7),3,5,9,11-hexaene, 10-methanesulfonyl-13-methoxy-5-[4-($^2H_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene, 5-(dimethyl-1H-1,2,3-triazol-5-yl)-8-[(S)-(2-fluorophenyl)(oxan-4-yl)methyl]-10-methanesulfonyl-13-methoxy-3,8,12-triazatricyclo[7.4.0.0$^{2,7}$]trideca-1(13),2(7),3,5,9,11-hexaene, 8-[(S)-(2-fluorophenyl)(oxan-4-yl)methyl]-10-methanesulfonyl-13-methoxy-5-[4-($^2H_3$)methyl-1-methyl-1H-1,2,3-triazol-5-yl]-3,8,12-triazatricyclo[7.4.0.0$^{2,7}$]trideca-1(13),2(7),3,5,9,11-hexaene, 5-(dimethyl-1H-1,2,3-triazol-5-yl)-8-[(S)-(4-fluorophenyl)(oxan-4-yl)methyl]-10-methanesulfonyl-13-methoxy-3,8,12-triazatricyclo[7.4.0.0$^{2,7}$]trideca-1(13),2(7),3,5,9,11-hexaene, 5-(dimethyl-1H-1,2,3-triazol-5-yl)-13-ethoxy-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaene, 10-methanesulfonyl-13-($^2H_3$)methoxy-5-[5-($^2H_3$)methyl-3-methyl-1,2-oxazol-4-yl]-8-[(S)-oxan-4-yl(phenyl)methyl]-3,8,12-triazatricyclo[7.4.0.0$^{2,7}$]trideca-1(13),2(7),3,5,9,11-hexaene, 8-[(S)-(4-fluorophenyl)(oxan-4-yl)methyl]-10-methanesulfonyl-13-($^2H_3$)methoxy-5-[5-($^2H_3$)methyl-3-methyl-1,2-oxazol-4-yl]-3,8,12-triazatricyclo[7.4.0.0$^{2,7}$]trideca-1(13),2(7),3,5,9,11-hexaene, 13-ethoxy-10-methanesulfonyl-5-[4-($^2H_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene, 13-(cyclopropylmethoxy)-10-methanesulfonyl-5-[4-($^2H_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaene, 8-[(S)-(3-fluoropyridin-2-yl)(oxan-4-yl)methyl]-10-methanesulfonyl-13-methoxy-5-[4-($^2H_3$)methyl-1-methyl-1H-1,2,3-triazol-5-yl]-3,8,12-triazatricyclo[7.4.0.0$^{2,7}$]trideca-1(13),2(7),3,5,9,11-hexaene, 8-[(S)-(4,4-difluorocyclohexyl)(3-fluoropyridin-2-yl)methyl]-10-methanesulfonyl-13-methoxy-5-[4-($^2H_3$)methyl-1-methyl-1H-1,2,3-triazol-5-yl]-3,8,12-triazatricyclo[7.4.0.0$^{2,7}$]trideca-1(13),2(7),3,5,9,11-hexaene, 13-(cyclopropylmethoxy)-8-[(S)-(2-fluorophenyl)(oxan-4-yl)methyl]-10-methanesulfonyl-5-[4-($^2H_3$)methyl-1-methyl-1H-1,2,3-triazol-5-yl]-3,8,12-triazatricyclo[7.4.0.0$^{2,7}$]trideca-1(13),2(7),3,5,9,11-hexaene, 13-ethoxy-8-[(S)-(4-fluorophenyl)(oxan-4-yl)methyl]-10-methanesulfonyl-5-[4-($^2H_3$)methyl-1-methyl-1H-1,2,3-triazol-5-yl]-3,8,12-triazatricyclo[7.4.0.0$^{2,7}$]trideca-1(13),2(7),3,5,9,11-hexaene, 13-(cyclopropylmethoxy)-8-[(S)-(4-fluorophenyl)(oxan-4-yl)methyl]-10-methanesulfonyl-5-[4-($^2H_3$)methyl-1-methyl-1H-1,2,3-triazol-5-yl]-3,8,12-triazatricyclo[7.4.0.0$^{2,7}$]trideca-1(13),2(7),3,5,9,11-hexaene, 8-[(S)-(4,4-difluorocyclohexyl)(phenyl)methyl]-10-methanesulfonyl-13-methoxy-5-[4-($^2H_3$)methyl-1-methyl-1H-1,2,3-triazol-5-yl]-3,8,12-triazatricyclo[7.4.0.0$^{2,7}$]trideca-1(13),2(7),3,5,9,11-hexaene, 10-methanesulfonyl-13-methoxy-5-[4-($^2H_3$)methyl-1-methyl-1H-1,2,3-triazol-5-yl]-8-[oxan-4-yl(2,4,6-trifluorophenyl)methyl]-3,8,12-triazatricyclo[7.4.0.0$^{2,7}$]trideca-1(13),2(7),3,5,9,11-hexaene, 8-[(4,4-difluorocyclohexyl)(phenyl)methyl]-5-(dimethyl-1H-1,2,3-triazol-5-yl)-10-methanesulfonyl-13-methoxy-3,8,12-triazatricyclo[7.4.0.0$^{2,7}$]trideca-1(13),2(7),3,5,9,11-hexaene, 13-(cyclopropylmethoxy)-8-[(S)-(4,4-difluorocyclohexyl)(phenyl)methyl]-10-methanesulfonyl-5-[4-($^2H_3$)methyl-1-methyl-1H-1,2,3-triazol-5-yl]-3,8,12-triazatricyclo[7.4.0.0$^{2,7}$]trideca-1(13),2(7),3,5,9,11-hexaene, N-[5-(dimethyl-1,2-oxazol-4-yl)-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaen-13-yl]cyclopropanesulfonamide, 13-(cyclopropylmethoxy)-5-(dimethyl-1H-1,2,3-triazol-5-yl)-10-methanesulfonyl-8-[(S)-oxan-4-yl(phenyl)methyl]-3,8,12-triazatricyclo[7.4.0.0$^{2,7}$]trideca-1(13),2(7),3,5,9,11-hexaene, 10-methanesulfonyl-13-methoxy-5-(4-methoxy-1-methyl-1H-1,2,3-triazol-5-yl)-8-[(S)-oxan-4-yl(phenyl)methyl]-3,8,12-triazatricyclo[7.4.0.0$^{2,7}$]trideca-1(9),2(7),3,5,10,12-hexaene

[5-(dimethyl-1H-1,2,3-triazol-5-yl)-13-methoxy-8-[(S)-oxan-4-yl(phenyl)methyl]-3,8,12-triazatricyclo[7.4.0.0$^{2,7}$]trideca-1(9),2,4,6,10,12-hexaen-10-yl]methanol, 2-{13-methoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(13),2(7),3,5,9,11-hexaen-10-yl}propan-2-ol, {13-methoxy-5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(9),2,4,6,10,12-hexaen-10-yl}methanol, 2-[5-(dimethyl-1H-1,2,3-triazol-5-yl)-13-methoxy-8-[(S)-oxan-4-yl(phenyl)methyl]-3,8,12-triazatricyclo[7.4.0.0$^{2,7}$]trideca-1(9),2,4,6,10,12-hexaen-10-yl]propan-2-ol, 2-[5-(dimethyl-1,2-oxazol-4-yl)-8-[(4-fluorophenyl)(oxan-4-yl)methyl]-3,8,12-triazatricyclo[7.4.0.0$^{2,7}$]trideca-1(9),2(7),3,5,10,12-hexaen-11-yl]propan-2-ol, 2-[5-(dimethyl-1,2-oxazol-4-yl)-13-methoxy-8-[(S)-oxan-4-yl(phenyl)methyl]-3,8,12-triazatricyclo[7.4.0.0$^{2,7}$]trideca-1(9),2,4,6,10,12-hexaen-10-yl]propan-2-ol, 2-{5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(9),2(7),3,5,10,12-hexaen-11-yl}propan-2-ol, 2-{5-[4-($^2$H$_3$)methyl-1-methyl-1H-1,2,3-triazol-5-yl]-8-[(S)-oxan-4-yl(phenyl)methyl]-3,8,12-triazatricyclo[7.4.0.0$^{2,7}$]trideca-1(9),2,4,6,10,12-hexaen-10-yl}propan-2-ol, 2-[5-(dimethyl-1H-1,2,3-triazol-5-yl)-8-[(S)-oxan-4-yl(phenyl)methyl]-3,8,12-triazatricyclo[7.4.0.0$^{2,7}$]trideca-1(9),2(7),3,5,10,12-hexaen-11-yl]propan-2-ol, 2-{5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(13),2(7),3,5,9,11-hexaen-12-yl}propan-2-ol, 2-[5-(dimethyl-1H-1,2,3-triazol-5-yl)-8-[(S)-oxan-4-yl(phenyl)methyl]-3,8,10-triazatricyclo[7.4.0.0$^{2,7}$]trideca-1(13),2(7),3,5,9,11-hexaen-12-yl]propan-2-ol, 2-[5-(dimethyl-1,2-oxazol-4-yl)-8-[(S)-oxan-4-yl(phenyl)methyl]-3,8,12-triazatricyclo[7.4.0.0$^{2,7}$]trideca-1(9),2(7),3,5,10,12-hexaen-11-yl]propan-2-ol, 2-[5-(4-ethyl-1-methyl-1H-1,2,3-triazol-5-yl)-8-[(S)-oxan-4-yl(phenyl)methyl]-3,8,12-triazatricyclo[7.4.0.0$^{2,7}$]trideca-1(9),2(7),3,5,10,12-hexaen-11-yl]propan-2-ol, 4-{5-[4-($^2$H$_3$)methyl-1-methyl-1H-1,2,3-triazol-5-yl]-8-[(S)-oxan-4-yl(phenyl)methyl]-3,8,10-triazatricyclo[7.4.0.0$^{2,7}$]trideca-1(9),2(7),3,5,10,12-hexaen-11-yl}-1λ$^6$,4-thiomorpholine-1,1-dione, or 2-{8-[(S)-(4-fluorophenyl)(oxan-4-yl)methyl]-5-[5-($^2$H$_3$)methyl-3-methyl-1,2-oxazol-4-yl]-3,8,12-triazatricyclo[7.4.0.0$^{2,7}$]trideca-1(13),2(7),3,5,9,11-hexaen-11-yl}propan-2-ol, or a pharmaceutically acceptable salt, tautomer or stereoisomer thereof.

15. A pharmaceutical composition which comprises a compound according to claim 1 or a pharmaceutically acceptable salt thereof and one or more pharmaceutically acceptable carriers, diluents or excipients.

16. A combination pharmaceutical product comprising a compound according to claim 1 or a pharmaceutically acceptable salt thereof together with one or more other therapeutically active agents.

17. A method of treating cancer, wherein the cancer is small cell lung cancer, non-small cell lung cancer, colorectal cancer, multiple myeloma or AML, comprising administering a therapeutically effective amount of one or more compounds according to claim 1 or a pharmaceutically acceptable salt thereof.

\* \* \* \* \*

SEQUENCE LISTING

<160> NUMBER OF SEQ ID NOS: 3

<210> SEQ ID NO 1
<211> LENGTH: 21
<212> TYPE: PRT
<213> ORGANISM: Tobacco vein mottling virus

<400> SEQUENCE: 1

Met Gly Ser Ser His His His His His His Ser Ser Gly Glu Thr Val
1               5                   10                  15

Arg Phe Gln Ser Met
            20

```
His Glu Asp Thr Gly His Met
            35

<210> SEQ ID NO 3
<211> LENGTH: 21
<212> TYPE: PRT
<213> ORGANISM: Artificial Sequence
<220> FEATURE:
<223> OTHER INFORMATION: Biotinylated histone peptide
<220> FEATURE:
<221> NAME/KEY: MOD_RES
<222> LOCATION: (5)..(5)
<223> OTHER INFORMATION: ACETYLATION
<220> FEATURE:
<221> NAME/KEY: MOD_RES
<222> LOCATION: (8)..(8)
<223> OTHER INFORMATION: ACETYLATION
<220> FEATURE:
<221> NAME/KEY: MOD_RES
<222> LOCATION: (12)..(12)
<223> OTHER INFORMATION: ACETYLATION
<220> FEATURE:
<221> NAME/KEY: MOD_RES
<222> LOCATION: (16)..(16)
<223> OTHER INFORMATION: ACETYLATION

<400> SEQUENCE: 3

Ser Gly Arg Gly Lys Gly Gly Lys Gly Leu Gly Lys Gly Gly Ala Lys
1               5                  10                  15

Arg His Arg Lys Val
            20
```